US010202452B2

(12) United States Patent
Tan et al.

(10) Patent No.: US 10,202,452 B2
(45) Date of Patent: Feb. 12, 2019

(54) CD3 BINDING POLYPEPTIDES

(71) Applicant: Aptevo Research and Development LLC, Seattle, WA (US)

(72) Inventors: Philip H Tan, Seattle, WA (US); Sateesh K Natarajan, Redmond, WA (US); Catherine J McMahan, Seattle, WA (US)

(73) Assignee: Aptevo Research and Development LLC, Seattle, WA (US)

( * ) Notice: Subject to any disclaimer, the term of this patent is extended or adjusted under 35 U.S.C. 154(b) by 457 days.

(21) Appl. No.: 14/395,689

(22) PCT Filed: Apr. 18, 2013

(86) PCT No.: PCT/US2013/037135

§ 371 (c)(1),
(2) Date: Oct. 20, 2014

(87) PCT Pub. No.: WO2013/158856

PCT Pub. Date: Oct. 24, 2013

(65) Prior Publication Data

US 2015/0232557 A1 Aug. 20, 2015

Related U.S. Application Data

(60) Provisional application No. 61/636,557, filed on Apr. 20, 2012, provisional application No. 61/718,635, filed on Oct. 25, 2012, provisional application No. 61/799,849, filed on Mar. 15, 2013.

(51) Int. Cl.

| | |
|---|---|
| ***C07K 16/28*** | (2006.01) |
| ***C07K 16/40*** | (2006.01) |
| *A61K 39/00* | (2006.01) |

(52) U.S. Cl.

CPC ...... *C07K 16/2809* (2013.01); *C07K 16/2896* (2013.01); *C07K 16/40* (2013.01); *A61K 2039/505* (2013.01); *C07K 2317/31* (2013.01); *C07K 2317/53* (2013.01); *C07K 2317/56* (2013.01); *C07K 2317/567* (2013.01); *C07K 2317/73* (2013.01)

(58) Field of Classification Search

None

See application file for complete search history.

(56) References Cited

U.S. PATENT DOCUMENTS

| | | | |
|---|---|---|---|
| 6,132,992 | A | 10/2000 | Ledbetter et al. |
| 6,423,498 | B1 | 7/2002 | Markland et al. |
| 6,809,185 | B1 | 10/2004 | Schoonjans et al. |
| 7,405,288 | B2 | 7/2008 | Galanis et al. |
| 7,695,936 | B2 | 4/2010 | Carter et al. |
| 7,754,208 | B2 | 7/2010 | Ledbetter et al. |
| 7,754,209 | B2 | 7/2010 | Ledbetter et al. |
| 7,829,084 | B2 | 11/2010 | Ledbetter et al. |
| 8,101,722 | B2 | 1/2012 | Kufer et al. |
| 8,106,161 | B2 | 1/2012 | Ledbetter et al. |
| 8,147,835 | B2 | 4/2012 | Ledbetter et al. |
| 8,188,237 | B2 | 5/2012 | Ledbetter et al. |
| 8,197,810 | B2 | 6/2012 | Ledbetter et al. |
| 2002/0150559 | A1 | 10/2002 | DeBoer et al. |
| 2003/0108548 | A1 | 6/2003 | Bluestone et al. |
| 2003/0133939 | A1 | 7/2003 | Ledbetter et al. |
| 2004/0044182 | A1 | 3/2004 | Hunt et al. |
| 2004/0058445 | A1 | 3/2004 | Ledbetter et al. |
| 2005/0175614 | A1 | 8/2005 | Ledbetter et al. |
| 2005/0180970 | A1 | 8/2005 | Ledbetter et al. |
| 2005/0186216 | A1 | 8/2005 | Ledbetter et al. |
| 2005/0202012 | A1 | 9/2005 | Ledbetter et al. |
| 2005/0202023 | A1 | 9/2005 | Ledbetter et al. |
| 2005/0202534 | A1 | 9/2005 | Ledbetter et al. |
| 2005/0238646 | A1 | 10/2005 | Ledbetter et al. |
| 2007/0237779 | A1 | 10/2007 | Ledbetter et al. |
| 2009/0148447 | A1 | 6/2009 | Ledbetter et al. |
| 2009/0175867 | A1 | 7/2009 | Thompson et al. |
| 2009/0196870 | A1 | 8/2009 | Ledbetter et al. |
| 2009/0324589 | A1 * | 12/2009 | Igawa .................. C07K 16/40 424/133.1 |
| 2010/0203052 | A1 | 8/2010 | Ledbetter et al. |
| 2010/0279932 | A1 | 11/2010 | Ledbetter et al. |

(Continued)

FOREIGN PATENT DOCUMENTS

| | | | |
|---|---|---|---|
| EP | 2006381 | A1 | 12/2008 |
| EP | 1940881 | B1 | 11/2016 |

(Continued)

OTHER PUBLICATIONS

Vajdos et al. (J Mol Biol. Jul. 5, 2002;320(2):415-28) (Year: 2002).*
Fang et al., "Characterization of an anti-human ovarian carcinoma x anti-human CD3 bispecific single-chain antibody with an albumin-original interlinker," Gynecologic Oncology 92:135-146 (2004).
Kobayashi et al., "The Pharmacokinetic Characteristics of Glycolated Humanized Anti-Tac Fabs Are Determined by Their Isoelectric Points," Cancer Res. 59:422-430 (1999).
Onda et al, "Lowering the Isoelectric Point of the Fv Portion of Recombinant Immunotoxins Leads to Decreased Nonspecific Animal Toxicity without Affecting Antitumor Activity," Cancer Res. 61:5070-5077 (2001).
Frankel et al., "Characterization of diphtheria fusion proteins targeted to the human interleukin-3 receptor," Protein Eng. 13(8):575-581 (2000).

(Continued)

*Primary Examiner* — Zachary S Skelding
(74) *Attorney, Agent, or Firm* — Cooley LLP

(57) ABSTRACT

The present invention relates to mono-specific and multi-specific polypeptides that specifically bind or interact with CD3. These polypeptides can be, but are not limited to, antibodies, fragments thereof, scFvs, Fabs, di-scFvs single domain antibodies, diabodies, dual variable domain binding proteins and polypeptides containing an antibody or antibody fragments. In one embodiment, a multi-specific polypeptide binds both a T-cell receptor complex on T-cells and a tumor antigen to induce target-dependent T-cell cytotoxicity, activation and proliferation.

33 Claims, 32 Drawing Sheets

Specification includes a Sequence Listing.

(56) References Cited

U.S. PATENT DOCUMENTS

| | | | |
|---|---|---|---|
| 2011/0033483 | A1 | 2/2011 | Ledbetter et al. |
| 2011/0142851 | A1 | 6/2011 | Misher et al. |
| 2011/0152173 | A1 | 6/2011 | Lofquist et al. |
| 2011/0158995 | A1 | 6/2011 | Tan et al. |
| 2011/0177070 | A1 | 7/2011 | Lofquist et al. |
| 2011/0217302 | A1 | 9/2011 | Odegard et al. |
| 2012/0100139 | A1 | 4/2012 | Thompson et al. |
| 2012/0213773 | A1 | 8/2012 | Ledbetter et al. |
| 2013/0052195 | A1 | 2/2013 | Misher et al. |
| 2013/0189261 | A1 | 7/2013 | Odegard et al. |
| 2017/0008960 | A1 | 1/2017 | Odegard et al. |

FOREIGN PATENT DOCUMENTS

| | | | |
|---|---|---|---|
| JP | 2006-512407 | A | 4/2006 |
| RU | 2179862 | C1 | 2/2002 |
| WO | WO 1994/028027 | A1 | 12/1994 |
| WO | WO 1997/044362 | A1 | 11/1997 |
| WO | WO 02/40545 | A2 | 5/2002 |
| WO | WO 2002/056910 | A1 | 7/2002 |
| WO | WO 2004/029207 | A2 | 4/2004 |
| WO | WO 2004/106381 | A1 | 12/2004 |
| WO | WO 2005/017148 | A1 | 2/2005 |
| WO | WO 2006/095164 | A1 | 9/2006 |
| WO | WO 2007/042261 | A2 | 4/2007 |
| WO | WO 2007/048037 | A2 | 4/2007 |
| WO | WO 2007/114319 | A1 | 10/2007 |
| WO | WO 2007/145941 | A2 | 12/2007 |
| WO | WO 2007/146968 | A2 | 12/2007 |
| WO | WO 2008/051448 | A2 | 5/2008 |
| WO | WO 2008/079713 | A2 | 7/2008 |
| WO | WO 2009/023386 | A2 | 2/2009 |
| WO | WO 2009/080251 | A1 | 7/2009 |
| WO | WO 2009/080254 | A1 | 7/2009 |
| WO | WO 2010/014629 | A1 | 2/2010 |
| WO | WO 2010/034441 | A1 | 4/2010 |
| WO | WO 2010/040508 | A1 | 4/2010 |
| WO | WO 2010/042904 | A2 | 4/2010 |
| WO | WO 2010/136172 | A1 | 12/2010 |
| WO | WO 2011/090754 | A1 | 7/2011 |
| WO | WO 2011/090761 | A1 | 7/2011 |
| WO | WO 2011/090762 | A1 | 7/2011 |
| WO | WO 2012/145714 | A2 | 10/2012 |
| WO | WO 2013/158856 | A2 | 10/2013 |

OTHER PUBLICATIONS

Pakula, A. A., and Sauer, R. T., "Genetic analysis of protein stability and function," Annu. Rev. Genet. 23:289-310 (1989).

Igawa et al., "Reduced elimination of IgG antibodies by engineering the variable region," Prot. Eng. Design Select. 23(5):385-392 (2010).

International Preliminary Report on Patentability, PCT appl. No. PCT/US2013/037135, 8 pages (dated Oct. 21, 2014).

Written Opinion of the International Searching Authority, PCT appl. No. PCT/US2013/037135, 7 pages (dated Jul. 5, 2013).

Bortoletto et al., "Optimizing anti-CD3 affinity for effective T cell targeting against tumor cells," Eur. J. Immunol. 32(11):3102-3107 (2002).

Kipriyanov et al., "Two amino acid mutations in an anti-human CD3 single-chain Fv antibody fragment that affect the yield on bacterial secretion but not the affinity," Protein Eng. 4(10):445-453 (1997).

Search Report, SG appl. No. 11201406346S, 6 pages (dated Apr. 5, 2016).

Serpieri et al., "Comparison of Humanized IgG and FvFc Anti-CD3 Monoclonal Antibodies Expressed in CHO Cells," Mol. Biotechnol. 45(3):218-225 (2010).

Supplementary European Search Report, EP appl. No. 13778209.0, 12 pages (dated Feb. 25, 2016).

Written Opinion, SG appl. No. 112014063465, 11 pages (dated Apr. 5, 2016).

Zhou et al., "Some characteristics and purification of anti-(human ovarian carcinoma) x anti-(human CD3) single chain bispecific antibody," Biotechnol. Appl. Biochem. 47(1):39-47 (2007).

Alberola-Ila et al., "Stimulation Through the TCR/CD3 Complex Up-regulates the CD2 Surface Expression on Human T Lymphocytes," J. Immunol. 146:1085-1092 (1991).

Alegre et al., "A Non-Activating "Humanized" Anti-CD3 Monoclonal Antibody Retains Immunosuppressive Properties In Vivo," Transplantation 67:1537-1543 (1994).

Anasetti, C. et al., "Induction of Specific Nonresponsiveness in Unprimed Human T Cells by Anti-CD3 Antibody and Alloantigen," J. Exp. Med 172:1691-1700, The Rockefeller University Press, United States (1990).

Boerman et al., "Tumour targetting of the anti-ovarian carcinoma X anti-CD3/TCR bispesific monoclonal antibody OC/TR and its parental MOv18 antibody in experimental ovarian cancer," Anticancer Res. 15(5B):2169-2174 (1995).

Caldas et al., "Humanization of the anti-CD18 antibody 6.7: an unexpected effect of a framework residue in binding to antigen," Mol. Immunol. 39:941-952 (2003).

Carpenter, P.A., et al., "A humanized non-FcR-binding anti-CD3 antibody, visilizumab, for treatment of steroid-refractory acute graft-versus-host disease," Blood 99: 2712-2719 (2002).

Carpenter, P.A., et al., "Non-Fc Receptor-Binding Humanized Anti-CD3 Antibodies Induce Apoptosis of Activated Human T Cells", The Journal of Immunology 165: 6205-6213 (2000).

Casset et al., "A peptide mimetic of an anti-CD4 monoclonal antibody by rational design," Biochem. Biophys. Res. Commun. 307:198-205 (2003).

Chang et al., "Loop-Sequence Features and Stability Determinants in Antibody Variable Domains by High Throughput Experiments," Structure 22: 9-21 (2014).

Chang, S.H. and Dong, C., "A novel heterodimeric cytokine consisting of IL-17 and IL-17F regulates inflammatory responses," Cell Research 17: 435-440 (2007).

Chatenoud, L., "CD3-Specific Antibody-Induced Active Tolerance: From Bench to Bedside," Nature Reviews Immunology 3:123-132 (2003).

Chatenoud, L., et al., "Restriction of the Human In Vivo Immune Response Against the Mouse Monoclonal Antibody OKT3," The Journal of Immunology 137(3):830-838 (1986).

Chien et al., "Significant structural and functional change of an antigen-binding site by a distant amino acid substitution: Proposal of a structural mechanism," Proc. Natl. Acad. Sci. USA 86: 5532-5536 (1989).

Choi, I., et al., "Recombinant chimeric OKT3 scFv IgM antibodies mediate immune suppression while reducing T cell activation in vitro," European Journal of Immunology, 31: 94-106 (2001).

De Pascalis et al., "Grafting of 'Abbreviated' Complementarity-Determining Regions Containing Specificity-Determining Residues Essential for Ligand Contact to Engineer a Less Immunogenic Humanized Monoclonal Antibody," J. Immunol. 169:3076-3084 (2002).

Giusti et al., "Somatic diversification of S107 from an antiphosphocholine to an anti-DNA autoantibody is due to a single base change in its heavy chain variable region," Proc. Natl. Acad. Sci. USA 84:2926-2930 (1987).

Güssow and Seemann, "Humanization of Monoclonal Antibodies," Meth. Enzymol. 203:99-121 (1991).

Herold, K.C., et al., "Activation of human T cells by FcR nonbinding anti-CD3 mAb, hOKT3y1(Ala-Ala)," Journal of Clinical Investigation 111(3):409-418 (2003).

Hirsch, R., et al., "Effects of In Vivo Administration of Anti-CD3 Monoclonal Antibody on T Cell Function in Mice: II. In Vivo Activation of T Cells", The Journal of Immunology 142(3):737-743 (1989).

Hoet, R.M., et al., "Generation of high-affinity human antibodies by combining donor-derived and synthetic complementarity-determining-region diversity," Nature Biotechnology 23:344-348 (2005).

Holm et al., "Functional mapping and single chain construction of the anti-cytokeratin 8 monoclonal antibody TS1," Mol. Immunol. 44:1075-1084 (2007).

Huston et al., "Protein engineering of antibody binding sites: Recovery of specific activity in an anti-digoxin single-chain Fv analogue produced in *Escherichia coli*," Proc. Natl. Acad. Sci. USA 85:5879-5883 (1988).

(56) References Cited

OTHER PUBLICATIONS

International Preliminary Report on Patentability, PCT Application No. PCT/US2009/060286, 14 pages, dated Apr. 12, 2011.
International Search Report for International Patent Application No. PCT/US2009/060286, dated Jul. 7, 2010.
Lavasani, S., et al., "Monoclonal Antibody against T-Cell Receptor αβ Induces Self Tolerance in Chronic Experimental Autoimmune Encephalomyelitis," Scandinavian Journal of Immunology 65: 39-47 (2007).
Le Gall, F., et al. "Immunosuppressive properties of anti-CD3 single-chain Fv and diabody," Journal of Immunological Methods 285:111-127 (2004).
Lv, Ming et al., "Structured to reduce the mitogenicity of anti-CD3 antibody based on computer-guided molecular design," International Journal of Biochemistry & Cell Biology 39:1142-1155 (2007).
MacCallum et al., "Antibody-antigen Interactions: Contact Analysis and Binding Site Topography," J. Mol. Biol. 262:732-745 (1996).
Mariuzza et al., "The Structural Basis of Antigen-Antibody Recognition," Ann. Rev. Biophys. Biophys. Chem. 16:139-159 (1987).
Oganesyan, V., et al., "Structural characterization of a human Fc fragment engineered for lack of effector functions," Acta Crystallographica Section D, 64:700-704 (2008).
Ortho Multicenter Transplant Study Group, "A Randomized Clinical Trial of OKT3 Monoclonal Antibody for Acute Rejection of Cadaveric Renal Transplants," The New England Journal of Medicine 313(6):337-342 (1985).
Plevy, S., et al., "A Phase I Study of Visilizumab, a Humanized Anti-CD3 Monoclonal Antibody, in Severe Steroid-Refractory Ulcerative Colitis," Gastroenterology 133:1414-1422 (2007).
Rudikoff et al., "Single amino acid substitution altering antigen-binding specificity," Proc. Natl. Acad. Sci. USA 79:1979-1983 (1982).
Samelson, L. et al., "Monoclonal antibodies against the antigen receptor on a cloned T-cell hybrid", Proc. Natl. Acad. Sci. U SA. (1983); 80 (22): 6972-6976.
Vajdos et al., "Comprehensive Functional Maps of the Antigen-binding Site of an Anti-ErbB2 Antibody Obtained with Shotgun Scanning Mutagenesis," J. Mol. Biol. 320:415-428 (2002).
Weisel, J.W., et al., "A Model for Fibrinogen: Domains and Sequence," Science 230:1388-1391 (1985).
Winkler et al., "Changing the Antigen Binding Specificity by Single Point Mutations of an Anti-p24 (HIV-1) Antibody," J. Immunol. 165: 4505-4514 (2000).
Written Opinion for International Patent Application No. PCT/US2009/060286, dated Jul. 7, 2010.
Wu et al., "Humanization of a Murine Monoclonal Antibody by Simultaneous Optimization of Framework and CDR Residues," J. Mol. Biol. 294:151-162 (1999).
Wu S. et al., "Use of Bispecific Heteroconjugated Antibodies (Anti-T Cell Antigen Receptor x Anti-MHC Class II) to Study Activation of T Cells with a Full Length or Truncated Antigen Receptor Chain", Journal of Immunology (1993); 150 (6): 2211-2221.
Yu et al., "Rationalization and Design of the Complementarity Determining Region Sequences in an Antibody-Antigen Recognition Interface," PLoS One 7(3):e33340, 15 pages (2012).
Zelensky and Gready, "The C-type lectin-like domain superfamily," FEBS Journal 272: 6179-6217 (2005).
European Patent No. 1940881 in the name of Amgen Research (Munich) GmbH, Notice of Opposition filed by Aptevo Research & Development LLC on Aug. 30, 2017, 27 pages.
European Patent No. 1940881 in the name of Amgen Research (Munich) GmbH, Reply to Notice of Opposition filed Feb. 19, 2018, 28 pages.

* cited by examiner

```
                (1) 1       10            20            30            40          51
Cris7 VH mouse  (1) QVQLQQSGAELARPGASVKMSCKASGYTFTRSTMHWVKQRPGQGLEWIGYI
      H1 chain  (1) QVQLVQSGAEVKKPGASVKVSCKASGYTFTRSTMHWVRQAPGQGLEWIGYI
      H2 chain  (1) QVQLVQSGGGVVQPGRSLRLSCKASGYTFTRSTMHWVRQAPGKGLEWIGYI
      H3 chain  (1) QVQLVQSGGGVVQPGRSLRLSCKASGYTFTRSTMHWVRQAPGKGLEWIGYI
      H4 chain  (1) QVQLVESGGGVVQPGRSLRLSCKASGYTFTRSTMHWVRQAPGQGLEWIGYI
      H6 chain  (1) EVQLVESGGGLVKPGGSLKLSCAASGFTFSRSTMHWVRQAPGKGLEWVSYI
      H5 chain  (1) QVQLVQSGAEVKKPGASVKVSCKASGYTFTRSTMHWVRQAPGQRLEWMGYI
     Consensus  (1) QVQLVQSGGGVVKPGASLRLSCKASGYTFTRSTMHWVRQAPGQGLEWIGYI
                                                                     Section 2
               (52) 52      60            70            80            90         102
Cris7 VH mouse (52) NPSSAYTNYNQKFKDKATLTADKSSSTAYMQLSSLTSEDSAVYYCASPQVH
      H1 chain (52) NPSSAYTNYNQKFKDKATLTADKSSSTAYMQLSSLRSEDTAVYYCARPQVH
      H2 chain (52) NPSSAYTNYNQKFKDKATLTADKSKNTAYMQLSSLRSEDTAVYYCARPQVH
      H3 chain (52) NPSSAYTNYNQKFKDRFTISADKSKSTAFLQMDSLRPEDTGVYFCARPQVH
      H4 chain (52) NPSSAYTNYNQKFKDRFTISADKSKSTAFLQMDSLRPEDTGVYFCARPQVH
      H6 chain (52) NPSSAYTNYNQKFKDRFTISRDNAKNSLYLQMNSLKAEDTAVYYCARPQVH
      H5 chain (52) NPSSAYTNYNQKFKDRVTITRDTSASTAYMELSSLRSEDTAVYYCARPQVH
     Consensus (52) NPSSAYTNYNQKFKDR TITADKSKSTAYMQLSSLRSEDTAVYYCARPQVH
                                                                     Section 3
              (103) 103    110        121
Cris7 VH mouse (103) YDYNGFPYWGQGTLVTVSA
      H1 chain (103) YDYNGFPYWGQGTLVTVSS
      H2 chain (103) YDYNGFPYWGQGTLVTVSS
      H3 chain (103) YDYNGFPYWGQGTPVTVSS
      H4 chain (103) YDYNGFPYWGQGTPVTVSS
      H6 chain (103) YDYNGFPYWGQGTLVTVSS
      H5 chain (103) YDYNGFPYWGQGTLVTVSS
     Consensus (103) YDYNGFPYWGQGTLVTVSS
```

FIG. 3

Section 1

| | | |
|---|---|---|
| | (1) | 1 10 20 30 40 52 |
| Cris7 VL mouse | (1) | AQQVVLTQSPAIMSAFPGEKVTMTCSASSSVSYMNWYQQKSGTSPKRWIYDS |
| L4 chain | (1) | --EIVLTQSPATLSLSPGERATLSCSASSSVSYMNWYQQKPGQAPRLLIYDS |
| L1 chain | (1) | AQDIQMTQSPSSLSASVGDRVTMTCSASSSVSYMNWYQQKPGKAPKRWIYDS |
| L2 chain | (1) | AQDIQMTQSPSSLSASVGDRVTITCSASSSVSYMNWYQQTPGKAPKRWIYDS |
| L3 chain | (1) | AQDIQMTQSPSSLSASVGDRVTMTCSASSSVSYMNWYQQKPGKAPKLLIYDS |
| Consensus | (1) | AQDIQMTQSFSSLSASVGDRVTMTCSASSSVSYMNWYQQKPGKAPKRWIYDS |

Section 2

| | | |
|---|---|---|
| | (53) | 53 60 70 80 90 104 |
| Cris7 VL mouse | (53) | SKLASGVPARFSGSGSGTSYSLTISSMETEDAATYYCQQWSRNPPTFGGGTK |
| L4 chain | (51) | SKLASGVPARFSGSGSGTDFTLTISSLEPEDFAVYYCQQWSRNPPTFGGGTK |
| L1 chain | (53) | SKLASGVPARFSGSGSGTDYTLTISSLQPEDFATYYCQQWSRNPPTFGGGTK |
| L2 chain | (53) | SKLASGVPARFSGSGSGTDFTLTISSLQPEDIATYYCQQWSRNPPTFGQGTK |
| L3 chain | (53) | SKLASGVPARFSGSGSGTDYTLTISSLQPEDFATYYCQQWSRNPPTFGGGTK |
| Consensus | (53) | SKLASGVPARFSGSGSGTDYTLTISSLQPEDFATYYCQQWSRNPPTFGGGTK |

Section 3

| | | |
|---|---|---|
| | (105) | 105108 |
| Cris7 VL mouse | (105) | LQIT |
| L4 chain | (103) | VEIK |
| L1 chain | (105) | LQIT |
| L2 chain | (105) | LQIT |
| L3 chain | (105) | VEIK |
| Consensus | (105) | LQIT |

FIG. 4

```
                                                                       Section 1
Jk region      (1)  1        10        20        30        40            54
IGKV1-5*01     (1)  --DIQMTQSPSTLSASVGDRVTITCRASQSISSWLAWYQQKPGKAPKLLIYDAS
L1 chain       (1)  AQDIQMTQSPSSLSASVGDRVTMTCSASSSVS-YMNWYQQKPGKAPKRWIYDSS
Consensus      (1)  · DIQMTQSPSSLSASVGDRVTITC AS SIS WL WYQQKPGKAPK  IYDAS
                                                                       Section 2
              (55)  55   60        70        80        90               108
IGKV1-5*01    (53)  SLESGVPSRFSGSGSGTEFTLTISSLQPDDFATYYCQQYNSYS-----------
L1 chain      (54)  KLASGVPARFSGSGSGTDYTLTISSLQPEDFATYYCQQWSRNPPTFGGGTKLQI
Consensus     (55)   L SGVPARFSGSGSGTDFTLTISSLQPDDFATYYCQQW
                                                                       Section 3
             (109)  109
IGKV1-5*01    (96)  -
L1 chain     (108)  T
Consensus    (109)
```

| Species | Gene | Allele | AccNum | Domain label | Functionality | Sequence |
|---|---|---|---|---|---|---|
| *Homsap* | IGKJ1 | IGKJ1*01 | J00242 | | F | WTFGQGTKVEIK |
| *Homsap* | IGKJ2 | IGKJ2*01 | J00242 | | F | YTFGQGTKLEIK |
| *Homsap* | IGKJ3 | IGKJ3*01 | J00242 | | F | FTFGPGTKVDIK |
| *Homsap* | IGKJ4 | IGKJ4*01 | J00242 | | F | LTFGGGTKVEIK |
| *Homsap* | IGKJ5 | IGKJ5*01 | J00242 | | F | ITFGQGTRLEIK |

JK4 is a better fit because of sequence Similarity to the end of the CDR3 sequence

FIG. 6

DRA233a and DRA234a Expressed in CHO cells

DRA161a, DRA233a and DRA234a Expressed in CHO cells (Bulk)

Non-reduced CE-SDS of pI Variant SMIPs

| Sample | % Area by CE-SDS "One-armed bandit" | Intact |
|---|---|---|
| 2404 DRA233a | 1.7 | 96.8 |
| 2405 DRA234a | 1.7 | 97.2 |

pI Variants of DRA161/209

Concentration over time for DRA233 and DRA234

| | Estimate | Units | DRA233 w/o 504 hr | DRA233 | DRA234 |
|---|---|---|---|---|---|
| pI Variants of DRA 161/209 | Rsq | | 0.9918 | 0.9481 | 0.9407 |
| | Rsq_adjusted | | 0.9898 | 0.9378 | 0.9308 |
| | Corr_XY | | -0.9959 | -0.9737 | -0.9699 |
| | No_points_lambda_z | | 6 | 7 | 8 |
| | Lambda_z | 1/hr | 0.0073 | 0.0107 | 0.0083 |
| | Lambda_z_lower | hr | 24 | 24 | 6 |
| | Lambda_z_upper | hr | 336 | 504 | 504 |
| | **HL_Lambda_z** | **hr** | **95.12** | **65.07** | **83.84** |
| | Tmax | hr | 0.25 | 0.25 | 0.25 |
| | Cmax | ug/mL | 223.67 | 223.67 | 198.91 |
| | SE_Cmax | ug/mL | 14.44 | 14.44 | 42.40 |
| | Cmax_D | kg*ug/mL/mg | 20.98 | 20.98 | 18.84 |
| | C0 | ug/mL | 239.3 | 239.3 | 215.5 |
| | Tlast | hr | 504 | 504 | 504 |
| PK Estimates for DRA233 and DRA234 | Clast | ug/mL | 0.2412 | 0.2412 | 2.0063 |
| | AUClast | hr*ug/mL | 10029 | 10029 | 10991 |
| | SE_AUClast | hr*ug/mL | 363.4 | 363.4 | 278.1 |
| | AUCall | hr*ug/mL | 10029 | 10029 | 10991 |
| | SE_AUCall | hr*ug/mL | 363.4 | 363.4 | 278.1 |
| | AUCINF_obs | hr*ug/mL | 10062 | 10051 | 11234 |
| | AUCINF_D_obs | hr*kg*ug/mL/mg | 943.9 | 942.9 | 1063.8 |
| | AUC_%Extrap_obs | % | 0.329 | 0.225 | 2.160 |
| | AUC_%Back_Ext_obs | % | 0.575 | 0.576 | 0.4612 |
| | **Vz_obs** | **mL/kg** | **145.39** | **99.55** | **113.7** |
| | **Cl_obs** | **mL/hr/kg** | **1.059** | **1.061** | **0.94** |
| | AUMClast | hr*hr*ug/mL | 1027660 | 1027660 | 1122005 |
| | AUMCINF_obs | hr*hr*ug/mL | 1048881 | 1041195 | 1273670 |
| | AUMC_%Extrap_obs | % | 2.023 | 1.300 | 11.91 |
| | MRTlast | hr | 102.47 | 102.47 | 102.08 |
| | MRTINF_obs | hr | 104.24 | 103.59 | 113.38 |
| | Vss_obs | mL/kg | 110.44 | 109.86 | 106.58 |
| | mean dose | mg/kg | 10.66 | 10.66 | 10.56 |

FIG. 19 pI Variants of DRA161/209

Humanized CRIS7 Constructs: Comparison of PK parameters

| Parameter | Estimates | | | |
|---|---|---|---|---|
| | DRA161 | DRA233 w/o 504 hr* | DRA233 | DRA234 |
| Empirical pI | 9.2 | 8.6 | 8.6 | 8.0 |
| (Half-life, hr) | 59.3 | 95.1 | 65.1 | 83.8 |
| (Clearance, mL/hr/kg) | 2.15 | 1.1 | 1.1 | 0.9 |

* Excluding the last time point

DRA 234 shows significantly higher half-life than DRA 161

FIG. 20

CD3 BINDING POLYPEPTIDES

CROSS REFERENCE TO RELATED APPLICATIONS

The present application is a U.S. National Stage Application pursuant to 35 U.S.C. § 371 of International Application No. PCT/US2013/037135, filed on Apr. 18, 2013, which claims priority to U.S. Provisional Application No. 61/636,557, filed on Apr. 20, 2012, and U.S. Provisional Application No. 61/718,635, filed on Oct. 25, 2012, and U.S. Provisional Application No. 61/799,849, filed on Mar. 15, 2013, each of which are hereby incorporated by reference in their entireties for all purposes.

RELATED INVENTIONS

This invention is related to PCT application PCT/US12/034575 filed Apr. 20, 2012 titled "Prostate-Specific Membrane Antigen Binding Proteins And Related Compositions And Methods" which claims priority to U.S. provisional patent application 61/478,449 filed Apr. 22, 2011, and is also related to U.S. Application No. 61/636,557, all three of which are incorporated by reference in their entireties.

FIELD OF INVENTION

The present invention relates to mono-specific and multi-specific protein therapeutics that bind or interact with CD3. This includes antibodies, fragments thereof, scFvs, Fabs, di-scFvs single domain antibodies and polypeptides containing an antibodies or antibody fragments.

ACCOMPANYING SEQUENCE LISTING

The contents of the text file submitted electronically herewith are incorporated herein by reference in their entirety: A computer readable format copy of the Sequence Listing (filename: EMER_031_03US_ST25.txt, date recorded: Nov. 6, 2014, file size: 450 kilobytes).

BACKGROUND

Targeting the TCR complex on human T-cells with anti-CD3 monoclonal antibodies has been used or suggested for treatment of autoimmune disease and related disorders such as in the treatment of organ allograft rejection. Mouse monoclonal antibodies specific for human CD3, such as OKT3 (Kung et al. (1979) Science 206: 347-9), were the first generation of such treatments. Although OKT3 has strong immunosuppressive potency, its clinical use was hampered by serious side effects linked to its immunogenic and mitogenic potentials (Chatenoud (2003) Nature Reviews 3:123-132). It induced an anti-globulin response, promoting its own rapid clearance and neutralization (Chatenoud et al. (1982) Eur. J. Immunol. 137:830-8). In addition, OKT3 induced T-cell proliferation and cytokine production in vitro and led to a large scale release of cytokine in vivo (Hirsch et al. (1989) J. Immunol 142: 737-43, 1989). The cytokine release (also referred to as "cytokine storm") in turn led to a "flu-like" syndrome, characterized by fever, chills, headaches, nausea, vomiting, diarrhea, respiratory distress, septic meningitis and hypotension (Chatenoud, 2003). Such serious side effects limited the more widespread use of OKT3 in transplantation as well as the extension of its use to other clinical fields such as autoimmunity (Id.).

To reduce the side effects of the first generation of anti-CD3 monoclonal antibodies, a second generation of genetically engineered anti-CD3 monoclonal antibodies had been developed not only by grafting complementarity-determining regions (CDRs) of murine anti-CD3 monoclonal antibodies into human IgG sequences, but also by introducing non-FcR-binding mutations into the Fc to reduce occurrence of cytokine storm (Cole et al. (1999) Transplantation 68: 563; Cole et al. (1997) J. Immunol. 159: 3613). See also PCT Publication No. WO2010/042904 which is herein incorporated by reference in its entirety.

In addition to monospecific therapeutics that target CD3, multispecific polypeptides that bind selectively to T-cells and tumor cells could offer a mechanism to redirect T-cell cytotoxicity towards the tumor cells and treatment of cancer. One problem, however, to designing a bispecific or multi-specific T-cell-recruiting antibody has been to maintain specificity while simultaneously overriding the regulation of T-cell activation by multiple regulatory pathways.

A need remains for improved anti-CD3 monospecific and multispecific molecules. Although previous improvements have been made in the Fc portion of CD3 targeting molecules to reduce the likelihood of cytokine storm, there is still a need for anti-CD3 therapeutics that have an increased half-life over prior art molecules, can be effectively manufactured, exhibit improved T-cell binding and/or improved redirected T-cell cytoxicity (in the case of multispecific molecules designed for treatment of cancer).

SUMMARY OF THE INVENTION

In one aspect, the present invention includes a CD3 binding polypeptide comprising a CD3 binding domain with a reduced isoelectric point as compared to a binding domain with the amino acid sequence of SEQ ID NO:41. In certain embodiments, the CD3 binding domain comprises a VH and VL region, each VH and VL region containing framework regions. To reduce the isoelectric point (pI) of the binding domain and/or polypeptide, two or more amino acids can be modified in the framework regions by substituting positively charged amino acids with neutral amino acids and/or substituting neutral amino acids with negatively charged amino acids. For instance, R and T can be substituted with S, Q can be substituted with E, Y can be substituted with F, and T can be substituted with V. In one embodiment, e.g., to reduce the risk of immunogenicity, the amino acids that are substituted into the sequence are prevalent in the human germline IgG sequence or contained in the human germline sequence at the same or proximate position, e.g., in a corresponding human germline IgG sequence. In some embodiments, the human germline IgG sequence comprises SEQ ID NOs:43 or 44.

In another embodiment of the invention, the CD3 binding polypeptide comprises modifications in the prehinge region that result in lowering the pI of the prehinge region or entire polypeptide. The prehinge region is in the junction between the binding domain and hinge region. For instance, a three amino acid prehinge region with the sequence RRT can be replaced with the sequence SSS to reduce the isoelectric point. In some embodiments, a prehinge region has a reduced isoelectric point as compared to a CD3 binding polypeptide with an RRT prehinge region.

CD3 binding polypeptides can be designed to lower the isoelectric point, e.g., by mutating the framework region(s) of the VH and/or VL regions and/or the prehinge region. The reduction in isoelectric point can be by 0.5 to 2.5 or more units.

In one embodiment of the invention, the CD3 binding polypeptide is an antibody, e.g., humanized. In another embodiment it is a small modular immunopharmaceutical protein (SMIP). In some embodiments, a CD3 binding polypeptide comprises a single-chain variable fragment (scFv).

In yet another embodiment, it is a multispecific or bispecific polypeptide. For instance, the CD3 binding polypeptide can comprise a CD3 binding domain and a tumor antigen binding domain. In one embodiment, the bispecific or multispecific molecule redirects T-cell cytotoxicity to a tumor cell.

In another embodiment of the invention, the CD3 polypeptide exists as a homodimer or a heterodimer.

DESCRIPTION OF THE FIGURES

FIG. 2A is a Capillary Electrophoresis in SDS that quantifies the low molecular weight clip content of purified proteins. FIG. 2B contains illustrations of clipped CD3 SMIP molecules. The sequences shown in FIG. 2B correspond to amino acids 252-260 of SEQ ID NO:4, 243-252 of SEQ ID NO:4 and 251-260 of SEQ ID NO:240.

FIG. 3 is an amino acid sequence alignment of Cris-7 mouse VH and derived humanized VH sequences. Cris7 VH mouse, H1, H2, H3, H4, H5, H6 and the consensus sequence correspond to SEQ ID NOs: 45, 22, 24, 26, 28, 30, 32 and 229, respectively.

FIG. 4 is an amino acid sequence alignment of Cris-7 mouse VL and derived humanized VL sequences. Cris7 VL mouse, L1, L2, L3, L4 and the consensus sequence correspond to SEQ ID NOs: 46, 34, 36, 38, 40 and 230, respectively.

FIG. 6 is an amino acid sequence alignment of the J kappa region of the VL region of the germline sequence IGKV1-5*01 and L1. The J kappa region of the VL region (IGKVI-5*01), L1 chain and consensus sequences correspond to SEQ ID NOs: 232, 34 and 233, respectively. The listed IGKJ1*01, IGKJ2*01, IGKJ3*01, IGKJ4*01 and IGKJ5*01 sequences correspond to SEQ ID NOs: 234-238, respectively.

FIG. 19 is a table of PK estimates for DRA233 and DRA234.

FIG. 20 is a table of PK parameters for DRA161 compared to DRA233 (with and without the 504 hour time point) and DRA234.

FIGS. 21A and 21B show results for CD4+ T-cell proliferation and CD8+ T-cell proliferation, respectively, as described in Example 10.

FIGS. 22A and 22B show results for CD8+ T-cell proliferation and CD4+ T-cell proliferation, respectively, as described in Example 10.

FIG. 23A shows results for the homodimeric bispecific polypeptides TSC129a, TSC233 and TSC234. FIG. 23B shows results for the heterodimeric bispecific polypeptides TSC127, TSC227 and TSC228.

FIG. 25 depicts results for T-cell binding of bispecific polypeptide heterodimers and homodimers.

FIG. 26 depicts results of target-dependent T-cell proliferation by polypeptide homodimers targeting PSMA.

DETAILED DESCRIPTION OF THE INVENTION

Figure 1:
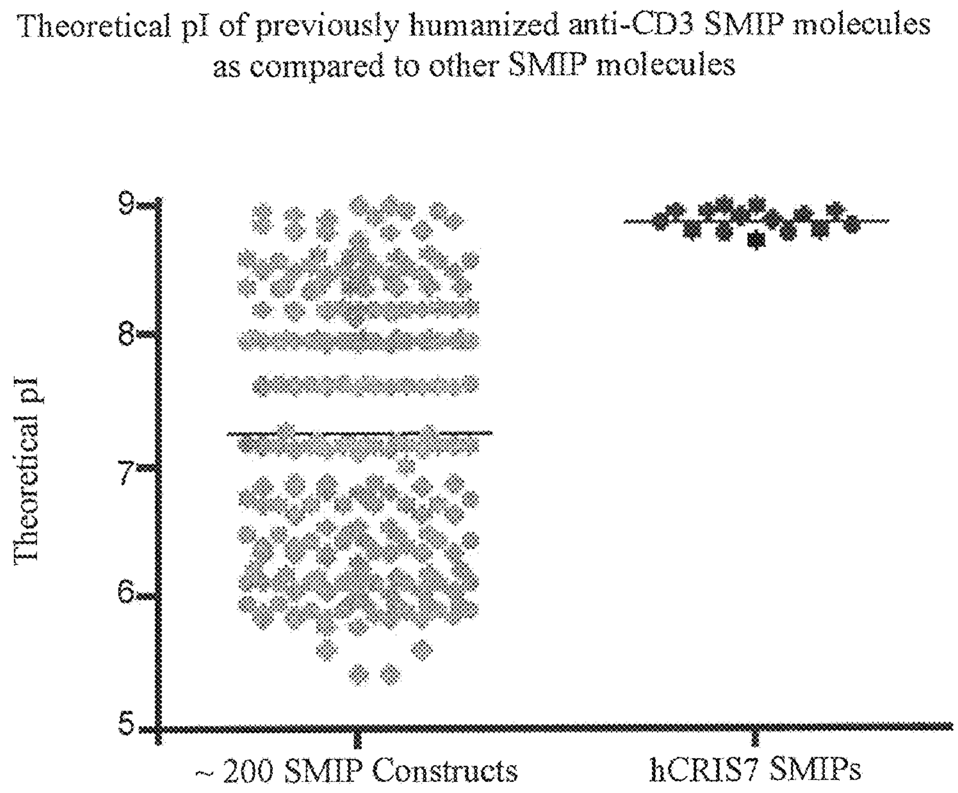
FIG. 1 is a graph depicting the theoretical pI of humanized Cris-7 SMIP polypeptides previously generated compared to the theoretical pI of about 200 other SMIP polypeptides.

The invention provides CD3 binding polypeptides with improved characteristics compared to prior art CD3 binding polypeptides. The molecules of the invention have been designed to exhibit a reduced isoelectric point by modifying amino acids in the heavy and/or light chain framework regions and/or a prehinge region to reduce the isoelectric point of the molecule. In one embodiment, the modifications are made in the J kappa region of the VL region. In some embodiments, modifications are made by substituting amino acids with a positive charge with amino acids with a neutral charge and/or substituting amino acids with a neutral charge with a negative charge.

In some embodiments, a CD3 binding polypeptide of the invention has a theoretical pI of about 0.5 to 2.5 units less than the anti-CD3 DRA209 SMIP (SEQ ID NO:4). For instance, DRA209 has a theoretical pI of 9, whereas pI variants DRA219 (SEQ ID NO:6) has a theoretical pI of 8.4, DRA221 (SEQ ID NO:10) has a theoretical pI of 8.2, DRA222 (SEQ ID NO:8) has a theoretical pI of 7.5, DRA223 (SEQ ID NO:12) has a theoretical pI of 7.2 and DRA224 (SEQ ID NO:14) has a theoretical pI of 6.8. In some embodiments, a CD3 binding polypeptide has an empirical isoelectric point of at least 1 pI unit less than a polypeptide of SEQ ID NO:4.

Surprisingly, pI variants exhibit an improved half-life and express better in CHO cells than DRA209, e.g., see Example 4 below which describes a method for measuring half-life. Moreover, multispecific constructs comprising the DRA222 scFv exhibited improved properties as compared to similar constructs with other anti-CD3 binding domains such as the DRA209 binding domain (see related PCT Publication No. WO2012/145714).

The section headings used herein are for organizational purposes only and are not to be construed as limiting the subject matter described. All documents, or portions of documents, cited herein, including but not limited to patents, patent applications, articles, books, and treatises, are hereby expressly incorporated by reference in their entirety for any purpose. In the event that one or more of the incorporated documents or portions of documents define a term that contradicts that term's definition in the application, the definition that appears in this application controls.

In the present description, any concentration range, percentage range, ratio range, or integer range is to be understood to include the value of any integer within the recited range and, when appropriate, fractions thereof (such as one tenth and one hundredth of an integer), unless otherwise indicated. As used herein, "about" means ±20% of the indicated range, value, or structure, unless otherwise indicated. It should be understood that the terms "a" and "an" as used herein refer to "one or more" of the enumerated components unless otherwise indicated. The use of the alternative (e.g., "or") should be understood to mean either one, both, or any combination thereof of the alternatives. As used herein, the terms "include" and "comprise" are used synonymously. In addition, it should be understood that the polypeptides comprising the various combinations of the components (e.g., domains or regions) and substituents described herein, are disclosed by the present application to the same extent as if each polypeptide was set forth individually. Thus, selection of particular components of individual polypeptides is within the scope of the present disclosure.

As used herein, the term "binding domain" or "binding region" refers to the domain, region, portion, or site of a protein, polypeptide, oligopeptide, or peptide that possesses the ability to specifically recognize and bind to a target molecule, such as an antigen, ligand, receptor, substrate, or inhibitor (e.g., CD3, or a tumor associated antigen such as RON, CD19, CD37 or PSMA). Exemplary binding domains include single-chain antibody variable regions (e.g., domain antibodies, sFv, scFv, and scFab), receptor ectodomains, and ligands (e.g., cytokines, chemokines). In certain embodiments, the binding domain comprises or consists of an antigen binding site (e.g., comprising a variable heavy chain sequence and variable light chain sequence or three light chain complementary determining regions (CDRs) and three heavy chain CDRs from an antibody placed into alternative framework regions (FRs) (e.g., human FRs optionally comprising one or more amino acid substitutions). A variety of assays are known for identifying binding domains of the present disclosure that specifically bind a particular target, including Western blot, ELISA, phage display library screening, and BIACORE® interaction analysis. As used herein, a CD3 binding polypeptide can have a "CD3 binding domain" and, optionally, a "second binding domain." The CD3 binding domain may be located at either the amino- or carboxyl-terminus. In certain embodiments, the CD3 binding domain comprises a humanized scFv derived from a mouse monoclonal antibody (e.g., Cris-7 or HuM291). For instance, the CD3 binding domain may be comprised of a VH region and VL region derived from a mouse monoclonal antibody wherein the VH and VL regions are joined with a linker such as a $(Gly_4Ser)_3$ (SEQ ID NO:76) linker. In other embodiments, the CD3 binding domain consists essentially of or consists of a humanized scFv derived from a mouse monoclonal antibody. In some embodiments, a CD3 binding domain of the invention comprises heavy chain CDR1, CDR2 and CDR3 and light chain CDR1, CDR2 and CDR3 of murine Cris-7 antibody or HuM291.

A binding domain "specifically binds" a target if it binds the target with an affinity or $K_a$ (i.e., an equilibrium association constant of a particular binding interaction with units of 1/M) equal to or greater than $10^5$ $M^{-1}$, while not significantly binding other components present in a test sample. Binding domains may be classified as "high affinity" binding domains and "low affinity" binding domains. "High affinity" binding domains refer to those binding domains with a $K_a$ of at least $10^7$ $M^{-1}$, at least $10^8$ $M^{-1}$, at least $10^9$ $M^{-1}$, at least $10^{10}$ $M^{-1}$, at least $10^{11}$ $M^{-1}$, at least $10^{12}$ $M^{-1}$ or at least $10^{13}$ $M^{-1}$. "Low affinity" binding domains refer to those binding domains with a $K_a$ of up to $10^7$ $M^{-1}$, up to $10^6$ $M^{-1}$, up to $10^5$ $M^{-1}$. Alternatively, affinity may be defined as an equilibrium dissociation constant ($K_d$) of a particular binding interaction with units of M (e.g., $10^{-5}$ M to $10^{-13}$ M). Affinities of binding domain polypeptides and single chain polypeptides according to the present disclosure can be readily determined using conventional techniques (see, e.g., Scatchard et al. (1949) Ann. N.Y. Acad. Sci. 51:660; and U.S. Pat. Nos. 5,283,173, 5,468,614, or the equivalent).

"CD3" is known in the art as a multi-protein complex of six chains (see, e.g., Abbas and Lichtman, 2003; Janeway et al., p. 172 and 178, 1999), which are subunits of the T-cell receptor complex. In mammals, the CD3 subunits of the T-cell receptor complex are a CD3γ chain, a CD3δ chain, two CD3ε chains, and a homodimer of CD3ζ chains. The CD3γ, CD3δ, and CD3ε chains are highly related cell surface proteins of the immunoglobulin superfamily containing a single immunoglobulin domain. The transmembrane regions of the CD3γ, CD3δ, and CD3ε chains are negatively charged, which is a characteristic that allows these chains to associate with the positively charged T-cell receptor chains. The intracellular tails of the CD3γ, CD3δ, and CD3ε chains each contain a single conserved motif known as an immunoreceptor tyrosine-based activation motif or ITAM, whereas each CD3ζ chain has three. It is believed the ITAMs are important for the signaling capacity of a TCR complex. CD3 as used in the present disclosure may be from various animal species, including human, monkey, mouse, rat, or other mammals.

As used herein, a "conservative substitution" is recognized in the art as a substitution of one amino acid for another amino acid that has similar properties. Exemplary conservative substitutions are well-known in the art (see, e.g., WO97/09433, page 10, published Mar. 13, 1997; Lehninger, Biochemistry, Second Edition; Worth Publishers, Inc. NY:NY (1975), pp. 71-77; Lewin, Genes IV, Oxford University Press, NY and Cell Press, Cambridge, Mass. (1990), p. 8). In certain embodiments, a conservative substitution includes a leucine to serine substitution.

As used herein, the term "derivative" refers to a modification of one or more amino acid residues of a peptide by chemical or biological means, either with or without an enzyme, e.g., by glycosylation, alkylation, acylation, ester formation, or amide formation.

As used herein, a polypeptide or amino acid sequence "derived from" a designated polypeptide or protein refers to the origin of the polypeptide. In one embodiment, the polypeptide or amino acid sequence which is derived from a particular sequence has an amino acid sequence that is essentially identical to that sequence or a portion thereof, wherein the portion consists of at least 10-20 amino acids, at least 20-30 amino acids, or at least 30-50 amino acids, or at least 50-150 amino acids, or which is otherwise identifiable to one of ordinary skill in the art as having its origin in the sequence. In one embodiment, a humanized or chimeric binding domain is derived from the VH and/or VL of an antibody generated by another animal. For instance, a humanized binding domain or chimeric binding domain can be derived from the VH and VL regions of a murine antibody. For example, humanization of murine antibodies can be performed by modifying framework regions by methods known in the art.

Polypeptides derived from another polypeptide may have one or more mutations relative to the starting polypeptide, e.g., one or more amino acid residues which have been substituted with another amino acid residue or which has one or more amino acid residue insertions or deletions. The polypeptide may comprise an amino acid sequence which is not naturally occurring. Such variations necessarily have less than 100% sequence identity or similarity with the starting polypeptide. In one embodiment, the variant will have an amino acid sequence from about 60% to less than 100% amino acid sequence identity or similarity with the amino acid sequence of the starting polypeptide. In another embodiment, the variant will have an amino acid sequence from about 75% to less than 100%, from about 80% to less than 100%, from about 85% to less than 100%, from about 90% to less than 100%, from about 95% to less than 100% amino acid sequence identity or similarity with the amino acid sequence of the starting polypeptide.

As used herein, unless otherwise provided, a position of an amino acid residue in a variable region of an immunoglobulin molecule is numbered according to the Kabat numbering convention (Kabat, Sequences of Proteins of Immunological Interest, $5^{th}$ ed. Bethesda, Md.: Public Health Service, National Institutes of Health (1991)), and a position of an amino acid residue in a constant region of an immunoglobulin molecule is numbered according to EU nomenclature (Ward et al., 1995 *Therap. Immunol.* 2:77-94).

As used herein, the term "dimer" refers to a biological entity that consists of two subunits associated with each other via one or more forms of intramolecular forces, including covalent bonds (e.g., disulfide bonds) and other interactions (e.g., electrostatic interactions, salt bridges, hydrogen bonding, and hydrophobic interactions), and is stable under appropriate conditions (e.g., under physiological conditions, in an aqueous solution suitable for expressing, purifying, and/or storing recombinant proteins, or under conditions for non-denaturing and/or non-reducing electrophoresis). A "heterodimer" or "heterodimeric protein," as used herein, refers to a dimer formed from two different polypeptides. A heterodimer does not include an antibody formed from four polypeptides (i.e., two light chains and two heavy chains). In one embodiment of the invention, a heterodimer is created using Emergent's Interceptor platform which comprises a heterodimerization domain. A "homodimer" or "homodimeric protein," as used herein, refers to a dimer formed from two identical polypeptides. In certain embodiments of the invention, the homodimer is created using Emergent's SMIP, PIMS or Scorpion platform.

As used herein, a "hinge region" or a "hinge" refers to a polypeptide derived from (a) an interdomain region of a transmembrane protein (e.g., a type I transmembrane protein); or (b) a stalk region of a type II C-lectin. For example, a hinge region may be derived from an interdomain region of an immunoglobulin superfamily member; suitable hinge regions within this particular class include (i) immunoglobulin hinge regions (made up of, for example, upper and/or core region(s)) or functional variants thereof, including wild-type and altered immunoglobulin hinges, and (ii) regions (or functional variants thereof) that connect immunoglobulin V-like or immunoglobulin C-like domains.

A "wild-type immunoglobulin hinge region" refers to a naturally occurring upper and middle hinge amino acid sequences interposed between and connecting the CH1 and CH2 domains (for IgG, IgA, and IgD) or interposed between and connecting the CH1 and CH3 domains (for IgE and IgM) found in the heavy chain of an antibody. In certain embodiments, a wild type immunoglobulin hinge region sequence is human, and may comprise a human IgG hinge region.

An "altered wild-type immunoglobulin hinge region" or "altered immunoglobulin hinge region" refers to (a) a wild type immunoglobulin hinge region with up to 30% amino acid changes (e.g., up to 25%, 20%, 15%, 10%, or 5% amino acid substitutions or deletions), or (b) a portion of a wild type immunoglobulin hinge region that has a length of about 5 amino acids (e.g., about 5, 6, 7, 8, 9, 10, 11, 12, 13, 14, 15, 16, 17, 18, 19, or 20 amino acids) up to about 120 amino acids (for instance, having a length of about 10 to about 40 amino acids or about 15 to about 30 amino acids or about 15 to about 20 amino acids or about 20 to about 25 amino acids), has up to about 30% amino acid changes (e.g., up to about 25%, 20%, 15%, 10%, 5%, 4%, 3%, 2%, or 1% amino acid substitutions or deletions or a combination thereof), and has an IgG core hinge region as disclosed in PCT Publications WO2011/090762 and WO2011/090754.

As used herein, the term "humanized" refers to a process of making an antibody or immunoglobulin binding proteins and polypeptides derived from a non-human species (e.g., mouse or rat) less immunogenic to humans, while still retaining antigen-binding properties of the original antibody, using genetic engineering techniques. In some embodiments, the binding domain(s) of an antibody or immunoglobulin binding proteins and polypeptides (e.g., light and heavy chain variable regions, Fab, scFv) are humanized. Non-human binding domains may be humanized using techniques known as CDR grafting (Jones et al., *Nature* 321:522 (1986)) and variants thereof, including "reshaping" (Verhoeyen, et al., 1988 *Science* 239:1534-1536; Riechmann, et al., 1988 *Nature* 332:323-337; Tempest, et al., *Bio/Technol* 1991 9:266-271), "hyperchimerization" (Queen, et al., 1989 *Proc Natl Acad Sci USA* 86:10029-10033; Co, et al., 1991 *Proc Natl Acad Sci USA* 88:2869-2873; Co, et al., 1992 *J Immunol* 148:1149-1154), and "veneering" (Mark, et al., "Derivation of therapeutically active humanized and veneered anti-CD18 antibodies. In: Metcalf B W, Dalton B J, eds. Cellular adhesion: molecular definition to therapeutic potential. New York: Plenum Press, 1994: 291-312). If derived from a non-human source, other regions of the antibody or immunoglobulin binding proteins and polypeptides, such as the hinge region and constant region domains, may also be humanized.

An "immunoglobulin constant region" or "constant region" is a term defined herein to refer to a peptide or polypeptide sequence that corresponds to or is derived from part or all of one or more constant region domains. In one embodiment, the constant region does contain all the constant region domains of a source antibody. In one embodiment, the constant region comprises IgG CH2 and CH3 domains, for instance, IgG1 CH2 and CH3 domains. In some embodiments, a constant region does not comprise a CH1 domain. In certain embodiments, the constant region domains making up the constant sub-region are human. In some embodiments, the constant region domains of a fusion protein of this disclosure lack or have minimal effector functions of antibody-dependent cell-mediated cytotoxicity (ADCC) and complement activation and complement-dependent cytotoxicity (CDC), while retaining the ability to bind some $F_c$ receptors (such as Fc Rn, the neonatal Fc receptor) and retaining a relatively long half life in vivo.

In other variations, a fusion protein of this disclosure includes constant domains that retain such effector function of one or both of ADCC and CDC. In certain embodiments, a binding domain of this disclosure is fused to a human IgG constant region (for instance, IgG1), wherein the constant region has one or more of the following amino acids mutated: leucine at position 234 (L234), leucine at position 235 (L235), glycine at position 237 (G237), glutamate at position 318 (E318), lysine at position 320 (K320), lysine at position 322 (K322), or any combination thereof (numbering according to EU). For example, any one or more of these amino acids can be changed to alanine. In a further embodiment, an IgG Fc domain such as IgG1 has each of L234, L235, G237, E318, K320, and K322 (according to EU numbering) mutated, e.g., to an alanine L234A, L235A, G237A, E318A, K320A, and K322A, respectively), and optionally an N297A mutation as well (i.e., essentially eliminating glycosylation of the CH2 domain).

As used here the term "small modular immunopharmaceutical proteins" or "SMIP" is used to refer to protein scaffold as generally disclosed in, for example, in US Patent Application Publication Nos. 2003/0133939, 2003/0118592, and 2005/0136049, which are incorporated herein by reference in their entirety. "SMIP molecules" described in the Examples and throughout the disclosure herein should be understood to be binding proteins comprising SMIP scaffolding, e.g., in order from amino to carboxyl-terminus, a first binding domain, a hinge region, and an immunoglobulin constant region. "CD3-specific SMIP molecules" should be understood to be CD3-binding proteins comprising SMIP scaffolding.

As used here the term "PIMS" is used to refer to protein scaffold as generally disclosed in, for example, in US Patent Application Publication No. 2009/0148447, which is incorporated herein in its entirety by reference. "PIMS molecules" described in the Examples and throughout the disclosure herein should be understood to be binding proteins comprising PIMS scaffolding, e.g., in order from amino to carboxyl-terminus, an immunoglobulin constant region, a hinge region and a first binding domain. "CD3-specific PIMS molecules" should be understood to be CD3-binding proteins comprising PIMS scaffolding.

"Fc region" or "Fc domain" refers to a polypeptide sequence corresponding to or derived from the portion of a source antibody that is responsible for binding to antibody receptors on cells and the C1q component of complement. Fc stands for "fragment crystalline," the fragment of an antibody that will readily form a protein crystal. Distinct protein fragments, which were originally described by proteolytic digestion, can define the overall general structure of an immunoglobulin protein. As originally defined in the literature, the Fc fragment consists of the disulfide-linked heavy chain hinge regions, CH2, and CH3 domains. However, more recently the term has been applied to a single chain consisting of CH3, CH2, and at least a portion of the hinge sufficient to form a disulfide-linked dimer with a second such chain. For a review of immunoglobulin structure and function, see Putnam, *The Plasma Proteins*, Vol. V (Academic Press, Inc., 1987), pp. 49-140; and Padlan, *Mol. Immunol.* 31:169-217, 1994. As used herein, the term Fc includes variants of naturally occurring sequences.

As used herein, "isoelectric point" or pI is the pH at which net charge is zero.

As used herein, the term "Interceptor" is used to refer to a monospecific or multispecific heterodimeric protein scaffold as generally disclosed in PCT Publications WO2011/090762 and WO2011/090754. The Interceptor molecules described herein should be understood to be CD3 binding proteins comprising two non-identical polypeptide chains, each polypeptide chain comprising an immunoglobulin heterodimerization domain. The interfacing immunoglobulin heterodimerization domains are different. In one embodiment, the immunoglobulin heterodimerization domain comprises a CH1 domain or a derivative thereof. In another embodiment, the immunoglobulin heterodimerization domain comprises a CL domain or a derivative thereof. In one embodiment, the CL domain is a Cκ or Cλ isotype or a derivative thereof.

As used herein, the "stalk region" of a type II C-lectin refers to the portion of the extracellular domain of the type II C-lectin that is located between the C-type lectin-like domain (CTLD; e.g., similar to CTLD of natural killer cell receptors) and the transmembrane domain. For example, in the human CD94 molecule (GenBank Accession No. AAC50291.1, PRI Nov. 30, 1995), the extracellular domain corresponds to amino acid residues 34-179, whereas the CTLD corresponds to amino acid residues 61-176. Accordingly, the stalk region of the human CD94 molecule includes amino acid residues 34-60, which is found between the membrane and the CTLD (see Boyington et al., *Immunity*

10:75, 1999; for descriptions of other stalk regions, see also Beavil et al., *Proc. Nat'l. Acad. Sci. USA* 89:753, 1992; and Figdor et al., *Nature Rev. Immunol.* 2:77, 2002). These type II C-lectins may also have from six to 10 junction amino acids between the stalk region and the transmembrane region or the CTLD. In another example, the 233 amino acid human NKG2A protein (GenBank Accession No. P26715.1, PRI Jun. 15, 2010) has a transmembrane domain ranging from amino acids 71-93 and an extracellular domain ranging from amino acids 94-233. The CTLD is comprised of amino acids 119-231, and the stalk region comprises amino acids 99-116, which is flanked by junctions of five and two amino acids. Other type II C-lectins, as well as their extracellular ligand-bind domains, interdomain or stalk regions, and CTLDs are known in the art (see, e.g., GenBank Accession Nos. NP_001993.2; AAH07037.1, PRI Jul. 15, 2006; NP_001773.1, PRI Jun. 20, 1010; AAL65234.1, PRI Jan. 17, 2002; and CAA04925.1, PRI Nov. 14, 2006, for the sequences of human CD23, CD69, CD72, NKG2A and NKG2D and their descriptions, respectively).

As used herein, the "interdomain region" of a transmembrane protein (e.g., a type I transmembrane protein) refers to a portion of the extracellular domain of the transmembrane protein that is located between two adjacent domains. Examples of interdomain regions include regions linking adjacent Ig domains of immunoglobulin superfamily members (e.g., an immunoglobulin hinge region from IgG, IgA, IgD, or IgE; the region linking the IgV and IgC2 domains of CD2; or the region linking the IgV and IgC domains of CD80 or CD86). Another example of an interdomain region is the region linking the non-Ig and IgC2 domain of CD22, a type I sialic acid-binding Ig-like lectin.

A polypeptide region "derived from" a stalk region of a type II C-lectin, or "derived from" a transmembrane protein interdomain region (e.g., an immunoglobulin hinge region), refers to an about five to about 150 amino acid sequence all or at least a portion of which includes (i) a wild-type stalk region or interdomain region sequence; (ii) a fragment of the wild-type stalk region or interdomain region sequence; (iii) a polypeptide having at least 80%, 85%, 90%, or 95% amino acid sequence identity with either (i) or (ii); or (iv) either (i) or (ii) in which one, two, three, four, or five amino acids have a deletion, insertion, substitution, or any combination thereof, for instance, the one or more changes are substitutions or the one or more mutations include only one deletion. In some embodiments, a derivative of a stalk region is more resistant to proteolytic cleavage as compared to the wild-type stalk region sequence, such as those derived from about eight to about 20, about 10 to about 25 or about 15 to about 25 amino acids of NKG2A, NKG2D, CD23, CD64, CD72, or CD94.

As used herein, the term "junction amino acids" or "junction amino acid residues" refers to one or more (e.g., about 2-10) amino acid residues between two adjacent regions or domains of a polypeptide, such as between a hinge and an adjacent immunoglobulin constant sub-region or between a hinge and an adjacent binding domain or between a peptide linker that links two immunoglobulin variable domains and an adjacent immunoglobulin variable domain. Junction amino acids may result from the construct design of a polypeptide (e.g., amino acid residues resulting from the use of a restriction enzyme site during the construction of a nucleic acid molecule encoding a polypeptide). Junction amino acids between a binding domain and hinge region are referred to herein as the prehinge region, e.g., can result from adding a restriction site into the encoding nucleotide sequence. In one embodiment, the prehinge region consists of about 1, 2, 3, 4, 5, 6, 7, 8, 9, 10 or 15 amino acids. The prehinge region sequence of DRA209 and DRA161 is not part of the murine Cris-7 or human immunoglobulin germline sequence. The prehinge region of DRA209 and DRA161 is the amino acid sequence RRT, while it is SSS for DRA219, DRA221, DRA222, DRA223, DRA224, DRA225, DRA228, DRA229, DRA233, DRA234, TSC249, TSC250, TSC251, TSC252, TSC295, TSC296, TSC301 and TSC302. Binding molecules of the invention may or may not include a prehinge region.

As used herein, the phrase a "linker between CH3 and CH1 or CL" refers to one or more (e.g., about 2-12) amino acid residues between the C-terminus of a CH3 domain (e.g., a wild type CH3 or a mutated CH3) and the N-terminus of a CH1 domain or CL domain (e.g., Ck).

As used herein, the term "patient in need" refers to a patient at risk of, or suffering from, a disease, disorder or condition that is amenable to treatment or amelioration with a CD3 binding protein or polypeptide or a composition thereof provided herein.

As used herein, the term "peptide linker" refers to an amino acid sequence that connects a heavy chain variable region to a light chain variable region and provides a spacer function compatible with interaction of the two sub-binding domains so that the resulting polypeptide retains a specific binding affinity to the same target molecule as an antibody that comprises the same light and heavy chain variable regions. In certain embodiments, a linker is comprised of five to about 35 amino acids, for instance, about 15 to about 25 amino acids.

As used herein, the term "pharmaceutically acceptable" refers to molecular entities and compositions that do not produce allergic or other serious adverse reactions in a majority of subjects when administered using routes well known in the art. Molecular entities and compositions approved by a regulatory agency of the Federal or a state government or listed in the U.S. Pharmacopeia or other generally recognized pharmacopeia for use in animals, and more particularly in humans are considered to be "pharmaceutically acceptable."

As used herein, the term "promoter" refers to a region of DNA involved in binding RNA polymerase to initiate transcription.

As used herein, the terms "nucleic acid," "nucleic acid molecule," or "polynucleotide" refer to deoxyribonucleotides or ribonucleotides and polymers thereof in either single- or double-stranded form. Unless specifically limited, the terms encompass nucleic acids containing analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al. (1991) *Nucleic Acid Res.* 19:5081; Ohtsuka et al. (1985) *J. Biol. Chem.* 260:2605-2608; Cassol et al. (1992); Rossolini et al. (1994) *Mol. Cell. Probes* 8:91-98). The term nucleic acid is used interchangeably with gene, cDNA, and mRNA encoded by a gene. As used herein, the terms "nucleic acid," "nucleic acid molecule," or "polynucleotide" are intended to include DNA molecules (e.g., cDNA or genomic DNA), RNA molecules (e.g., mRNA), analogs of the DNA or RNA generated using nucleotide analogs, and derivatives, fragments and homologs thereof.

The term "expression" refers to the biosynthesis of a product encoded by a nucleic acid. For example, in the case of nucleic acid segment encoding a polypeptide of interest, expression involves transcription of the nucleic acid segment into mRNA and the translation of mRNA into one or more polypeptides.

The terms "expression unit" and "expression cassette" are used interchangeably herein and denote a nucleic acid segment encoding a polypeptide of interest and capable of providing expression of the nucleic acid segment in a host cell. An expression unit typically comprises a transcription promoter, an open reading frame encoding the polypeptide of interest, and a transcription terminator, all in operable configuration. In addition to a transcriptional promoter and terminator, an expression unit may further include other nucleic acid segments such as, e.g., an enhancer or a polyadenylation signal.

The term "expression vector," as used herein, refers to a nucleic acid molecule, linear or circular, comprising one or more expression units. In addition to one or more expression units, an expression vector may also include additional nucleic acid segments such as, for example, one or more origins of replication or one or more selectable markers. Expression vectors are generally derived from plasmid or viral DNA, or may contain elements of both.

As used herein, Scorpion is a term used to refer to a multi-specific binding protein scaffold. Multi-specific binding proteins and polypeptides are disclosed, for instance, in PCT Application Publication No. WO 2007/146968, U.S. Patent Application Publication No. 2006/0051844, PCT Application Publication No. WO 2010/040105, PCT Application Publication No. WO2010/003108, and U.S. Pat. No. 7,166,707. A Scorpion polypeptide comprises two binding domains (the domains can be designed to specifically bind the same or different targets), two linkers, and an immunoglobulin constant sub-region. Linkers for Scorpion molecules are described in PCT Application Publication No. WO2010/003108. In some embodiments, a linker sequence is between about 2-45 amino acids, or 2-38 amino acids, or 5-45 amino acids. In some embodiments, a linker is an antibody hinge region (e.g., from IgG) or a C-lectin stalk region. Scorpion proteins are homodimeric proteins comprising two identical, disulfide-bonded Scorpion polypeptides.

As used herein, the term "sequence identity" refers to a relationship between two or more polynucleotide sequences or between two or more polypeptide sequences. When a position in one sequence is occupied by the same nucleic acid base or amino acid residue in the corresponding position of the comparator sequence, the sequences are said to be "identical" at that position. The percentage "sequence identity" is calculated by determining the number of positions at which the identical nucleic acid base or amino acid residue occurs in both sequences to yield the number of "identical" positions. The number of "identical" positions is then divided by the total number of positions in the comparison window and multiplied by 100 to yield the percentage of "sequence identity." Percentage of "sequence identity" is determined by comparing two optimally aligned sequences over a comparison window. The comparison window for nucleic acid sequences may be, for instance, at least 20, 30, 40, 50, 60, 70, 80, 90, 100, 110, 120, 130, 140, 150, 160, 170, 180, 190, 200, 300, 400, 500, 600, 700, 800, 900 or 1000 or more nucleic acids in length. The comparison window for polypeptide sequences may be, for instance, at least 20, 30, 40, 50, 60, 70, 80, 90, 100, 110, 120, 130, 140, 150, 160, 170, 180, 190, 200, 300 or more amino acids in length. In order to optimally align sequences for comparison, the portion of a polynucleotide or polypeptide sequence in the comparison window may comprise additions or deletions termed gaps while the reference sequence is kept constant. An optimal alignment is that alignment which, even with gaps, produces the greatest possible number of "identical" positions between the reference and comparator sequences. Percentage "sequence identity" between two sequences can be determined using the version of the program "BLAST 2 Sequences" which was available from the National Center for Biotechnology Information as of Sep. 1, 2004, which program incorporates the programs BLASTN (for nucleotide sequence comparison) and BLASTP (for polypeptide sequence comparison), which programs are based on the algorithm of Karlin and Altschul (Proc. Natl. Acad. Sci. USA 90(12):5873-5877, 1993). When utilizing "BLAST 2 Sequences," parameters that were default parameters as of Sep. 1, 2004, can be used for word size (3), open gap penalty (11), extension gap penalty (1), gap dropoff (50), expect value (10) and any other required parameter including but not limited to matrix option. Two nucleotide or amino acid sequences are considered to have "substantially similar sequence identity" or "substantial sequence identity" if the two sequences have at least 80%, at least 85%, at least 90%, at least 95%, at least 96%, at least 97%, at least 98%, or at least 99% sequence identity relative to each other.

As used herein, a "polypeptide" or "polypeptide chain" is a single, linear and contiguous arrangement of covalently linked amino acids. It does not include two polypeptide chains that link together in a non-linear fashion, such as via an interchain disulfide bond (e.g., a half immunoglobulin molecule in which a light chain links with a heavy chain via a disulfide bond). Polypeptides may have or form one or more intrachain disulfide bonds. With regard to polypeptides as described herein, reference to amino acid residues corresponding to those specified by a SEQ ID NO includes post-translational modifications of such residues.

A "protein" is a macromolecule comprising one or more polypeptide chains. A protein may also comprise non-peptidic components, such as carbohydrate groups. Carbohydrates and other non-peptidic substituents may be added to a protein by the cell in which the protein is produced, and will vary with the type of cell. Proteins are defined herein in terms of their amino acid backbone structures; substituents such as carbohydrate groups are generally not specified, but may be present nonetheless.

The terms "amino-terminal" (N-terminal) and "carboxyl-terminal" (C-terminal) are used herein to denote positions within polypeptides. Where the context allows, these terms are used with reference to a particular sequence or portion of a polypeptide to denote proximity or relative position. For example, a certain sequence positioned carboxyl-terminal to a reference sequence within a polypeptide is located proximal to the carboxyl-terminus of the reference sequence, but is not necessarily at the carboxyl-terminus of the complete polypeptide.

"T-cell receptor" (TCR) is a molecule found on the surface of T-cells that, along with CD3, is generally responsible for recognizing antigens bound to major histocompatibility complex (MHC) molecules. It consists of a disulfide-linked heterodimer of the highly variable α and β chains in most T-cells. In other T-cells, an alternative receptor made up of variable γ and δ chains is expressed. Each chain of the TCR is a member of the immunoglobulin superfamily and possesses one N-terminal immunoglobulin variable domain, one immunoglobulin constant domain, a transmembrane region, and a short cytoplasmic tail at the C-terminal end (see Abbas and Lichtman, *Cellular and Molecular Immunology* (5th Ed.), Editor: Saunders, Philadelphia, 2003; Janeway et al., *Immunobiology: The Immune System in Health and Disease,* $4^{th}$ Ed., Current Biology Publications, p148, 149, and 172, 1999). TCR as used in the present disclosure may be from various animal species, including human, mouse, rat, or other mammals.

"TCR complex," as used herein, refers to a complex formed by the association of CD3 chains with other TCR chains. For example, a TCR complex can be composed of a CD3γ chain, a CD3δ chain, two CD3ε chains, a homodimer of CD3ζ chains, a TCRα chain, and a TCRβ chain. Alternatively, a TCR complex can be composed of a CD3γ chain, a CD3δ chain, two CD3ε chains, a homodimer of CD3ζ chains, a TCRγ chain, and a TCRδ chain.

"A component of a TCR complex," as used herein, refers to a TCR chain (e.g., TCRα, TCRβ, TCRγ or TCRδ), a CD3 chain (e.g., CD3γ, CD3δ, CD3ε or CD3ζ), or a complex formed by two or more TCR chains or CD3 chains (e.g., a complex of TCRα and TCRβ, a complex of TCRγ and TCRδ, a complex of CD3ε and CD3δ, a complex of CD3γ and CD3ε, or a sub-TCR complex of TCRα, TCRβ, CD3γ, CD3δ, and two CD3ε chains).

"Antibody-dependent cell-mediated cytotoxicity" and "ADCC," as used herein, refer to a cell-mediated process in which nonspecific cytotoxic cells that express FcγRs (e.g., monocytic cells such as Natural Killer (NK) cells and macrophages) recognize bound antibody (or other protein capable of binding FcγRs) on a target cell and subsequently cause lysis of the target cell. In principle, any effector cell with an activating FcγR can be triggered to mediate ADCC. The primary cells for mediating ADCC are NK cells, which express only FcγRIII, whereas monocytes, depending on their state of activation, localization, or differentiation, can express FcγRI, FcγRII, and FcγRIII. For a review of FcγR expression on hematopoietic cells, see, e.g., Ravetch et al., 1991*, Annu. Rev. Immunol.,* 9:457-92.

The term "having ADCC activity," as used herein in reference to a polypeptide or protein, means that the polypeptide or protein (for example, one comprising an immunoglobulin hinge region and an immunoglobulin constant sub-region having CH2 and CH3 domains, such as derived from IgG (e.g., IgG1)), is capable of mediating antibody-dependent cell-mediated cytotoxicity (ADCC) through binding of a cytolytic Fc receptor (e.g., FcγRIII) on a cytolytic immune effector cell expressing the Fc receptor (e.g., an NK cell).

"Complement-dependent cytotoxicity" and "CDC," as used herein, refer to a process in which components in normal serum ("complement"), together with an antibody or other C1q-complement-binding protein bound to a target antigen, exhibit lysis of a target cell expressing the target antigen. Complement consists of a group of serum proteins that act in concert and in an orderly sequence to exert their effect.

The terms "classical complement pathway" and "classical complement system," as used herein, are synonymous and refer to a particular pathway for the activation of complement. The classical pathway requires antigen-antibody complexes for initiation and involves the activation, in an orderly fashion, of nine major protein components designated C1 through C9. For several steps in the activation process, the product is an enzyme that catalyzes the subsequent step. This cascade provides amplification and activation of large amounts of complement by a relatively small initial signal.

The term "having CDC activity," as used herein in reference to a polypeptide or protein, means that the polypeptide or protein (for example, one comprising an immunoglobulin hinge region and an immunoglobulin constant sub-region having CH2 and CH3 domains, such as derived from IgG (e.g., IgG1)) is capable of mediating complement-dependent cytotoxicity (CDC) through binding of C1q complement protein and activation of the classical complement system.

"Redirected T-cell cytotoxicity" and "RTCC," as used herein, refer to a T-cell-mediated process in which a cytotoxic T-cell is recruited to a target cell using a multi-specific protein that is capable of specifically binding both the cytotoxic T-cell and the target cell, and whereby a target-dependent cytotoxic T-cell response is elicited against the target cell.

As used herein, the term "treatment," "treating," or "ameliorating" refers to either a therapeutic treatment or prophylactic/preventative treatment. A treatment is therapeutic if at least one symptom of disease in an individual receiving treatment improves or a treatment may delay worsening of a progressive disease in an individual, or prevent onset of additional associated diseases.

As used herein, the term "transformation," "transfection," and "transduction" refer to the transfer of nucleic acid (e.g., a nucleotide polymer) into a cell. As used herein, the term "genetic transformation" refers to the transfer and incorporation of DNA, especially recombinant DNA, into a cell. The transferred nucleic acid may be introduced into a cell via an expression vector.

As used herein, the term "variant" or "variants" refers to a nucleic acid or polypeptide differing from a reference nucleic acid or polypeptide, but retaining essential properties thereof. Generally, variants are overall closely similar, and, in many regions, identical to the reference nucleic acid or polypeptide. For instance, a variant may exhibit at least about 70%, at least about 80%, at least about 90%, at least about 95%, at least about 96%, at least about 97%, at least about 98% or at least about 99% sequence identity compared to the active portion or full length reference nucleic acid or polypeptide.

The terms "light chain variable region" (also referred to as "light chain variable domain" or "VL") and "heavy chain variable region" (also referred to as "heavy chain variable domain" or "VH") refer to the variable binding region from an antibody light and heavy chain, respectively. The variable binding regions are made up of discrete, well-defined sub-regions known as "complementarity determining regions" (CDRs) and "framework regions" (FRs). In one embodiment, the FRs are humanized. The term "CL" refers to an "immunoglobulin light chain constant region" or a "light chain constant region," i.e., a constant region from an antibody light chain. The term "CH" refers to an "immunoglobulin heavy chain constant region" or a "heavy chain constant region," which is further divisible, depending on the antibody isotype into CH1, CH2, and CH3 (IgA, IgD, IgG), or CH1, CH2, CH3, and CH4 domains (IgE, IgM). A "Fab" (fragment antigen binding) is the part of an antibody that binds to antigens and includes the variable region and CH1 domain of the heavy chain linked to the light chain via an inter-chain disulfide bond.

The present disclosure provides, inter alia, polypeptides and proteins comprising binding domains, in particular, a first binding domain that specifically binds CD3. The polypeptides and proteins comprising binding domains of this disclosure may comprise one or more of the following: an immunoglobulin constant sub-region(s), a linker peptide(s), a hinge region(s), an immunoglobulin heterodimerization domain(s), an immunoglobulin dimerization domain(s), one or more junctional amino acids, a tag(s), etc. These components of the disclosed polypeptides and proteins are described in further detail herein.

Additionally, the CD3 binding polypeptides and proteins disclosed herein may be in the form of an antibody or a fusion protein of any of a variety of different formats (e.g., the fusion protein may be in the form of a SMIP protein, a PIMS protein, a Scorpion protein or an Interceptor protein).

In some embodiments, a CD3 binding polypeptide comprises a second binding domain. In some embodiments, a CD3 binding polypeptide comprises, from amino to carboxyl terminus, a CD3 binding domain, a hinge region, a constant region, and a second binding domain. In other embodiments, a CD3 binding polypeptide comprises, from amino to carboxyl terminus, a second binding domain, a hinge region, a constant region, and a CD3 binding domain.

A CD3 binding protein in accordance with the present invention generally includes (a) at least one CD3 binding polypeptide chain comprising a CD3 binding domain as set forth herein. In certain variations, the CD3 binding polypeptide further includes (b) a hinge region carboxyl-terminal to the CD3 binding domain, and (c) an immunoglobulin constant region (e.g., a SMIP polypeptide). In further variations, the CD3 binding polypeptide further includes (d) a second hinge region carboxyl-terminal to the immunoglobulin constant sub-region, and (e) a second binding domain carboxyl-terminal to the second hinge region (e.g., a Scorpion polypeptide). In some embodiments, a CD3 binding polypeptide comprises a CD3 binding domain with framework regions, a prehinge region and a hinge region.

In some embodiments, a CD3 binding polypeptide comprises three or more modified amino acids as compared to SEQ ID NO:42, for example, the modifications being substitutions of positively charged amino acids with neutral amino acids and/or substitutions of neutral amino acids with negatively charged amino acids, e.g., in the framework and/or prehinge regions. In some embodiments, at least two, at least three, at least four, 3-5 or 3-10 amino acids are modified in the framework regions of VH and/or VL by substituting positively charged amino acids with neutral amino acids and/or substituting neutral amino acids with negatively charged amino acids.

In some embodiment of the invention, a CD3 binding polypeptide comprises modifications in the prehinge region, e.g., that result in lowering the pI of the prehinge region or entire polypeptide. The prehinge region is in the junction between the binding domain and hinge region. For instance, a three amino acid prehinge region with the sequence RRT can be replaced with the sequence SSS or SST to reduce the isoelectric point. In some embodiments, a prehinge region has a reduced isoelectric point as compared to a CD3 binding polypeptide with an RRT prehinge region.

In one embodiment, to reduce the risk of immunogenicity, amino acids are substituted into the sequence that are prevalent in the human germline IgG sequence or contained in the human germline sequence at the same or proximate position, e.g., in a corresponding human germline IgG sequence. In some embodiments, the human germline IgG sequence comprises SEQ ID NOs:43 or 44.

In some embodiments, at least one amino acid modification is within the J kappa (Jk) region of the VL region as compared to the Cris-7 VL Jk region mouse sequence LQIT (SEQ ID NO:252). In some embodiments, a Jk region comprises the amino acid sequence VEIK (SEQ ID NO:253), e.g., in place of LQIT (SEQ ID NO:252).

In some embodiments, a CD3 binding polypeptide comprises a hinge region and a constant region, for example, a CD3 binding polypeptide may comprise (a) a hinge region amino-terminal to the CD3 binding domain, and (b) an immunoglobulin constant region amino-terminal to the hinge region (e.g., a PIMS polypeptide). In some embodiments, a CD3 binding polypeptide comprises, from amino to carboxyl terminus, a CD3 binding domain, a hinge region and a constant region. In some embodiments, a CD3 binding polypeptide comprises, from amino to carboxyl terminus, a constant region, a hinge region and a CD3 binding domain.

Typically, CD3 binding polypeptides of the above formats (SMIP, Scorpion, or PIMS) are capable of homodimerization, typically through disulfide bonding, via the immunoglobulin constant region and/or hinge region (e.g., via an immunoglobulin constant region comprising IgG CH2 and CH3 domains and an IgG hinge region). Thus, in certain aspects of the present invention, two identical CD3 binding polypeptides homodimerize to form a dimeric CD3 binding protein.

In other embodiments, a CD3 binding polypeptide further includes a heterodimerization domain that is capable of heterodimerization with a different heterodimerization domain in a second, non-identical polypeptide chain. In certain variations, the second polypeptide chain for heterodimerization includes a second binding domain. Accordingly, in certain aspects of the present invention, two non-identical polypeptide chains, one comprising the CD3 binding domain and the second optionally comprising a second binding domain, dimerize to form a heterodimeric protein with one to four binding domains. In some embodiments, a CD3 binding polypeptide comprises, from amino to carboxyl terminus, a CD3 binding domain, a hinge region, a constant region, a heterodimerization domain and optionally a second binding domain.

In some embodiments, a second binding domain binds or interacts with a target molecule and the CD3 binding polypeptide induces T-cell cytotoxicity. This could be in a non-dimer, heterodimer or homodimer format. In some embodiments, a second binding domain binds or interacts with a tumor associated antigen. In some embodiments, a CD3 binding polypeptide induces T-cells to lyse tumor cells and/or induces polyclonal T-cell activation and expansion in the vicinity of a tumor.

Polypeptides comprising an anti-CD3 binding domain of the invention can be or comprise antibodies or antibody derivatives including functional antibody fragments or derivatives of fragments which retain binding specificity. In some embodiments, the invention includes fusion proteins and other polypeptides that contain variable heavy and/or light chain domains.

In some embodiments of the invention, a CD3 binding polypeptide comprises a CD3 binding domain that comprises a VH region sequence or VL region sequence selected from the group consisting of SEQ ID NOs:28, 30, 32, 38 and 40. In some embodiments, a CD3 binding domain comprises a VH region selected from the group consisting of SEQ ID NOs:22, 24, 26, 28, 30 and 32 and a VL region selected from the group consisting of SEQ ID NOs:38 and 40. In some embodiments, a CD3 binding domain comprises a VH region selected from the group consisting of SEQ ID NO:28, 30 and 32 and a VL region selected from the group consisting of SEQ ID NO:34, 36, 38 and 40. In some embodiments, the VH region comprises SEQ ID NO:28 and the VL region comprises SEQ ID NO:34; the VH region comprises SEQ ID NO:28 and the VL region comprises SEQ ID NO:38.; the VH region comprises SEQ ID NO:26 and the VL region comprises SEQ ID NO:38; or the VH region comprises SEQ ID NO:26 and the VL region comprises SEQ ID NO:34. In some embodiments, a CD3 binding polypeptide comprises a CD3 binding domain that comprises a heavy chain CDR1, CDR2 and CDR3 and a light chain CDR1, CDR2 and CDR3 and wherein the heavy chain CDR3 comprises SEQ ID NO:51. In some embodiments, a CD3 binding polypeptide includes a heavy chain CDR1 comprising SEQ ID NO:49, a CDR2 comprising SEQ ID NO:50 and a CDR3 comprising SEQ ID NO:51 and a light chain CDR1 comprising SEQ ID NO:52, a CDR2 comprising SEQ ID NO:53, and a CDR3 comprising SEQ ID NO:54.

In some embodiments, a CD3 binding polypeptide comprises an amino acid sequence selected from the group consisting of SEQ ID NOs:6, 8, 10, 12, 14, 16, 18 and 20.

The invention includes a multispecific binding protein comprising dimerized single chain polypeptides, each single chain polypeptide comprising, from amino to carboxyl terminus, a first binding domain, an N-terminus linker, an immunoglobulin constant region, a C-terminus linker and a CD3 binding domain of the invention. Likewise, the invention includes a multispecific binding protein comprising dimerized single chain polypeptides, each single chain polypeptide comprising, from amino to carboxyl terminus, a CD3 binding domain of the invention, an N-terminus linker, an immunoglobulin constant region, a C-terminus linker and a first binding domain. In some embodiments, the N-terminus linker may comprise or may consist essentially of an immunoglobulin hinge region.

In another aspect of the invention, the multispecific binding protein comprises a single chain polypeptide comprising, from amino to carboxyl terminus, a first binding domain, an N-terminus linker, an immunoglobulin constant region, a C-terminus linker and a CD3 binding domain. Likewise, the invention includes a multispecific binding protein comprising, from amino to carboxyl terminus, a CD3 binding domain, an N-terminus linker, an immunoglobulin constant region, a C-terminus linker and a first binding domain.

The invention includes a multispecific binding protein comprising a first binding domain linked via a linker domain to a second binding domain (e.g., a scFv linked via a linker to another scFv). For instance, the invention includes a multispecific binding protein comprising a first binding domain (in $V_H$-linker-$V_L$ or $V_L$-linker-$V_H$ orientation) linked via a peptide linker domain to a CD3 binding domain (in $V_H$-linker-$V_L$ or $V_L$-linker-$V_H$ orientation). In some embodiments, a bispecific protein in the scFv-linker-scFv format may comprise variable heavy and variable light domains derived from an antibody to a T-cell antigen (such as CD3) including, but not limited to, the variable domains disclosed herein. A linker separating the scFv domains may comprise $((Gly_4)Ser)_n$ wherein n=1-5 (SEQ ID NOs:74-78). In one embodiment, the linker is $((Gly_4)Ser)_3$ (SEQ ID NO:76). The linker may also comprise about 8-12 amino acids. In some embodiments, a protein of the invention in this format ("bispecific single chain antibody"), does not comprise an Fc region and as a result, has no Fc-related effector function.

The invention includes essentially any type of polypeptide containing a binding domain or domains as described herein. This includes antibodies, fragments thereof, scFvs, Fabs, di-scFvs single domain antibodies, diabodies, dual variable domain binding proteins and polypeptides containing an antibody or antibody fragments. Further types of polypeptides that are included in the invention are described herein.

In some embodiments, $V_H$ and $V_L$ domains are used as scFvs and attached/fused to other polypeptides or amino acid sequences in a manner that allows the scFvs and $V_H/V_L$ to bind the target. In some embodiments, a $V_H$ and $V_L$ domain as described herein is used in an antibody or fragment thereof. For example the $V_H$ and $V_L$ domains are incorporated into the natural position for $V_H$ and $V_L$ domains in an antibody. In some embodiments, a CD3 binding polypeptide of the invention is an antibody, e.g., with a $V_L$ chain and $V_H$ chain as described herein.

In one embodiment of the invention, a multispecific protein is a scFv dimer or diabody rather than a whole antibody. Diabodies and scFv dimers can be constructed without an Fc region, using only variable domains. Diabodies are bivalent, bispecific antibodies in which $V_H$ and $V_L$ domains are expressed on a single polypeptide chain, but using a peptide linker that is too short to allow for pairing between the two domains on the same chain, thereby forcing the domains to pair with complementary domains of another chain and creating two antigen binding sites (see e.g., Holliger, P., et al. (1993) Proc. Natl. Acad. Sci. USA 90:6444-6448; Poljak, R. J., et al. (1994) Structure 2:1121-1123). Such antibody binding portions are known in the art (Kontermann and Dubel eds., Antibody Engineering (2001) Springer-Verlag. New York. 790 pp. (ISBN 3-540-41354-5).

In one embodiment of the invention, a multispecific protein is a disulfide-stabilized diabody. For instance, a multispecific antibody may comprise two distinct polypeptides that are co-expressed to generate a covalently linked heterodimeric complex with one binding site for each of 2 specificities. In this embodiment, each Fv is formed by the association of a $V_L$ partner on one chain with a $V_H$ partner on the second chain in a $V_{LA}$-$V_{HB}$ (first chain) and $V_{LB}$-$V_{HA}$ (second chain) configuration. This can be stabilized by either of two alternative carboxy terminal heterodimerization domains: a pairing of VEPKSC (SEQ ID NO:254) on one chain and FNRGEC (SEQ ID NO:255) on the other or a pairing of oppositely charged coiled-coil domains. See, for instance, Moore et al., 2011, *Blood.* 117:4542-4551. In this embodiment, a multispecific binding protein may comprise a first chain with a CD3 binding domain $V_H$ linked to first binding domain $V_L$ and the second chain comprises a CD3 binding domain $V_L$ linked to a first binding domain $V_H$, and the two chains are linked via a disulfide bond at the C-termini. A disulfide-stabilized diabody may be designed using variable heavy and light chains derived from known antibodies including, for instance, the variable heavy and light chains disclosed herein.

In another embodiment, a multispecific binding protein is a dual variable domain binding protein capable of binding a first binding site (e.g., a tumor antigen) and a TCR complex with specificity. In this embodiment, a recombinant protein comprises a polypeptide chain, wherein said polypeptide chain comprises VD1-(X1)n-VD2-C-(X2)n, wherein VD1 is a first variable domain, VD2 is a second variable domain, C is a constant domain, X1 is a linker (e.g., a polypeptide linker of about 10 to 20 amino acids in length), X2 represents an Fc region and n is 0 or 1. See, for instance, U.S. Pat. No. 8,258,268.

In one embodiment of the invention, a multispecific binding protein comprises one, two, three or more polypeptide chains. For instance, the invention includes a multispecific protein with a first chain comprising $V_{H1}$-$V_{L2}$, a second chain comprising CH2-CH3-$V_{L1}$-$V_{H2}$ and a third chain comprising CH2-CH3. In this embodiment, the $V_{H1}$ and $V_{L1}$ may correspond to a first binding domain's variable domains, and $V_{H2}$ and $V_{L2}$ may correspond to anti-CD3 variable domains. Alternatively, the $V_{H1}$ and $V_{L1}$ may correspond to anti-CD3 variable domains, and the $V_{H2}$ and $V_{L2}$ may correspond to a first binding domain's variable domains.

In other embodiments, a multispecific binding protein is composed of dimerized single chain polypeptide chains comprising different single chain polypeptides (a heterodimer). In this format ("multispecific heterodimer"), each polypeptide chain comprising a binding domain, N-terminus linker, constant region, C-terminus linker and optionally another binding domain and does further include a heterodimerization domain. In certain variations, the second polypeptide chain for heterodimerization includes additional binding domains. Accordingly, in certain embodiments of the present invention, a heterodimeric recombinant protein may contain two, three or four binding different binding domains. See PCT publication No. WO2011/090762 for some examples and related methods.

As indicated above, a CD3 binding polypeptide of the present disclosure comprises a binding domain that specifically binds CD3. In some variations, the CD3 binding domain is capable of competing for binding to CD3 with a single-chain Fv (scFv) having an amino acid sequence as shown in SEQ ID NO:41. In particular embodiments, the CD3 binding domain comprises (i) an immunoglobulin heavy chain variable region ($V_H$) comprising CDRs HCDR1, HCDR2, and HCDR3, and (ii) an immunoglobulin light chain variable region ($V_L$) comprising CDRs LCDR1, LCDR2, and LCDR3. Suitable CD3 binding domains include those having $V_L$ and $V_H$ regions derived from murine monoclonal antibody Cris-7 (Reinherz, E. L. et al. (eds.), Leukocyte typing II., Springer Verlag, New York, (1986). In some such embodiments, LCDR3 has the amino acid sequence set forth in SEQ ID NO:54 and/or HCDR3 has the amino acid sequence set forth in SEQ ID NO:51; and LCDR1 and LCDR2 optionally have the amino acid sequences as set forth in SEQ ID NO:52 and SEQ ID NO:53, respectively, and HCDR1 and HCDR2 optionally have the amino acid sequences as set forth in SEQ ID NO:49 and SEQ ID NO:50, respectively. In some embodiments, for example, LCDR1, LCDR2, and LCDR3 have the amino acid sequences respectively shown in SEQ ID NOs:52, 53, and 54; and/or HCDR1, HCDR2, and HCDR3 have the amino acid sequences as respectively shown in SEQ ID NOs:49, 50, and 51.

Exemplary anti-CD3 antibodies from which the binding domain of this disclosure may be derived include Cris-7 monoclonal antibody (Reinherz, E. L. et al. (eds.), *Leukocyte typing II.*, Springer Verlag, New York, (1986)

($V_L$ = QVVLTQSPAIMSAFPGEKVTMTCSASSSVSYMNWYQQKSGTSP

KRWIYDSSKLASGVPARFSGSGSGTSYSLTISSMETEDAATYYCQQWSR

NPPTFGGGTKLQITR (SEQ ID NO: 46)
and $V_H$ = QVQLQQSGAELARPGASVKMSCKASGYTFTRSTMHWVKQRPGQG

LEWIGYINPSSAYTNYNQKFKDKATLTADKSSSTAYMQLSSLTSEDSAV

YYCASPQVHYDYNGFPYWGQGTLVTVSA (SEQ ID NO: 45));

HuM291 (Chau et al. (2001) Transplantation
71: 941-950

-continued ($V_L$ = DIQMTQSPSSLSASVGDRVTITCSASSSVSYMNWYQQKPGKAP

KRLIYDTSKLASGVPSRFSGSGSGTDFTLTISSLQPEDFATYYCQQWSS

NPPTFGGGTKVEIK (SEQ ID NO: 72)
and $V_H$ = QVQLVQSGAEVKKPGASVKVSCKASGYTFISYTMHWVRQAPGQG

LEWMGYINPRSGYTHYNQKLKDKATLTADKSASTAYMELSSLRSEDTAV

YYCARSAYYDYDGFAYWGQGTLVTVSS (SEQ ID NO: 73);

BC3 monoclonal antibody (Anasetti et al. (1990) *J. Exp. Med.* 172:1691); OKT3 monoclonal antibody (Ortho multicenter Transplant Study Group (1985) *N. Engl. J. Med.* 313:337) and derivatives thereof such as OKT3 ala-ala (also referred to as OKT3 AA-FL or OKT3 FL), a humanized, Fc variant with alanine substitutions at positions 234 and 235 (Herold et al. (2003) *J. Clin. Invest.* 11:409); visilizumab (Carpenter et al. (2002) *Blood* 99:2712), G19-4 monoclonal antibody (Ledbetter et al., 1986, *J. Immunol.* 136:3945) and 145-2C11 monoclonal antibody (Hirsch et al. (1988) *J. Immunol.* 140: 3766). An exemplary anti-TCR antibody is the BMA031 monoclonal antibody (Borst et al. (1990) *Human Immunology* 29:175-188).

In some embodiments, a binding domain is a single-chain Fv fragment (scFv) that comprises $V_H$ and $V_L$ regions specific for a target of interest. In certain embodiments, the $V_H$ and $V_L$ regions are human.

In one embodiment of the invention, CD3 binding polypeptides have an empirical and/or theoretical pI that is at least 0.25, 0.5, 0.75, 1, 1.25, 1.5, 2, 2.5 or more units less than that of the DRA209 SMIP. In some embodiments, a CD3 binding polypeptide of the invention has an empirical and/or theoretical pI that is from about 0.25 to about 2.5, 0.5 to about 2.5, about 0.5 to about 2.0, about 0.5 to about 1.5, about 0.5 to about 1.25, about 0.5 to about 1.0, about 0.5 to about 0.75, about 0.75 to about 1.0, about 0.75 to about 1.25, about 0.75 to about 1.5, about 0.75 to about 2.0, about 1.0 to about 1.5, about 1.0 to about 2.0, or about 1.0 to about 2.5 units less than that of the DRA209 SMIP. In some embodiments, the CD3 polypeptides of the invention have an empirical or theoretical pI that is less than about 8.9, 8.8, 8.7, 8.6, 8.5, 8.4, 8.3, 8.2, 8.1, 8, 7.5, 7.25, 7.0 or 6.75. In some embodiments, the CD3 polypeptides of the invention have an empirical or theoretical pI that is about 8.9, 8.8, 8.7, 8.6, 8.5, 8.4, 8.3, 8.2, 8.1, 8, 7.5, 7.25, 7.2 7.0, 6.8 or 6.75. In some embodiments, the CD3 polypeptides of the invention have an empirical or theoretical pI that is from about 7.9 to about 8.7, 7.9 to about 8.6, 8.0 to about 8.6, 8.0 to about 8.5, 8.0 to about 8.4, 8.0 to about 8.3, 8.0 to about 8.2, 8.0 to about 8.1, about 8.1 to about 8.6, about 8.2 to about 8.6, about 8.3 to about 8.6, about 8.4 to about 8.6, about 8.5 to about 8.6, about 8.5 to about 8.3, about 8.4 to about 8.2, or about 8.3 to about 8.1.

In certain embodiments, a CD3 binding domain comprises or is a scFv with a reduced pI (empirical and/or theoretical) by at least about 0.25, 0.5, 1, 1.25, 1.5, 2, 2.5 or more units as compared to the scFv of SEQ ID NO:41. In some embodiments, a CD3 binding domain comprises or is a scFv with a reduced pI (empirical and/or theoretical) that is from about 0.25 to about 2.5, 0.5 to about 2.5, about 0.5 to about 2.0, about 0.5 to about 1.5, about 0.5 to about 1.25, about 0.5 to about 1.0, about 0.5 to about 0.75, about 0.75 to about 1.0, about 0.75 to about 1.25, about 0.75 to about 1.5, about 0.75 to about 2.0, about 1.0 to about 1.5, about 1.0 to about 2.0, or about 1.0 to about 2.5 units less than that of the scFv of SEQ ID NO:41. Such scFvs include the scFvs contained within SEQ ID NOs: 6, 8, 10, 12, 14, 16, 18, and 20 or an scFv that is at least about 90%, at least about 91%, at least about 92%, at least about 93%, at least about 94%, at least about 95%, at least about 96%, at least about 97%, at least about 98%, at least about 99%, at least about 99.5%, or 100% identical to an amino acid sequence of scFvs contained within SEQ ID NOs: 6, 8, 10, 12, 14, 16, 18, and 20.

In some embodiments, a CD3 binding domain of the invention is about 80% to about 99%, about 82% to about 99%, about 84% to about 99%, about 86% to about 99%, about 88% to about 99%, about 90% to about 99%, about 92% to about 99%, about 94% to about 99%, about 96% to about 99%, about 97% to about 99%, about 98% to about 99%, about 80% to about 85%, about 85% to about 90%, about 85% to about 95%, about 90% to about 97%, about 90% to about 95%, about 90% to about 93%, about 90% to about 91%, about 95% to about 96%, about 96% to about 97%, about 97% to about 98%, about 96% to about 97% or about 96% to about 98% identical to SEQ ID NO:41.

In some embodiments, a CD3 binding domain of the invention is a variant of SEQ ID NO:41, wherein one or more amino acids in the amino acid sequence have been mutated to decrease the pI of the binding domain. Mutations include substitution of an amino acid(s) with another amino acid(s) to lower the pI of the binding domain, insertion of an amino acid(s) to lower the pI of the binding molecule and/or deletion of an amino acid(s) to lower the pI of the binding domain. In one embodiment, the mutations are substitutions. In some embodiments, the mutation(s) are in the framework regions of the variable chain(s). In some embodiments, a variant has a mutation of 1, 2, 3, 4, 5, 6, 7, 8, 9, 10 or more amino acids In one embodiment, the CD3 binding domain comprises or is a scFv comprising a heavy chain or a light chain selected from the group consisting of SEQ ID NOs: 28, 30, 32, 38 and 40. In another embodiment, the CD3 binding domain comprises a VH region selected from the group consisting of SEQ ID NOs: 22, 24, 26, 28, 30 and 32, and a VL region selected from the group consisting of SEQ ID NOs: 38 and 40. In another embodiment, the CD3 binding domain comprises a VH region selected from the group consisting of SEQ ID NOs: 28, 30 and 32 and a VL region selected from the group consisting of SEQ ID NOs: 34, 36, 38 and 40. In another embodiment, the CD3 binding domain comprises SEQ ID NOs: 28 and 34. In another embodiment, the CD3 binding domain comprises SEQ ID NOs: 28 and 38. In another embodiment, the CD3 binding domain comprises SEQ ID NOs: 26 and 38. In another embodiment, the CD3 binding domain comprises SEQ ID NOs: 26 and 34. In some embodiments, a CD3 binding domain comprises a VL region selected from the group consisting of SEQ ID NOs: 38 and 40 and a VH region selected from the group consisting of SEQ ID NOs: 22, 24, 26, 28, 30 and 32. In further embodiments, each CDR comprises no more than one, two, or three substitutions, insertions or deletions, as compared to that from a monoclonal antibody or fragment or derivative thereof that specifically binds to a target of interest (e.g., CD3).

In some embodiments, a CD3 binding domain binds or interacts with the CD3c subunit of the T-cell receptor complex on T-cells. In some embodiments, the CD3 binding domain competes for binding to CD3c with the Cris-7 or HuM291 monoclonal antibody.

In some embodiments, a CD3 binding polypeptide induces internalization of a T-cell receptor complex.

In some variations, the binding domain is a single-chain Fv (scFv) comprising immunoglobulin $V_L$ and $V_H$ regions joined by a peptide linker. The use of peptide linkers for joining $V_L$ and $V_H$ regions is well-known in the art, and a large number of publications exist within this particular field. A widely used peptide linker is a 15mer consisting of three repeats of a Gly-Gly-Gly-Gly-Ser (SEQ ID NO:74) amino acid sequence $(Gly_4Ser)_3$ (SEQ ID NO:76). In some embodiments, a peptide linker comprises or consists of any one of SEQ ID NOs:74-78. Other linkers have been used, and phage display technology, as well as selective infective phage technology, has been used to diversify and select appropriate linker sequences (Tang et al., *J. Biol. Chem.* 271, 15682-15686, 1996; Hennecke et al., *Protein Eng.* 11, 405-410, 1998). In certain embodiments, the $V_H$ and $V_L$ regions are joined by a peptide linker having an amino acid sequence comprising the formula $(Gly_4Ser)_n$, wherein n=1-5 (SEQ ID NOs:74-78, respectively). Other suitable linkers may be obtained by optimizing a simple linker (e.g., $(Gly_4Ser)_n$) through random mutagenesis.

In particular embodiments, a binding domain comprises humanized immunoglobulin $V_L$ and/or $V_H$ regions. Techniques for humanizing immunoglobulin $V_L$ and $V_H$ regions are known in the art and are discussed, for example, in United States Patent Application Publication No. 2006/0153837.

"Humanization" is expected to result in an antibody that is less immunogenic, with complete retention of the antigen-binding properties of the original molecule. In order to retain all of the antigen-binding properties of the original antibody, the structure of its antigen binding site should be reproduced in the "humanized" version. This can be achieved by grafting only the nonhuman CDRs onto human variable framework domains and constant regions, with or without retention of critical framework residues (Jones et al., *Nature* 321:522 (1986); Verhoeyen et al., *Science* 239:1539 (1988)) or by recombining the entire nonhuman variable domains (to preserve ligand-binding properties), but "cloaking" them with a human-like surface through judicious replacement of exposed residues (to reduce antigenicity) (Padlan, *Molec. Immunol.* 28:489 (1991)).

Essentially, humanization by CDR grafting involves recombining only the CDRs of a non-human antibody onto a human variable region framework and a human constant region. Theoretically, this should substantially reduce or eliminate immunogenicity (except if allotypic or idiotypic differences exist). However, it has been reported that some framework residues of the original antibody also may need to be preserved (Reichmann et al., *Nature,* 332:323 (1988); Queen et al., *Proc. Natl. Acad. Sci. USA,* 86:10, 029 (1989)).

The framework residues that need to be preserved are amenable to identification through computer modeling. Alternatively, critical framework residues may potentially be identified by comparing known antigen-binding site structures (Padlan, *Molec. Immunol.,* 31(3):169-217 (1994), incorporated herein by reference).

The residues that potentially affect antigen binding fall into several groups. The first group comprises residues that are contiguous with the antigen site surface, which could therefore make direct contact with antigens. These residues include the amino-terminal residues and those adjacent to the CDRs. The second group includes residues that could alter the structure or relative alignment of the CDRs, either by contacting the CDRs or another peptide chain in the antibody. The third group comprises amino acids with buried side chains that could influence the structural integrity of the variable domains. The residues in these groups are usually found in the same positions (Padlan, 1994, supra) although their positions as identified may differ depending on the numbering system (see Kabat et al., "Sequences of proteins of immunological interest, 5th ed., Pub. No. 91-3242, U.S. Dept. Health & Human Services, NIH, Bethesda, Md., 1991).

Although some examples described herein involve the humanization of scFv, SMIP, Scorpion, and Interceptor molecules, and not antibodies, knowledge about humanized antibodies in the art is applicable to the polypeptides according to the invention.

In certain embodiments, a hinge is a wild-type human immunoglobulin hinge region. In certain other embodiments, one or more amino acid residues may be added at the amino- or carboxyl-terminus of a wild type immunoglobulin hinge region as part of a fusion protein construct design. For example, additional junction amino acid residues at the hinge amino-terminus can be "RT," "RSS," "TG," or "T," or at the hinge carboxyl-terminus can be "SG", or a hinge deletion can be combined with an addition, such as ΔP with "SG" added at the carboxyl-terminus.

In certain embodiments, a hinge is an altered immunoglobulin hinge in which one or more cysteine residues in a wild type immunoglobulin hinge region is substituted with one or more other amino acid residues (e.g., serine or alanine).

Exemplary altered immunoglobulin hinges include, but are not limited to, an immunoglobulin human IgG1 hinge region having one, two or three cysteine residues found in a wild type human IgG1 hinge substituted by one, two or three different amino acid residues (e.g., serine or alanine). An altered immunoglobulin hinge may additionally have a proline substituted with another amino acid (e.g., serine or alanine). For example, the above-described altered human IgG1 hinge may additionally have a proline located carboxyl-terminal to the three cysteines of wild type human IgG1 hinge region substituted by another amino acid residue (e.g., serine, alanine). In one embodiment, the prolines of the core hinge region are not substituted.

In certain embodiments, a hinge polypeptide comprises or is a sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to a wild type immunoglobulin hinge region, such as a wild type human IgG1 hinge, a wild type human IgG2 hinge, or a wild type human IgG4 hinge.

In further embodiments, a hinge present in a CD3 binding polypeptide may be a hinge that is not based on or derived from an immunoglobulin hinge (i.e., not a wild-type immunoglobulin hinge or an altered immunoglobulin hinge). Examples for such hinges include peptides of about five to about 150 amino acids derived from an interdomain region of a transmembrane protein or stalk region of a type II C-lectin, for instance, peptides of about eight to 25 amino acids and peptides of about seven to 18 amino acids.

In certain embodiments, interdomain or stalk region hinges have seven to 18 amino acids and can form an α-helical coiled coil structure. In certain embodiments, interdomain or stalk region hinges contain 0, 1, 2, 3, or 4 cysteines. Exemplary interdomain or stalk region hinges are peptide fragments of the interdomain or stalk regions, such as ten to 150 amino acid fragments from the stalk regions of CD69, CD72, CD94, NKG2A and NKG2D.

In certain embodiments, hinge sequences have about 5 to 150 amino acids, 5 to 10 amino acids, 10 to 20 amino acids, 20 to 30 amino acids, 30 to 40 amino acids, 40 to 50 amino acids, 50 to 60 amino acids, 5 to 60 amino acids, 5 to 40 amino acids, 8 to 20 amino acids, or 10 to 15 amino acids. The hinge may be primarily flexible, but may also provide more rigid characteristics or may contain primarily α-helical structure with minimal β-sheet structure. The lengths or the sequences of the hinges may affect the binding affinities of the binding domains to which the hinges are directly or indirectly (via another region or domain, such as an heterodimerization domain) connected as well as one or more activities of the Fc region portions to which the hinges are directly or indirectly connected.

In certain embodiments, hinge sequences are stable in plasma and serum and are resistant to proteolytic cleavage. The first lysine in the IgG1 upper hinge region may be mutated to minimize proteolytic cleavage, for instance, the lysine may be substituted with methionine, threonine, alanine or glycine, or is deleted.

In some embodiments of the invention, the CD3 binding polypeptide is capable of forming a heterodimer with a second polypeptide chain and comprises a hinge region: (a) immediately amino-terminal to an immunoglobulin constant region (e.g., amino-terminal to a CH2 domain wherein the immunoglobulin constant region includes CH2 and CH3 domains, or amino-terminal to a CH3 domain wherein the immunoglobulin regions includes CH3 and CH4 domains), (b) interposed between and connecting a binding domain (e.g., scFv) and a immunoglobulin heterodimerization domain, (c) interposed between and connecting an immunoglobulin heterodimerization domain and an immunoglobulin constant region (e.g., wherein the immunoglobulin constant region includes CH2 and CH3 domains or CH3 and CH4 domains), (d) interposed between and connecting an immunoglobulin constant region and a binding domain, (e) at the amino-terminus of a polypeptide chain, or (f) at the carboxyl-terminus of a polypeptide chain. A polypeptide chain comprising a hinge region as described herein can be capable of associating with a different polypeptide chain to form a homodimeric or heterodimeric protein provided herein, and the dimer formed will contain a binding domain that retains its target specificity and/or its specific target binding affinity.

In certain embodiments, a hinge present in a polypeptide that forms a heterodimer with another polypeptide chain may be an immunoglobulin hinge, such as a wild-type immunoglobulin hinge region or an altered immunoglobulin hinge region thereof. In certain embodiments, a hinge of one polypeptide chain of a heterodimeric protein is identical to a corresponding hinge of the other polypeptide chain of the heterodimer. In certain other embodiments, a hinge of one chain is different from that of the other chain (e.g., in their length and/or sequence). The different hinges in the different chains allow different manipulation of the binding affinities of the binding domains to which the hinges are connected, so that the heterodimer is able to bind to the target of one binding domain over the target of the other binding domain. For example, in certain embodiments, a heterodimeric protein has a CD3- or TCR-binding domain in one chain and a second binding domain (such as a tumor antigen binding domain) in another chain. Having two different hinges in the two chains may allow the heterodimer to bind to the tumor antigen first, and then to a CD3 or other TCR component second. Thus, the heterodimer may recruit $CD3^+$ T-cells to tumor antigen-expressing cells (e.g., PSMA-expressing tumor cells), which in turn may damage or destroy the tumor antigen-expressing cells.

Exemplary hinge regions suitable for use in accordance with the present invention are shown in the Tables 1 and 2 below.

TABLE 1

Exemplary hinge regions

| Hinge Region | Amino Acid Sequence |
|---|---|
| sss(s)-hIgG1 hinge | EPKSSDKTHTSPPSS (SEQ ID NO: 112) |
| csc(s)-hIgG1 hinge | EPKSCDKTHTSPPCS (SEQ ID NO: 113) |
| ssc(s)-hIgG1 hinge | EPKSSDKTHTSPPCS (SEQ ID NO: 114) |
| scc(s)-hIgG1 hinge | EPKSSDKTHTCPPCS (SEQ ID NO: 115) |
| css(s)-hIgG1 hinge | EPKSCDKTHTSPPSS (SEQ ID NO: 116) |
| scs(s)-hIgG1 hinge | EPKSSDKTHTCPPSS (SEQ ID NO: 117) |
| ccc(s)-hIgG1 hinge | EPKSCDKTHTSPPCS (SEQ ID NO: 118) |
| ccc(p)-hIgG1 hinge | EPKSCDKTHTSPPCP (SEQ ID NO: 119) |
| sss(p)-hIgG1 hinge | EPKSSDKTHTSPPSP (SEQ ID NO: 120) |
| csc(p)-hIgG1 hinge | EPKSCDKTHTSPPCP (SEQ ID NO: 121) |
| ssc(p)-hIgG1 hinge | EPKSSDKTHTSPPCP (SEQ ID NO: 122) |
| scc(p)-hIgG1 hinge | EPKSSDKTHTCPPCP (SEQ ID NO: 123) |
| css(p)-hIgG1 hinge | EPKSCDKTHTSPPSP (SEQ ID NO: 124) |
| scs(p)-hIgG1 hinge | EPKSSDKTHTCPPSP (SEQ ID NO: 125) |
| Scppcp | SCPPCP (SEQ ID NO: 126) |
| STD1 | NYGGGGSGGGGSGGGGSGNS (SEQ ID NO: 127) |
| STD2 | NYGGGGSGGGGSGGGGSGNY GGGGSGGGGSGGGGSGNS (SEQ ID NO: 128) |
| H1 | NS (SEQ ID NO: 129) |
| H2 | GGGGSGNS (SEQ ID NO: 130) |
| H3 | NYGGGGSGNS (SEQ ID NO: 131) |
| H4 | GGGGSGGGGSGNS (SEQ ID NO: 132) |
| H5 | NYGGGGSGGGGSGNS (SEQ ID NO: 133) |
| H6 | GGGGSGGGGSGGGGSGNS (SEQ ID NO: 134) |

TABLE 1-continued

Exemplary hinge regions

| Hinge Region | Amino Acid Sequence |
|---|---|
| H7 | GCPPCPNS (SEQ ID NO: 135) |
| H9 | GSPPSPNS (SEQ ID NO: 136) |
| (G4S)3 | GGGGSGGGGSGGGGS (SEQ ID NO: 137) |
| H105 | SGGGGSGGGGSGGGGS (SEQ ID NO: 138) |
| (G4S)4 | GGGGSGGGGSGGGGSGGGGS (SEQ ID NO: 139) |
| H75 (NKG2A quadruple mutant) | QRHNNSSLNTGTQMAGHSPNS (SEQ ID NO: 140) |
| H83 (NKG2A derived) | SSLNTGTQMAGHSPNS (SEQ ID NO: 141) |
| H106 (NKG2A derived) | QRHNNSSLNTGTQMAGHS (SEQ ID NO: 142) |
| H81 (NKG2D derived) | EVQIPLTESYSPNS (SEQ ID NO: 143) |
| H91 (NKG2D derived) | NSLANQEVQIPLTESYSPNS (SEQ ID NO: 144) |
| H94 | SGGGGSGGGGSGGGGSPNS (SEQ ID NO: 145) |

TABLE 2

Exemplary hinge regions (derived from H7 hinge, stalk region of a type II C-lectin, or interdomain region of a type I transmembrane protein)

| Hinge Region | Amino Acid Sequence | Molecule and/or hinge from which derived |
|---|---|---|
| H16 | LSVKADFLTPSIGNS (SEQ ID NO: 146) | CD80 |
| H17 | LSVKADFLTPSISCPPCPNS (SEQ ID NO: 147) | CD80 + H7 |
| H18 | LSVLANFSQPEIGNS (SEQ ID NO: 148) | CD86 |
| H19 | LSVLANFSQPEISCPPCPNS (SEQ ID NO: 149) | CD86 + H7 |
| H20 | LKIQERVSKPKISNS (SEQ ID NO: 150) | CD2 |
| H21 | LKIQERVSKPKISCPPCPNS (SEQ ID NO: 151) | CD2 + H7 |
| H22 | LNVSERPFPPHIQNS (SEQ ID NO: 152) | CD22 |
| H23 | LDVSERPFPPHIQSCPPCPNS (SEQ ID NO: 153) | CD22 + H7 |
| H24 | REQLAEVTLSLKANS (SEQ ID NO: 154) | CD80 |
| H25 | REQLAEVTLSLKACPPCPNS (SEQ ID NO: 155) | CD80 + H7 |

TABLE 2-continued

Exemplary hinge regions (derived from H7 hinge, stalk region of a type II C-lectin, or interdomain region of a type I transmembrane protein)

| Hinge Region | Amino Acid Sequence | Molecule and/or hinge from which derived |
|---|---|---|
| H26 | RIHQMNSELSVLANS (SEQ ID NO: 156) | CD86 |
| H27 | RIHQMNSELSVLACPPCPNS (SEQ ID NO: 157) | CD86 + H7 |
| H28 | DTKGKNVLEKIFSNS (SEQ ID NO: 158) | CD2 |
| H30 | LPPETQESQEVTLNS (SEQ ID NO: 159) | CD22 |
| H32 | RIHLNVSERPFPPNS (SEQ ID NO: 160) | CD22 |
| H33 | RIHLNVSERPFPPCPPCPNS (SEQ ID NO: 161) | CD22 + H7 |
| H36 | GCPPCPGGGGSNS (SEQ ID NO: 162) | H7 |
| H40 | GCPPCPANS (SEQ ID NO: 163) | H7 |
| H41 | GCPPCPANS (SEQ ID NO: 164) | H7 |
| H42 | GCPPCPNS (SEQ ID NO: 165) | H7 |
| H44 | GGGASCPPCPGNS (SEQ ID NO: 166) | H7 |
| H45 | GGGASCPPCAGNS (SEQ ID NO: 167) | H7 |
| H46 | GGGASCPPCANS (SEQ ID NO: 168) | H7 |
| H47 | LSVKADFLTPSIGNS (SEQ ID No; 169) | CD80 |
| H48 | ADFLTPSIGNS (SEQ ID NO: 170) | CD80 |
| H50 | LSVLANFSQPEIGNS (SEQ ID NO: 171) | CD86 |
| H51 | LSVLANFSQPEIGNS (SEQ ID NO: 172) | CD86 |
| H52 | SQPEIVPISNS SEQ ID NO: 173) | CD86 |
| H53 | SQPEIVPISCPPCPNS SEQ ID NO: 174) | CD86 + H7 |
| H54 | SVLANFSQPEISCPPCPNS SEQ ID NO: 175) | CD86 + H7 |
| H55 | RIHQMNSELSVLANS SEQ ID NO: 176) | CD86 |
| H56 | QMNSELSVLANS SEQ ID NO: 177) | CD86 |
| H57 | VSERPFPPNS SEQ ID NO: 178) | CD22 |
| H58 | KPFFTCGSADTCPNS SEQ ID NO: 179) | CD72 |

TABLE 2-continued

Exemplary hinge regions (derived from H7 hinge, stalk region of a type II C-lectin, or interdomain region of a type I transmembrane protein)

| Hinge Region | Amino Acid Sequence | Molecule and/or hinge from which derived |
|---|---|---|
| H59 | KPFFTCGSADTCPNS SEQ ID NO: 180) | CD72 |
| H60 | QYNCPGQYTFSMPNS SEQ ID NO: 181) | CD69 |
| H61 | EPAFTPGPNIELQKDSDCPNS SEQ ID NO: 182) | CD94 |
| H62 | QRHNNSSLNTRTQKARHCPNS SEQ ID NO: 183) | NKG2A |
| H63 | NSLFNQEVQIPLTESYCPNS SEQ ID NO: 184) | NKG2D |

In certain embodiments, a CD3 binding polypeptide or protein of the invention may comprise an “immunoglobulin dimerization domain” or “immunoglobulin heterodimerization domain.”

An “immunoglobulin dimerization domain” or “immunoglobulin heterodimerization domain,” as used herein, refers to an immunoglobulin domain of a polypeptide chain that interacts or associates with a second immunoglobulin domain of a second polypeptide chain, wherein the interaction of the first and second immunoglobulin heterodimerization domains substantially contributes to or efficiently promotes heterodimerization of the first and second polypeptide chains (i.e., the formation of a dimer between two different polypeptide chains, which is also referred to as a “heterodimer” or “heterodimeric protein”). The interactions between immunoglobulin heterodimerization domains “substantially contributes to or efficiently promotes” the heterodimerization of first and second polypeptide chains if there is a statistically significant reduction in the dimerization between the first and second polypeptide chains in the absence of the immunoglobulin heterodimerization domain of the first polypeptide chain and/or the immunoglobulin heterodimerization domain of the second polypeptide chain. In certain embodiments, when the first and second polypeptide chains are co-expressed, at least 60%, at least about 60% to about 70%, at least about 70% to about 80%, at least 80% to about 90%, 91%, 92%, 93%, 94%, 95%, 96%, 97%, 98%, or 99% of the first and second polypeptide chains form heterodimers with each other. Representative immunoglobulin heterodimerization domains include an immunoglobulin CH1 domain, an immunoglobulin CL domain (e.g., Cκ or Cλ isotypes), or derivatives thereof, including wild-type immunoglobulin CH1 and CL domains and altered (or mutated) immunoglobulin CH1 and CL domains, such as provided herein.

Dimerization/heterodimerization domains may be used where it is desired to form heterodimers from two non-identical polypeptide chains, where one or both polypeptide chains comprise a binding domain. In certain embodiments, one polypeptide chain member of certain heterodimers described herein does not contain a binding domain. As indicated above, a heterodimeric protein of the present disclosure comprises an immunoglobulin heterodimerization domain in each polypeptide chain. The immunoglobulin heterodimerization domains in the polypeptide chains of a heterodimer are different from each other and thus may be differentially modified to facilitate heterodimerization of both chains and to minimize homodimerization of either chain. As shown in PCT Publication No. WO2011/090762, immunoglobulin heterodimerization domains provided herein allow for efficient heterodimerization between different polypeptides and facilitate purification of the resulting heterodimeric protein.

As provided herein, immunoglobulin heterodimerization domains useful for promoting heterodimerization of two different single chain polypeptides (e.g., one short and one long) according to the present disclosure include immunoglobulin CH1 and CL domains, for instance, human CH1 and CL domains. In certain embodiments, an immunoglobulin heterodimerization domain is a wild-type CH1 domain, such as a wild type IgG1, IgG2, IgG3, IgG4, IgA1, IgA2, IgD, IgE, or IgM CH1 domain. In further embodiments, an immunoglobulin heterodimerization domain is a wild-type human IgG1, IgG2, IgG3, IgG4, IgA1, IgA2, IgD, IgE, or IgM CH1 domain as set forth in SEQ ID NOS:114, 186-192 and 194, respectively, of PCT Publication No. WO2011/090762 (said sequences incorporated by reference herein). In certain embodiments, an immunoglobulin heterodimerization domain is a wild-type human IgG1 CH1 domain as set forth in SEQ ID NO:114 of WO2011/090762 (said sequence incorporated by reference herein), which is the same as SEQ ID NO:80 of the present application.

In further embodiments, an immunoglobulin heterodimerization domain is an altered immunoglobulin CH1 domain, such as an altered IgG1, IgG2, IgG3, IgG4, IgA1, IgA2 IgD, IgE, or IgM CH1 domain. In certain embodiments, an immunoglobulin heterodimerization domain is an altered human IgG1, IgG2, IgG3, IgG4, IgA1, IgA2, IgD, IgE, or IgM CH1 domain. In still further embodiments, a cysteine residue of a wild-type CH1 domain (e.g., a human CH1) involved in forming a disulfide bond with a wild type immunoglobulin CL domain (e.g., a human CL) is deleted or substituted in the altered immunoglobulin CH1 domain such that a disulfide bond is not formed between the altered CH1 domain and the wild-type CL domain.

In certain embodiments, an immunoglobulin heterodimerization domain is a wild-type CL domain, such as a wild type Cκ domain or a wild type Cλ domain. In particular embodiments, an immunoglobulin heterodimerization domain is a wild type human Cκ or human Cλ domain as set forth in SEQ ID NOS:112 and 113, respectively, of WO2011/090762 (said sequences incorporated by reference herein), which are the same as SEQ ID NOs:81 & 82, respectively, of the present application. In further embodiments, an immunoglobulin heterodimerization domain is an altered immunoglobulin CL domain, such as an altered Cκ or Cλ domain, for instance, an altered human Cκ or human Cλ domain.

In certain embodiments, a cysteine residue of a wild-type CL domain (e.g., a human CL) involved in forming a disulfide bond with a wild type immunoglobulin CH1 domain (e.g., a human CH1) is deleted or substituted in the altered immunoglobulin CL domain. Such altered CL domains may further comprise an amino acid deletion at their amino-termini. An exemplary Cκ domain is set forth in SEQ ID NO:141 of WO2011/090762 (said sequence incorporated by reference herein, which is SEQ ID NO:83 of the present application), in which the first arginine and the last cysteine of the wild type human Ck domain are both deleted. In certain embodiments, only the last cysteine of the wild type human Ck domain is deleted in the altered Ck domain because the first arginine deleted from the wild type human Ck domain may be provided by a linker that has an arginine at its carboxyl-terminus and links the amino-terminus of the altered Ck domain with another domain (e.g., an immunoglobulin sub-region, such as a sub-region comprising immunoglobulin CH2 and CH3 domains). An exemplary Cλ domain is set forth in SEQ ID NO:140 of WO2011/090762 (said sequence incorporated by reference herein, which is SEQ ID NO:84 of the present application), in which the first arginine of a wild type human Cλ domain is deleted and the cysteine involved in forming a disulfide bond with a cysteine in a CH1 domain is substituted by a serine.

In further embodiments, an immunoglobulin heterodimerization domain is an altered Cκ domain that contains one or more amino acid substitutions, as compared to a wild type Cκ domain, at positions that may be involved in forming the interchain-hydrogen bond network at a Cκ-Cκ interface. For example, in certain embodiments, an immunoglobulin heterodimerization domain is an altered human Cκ domain having one or more amino acids at positions N29, N30, Q52, V55, T56, S68 or T70 that are substituted with a different amino acid. The numbering of the amino acids is based on their positions in the altered human Cκ sequence as set forth in SEQ ID NO:141 of WO2011/090762 (said sequence incorporated by reference herein, which is SEQ ID NO:83 of the present application). In certain embodiments, an immunoglobulin heterodimerization domain is an altered human Cκ domain having one, two, three or four amino acid substitutions at positions N29, N30, V55, or T70. The amino acid used as a substitute at the above-noted positions may be an alanine, or an amino acid residue with a bulk side chain moiety such as arginine, tryptophan, tyrosine, glutamate, glutamine, or lysine. Additional amino acid residues that may be used to substitute amino acid residues of the wild type human Ck sequence at the above noted positions (e.g., N30) include aspartate, methionine, serine and phenylalanine. Exemplary altered human Cκ domains are set forth in SEQ ID NOS:142-178 of WO2011/090762 (said sequences incorporated by reference herein). Altered human CK domains are those that facilitate heterodimerization with a CH1 domain, but minimize homodimerization with another Cκ domain. Representative altered human Cκ domains are set forth in SEQ ID NOS:160 (N29W V55A T70A), 161 (N29Y V55A T70A), 202 (T70E N29A N30A V55A), 167 (N30R V55A T70A), 168 (N30K V55A T70A), 170 (N30E V55A T70A), 172 (V55R N29A N30A), 175 (N29W N30Y V55A T70E), 176 (N29Y N30Y V55A T70E), 177 (N30E V55A T70E), 178 (N30Y V55A T70E), 838 (N30D V55A T70E), 839 (N30M V55A T70E), 840 (N30S V55A T70E), and 841 (N30F V55A T70E) of WO2011/090762 (said sequences incorporated by reference herein).

In certain embodiments, in addition to or alternative to the mutations in Ck domains described herein, both the immunoglobulin heterodimerization domains (e.g., immunoglobulin CH1 and CL domains) of a polypeptide heterodimer have mutations so that the resulting immunoglobulin heterodimerization domains form salt bridges (i.e., ionic interactions) between the amino acid residues at the mutated sites. For example, the immunoglobulin heterodimerization domains of a polypeptide heterodimer may be a mutated CH1 domain in combination with a mutated Ck domain. In the mutated CH1 domain, valine at position 68 (V68) of the wild type human CH1 domain is substituted by an amino acid residue having a negative charge (e.g., aspartate or glutamate), whereas leucine at position 29 (L29) of a mutated human Ck domain in which the first arginine and the last cysteine have been deleted is substituted by an amino acid residue having a positive charge (e.g., lysine, arginine or histidine). The charge-charge interaction between the amino acid residue having a negative charge of the resulting mutated CH1 domain and the amino acid residue having a positive charge of the resulting mutated Ck domain forms a salt bridge, which stabilizes the heterodimeric interface between the mutated CH1 and Ck domains. Alternatively, V68 of the wild type CH1 may be substituted by an amino acid residue having a positive charge, whereas L29 of a mutated human Ck domain in which the first arginine and the last cysteine have been deleted may be substituted by an amino acid residue having a negative charge. Exemplary mutated CH1 sequences in which V68 is substituted by an amino acid with either a negative or positive charge are set forth in SEQ ID NOS:844 and 845 of WO2011/090762 (said sequences incorporated by reference herein). Exemplary mutated Ck sequences in which L29 is substituted by an amino acid with either a negative or positive charge are set forth in SEQ ID NOS:842 and 843 of WO2011/090762 (said sequences incorporated by reference herein).

Positions other than V68 of human CH1 domain and L29 of human Ck domain may be substituted with amino acids having opposite charges to produce ionic interactions between the amino acids in addition or alternative to the mutations in V68 of CH1 domain and L29 of Ck domain. Such positions can be identified by any suitable method, including random mutagenesis, analysis of the crystal structure of the CH1-Ck pair to identify amino acid residues at the CH1-Ck interface, and further identifying suitable positions among the amino acid residues at the CH1-Ck interface using a set of criteria (e.g., propensity to engage in ionic interactions, proximity to a potential partner residue, etc.).

In certain embodiments, polypeptide heterodimers of the present disclosure contain only one pair of immunoglobulin heterodimerization domains. For example, a first chain of a polypeptide heterodimer may comprise a CH1 domain as an immunoglobulin heterodimerization domain, while a second chain may comprise a CL domain (e.g., a Cκ or Cλ) as an immunoglobulin heterodimerization domain. Alternatively, a first chain may comprise a CL domain (e.g., a Cκ or Cλ) as an immunoglobulin heterodimerization domain, while a second chain may comprise a CH1 domain as an immunoglobulin heterodimerization domain. As set forth herein, the immunoglobulin heterodimerization domains of the first and second chains are capable of associating to form a heterodimeric protein of this disclosure.

In certain other embodiments, heterodimeric proteins of the present disclosure may have two pairs of immunoglobulin heterodimerization domains. For example, a first chain of a heterodimer may comprise two CH1 domains, while a second chain may have two CL domains that associate with the two CH1 domains in the first chain. Alternatively, a first chain may comprise two CL domains, while a second chain may have two CH1 domains that associate with the two CL domains in the first chain. In certain embodiments, a first polypeptide chain comprises a CH1 domain and a CL domain, while a second polypeptide chain comprises a CL domain and a CH1 domain that associate with the CH1 domain and the CL domain, respectively, of the first polypeptide chain.

In the embodiments where a heterodimeric protein comprises only one heterodimerization pair (e.g., one immunoglobulin heterodimerization domain in each chain), the immunoglobulin heterodimerization domain of each chain may be located amino-terminal to the immunoglobulin constant sub-region of that chain. Alternatively, the immunoglobulin heterodimerization domain in each chain may be located carboxyl-terminal to the immunoglobulin constant sub-region of that chain.

In the embodiments where a heterodimeric protein comprises two heterodimerization pairs (e.g., two immunoglobulin heterodimerization domains in each chain), both immunoglobulin heterodimerization domains in each chain may be located amino-terminal to the immunoglobulin constant sub-region of that chain. Alternatively, both immunoglobulin heterodimerization domains in each chain may be located carboxyl-terminal to the immunoglobulin constant sub-region of that chain. In further embodiments, one immunoglobulin heterodimerization domain in each chain may be located amino-terminal to the immunoglobulin constant sub-region of that chain, while the other immunoglobulin heterodimerization domain of each chain may be located carboxyl-terminal to the immunoglobulin constant sub-region of that chain. In other words, in those embodiments, the immunoglobulin constant sub-region is interposed between the two immunoglobulin heterodimerization domains of each chain.

As indicated herein, in certain embodiments, CD3 binding polypeptides of the present disclosure (e.g., small modular immunopharmaceutical proteins (SMIPs), homodimer bispecifics (e.g., Scorpion), heterodimer mono- and multi-specific therapeutics (e.g., Interceptor) comprise an immunoglobulin constant region in each polypeptide chain. The term "constant region" is used interchangeably with constant sub-region and immunoglobulin constant region herein. The inclusion of an immunoglobulin constant region can slow clearance of the homodimeric and heterodimeric proteins formed from two CD3 binding polypeptide chains from circulation after administration to a subject.

By mutations or other alterations, the immunoglobulin constant region further enables relatively easy modulation of dimeric polypeptide effector functions (e.g., ADCC, ADCP, CDC, complement fixation, and binding to Fc receptors), which can either be increased or decreased depending on the disease being treated, as known in the art and described herein.

In certain embodiments, an immunoglobulin constant region of one or both of the polypeptide chains of the polypeptide homodimers and heterodimers of the present disclosure will be capable of mediating one or more of these effector functions.

In other embodiments, one or more of these effector functions are reduced or absent in an immunoglobulin constant region of one or both of the polypeptide chains of the polypeptide homodimers and heterodimers of the present disclosure, as compared to a corresponding wild-type immunoglobulin constant region. For instance, it is particularly useful for monospecific CD3 binding polypeptides as well as CD3 binding polypeptides comprising a second binding domain, e.g., designed to elicit redirected T-cell toxicity (RTCC), to have an immunoglobulin constant region with reduced or no effector function relative to a corresponding wild-type immunoglobulin constant region. In one embodiment, the constant region is modified to not fix complement. The constant region can also be modified to not bind to one or more Fcγ receptors such as CD16, CD32 and CD64.

An immunoglobulin constant sub-region present in CD3 binding polypeptides of the present disclosure may comprise of or is derived from part or all of: a CH2 domain, a CH3 domain, a CH4 domain, or any combination thereof. For example, an immunoglobulin constant sub-region may comprise a CH2 domain, a CH3 domain, both CH2 and CH3 domains, both CH3 and CH4 domains, two CH3 domains, a CH4 domain, two CH4 domains, and a CH2 domain and part of a CH3 domain. In some embodiments, a constant region comprises CH2 and CH3 domains of IgG1, IgG2, IgG3, IgG4, IgA1, IgA2, IgD or any combination thereof; an immunoglobulin CH3 domain of IgG1, IgG2, IgG3, IgG4, IgA1, IgA2, IgD, IgE, IgM or any combination thereof; or immunoglobulin CH3 and CH4 domains of IgE, IgM or a combination thereof. In some embodiments, a constant region consists essentially of a CH2 domain and CH3 domain.

A CH2 domain that may form an immunoglobulin constant region of a CD3 binding polypeptide of the present disclosure may be a wild type immunoglobulin CH2 domain or an altered immunoglobulin CH2 domain thereof from certain immunoglobulin classes or subclasses (e.g., IgG1, IgG2, IgG3, IgG4, IgA1, IgA2, or IgD) and from various species (including human, mouse, rat, and other mammals). In some embodiments, a constant region is modified to reduce or eliminate effector function, reduce or not fix complement and/or reduce binding to or not bind to Fcγ receptors. In some embodiments, an Fcγ receptor is selected from the group consisting of CD16, CD32 and CD64.

In certain embodiments, a CH2 domain is a wild type human immunoglobulin CH2 domain, such as wild type CH2 domains of human IgG1, IgG2, IgG3, IgG4, IgA1, IgA2, or IgD, as set forth in SEQ ID NOS:115, 199-201 and 195-197, respectively, of PCT Publication WO2011/090762 (said sequences incorporated by reference herein). In certain embodiments, the CH2 domain is a wild type human IgG1 CH2 domain as set forth in SEQ ID NO:115 of WO2011/090762 (said sequence incorporated by reference herein, which is SEQ ID NO:85 of the present application). In some embodiments, a constant region comprises or consists of the amino acid sequence of SEQ ID NO:55

In certain embodiments, a CH2 domain is an altered immunoglobulin CH2 region (e.g., an altered human IgG1 CH2 domain) that comprises an amino acid substitution at the asparagine of position 297 (e.g., asparagine to alanine). Such an amino acid substitution reduces or eliminates glycosylation at this site and abrogates efficient Fc binding to FcγR and C1q. The sequence of an altered human IgG1 CH2 domain with an Asn to Ala substitution at position 297 is set forth in SEQ ID NO:324 of WO2011/090762 said (sequence incorporated by reference herein, which is SEQ ID NO:86 of the present application).

In certain embodiments, a CH2 domain is an altered immunoglobulin CH2 region (e.g., an altered human IgG1 CH2 domain) that comprises at least one substitution or deletion at positions 234 to 238. For example, an immunoglobulin CH2 region can comprise a substitution at position 234, 235, 236, 237 or 238, positions 234 and 235, positions 234 and 236, positions 234 and 237, positions 234 and 238, positions 234-236, positions 234, 235 and 237, positions 234, 236 and 238, positions 234, 235, 237, and 238, positions 236-238, or any other combination of two, three, four, or five amino acids at positions 234-238. In addition or alternatively, an altered CH2 region may comprise one or more (e.g., two, three, four or five) amino acid deletions at positions 234-238, for instance, at one of position 236 or position 237 while the other position is substituted. The above-noted mutation(s) decrease or eliminate the antibody-dependent cell-mediated cytotoxicity (ADCC) activity or Fc receptor-binding capability of a polypeptide heterodimer that comprises the altered CH2 domain. In certain embodiments, the amino acid residues at one or more of positions 234-238 has been replaced with one or more alanine residues. In further embodiments, only one of the amino acid residues at positions 234-238 have been deleted while one or more of the remaining amino acids at positions 234-238 can be substituted with another amino acid (e.g., alanine or serine).

In certain other embodiments, a CH2 domain is an altered immunoglobulin CH2 region (e.g., an altered human IgG1 CH2 domain) that comprises one or more amino acid substitutions at positions 253, 310, 318, 320, 322, and 331. For example, an immunoglobulin CH2 region can comprise a substitution at position 253, 310, 318, 320, 322, or 331, positions 318 and 320, positions 318 and 322, positions 318, 320 and 322, or any other combination of two, three, four, five or six amino acids at positions 253, 310, 318, 320, 322, and 331. The above-noted mutation(s) decrease or eliminate the complement-dependent cytotoxicity (CDC) of a polypeptide heterodimer that comprises the altered CH2 domain.

In certain other embodiments, in addition to the amino acid substitution at position 297, an altered CH2 region (e.g., an altered human IgG1 CH2 domain) can further comprise one or more (e.g., two, three, four, or five) additional substitutions at positions 234-238. For example, an immunoglobulin CH2 region can comprise a substitution at positions 234 and 297, positions 234, 235, and 297, positions 234, 236 and 297, positions 234-236 and 297, positions 234, 235, 237 and 297, positions 234, 236, 238 and 297, positions 234, 235, 237, 238 and 297, positions 236-238 and 297, or any combination of two, three, four, or five amino acids at positions 234-238 in addition to position 297. In addition or alternatively, an altered CH2 region may comprise one or more (e.g., two, three, four or five) amino acid deletions at positions 234-238, such as at position 236 or position 237. The additional mutation(s) decreases or eliminates the antibody-dependent cell-mediated cytotoxicity (ADCC) activity or Fc receptor-binding capability of a polypeptide heterodimer that comprises the altered CH2 domain. In certain embodiments, the amino acid residues at one or more of positions 234-238 have been replaced with one or more alanine residues. In further embodiments, only one of the amino acid residues at positions 234-238 has been deleted while one or more of the remaining amino acids at positions 234-238 can be substituted with another amino acid (e.g., alanine or serine).

In certain embodiments, in addition to one or more (e.g., 2, 3, 4, or 5) amino acid substitutions at positions 234-238, a mutated CH2 region (e.g., an altered human IgG1 CH2 domain) in a fusion protein of the present disclosure may contain one or more (e.g., 2, 3, 4, 5, or 6) additional amino acid substitutions (e.g., substituted with alanine) at one or more positions involved in complement fixation (e.g., at positions I253, H310, E318, K320, K322, or P331). Examples of mutated immunoglobulin CH2 regions include human IgG1, IgG2, IgG4 and mouse IgG2a CH2 regions with alanine substitutions at positions 234, 235, 237 (if present), 318, 320 and 322. An exemplary mutated immunoglobulin CH2 region is mouse IGHG2c CH2 region with alanine substitutions at L234, L235, G237, E318, K320, and K322.

In still further embodiments, in addition to the amino acid substitution at position 297 and the additional deletion(s) or substitution(s) at positions 234-238, an altered CH2 region (e.g., an altered human IgG1 CH2 domain) can further comprise one or more (e.g., two, three, four, five, or six) additional substitutions at positions 253, 310, 318, 320, 322, and 331. For example, an immunoglobulin CH2 region can comprise a (1) substitution at position 297, (2) one or more substitutions or deletions or a combination thereof at positions 234-238, and one or more (e.g., 2, 3, 4, 5, or 6) amino acid substitutions at positions 1253, H310, E318, K320, K322, and P331, such as one, two, three substitutions at positions E318, K320 and K322. The amino acids at the above-noted positions may be substituted by alanine or serine.

In certain embodiments, an immunoglobulin CH2 region polypeptide comprises: (i) an amino acid substitution at the asparagines of position 297 and one amino acid substitution at position 234, 235, 236 or 237; (ii) an amino acid substitution at the asparagine of position 297 and amino acid substitutions at two of positions 234-237; (iii) an amino acid substitution at the asparagine of position 297 and amino acid substitutions at three of positions 234-237; (iv) an amino acid substitution at the asparagine of position 297, amino acid substitutions at positions 234, 235 and 237, and an amino acid deletion at position 236; (v) amino acid substitutions at three of positions 234-237 and amino acid substitutions at positions 318, 320 and 322; or (vi) amino acid substitutions at three of positions 234-237, an amino acid deletion at position 236, and amino acid substitutions at positions 318, 320 and 322.

Exemplary altered immunoglobulin CH2 regions with amino acid substitutions at the asparagine of position 297 include: human IgG1 CH2 region with alanine substitutions at L234, L235, G237 and N297 and a deletion at G236 (SEQ ID NO:325 of WO2011/090762, said sequence incorporated by reference herein), human IgG2 CH2 region with alanine substitutions at V234, G236, and N297 (SEQ ID NO:326 of WO2011/090762, said sequence incorporated by reference herein), human IgG4 CH2 region with alanine substitutions at F234, L235, G237 and N297 and a deletion of G236 (SEQ ID NO:322 of WO2011/090762, said sequence incorporated by reference herein), human IgG4 CH2 region with alanine substitutions at F234 and N297 (SEQ ID NO:343 of WO2011/090762, said sequence incorporated by reference herein), human IgG4 CH2 region with alanine substitutions at L235 and N297 (SEQ ID NO:344 of WO2011/090762, said sequence incorporated by reference herein), human IgG4 CH2 region with alanine substitutions at G236 and N297 (SEQ ID NO:345 of WO2011/090762, said sequence incorporated by reference herein), and human IgG4 CH2 region with alanine substitutions at G237 and N297 (SEQ ID NO:346 of WO2011/090762, said sequence incorporated by reference herein).

In certain embodiments, in addition to the amino acid substitutions described above, an altered CH2 region (e.g., an altered human IgG1 CH2 domain) may contain one or more additional amino acid substitutions at one or more positions other than the above-noted positions. Such amino acid substitutions may be conservative or non-conservative amino acid substitutions. For example, in certain embodiments, P233 may be changed to E233 in an altered IgG2 CH2 region (see, e.g., SEQ ID NO:326 of WO2011/090762, said sequence incorporated by reference herein). In addition or alternatively, in certain embodiments, the altered CH2 region may contain one or more amino acid insertions, deletions, or both. The insertion(s), deletion(s) or substitution(s) may anywhere in an immunoglobulin CH2 region, such as at the N- or C-terminus of a wild type immunoglobulin CH2 region resulting from linking the CH2 region with another region (e.g., a binding domain or an immunoglobulin heterodimerization domain) via a hinge.

In certain embodiments, an altered CH2 region in a polypeptide of the present disclosure comprises or is a sequence that is at least 90%, at least 91%, at least 92%, at least 93%, at least 94%, at least 95%, at least 96%, at least 97%, at least 98% or at least 99% identical to a wild type immunoglobulin CH2 region, such as the CH2 region of wild type human IgG1, IgG2, or IgG4, or mouse IgG2a (e.g., IGHG2c).

An altered immunoglobulin CH2 region in a CD3 binding polypeptide of the present disclosure may be derived from a CH2 region of various immunoglobulin isotypes, such as IgG1, IgG2, IgG3, IgG4, IgA1, IgA2, and IgD, from various species (including human, mouse, rat, and other mammals). In certain embodiments, an altered immunoglobulin CH2 region in a fusion protein of the present disclosure may be derived from a CH2 region of human IgG1, IgG2 or IgG4, or mouse IgG2a (e.g., IGHG2c), whose sequences are set forth in SEQ ID NOS:115, 199, 201, and 320 of WO2011/090762 (said sequences incorporated by reference herein).

In certain embodiments, an altered CH2 domain is a human IgG1 CH2 domain with alanine substitutions at positions 235, 318, 320, and 322 (i.e., a human IgG1 CH2 domain with L235A, E318A, K320A and K322A substitutions) (SEQ ID NO:595 of WO2011/090762, said sequence incorporated by reference herein), and optionally an N297 mutation (e.g., to alanine). In certain other embodiments, an altered CH2 domain is a human IgG1 CH2 domain with alanine substitutions at positions 234, 235, 237, 318, 320 and 322 (i.e., a human IgG1 CH2 domain with L234A, L235A, G237A, E318A, K320A and K322A substitutions) (SEQ ID NO:596 of WO2011/090762, said sequence incorporated by reference herein), and optionally an N297 mutation (e.g., to alanine).

In certain embodiments, an altered CH2 domain is an altered human IgG1 CH2 domain with mutations known in the art that enhance immunological activities such as ADCC, ADCP, CDC, complement fixation, Fc receptor binding, or any combination thereof.

The CH3 domain that may form an immunoglobulin constant region of a CD3 binding polypeptide of the present disclosure may be a wild type immunoglobulin CH3 domain or an altered immunoglobulin CH3 domain thereof from certain immunoglobulin classes or subclasses (e.g., IgG1, IgG2, IgG3, IgG4, IgA1, IgA2, IgD, IgE, IgM) of various species (including human, mouse, rat, and other mammals). In certain embodiments, a CH3 domain is a wild type human immunoglobulin CH3 domain, such as wild type CH3 domains of human IgG1, IgG2, IgG3, IgG4, IgA1, IgA2, IgD, IgE, or IgM as set forth in SEQ ID NOS:116, 208-210, 204-207, and 212, respectively of WO2011/090762 (said sequences incorporated by reference herein). In certain embodiments, the CH3 domain is a wild type human IgG1 CH3 domain as set forth in SEQ ID NO:116 of WO2011/090762 (said sequence incorporated by reference herein). In certain embodiments, a CH3 domain is an altered human immunoglobulin CH3 domain, such as an altered CH3 domain based on or derived from a wild-type CH3 domain of human IgG1, IgG2, IgG3, IgG4, IgA1, IgA2, IgD, IgE, or IgM antibodies. For example, an altered CH3 domain may be a human IgG1 CH3 domain with one or two mutations at positions H433 and N434 (positions are numbered according to EU numbering). The mutations in such positions may be involved in complement fixation. In certain other embodiments, an altered CH3 domain may be a human IgG1 CH3 domain but with one or two amino acid substitutions at position F405 or Y407. The amino acids at such positions are involved in interacting with another CH3 domain. In certain embodiments, an altered CH3 domain may be an altered human IgG1 CH3 domain with its last lysine deleted. The sequence of this altered CH3 domain is set forth in SEQ ID NO:761 of WO2011/090762 (said sequence incorporated by reference herein).

In certain embodiments, CD3 binding polypeptides forming a polypeptide heterodimer comprise a CH3 pair that comprises so called "knobs-into-holes" mutations (see, Marvin and Zhu, Acta Pharmacologica Sinica 26:649-58, 2005; Ridgway et al., Protein Engineering 9:617-21, 1966). More specifically, mutations may be introduced into each of the two CH3 domains of each polypeptide chain so that the steric complementarity required for CH3/CH3 association obligates these two CH3 domains to pair with each other. For example, a CH3 domain in one single chain polypeptide of a polypeptide heterodimer may contain a T366W mutation (a "knob" mutation, which substitutes a small amino acid with a larger one), and a CH3 domain in the other single chain polypeptide of the polypeptide heterodimer may contain a Y407A mutation (a "hole" mutation, which substitutes a large amino acid with a smaller one). Other exemplary knobs-into-holes mutations include (1) a T366Y mutation in one CH3 domain and a Y407T in the other CH3 domain, and (2) a T366W mutation in one CH3 domain and T366S, L368A and Y407V mutations in the other CH3 domain.

The CH4 domain that may form an immunoglobulin constant region of CD3 binding polypeptides of the present disclosure may be a wild type immunoglobulin CH4 domain or an altered immunoglobulin CH4 domain thereof from IgE or IgM molecules. In certain embodiments, the CH4 domain is a wild type human immunoglobulin CH4 domain, such as wild type CH4 domains of human IgE and IgM molecules as set forth in SEQ ID NOS:213 and 214, respectively, of WO2011/090762 (said sequences incorporated by reference herein). In certain embodiments, a CH4 domain is an altered human immunoglobulin CH4 domain, such as an altered CH4 domain based on or derived from a CH4 domain of human IgE or IgM molecules, which have mutations that increase or decrease an immunological activity known to be associated with an IgE or IgM Fc region.

In certain embodiments, an immunoglobulin constant region of CD3 binding polypeptides of the present disclosure comprises a combination of CH2, CH3 or CH4 domains (i.e., more than one constant region domain selected from CH2, CH3 and CH4). For example, the immunoglobulin constant sub-region may comprise CH2 and CH3 domains or CH3 and CH4 domains. In certain other embodiments, the immunoglobulin constant region may comprise two CH3 domains and no CH2 or CH4 domains (i.e., only two or more CH3). The multiple constant region domains that form an immunoglobulin constant sub-region may be based on or derived from the same immunoglobulin molecule, or the same class or subclass immunoglobulin molecules. In certain embodiments, the immunoglobulin constant sub-region is an IgG CH2CH3 (e.g., IgG1 CH2CH3, IgG2 CH2CH3, and IgG4 CH2CH3) and may be a human (e.g., human IgG1, IgG2, and IgG4) CH2CH3. For example, in certain embodiments, the immunoglobulin constant sub-region comprises (1) wild type human IgG1 CH2 and CH3 domains, (2) human IgG1 CH2 with N297A substitution (i.e., CH2 (N297A)) and wild type human IgG1 CH3, or (3) human IgG1 CH2(N297A) and an altered human IgG1 CH3 with the last lysine deleted.

Alternatively, the multiple constant region domains may be based on or derived from different immunoglobulin molecules, or different classes or subclasses immunoglobulin molecules. For example, in certain embodiments, an immunoglobulin constant sub-region comprises both human IgM CH3 domain and human IgG1 CH3 domain. The multiple constant region domains that form an immunoglobulin constant sub-region may be directly linked together or may be linked to each other via one or more (e.g., about 2-10) amino acids.

Exemplary immunoglobulin constant sub-regions are set forth in SEQ ID NOS:305-309, 321, 323, 341, 342, and 762 of WO2011/090762 (said sequences incorporated by reference herein).

In certain embodiments, the immunoglobulin constant regions of both CD3 binding polypeptide chains of a homodimer or heterodimer are identical to each other. In certain other embodiments, the immunoglobulin constant sub-region of one polypeptide chain of a heterodimeric protein is different from the immunoglobulin constant sub-region of the other polypeptide chain of the heterodimer. For example, one immunoglobulin constant sub-region of a heterodimeric protein may contain a CH3 domain with a "knob" mutation, whereas the other immunoglobulin constant sub-region of the heterodimeric protein may contain a CH3 domain with a "hole" mutation.

Some embodiments of the invention involve using bispecific or multispecific binding molecules that (i) target a TCR complex (e.g., CD3) on human T-cells and (ii) a cell surface protein, e.g., to redirect T-cell cytotoxicity towards the cell with the cell surface protein, e.g., towards a tumor cell expressing a tumor antigen for the treatment of cancer.

In certain embodiments, a CD3 binding protein may comprise one or more additional binding domains (e.g., a second binding domain) that bind a target other than CD3. These other target molecules may comprise, for example, a tumor associated antigen. In one embodiment of the invention, the one or more additional binding domains bind or interact with one or more of the following tumor antigens: RON, c-Met, CEACAM-6, PSMA, EpCAM, CEA, PCTA-1, STEAP-1, STEAP-2, PSCA, PSA, PAP, ALCAM (CD166), PECAM-1, EphA2, CD151, CA-125/MUC16, MUC-1, MAGE-1, TROP2, IGF1R, TGFBR2, GHRHR, GHR, IL-6R, gp130, TNFR2, OSMRβ, Patched-1, Frizzled, Robo1, LTβR, CD19, CD25, CD26, CD27, CD30, CD33, CD44, CD44v6, CD63, CD80, CD81, CD86, CD100, CD151, CXCR4, CCR5, HER-2/ErbB1, HER-3/ErbB3, HER-4/ErbB4, EGFR/ErbB1, EGFRvIII isoform, MUC2, MUC3, MUC4, $MUC5_{AC}$, $MUC5_{b}$, MUC7, βhCG, Lewis-Y, ganglioside GD3, 9-O-Acetyl-GD3, GM2, Globo H, fucosyl GM1, Poly SA, GD2, Carbonic anhydrase IX (MN/CA IX), Sonic Hedgehog (Shh), Wue-1, Plasma Cell Antigen, (membrane-bound) IgE, Melanoma Chondroitin Sulfate Proteoglycan (MCSP), CCR8, TNF-alpha precursor, mesothelin, A33 Antigen, Ly-6; desmoglein 4, E-cadherin neoepitope, Fetal Acetylcholine Receptor, CA19-9 marker, Muellerian Inhibitory Substance (MIS) Receptor type II, sTn (sialylated Tn antigen; TAG-72), FAP (fibroblast activation antigen), endosialin, LG, SAS, BCMA, TWEAKR/Fn14, FGFR4, VEGFR1, VEGFR2, SSX1, and SSX2.

In certain embodiments, the CD3 binding domain binds the TCR binding domain for recruitment of T-cells to target cells expressing a tumor antigen. In certain embodiments, a CD3 binding polypeptide may comprise a CD3 binding domain that specifically binds a TCR complex or a component thereof (e.g., TCRα, TCRβ, CD3γ, CD3δ, and CD3ε) and another binding domain that specifically binds to a tumor associated antigen.

PSMA is a highly restricted prostate-cancer-related cell membrane antigen. In prostate cancer cells, PSMA is expressed 1000-fold higher than on normal prostate epithelium (Su et al., *Cancer Res.* 1995 44:1441-1443). Expression of PSMA increases with prostate cancer progression and is typically highest in metastatic disease, hormone refractory cases, and higher-grade lesions (Israeli et al., *Cancer Res.* 1994, 54:1807-1811; Wright et al., *Urologic Oncology: Seminars and Original Investigations* 1995 1:18-28; Wright et al., *Urology* 1996 48:326-332; Sweat et al., *Urology* 1998 52:637-640). Additionally, PSMA is abundantly expressed on the neovasculature of a variety of other solid tumors, including bladder, pancreas, melanoma, lung and kidney cancers, but not on normal neovasculature (Chang et al., *Urology* 2001 57:801-805; Divgi et al., *Clin. Cancer Res.* 1998 4:2729-3279). Binding domains for targeting PSMA include, but are not limited to, those described in PCT Publication No. WO2012/145714, which is herein incorporated by reference in its entirety.

In some embodiments, a PSMA binding domain comprises an amino acid sequence that is at least 90%, at least 95% or 100% identical to an amino acid sequence selected from the group consisting of (i) amino acids 1-107 and 124-243 of SEQ ID NO:212; (ii) amino acids 1-107 and 124-243 of SEQ ID NO:226; or (iii) amino acids 1-107 and 124-243 of SEQ ID NO:216. In some embodiments, a protein or molecule of the invention comprises an amino acid sequence selected from the group consisting of SEQ ID NO:212, 214, 216 and 226. PSMA binding domains that can be used in accordance with the invention are also described in PCT Publication No. WO2012/145714 including PSMA binding domains comprising amino acid sequences SEQ ID NOs:19, 21, 30, 31, 34, or 35 of WO2012/145714 or comprises a VL chain comprising an amino acid sequence selected from the group consisting of SEQ ID NO:5 and 23 and a VH chain comprising an amino acid sequence selected from the group consisting of SEQ ID NO: 2, 25 and 27 of WO2012/145714.

RON (recepteur d'origine Nantaise, also known as MST1R) is a receptor-type protein tyrosine kinase that is essential to embryonic development and also plays an important role in inflammatory responses (Camp et al. Ann. Surg. Oncol. 12:273-281 (2005)). RON is mostly expressed in epithelial-derived cell types, and it has been suggested that RON, like a number of other receptor-type tyrosine kinases, may play a role in the progression of malignant epithelial cancers (Wang et al. Carcinogenesis 23:1291-1297 (2003)). Activation of RON initiates downstream signaling pathways that have been implicated in tumorigenic activities such as cell proliferation, inhibition of apoptosis, and cell motility. RON represents a therapeutic target for epithelial cancers, inter alia, because of its signaling properties and/or the overexpression of RON in colorectal, breast, ovarian, and pancreatic carcinomas.

Binding domains for targeting RON include, but are not limited to, those described in the Examples section and those described in PCT Publication WO2011/090761 which is herein incorporated by reference in its entirety. In some embodiments, an anti-RON binding domain comprises (a) a VL domain comprising i. a CDR1 amino acid sequence of SEQ ID NO:87, a CDR2 amino acid sequence of SEQ ID NO:88, and a CDR3 amino acid sequence of SEQ ID NO:89; or ii. a CDR1 amino acid sequence of SEQ ID NO:90, a CDR2 amino acid sequence of SEQ ID NO:91, and a CDR3 amino acid sequence of SEQ ID NO:92; or (b) a VH domain comprising i. a CDR1 amino acid sequence of SEQ ID NO:93, a CDR2 amino acid sequence of SEQ ID NO:94, and a CDR3 amino acid sequence of SEQ ID NO:95; or ii. a CDR1 amino acid sequence of SEQ ID NO:96, a CDR2 amino acid sequence of SEQ ID NO:97, and a CDR3 amino acid sequence of SEQ ID NO:98; or (c) a VL of (a) and a VH of (b). In one embodiment, the VL domain comprises an amino acid sequence of any one of SEQ ID NOS:99 or 100, and the VH domain comprises an amino acid sequence of any one of SEQ ID NOS:101, 102 and 103. In another embodiment, the VL and VH domains are humanized. In certain embodiments, the humanized VL comprises an amino acid sequence of any one of SEQ ID NOS:104, 105 and 106, and the humanized VH domain comprises an amino acid sequence of any one of SEQ ID NOS:107-111. In some embodiments, an anti-RON binding domain comprises a VL domain comprising an amino acid sequence of any one of SEQ ID NO:99 and 100, and a VH domain comprising an amino acid sequence of any one of SEQ ID NO:101, 102 and 103. In some embodiments, an anti-RON binding domain comprises a VL domain comprises an amino acid sequence of any one of SEQ ID NOS:104, 105, and 106, and a VH domain comprising an amino acid sequence of any one of SEQ ID NOS:107-111.

In some embodiments, a RON binding domain comprises an amino acid sequence that is at least 90%, 92%, 94%, 96%, 97%, 98%, 99% or 100% identical to SEQ ID NO:187 and/or comprises an amino acid sequence that is at least 90%, 92%, 94%, 96%, 97%, 98%, 99% or 100% identical to SEQ ID NO:188. In some embodiments, a RON binding domain comprises (i) SEQ ID NO:187, wherein amino acid 43 (alanine) is substituted with another amino acid, e.g., with lysine (A43K) or threonine (A43T), (ii) SEQ ID NO:188, wherein amino acid 38 (glutamine) and/or 113 (glutamine) is substituted with another amino acid, e.g., with glutamic acid and/or arginine such as Q38R and/or Q113E, or (iii) any combination thereof. In some embodiments, an anti-RON/anti-CD3 bispecific molecule comprises or consists of an amino acid sequence that is at least 90%, 92%, 94%, 96%, 97%, 98%, 99% or 100% identical to any one of SEQ ID NOs:186, 190, 192 or 194. In some embodiments, the invention provides a nucleic acid that encodes an anti-RON/anti-CD3 bispecific molecule, wherein the nucleic acid comprises a nucleotide sequence that is at least 90%, 92%, 94%, 96%, 97%, 98%, 99% or 100% identical to any one of SEQ ID NOs:185, 189, 191 or 193.

CD19 is found on the surface of B-cells including most malignant B cells. Targeting CD19 can be used to inhibit and treat B-cell related diseases, leukemias and lymphomas.

In some embodiments, a CD19 binding domain comprises an amino acid sequence that is at least 90%, 92%, 94%, 96%, 97%, 98%, 99% or 100% identical to amino acids 1-111 of SEQ ID NO:196 and/or comprises an amino acid sequence that is at least 90%, 92%, 94%, 96%, 97%, 98%, 99% or 100% identical to amino acids 128-251 of SEQ ID NO:196. In some embodiments, an anti-CD19/anti-CD3 bispecific molecule comprises or consists of an amino acid sequence that is at least 90%, 92%, 94%, 96%, 97%, 98%, 99% or 100% identical to any one of SEQ ID NOs:196, 198, 200, 202, 204 or 206. In some embodiments, the invention provides a nucleic acid that encodes an anti-CD19/anti-CD3 bispecific molecule, wherein the nucleic acid comprises a nucleotide sequence that is at least 90%, 92%, 94%, 96%, 97%, 98%, 99% or 100% identical to any one of SEQ ID NOs:195, 197, 199, 201, 203 or 206.

HER2 is also known as human ErbB2. Overexpression of HER2 (frequently but not uniformly due to gene amplification) has also been observed in breast cancers, ovarian cancers and other carcinomas including carcinomas of the stomach, endometrium, salivary gland, lung, kidney, colon, thyroid, pancreas and bladder. Binding domains for targeting HER2 include, but are not limited to, those described in PCT Publication WO2009/055074 which is herein incorporated by reference in its entirety.

In some embodiments, a CD3 binding polypeptide comprises an amino acid sequence that is at least 90%, at least 95% or 100% identical to SEQ ID NO: 57, 59, 61, 63, 65, 67, 69, 71, 186, 190, 192, 194, 196, 198, 200, 202, 204 or 206.

In some embodiments, a CD3 binding polypeptide is part of a heterodimer. In some embodiments, a heterodimer comprises a pair of single chain polypeptides wherein the single chain pair comprises amino acid sequences that are at least 90%, at least 95% or 100% identical to the pairs selected from SEQ ID NO:210 & 247, SEQ ID NO:210 & 218, SEQ ID NO:210 & 220, SEQ ID NO:208 & 249, SEQ ID NO:208 & 222, or SEQ ID NO:208 & 224, SEQ ID NO:212 & 218, SEQ ID NO:216 & 222, SEQ ID NO:228 & 226, or SEQ ID NO:214 & 218.

The invention also includes nucleic acids (e.g., DNA or RNA) encoding a CD3 binding polypeptide as described herein, or one or more polypeptide chains of a dimeric or heterodimeric CD3 binding protein as described herein. Nucleic acids of the invention include nucleic acids having a region that is substantially identical to a polynucleotide as provided in SEQ ID NOs: 5, 7, 9, 11, 13, 15, 17, 19, 27, 29, 31, 37 and 39 or nucleic acids comprising a coding region that codes for the same or a similar polypeptide. In certain embodiments, a nucleic acid in accordance with the present invention has at least 80%, typically at least about 90%, and more typically at least about 95% or at least about 98% identity to a polypeptide-encoding polynucleotide as provided in SEQ ID NOs: 5, 7, 9, 11, 13, 15, 17, 19, 27, 29, 31, 37 and 39. Nucleic acids of the invention also include complementary nucleic acids. In some instances, the sequences will be fully complementary (no mismatches) when aligned. In other instances, there may be up to about a 20% mismatch in the sequences. In some embodiments of the invention are provided nucleic acids encoding both first and second polypeptide chains of a heterodimeric CD3 binding protein of the invention. The nucleic acid sequences provided herein can be exploited using codon optimization, degenerate sequence, silent mutations, and other DNA techniques to optimize expression in a particular host, and the present invention encompasses such sequence modifications.

Polynucleotide molecules comprising a desired polynucleotide sequence are propagated by placing the molecule in a vector. The invention also includes expression vectors containing nucleic acids of the invention and/or that express polypeptides of the invention. Viral and non-viral vectors are used, including plasmids. The choice of plasmid will depend on the type of cell in which propagation is desired and the purpose of propagation. Certain vectors are useful for amplifying and making large amounts of the desired DNA sequence. Other vectors are suitable for expression in cells in culture. Still other vectors are suitable for transfer and expression in cells in a whole animal or person. The choice of appropriate vector is well within the skill of the art. Many such vectors are available commercially. The partial or full-length polynucleotide is inserted into a vector typically by means of DNA ligase attachment to a cleaved restriction enzyme site in the vector. Alternatively, the desired nucleotide sequence can be inserted by homologous recombination in vivo. Typically this is accomplished by attaching regions of homology to the vector on the flanks of the desired nucleotide sequence. Regions of homology are added by ligation of oligonucleotides, or by polymerase chain reaction using primers comprising both the region of homology and a portion of the desired nucleotide sequence, for example.

For expression, an expression cassette or system may be employed. To express a nucleic acid encoding a polypeptide disclosed herein, a nucleic acid molecule encoding the polypeptide, operably linked to regulatory sequences that control transcriptional expression in an expression vector, is introduced into a host cell. The invention includes host cells comprising a nucleic acid and/or expression vector of the invention, e.g., those that code for a polypeptide of the invention. In addition to transcriptional regulatory sequences, such as promoters and enhancers, expression vectors can include translational regulatory sequences and a marker gene which is suitable for selection of cells that carry the expression vector. The gene product encoded by a polynucleotide of the invention is expressed in any convenient expression system, including, for example, bacterial, yeast, insect, amphibian and mammalian systems. In the expression vector, the polypeptide-encoding polynucleotide is linked to a regulatory sequence as appropriate to obtain the desired expression properties. These can include promoters, enhancers, terminators, operators, repressors, and inducers. The promoters can be regulated (e.g., the promoter from the steroid inducible pIND vector (Invitrogen)) or constitutive (e.g., promoters from CMV, SV40, Elongation Factor, or LTR sequences). These are linked to the desired nucleotide sequence using the techniques described above for linkage to vectors. Any techniques known in the art can be used. Accordingly, the expression vector will generally provide a transcriptional and translational initiation region, which may be inducible or constitutive, where the coding region is operably linked under the transcriptional control of the transcriptional initiation region, and a transcriptional and translational termination region.

An expression cassette ("expression unit") may be introduced into a variety of vectors, e.g., plasmid, BAC, YAC, bacteriophage such as lambda, P1, M13, etc., plant or animal viral vectors (e.g., retroviral-based vectors, adenovirus vectors), and the like, where the vectors are normally characterized by the ability to provide selection of cells comprising the expression vectors. The vectors may provide for extrachromosomal maintenance, particularly as plasmids or viruses, or for integration into the host chromosome. Where extrachromosomal maintenance is desired, an origin sequence is provided for the replication of the plasmid, which may be low- or high copy-number. A wide variety of markers are available for selection, particularly those which protect against toxins, more particularly against antibiotics. The particular marker that is chosen is selected in accordance with the nature of the host, where in some cases, complementation may be employed with auxotrophic hosts. Introduction of the DNA construct may use any convenient method, including, e.g., conjugation, bacterial transformation, calcium-precipitated DNA, electroporation, fusion, transfection, infection with viral vectors, biolistics, and the like.

Accordingly, proteins for use within the present invention can be produced in genetically engineered host cells according to conventional techniques. Suitable host cells are those cell types that can be transformed or transfected with exogenous DNA and grown in culture, and include bacteria, fungal cells, and cultured higher eukaryotic cells (including cultured cells of multicellular organisms), particularly cultured mammalian cells. Techniques for manipulating cloned DNA molecules and introducing exogenous DNA into a variety of host cells are disclosed by Sambrook and Russell, *Molecular Cloning: A Laboratory Manual* (3rd ed., Cold Spring Harbor Laboratory Press, Cold Spring Harbor, N.Y., 2001), and Ausubel et al., *Short Protocols in Molecular Biology* (4th ed., John Wiley & Sons, 1999).

For example, for recombinant expression of a homodimeric CD3 binding protein comprising two identical CD3 binding polypeptide chains as described herein, an expression vector will generally include a nucleic acid segment encoding the CD3 binding polypeptide, operably linked to a promoter. For recombinant expression of a heterodimeric CD3 binding protein, comprising different first and second polypeptide chains, the first and second polypeptide chains may be co-expressed from separate vectors in the host cell for expression of the entire heterodimeric protein. Alternatively, for the expression of heterodimeric CD3 binding proteins, the first and second polypeptide chains are co-expressed from separate expression units in the same vector in the host cell for expression of the entire heterodimeric protein. The expression vector(s) are transferred to a host cell by conventional techniques, and the transfected cells are then cultured by conventional techniques to produce the encoded polypeptide(s) to produce the corresponding CD3 binding protein.

To direct a recombinant protein into the secretory pathway of a host cell, a secretory signal sequence (also known as a leader sequence) is provided in the expression vector. The secretory signal sequence may be that of the native form of the recombinant protein, or may be derived from another secreted protein or synthesized de novo. The secretory signal sequence is operably linked to the polypeptide-encoding DNA sequence, i.e., the two sequences are joined in the correct reading frame and positioned to direct the newly synthesized polypeptide into the secretory pathway of the host cell. Secretory signal sequences are commonly positioned 5' to the DNA sequence encoding the polypeptide of interest, although certain signal sequences may be positioned elsewhere in the DNA sequence of interest (see, e.g., Welch et al., U.S. Pat. No. 5,037,743; Holland et al., U.S. Pat. No. 5,143,830). In particular variations, a secretory signal sequence for use in accordance with the present invention has the amino acid sequence MEAPAQLLFLLLLWLPDTTG (SEQ ID NO:79).

Cultured mammalian cells are suitable hosts for production of recombinant proteins for use within the present invention. Methods for introducing exogenous DNA into mammalian host cells include calcium phosphate-mediated transfection (Wigler et al., *Cell* 14:725, 1978; Corsaro and Pearson, *Somatic Cell Genetics* 7:603, 1981: Graham and Van der Eb, *Virology* 52:456, 1973), electroporation (Neumann et al., *EMBO J.* 1:841-845, 1982), DEAE-dextran mediated transfection (Ausubel et al., supra), and liposome-mediated transfection (Hawley-Nelson et al., *Focus* 15:73, 1993; Ciccarone et al., Focus 15:80, 1993). The production of recombinant polypeptides in cultured mammalian cells is disclosed by, for example, Levinson et al., U.S. Pat. No. 4,713,339; Hagen et al., U.S. Pat. No. 4,784,950; Palmiter et al., U.S. Pat. No. 4,579,821; and Ringold, U.S. Pat. No. 4,656,134. Examples of suitable mammalian host cells include African green monkey kidney cells (Vero; ATCC CRL 1587), human embryonic kidney cells (293-HEK; ATCC CRL 1573), baby hamster kidney cells (BHK-21, BHK-570; ATCC CRL 8544, ATCC CRL 10314), canine kidney cells (MDCK; ATCC CCL 34), Chinese hamster ovary cells (CHO-K1; ATCC CCL61; CHO DG44; CHO DXB11 (Hyclone, Logan, Utah); see also, e.g., Chasin et al., *Som. Cell. Molec. Genet.* 12:555, 1986)), rat pituitary cells (GH1; ATCC CCL82), HeLa S3 cells (ATCC CCL2.2), rat hepatoma cells (H-4-II-E; ATCC CRL 1548) SV40-transformed monkey kidney cells (COS-1; ATCC CRL 1650) and murine embryonic cells (NIH-3T3; ATCC CRL 1658). Additional suitable cell lines are known in the art and available from public depositories such as the American Type Culture Collection, Manassas, Va. Strong transcription promoters can be used, such as promoters from SV-40 or cytomegalovirus. See, e.g., U.S. Pat. No. 4,956,288. Other suitable promoters include those from metallothionein genes (U.S. Pat. Nos. 4,579,821 and 4,601,978) and the adenovirus major late promoter.

Drug selection is generally used to select for cultured mammalian cells into which foreign DNA has been inserted. Such cells are commonly referred to as "transfectants." Cells that have been cultured in the presence of the selective agent and are able to pass the gene of interest to their progeny are referred to as "stable transfectants." Exemplary selectable markers include a gene encoding resistance to the antibiotic neomycin, which allows selection to be carried out in the presence of a neomycin-type drug, such as G-418 or the like; the gpt gene for xanthine-guanine phosphoribosyl transferase, which permits host cell growth in the presence of mycophenolic acid/xanthine; and markers that provide resistance to zeocin, bleomycin, blastocidin, and hygromycin (see, e.g., Gatignol et al., *Mol. Gen. Genet.* 207:342, 1987; Drocourt et al., *Nucl. Acids Res.* 18:4009, 1990). Selection systems can also be used to increase the expression level of the gene of interest, a process referred to as "amplification." Amplification is carried out by culturing transfectants in the presence of a low level of the selective agent and then increasing the amount of selective agent to select for cells that produce high levels of the products of the introduced genes. An exemplary amplifiable selectable marker is dihydrofolate reductase, which confers resistance to methotrexate. Other drug resistance genes (e.g., hygromycin resistance, multi-drug resistance, puromycin acetyltransferase) can also be used.

Other higher eukaryotic cells can also be used as hosts, including insect cells, plant cells and avian cells. The use of *Agrobacterium rhizogenes* as a vector for expressing genes in plant cells has been reviewed by Sinkar et al., *J. Biosci. (Bangalore)* 11:47-58, 1987. Transformation of insect cells and production of foreign polypeptides therein is disclosed by Guarino et al., U.S. Pat. No. 5,162,222 and WIPO publication WO 94/06463.

Insect cells can be infected with recombinant baculovirus, commonly derived from *Autographa californica* nuclear polyhedrosis virus (AcNPV). See King and Possee, *The Baculovirus Expression System: A Laboratory Guide* (Chapman & Hall, London); O'Reilly et al., *Baculovirus Expression Vectors: A Laboratory Manual* (Oxford University Press., New York 1994); and *Baculovirus Expression Protocols. Methods in Molecular Biology* (Richardson ed., Humana Press, Totowa, N.J., 1995). Recombinant baculovirus can also be produced through the use of a transposon-based system described by Luckow et al. (*J. Virol.* 67:4566-4579, 1993). This system, which utilizes transfer vectors, is commercially available in kit form (BAC-TO-BAC kit; Life Technologies, Gaithersburg, Md.). The transfer vector (e.g., PFASTBAC1; Life Technologies) contains a Tn7 transposon to move the DNA encoding the protein of interest into a baculovirus genome maintained in *E. coli* as a large plasmid called a "bacmid." See Hill-Perkins and Possee, *J. Gen. Virol.* 71:971-976, 1990; Bonning et al., *J. Gen. Virol.* 75:1551-1556, 1994; and Chazenbalk and Rapoport, *J. Biol. Chem.* 270:1543-1549, 1995. In addition, transfer vectors can include an in-frame fusion with DNA encoding a polypeptide extension or affinity tag as disclosed above. Using techniques known in the art, a transfer vector containing a protein-encoding DNA sequence is transformed into *E. coli* host cells, and the cells are screened for bacmids which contain an interrupted lacZ gene indicative of recombinant baculovirus. The bacmid DNA containing the recombinant baculovirus genome is isolated, using common techniques, and used to transfect *Spodoptera frugiperda* cells, such as Sf9 cells. Recombinant virus that expresses the protein or interest is subsequently produced. Recombinant viral stocks are made by methods commonly used in the art.

For protein production, the recombinant virus is used to infect host cells, typically a cell line derived from the fall armyworm, *Spodoptera frugiperda* (e.g., Sf9 or Sf21 cells) or *Trichoplusia ni* (e.g., HIGH FIVE cells; Invitrogen, Carlsbad, Calif.). See generally Glick and Pasternak, *Molecular Biotechnology, Principles & Applications of Recombinant DNA* (ASM Press, Washington, D.C., 1994). See also U.S. Pat. No. 5,300,435. Serum-free media are used to grow and maintain the cells. Suitable media formulations are known in the art and can be obtained from commercial suppliers. The cells are grown up from an inoculation density of approximately $2\text{-}5\times10^5$ cells to a density of $1\text{-}2\times10^6$ cells, at which time a recombinant viral stock is added at a multiplicity of infection (MOI) of 0.1 to 10, more typically near 3. Procedures used are generally described in available laboratory manuals (see, e.g., King and Possee, supra; O'Reilly et al., supra; Richardson, supra).

Fungal cells, including yeast cells, can also be used within the present invention. Yeast species of particular interest in this regard include *Saccharomyces cerevisiae, Pichia pastoris*, and *Pichia methanolica*. Methods for transforming *S. cerevisiae* cells with exogenous DNA and producing recombinant polypeptides therefrom are disclosed by, for example, Kawasaki, U.S. Pat. No. 4,599,311; Kawasaki et al., U.S. Pat. No. 4,931,373; Brake, U.S. Pat. No. 4,870,008; Welch et al., U.S. Pat. No. 5,037,743; and Murray et al., U.S. Pat. No. 4,845,075. Transformed cells are selected by phenotype determined by the selectable marker, commonly drug resistance or the ability to grow in the absence of a particular nutrient (e.g., leucine). An exemplary vector system for use in *Saccharomyces cerevisiae* is the POT1 vector system disclosed by Kawasaki et al. (U.S. Pat. No. 4,931,373), which allows transformed cells to be selected by growth in glucose-containing media. Suitable promoters and terminators for use in yeast include those from glycolytic enzyme genes (see, e.g., Kawasaki, U.S. Pat. No. 4,599,311; Kingsman et al., U.S. Pat. No. 4,615,974; and Bitter, U.S. Pat. No. 4,977,092) and alcohol dehydrogenase genes. See also U.S. Pat. Nos. 4,990,446; 5,063,154; 5,139,936; and 4,661,454. Transformation systems for other yeasts, including *Hansenula polymorpha, Schizosaccharomyces pombe, Kluyveromyces lactis, Kluyveromyces fragilis, Ustilago maydis, Pichia pastoris, Pichia methanolica, Pichia guillermondii*, and *Candida maltosa* are known in the art. See, e.g., Gleeson et al., *J. Gen. Microbiol.* 132:3459-3465, 1986; Cregg, U.S. Pat. No. 4,882,279; and Raymond et al., *Yeast* 14:11-23, 1998. *Aspergillus* cells may be utilized according to the methods of McKnight et al., U.S. Pat. No. 4,935,349. Methods for transforming *Acremonium chrysogenum* are disclosed by Sumino et al., U.S. Pat. No. 5,162,228. Methods for transforming *Neurospora* are disclosed by Lambowitz, U.S. Pat. No. 4,486,533. Production of recombinant proteins in *Pichia methanolica* is disclosed in U.S. Pat. Nos. 5,716,808; 5,736,383; 5,854,039; and 5,888,768.

Prokaryotic host cells, including strains of the bacteria *Escherichia coli, Bacillus*, and other genera are also useful host cells within the present invention. Techniques for transforming these hosts and expressing foreign DNA sequences cloned therein are well-known in the art (see, e.g., Sambrook and Russell, supra). When expressing a recombinant protein in bacteria such as *E. coli*, the protein may be retained in the cytoplasm, typically as insoluble granules, or may be directed to the periplasmic space by a bacterial secretion sequence. In the former case, the cells are lysed, and the granules are recovered and denatured using, for example, guanidine isothiocyanate or urea. The denatured protein can then be refolded and dimerized by diluting the denaturant, such as by dialysis against a solution of urea and a combination of reduced and oxidized glutathione, followed by dialysis against a buffered saline solution. In the alternative, the protein may be recovered from the cytoplasm in soluble form and isolated without the use of denaturants. The protein is recovered from the cell as an aqueous extract in, for example, phosphate buffered saline. To capture the protein of interest, the extract is applied directly to a chromatographic medium, such as an immobilized antibody or heparin-Sepharose column. Secreted proteins can be recovered from the periplasmic space in a soluble and functional form by disrupting the cells (by, for example, sonication or osmotic shock) to release the contents of the periplasmic space and recovering the protein, thereby obviating the need for denaturation and refolding. Antibodies, including single-chain antibodies, can be produced in bacterial host cells according to known methods. See, e.g., Bird et al., *Science* 242:423-426, 1988; Huston et al., *Proc. Natl. Acad. Sci. USA* 85:5879-5883, 1988; and Pantoliano et al., *Biochem.* 30:10117-10125, 1991.

Transformed or transfected host cells are cultured according to conventional procedures in a culture medium containing nutrients and other components required for the growth of the chosen host cells. A variety of suitable media, including defined media and complex media, are known in the art and generally include a carbon source, a nitrogen source, essential amino acids, vitamins and minerals. Media may also contain such components as growth factors or serum, as required. The growth medium will generally select for cells containing the exogenously added DNA by, for example, drug selection or deficiency in an essential nutrient which is complemented by the selectable marker carried on the expression vector or co-transfected into the host cell.

CD3 binding proteins can be purified by conventional protein purification methods, typically by a combination of chromatographic techniques. See generally *Affinity Chromatography: Principles & Methods* (Pharmacia LKB Biotechnology, Uppsala, Sweden, 1988); Scopes, *Protein Purification: Principles and Practice* (Springer-Verlag, New York 1994). Proteins comprising an immunoglobulin Fc region can be purified by affinity chromatography on immobilized protein A or protein G. Additional purification steps, such as gel filtration, can be used to obtain the desired level of purity or to provide for desalting, buffer exchange, and the like.

The invention also includes compositions comprising a CD3 binding polypeptide of the invention and a pharmaceutically acceptable carrier, diluent and/or excipient.

In one embodiment of the invention, a monospecific CD3 binding polypeptide is administering to a patient suffering from an autoimmune disease such as rheumatoid arthritis. In another embodiment of the invention, a monospecific CD3 binding polypeptide of the invention is administered to a subject about to undergo an organ transplant.

In another aspect, the present invention provides a method for treating a disorder characterized by overexpression of a tumor antigen, such as cancer. Generally, such methods include administering to a subject in need of such treatment a therapeutically effective amount of a CD3 binding protein comprising a second binding domain that binds the tumor antigen as described herein. In some embodiments, the CD3 binding protein induces redirected T-cell cytotoxicity (RTCC) against tumor antigen-expressing cells in the subject.

In certain variations of the method, the disorder is a cancer. In other variations, the disorder is an autoimmune disease. The invention also provides methods for treating cancer or an autoimmune disorder comprising administering a therapeutically effective amount of the compositions or CD3 binding polypeptides described herein to a patient in need thereof.

In each of the embodiments of the treatment methods described herein, the CD3 binding protein is delivered in a manner consistent with conventional methodologies associated with management of the disease or disorder for which treatment is sought. In accordance with the disclosure herein, an effective amount of the CD3 binding protein is administered to a subject in need of such treatment for a time and under conditions sufficient to prevent or treat the disease or disorder.

For administration, the CD3 binding protein is formulated as a pharmaceutical composition. A pharmaceutical composition comprising a CD3 binding protein can be formulated according to known methods to prepare pharmaceutically useful compositions, whereby the therapeutic molecule is combined in a mixture with a pharmaceutically acceptable carrier. A composition is said to be a "pharmaceutically acceptable carrier" if its administration can be tolerated by a recipient patient. Sterile phosphate-buffered saline is one example of a pharmaceutically acceptable carrier. Other suitable carriers are well-known to those in the art. (See, e.g., Gennaro (ed.), *Remington's Pharmaceutical Sciences* (Mack Publishing Company, 19th ed. 1995).) Formulations may further include one or more excipients, preservatives, solubilizers, buffering agents, albumin to prevent protein loss on vial surfaces, etc.

A pharmaceutical composition comprising a CD3 binding protein is administered to a subject in a therapeutically effective amount. According to the methods of the present invention, a CD3 binding protein may be administered to subjects by a variety of administration modes, including, for example, by intramuscular, subcutaneous, intravenous, intra-atrial, intra-articular, parenteral, intranasal, intrapulmonary, transdermal, intrapleural, intrathecal, and oral routes of administration. For prevention and treatment purposes, administration to a subject may be, e.g., in a single bolus delivery, via continuous delivery (e.g., continuous transdermal delivery) over an extended time period, or in a repeated administration protocol (e.g., on an hourly, daily, or weekly basis).

A "therapeutically effective amount (or dose)" or "effective amount (or dose)" of a molecule or composition is that amount that produces a statistically significant effect in amelioration of one or more symptoms of the disorder, such as a statistically significant reduction in disease progression or a statistically significant improvement in organ function. The exact dose will be determined by the clinician according to accepted standards, taking into account the nature and severity of the condition to be treated, patient traits, etc. Determination of dose is within the level of ordinary skill in the art. When referring to a combination, a therapeutically effective dose refers to combined amounts of the active ingredients that result in the therapeutic effect, whether administered serially or simultaneously (e.g., in the same formulation or concurrently in separate formulations).

Determination of effective dosages in this context is typically based on animal model studies followed up by human clinical trials and is guided by determining effective dosages and administration protocols that significantly reduce the occurrence or severity of the subject disorder in model subjects. Effective doses of the compositions of the present invention vary depending upon many different factors, including means of administration, target site, physiological state of the patient, whether the patient is human or an animal, other medications administered, whether treatment is prophylactic or therapeutic, as well as the specific activity of the composition itself and its ability to elicit the desired response in the individual. Usually, the patient is a human, but in some diseases, the patient can be a nonhuman mammal. Typically, dosage regimens are adjusted to provide an optimum therapeutic response, e.g., to optimize safety and efficacy.

EXAMPLES

Figure 2A:
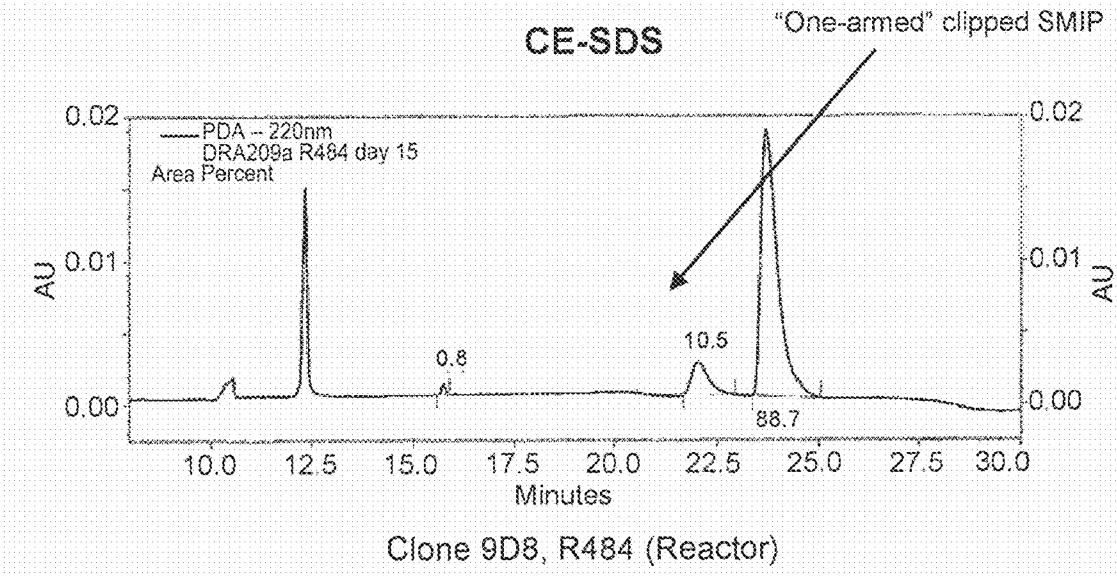
FIGS. 2A and 2B illustrate the clipping of CD3 binding SMIP polypeptides that contain a higher pI than the CD3 polypeptides of the invention.
Figure 2B:
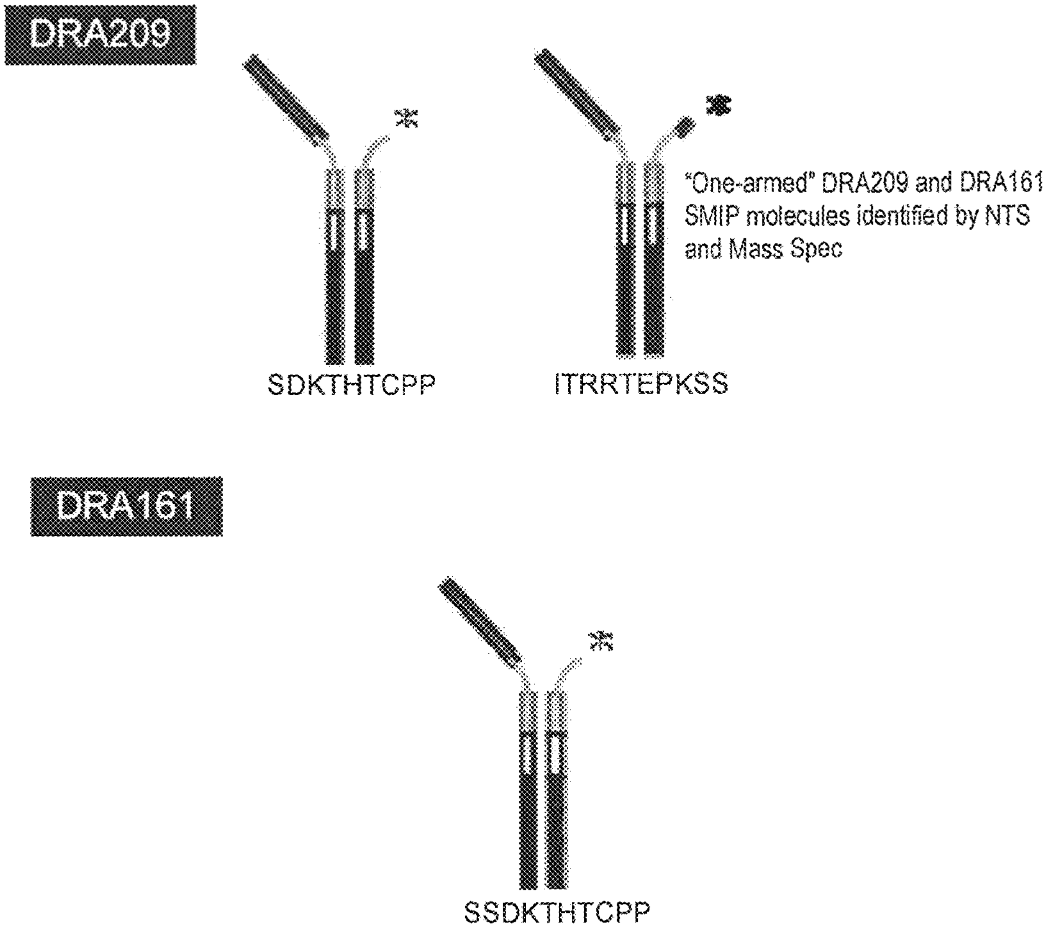

Example 1: Design and Construction of Anti-CD3 SMIP Molecules with Reduced Theoretical pI L1, L2, H1, H2 and H3 (see FIGS. 3 & 4) are heavy and light chains of humanized Cris-7 that were previously constructed and analyzed for binding and activity. H3L1 was used to make SMIP DRA209 (SEQ ID NOs: 3 and 4; IgG4 AA ADCC-CDC null Fc) and SMIP DRA161 (IgG4 AA N297A Fc). Although these constructs exhibit improved characteristics over OKT3 and other anti-CD3 therapeutics in the prior art, the constructs exhibit significantly shorter half-life, higher theoretical pI (see FIG. 1) and "clipping" at the binding domain or prehinge region when expressed in CHO cells (see FIGS. 2A and 2B) as compared to other SMIP molecules.

Anti-CD3 pI variants were designed to reduce the pI of the binding domain and/or prehinge region. To make the anti-CD3 pI variants, new heavy and light chains (L3, L4, H4, H5, and H6) were ordered and synthesized by Blue Heron. See Table 3 and FIGS. 3 and 4.

TABLE 3

CD3 Variable Heavy and Light Chains

| Name | SEQ ID NOs: |
|---|---|
| H1 | SEQ ID NO: 21 nucleic acid (na)<br>SEQ ID NO: 22 amino acid (aa) |
| H2 | SEQ ID NO: 23 (na)<br>SEQ ID NO: 24 (aa) |
| H3 | SEQ ID NO: 25 (na)<br>SEQ ID NO: 26 (aa) |
| H4 | SEQ ID NO: 27 (na)<br>SEQ ID NO: 28 (aa) |
| H5 | SEQ ID NO: 29 (na)<br>SEQ ID NO: 30 (aa) |
| H6 | SEQ ID NO: 31 (na)<br>SEQ ID NO: 32 (aa) |
| L1 | SEQ ID NO: 33 (na)<br>SEQ ID NO: 34 (aa) |
| L2 | SEQ ID NO: 35 (na)<br>SEQ ID NO: 36 (aa) |
| L3 | SEQ ID NO: 37 (na)<br>SEQ ID NO: 38 (aa) |
| L4 | SEQ ID NO: 39 (na)<br>SEQ ID NO: 40 (aa) |

Figure 5:
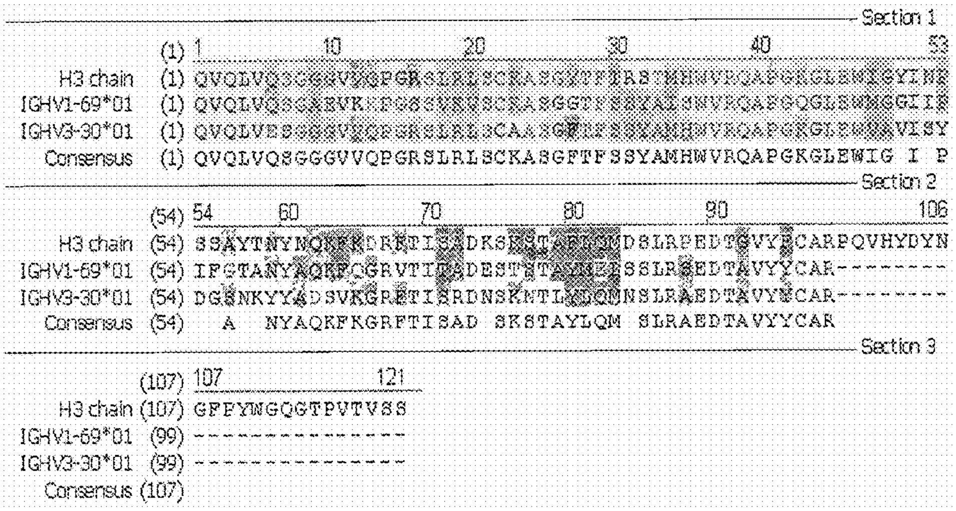
FIG. 5 is an amino acid sequence alignment of the H3 and germline sequences IGHV1-69*01 and IGHV3-30*01. The H3, IGHV1-69*01, IGHV3-30*01 and consensus sequences correspond to SEQ ID NOs: 26, 43, 44 and 331, respectively.

H4 has 2 point mutations compared to H3. One mutation replaced a positive charge residue (K to Q) while the other mutation introduced a negative charge (Q to E). Both changes were designed to reduce the pI of the protein (either by removing a positive charge or introducing a negative charge). The mutations were performed on the framework sequence to avoid loss of affinity and new residues introduced were verified to be present in the germline sequence at that position to avoid the risk of immunogenicity. By using the germline sequence as a guide to reduce the pI of an already humanized binding domain, amino acid substitutions can be made to add amino acids that are prevalent in the germline sequence. These amino acids may be at the same location in the germline sequence or a proximate position. See FIG. 5.

H5 was designed by "re-humanizing" the heavy chain sequence (as compared to DRA209 and DRA161) in such a way to create a lower pI as compared to DRA209 and DRA161. This was done by designing the heavy chain as compared to the VH1 framework of IGHV1-3*01 heavy chain germline sequence.

H6 was designed by "re-humanizing" the heavy chain sequence (as compared to DRA209 and DRA161) in such a way to create a lower pI as compared to DRA209 and DRA161. In other words, the starting sequence used to design H6 was the germline sequence rather than a previously humanized sequence. Specifically, this was done by designing the heavy chain using the VH3 framework of IGHV3-21*01 heavy chain sequence.

L3 has 6 points mutation compared to L1 where RW were mutated (i.e., replacing the positive charge residue, R to L) to LL (LL was used because LL is more common in the germline sequence than LW) and part of the J kappa (Jk) region (LQIT; SEQ ID NO:252) was replaced with Jk4 sequence (VEIK; SEQ ID NO:253). Jk4 is a better match Jk region based on the Cris-7 H_CDR3 sequence. See FIG. 6. Again, mutations were only performed in the framework region and new residues introduced were verified to be present at that position in the germline sequence to avoid the risk of immunogenicity.

L4 was designed by "re-humanizing" the light chain sequence (as compared to DRA209 and DRA161) in such a way to create a lower pI as compared to DRA209 and DRA161. L4 was re-humanized using the framework of Vk3 of IGKV3-11*01 light chain sequence as a guide.

All the new light and heavy chains are expected to have lower pI based on theoretical calculations. Vector NTI (Invitrogen) was used to help put together the sequences (the sequences are attached). The germline sequences were obtained from NCBI website (http://www.ncbi.nlm.nih.gov/igblast/).

Variants were constructed that comprised substituted amino acids in the prehinge region of SMIP molecules that are otherwise identical to DRA209 and DRA161. The prehinge region is a short amino acid sequence that connects the binding domain to the hinge region, e.g., can result from adding a restriction site into the encoding nucleotide sequence.

One variant made involved replacing the RRT sequence in the prehinge region of DRA209 with SSS by PCR mutagenesis. This was done intentionally to remove two positively charged residues (arginine). We have experimentally shown that this change translated to reduction in pI of the protein. This construct still had the H3L1 combination and was given the new name, DRA219. Aside from removing positive charged residues (two arginine), this SSS mutation also introduced an XhoI restriction site that allowed for easy assembly of the newer pI variant constructs.

Figure 7A:
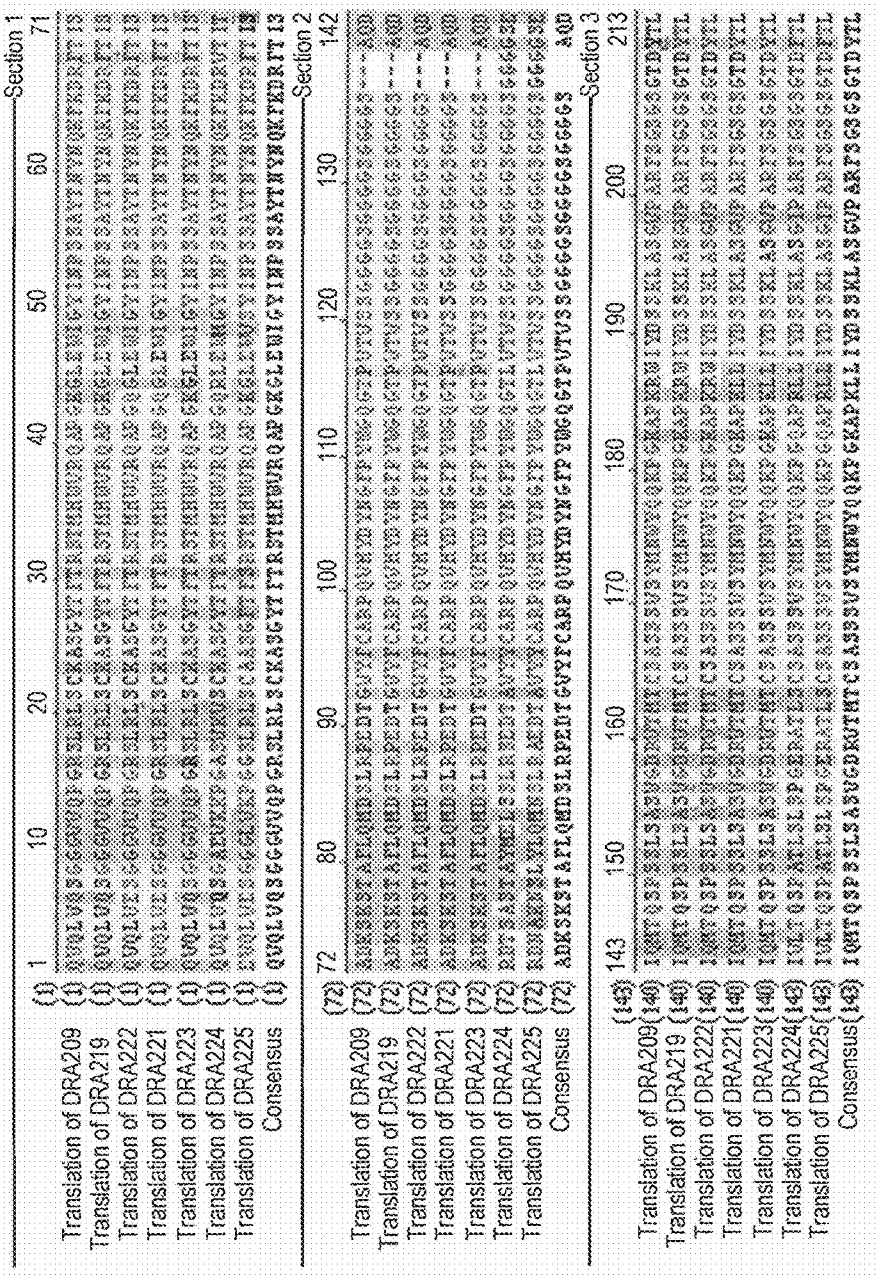
FIGS. 7A and 7B depicts an amino acid sequence alignment of various CD3 binding polypeptide SMIP molecules with reduced theoretical pI as compared to DRA209. The sequences listed for DRA209, DRA219, DRA222, DRA221, DRA223, DRA224, DRA225 and the consensus sequence correspond to amino acids 1-423 of SEQ ID NO:4, amino acids 1-423 of SEQ ID NO:6, amino acids 1-423 of SEQ ID NO:8, amino acids 1-423 of SEQ ID NO:10, amino acids 1-423 of SEQ ID NO:12, amino acids 1-426 of SEQ ID NO:14, amino acids 1-426 of SEQ ID NO:16 and SEQ ID NO:239, respectively.
Figure 7B:
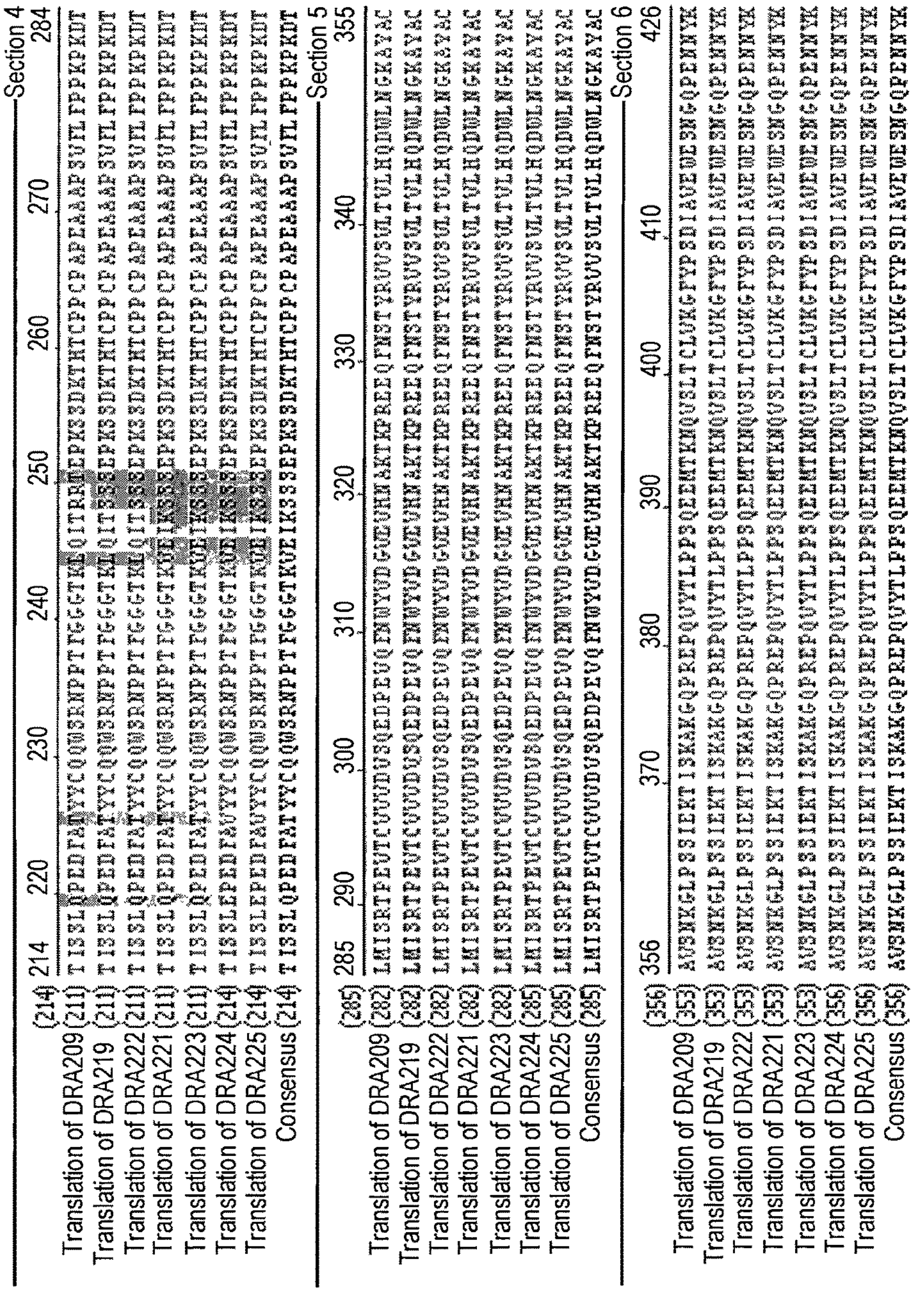

Using the same Fc tail as DRA209, the following combinations of H and L were used to construct SMIP constructs using standard molecular biology techniques: a) H4 L1 (with IgG4 AA ADCC-CDC null FC; also referred to herein as DRA222; SEQ ID NOs: 7 and 8), b) H4L3 (with IgG4 AA ADCC-CDC null Fc; also referred to herein as DRA221; SEQ ID NOs:9 and 10), c) H3L3 (with IgG4 AA ADCC-CDC null Fc; also referred to herein as DRA223; SEQ ID NOs: 11 and 12), d) H5L4 (with IgG4 AA ADCC-CDC null Fc; also referred to herein as DRA224; SEQ ID NOs: 13 and 14), and e) H6L4 (with IgG4 AA ADCC-CDC null Fc; also referred to herein as DRA225; SEQ ID NOs: 15 and 16). See FIGS. 7A and 7B.

All these constructs were transfected into HEK cells to generate protein for in vitro binding studies. All of the constructs expressed the desired protein except the DRA225 construct, which had no apparent expression. All of the other constructs were found (i) to bind CD3 with varying degrees (DRA222 having some of the best binding) and (ii) to have a lower pI than the parent molecule, DRA209. The measured pIs are found in Table 4.

TABLE 4

| Measured pIs | |
|---|---|
| Construct | Measured pI |
| DRA209 | 9.0 |
| DRA219 | 8.4 |
| DRA221 | 8.2 |
| DRA222 | 7.5 |
| DRA223 | 7.2 |
| DRA224 | 6.8 |

DRA219, DRA221, DRA222, DRA223 and DRA224 all inhibited human mixed lymphocyte reactions (MLR; data not shown) and the amount of inhibition correlated with their measured ability to bind CD3.

Figure 8:
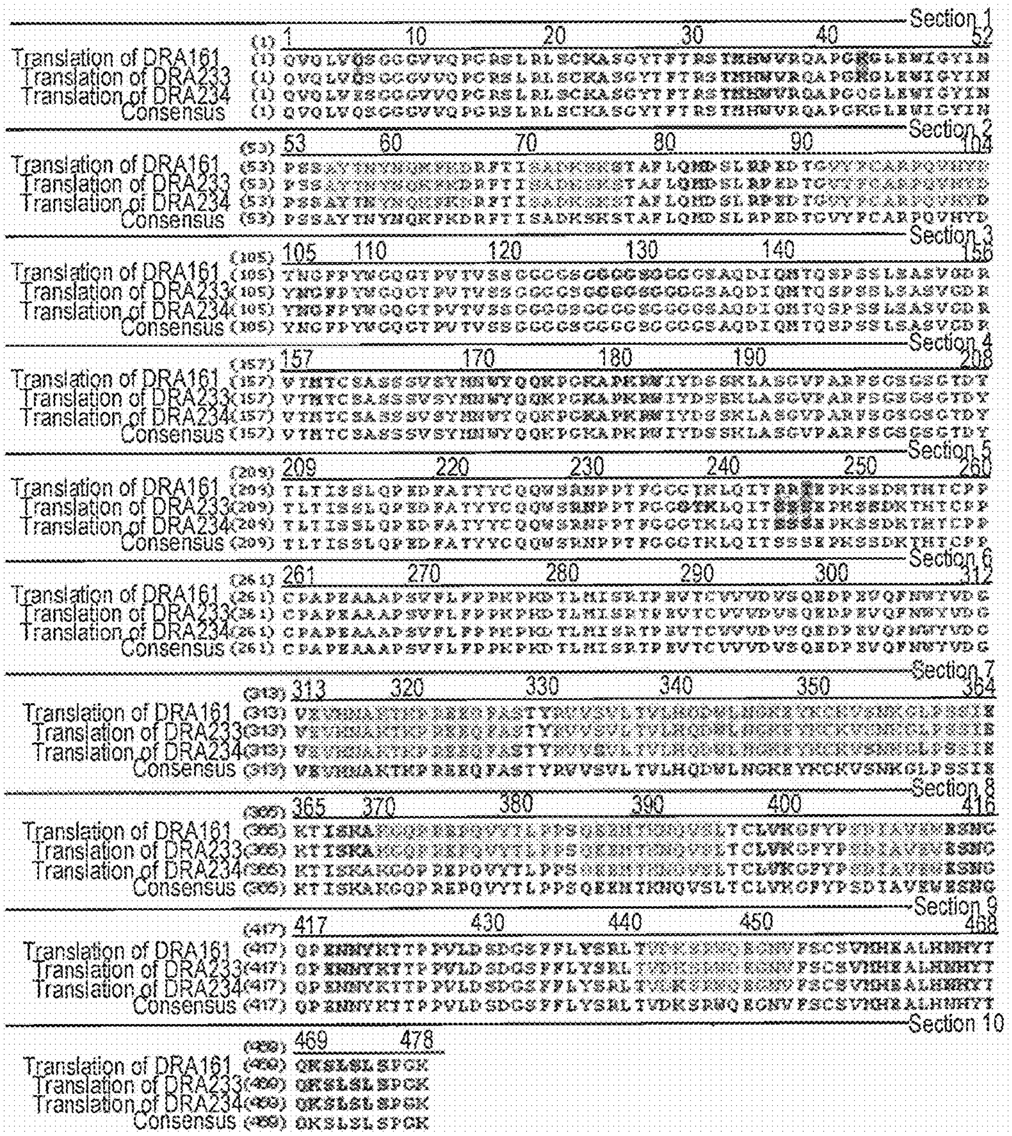
FIG. 8 is an amino acid sequence alignment of pI variants DRA233 and DRA234 compared to DRA161. The sequences listed for DRA161, DRA233, DRA234 and the consensus sequence correspond to SEQ ID NOs: 240, 18, 20 and 241, respectively.

DRA219 (H3 L1 IgG4 AA ADCC-CDC null FC; SEQ ID NOs: 5 and 6) and DRA222 (SEQ ID NOs: 7 and 8) both retained binding to CD3 and had a lower measured pI and were further cloned into the pEE12.4 vector which codes for a different Fc tail (IgG4 AA N297A) to generate two additional constructs—DRA233 (H3L1; SEQ ID NOs: 17 and 18) and DRA234 (H4L1; SEQ ID NOs: 19 and 20) respectively. Furthermore, DRA219 and DRA222 were cloned into pEE12.4 vector for expression in CHO and named as DRA228 and DRA229 respectively. Essentially DRA219 is equivalent to DRA228 and DRA222 is equivalent to DRA229. All the constructs (DRA228, DRA229, DRA233 and DRA234) were subsequently transfected into CHO cells to generate proteins for binding studies, protein characterization and PK studies. See FIG. 8.

Proteins were purified from cell supernatant by Protein A affinity chromatography using an AKTA Purifier HPLC system. Pre-packed POROS A columns (Life Technologies) were used for in vitro preparations and pre-packed MabSuRe Protein A columns (GE Healthcare) were used for in vivo material. Samples were loaded in the presence of PBS and eluted with citrate buffer. Eluents were neutralized with TRIS buffer.

Figure 9:
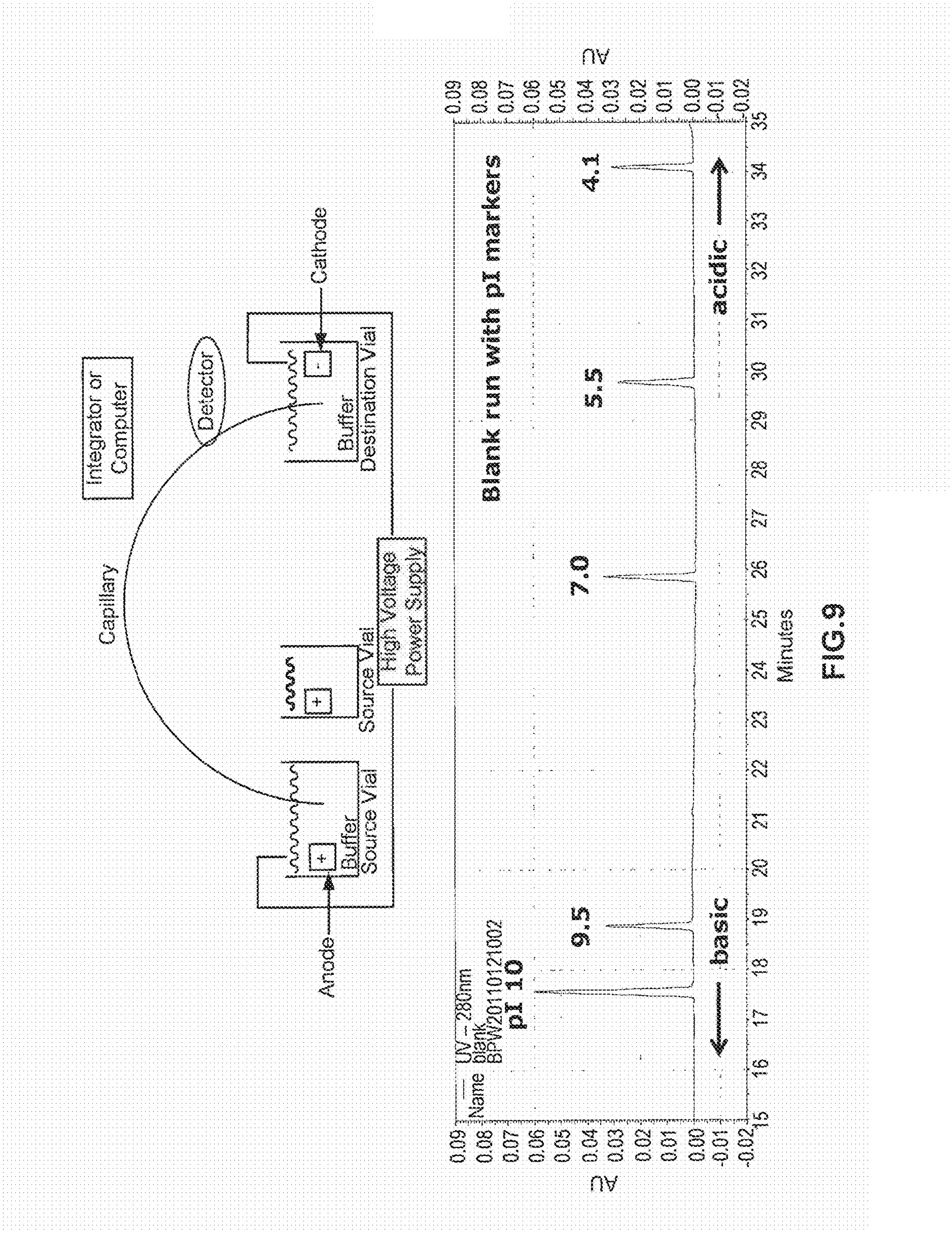
FIG. 9 is an illustration of how empirical pI values were determined.
Figure 10:
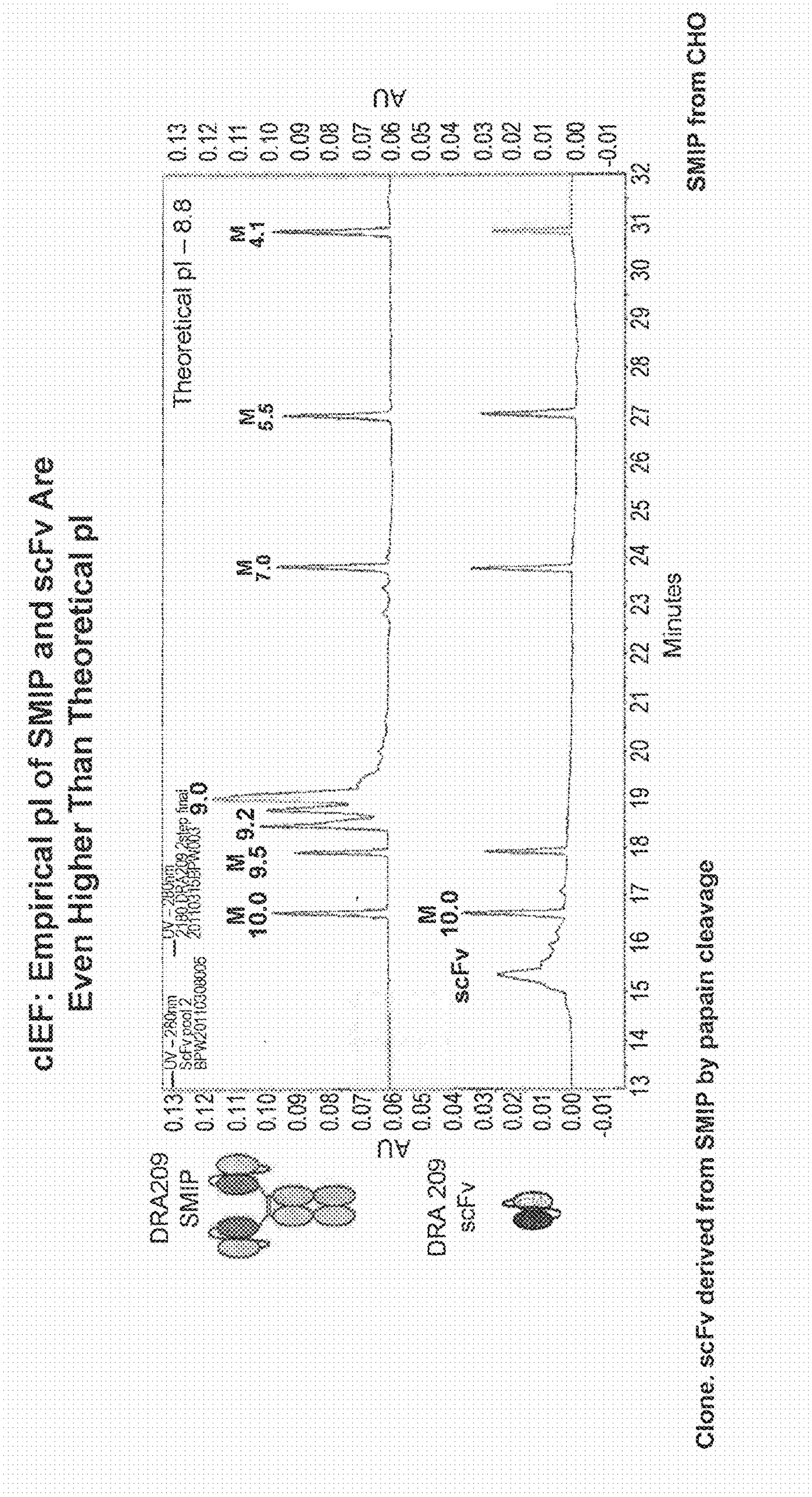
FIG. 10 is a graph showing the empirical pI of DRA209 SMIP and scFv.
Figure 11:
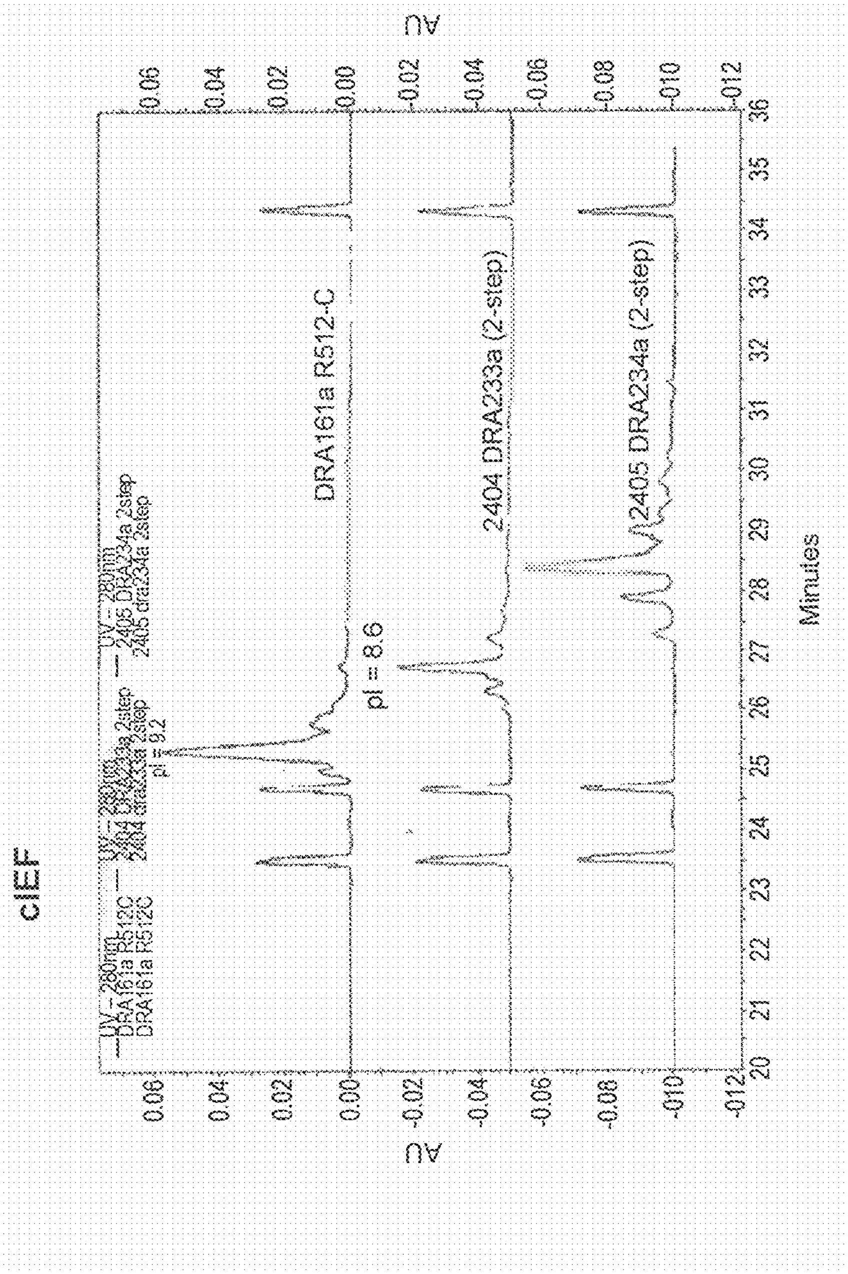
FIG. 11 is a graph showing the empirical pI of DRA161 SMIP compared to pI variants DRA233 and DRA234.

Capillary Isoelectric Focusing was performed on a Beckman PA 800 instrument and used to determine the isoelectric point (pI) of purified proteins. Analysis was performed according to standard Beckman cIEF protocol. Samples were prepared in a solution of 3M urea in cIEF gel (Beckman) supplemented with Pharmalyte 3-10 ampholytes (GE Healthcare), cathodic and anodic stabilizers, and synthetic peptide pI markers (Beckman). Samples were introduced into a neutral capillary (Beckman) and then focused by submerging the capillary inlet in anolyte solution, the outlet in catholyte solution, and applying a 25 kV electrical potential across the capillary for 15 minutes. After focusing, the sample was mobilized by chemical means to pass all separated components across a fixed wavelength detector measuring absorbance at 280 nm. The isoelectric point (pI) was calculated for all samples from a standard curve constructed of results for the synthetic peptide pI markers. See FIGS. 9-11. The constructs had the following measured pIs: DRA228=8.4; DRA229=7.5; DRA233=8.6; DRA234=8.0, whereas the DRA161=9.2 and DRA209=8.8. Therefore, all of the pI variants that were expressed had a lower pI than their respective parental constructs, DRA161 or DRA209.

Example 2: Anti-CD3 SMIP Molecules Bind T-Cells

Figure 12:
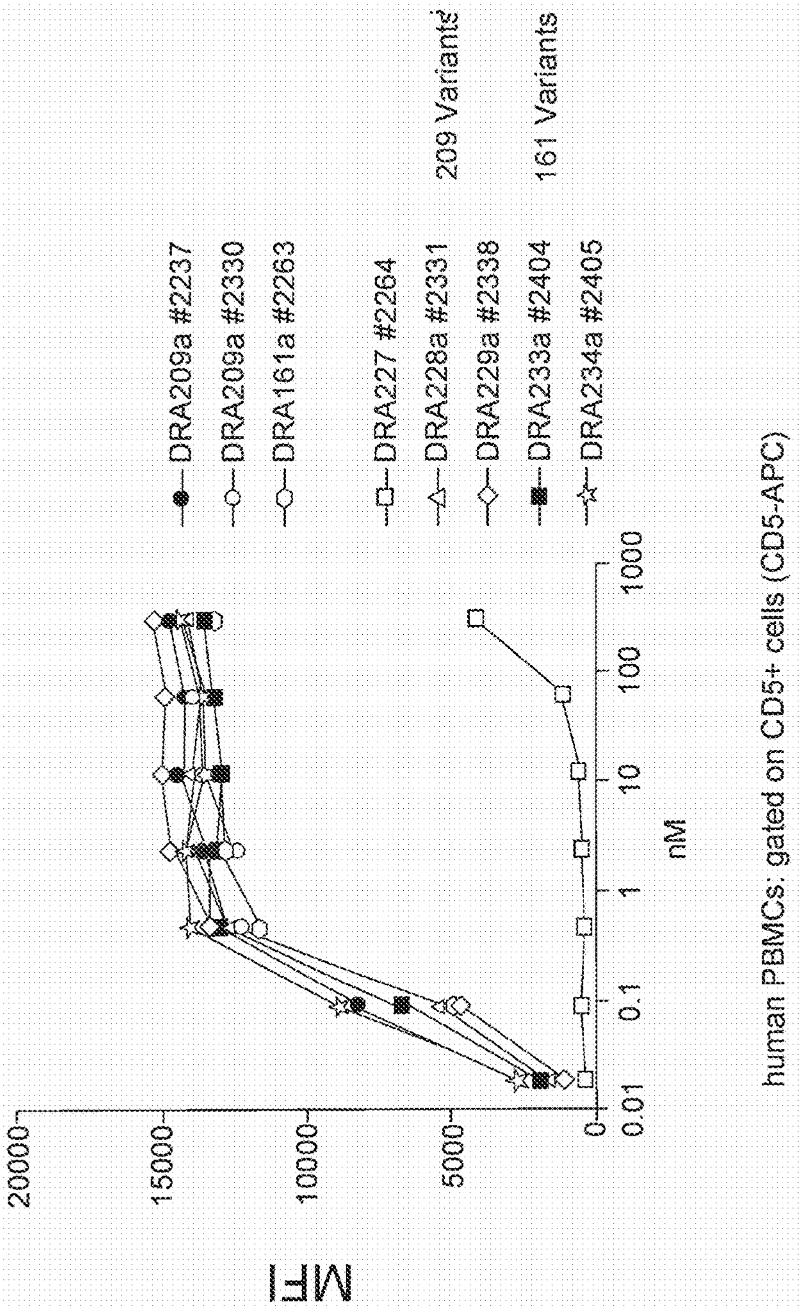
FIG. 12 is a graph showing that the SMIP pI variants bound to T-cells the same as DRA209 and DRA161 with the exception of DRA227. DRA227 SMIP is used as a control and it does not contain a CD3 or T-cell binding domain. The letter "a" following each molecule designation indicates that the particular molecule was produced in CHO cells and the four digit number is the lot number.

Human peripheral blood mononuclear cells (PBMC) were isolated from fresh whole blood using standard density gradient centrifugation and washed three times in PBS with 0.2% BSA. Cells were plated in 96-well plates U-bottom plates at 200,000 PBMCs/well and labeled with 50 ul of antibodies at the nM concentrations as indicated in FIG. 12 for 30 min on ice. Plates were washed three times and labeled for 30 min with 50 ul of an antibody cocktail containing optimal concentrations of anti-CD5-APC plus F(ab')2 goat anti-hu IgG Fc-PE. Plates were washed three times and fixed in 120 ul of 1% paraformaldehyde in PBS, at 4 C overnight. All antibody incubations and washes were performed on ice, with cold PBS, 0.2% BSA, 2 nM EDTA. Samples were analyzed by flow cytometry using a BD LSRII analyzer. Sixty microliters were collected from each well. Collected samples were analyzed using Flowjo software by gating on T-cells (FCS vs SSC, CD5+ cells). The mean fluorescence intensity (MFI) on the PE channel is shown in the graph. The DRA227 SMIP was used only as a control and does not contain a CD3 or T-cell binding domain and was not modified to reduce pI. See FIG. 12. All the tested pI variants bound to CD3 and DRA228 and DRA229 retained binding activity very similar to their parental constructs.

Example 3: Anti-CD3 SMIP Molecules with Reduced pI Express Better in Cho Cells

Size Exclusion Chromatography:

Size exclusion chromatography was used to assess the high-molecular weight aggregate content of purified proteins. The HPLC system was an Agilent 1200 series equipped with a quaternary pump, solvent degasser, DAD, and temperature-controlled autosampler. A Tosoh TSKgel G3000SWxl column equilibrated in a running buffer of 200 mM potassium phosphate and 250 mM potassium chloride at pH 7.2 was used for chromatographic separation. Solvent flow rate was 1 mL/min and sample injection mass was 50 μg, Column effluent was monitored with the Agilent DAD detector at a wavelength of 280 nm.

Figure 13:
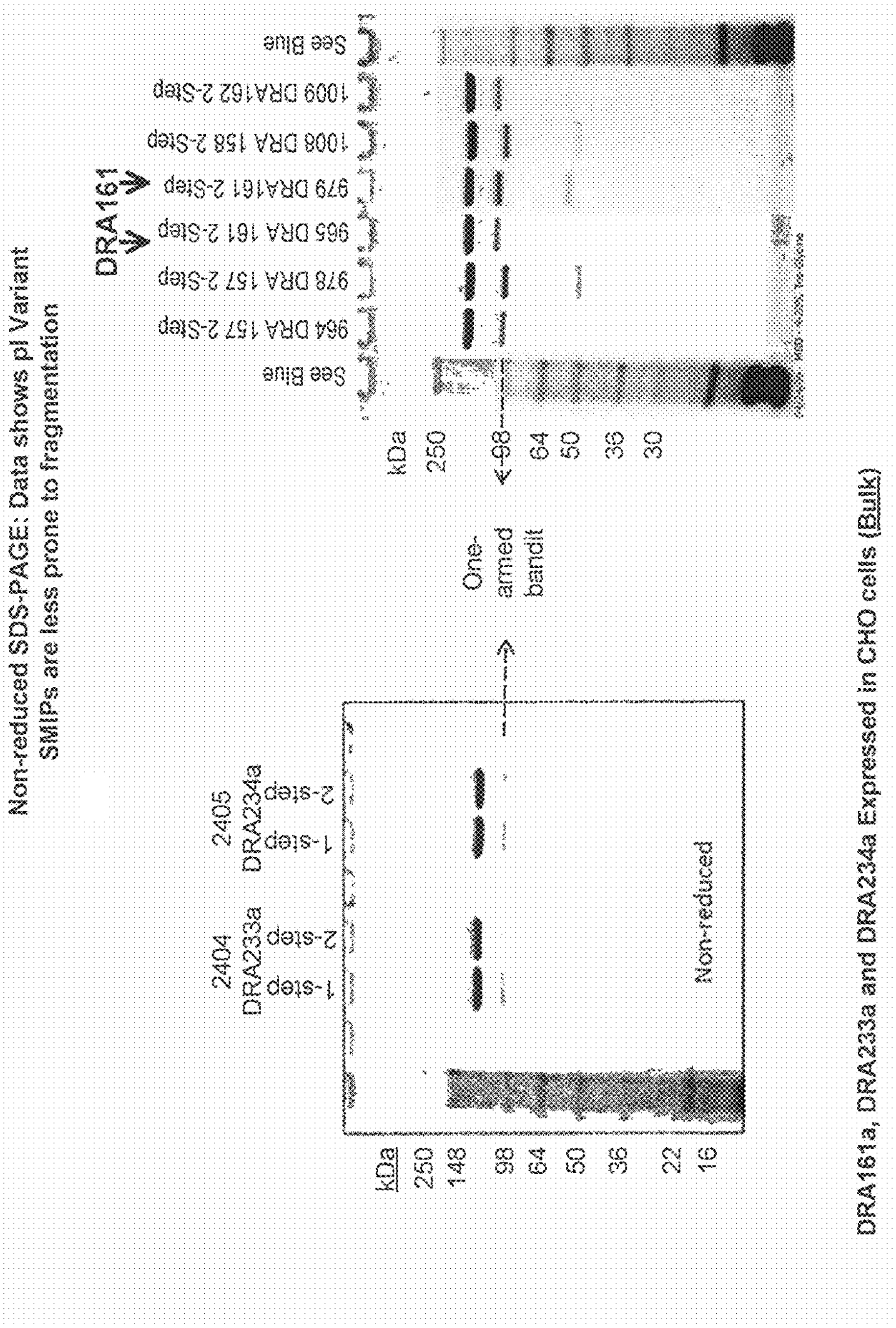
FIG. 13 depicts images of non-reduced SDS-PAGE showing that the CD3 binding SMIP constructs DRA233 and DRA234 are less prone to fragmentation than SMIP DRA161 (which shares the same VH and VL as DRA209).
Figure 14:
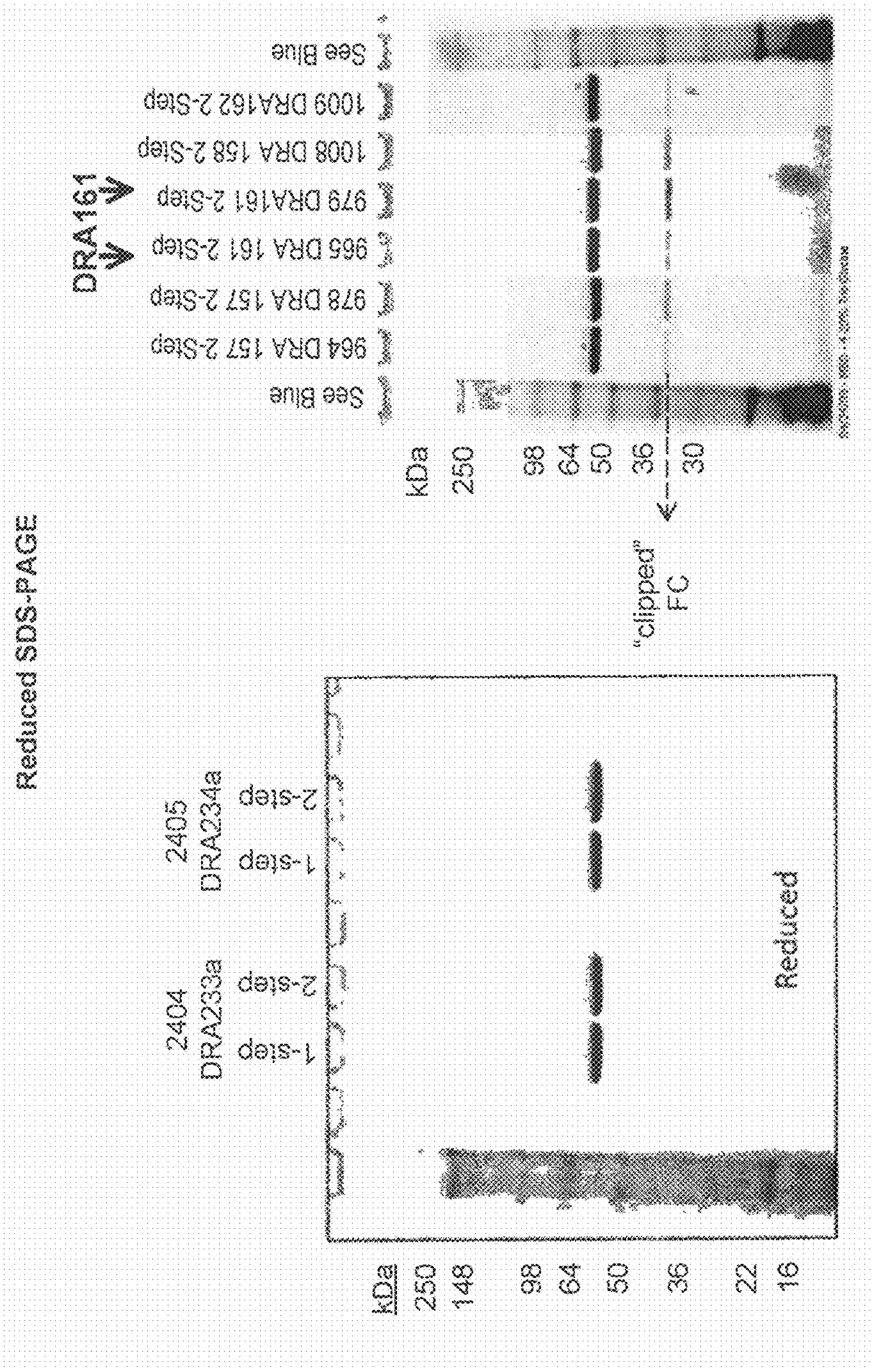
FIG. 14 depicts images of reduced SDS-PAGE showing that the CD3 binding SMIP constructs DRA233 and DRA234 are less prone to fragmentation than SMIP DRA161 (which shares the same VH and VL as DRA209).

SDS-PAGE:

Denaturing sodium dodecyl sulfate polyacrylamide gel electrophoresis (SDS-PAGE) was used to assess the integrity of purified proteins. Samples were prepared with Novex sample buffer (Invitrogen) and heated at 85° C. for 3 minutes to ensure full denaturation prior to loading into 4-20% Novex Tris-Glycine gels (Invitrogen). Samples were optionally reduced by adding Novex reducing agent prior to the heating step. Proteins were mobilized and separated by applying 125V across the gels for 110 minutes in an electrophoresis chamber filled with Tris-Glycine buffer (Invitrogen, from 10× stock). Protein bands were visualized by staining with SimplyBlue Safe Stain (Invitrogen). See FIGS. 13-14. The tested pI variants demonstrated reduced clipping as compared to their parental molecule, DRA161.

Figure 15:
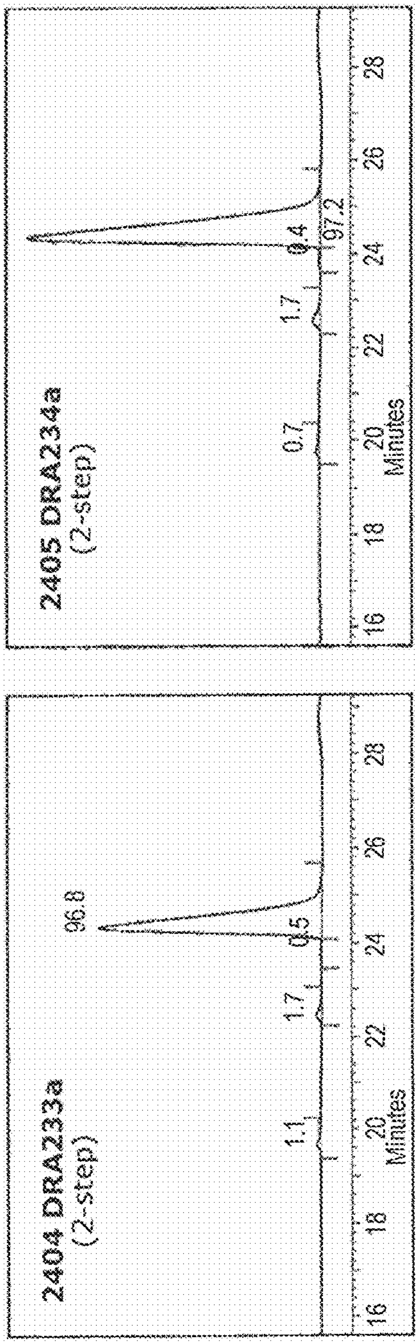
FIG. 15 are graphs and a table showing that pI variants DRA233 and DRA234 are predominately expressed intact (e.g., no clipping).
Figure 16:
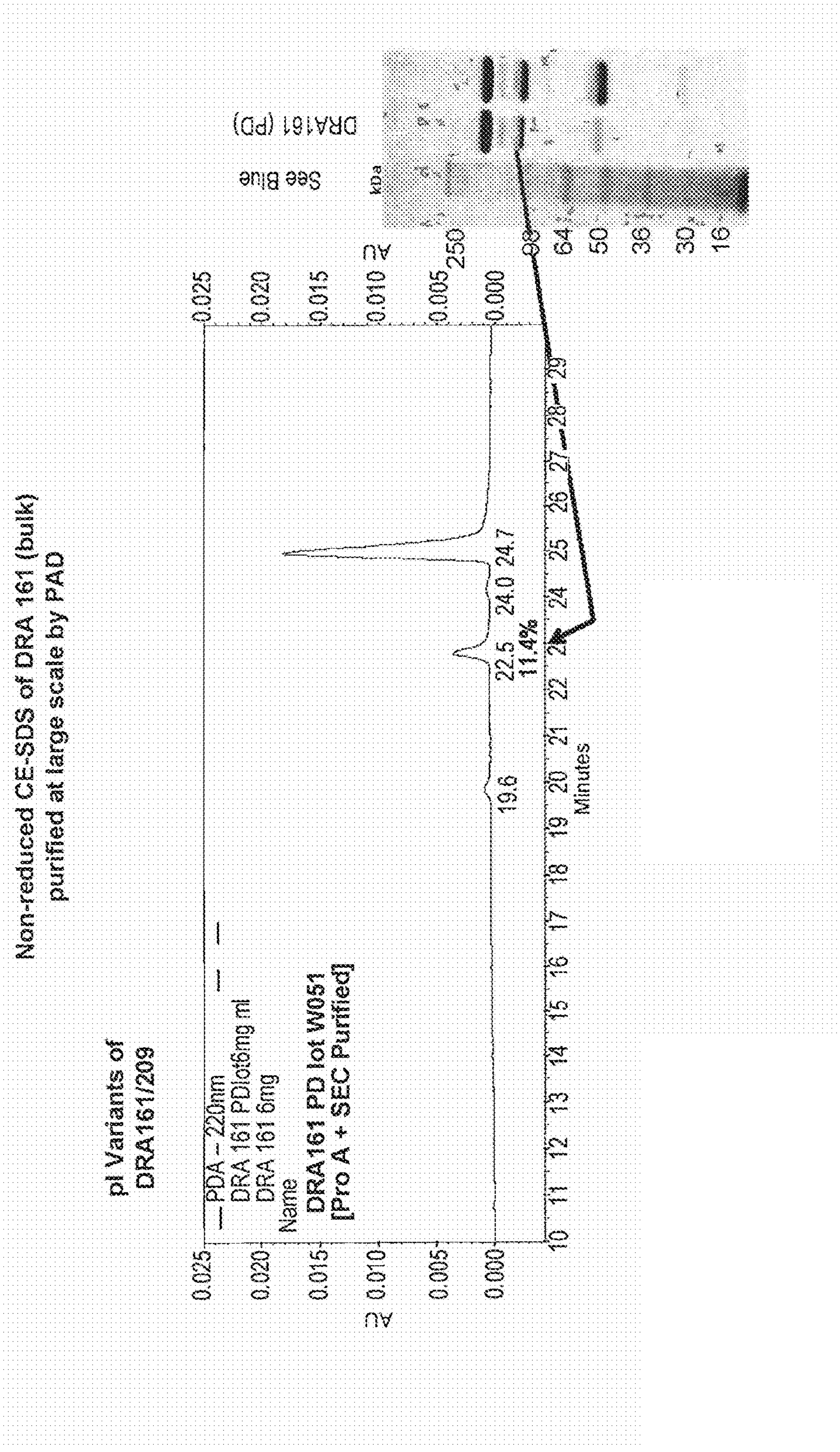
FIG. 16 are images showing non-reduced CE-SDS of DRA161 (purified).

CE-SDS:

Capillary Electrophoresis in SDS was performed on a Beckman PA 800 instrument and used to quantify the low molecular weight clip content of purified proteins. Samples were prepared at a 1 mg/mL concentration in 50% SDS sample buffer (Beckman) and heated at 85° C. for 3 minutes to ensure full denaturation prior to analysis. Samples were electrokinetically injected (10 kV for 20 s) into a bare-fused silica capillary filled with SDS gel buffer (Beckman) and separated by applying a voltage of 15 kV across the capillary (reverse polarity) for 30 minutes, Absorbance at 220 nm and 280 nm was measured at the detector window. See FIGS. 15-16. This showed that the quality of protein of the pI variants was better than the parental molecule, e.g., because of lower apparent proteolysis, sometimes referred to herein as "clipping".

Example 4: Anti-CD3 SMIP pI Variant Molecules Exhibit Increased Half-Life

Female BALB/c mice were injected intravenously (IV) at time 0 with 200 μL of PBS containing 200 μg of DRA234 or DRA233. Three mice per group were injected for each time point. Anesthetized mice were exsanguinated via cardiac puncture at the indicted time points after injection, and serum was collected as described below. Serum concentrations of DRA234 and DRA233 were determined using enzyme linked immunosorbent assays (ELISA). Pharmacokinetic disposition parameters for each protein were estimated by non-compartmental analysis using WinNonlin™ Professional software (v5.3) and applying the precompiled model 201 for IV bolus administration and sparse sampling.

Figure 17:
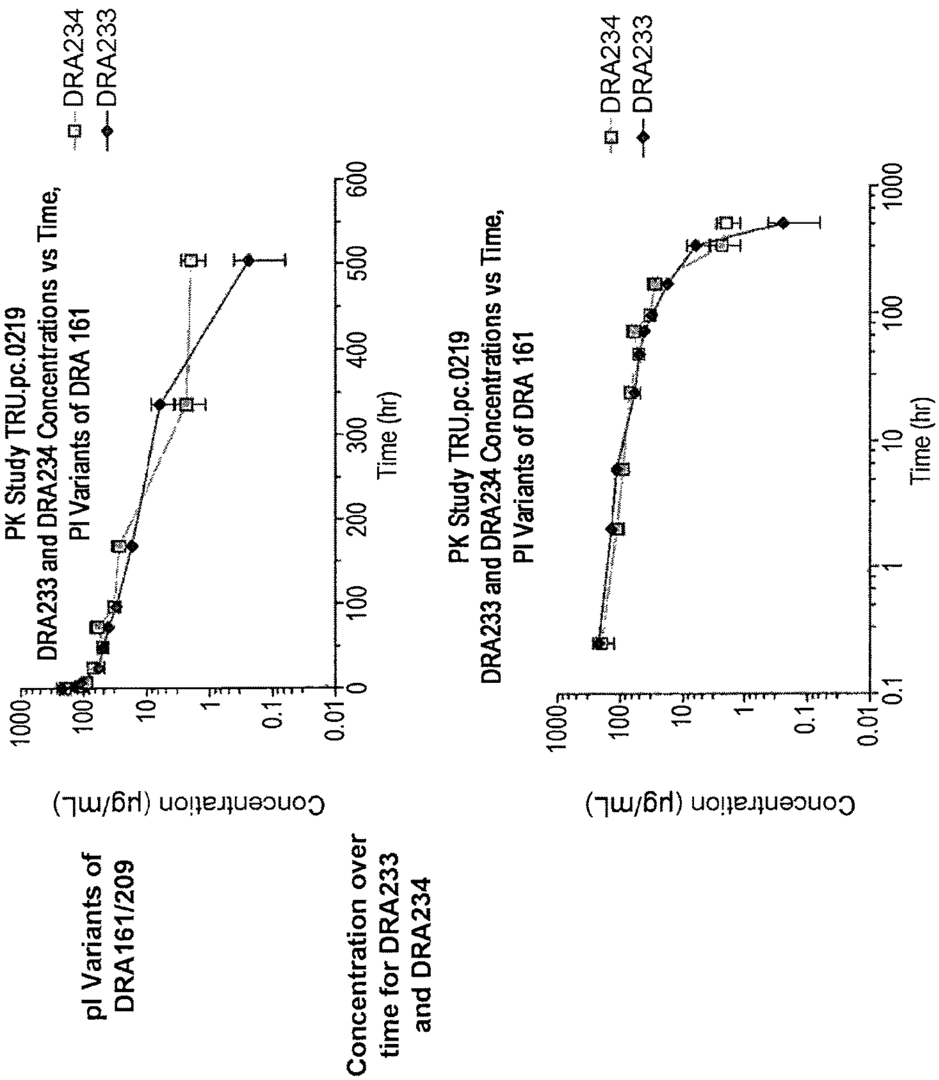
FIG. 17 shows data of a PK study of DRA234 and DRA233.

At time 0, mice were injected IV with 200 μL of PBS containing 200 μg (~10 mg/kg) of DRA233 or DRA234. Three mice per group were injected for each time point. Anesthetized mice were exsanguinated via cardiac puncture and serum was collected at t=15 minutes, and 2, 6, 24, 48, 72, 96, 168, 336 and 504 hours after injection. Serum concentrations for each protein were determined using a specific sandwich ELISA. Results are expressed as mean serum concentration (in μg/mL)±SD over time. Data are shown in linear (A) and log (B) format. See FIG. 17.

Anti-drug antibodies (ADA) were detected using a sandwich ELISA, with DRA161 (original form of DRA233 and DRA234) coated on plates to capture ADA, and anti-mouse IgG (H&L) HRP to detect bound ADA. Bound complexes were measured using a peroxidase substrate, with results being read on a fluorescent plate reader. Results were expressed as mean fluorescent units (FU) vs. serum dilution. Levels of ADA were clearly seen at 504 hours for DRA233, with possible low levels starting at 336 hours; however there did not appear to be ADA in any of the DRA234 samples. (Data not shown).

Figure 18:
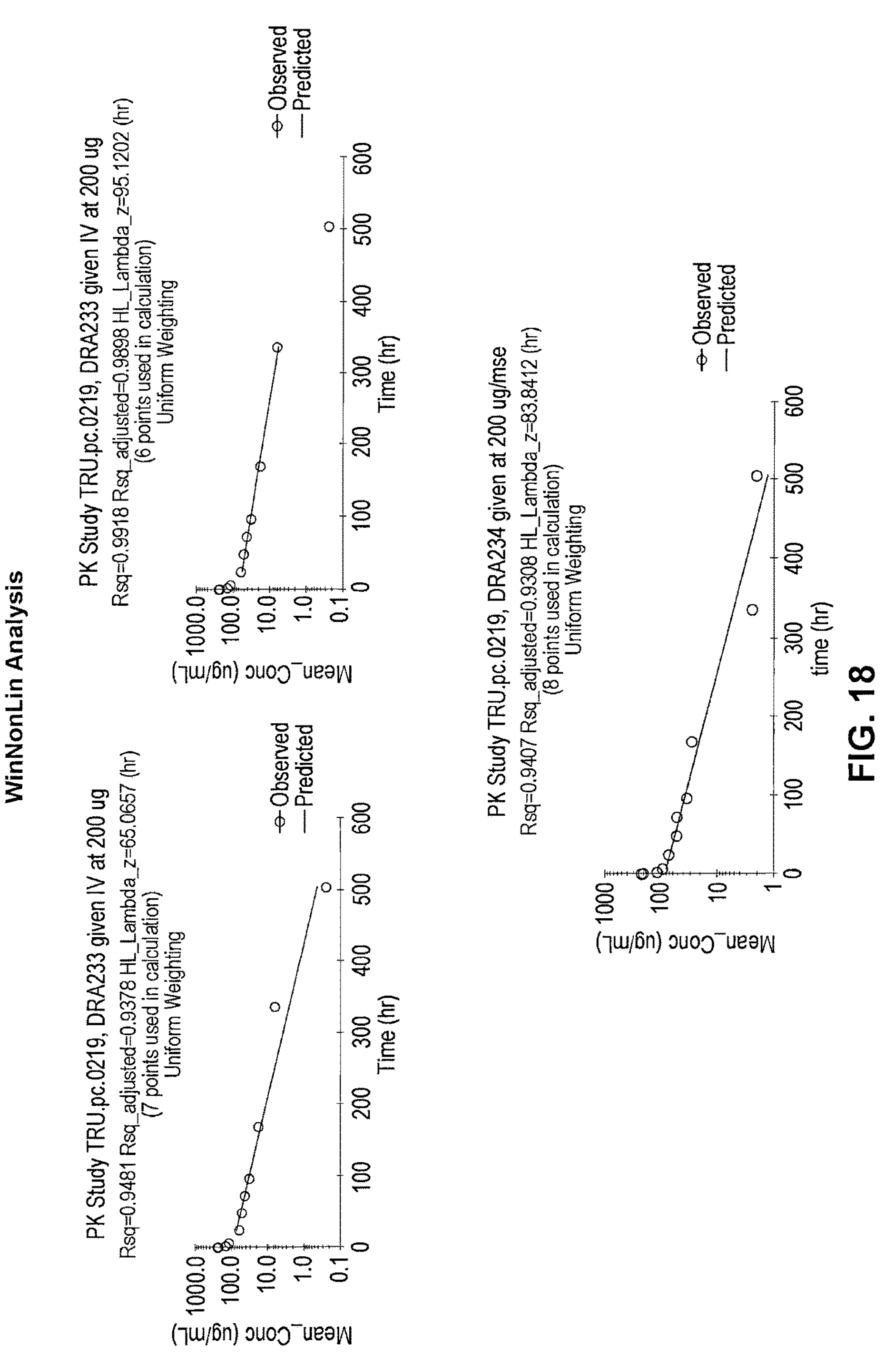
FIG. 18 provides data from a WinNonLin Analysis for DRA233 and DRA234 as described in Example 14.

The mean serum concentration vs time profile is plotted for all DRA233 PK time points in and without data from 504 hours. The serum concentration vs time profile for DRA234 is found in FIG. 18C. Results are expressed as the observed data set and the predicted values calculated by WinNonLin™ software. The Rsq value and Rsq adjusted values are the goodness of fit statistics for the terminal elimination phase, before and after adjusting for the number of points used in the estimation of HL_Lambda z. The approximate half-life for DRA233 was 95 hours using only time points without detectable levels of anti-drug antibodies, and 84 hours for DRA234. See FIG. 18.

PK estimates from WinNonLin program in tabular format: The pharmacokinetic analysis was carried out using WinNonlin™ Professional (v5.3) software, applying non-compartmental analysis using sparse sampling and the precompiled model 201 for IV bolus administration with uniform weighting. The area under the serum concentration-time curve (AUC) from time 0 to the last measurable concentration (Tlast) was estimated using the linear trapezoidal with linear/log interpolation calculation method. The following pharmacokinetic disposition parameters were estimated: maximum observed serum concentration (Cmax), concentration at the last measurable concentration (Clast), time to reach the maximum observed serum concentration (Tmax), apparent terminal elimination half-life (HL lambda z), AUC from time of dosing to the last measurable concentration (AUCaII), AUC from dosing with time extrapolated to infinity (AUCINF_obs), serum clearance (Cl_obs), volume of distribution based on the terminal phase (Vz_obs), and mean residence time (MRT). See FIGS. 19 and 20. This Example shows that the tested pI variants had longer in vivo serum half-life and slower clearance in mice as compared to the parent molecule, DRA161.

Example 5: Bispecific Homodimer Molecules—Anti-CD3 and Anti-PSMA

Bispecific CD3 and PSMA binding homodimers were constructed using standard techniques. These constructs, TSC249, TSC250, TSC251, TSC252, TSC295, TSC296, TSC301 and TSC302 are described in Table 5. Insertion of the N-terminal scFv binding domain was accomplished through digestion of the parental template and scFv insert with either the restriction enzymes HindIII and XhoI or AgeI and XhoI, desired fragments were identified and isolated by agarose gel purification, and ligation. Insertion of the C-terminal scFv binding domain was accomplished through digestion of the parental template and scFv insert with the restriction enzymes EcoRI and NotI, desired fragments were identified and isolated by agarose gel purification, and ligation.

TABLE 5

Binding Polypeptide Sequences and Components

| Name | SEQ ID NOs |
|---|---|
| humanized TSC249 Scorpion (huVL-VH#2 107-1A4 scFv-Fc-DRA222 scFv) | SEQ ID NO: 56 nucleic acid (na) SEQ ID NO: 57 amino acid (aa) |
| humanized TSC250 Scorpion (huVL-VH#2 107-1A4 scFv-Fc-DRA222 scFv, with H81 linker) | SEQ ID NO: 58 (na) SEQ ID NO: 59 (aa) |
| humanized TSC251 Scorpion (huVL-VH#2 107-1A4 scFv-Fc-DRA222 scFv, with H83 linker) | SEQ ID NO: 60 (na) SEQ ID NO: 61 (aa) |
| humanized TSC252 Scorpion (huVL-VH#2 107-1A4 scFv-Fc-DRA222 scFv, with H91 linker) | SEQ ID NO: 62 (na) SEQ ID NO: 63 (aa) |
| Humanized TSC295 Scorpion (huVL-VH#2 107-1A4 scFv-Fc-DRA222 scFv, with H9 linker) | SEQ ID NO: 64 (na) SEQ ID NO: 65 (aa) |
| Humanized TSC296 Scorpion (huVL-VH#2 107-1A4 scFv-Fc-DRA222 scFv, with H94 linker) | SEQ ID NO: 66 (na) SEQ ID NO: 67 (aa) |
| Humanized TSC301 Scorpion (huVL-VH#2 107-1A4 scFv-Fc-DRA222 scFv, with H105 linker) | SEQ ID NO: 68 (na) SEQ ID NO: 69 (aa) |
| Humanized TSC302 Scorpion (huVL-VH#2 107-1A4 scFv-Fc-DRA222 scFv, with H106 linker) | SEQ ID NO: 70 (na) SEQ ID NO: 71 (aa) |

Example 6: Bispecific Homodimer Molecules—Anti-CD3 and Anti-RON

Bispecific molecules with both CD3 and RON binding homodimers were constructed using standard techniques. These constructs, TSC275, TSC277, TSC278 and TSC279, are described in Table 6. TSC275 contains the VL and VH chains of hu4C04, SEQ ID NOs:187 and 188, respectively, which are part of the RON binding domain. TSC277, TSC278 and TSC279 are the same as TSC275 except for the mutations/substitutions as indicated in Table 6.

TABLE 6

Binding Polypeptide Sequences and Components

| Name | Brief Description | Nucleic Acid Sequence (SEQ ID NO) | Amino Acid Sequence (SEQ ID NO) |
|---|---|---|---|
| TSC275 | hu4C04 × DRA222 null2 | 185 | 186 |
| TSC277 | hu4C04 (A43K Q240E) × DRA222 null2 | 189 | 190 |
| TSC278 | hu4C04 (A43T) × DRA222 null2 | 191 | 192 |
| TSC279 | hu4C04 (Q165R) × DRA222 null2 | 193 | 194 |

Example 7: Bispecific Homodimer Molecules—Anti-CD3 and Anti-CD19

Bispecific molecules with both CD3 and CD19 binding homodimers were constructed using standard techniques, e.g., see PCT Publication No. WO2007/146968. These constructs, TSC233, TSC234, TSC235, TSC240, TSC241 and TSC242, are described in Table 7. TSC233 contains the VL (amino acids 1-111 of SEQ ID NO:196) and VH (amino acids 128-251 of SEQ ID NO:196) chains of HD37 which are part of the CD19 binding domain.

TABLE 7

Binding Polypeptide Sequences and Components

| Name | Brief Description | Nucleic Acid Sequence (SEQ ID NO) | Amino Acid Sequence (SEQ ID NO) |
|---|---|---|---|
| TSC129a | HD37 × Cris7 scorpion, H75 linker | 244 | 245 |
| TSC233 | HD37 × DRA221 scorpion, H75 linker | 195 | 196 |
| TSC234 | HD37 × DRA222 scorpion, H75 linker | 197 | 198 |
| TSC235 | HD37 × DRA224 scorpion, H75 linker | 199 | 200 |
| TSC240 | HD37 × DRA222 scorpion, H81 linker | 201 | 202 |
| TSC241 | HD37 × DRA222 scorpion, H83 linker | 203 | 204 |
| TSC242 | HD37 × DRA222 scorpion, H91 linker | 205 | 206 |

Example 8: Bispecific Heterodimer Molecules—Anti-CD3 and Anti-CD19

Different heterodimeric bispecific molecules comprising a CD19 binding domain and a CD3 binding domain were constructed similar to as described in PCT Publication WO2011/090762 by performing co-transfections of nucleic acids encoding the amino acid sequences as indicated in Table 8. Heterodimers were made by co-expressing two different polypeptides chains, one polypeptide chain comprising an immunoglobulin CH1 heterodimerization domain and the other polypeptide chain comprising an immunoglobulin CL heterodimerization domain.

TABLE 8

Cotransfection for ANTI-CD3 AND ANTI-CD19 Heterodimer Constructions

| Heterodimer Designation | Binding Domain in Each Heterodimer | Constructs Used in Co-transfection (na & aa sequences) | |
|---|---|---|---|
| TSC127 | Cris 7 scFv × HD37 | TSC096<br>SEQ ID NOs: 209 & 210 | TSC125<br>SEQ ID NOs 242 & 243 |
| TSC224 | DRA221 scFv* × HD37 | TSC096<br>SEQ ID NOs: 209 & 210 | TSC218<br>SEQ ID NOs: 246 & 247 |
| TSC225 | DRA222 scFv** × HD37 | TSC096<br>SEQ ID NOs: 209 & 210 | TSC219<br>SEQ ID NOs: 217 & 218 |
| TSC226 | DRA224 scFv*** × HD37 | TSC096<br>SEQ ID NOs: 209 & 210 | TSC220<br>SEQ ID NOs: 219 & 220 |
| TSC227 | HD37 × DRA221 scFv* | TSC049<br>SEQ ID NOs: 207 & 208 | TSC221<br>SEQ ID NOs: 248 & 249 |
| TSC228 | HD37 × DRA222 scFv** | TSC049<br>SEQ ID NOs: 207 & 208 | TSC222<br>SEQ ID NOs: 221 & 222 |
| TSC229 | HD37 × DRA224 scFv*** | TSC049<br>SEQ ID NOs: 207 & 208 | TSC223<br>SEQ ID NOs: 223 & 224 |

*amino acid 1-244 of SEQ ID NO: 10
**amino acid 1-244 of SEQ ID NO: 8
***amino acid 1-247 of SEQ ID NO: 14

TSC049 comprises from its amino- to carboxyl-terminus: HD37 (anti-CD19) scFv, human IgG1 SCC-P hinge, human IgG1 CH2, human IgG1 CH3, and human CH1. TSC096 comprises from its amino- to carboxyl-terminus: HD37 (anti-CD19) scFv, human IgG1 SCC-P hinge, human IgG1 CH2, human IgG1 CH3, and human Cκ (YAE). TSC125 comprises from its amino- to carboxyl-terminus: Cris7 (anti-CD3) scFv, human IgG1 SCC-P hinge, human IgG1 CH2, human IgG1 CH3, and human CH1. TSC218 comprises from its amino- to carboxyl-terminus: DRA221 (anti-CD3) scFv, human IgG1 SCC-P hinge, human IgG1 CH2, human IgG1 CH3, and human CH1. TSC219 comprises from its amino- to carboxyl-terminus: DRA222 (anti-CD3) scFv, human IgG1 SCC-P hinge, human IgG1 CH2, human IgG1 CH3, and human CH1. TSC220 comprises from its amino- to carboxyl-terminus: DRA224 (anti-CD3) scFv, human IgG1 SCC-P hinge, human IgG1 CH2, human IgG1 CH3, and human CH1. TSC221 comprises from its amino- to carboxyl-terminus: DRA221 (anti-CD3) scFv, human IgG1 SCC-P hinge, human IgG1 CH2, human IgG1 CH3, and human Cκ (YAE). TSC222 comprises from its amino- to carboxyl-terminus: DRA222 (anti-CD3) scFv, human IgG1 SCC-P hinge, human IgG1 CH2, human IgG1 CH3, and human Cκ (YAE). TSC223 comprises from its amino- to carboxyl-terminus: DRA224 (anti-CD3) scFv, human IgG1 SCC-P hinge, human IgG1 CH2, human IgG1 CH3, and human Cκ (YAE).

Example 9: Bispecific Heterodimer Molecules—Anti-CD3 and Anti-PSMA

Different heterodimeric bispecific molecules comprising a PSMA binding domain and a CD3 binding domain were constructed similar to as described in PCT Publication WO2011/090762 by performing co-transfections of nucleic acids encoding the amino acid sequences as indicated in Table 9. Heterodimers were made by co-expressing two different polypeptides chains, one polypeptide chain comprising an immunoglobulin CH1 heterodimerization domain and the other polypeptide chain comprising an immunoglobulin CL heterodimerization domain. Some PSMA binding domains are described in PCT Publication No. WO2011/090761.

TABLE 9

Cotransfection for ANTI-CD3 AND ANTI-PSMA Heterodimer Constructions

| Heterodimer Designation | Binding Domain in Each Heterodimer | Constructs Used in Co-transfection (na & aa sequences) | |
|---|---|---|---|
| TSC236 | DRA222 scFv* × humanized 107-1A4 VL-VH#2 scFv** | TSC192<br>SEQ ID NOs: 211 & 212 | TSC219<br>SEQ ID NOs: 217 & 218 |
| TSC237 | humanized 107-1A4 scFv** × DRA222 scFv* | TSC195<br>SEQ ID NOs: 215 & 216 | TSC222<br>SEQ ID NOs: 221 & 222 |
| TSC264 | humanized 107-1A4 VL-VH#1 scFv*** × DRA222 scFv* | TSC258<br>SEQ ID NOs: 227 & 228 | TSC254<br>SEQ ID NOs: 225 & 226 |
| TSC265 | DRA222 scFv* × humanized 107-1A4 VL-VH#1 scFv** | TSC193<br>SEQ ID NOs: 213 & 214 | TSC219<br>SEQ ID NOs: 217 & 218 |

*amino acid 1-244 of SEQ ID NO: 8
**amino acid 1-243 of SEQ ID NO: 216
***amino acid 1-243 of SEQ ID NO: 226

"Humanized 107-1A4 VL-VH#2 scFv" and "humanized 107-1A4 VL-VH#1 scFv" are humanized scFvs based on the anti-human-PSMA 107-1A4 monoclonal antibody and are also described in PCT Publication No. WO2011/090761. The "humanized 107-1A4 VL-VH#2 scFv" and "humanized 107-1A4 VL-VH#1 scFv" correspond to amino acids amino acid 1-243 of SEQ ID NO:216 & 226, respectively.

TSC192 comprises from its amino- to carboxyl-terminus: humanized 107-1A4 (anti-PSMA) VL-VH#2 scFv, human IgG1 SCC-P hinge, human IgG1 CH2, human IgG1 CH3, and human Cκ(YAE). TSC195 comprises from its amino- to carboxyl-terminus: humanized 107-1A4 (anti-PSMA) VL-VH#2 scFv, human IgG1 SCC-P hinge, human IgG1 CH2, human IgG1 CH3, and human CH1. TSC193 comprises from its amino- to carboxyl-terminus: humanized 107-1A4 (anti-PSMA) VL-VH#1 scFv, human IgG1 SCC-P hinge, human IgG1 CH2, human IgG1 CH3, and human Cκ(YAE).

TSC219 comprises from its amino- to carboxyl-terminus: DRA222 (anti-CD3) scFv, human IgG1 SCC-P hinge, human IgG1 CH2, human IgG1 CH3, and human CH1. TSC222 comprises from its amino- to carboxyl-terminus: DRA222 (anti-CD3) scFv, human IgG1 SCC-P hinge, human IgG1 CH2, human IgG1 CH3, and human Cκ(YAE).

TSC254 comprises from its amino- to carboxyl-terminus: humanized 107-1A4 (anti-PSMA) VL-VH#1 scFv, human IgG1 SCC-P hinge, human IgG1 CH2, human IgG1 CH3, linker, and human CH1. TSC258 comprises from its amino- to carboxyl-terminus: DRA222 (anti-CD3) scFv, human IgG1 SCC-P hinge, human IgG1 CH2, human IgG1 CH3, linker, and human Cκ(YAE).

Example 10: Target-Dependent T-Cell Proliferation by Polypeptide Heterodimers and Homodimers Targeting CD19

To compare the effectiveness of different bispecific polypeptide heterodimer molecules at inducing target-dependent T-cell activation and proliferation, three different homodimeric bispecific molecules (TSC129a, TSC233, and TSC234 (SEQ ID NOs: 245, 196 and 198, respectively)) with a common anti-CD19 binding domain (HD37) and three different anti-CD3 binding domains (Cris7 for TSC129a, the scFv binding domain from DRA221 (amino acid 1-244 of SEQ ID NO:10) for TSC233, the scFv binding domain from DRA222 (amino acid 1-244 of SEQ ID NO:8) for TSC234) were compared. Additionally, three different heterodimeric bispecific molecules (TSC127, TSC227, TSC228) with three different anti-CD3 binding domains (Cris7 for TSC127, scFv binding domain from DRA221 (amino acid 1-244 of SEQ ID NO:10) for TSC227, and scFv binding domain from DRA222 (amino acid 1-244 of SEQ ID NO:8) for TSC228) were also compared.

Daudi Burkitt's lymphoma cells (CD19+) were obtained from ATCC (Manassas, Va.) and cultured according to the provided protocol. Peripheral blood mononuclear cells (PBMC) were isolated from human blood using standard ficoll gradients. The isolated cells were washed in saline buffer. T-cells were additionally isolated from these PBMC using a Pan T-cell Isolation Kit II from Miltenyi Biotec (Bergisch Gladbach, Germany) using the manufacturer's protocol.

Proliferation was assessed by labeling isolated T-cell populations with carboxyfluorescein diacetate succinimidyl ester (CFSE). CFSE-labeled T-cells were plated in U-bottom 96-well plates at 100,000 T-cells/well, with 33,000 tumor cells/well, to achieve T-cell to tumor cell ratios of approximately 3:1. Concentrations of test molecules ranging from 1 nM to 5 fM were added to the cell mixtures in a total of 200 uL/well in RPMI 1640 media supplemented with 10% human or bovine serum, sodium pyruvate and non-essential amino acids. Plates were incubated at 37° C., 5% $CO_2$ in humidified incubators. After 3 days, cells were labeled with antibodies for flow cytometric analysis. Cells were labeled and washed in their original plates to minimize cell losses during transfers, and all labeling was done in saline buffer with 0.2% bovine serum albumin. First, cells were pre-incubated with 100 ug/ml human IgG at room temperature for 15 min. Subsequently, cells were incubated with a mixture (total volume 50 ul) of the following dye-labeled antibodies: CD5-PE, CD4-APC, CD8-Pacific Blue, CD25-PE-Cy7, as well as 7-Amino Actinomycin D (7AAD hereafter) for 40 min. Plates were washed twice, resuspended in 80 to 120 ul volumes and ran immediately in a BD LSRII flow cytometer to acquire 80% of the contents of each well. The sample files were analyzed using FlowJo software to calculate the percentages and numbers of cells that had undergone at least one cell division, according to their CFSE profile, by gating sequentially on activated, live CD4+ or CD8+ T-cells (7AAD−, CD5+ CD25+ CD4+ or 7AAD− CD5+ CD25+ CD8+, respectively). Mean values and standard deviations were calculated using Microsoft Excel software. Graphs were plotted using Microsoft Excel or Graphpad Prism.

Figure 21:
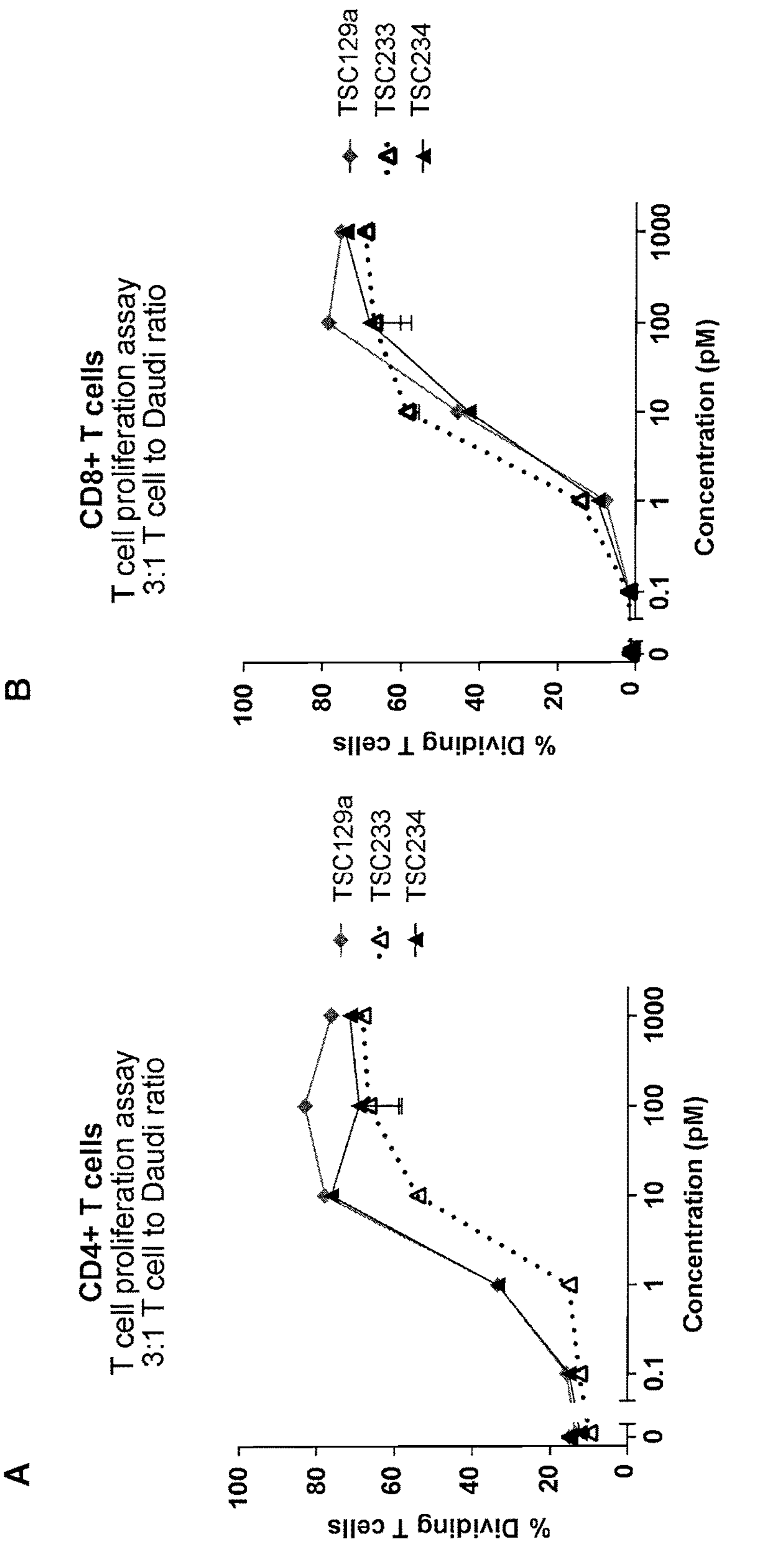
FIG. 21 depicts results from target-dependent T-cell proliferation assays using different homodimer bispecific polypeptide molecules that target CD19.
Figure 22:
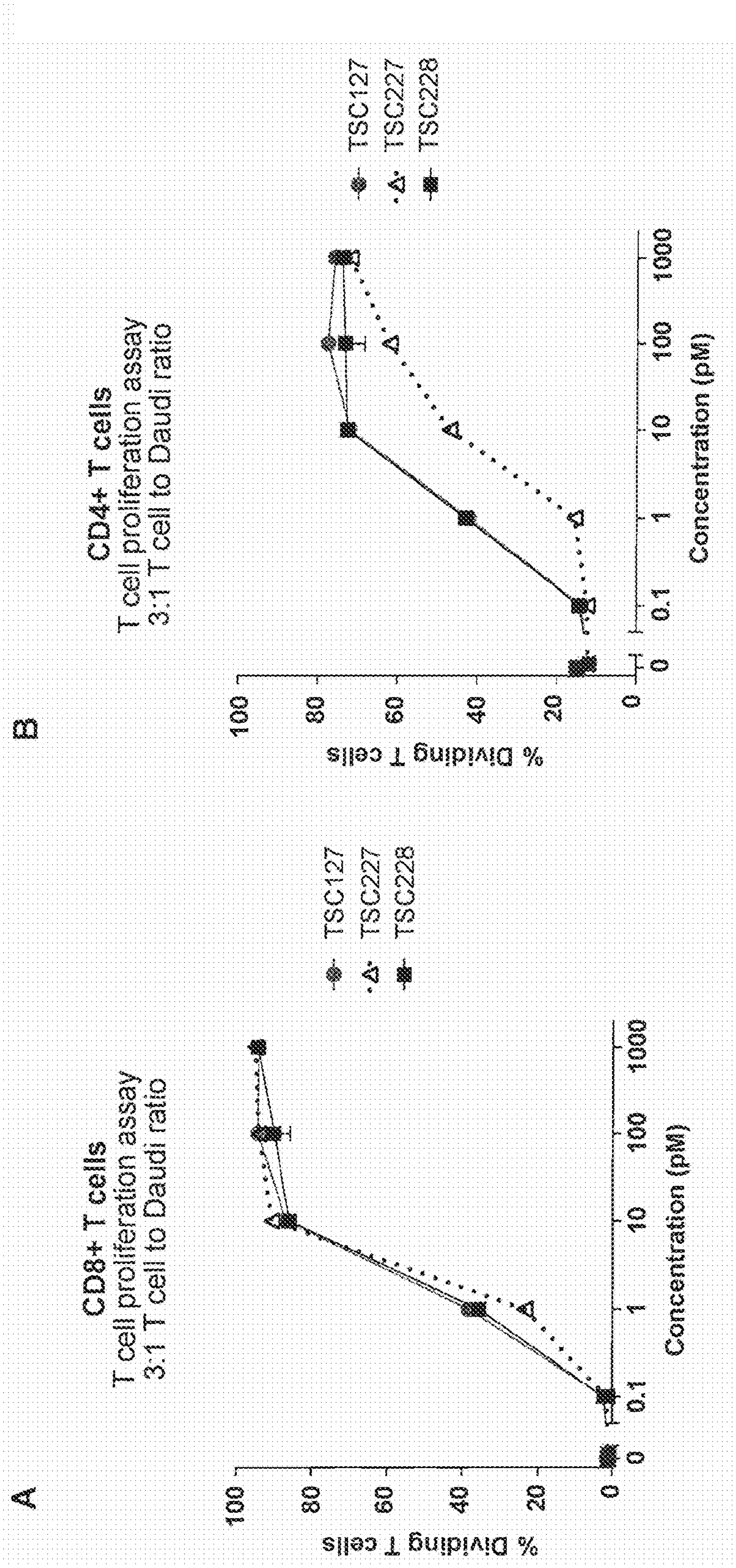
FIG. 22 depicts results from a target-dependent T-cell proliferation assay using different heterodimer bispecific polypeptide molecules that target CD19.

Analysis of live CD4+ and CD8+ populations from Daudi cells treated with whole T-cells revealed a significant increase in both the total number of cells and percent proliferating cells in the presence of Daudi cells displaying the target CD19 antigen (FIGS. 21 & 22).

For the homodimeric bispecific polypeptides (TSC129a, TSC233, TSC234), proliferation was comparable between CD4+ and CD8+ cells (FIG. 21). Proliferation induced by TSC129a and TSC234 was comparable between CD4+ and CD8+ cells (FIG. 21), suggesting that pI variant anti-CD3 scFv binding domain from DRA222 had essentially equivalent activity to the parental Cris7 binding domain. The profile of T-cell proliferation induced by TSC233 differed slightly from TSC129a and TSC234, with a decreased induction of CD4+ proliferation (FIG. 21A) and a slightly increased induction of CD8+ proliferation (FIG. 21B). This suggested that the pI variant anti-CD3 scFv binding domain from DRA221 was not completely equivalent in activity to the parental Cris7 binding domain.

For the heterodimeric bispecific polypeptides (TSC127, TSC227, TSC228), proliferation was higher for CD8+ T-cells than CD4+ T-cells in the presence of Daudi cells (FIG. 22). Proliferation induced by TSC127 and TSC228 was comparable between CD4+ and CD8+ cells (FIG. 22), suggesting that pI variant anti-CD3 scFv binding domain from DRA222 had essentially equivalent activity to the parental Cris7 binding domain. The profile of T-cell proliferation induced by TSC227 differed slightly from TSC127 and TSC228, with a decreased induction of CD4+ proliferation, and comparable induction of CD8+ proliferation. Again, this suggested that the pI variant anti-CD3 scFv binding domain from DRA221 was not completely equivalent in activity to the parental Cris7 binding domain.

Example 11: Redirected T-Cell Cytotoxicity by Polypeptide Heterodimers and Homodimers Targeting CD19

To compare the effectiveness of different bispecific polypeptide heterodimer molecules at inducing target-dependent T-cell cytotoxicity, three different homodimeric bispecific molecules (TSC129a, TSC233, and TSC234 (SEQ ID NOs: 245, 196 and 198, respectively)) with a common anti-CD19 binding domain (HD37) and three different anti-CD3 binding domains (Cris7 for TSC129a, the scFv binding domain from DRA221 (amino acid 1-244 of SEQ ID NO:10) for TSC233, the scFv binding domain from DRA222 (amino acid 1-244 of SEQ ID NO:8) for TSC234)) were compared. Additionally, three different heterodimeric bispecific molecules (TSC127, TSC227, TSC228) with three different anti-CD3 binding domains (Cris7 for TSC127, scFv binding domain from DRA221 (amino acid 1-244 of SEQ ID NO:10) for TSC227, and scFv binding domain from DRA222 (amino acid 1-244 of SEQ ID NO:8) for TSC228) were also compared.

Daudi Burkitt's lymphoma cells (CD19+) were obtained from ATCC (Manassas, Va.) and cultured according to the provided protocol. Peripheral blood mononuclear cells (PBMC) were isolated from human blood using standard ficoll gradients and washed in saline buffer. T cells were additionally isolated from PBMC using a Pan T-cell Isolation Kit II from Miltenyi Biotec (Bergisch Gladbach, Germany) using the manufacturer's protocol.

Cytotoxicity was assessed by a $^{51}Cr$ release assay. Approximately $5\times10^6$ Daudi cells were treated with 0.3 mCi of $^{51}Cr$ and incubated for 75 minutes at 37° C. After 75 minutes, cells were washed 3 times with media (RPMI +10% FBS) and resuspended in 11.5 mL of media. From this suspension, 50 μL was dispensed per well into 96 well U-bottom plates (approximately 20,000 cells/well). Concentrations of bispecific molecules ranging from 500 pM to 0.1 pM were added to the Daudi cells, bringing the total volume to 100 μL/well. Target cells were incubated at room temperature for 15 minutes. Then 100 μL of isolated T-cells (approximately 200,000) were added to bring the T-cell to target cell ratio to 10:1. 50 μL of 0.8% NP-40 was added to a control well containing target cells, left for 15 minutes, then 100 μL of media was added to provide a total lysis control.

Plates were incubated for 4 hours, then spun at 1500 rpm for 3 minutes and 25 μL of supernatant was transferred from each well to the corresponding well of a 96-well Luma sample plate. Sample plates were allowed to air dry in a chemical safety hood for 18 hours, and then radioactivity was read on a Topcount scintillation counter using a standard protocol.

Figure 23:
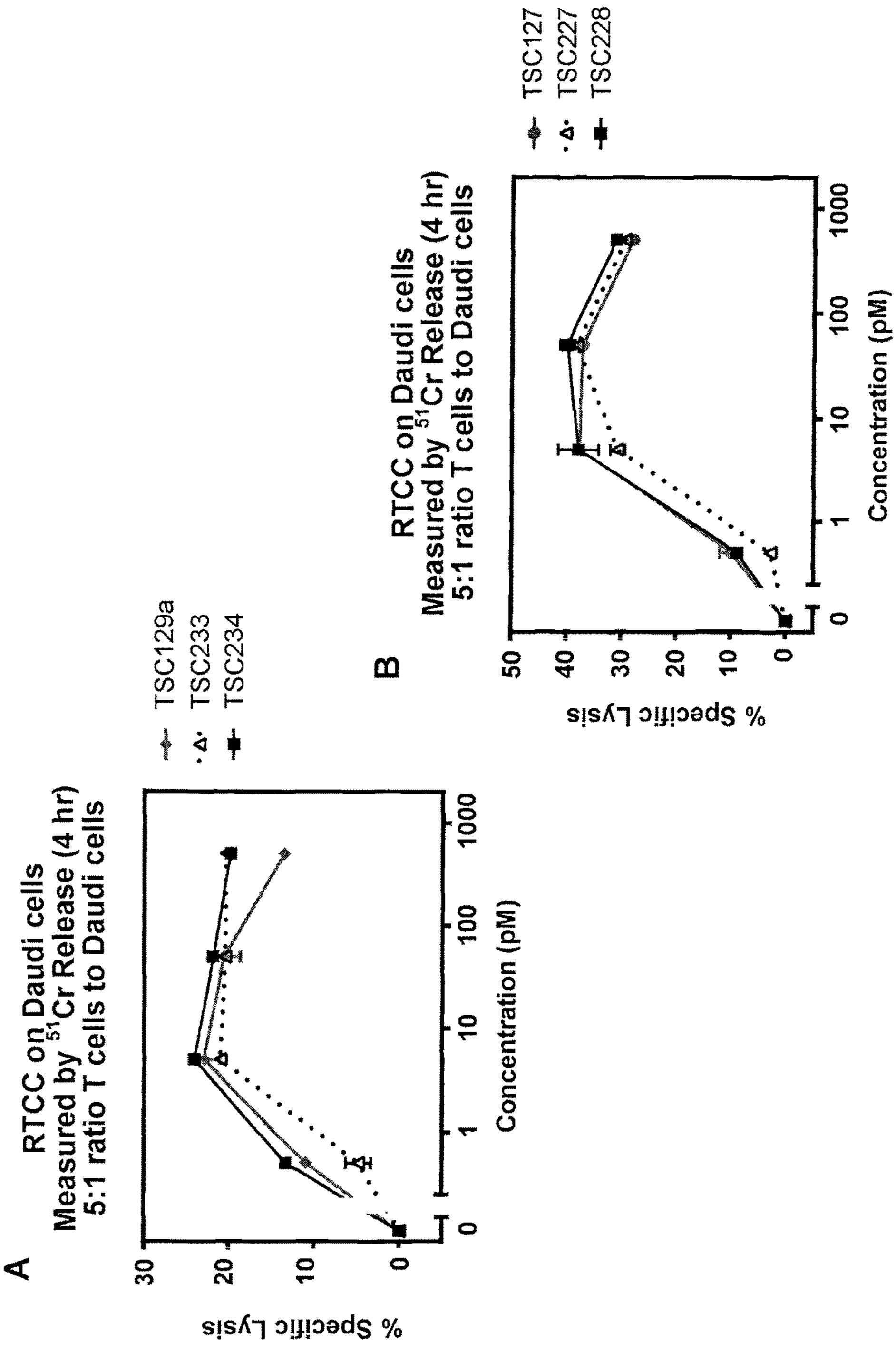
FIG. 23 depicts results from a redirected T-cell cytotoxicity assay using different polypeptide heterodimers and homodimers that target CD19.

Analysis of cytotoxicity data showed T-cell directed cytotoxicity with the Daudi cells in the presence of T-cells and anti-CD19 directed bispecific molecules (FIG. 23).

For the homodimeric bispecific polypeptides (TSC129a, TSC233, TSC234), observed cytotoxicity was comparable between TSC129a and TSC234 (FIG. 23A), suggesting that the DRA222 pI variant had equivalent activity to the parental Cris7 binding domain. A slight decrease in cytotoxicity was observed with TSC233, suggesting that the DRA221 pI variant had less activity than the parental Cris7 binding domain.

For the heterodimeric bispecific polypeptides (TSC127, TSC227, TSC228), observed cytotoxicity was comparable between TSC127 and TSC228 (FIG. 23B), suggesting that the DRA222 scFv binding domain pI variant had equivalent activity to the parental Cris7 binding domain. A slight decrease in cytotoxicity was observed with TSC227, suggesting that the DRA221 scFv binding domain pI variant had less activity than the parental Cris7 binding domain.

Example 12: Redirected T-Cell Cytotoxicity by Polypeptide Homodimers Targeting Ron To compare the effectiveness of different bispecific polypeptide heterodimer molecules at inducing target-dependent T-cell cytotoxicity, four different homodimeric bispecific molecules (TSC275, TSC277, TSC278, and TSC279) with a common anti-CD3 binding domain (scFv binding domain from DRA222 (amino acid 1-244 of SEQ ID NO:8)) and four variants of the same anti-RON binding domain (hu4C04 scFv for TSC275, hu4C04 scFv (A43K/Q240E) for TSC277, hu4C04 scFv (A43T) for TSC278, and hu4C04 scFv (Q165R) for TSC279) were compared.

MDA-MB-453 breast cancer cells (RON+) were obtained from ATCC (Manassas, Va.) and cultured according to the protocol provided by ATCC. Peripheral blood mononuclear cells (PBMC) were isolated from human blood using standard ficoll gradients and washed in saline buffer. T-cells were additionally isolated from PBMC using a Pan T-cell Isolation Kit II from Miltenyi Biotec (Bergisch Gladbach, Germany) using the manufacturer's protocol.

Cytotoxicity was assessed by a $^{51}Cr$ release assay. Approximately $5\times10^6$ Daudi cells were treated with 0.3 mCi of $^{51}Cr$ and incubated for 75 minutes at 37° C. After 75 minutes, cells were washed 3 times with media (RPMI+10% FBS) and resuspended in 11.5 mL of media. From this suspension, 50 μL was dispensed per well into 96 well U-bottom plates (approximately 20,000 cells/well). Concentrations of bispecific molecules ranging from 10 nM to 0.005 fM were added to the Daudi cells, bringing the total volume to 100 μL/well. Target cells were incubated at room temperature for 15 minutes. Then 100 μL of isolated T-cells (approximately 100,000) were added to bring the T-cell to target cell ratio to 5:1. 50 μL of 0.8% NP-40 was added to a control well containing target cells, left for 15 minutes, then 100 μL of media was added to provide a total lysis control.

Plates were incubated for 24 hours, spun at 1500 rpm for 3 minutes, and 25 μL of supernatant was transferred from each well to the corresponding well of a 96-well Luma sample plate. Sample plates were allowed to air dry in a chemical safety hood for 18 hours, and then radioactivity was read on a Topcount scintillation counter using a standard protocol.

Figure 24:
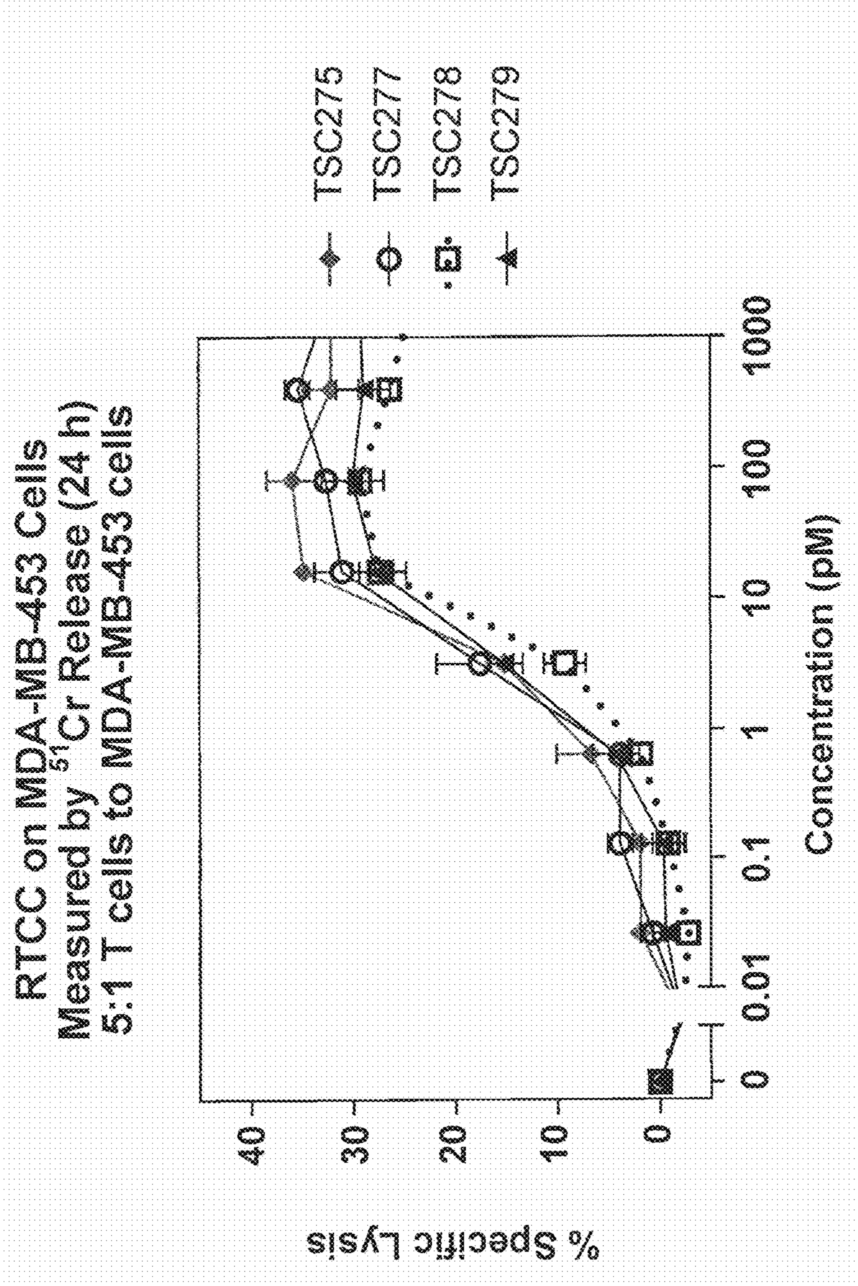
FIG. 24 depicts results from a redirected T-cell cytotoxicity assay using TSC275, TSC277, TSC278 and TSC279 which are different bispecific polypeptide homodimers that target RON.

Analysis of cytotoxicity data showed T-cell directed cytotoxicity with the MDA-MB-453 cells in the presence of T-cells and anti-RON directed bispecific molecules (FIG. 24).

For the homodimeric bispecific polypeptides (TSC275, TSC277, TSC278 and TSC279), observed cytotoxicity was generally comparable (FIG. 24), suggesting that mutations within the ORN196 binding domain did not significantly affect overall activity. However, slightly lower maximum lysis was observed for TSC278 compared to the other three variants (FIG. 24). Maximum lysis was observed between concentrations of 10 pM and 10 nM.

Example 13: T-Cell Binding of Bispecific Polypeptide Heterodimers and Homodimers To compare the effectiveness of bispecific polypeptide molecules featuring a pI variant CD3 binding domain (the scFv found in DRA222 (amino acid 1-244 of SEQ ID NO:8)) at binding to T-cells, the on-cell binding characteristics of an anti-CD19×anti-CD3 bispecific polypeptide heterodimer, TSC228 (as described in Example 8, Table 8), were compared to that of an anti-PSMA×anti-CD3 bispecific polypeptide homodimer TSC249 (as described in Example 5, Table 5), were compared in two independent experiments.

Jurkat ($CD3^+$) T cell leukemia cells were obtained from ATCC (Manassas, Va.), and cultured according to the protocol provided by ATCC. Binding was assessed by incubating $5\times10^5$ Jurkat cells for 30 minutes at 4° C. with serially diluted bispecific molecules TSC228 or TSC249, in concentrations from 250 nM to 0.125 nM (TSC249) or 125 nM to 1 pM (TSC228). The cells were washed three times and then incubated with goat anti-human IgG-FITC (1:200 dilution) for another 30 minutes at 4° C. The cells were then washed again three times, fixed in 1% paraformaldehyde and read on a FACS-Calibur instrument.

Figure 25A:
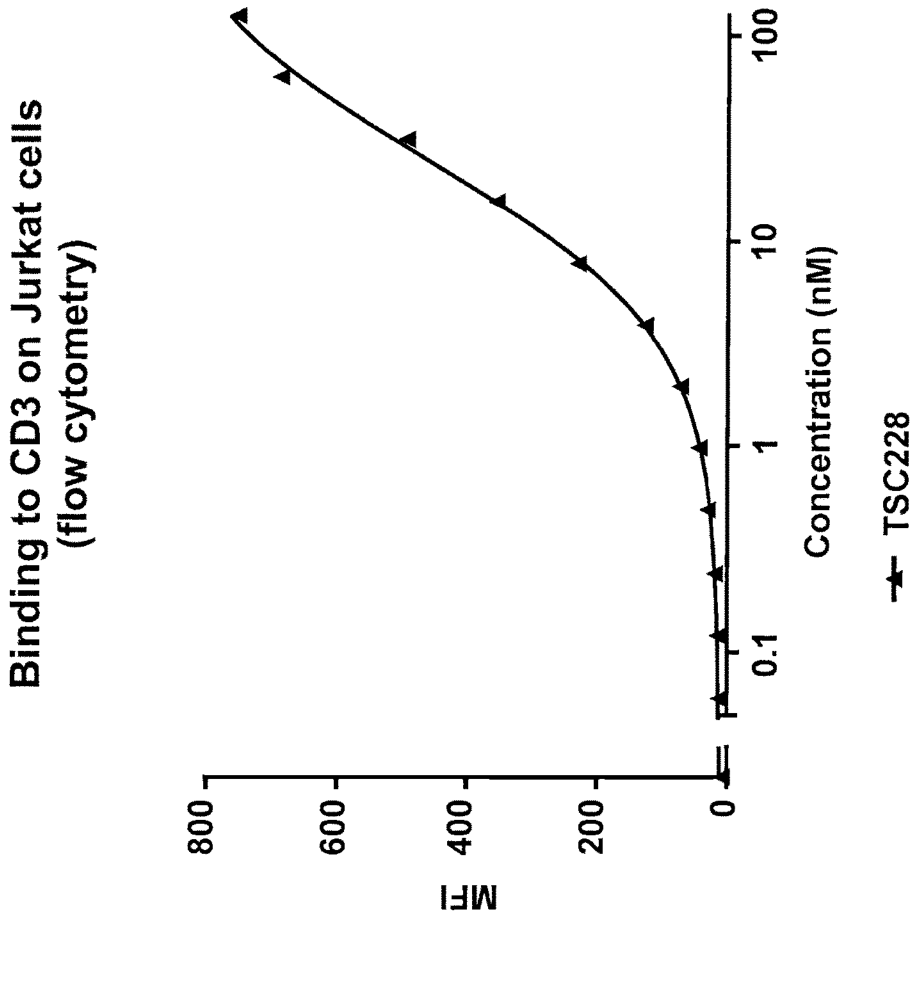
FIGS. 25A and 25B show dose-dependent binding of bispecific molecules TSC228 (heterodimer) and TSC249 (homodimer) to Jurkat cells.
Figure 25B:
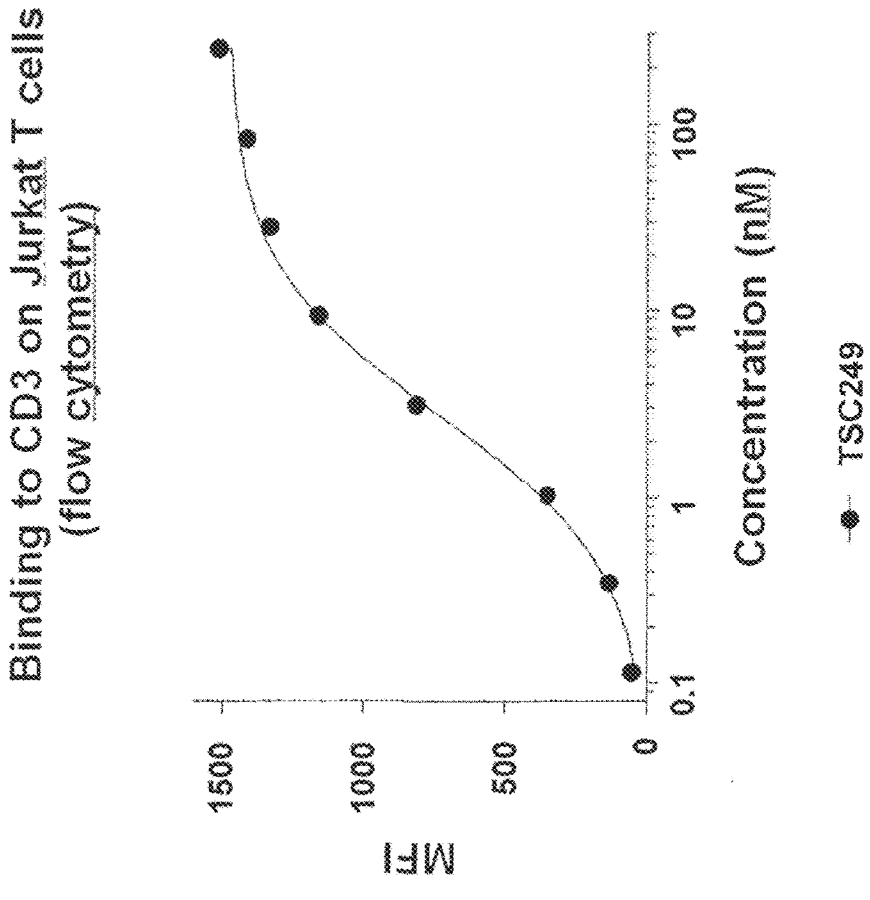

Analysis of the FSC high, SSC high subset in FlowJo v7.5 (Tree Star, Inc, Ashland, Oreg.) showed dose-dependent binding of bispecific molecules TSC228 and TSC249 to Jurkat cells (FIGS. 25A & B, respectively). The TSC228 bispecific polypeptide heterodimer, which possessed only one anti-CD3 binding domain, bound with a lower apparent affinity ($EC_{50}$=24.5 nM) than the TSC249 bispecific polypeptide homodimer ($EC_{50}$=1.9 nM), which possessed two anti-CD3 binding domains. This suggests that the TSC249 bispecific polypeptide heterodimer bound with some avidity.

Example 14: Target-Dependent T-Cell Proliferation by Bispecific Polypeptide Homodimers Targeting PSMA To determine the effectiveness of different bispecific polypeptide heterodimer molecules at inducing target-dependent T-cell activation and proliferation, a homodimeric bispecific molecule (TSC249, see Example 5, Table 5) with an anti-PSMA binding domain (hu107-1A4) and an anti-CD3 binding domain (the scFv from DRA222 (amino acid 1-244 of SEQ ID NO:8)) was tested on prostate cancer cell lines expressing PSMA, prostate cancer cell lines not expressing PSMA, and T-cells without target cells present.

C4-2B prostate carcinoma cells (PSMA+) were obtained from MD Anderson Cancer Center (Houston, Tex.) and cultured according to the provided protocol. DU-145 prostate carcinoma cells ($PSMA^-$) were obtained from ATCC (Manassas, Va.) and cultured according to the provided protocol. Peripheral blood mononuclear cells (PBMC) were isolated from human blood using standard ficoll gradients, and further were washed in saline buffer. T-cells were then isolated from these PBMC using a Pan T-cell Isolation Kit II from Miltenyi Biotec (Bergisch Gladbach, Germany) using the manufacturer's protocol.

Proliferation was assessed by labeling isolated T cell populations with carboxyfluorescein diacetate succinimidyl ester (CFSE). Three individual experiments were set up simultaneously. CFSE-labeled T cells were mixed with the TSC249 molecule alone; CFSE-labeled T cells were mixed with DU-145 cells and the TSC249 molecule; and CFSE-labeled T cells were mixed with C4-2B cells and the TSC249 molecule. CFSE-labeled T-cells were plated in U-bottom 96-well plates at 100,000 cells/well, with 33,000 tumor cells/well, to achieve approximate T-cell to tumor cell ratios of 3:1. Concentrations of test molecules ranging from 20 nM to 5 fM were added to the cell mixtures in a total of 200 uL/well in RPMI 1640 media supplemented with 10% human or bovine serum, sodium pyruvate and non-essential amino acids. Plates were incubated at 37° C., 5% $CO_2$ in humidified incubators. After 3 days, cells were labeled with antibodies for flow cytometric analysis. Cells were labeled and washed in their original plates to minimize cell losses during transfers, and all labeling was done in saline buffer with 0.2% bovine serum albumin. First, cells were pre-incubated with 100 ug/ml human IgG at room temperature for 15 min. Subsequently, cells were incubated with a mixture (total volume 50 ul) of the following dye-labeled antibodies: CD5-PE, CD4-APC, CD8-Pacific Blue, CD25-PE-Cy7, as well as 7-Amino Actinomycin D (7AAD hereafter) for 40 min. Plates were washed twice, resuspended in 80 to 120 ul volumes and ran immediately in a BD LSRII flow cytometer to acquire 80% of the contents of each well. The sample files were analyzed using FlowJo software to calculate the percentages and numbers of cells that had undergone at least one cell division, according to their CFSE profile, by gating sequentially on activated, live CD4+ or CD8+ T cells (7AAD-, CD5+CD25+CD4+ or 7AAD-CD5+CD25+CD8+, respectively). Mean values and standard deviations were calculated using Microsoft Excel software. Graphs were plotted using Microsoft Excel or Graphpad Prism.

Figure 26A:
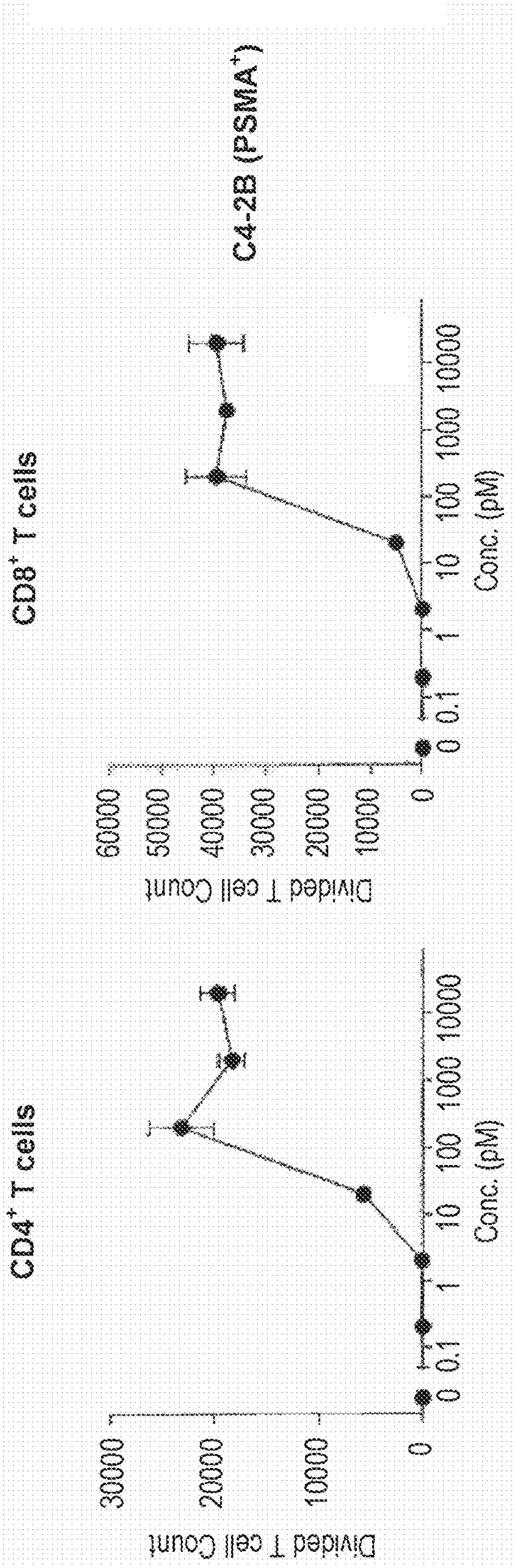
FIG. 26A shows results for C4-2B cells expressing the target PSMA antigen upon treatment with TSC249.
Figure 26B:
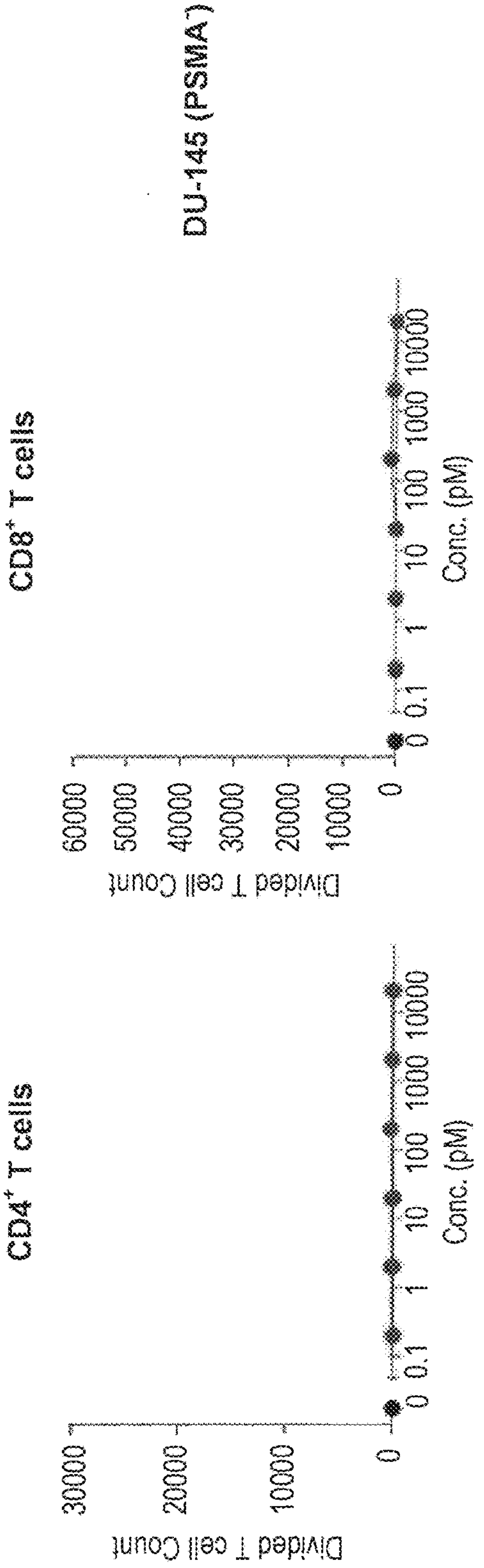
FIG. 26B shows results for DU-145 cells that did not express the target PSMA antigen upon treatment with TSC249.
Figure 26C:
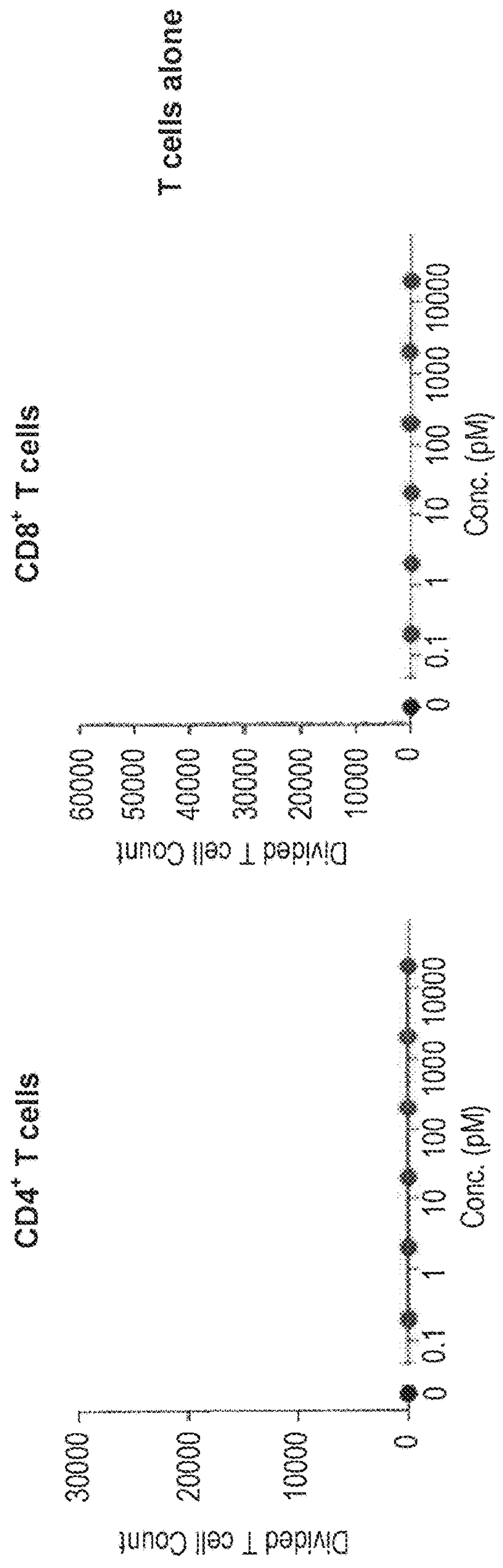
FIG. 26C shows the results when isolated T-cells were treated with TSC249.

Analysis of live CD4+ and CD8+ populations from C4-2B cells treated with whole T cells revealed a significant increase in both the total number of cells in the presence of C4-2B cells expressing the target PSMA antigen upon treatment with TSC249 (FIG. 26A). This increase was not seen in the presence of DU-145 cells that did not express the target PSMA antigen after treatment with TSC249 (FIG. 26B). Finally, this increase was also not seen when isolated T cells were treated with TSC249 (FIG. 26C). This confirmed the target-dependent nature of the T cell proliferation induced by TSC249 in the presence of tumor cells expressing the target antigen.

Example 15: In Vivo Testing of Bispecific Targeting of CD3 and PSMA

To confirm effectiveness of an anti-CD3 and anti-PSMA bispecific molecule at inhibiting tumor growth in vivo, a PSMA-directed molecule can be evaluated using any one or more of the following.

Prophylactic treatment, or prevention of tumor engraftment of subcutaneous tumors: Cultured, PSMA-expressing tumor cell lines (such as LNCaP, LNCaP C4-2, LNCaP C4-2B, VCaP, CWR22Rv1, LAPC4, MDA-PCa-2b, LuCaP 23.1, LuCaP 58, LuCaP 70, LuCaP 77) are mixed with human lymphocytes (either human peripheral blood mononuclear cells or purified T-cells) and injected subcutaneously into immunodeficient mice (such as SCID, NOD/SCID, etc.). An anti-PSMA bispecific molecule is injected intravenously on the day of injection and on several subsequent days. Dose-dependent inhibition of tumor outgrowth, as assessed by tumor volume, indicates that the respective molecule has efficacy against PSMA-expressing tumors in vivo.

Therapeutic treatment or regression of previously established subcutaneous tumors: Cultured, PSMA-expressing tumor cell lines (such as LNCaP, LNCaP C4-2, LNCaP C4-2B, VCaP, CWR22Rv1, LAPC4, MDA-PCa-2b, LuCaP 23.1AI, LuCaP 58, LuCaP 70, and LuCaP 77) are injected subcutaneously into immunodeficient mice (such as SCID, NOD/SCID, etc.). Tumor growth is monitored, and the study is initiated when tumors show signs of established growth (typically a volume of ~200 mm3). Human lymphocytes (either human peripheral blood mononuclear cells or purified T-cells) are injected intravenously along with an anti-PSMA bispecific molecule on the day of injection. The anti-PSMA bispecific molecule is injected several subsequent days. Dose-dependent inhibition of tumor growth, as assessed by tumor volume, indicates that the respective molecule has efficacy against PSMA-expressing tumors in vivo.

Prophylactic treatment, or prevention of tumor engraftment of intra-tibial tumors: Cultured, PSMA-expressing tumor cell lines (such as LNCaP C4-2, LNCaP C4-2B, VCaP, CWR22Rv1, LAPC4, MDA-PCa-2b, LuCaP 23.1, LuCaP 58, LuCaP 70, LuCaP 77) are mixed with human lymphocytes (either human peripheral blood mononuclear cells or purified T-cells) and injected intra-tibially into immunodeficient mice (such as SCID, NOD/SCID, etc.). An anti-PSMA bispecific molecule is injected intravenously on the day of injection and on several subsequent days. Dose-dependent inhibition of tumor growth, as assessed by serum biomarkers, radiography, fluorescent imaging, weight loss, and other proxy measurements of tumor volume, indicates that the respective molecule has efficacy against PSMA-expressing tumors in vivo.

Therapeutic treatment or regression of previously established intra-tibial tumors: Cultured, PSMA-expressing tumor cell lines (such as LNCaP C4-2, LNCaP C4-2B, VCaP, CWR22Rv1, LAPC4, MDA-PCa-2b, LuCaP 23.1AI, LuCaP 58, LuCaP 70, and LuCaP 77) are injected intra-tibially into immunodeficient mice (such as SCID, NOD/SCID, etc.). Tumor growth is monitored, and the study is initiated when tumors show signs of established growth (typically a volume of ~200 mm3). Human lymphocytes (either human peripheral blood mononuclear cells or purified T-cells) are injected intravenously along with an anti-PSMA bispecific molecule on the day of injection. The anti-PSMA bispecific molecule is injected several subsequent days. Dose-dependent inhibition of tumor growth, as assessed by serum biomarkers, radiography, fluorescent imaging, weight loss, and other proxy measurements of tumor volume, indicates that the respective molecule has efficacy against PSMA expressing tumors in vivo.

Example 16: Redirected T-Cell Cytotoxicity by Polypeptide Heterodimers and Homodimers Targeting PSMA To compare the effectiveness of different bispecific polypeptide heterodimer molecules at inducing target-dependent T-cell cytotoxicity, two different homodimeric bispecific molecules (TSC194, TSC249) with a common anti-PSMA binding domain (hu107-1A4) and two different anti-CD3 binding domains (a Cris7 scFV for TSC194, the scFv from DRA222 for TSC249) were compared. TSC194 is a homodimeric bispecific ((huVL-VH#2 107-1A4 scFv-Fc-Cris7 scFv) (SEQ ID NO:250 & 251)

C4-2B cells (PSMA+) were obtained from MD Anderson and cultured according to published culture conditions in RPMI-1640 media (Life Technologies, Carlsbad, Calif.) plus 10% FBS. Peripheral blood mononuclear cells (PBMCs) were isolated from human blood using standard Ficoll gradients and washed in saline buffer. T-cells were additionally isolated from PBMC using a Pan T-cell Isolation Kit II from Miltenyi Biotec (Bergisch Gladbach, Germany) using the manufacturer's protocol.

Cytotoxicity was assessed by a $^{51}$Cr release assay. Approximately $5\times10^6$ C4-2 cells were treated with 0.3 mCi of $^{51}$Cr and incubated for 75 minutes at 37° C. After 75 minutes, cells were washed 3 times with media (RPMI +10% FBS) and resuspended in 11.5 mL of media. From this suspension, 50 μL was dispensed per well into 96 well U-bottom plates (approximately 20,000 cells/well). Concentrations of bispecific molecules ranging from 500 pM to 0.2 pM were added to the C4-2 cells, bringing the total volume to 100 μL/well. Target cells were incubated at room temperature for 15 minutes. Then 100 μL of isolated T-cells (approximately 200,000) were added to bring the T-cell to target cell ratio to 10:1. 50 μL of 0.8% NP-40 was added to a control well containing target cells, left for 15 minutes, then 100 μL of media was added to provide a total lysis control.

Plates were incubated for 4 hours, spun at 1500 rpm for 3 minutes, and 25 μL of supernatant was transferred from each well to the corresponding well of a 96-well Luma sample plate. Sample plates were allowed to air dry in a chemical safety hood for 18 hours, and then radioactivity was read on a Topcount scintillation counter using a standard protocol.

Figure 27:
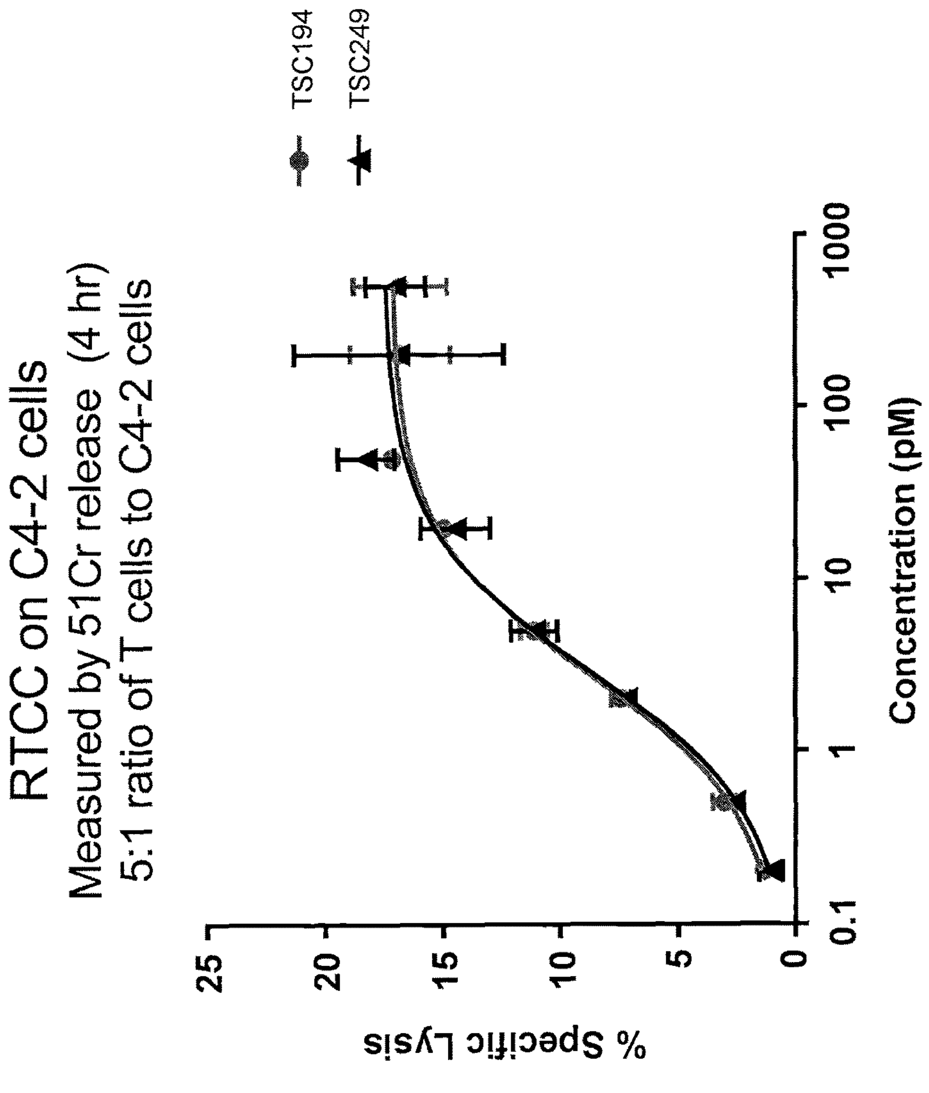
FIG. 27 depicts results from a redirected T-cell cytotoxicity assay using the homodimeric bispecific polypeptides TSC194 and TSC249 that target both PSMA.

Analysis of cytotoxicity data showed T-cell directed cytotoxicity with the C4-2 cells in the presence of T-cells and anti-PSMA directed bispecific molecules (FIG. 27). For the homodimeric bispecific polypeptides (TSC194, TSC249), observed cytotoxicity was comparable between TSC194 and TSC249 (Table 10), suggesting that the DRA222 anti-CD3 scFv binding domain pI variant had equivalent activity to the parental Cris7 binding domain.

TABLE 10

Observed Cytotoxicity

| | $EC_{50}$ for RTCC |
|---|---|
| TSC194 | 2.8 ± 0.6 pM |
| TSC249 | 2.9 ± 1.0 pM |

SEQUENCE LISTING

```
<160> NUMBER OF SEQ ID NOS: 255

<210> SEQ ID NO 1
<211> LENGTH: 66
<212> TYPE: DNA
<213> ORGANISM: Artificial
<220> FEATURE:
<223> OTHER INFORMATION: Signal peptide

<400> SEQUENCE: 1

atggattttc aagtgcagat tttcagcttc ctgctaatca gtgcttcagt cataatgtcg     60

cgagga                                                                 66


<210> SEQ ID NO 2
<211> LENGTH: 22
<212> TYPE: PRT
<213> ORGANISM: Artificial
```

<220> FEATURE:
<223> OTHER INFORMATION: Signal peptide

<400> SEQUENCE: 2

Met Asp Phe Gln Val Gln Ile Phe Ser Phe Leu Leu Ile Ser Ala Ser
1               5                   10                  15

Val Ile Met Ser Arg Gly
            20

<210> SEQ ID NO 3
<211> LENGTH: 1434
<212> TYPE: DNA
<213> ORGANISM: Artificial
<220> FEATURE:
<223> OTHER INFORMATION: DRA209 (H2 L1 with IgG4 AA ADCC-CDC null Fc)

<400> SEQUENCE: 3
caggtccagc tggtgcagtc tgggggcgga gtggtgcagc ctgggcggtc actgaggctg 60
tcctgcaagg cttctggcta cacctttact agatctacga tgcactgggt aaggcaggcc 120
cctggaaagg gtctggaatg gattggatac attaatccta gcagtgctta tactaattac 180
aatcagaaat tcaaggacag gttcacaatc agcgcagaca aatccaagag cacagccttc 240
ctgcagatgg acagcctgag gcccgaggac accggcgtct atttctgtgc acggccccaa 300
gtccactatg attacaacgg gtttccttac tggggccaag ggactcccgt cactgtctct 360
agcggtggcg gagggtctgg gggtggcgga tccggaggtg gtggctctgc acaagacatc 420
cagatgaccc agtctccaag cagcctgtct gcaagcgtgg gggacagggt caccatgacc 480
tgcagtgcca gctcaagtgt aagttacatg aactggtacc agcagaagcc gggcaaggcc 540
cccaaaagat ggatttatga ctcatccaaa ctggcttctg gagtccctgc tcgcttcagt 600
ggcagtgggt ctgggaccga ctataccctc acaatcagca gcctgcagcc cgaagatttc 660
gccacttatt actgccagca gtggagtcgt aacccaccca cgttcggagg ggggaccaag 720
ctacaaatta cacgacgaac tgagcccaaa tcttctgaca aaactcacac atgcccaccg 780
tgcccagcac ctgaagccgc agctccgtca gtcttcctct tccccccaaa acccaaggac 840
accctcatga tctcccggac ccctgaggtc acgtgcgtgg tggtggacgt gagccaggaa 900
gaccccgagg tccagttcaa ctggtacgtg gatggcgtgg aggtgcataa tgccaagaca 960
aagccgcggg aggagcagtt caacagcacg taccgtgtgg tcagcgtcct caccgtcctg 1020
caccaggact ggctgaacgg caaggcatac gcctgcgctg tctccaacaa aggcctcccg 1080
tcctccatcg agaaaaccat ctccaaagcc aaagggcagc cccgagagcc acaggtgtac 1140
accctgcccc catcccagga ggagatgacc aagaaccagg tcagcctgac ctgcctggtc 1200
aaaggcttct accccagcga catcgccgtg gagtgggaga gcaatgggca gccggagaac 1260
aactacaaga ccacgcctcc cgtgctggac tccgacggct ccttcttcct ctacagcagg 1320
ctaaccgtgg acaagagccg gtggcaggag gggaatgtct tctcatgctc cgtgatgcat 1380
gaggctctgc acaaccacta cacacagaag agcctctccc tgtctccggg taaa 1434

<210> SEQ ID NO 4
<211> LENGTH: 478
<212> TYPE: PRT
<213> ORGANISM: Artificial
<220> FEATURE:
<223> OTHER INFORMATION: DRA209 (H3 L1 with IgG4 AA ADCC-CDC null Fc)

<400> SEQUENCE: 4

-continued

```
Gln Val Gln Leu Val Gln Ser Gly Gly Gly Val Val Gln Pro Gly Arg
1               5                   10                  15

Ser Leu Arg Leu Ser Cys Lys Ala Ser Gly Tyr Thr Phe Thr Arg Ser
            20                  25                  30

Thr Met His Trp Val Arg Gln Ala Pro Gly Lys Gly Leu Glu Trp Ile
        35                  40                  45

Gly Tyr Ile Asn Pro Ser Ser Ala Tyr Thr Asn Tyr Asn Gln Lys Phe
    50                  55                  60

Lys Asp Arg Phe Thr Ile Ser Ala Asp Lys Ser Lys Ser Thr Ala Phe
65                  70                  75                  80

Leu Gln Met Asp Ser Leu Arg Pro Glu Asp Thr Gly Val Tyr Phe Cys
                85                  90                  95

Ala Arg Pro Gln Val His Tyr Asp Tyr Asn Gly Phe Pro Tyr Trp Gly
            100                 105                 110

Gln Gly Thr Pro Val Thr Val Ser Ser Gly Gly Gly Gly Ser Gly Gly
        115                 120                 125

Gly Gly Ser Gly Gly Gly Gly Ser Ala Gln Asp Ile Gln Met Thr Gln
    130                 135                 140

Ser Pro Ser Ser Leu Ser Ala Ser Val Gly Asp Arg Val Thr Met Thr
145                 150                 155                 160

Cys Ser Ala Ser Ser Ser Val Ser Tyr Met Asn Trp Tyr Gln Gln Lys
                165                 170                 175

Pro Gly Lys Ala Pro Lys Arg Trp Ile Tyr Asp Ser Ser Lys Leu Ala
            180                 185                 190

Ser Gly Val Pro Ala Arg Phe Ser Gly Ser Gly Ser Gly Thr Asp Tyr
        195                 200                 205

Thr Leu Thr Ile Ser Ser Leu Gln Pro Glu Asp Phe Ala Thr Tyr Tyr
    210                 215                 220

Cys Gln Gln Trp Ser Arg Asn Pro Pro Thr Phe Gly Gly Gly Thr Lys
225                 230                 235                 240

Leu Gln Ile Thr Arg Arg Thr Glu Pro Lys Ser Ser Asp Lys Thr His
                245                 250                 255

Thr Cys Pro Pro Cys Pro Ala Pro Glu Ala Ala Ala Pro Ser Val Phe
            260                 265                 270

Leu Phe Pro Pro Lys Pro Lys Asp Thr Leu Met Ile Ser Arg Thr Pro
        275                 280                 285

Glu Val Thr Cys Val Val Val Asp Val Ser Gln Glu Asp Pro Glu Val
    290                 295                 300

Gln Phe Asn Trp Tyr Val Asp Gly Val Glu Val His Asn Ala Lys Thr
305                 310                 315                 320

Lys Pro Arg Glu Glu Gln Phe Asn Ser Thr Tyr Arg Val Val Ser Val
                325                 330                 335

Leu Thr Val Leu His Gln Asp Trp Leu Asn Gly Lys Ala Tyr Ala Cys
            340                 345                 350

Ala Val Ser Asn Lys Gly Leu Pro Ser Ser Ile Glu Lys Thr Ile Ser
        355                 360                 365

Lys Ala Lys Gly Gln Pro Arg Glu Pro Gln Val Tyr Thr Leu Pro Pro
    370                 375                 380

Ser Gln Glu Glu Met Thr Lys Asn Gln Val Ser Leu Thr Cys Leu Val
385                 390                 395                 400

Lys Gly Phe Tyr Pro Ser Asp Ile Ala Val Glu Trp Glu Ser Asn Gly
                405                 410                 415

Gln Pro Glu Asn Asn Tyr Lys Thr Thr Pro Pro Val Leu Asp Ser Asp
```

-continued

```
            420                 425                 430

Gly Ser Phe Phe Leu Tyr Ser Arg Leu Thr Val Asp Lys Ser Arg Trp
        435                 440                 445

Gln Glu Gly Asn Val Phe Ser Cys Ser Val Met His Glu Ala Leu His
    450                 455                 460

Asn His Tyr Thr Gln Lys Ser Leu Ser Leu Ser Pro Gly Lys
465                 470                 475
```

<210> SEQ ID NO 5
<211> LENGTH: 1434
<212> TYPE: DNA
<213> ORGANISM: Artificial
<220> FEATURE:
<223> OTHER INFORMATION: DRA219 (H3 L1 IgG4 AA ADCC-CDC null Fc)

<400> SEQUENCE: 5

```
caggtccagc tggtgcagtc tgggggcgga gtggtgcagc ctgggcggtc actgaggctg     60

tcctgcaagg cttctggcta cacctttact agatctacga tgcactgggt aaggcaggcc    120

cctggaaagg gtctggaatg gattggatac attaatccta gcagtgctta tactaattac    180

aatcagaaat tcaaggacag gttcacaatc agcgcagaca aatccaagag cacagccttc    240

ctgcagatgg acagcctgag gcccgaggac accggcgtct atttctgtgc acggccccaa    300

gtccactatg attacaacgg gtttccttac tggggccaag ggactcccgt cactgtctct    360

agcggtggcg gagggtctgg gggtggcgga tccggaggtg gtggctctgc acaagacatc    420

cagatgaccc agtctccaag cagcctgtct gcaagcgtgg gggacagggt caccatgacc    480

tgcagtgcca gctcaagtgt aagttacatg aactggtacc agcagaagcc gggcaaggcc    540

cccaaaagat ggatttatga ctcatccaaa ctggcttctg gagtccctgc tcgcttcagt    600

ggcagtgggt ctgggaccga ctataccctc acaatcagca gcctgcagcc cgaagatttc    660

gccacttatt actgccagca gtggagtcgt aacccaccca cgttcggagg ggggaccaag    720

ctacaaatta catcctcgag cgagcccaaa tcttctgaca aaactcacac atgcccaccg    780

tgcccagcac ctgaagccgc agctccgtca gtcttcctct tccccccaaa acccaaggac    840

accctcatga tctcccggac ccctgaggtc acgtgcgtgg tggtggacgt gagccaggaa    900

gaccccgagg tccagttcaa ctggtacgtg gatggcgtgg aggtgcataa tgccaagaca    960

aagccgcggg aggagcagtt caacagcacg taccgtgtgg tcagcgtcct caccgtcctg   1020

caccaggact ggctgaacgg caaggcatac gcctgcgctg tctccaacaa aggcctcccg   1080

tcctccatcg agaaaaccat ctccaaagcc aaagggcagc cccgagagcc acaggtgtac   1140

accctgcccc catcccagga ggagatgacc aagaaccagg tcagcctgac ctgcctggtc   1200

aaaggcttct accccagcga catcgccgtg gagtgggaga gcaatgggca gccggagaac   1260

aactacaaga ccacgcctcc cgtgctggac tccgacggct ccttcttcct ctacagcagg   1320

ctaaccgtgg acaagagccg gtggcaggag gggaatgtct tctcatgctc cgtgatgcat   1380

gaggctctgc acaaccacta cacacagaag agcctctccc tgtctccggg taaa         1434
```

<210> SEQ ID NO 6
<211> LENGTH: 478
<212> TYPE: PRT
<213> ORGANISM: Artificial
<220> FEATURE:
<223> OTHER INFORMATION: DRA219 (H3 L1 IgG4 AA ADCC-CDC null Fc)

<400> SEQUENCE: 6

-continued

```
Gln Val Gln Leu Val Gln Ser Gly Gly Gly Val Val Gln Pro Gly Arg
1               5                   10                  15

Ser Leu Arg Leu Ser Cys Lys Ala Ser Gly Tyr Thr Phe Thr Arg Ser
            20                  25                  30

Thr Met His Trp Val Arg Gln Ala Pro Gly Lys Gly Leu Glu Trp Ile
        35                  40                  45

Gly Tyr Ile Asn Pro Ser Ser Ala Tyr Thr Asn Tyr Asn Gln Lys Phe
    50                  55                  60

Lys Asp Arg Phe Thr Ile Ser Ala Asp Lys Ser Lys Ser Thr Ala Phe
65                  70                  75                  80

Leu Gln Met Asp Ser Leu Arg Pro Glu Asp Thr Gly Val Tyr Phe Cys
                85                  90                  95

Ala Arg Pro Gln Val His Tyr Asp Tyr Asn Gly Phe Pro Tyr Trp Gly
            100                 105                 110

Gln Gly Thr Pro Val Thr Val Ser Ser Gly Gly Gly Gly Ser Gly Gly
        115                 120                 125

Gly Gly Ser Gly Gly Gly Gly Ser Ala Gln Asp Ile Gln Met Thr Gln
    130                 135                 140

Ser Pro Ser Ser Leu Ser Ala Ser Val Gly Asp Arg Val Thr Met Thr
145                 150                 155                 160

Cys Ser Ala Ser Ser Ser Val Ser Tyr Met Asn Trp Tyr Gln Gln Lys
                165                 170                 175

Pro Gly Lys Ala Pro Lys Arg Trp Ile Tyr Asp Ser Ser Lys Leu Ala
            180                 185                 190

Ser Gly Val Pro Ala Arg Phe Ser Gly Ser Gly Ser Gly Thr Asp Tyr
        195                 200                 205

Thr Leu Thr Ile Ser Ser Leu Gln Pro Glu Asp Phe Ala Thr Tyr Tyr
    210                 215                 220

Cys Gln Gln Trp Ser Arg Asn Pro Pro Thr Phe Gly Gly Gly Thr Lys
225                 230                 235                 240

Leu Gln Ile Thr Ser Ser Ser Glu Pro Lys Ser Ser Asp Lys Thr His
                245                 250                 255

Thr Cys Pro Pro Cys Pro Ala Pro Glu Ala Ala Ala Pro Ser Val Phe
            260                 265                 270

Leu Phe Pro Pro Lys Pro Lys Asp Thr Leu Met Ile Ser Arg Thr Pro
        275                 280                 285

Glu Val Thr Cys Val Val Val Asp Val Ser Gln Glu Asp Pro Glu Val
    290                 295                 300

Gln Phe Asn Trp Tyr Val Asp Gly Val Glu Val His Asn Ala Lys Thr
305                 310                 315                 320

Lys Pro Arg Glu Glu Gln Phe Asn Ser Thr Tyr Arg Val Val Ser Val
                325                 330                 335

Leu Thr Val Leu His Gln Asp Trp Leu Asn Gly Lys Ala Tyr Ala Cys
            340                 345                 350

Ala Val Ser Asn Lys Gly Leu Pro Ser Ser Ile Glu Lys Thr Ile Ser
        355                 360                 365

Lys Ala Lys Gly Gln Pro Arg Glu Pro Gln Val Tyr Thr Leu Pro Pro
    370                 375                 380

Ser Gln Glu Glu Met Thr Lys Asn Gln Val Ser Leu Thr Cys Leu Val
385                 390                 395                 400

Lys Gly Phe Tyr Pro Ser Asp Ile Ala Val Glu Trp Glu Ser Asn Gly
                405                 410                 415

Gln Pro Glu Asn Asn Tyr Lys Thr Thr Pro Pro Val Leu Asp Ser Asp
```

```
            420                 425                 430

Gly Ser Phe Phe Leu Tyr Ser Arg Leu Thr Val Asp Lys Ser Arg Trp
        435                 440                 445

Gln Glu Gly Asn Val Phe Ser Cys Ser Val Met His Glu Ala Leu His
    450                 455                 460

Asn His Tyr Thr Gln Lys Ser Leu Ser Leu Ser Pro Gly Lys
465                 470                 475


<210> SEQ ID NO 7
<211> LENGTH: 1434
<212> TYPE: DNA
<213> ORGANISM: Artificial
<220> FEATURE:
<223> OTHER INFORMATION: DRA222 (H4 L1 with IgG4 AA ADCC-CDC null Fc)

<400> SEQUENCE: 7

caggtccagc tggtggagtc tgggggcgga gtggtgcagc ctgggcggtc actgaggctg     60

tcctgcaagg cttctggcta cacctttact agatctacga tgcactgggt aaggcaggcc    120

cctggacaag gtctggaatg gattggatac attaatccta gcagtgctta tactaattac    180

aatcagaaat tcaaggacag gttcacaatc agcgcagaca aatccaagag cacagccttc    240

ctgcagatgg acagcctgag gcccgaggac accggcgtct atttctgtgc acggccccaa    300

gtccactatg attacaacgg gtttccttac tggggccaag ggactcccgt cactgtctct    360

agcggtggcg gagggtctgg gggtggcgga tccggaggtg gtggctctgc acaagacatc    420

cagatgaccc agtctccaag cagcctgtct gcaagcgtgg gggacagggt caccatgacc    480

tgcagtgcca gctcaagtgt aagttacatg aactggtacc agcagaagcc gggcaaggcc    540

cccaaaagat ggatttatga ctcatccaaa ctggcttctg gagtccctgc tcgcttcagt    600

ggcagtgggt ctgggaccga ctataccctc acaatcagca gcctgcagcc cgaagatttc    660

gccacttatt actgccagca gtggagtcgt aacccaccca cgttcggagg ggggaccaag    720

ctacaaatta catcctcgag cgagcccaaa tcttctgaca aaactcacac atgcccaccg    780

tgcccagcac ctgaagccgc agctccgtca gtcttcctct tccccccaaa acccaaggac    840

accctcatga tctcccggac ccctgaggtc acgtgcgtgg tggtggacgt gagccaggaa    900

gaccccgagg tccagttcaa ctggtacgtg gatggcgtgg aggtgcataa tgccaagaca    960

aagccgcggg aggagcagtt caacagcacg taccgtgtgg tcagcgtcct caccgtcctg   1020

caccaggact ggctgaacgg caaggcatac gcctgcgctg tctccaacaa aggcctcccg   1080

tcctccatcg agaaaaccat ctccaaagcc aaagggcagc cccgagagcc acaggtgtac   1140

accctgcccc catcccagga ggagatgacc aagaaccagg tcagcctgac ctgcctggtc   1200

aaaggcttct accccagcga catcgccgtg gagtgggaga gcaatgggca gccggagaac   1260

aactacaaga ccacgcctcc cgtgctggac tccgacggct ccttcttcct ctacagcagg   1320

ctaaccgtgg acaagagccg gtggcaggag gggaatgtct tctcatgctc cgtgatgcat   1380

gaggctctgc acaaccacta cacacagaag agcctctccc tgtctccggg taaa         1434


<210> SEQ ID NO 8
<211> LENGTH: 478
<212> TYPE: PRT
<213> ORGANISM: Artificial
<220> FEATURE:
<223> OTHER INFORMATION: DRA222 (H4 L1 with IgG4 AA ADCC-CDC null Fc)

<400> SEQUENCE: 8
```

-continued

```
Gln Val Gln Leu Val Glu Ser Gly Gly Gly Val Val Gln Pro Gly Arg
1               5                   10                  15

Ser Leu Arg Leu Ser Cys Lys Ala Ser Gly Tyr Thr Phe Thr Arg Ser
            20                  25                  30

Thr Met His Trp Val Arg Gln Ala Pro Gly Gln Gly Leu Glu Trp Ile
        35                  40                  45

Gly Tyr Ile Asn Pro Ser Ser Ala Tyr Thr Asn Tyr Asn Gln Lys Phe
    50                  55                  60

Lys Asp Arg Phe Thr Ile Ser Ala Asp Lys Ser Lys Ser Thr Ala Phe
65                  70                  75                  80

Leu Gln Met Asp Ser Leu Arg Pro Glu Asp Thr Gly Val Tyr Phe Cys
                85                  90                  95

Ala Arg Pro Gln Val His Tyr Asp Tyr Asn Gly Phe Pro Tyr Trp Gly
            100                 105                 110

Gln Gly Thr Pro Val Thr Val Ser Ser Gly Gly Gly Gly Ser Gly Gly
        115                 120                 125

Gly Gly Ser Gly Gly Gly Gly Ser Ala Gln Asp Ile Gln Met Thr Gln
    130                 135                 140

Ser Pro Ser Ser Leu Ser Ala Ser Val Gly Asp Arg Val Thr Met Thr
145                 150                 155                 160

Cys Ser Ala Ser Ser Ser Val Ser Tyr Met Asn Trp Tyr Gln Gln Lys
                165                 170                 175

Pro Gly Lys Ala Pro Lys Arg Trp Ile Tyr Asp Ser Ser Lys Leu Ala
            180                 185                 190

Ser Gly Val Pro Ala Arg Phe Ser Gly Ser Gly Ser Gly Thr Asp Tyr
        195                 200                 205

Thr Leu Thr Ile Ser Ser Leu Gln Pro Glu Asp Phe Ala Thr Tyr Tyr
    210                 215                 220

Cys Gln Gln Trp Ser Arg Asn Pro Pro Thr Phe Gly Gly Gly Thr Lys
225                 230                 235                 240

Leu Gln Ile Thr Ser Ser Ser Glu Pro Lys Ser Ser Asp Lys Thr His
                245                 250                 255

Thr Cys Pro Pro Cys Pro Ala Pro Glu Ala Ala Ala Pro Ser Val Phe
            260                 265                 270

Leu Phe Pro Pro Lys Pro Lys Asp Thr Leu Met Ile Ser Arg Thr Pro
        275                 280                 285

Glu Val Thr Cys Val Val Val Asp Val Ser Gln Glu Asp Pro Glu Val
    290                 295                 300

Gln Phe Asn Trp Tyr Val Asp Gly Val Glu Val His Asn Ala Lys Thr
305                 310                 315                 320

Lys Pro Arg Glu Glu Gln Phe Asn Ser Thr Tyr Arg Val Val Ser Val
                325                 330                 335

Leu Thr Val Leu His Gln Asp Trp Leu Asn Gly Lys Ala Tyr Ala Cys
            340                 345                 350

Ala Val Ser Asn Lys Gly Leu Pro Ser Ser Ile Glu Lys Thr Ile Ser
        355                 360                 365

Lys Ala Lys Gly Gln Pro Arg Glu Pro Gln Val Tyr Thr Leu Pro Pro
    370                 375                 380

Ser Gln Glu Glu Met Thr Lys Asn Gln Val Ser Leu Thr Cys Leu Val
385                 390                 395                 400

Lys Gly Phe Tyr Pro Ser Asp Ile Ala Val Glu Trp Glu Ser Asn Gly
                405                 410                 415

Gln Pro Glu Asn Asn Tyr Lys Thr Thr Pro Pro Val Leu Asp Ser Asp
```

```
            420                 425                 430

Gly Ser Phe Phe Leu Tyr Ser Arg Leu Thr Val Asp Lys Ser Arg Trp
        435                 440                 445

Gln Glu Gly Asn Val Phe Ser Cys Ser Val Met His Glu Ala Leu His
    450                 455                 460

Asn His Tyr Thr Gln Lys Ser Leu Ser Leu Ser Pro Gly Lys
465                 470                 475
```

<210> SEQ ID NO 9
<211> LENGTH: 1434
<212> TYPE: DNA
<213> ORGANISM: Artificial
<220> FEATURE:
<223> OTHER INFORMATION: DRA221 (H4 L3 with IgG4 AA ADCC-CDC null Fc)

<400> SEQUENCE: 9

```
caggtccagc tggtggagtc tgggggcgga gtggtgcagc ctgggcggtc actgaggctg     60
tcctgcaagg cttctggcta cacctttact agatctacga tgcactgggt aaggcaggcc    120
cctggacaag gtctggaatg gattggatac attaatccta gcagtgctta tactaattac    180
aatcagaaat tcaaggacag gttcacaatc agcgcagaca aatccaagag cacagccttc    240
ctgcagatgg acagcctgag gcccgaggac accggcgtct atttctgtgc acggccccaa    300
gtccactatg attacaacgg gtttccttac tggggccaag ggactcccgt cactgtctct    360
agcggtggcg gagggtctgg gggtggcgga tccggaggtg gtggctctgc acaagacatc    420
cagatgaccc agtctccaag cagcctgtct gcaagcgtgg gggacagggt caccatgacc    480
tgcagtgcca gctcaagtgt aagttacatg aactggtacc agcagaagcc gggcaaggcc    540
cccaaactcc tcatttatga ctcatccaaa ctggcttctg gagtccctgc tcgcttcagt    600
ggcagtgggt ctgggaccga ctataccctc acaatcagca gcctgcagcc cgaagatttc    660
gccacttatt actgccagca gtggagtcgt aacccaccca ctttcggcgg agggaccaag    720
gtggagatca aatcctcgag cgagcccaaa tcttctgaca aaactcacac atgcccaccg    780
tgcccagcac ctgaagccgc agctccgtca gtcttcctct tccccccaaa acccaaggac    840
accctcatga tctcccggac ccctgaggtc acgtgcgtgg tggtggacgt gagccaggaa    900
gaccccgagg tccagttcaa ctggtacgtg gatggcgtgg aggtgcataa tgccaagaca    960
aagccgcggg aggagcagtt caacagcacg taccgtgtgg tcagcgtcct caccgtcctg   1020
caccaggact ggctgaacgg caaggcatac gcctgcgctg tctccaacaa aggcctcccg   1080
tcctccatcg agaaaaccat ctccaaagcc aaagggcagc cccgagagcc acaggtgtac   1140
accctgcccc catcccagga ggagatgacc aagaaccagg tcagcctgac ctgcctggtc   1200
aaaggcttct accccagcga catcgccgtg gagtgggaga gcaatgggca gccggagaac   1260
aactacaaga ccacgcctcc cgtgctggac tccgacggct ccttcttcct ctacagcagg   1320
ctaaccgtgg acaagagccg gtggcaggag gggaatgtct tctcatgctc cgtgatgcat   1380
gaggctctgc acaaccacta cacacagaag agcctctccc tgtctccggg taaa         1434
```

<210> SEQ ID NO 10
<211> LENGTH: 478
<212> TYPE: PRT
<213> ORGANISM: Artificial
<220> FEATURE:
<223> OTHER INFORMATION: DRA221 (H4 L3 with IgG4 AA ADCC-CDC null Fc)

<400> SEQUENCE: 10

-continued

```
Gln Val Gln Leu Val Glu Ser Gly Gly Gly Val Val Gln Pro Gly Arg
1               5                   10                  15

Ser Leu Arg Leu Ser Cys Lys Ala Ser Gly Tyr Thr Phe Thr Arg Ser
            20                  25                  30

Thr Met His Trp Val Arg Gln Ala Pro Gly Gln Gly Leu Glu Trp Ile
        35                  40                  45

Gly Tyr Ile Asn Pro Ser Ser Ala Tyr Thr Asn Tyr Asn Gln Lys Phe
    50                  55                  60

Lys Asp Arg Phe Thr Ile Ser Ala Asp Lys Ser Lys Ser Thr Ala Phe
65                  70                  75                  80

Leu Gln Met Asp Ser Leu Arg Pro Glu Asp Thr Gly Val Tyr Phe Cys
                85                  90                  95

Ala Arg Pro Gln Val His Tyr Asp Tyr Asn Gly Phe Pro Tyr Trp Gly
            100                 105                 110

Gln Gly Thr Pro Val Thr Val Ser Ser Gly Gly Gly Gly Ser Gly Gly
        115                 120                 125

Gly Gly Ser Gly Gly Gly Gly Ser Ala Gln Asp Ile Gln Met Thr Gln
    130                 135                 140

Ser Pro Ser Ser Leu Ser Ala Ser Val Gly Asp Arg Val Thr Met Thr
145                 150                 155                 160

Cys Ser Ala Ser Ser Ser Val Ser Tyr Met Asn Trp Tyr Gln Gln Lys
                165                 170                 175

Pro Gly Lys Ala Pro Lys Leu Leu Ile Tyr Asp Ser Ser Lys Leu Ala
            180                 185                 190

Ser Gly Val Pro Ala Arg Phe Ser Gly Ser Gly Ser Gly Thr Asp Tyr
        195                 200                 205

Thr Leu Thr Ile Ser Ser Leu Gln Pro Glu Asp Phe Ala Thr Tyr Tyr
    210                 215                 220

Cys Gln Gln Trp Ser Arg Asn Pro Pro Thr Phe Gly Gly Gly Thr Lys
225                 230                 235                 240

Val Glu Ile Lys Ser Ser Ser Glu Pro Lys Ser Ser Asp Lys Thr His
                245                 250                 255

Thr Cys Pro Pro Cys Pro Ala Pro Glu Ala Ala Ala Pro Ser Val Phe
            260                 265                 270

Leu Phe Pro Pro Lys Pro Lys Asp Thr Leu Met Ile Ser Arg Thr Pro
        275                 280                 285

Glu Val Thr Cys Val Val Val Asp Val Ser Gln Glu Asp Pro Glu Val
    290                 295                 300

Gln Phe Asn Trp Tyr Val Asp Gly Val Glu Val His Asn Ala Lys Thr
305                 310                 315                 320

Lys Pro Arg Glu Glu Gln Phe Asn Ser Thr Tyr Arg Val Val Ser Val
                325                 330                 335

Leu Thr Val Leu His Gln Asp Trp Leu Asn Gly Lys Ala Tyr Ala Cys
            340                 345                 350

Ala Val Ser Asn Lys Gly Leu Pro Ser Ser Ile Glu Lys Thr Ile Ser
        355                 360                 365

Lys Ala Lys Gly Gln Pro Arg Glu Pro Gln Val Tyr Thr Leu Pro Pro
    370                 375                 380

Ser Gln Glu Glu Met Thr Lys Asn Gln Val Ser Leu Thr Cys Leu Val
385                 390                 395                 400

Lys Gly Phe Tyr Pro Ser Asp Ile Ala Val Glu Trp Glu Ser Asn Gly
                405                 410                 415

Gln Pro Glu Asn Asn Tyr Lys Thr Thr Pro Pro Val Leu Asp Ser Asp
```

```
        420                 425                 430

Gly Ser Phe Phe Leu Tyr Ser Arg Leu Thr Val Asp Lys Ser Arg Trp
        435                 440                 445

Gln Glu Gly Asn Val Phe Ser Cys Ser Val Met His Glu Ala Leu His
    450                 455                 460

Asn His Tyr Thr Gln Lys Ser Leu Ser Leu Ser Pro Gly Lys
465                 470                 475


<210> SEQ ID NO 11
<211> LENGTH: 1434
<212> TYPE: DNA
<213> ORGANISM: Artificial
<220> FEATURE:
<223> OTHER INFORMATION: DRA223 (H3 L3 with IgG4 AA ADCC-CDC null Fc)

<400> SEQUENCE: 11

caggtccagc tggtgcagtc tgggggcgga gtggtgcagc ctgggcggtc actgaggctg     60

tcctgcaagg cttctggcta cacctttact agatctacga tgcactgggt aaggcaggcc    120

cctggaaagg gtctggaatg gattggatac attaatccta gcagtgctta tactaattac    180

aatcagaaat tcaaggacag gttcacaatc agcgcagaca aatccaagag cacagccttc    240

ctgcagatgg acagcctgag gcccgaggac accggcgtct atttctgtgc acggccccaa    300

gtccactatg attacaacgg gtttccttac tggggccaag ggactcccgt cactgtctct    360

agcggtggcg gagggtctgg gggtggcgga tccggaggtg gtggctctgc acaagacatc    420

cagatgaccc agtctccaag cagcctgtct gcaagcgtgg gggacagggt caccatgacc    480

tgcagtgcca gctcaagtgt aagttacatg aactggtacc agcagaagcc gggcaaggcc    540

cccaaactcc tcatttatga ctcatccaaa ctggcttctg gagtccctgc tcgcttcagt    600

ggcagtgggt ctgggaccga ctataccctc acaatcagca gcctgcagcc cgaagatttc    660

gccacttatt actgccagca gtggagtcgt aacccaccca ctttcggcgg agggaccaag    720

gtggagatca aatcctcgag cgagcccaaa tcttctgaca aaactcacac atgcccaccg    780

tgcccagcac ctgaagccgc agctccgtca gtcttcctct tccccccaaa acccaaggac    840

accctcatga tctcccggac ccctgaggtc acgtgcgtgg tggtggacgt gagccaggaa    900

gaccccgagg tccagttcaa ctggtacgtg gatggcgtgg aggtgcataa tgccaagaca    960

aagccgcggg aggagcagtt caacagcacg taccgtgtgg tcagcgtcct caccgtcctg   1020

caccaggact ggctgaacgg caaggcatac gcctgcgctg tctccaacaa aggcctcccg   1080

tcctccatcg agaaaaccat ctccaaagcc aaagggcagc cccgagagcc acaggtgtac   1140

accctgcccc catcccagga ggagatgacc aagaaccagg tcagcctgac ctgcctggtc   1200

aaaggcttct accccagcga catcgccgtg gagtgggaga gcaatgggca gccggagaac   1260

aactacaaga ccacgcctcc cgtgctggac tccgacggct ccttcttcct ctacagcagg   1320

ctaaccgtgg acaagagccg gtggcaggag gggaatgtct tctcatgctc cgtgatgcat   1380

gaggctctgc acaaccacta cacacagaag agcctctccc tgtctccggg taaa          1434


<210> SEQ ID NO 12
<211> LENGTH: 478
<212> TYPE: PRT
<213> ORGANISM: Artificial
<220> FEATURE:
<223> OTHER INFORMATION: DRA223 (H3 L3 with IgG4 AA ADCC-CDC null Fc)

<400> SEQUENCE: 12
```

-continued

```
Gln Val Gln Leu Val Gln Ser Gly Gly Gly Val Val Gln Pro Gly Arg
1               5                   10                  15

Ser Leu Arg Leu Ser Cys Lys Ala Ser Gly Tyr Thr Phe Thr Arg Ser
            20                  25                  30

Thr Met His Trp Val Arg Gln Ala Pro Gly Lys Gly Leu Glu Trp Ile
        35                  40                  45

Gly Tyr Ile Asn Pro Ser Ser Ala Tyr Thr Asn Tyr Asn Gln Lys Phe
    50                  55                  60

Lys Asp Arg Phe Thr Ile Ser Ala Asp Lys Ser Lys Ser Thr Ala Phe
65                  70                  75                  80

Leu Gln Met Asp Ser Leu Arg Pro Glu Asp Thr Gly Val Tyr Phe Cys
                85                  90                  95

Ala Arg Pro Gln Val His Tyr Asp Tyr Asn Gly Phe Pro Tyr Trp Gly
            100                 105                 110

Gln Gly Thr Pro Val Thr Val Ser Ser Gly Gly Gly Gly Ser Gly Gly
        115                 120                 125

Gly Gly Ser Gly Gly Gly Gly Ser Ala Gln Asp Ile Gln Met Thr Gln
    130                 135                 140

Ser Pro Ser Ser Leu Ser Ala Ser Val Gly Asp Arg Val Thr Met Thr
145                 150                 155                 160

Cys Ser Ala Ser Ser Ser Val Ser Tyr Met Asn Trp Tyr Gln Gln Lys
                165                 170                 175

Pro Gly Lys Ala Pro Lys Leu Leu Ile Tyr Asp Ser Ser Lys Leu Ala
            180                 185                 190

Ser Gly Val Pro Ala Arg Phe Ser Gly Ser Gly Ser Gly Thr Asp Tyr
        195                 200                 205

Thr Leu Thr Ile Ser Ser Leu Gln Pro Glu Asp Phe Ala Thr Tyr Tyr
    210                 215                 220

Cys Gln Gln Trp Ser Arg Asn Pro Pro Thr Phe Gly Gly Gly Thr Lys
225                 230                 235                 240

Val Glu Ile Lys Ser Ser Ser Glu Pro Lys Ser Ser Asp Lys Thr His
                245                 250                 255

Thr Cys Pro Pro Cys Pro Ala Pro Glu Ala Ala Ala Pro Ser Val Phe
            260                 265                 270

Leu Phe Pro Pro Lys Pro Lys Asp Thr Leu Met Ile Ser Arg Thr Pro
        275                 280                 285

Glu Val Thr Cys Val Val Val Asp Val Ser Gln Glu Asp Pro Glu Val
    290                 295                 300

Gln Phe Asn Trp Tyr Val Asp Gly Val Glu Val His Asn Ala Lys Thr
305                 310                 315                 320

Lys Pro Arg Glu Glu Gln Phe Asn Ser Thr Tyr Arg Val Val Ser Val
                325                 330                 335

Leu Thr Val Leu His Gln Asp Trp Leu Asn Gly Lys Ala Tyr Ala Cys
            340                 345                 350

Ala Val Ser Asn Lys Gly Leu Pro Ser Ser Ile Glu Lys Thr Ile Ser
        355                 360                 365

Lys Ala Lys Gly Gln Pro Arg Glu Pro Gln Val Tyr Thr Leu Pro Pro
    370                 375                 380

Ser Gln Glu Glu Met Thr Lys Asn Gln Val Ser Leu Thr Cys Leu Val
385                 390                 395                 400

Lys Gly Phe Tyr Pro Ser Asp Ile Ala Val Glu Trp Glu Ser Asn Gly
                405                 410                 415

Gln Pro Glu Asn Asn Tyr Lys Thr Thr Pro Pro Val Leu Asp Ser Asp
```

-continued

```
            420                 425                 430

Gly Ser Phe Phe Leu Tyr Ser Arg Leu Thr Val Asp Lys Ser Arg Trp
        435                 440                 445

Gln Glu Gly Asn Val Phe Ser Cys Ser Val Met His Glu Ala Leu His
    450                 455                 460

Asn His Tyr Thr Gln Lys Ser Leu Ser Leu Ser Pro Gly Lys
465                 470                 475


<210> SEQ ID NO 13
<211> LENGTH: 1443
<212> TYPE: DNA
<213> ORGANISM: Artificial
<220> FEATURE:
<223> OTHER INFORMATION: DRA224 (H5 L4 with IgG4 AA ADCC-CDC null Fc)

<400> SEQUENCE: 13

caggtccagc ttgtgcagtc tggggctgag gtgaagaagc ctggggcctc agtgaaggtt     60

tcctgcaagg cttctggata caccttcact agatctacga tgcactgggt gcgccaggcc    120

cccggacaaa ggcttgagtg gatgggatac attaatccta gcagtgctta tactaattac    180

aatcagaaat tcaaggacag agtcaccatt accagggaca catccgcgag cacagcctac    240

atggagctga gcagcctgag atctgaagac acggctgtgt attactgtgc gagaccccaa    300

gtccactatg attacaacgg gtttccttac tggggccaag gaaccctggt caccgtctcc    360

tcaggtggag gcggttcagg cggaggtgga tccggcggtg gcggatcggg tggcggcgga    420

tctgaaattg tgttgacaca gtctccagcc accctgtctt tgtctccagg ggaaagagcc    480

accctctcct gcagtgccag ctcaagtgta agttacatga actggtacca acagaaacct    540

ggccaggctc ccaggctcct catctatgac tcatccaaac tggcttctgg catcccagcc    600

aggttcagtg gcagtgggtc tgggacagac ttcactctca ccatcagcag cctagagcct    660

gaagattttg cagtttatta ctgtcagcag tggagtcgta acccacccac tttcggcgga    720

gggaccaagg tggagatcaa atcctcgagc gagcccaaat cttctgacaa aactcacaca    780

tgcccaccgt gcccagcacc tgaagccgca gctccgtcag tcttcctctt ccccccaaaa    840

cccaaggaca ccctcatgat ctcccggacc cctgaggtca cgtgcgtggt ggtggacgtg    900

agccaggaag accccgaggt ccagttcaac tggtacgtgg atggcgtgga ggtgcataat    960

gccaagacaa agccgcggga ggagcagttc aacagcacgt accgtgtggt cagcgtcctc   1020

accgtcctgc accaggactg gctgaacggc aaggcatacg cctgcgctgt ctccaacaaa   1080

ggcctcccgt cctccatcga gaaaaccatc tccaaagcca aagggcagcc ccgagagcca   1140

caggtgtaca ccctgccccc atcccaggag gagatgacca agaaccaggt cagcctgacc   1200

tgcctggtca aaggcttcta ccccagcgac atcgccgtgg agtgggagag caatgggcag   1260

ccggagaaca actacaagac cacgcctccc gtgctggact ccgacggctc cttcttcctc   1320

tacagcaggc taaccgtgga caagagccgg tggcaggagg ggaatgtctt ctcatgctcc   1380

gtgatgcatg aggctctgca caaccactac acacagaaga gcctctccct gtctccgggt   1440

aaa                                                                 1443


<210> SEQ ID NO 14
<211> LENGTH: 481
<212> TYPE: PRT
<213> ORGANISM: Artificial
<220> FEATURE:
<223> OTHER INFORMATION: DRA224 (H5 L4 with IgG4 AA ADCC-CDC null Fc)
```

<400> SEQUENCE: 14

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Arg Ser
            20                  25                  30

Thr Met His Trp Val Arg Gln Ala Pro Gly Gln Arg Leu Glu Trp Met
        35                  40                  45

Gly Tyr Ile Asn Pro Ser Ser Ala Tyr Thr Asn Tyr Asn Gln Lys Phe
    50                  55                  60

Lys Asp Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Pro Gln Val His Tyr Asp Tyr Asn Gly Phe Pro Tyr Trp Gly
            100                 105                 110

Gln Gly Thr Leu Val Thr Val Ser Ser Gly Gly Gly Gly Ser Gly Gly
        115                 120                 125

Gly Gly Ser Gly Gly Gly Gly Ser Gly Gly Gly Gly Ser Glu Ile Val
    130                 135                 140

Leu Thr Gln Ser Pro Ala Thr Leu Ser Leu Ser Pro Gly Glu Arg Ala
145                 150                 155                 160

Thr Leu Ser Cys Ser Ala Ser Ser Ser Val Ser Tyr Met Asn Trp Tyr
                165                 170                 175

Gln Gln Lys Pro Gly Gln Ala Pro Arg Leu Leu Ile Tyr Asp Ser Ser
            180                 185                 190

Lys Leu Ala Ser Gly Ile Pro Ala Arg Phe Ser Gly Ser Gly Ser Gly
        195                 200                 205

Thr Asp Phe Thr Leu Thr Ile Ser Ser Leu Glu Pro Glu Asp Phe Ala
    210                 215                 220

Val Tyr Tyr Cys Gln Gln Trp Ser Arg Asn Pro Pro Thr Phe Gly Gly
225                 230                 235                 240

Gly Thr Lys Val Glu Ile Lys Ser Ser Ser Glu Pro Lys Ser Ser Asp
                245                 250                 255

Lys Thr His Thr Cys Pro Pro Cys Pro Ala Pro Glu Ala Ala Ala Pro
            260                 265                 270

Ser Val Phe Leu Phe Pro Pro Lys Pro Lys Asp Thr Leu Met Ile Ser
        275                 280                 285

Arg Thr Pro Glu Val Thr Cys Val Val Val Asp Val Ser Gln Glu Asp
    290                 295                 300

Pro Glu Val Gln Phe Asn Trp Tyr Val Asp Gly Val Glu Val His Asn
305                 310                 315                 320

Ala Lys Thr Lys Pro Arg Glu Glu Gln Phe Asn Ser Thr Tyr Arg Val
                325                 330                 335

Val Ser Val Leu Thr Val Leu His Gln Asp Trp Leu Asn Gly Lys Ala
            340                 345                 350

Tyr Ala Cys Ala Val Ser Asn Lys Gly Leu Pro Ser Ser Ile Glu Lys
        355                 360                 365

Thr Ile Ser Lys Ala Lys Gly Gln Pro Arg Glu Pro Gln Val Tyr Thr
    370                 375                 380

Leu Pro Pro Ser Gln Glu Glu Met Thr Lys Asn Gln Val Ser Leu Thr
385                 390                 395                 400

Cys Leu Val Lys Gly Phe Tyr Pro Ser Asp Ile Ala Val Glu Trp Glu
                405                 410                 415
```

Ser Asn Gly Gln Pro Glu Asn Asn Tyr Lys Thr Thr Pro Pro Val Leu
420 425 430

Asp Ser Asp Gly Ser Phe Phe Leu Tyr Ser Arg Leu Thr Val Asp Lys
435 440 445

Ser Arg Trp Gln Glu Gly Asn Val Phe Ser Cys Ser Val Met His Glu
450 455 460

Ala Leu His Asn His Tyr Thr Gln Lys Ser Leu Ser Leu Ser Pro Gly
465 470 475 480

Lys

<210> SEQ ID NO 15
<211> LENGTH: 1443
<212> TYPE: DNA
<213> ORGANISM: Artificial
<220> FEATURE:
<223> OTHER INFORMATION: DRA225 (H6 L4 with IgG4 AA ADCC-CDC null Fc)

<400> SEQUENCE: 15
gaggtgcagc tggtggagtc tgggggaggc ctggtcaagc ctgggggtc cctgagactc 60 tcctgtgcag cctctggatt caccttcagt agatctacga tgcactgggt ccgccaggct 120
ccagggaagg ggctggagtg ggtctcatac attaatccta gcagtgctta tactaattac 180
aatcagaaat tcaaggaccg attcaccatc tccagagaca acgccaagaa ctcactgtat 240
ctgcaaatga acagcctgag agccgaggac acggctgtgt attactgtgc gagaccccaa 300
gtccactatg attacaacgg gtttccttac tggggccaag gaaccctggt caccgtctcc 360
tcaggtggag gcggttcagg cggaggtgga tccggcggtg gcggatcggg tggcggcgga 420
tctgaaattg tgttgacaca gtctccagcc accctgtctt tgtctccagg ggaaagagcc 480
accctctcct gcagtgccag ctcaagtgta agttacatga actggtacca acagaaacct 540
ggccaggctc ccaggctcct catctatgac tcatccaaac tggcttctgg catcccagcc 600
aggttcagtg gcagtgggtc tgggacagac ttcactctca ccatcagcag cctagagcct 660
gaagattttg cagtttatta ctgtcagcag tggagtcgta acccacccac tttcggcgga 720
gggaccaagg tggagatcaa atcctcgagc gagcccaaat cttctgacaa aactcacaca 780
tgcccaccgt gcccagcacc tgaagccgca gctccgtcag tcttcctctt ccccccaaaa 840
cccaaggaca ccctcatgat ctcccggacc cctgaggtca cgtgcgtggt ggtggacgtg 900
agccaggaag accccgaggt ccagttcaac tggtacgtgg atggcgtgga ggtgcataat 960
gccaagacaa agccgcggga ggagcagttc aacagcacgt accgtgtggt cagcgtcctc 1020
accgtcctgc accaggactg gctgaacggc aaggcatacg cctgcgctgt ctccaacaaa 1080
ggcctcccgt cctccatcga gaaaaccatc tccaaagcca aagggcagcc ccgagagcca 1140
caggtgtaca ccctgccccc atcccaggag gagatgacca agaaccaggt cagcctgacc 1200
tgcctggtca aaggcttcta ccccagcgac atcgccgtgg agtgggagag caatgggcag 1260
ccggagaaca actacaagac cacgcctccc gtgctggact ccgacggctc cttcttcctc 1320
tacagcaggc taaccgtgga caagagccgg tggcaggagg ggaatgtctt ctcatgctcc 1380
gtgatgcatg aggctctgca caaccactac acacagaaga gcctctccct gtctccgggt 1440
aaa 1443

<210> SEQ ID NO 16
<211> LENGTH: 481
<212> TYPE: PRT

<213> ORGANISM: Artificial
<220> FEATURE:
<223> OTHER INFORMATION: DRA225 (H6 L4 with IgG4 AA ADCC-CDC null Fc)

<400> SEQUENCE: 16

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Arg Ser
            20                  25                  30

Thr Met His Trp Val Arg Gln Ala Pro Gly Lys Gly Leu Glu Trp Val
        35                  40                  45

Ser Tyr Ile Asn Pro Ser Ser Ala Tyr Thr Asn Tyr Asn Gln Lys Phe
    50                  55                  60

Lys Asp Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Pro Gln Val His Tyr Asp Tyr Asn Gly Phe Pro Tyr Trp Gly
            100                 105                 110

Gln Gly Thr Leu Val Thr Val Ser Ser Gly Gly Gly Gly Ser Gly Gly
        115                 120                 125

Gly Gly Ser Gly Gly Gly Gly Ser Gly Gly Gly Gly Ser Glu Ile Val
    130                 135                 140

Leu Thr Gln Ser Pro Ala Thr Leu Ser Leu Ser Pro Gly Glu Arg Ala
145                 150                 155                 160

Thr Leu Ser Cys Ser Ala Ser Ser Ser Val Ser Tyr Met Asn Trp Tyr
                165                 170                 175

Gln Gln Lys Pro Gly Gln Ala Pro Arg Leu Leu Ile Tyr Asp Ser Ser
            180                 185                 190

Lys Leu Ala Ser Gly Ile Pro Ala Arg Phe Ser Gly Ser Gly Ser Gly
        195                 200                 205

Thr Asp Phe Thr Leu Thr Ile Ser Ser Leu Glu Pro Glu Asp Phe Ala
    210                 215                 220

Val Tyr Tyr Cys Gln Gln Trp Ser Arg Asn Pro Pro Thr Phe Gly Gly
225                 230                 235                 240

Gly Thr Lys Val Glu Ile Lys Ser Ser Ser Glu Pro Lys Ser Ser Asp
                245                 250                 255

Lys Thr His Thr Cys Pro Pro Cys Pro Ala Pro Glu Ala Ala Ala Pro
            260                 265                 270

Ser Val Phe Leu Phe Pro Pro Lys Pro Lys Asp Thr Leu Met Ile Ser
        275                 280                 285

Arg Thr Pro Glu Val Thr Cys Val Val Val Asp Val Ser Gln Glu Asp
    290                 295                 300

Pro Glu Val Gln Phe Asn Trp Tyr Val Asp Gly Val Glu Val His Asn
305                 310                 315                 320

Ala Lys Thr Lys Pro Arg Glu Glu Gln Phe Asn Ser Thr Tyr Arg Val
                325                 330                 335

Val Ser Val Leu Thr Val Leu His Gln Asp Trp Leu Asn Gly Lys Ala
            340                 345                 350

Tyr Ala Cys Ala Val Ser Asn Lys Gly Leu Pro Ser Ser Ile Glu Lys
        355                 360                 365

Thr Ile Ser Lys Ala Lys Gly Gln Pro Arg Glu Pro Gln Val Tyr Thr
    370                 375                 380

Leu Pro Pro Ser Gln Glu Glu Met Thr Lys Asn Gln Val Ser Leu Thr

-continued

```
385                 390                 395                 400

Cys Leu Val Lys Gly Phe Tyr Pro Ser Asp Ile Ala Val Glu Trp Glu
                405                 410                 415

Ser Asn Gly Gln Pro Glu Asn Asn Tyr Lys Thr Thr Pro Pro Val Leu
            420                 425                 430

Asp Ser Asp Gly Ser Phe Phe Leu Tyr Ser Arg Leu Thr Val Asp Lys
        435                 440                 445

Ser Arg Trp Gln Glu Gly Asn Val Phe Ser Cys Ser Val Met His Glu
    450                 455                 460

Ala Leu His Asn His Tyr Thr Gln Lys Ser Leu Ser Leu Ser Pro Gly
465                 470                 475                 480

Lys
```

<210> SEQ ID NO 17
<211> LENGTH: 1434
<212> TYPE: DNA
<213> ORGANISM: Artificial
<220> FEATURE:
<223> OTHER INFORMATION: DRA233 (H3 L1 with IgG4 AA N297A mutations - different Fc tail than the top constructs)

<400> SEQUENCE: 17

```
caggtccagc tggtgcagtc tgggggcgga gtggtgcagc ctgggcggtc actgaggctg     60

tcctgcaagg cttctggcta cacctttact agatctacga tgcactgggt aaggcaggcc    120

cctggaaagg gtctggaatg gattggatac attaatccta gcagtgctta tactaattac    180

aatcagaaat tcaaggacag gttcacaatc agcgcagaca aatccaagag cacagccttc    240

ctgcagatgg acagcctgag gcccgaggac accggcgtct atttctgtgc acggccccaa    300

gtccactatg attacaacgg gtttccttac tggggccaag ggactcccgt cactgtctct    360

agcggtggcg gagggtctgg gggtggcgga tccggaggtg gtggctctgc acaagacatc    420

cagatgaccc agtctccaag cagcctgtct gcaagcgtgg gggacagggt caccatgacc    480

tgcagtgcca gctcaagtgt aagttacatg aactggtacc agcagaagcc gggcaaggcc    540

cccaaaagat ggatttatga ctcatccaaa ctggcttctg gagtccctgc tcgcttcagt    600

ggcagtgggt ctgggaccga ctataccctc acaatcagca gcctgcagcc cgaagatttc    660

gccacttatt actgccagca gtggagtcgt aacccaccca cgttcggagg ggggaccaag    720

ctacaaatta catcctcgag cgagcccaaa tcttctgaca aaactcacac atgcccaccg    780

tgcccagcac ctgaagccgc agctccgtca gtcttcctct tcccccccaaa acccaaggac    840

accctcatga tctcccggac ccctgaggtc acgtgcgtgg tggtggacgt gagccaggaa    900

gaccccgagg tccagttcaa ctggtacgtg gatggcgtgg aggtgcataa tgccaagaca    960

aagccgcggg aggagcagtt cgccagcacg taccgtgtgg tcagcgtcct caccgtcctg   1020

caccaggact ggctgaacgg caaggagtac aagtgcaagg tctccaacaa aggcctcccg   1080

tcctccatcg agaaaaccat ctccaaagcc aaagggcagc cccgagagcc acaggtgtac   1140

accctgcccc catcccagga ggagatgacc aagaaccagg tcagcctgac ctgcctggtc   1200

aaaggcttct accccagcga catcgccgtg gagtgggaga gcaatgggca gccggagaac   1260

aactacaaga ccacgcctcc cgtgctggac tccgacggct ccttcttcct ctacagcagg   1320

ctaaccgtgg acaagagccg gtggcaggag gggaatgtct tctcatgctc cgtgatgcat   1380

gaggctctgc acaaccacta cacacagaag agcctctccc tgtctccggg taaa         1434
```

-continued

<210> SEQ ID NO 18
<211> LENGTH: 478
<212> TYPE: PRT
<213> ORGANISM: Artificial
<220> FEATURE:
<223> OTHER INFORMATION: DRA233 (H3 L1 with IgG4 AA N297A mutations - different Fc tail than the top constructs)

<400> SEQUENCE: 18

```
Gln Val Gln Leu Val Gln Ser Gly Gly Gly Val Val Gln Pro Gly Arg
1               5                   10                  15

Ser Leu Arg Leu Ser Cys Lys Ala Ser Gly Tyr Thr Phe Thr Arg Ser
            20                  25                  30

Thr Met His Trp Val Arg Gln Ala Pro Gly Lys Gly Leu Glu Trp Ile
        35                  40                  45

Gly Tyr Ile Asn Pro Ser Ser Ala Tyr Thr Asn Tyr Asn Gln Lys Phe
    50                  55                  60

Lys Asp Arg Phe Thr Ile Ser Ala Asp Lys Ser Lys Ser Thr Ala Phe
65                  70                  75                  80

Leu Gln Met Asp Ser Leu Arg Pro Glu Asp Thr Gly Val Tyr Phe Cys
                85                  90                  95

Ala Arg Pro Gln Val His Tyr Asp Tyr Asn Gly Phe Pro Tyr Trp Gly
            100                 105                 110

Gln Gly Thr Pro Val Thr Val Ser Ser Gly Gly Gly Gly Ser Gly Gly
        115                 120                 125

Gly Gly Ser Gly Gly Gly Gly Ser Ala Gln Asp Ile Gln Met Thr Gln
    130                 135                 140

Ser Pro Ser Ser Leu Ser Ala Ser Val Gly Asp Arg Val Thr Met Thr
145                 150                 155                 160

Cys Ser Ala Ser Ser Ser Val Ser Tyr Met Asn Trp Tyr Gln Gln Lys
                165                 170                 175

Pro Gly Lys Ala Pro Lys Arg Trp Ile Tyr Asp Ser Ser Lys Leu Ala
            180                 185                 190

Ser Gly Val Pro Ala Arg Phe Ser Gly Ser Gly Ser Gly Thr Asp Tyr
        195                 200                 205

Thr Leu Thr Ile Ser Ser Leu Gln Pro Glu Asp Phe Ala Thr Tyr Tyr
    210                 215                 220

Cys Gln Gln Trp Ser Arg Asn Pro Pro Thr Phe Gly Gly Gly Thr Lys
225                 230                 235                 240

Leu Gln Ile Thr Ser Ser Ser Glu Pro Lys Ser Ser Asp Lys Thr His
                245                 250                 255

Thr Cys Pro Pro Cys Pro Ala Pro Glu Ala Ala Ala Pro Ser Val Phe
            260                 265                 270

Leu Phe Pro Pro Lys Pro Lys Asp Thr Leu Met Ile Ser Arg Thr Pro
        275                 280                 285

Glu Val Thr Cys Val Val Val Asp Val Ser Gln Glu Asp Pro Glu Val
    290                 295                 300

Gln Phe Asn Trp Tyr Val Asp Gly Val Glu Val His Asn Ala Lys Thr
305                 310                 315                 320

Lys Pro Arg Glu Glu Gln Phe Ala Ser Thr Tyr Arg Val Val Ser Val
                325                 330                 335

Leu Thr Val Leu His Gln Asp Trp Leu Asn Gly Lys Glu Tyr Lys Cys
            340                 345                 350

Lys Val Ser Asn Lys Gly Leu Pro Ser Ser Ile Glu Lys Thr Ile Ser
        355                 360                 365
```

-continued

```
Lys Ala Lys Gly Gln Pro Arg Glu Pro Gln Val Tyr Thr Leu Pro Pro
    370                 375                 380

Ser Gln Glu Glu Met Thr Lys Asn Gln Val Ser Leu Thr Cys Leu Val
385                 390                 395                 400

Lys Gly Phe Tyr Pro Ser Asp Ile Ala Val Glu Trp Glu Ser Asn Gly
                405                 410                 415

Gln Pro Glu Asn Asn Tyr Lys Thr Thr Pro Pro Val Leu Asp Ser Asp
            420                 425                 430

Gly Ser Phe Phe Leu Tyr Ser Arg Leu Thr Val Asp Lys Ser Arg Trp
        435                 440                 445

Gln Glu Gly Asn Val Phe Ser Cys Ser Val Met His Glu Ala Leu His
    450                 455                 460

Asn His Tyr Thr Gln Lys Ser Leu Ser Leu Ser Pro Gly Lys
465                 470                 475


<210> SEQ ID NO 19
<211> LENGTH: 1434
<212> TYPE: DNA
<213> ORGANISM: Artificial
<220> FEATURE:
<223> OTHER INFORMATION: DRA234 (H4 L1 with IgG4 AA N297A mutations -
      same Fc tails as DRA233)

<400> SEQUENCE: 19

caggtccagc tggtggagtc tgggggcgga gtggtgcagc ctgggcggtc actgaggctg     60

tcctgcaagg cttctggcta cacctttact agatctacga tgcactgggt aaggcaggcc    120

cctggacaag gtctggaatg gattggatac attaatccta gcagtgctta tactaattac    180

aatcagaaat tcaaggacag gttcacaatc agcgcagaca aatccaagag cacagccttc    240

ctgcagatgg acagcctgag gcccgaggac accggcgtct atttctgtgc acggccccaa    300

gtccactatg attacaacgg gtttccttac tggggccaag ggactcccgt cactgtctct    360

agcggtggcg gagggtctgg gggtggcgga tccggaggtg gtggctctgc acaagacatc    420

cagatgaccc agtctccaag cagcctgtct gcaagcgtgg gggacagggt caccatgacc    480

tgcagtgcca gctcaagtgt aagttacatg aactggtacc agcagaagcc gggcaaggcc    540

cccaaaagat ggatttatga ctcatccaaa ctggcttctg gagtccctgc tcgcttcagt    600

ggcagtgggt ctgggaccga ctataccctc acaatcagca gcctgcagcc cgaagatttc    660

gccacttatt actgccagca gtggagtcgt aacccaccca cgttcggagg ggggaccaag    720

ctacaaatta catcctcgag cgagcccaaa tcttctgaca aaactcacac atgcccaccg    780

tgcccagcac ctgaagccgc agctccgtca gtcttcctct tccccccaaa acccaaggac    840

accctcatga tctcccggac ccctgaggtc acgtgcgtgg tggtggacgt gagccaggaa    900

gaccccgagg tccagttcaa ctggtacgtg gatggcgtgg aggtgcataa tgccaagaca    960

aagccgcggg aggagcagtt cgccagcacg taccgtgtgg tcagcgtcct caccgtcctg   1020

caccaggact ggctgaacgg caaggagtac aagtgcaagg tctccaacaa aggcctcccg   1080

tcctccatcg agaaaaccat ctccaaagcc aaagggcagc cccgagagcc acaggtgtac   1140

accctgcccc catcccagga ggagatgacc aagaaccagg tcagcctgac ctgcctggtc   1200

aaaggcttct accccagcga catcgccgtg gagtgggaga gcaatgggca gccggagaac   1260

aactacaaga ccacgcctcc cgtgctggac tccgacggct ccttcttcct ctacagcagg   1320

ctaaccgtgg acaagagccg gtggcaggag gggaatgtct tctcatgctc cgtgatgcat   1380

gaggctctgc acaaccacta cacacagaag agcctctccc tgtctccggg taaa         1434
```

<210> SEQ ID NO 20
<211> LENGTH: 478
<212> TYPE: PRT
<213> ORGANISM: Artificial
<220> FEATURE:
<223> OTHER INFORMATION: DRA234 (H4 L1 with IgG4 AA N297A mutations - same Fc tails as DRA233)

<400> SEQUENCE: 20

```
Gln Val Gln Leu Val Glu Ser Gly Gly Gly Val Val Gln Pro Gly Arg
1               5                   10                  15

Ser Leu Arg Leu Ser Cys Lys Ala Ser Gly Tyr Thr Phe Thr Arg Ser
            20                  25                  30

Thr Met His Trp Val Arg Gln Ala Pro Gly Gln Gly Leu Glu Trp Ile
        35                  40                  45

Gly Tyr Ile Asn Pro Ser Ser Ala Tyr Thr Asn Tyr Asn Gln Lys Phe
    50                  55                  60

Lys Asp Arg Phe Thr Ile Ser Ala Asp Lys Ser Lys Ser Thr Ala Phe
65                  70                  75                  80

Leu Gln Met Asp Ser Leu Arg Pro Glu Asp Thr Gly Val Tyr Phe Cys
                85                  90                  95

Ala Arg Pro Gln Val His Tyr Asp Tyr Asn Gly Phe Pro Tyr Trp Gly
            100                 105                 110

Gln Gly Thr Pro Val Thr Val Ser Ser Gly Gly Gly Gly Ser Gly Gly
        115                 120                 125

Gly Gly Ser Gly Gly Gly Gly Ser Ala Gln Asp Ile Gln Met Thr Gln
    130                 135                 140

Ser Pro Ser Ser Leu Ser Ala Ser Val Gly Asp Arg Val Thr Met Thr
145                 150                 155                 160

Cys Ser Ala Ser Ser Ser Val Ser Tyr Met Asn Trp Tyr Gln Gln Lys
                165                 170                 175

Pro Gly Lys Ala Pro Lys Arg Trp Ile Tyr Asp Ser Ser Lys Leu Ala
            180                 185                 190

Ser Gly Val Pro Ala Arg Phe Ser Gly Ser Gly Ser Gly Thr Asp Tyr
        195                 200                 205

Thr Leu Thr Ile Ser Ser Leu Gln Pro Glu Asp Phe Ala Thr Tyr Tyr
    210                 215                 220

Cys Gln Gln Trp Ser Arg Asn Pro Pro Thr Phe Gly Gly Gly Thr Lys
225                 230                 235                 240

Leu Gln Ile Thr Ser Ser Ser Glu Pro Lys Ser Ser Asp Lys Thr His
                245                 250                 255

Thr Cys Pro Pro Cys Pro Ala Pro Glu Ala Ala Ala Pro Ser Val Phe
            260                 265                 270

Leu Phe Pro Pro Lys Pro Lys Asp Thr Leu Met Ile Ser Arg Thr Pro
        275                 280                 285

Glu Val Thr Cys Val Val Val Asp Val Ser Gln Glu Asp Pro Glu Val
    290                 295                 300

Gln Phe Asn Trp Tyr Val Asp Gly Val Glu Val His Asn Ala Lys Thr
305                 310                 315                 320

Lys Pro Arg Glu Glu Gln Phe Ala Ser Thr Tyr Arg Val Val Ser Val
                325                 330                 335

Leu Thr Val Leu His Gln Asp Trp Leu Asn Gly Lys Glu Tyr Lys Cys
            340                 345                 350

Lys Val Ser Asn Lys Gly Leu Pro Ser Ser Ile Glu Lys Thr Ile Ser
```

```
        355                 360                 365

Lys Ala Lys Gly Gln Pro Arg Glu Pro Gln Val Tyr Thr Leu Pro Pro
    370                 375                 380

Ser Gln Glu Glu Met Thr Lys Asn Gln Val Ser Leu Thr Cys Leu Val
385                 390                 395                 400

Lys Gly Phe Tyr Pro Ser Asp Ile Ala Val Glu Trp Glu Ser Asn Gly
                405                 410                 415

Gln Pro Glu Asn Asn Tyr Lys Thr Thr Pro Pro Val Leu Asp Ser Asp
            420                 425                 430

Gly Ser Phe Phe Leu Tyr Ser Arg Leu Thr Val Asp Lys Ser Arg Trp
        435                 440                 445

Gln Glu Gly Asn Val Phe Ser Cys Ser Val Met His Glu Ala Leu His
    450                 455                 460

Asn His Tyr Thr Gln Lys Ser Leu Ser Leu Ser Pro Gly Lys
465                 470                 475


<210> SEQ ID NO 21
<211> LENGTH: 363
<212> TYPE: DNA
<213> ORGANISM: Artificial
<220> FEATURE:
<223> OTHER INFORMATION: H1 chain

<400> SEQUENCE: 21

caggtccagc tggtgcagtc tggggctgaa gtgaagaagc ctggggcctc agtgaaggtg      60

tcctgcaagg cttctggcta cacctttact agatctacga tgcactgggt aaaacaggcc     120

cctggacagg gtctggaatg gattggatac attaatccta gcagtgctta tactaattac     180

aatcagaaat tcaaggacaa ggccacattg actgcagaca aatcctccag tacagcctac     240

atgcaactga gtagcctgag gtctgaggac accgcagtct attactgtgc acggccccaa     300

gtccactatg attacaacgg gtttccttac tggggccaag ggactctggt cactgtctct     360

agc                                                                   363


<210> SEQ ID NO 22
<211> LENGTH: 121
<212> TYPE: PRT
<213> ORGANISM: Artificial
<220> FEATURE:
<223> OTHER INFORMATION: H1 chain

<400> SEQUENCE: 22

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Arg Ser
            20                  25                  30

Thr Met His Trp Val Lys Gln Ala Pro Gly Gln Gly Leu Glu Trp Ile
        35                  40                  45

Gly Tyr Ile Asn Pro Ser Ser Ala Tyr Thr Asn Tyr Asn Gln Lys Phe
    50                  55                  60

Lys Asp Lys Ala Thr Leu Thr Ala Asp Lys Ser Ser Ser Thr Ala Tyr
65                  70                  75                  80

Met Gln Leu Ser Ser Leu Arg Ser Glu Asp Thr Ala Val Tyr Tyr Cys
                85                  90                  95

Ala Arg Pro Gln Val His Tyr Asp Tyr Asn Gly Phe Pro Tyr Trp Gly
            100                 105                 110

Gln Gly Thr Leu Val Thr Val Ser Ser
```

```
        115                 120


<210> SEQ ID NO 23
<211> LENGTH: 363
<212> TYPE: DNA
<213> ORGANISM: Artificial
<220> FEATURE:
<223> OTHER INFORMATION: H2 chain

<400> SEQUENCE: 23

caggtccagc tggtgcagtc tgggggcgga gtggtgcagc ctgggcggtc actgaggctg     60

tcctgcaagg cttctggcta cacctttact agatctacga tgcactgggt aaggcaggcc    120

cctggaaagg gtctggaatg gattggatac attaatccta gcagtgctta tactaattac    180

aatcagaaat tcaaggacaa ggccacattg actgcagaca aatccaagaa cacagcctac    240

atggagctga gtagcctgag gtctgaggac accgcagtct attactgtgc acggccccaa    300

gtccactatg attacaacgg gtttccttac tggggccaag ggactctggt cactgtctct    360

agc                                                                  363


<210> SEQ ID NO 24
<211> LENGTH: 121
<212> TYPE: PRT
<213> ORGANISM: Artificial
<220> FEATURE:
<223> OTHER INFORMATION: H2 chain

<400> SEQUENCE: 24

Gln Val Gln Leu Val Gln Ser Gly Gly Gly Val Val Gln Pro Gly Arg
1               5                   10                  15

Ser Leu Arg Leu Ser Cys Lys Ala Ser Gly Tyr Thr Phe Thr Arg Ser
            20                  25                  30

Thr Met His Trp Val Arg Gln Ala Pro Gly Lys Gly Leu Glu Trp Ile
        35                  40                  45

Gly Tyr Ile Asn Pro Ser Ser Ala Tyr Thr Asn Tyr Asn Gln Lys Phe
    50                  55                  60

Lys Asp Lys Ala Thr Leu Thr Ala Asp Lys Ser Lys Asn Thr Ala Tyr
65                  70                  75                  80

Met Glu Leu Ser Ser Leu Arg Ser Glu Asp Thr Ala Val Tyr Tyr Cys
                85                  90                  95

Ala Arg Pro Gln Val His Tyr Asp Tyr Asn Gly Phe Pro Tyr Trp Gly
            100                 105                 110

Gln Gly Thr Leu Val Thr Val Ser Ser
        115                 120


<210> SEQ ID NO 25
<211> LENGTH: 363
<212> TYPE: DNA
<213> ORGANISM: Artificial
<220> FEATURE:
<223> OTHER INFORMATION: H3 chain

<400> SEQUENCE: 25

caggtccagc tggtgcagtc tgggggcgga gtggtgcagc ctgggcggtc actgaggctg     60

tcctgcaagg cttctggcta cacctttact agatctacga tgcactgggt aaggcaggcc    120

cctggaaagg gtctggaatg gattggatac attaatccta gcagtgctta tactaattac    180

aatcagaaat tcaaggacag gttcacaatc agcgcagaca aatccaagag cacagccttc    240

ctgcagatgg acagcctgag gcccgaggac accggcgtct atttctgtgc acggccccaa    300
```

gtccactatg attacaacgg gtttccttac tggggccaag ggactcccgt cactgtctct 360
agc 363

<210> SEQ ID NO 26
<211> LENGTH: 121
<212> TYPE: PRT
<213> ORGANISM: Artificial
<220> FEATURE:
<223> OTHER INFORMATION: H3 chain

<400> SEQUENCE: 26

Gln Val Gln Leu Val Gln Ser Gly Gly Gly Val Val Gln Pro Gly Arg
1 5 10 15

Ser Leu Arg Leu Ser Cys Lys Ala Ser Gly Tyr Thr Phe Thr Arg Ser
20 25 30

Thr Met His Trp Val Arg Gln Ala Pro Gly Lys Gly Leu Glu Trp Ile
35 40 45

Gly Tyr Ile Asn Pro Ser Ser Ala Tyr Thr Asn Tyr Asn Gln Lys Phe
50 55 60

Lys Asp Arg Phe Thr Ile Ser Ala Asp Lys Ser Lys Ser Thr Ala Phe
65 70 75 80

Leu Gln Met Asp Ser Leu Arg Pro Glu Asp Thr Gly Val Tyr Phe Cys
85 90 95

Ala Arg Pro Gln Val His Tyr Asp Tyr Asn Gly Phe Pro Tyr Trp Gly
100 105 110

Gln Gly Thr Pro Val Thr Val Ser Ser
115 120

<210> SEQ ID NO 27
<211> LENGTH: 363
<212> TYPE: DNA
<213> ORGANISM: Artificial
<220> FEATURE:
<223> OTHER INFORMATION: H4 chain

<400> SEQUENCE: 27
caggtccagc tggtggagtc tgggggcgga gtggtgcagc ctgggcggtc actgaggctg 60
tcctgcaagg cttctggcta cacctttact agatctacga tgcactgggt aaggcaggcc 120
cctggacaag gtctggaatg gattggatac attaatccta gcagtgctta tactaattac 180
aatcagaaat tcaaggacag gttcacaatc agcgcagaca aatccaagag cacagccttc 240
ctgcagatgg acagcctgag gcccgaggac accggcgtct atttctgtgc acggccccaa 300
gtccactatg attacaacgg gtttccttac tggggccaag ggactcccgt cactgtctct 360
agc 363

<210> SEQ ID NO 28
<211> LENGTH: 121
<212> TYPE: PRT
<213> ORGANISM: Artificial
<220> FEATURE:
<223> OTHER INFORMATION: H4 chain

<400> SEQUENCE: 28

Gln Val Gln Leu Val Glu Ser Gly Gly Gly Val Val Gln Pro Gly Arg
1 5 10 15

Ser Leu Arg Leu Ser Cys Lys Ala Ser Gly Tyr Thr Phe Thr Arg Ser
20 25 30

-continued

```
Thr Met His Trp Val Arg Gln Ala Pro Gly Gln Gly Leu Glu Trp Ile
        35                  40                  45

Gly Tyr Ile Asn Pro Ser Ser Ala Tyr Thr Asn Tyr Asn Gln Lys Phe
    50                  55                  60

Lys Asp Arg Phe Thr Ile Ser Ala Asp Lys Ser Lys Ser Thr Ala Phe
65                  70                  75                  80

Leu Gln Met Asp Ser Leu Arg Pro Glu Asp Thr Gly Val Tyr Phe Cys
                85                  90                  95

Ala Arg Pro Gln Val His Tyr Asp Tyr Asn Gly Phe Pro Tyr Trp Gly
            100                 105                 110

Gln Gly Thr Pro Val Thr Val Ser Ser
        115                 120
```

<210> SEQ ID NO 29
<211> LENGTH: 363
<212> TYPE: DNA
<213> ORGANISM: Artificial
<220> FEATURE:
<223> OTHER INFORMATION: H5 chain

<400> SEQUENCE: 29

```
caggtccagc ttgtgcagtc tggggctgag gtgaagaagc ctggggcctc agtgaaggtt      60

tcctgcaagg cttctggata caccttcact agatctacga tgcactgggt gcgccaggcc     120

cccggacaaa ggcttgagtg gatgggatac attaatccta gcagtgctta tactaattac     180

aatcagaaat tcaaggacag agtcaccatt accagggaca catccgcgag cacagcctac     240

atggagctga gcagcctgag atctgaagac acggctgtgt attactgtgc gagaccccaa     300

gtccactatg attacaacgg gtttccttac tggggccaag gaaccctggt caccgtctcc     360

tca                                                                   363
```

<210> SEQ ID NO 30
<211> LENGTH: 121
<212> TYPE: PRT
<213> ORGANISM: Artificial
<220> FEATURE:
<223> OTHER INFORMATION: H5 chain

<400> SEQUENCE: 30

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Arg Ser
            20                  25                  30

Thr Met His Trp Val Arg Gln Ala Pro Gly Gln Arg Leu Glu Trp Met
        35                  40                  45

Gly Tyr Ile Asn Pro Ser Ser Ala Tyr Thr Asn Tyr Asn Gln Lys Phe
    50                  55                  60

Lys Asp Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Pro Gln Val His Tyr Asp Tyr Asn Gly Phe Pro Tyr Trp Gly
            100                 105                 110

Gln Gly Thr Leu Val Thr Val Ser Ser
        115                 120
```

<210> SEQ ID NO 31
<211> LENGTH: 363

<212> TYPE: DNA
<213> ORGANISM: Artificial
<220> FEATURE:
<223> OTHER INFORMATION: H6 chain

<400> SEQUENCE: 31
gaggtgcagc tggtggagtc tgggggaggc ctggtcaagc ctggggggtc cctgagactc 60
tcctgtgcag cctctggatt caccttcagt agatctacga tgcactgggt ccgccaggct 120
ccagggaagg ggctggagtg ggtctcatac attaatccta gcagtgctta tactaattac 180
aatcagaaat tcaaggaccg attcaccatc tccagagaca acgccaagaa ctcactgtat 240
ctgcaaatga acagcctgag agccgaggac acggctgtgt attactgtgc gagaccccaa 300
gtccactatg attacaacgg gtttccttac tggggccaag gaaccctggt caccgtctcc 360
tca 363

<210> SEQ ID NO 32
<211> LENGTH: 121
<212> TYPE: PRT
<213> ORGANISM: Artificial
<220> FEATURE:
<223> OTHER INFORMATION: H6 chain

<400> SEQUENCE: 32

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Arg Ser
            20                  25                  30

Thr Met His Trp Val Arg Gln Ala Pro Gly Lys Gly Leu Glu Trp Val
        35                  40                  45

Ser Tyr Ile Asn Pro Ser Ser Ala Tyr Thr Asn Tyr Asn Gln Lys Phe
    50                  55                  60

Lys Asp Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Pro Gln Val His Tyr Asp Tyr Asn Gly Phe Pro Tyr Trp Gly
            100                 105                 110

Gln Gly Thr Leu Val Thr Val Ser Ser
        115                 120

<210> SEQ ID NO 33
<211> LENGTH: 324
<212> TYPE: DNA
<213> ORGANISM: Artificial
<220> FEATURE:
<223> OTHER INFORMATION: L1 chain

<400> SEQUENCE: 33
gcacaagaca tccagatgac ccagtctcca agcagcctgt ctgcaagcgt gggggacagg 60
gtcaccatga cctgcagtgc cagctcaagt gtaagttaca tgaactggta ccagcagaag 120
ccgggcaagg cccccaaaag atggatttat gactcatcca aactggcttc tggagtccct 180
gctcgcttca gtggcagtgg gtctgggacc gactataccc tcacaatcag cagcctgcag 240
cccgaagatt tcgccactta ttactgccag cagtggagtc gtaacccacc cacgttcgga 300
ggggggacca agctacaaat taca 324

<210> SEQ ID NO 34

<211> LENGTH: 108
<212> TYPE: PRT
<213> ORGANISM: Artificial
<220> FEATURE:
<223> OTHER INFORMATION: L1 chain

<400> SEQUENCE: 34

Ala Gln Asp Ile Gln Met Thr Gln Ser Pro Ser Ser Leu Ser Ala Ser
1               5                   10                  15

Val Gly Asp Arg Val Thr Met Thr Cys Ser Ala Ser Ser Ser Val Ser
            20                  25                  30

Tyr Met Asn Trp Tyr Gln Gln Lys Pro Gly Lys Ala Pro Lys Arg Trp
        35                  40                  45

Ile Tyr Asp Ser Ser Lys Leu Ala Ser Gly Val Pro Ala Arg Phe Ser
    50                  55                  60

Gly Ser Gly Ser Gly Thr Asp Tyr Thr Leu Thr Ile Ser Ser Leu Gln
65                  70                  75                  80

Pro Glu Asp Phe Ala Thr Tyr Tyr Cys Gln Gln Trp Ser Arg Asn Pro
                85                  90                  95

Pro Thr Phe Gly Gly Gly Thr Lys Leu Gln Ile Thr
            100                 105

<210> SEQ ID NO 35
<211> LENGTH: 324
<212> TYPE: DNA
<213> ORGANISM: Artificial
<220> FEATURE:
<223> OTHER INFORMATION: L2 chain

<400> SEQUENCE: 35
gcacaagaca tccagatgac ccagtctcca agcagcctgt ctgcaagcgt gggggacagg 60
gtcaccatca cctgcagtgc cagctcaagt gtaagttaca tgaactggta ccagcagacc 120
cccggcaagg cccccaaaag atggatttat gactcatcca aactggcttc tggagtccct 180
agccgcttca gtggcagtgg gtctgggacc gacttcaccc tcacaatcag cagcctgcag 240
cccgaagata tcgccactta ttactgccag cagtggagtc gtaacccacc cacgttcgga 300
caggggacca agctacaaat taca 324

<210> SEQ ID NO 36
<211> LENGTH: 108
<212> TYPE: PRT
<213> ORGANISM: Artificial
<220> FEATURE:
<223> OTHER INFORMATION: L2 chain

<400> SEQUENCE: 36

Ala Gln Asp Ile Gln Met Thr Gln Ser Pro Ser Ser Leu Ser Ala Ser
1               5                   10                  15

Val Gly Asp Arg Val Thr Ile Thr Cys Ser Ala Ser Ser Ser Val Ser
            20                  25                  30

Tyr Met Asn Trp Tyr Gln Gln Thr Pro Gly Lys Ala Pro Lys Arg Trp
        35                  40                  45

Ile Tyr Asp Ser Ser Lys Leu Ala Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Ile Ala Thr Tyr Tyr Cys Gln Gln Trp Ser Arg Asn Pro
                85                  90                  95

Pro Thr Phe Gly Gln Gly Thr Lys Leu Gln Ile Thr
100 105

<210> SEQ ID NO 37
<211> LENGTH: 324
<212> TYPE: DNA
<213> ORGANISM: Artificial
<220> FEATURE:
<223> OTHER INFORMATION: L3 chain

<400> SEQUENCE: 37
gcacaagaca tccagatgac ccagtctcca agcagcctgt ctgcaagcgt gggggacagg 60
gtcaccatga cctgcagtgc cagctcaagt gtaagttaca tgaactggta ccagcagaag 120
ccgggcaagg cccccaaact cctcatttat gactcatcca aactggcttc tggagtccct 180
gctcgcttca gtggcagtgg gtctgggacc gactataccc tcacaatcag cagcctgcag 240
cccgaagatt tcgccactta ttactgccag cagtggagtc gtaacccacc cactttcggc 300
ggagggacca aggtggagat caaa 324

<210> SEQ ID NO 38
<211> LENGTH: 108
<212> TYPE: PRT
<213> ORGANISM: Artificial
<220> FEATURE:
<223> OTHER INFORMATION: L3 chain

<400> SEQUENCE: 38

Ala Gln Asp Ile Gln Met Thr Gln Ser Pro Ser Ser Leu Ser Ala Ser
1 5 10 15

Val Gly Asp Arg Val Thr Met Thr Cys Ser Ala Ser Ser Ser Val Ser
20 25 30

Tyr Met Asn Trp Tyr Gln Gln Lys Pro Gly Lys Ala Pro Lys Leu Leu
35 40 45

Ile Tyr Asp Ser Ser Lys Leu Ala Ser Gly Val Pro Ala Arg Phe Ser
50 55 60

Gly Ser Gly Ser Gly Thr Asp Tyr Thr Leu Thr Ile Ser Ser Leu Gln
65 70 75 80

Pro Glu Asp Phe Ala Thr Tyr Tyr Cys Gln Gln Trp Ser Arg Asn Pro
85 90 95

Pro Thr Phe Gly Gly Gly Thr Lys Val Glu Ile Lys
100 105

<210> SEQ ID NO 39
<211> LENGTH: 318
<212> TYPE: DNA
<213> ORGANISM: Artificial
<220> FEATURE:
<223> OTHER INFORMATION: L4 chain

<400> SEQUENCE: 39
gaaattgtgt tgacacagtc tccagccacc ctgtctttgt ctccagggga aagagccacc 60
ctctcctgca gtgccagctc aagtgtaagt tacatgaact ggtaccaaca gaaacctggc 120
caggctccca ggctcctcat ctatgactca tccaaactgg cttctggcat cccagccagg 180
ttcagtggca gtgggtctgg gacagacttc actctcacca tcagcagcct agagcctgaa 240
gattttgcag tttattactg tcagcagtgg agtcgtaacc cacccacttt cggcggaggg 300
accaaggtgg agatcaaa 318

<210> SEQ ID NO 40
<211> LENGTH: 106
<212> TYPE: PRT
<213> ORGANISM: Artificial
<220> FEATURE:
<223> OTHER INFORMATION: L4 chain

<400> SEQUENCE: 40

Glu Ile Val Leu Thr Gln Ser Pro Ala Thr Leu Ser Leu Ser Pro Gly
1               5                   10                  15

Glu Arg Ala Thr Leu Ser Cys Ser Ala Ser Ser Ser Val Ser Tyr Met
            20                  25                  30

Asn Trp Tyr Gln Gln Lys Pro Gly Gln Ala Pro Arg Leu Leu Ile Tyr
        35                  40                  45

Asp Ser Ser Lys Leu Ala Ser Gly Ile Pro Ala Arg Phe Ser Gly Ser
    50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys Gln Gln Trp Ser Arg Asn Pro Pro Thr
                85                  90                  95

Phe Gly Gly Gly Thr Lys Val Glu Ile Lys
            100                 105

<210> SEQ ID NO 41
<211> LENGTH: 244
<212> TYPE: PRT
<213> ORGANISM: Artificial
<220> FEATURE:
<223> OTHER INFORMATION: DRA209 binding domains

<400> SEQUENCE: 41

Gln Val Gln Leu Val Gln Ser Gly Gly Gly Val Val Gln Pro Gly Arg
1               5                   10                  15

Ser Leu Arg Leu Ser Cys Lys Ala Ser Gly Tyr Thr Phe Thr Arg Ser
            20                  25                  30

Thr Met His Trp Val Arg Gln Ala Pro Gly Lys Gly Leu Glu Trp Ile
        35                  40                  45

Gly Tyr Ile Asn Pro Ser Ser Ala Tyr Thr Asn Tyr Asn Gln Lys Phe
    50                  55                  60

Lys Asp Arg Phe Thr Ile Ser Ala Asp Lys Ser Lys Ser Thr Ala Phe
65                  70                  75                  80

Leu Gln Met Asp Ser Leu Arg Pro Glu Asp Thr Gly Val Tyr Phe Cys
                85                  90                  95

Ala Arg Pro Gln Val His Tyr Asp Tyr Asn Gly Phe Pro Tyr Trp Gly
            100                 105                 110

Gln Gly Thr Pro Val Thr Val Ser Ser Gly Gly Gly Gly Ser Gly Gly
        115                 120                 125

Gly Gly Ser Gly Gly Gly Gly Ser Ala Gln Asp Ile Gln Met Thr Gln
    130                 135                 140

Ser Pro Ser Ser Leu Ser Ala Ser Val Gly Asp Arg Val Thr Met Thr
145                 150                 155                 160

Cys Ser Ala Ser Ser Ser Val Ser Tyr Met Asn Trp Tyr Gln Gln Lys
                165                 170                 175

Pro Gly Lys Ala Pro Lys Arg Trp Ile Tyr Asp Ser Ser Lys Leu Ala
            180                 185                 190

Ser Gly Val Pro Ala Arg Phe Ser Gly Ser Gly Ser Gly Thr Asp Tyr
        195                 200                 205

Thr Leu Thr Ile Ser Ser Leu Gln Pro Glu Asp Phe Ala Thr Tyr Tyr
210 215 220

Cys Gln Gln Trp Ser Arg Asn Pro Pro Thr Phe Gly Gly Gly Thr Lys
225 230 235 240

Leu Gln Ile Thr

<210> SEQ ID NO 42
<211> LENGTH: 247
<212> TYPE: PRT
<213> ORGANISM: Artificial
<220> FEATURE:
<223> OTHER INFORMATION: DRA209 plus junction sequence

<400> SEQUENCE: 42

Gln Val Gln Leu Val Gln Ser Gly Gly Gly Val Val Gln Pro Gly Arg
1 5 10 15

Ser Leu Arg Leu Ser Cys Lys Ala Ser Gly Tyr Thr Phe Thr Arg Ser
20 25 30

Thr Met His Trp Val Arg Gln Ala Pro Gly Lys Gly Leu Glu Trp Ile
35 40 45

Gly Tyr Ile Asn Pro Ser Ser Ala Tyr Thr Asn Tyr Asn Gln Lys Phe
50 55 60

Lys Asp Arg Phe Thr Ile Ser Ala Asp Lys Ser Lys Ser Thr Ala Phe
65 70 75 80

Leu Gln Met Asp Ser Leu Arg Pro Glu Asp Thr Gly Val Tyr Phe Cys
85 90 95

Ala Arg Pro Gln Val His Tyr Asp Tyr Asn Gly Phe Pro Tyr Trp Gly
100 105 110

Gln Gly Thr Pro Val Thr Val Ser Ser Gly Gly Gly Gly Ser Gly Gly
115 120 125

Gly Gly Ser Gly Gly Gly Gly Ser Ala Gln Asp Ile Gln Met Thr Gln
130 135 140

Ser Pro Ser Ser Leu Ser Ala Ser Val Gly Asp Arg Val Thr Met Thr
145 150 155 160

Cys Ser Ala Ser Ser Ser Val Ser Tyr Met Asn Trp Tyr Gln Gln Lys
165 170 175

Pro Gly Lys Ala Pro Lys Arg Trp Ile Tyr Asp Ser Ser Lys Leu Ala
180 185 190

Ser Gly Val Pro Ala Arg Phe Ser Gly Ser Gly Ser Gly Thr Asp Tyr
195 200 205

Thr Leu Thr Ile Ser Ser Leu Gln Pro Glu Asp Phe Ala Thr Tyr Tyr
210 215 220

Cys Gln Gln Trp Ser Arg Asn Pro Pro Thr Phe Gly Gly Gly Thr Lys
225 230 235 240

Leu Gln Ile Thr Arg Arg Thr
245

<210> SEQ ID NO 43
<211> LENGTH: 98
<212> TYPE: PRT
<213> ORGANISM: Artificial
<220> FEATURE:
<223> OTHER INFORMATION: IGHV1-69*1

<400> SEQUENCE: 43

Gln Val Gln Leu Val Gln Ser Gly Ala Glu Val Lys Lys Pro Gly Ser
1 5 10 15

```
Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg


<210> SEQ ID NO 44
<211> LENGTH: 98
<212> TYPE: PRT
<213> ORGANISM: Artificial
<220> FEATURE:
<223> OTHER INFORMATION: IGHV3-30*01

<400> SEQUENCE: 44

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg


<210> SEQ ID NO 45
<211> LENGTH: 115
<212> TYPE: PRT
<213> ORGANISM: Artificial
<220> FEATURE:
<223> OTHER INFORMATION: CRIS7 VH

<400> SEQUENCE: 45

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Arg Ser
            20                  25                  30

Thr Met His Trp Val Lys Gln Arg Pro Gly Gln Gly Leu Glu Trp Ile
        35                  40                  45

Gly Tyr Ile Asn Pro Ser Ser Ala Tyr Thr Asn Tyr Asn Gln Lys Phe
    50                  55                  60

Lys Asp Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Ser Pro Gln Val His Tyr Asp Tyr Asn Gly Phe Pro Tyr Trp Gly
            100                 105                 110

Gln Gly Thr
```

115

<210> SEQ ID NO 46
<211> LENGTH: 107
<212> TYPE: PRT
<213> ORGANISM: Artificial
<220> FEATURE:
<223> OTHER INFORMATION: CRIS7 VL

<400> SEQUENCE: 46

```
Gln Val Val Leu Thr Gln Ser Pro Ala Ile Met Ser Ala Phe Pro Gly
1               5                   10                  15

Glu Lys Val Thr Met Thr Cys Ser Ala Ser Ser Ser Val Ser Tyr Met
            20                  25                  30

Asn Trp Tyr Gln Gln Lys Ser Gly Thr Ser Pro Lys Arg Trp Ile Tyr
        35                  40                  45

Asp Ser Ser Lys Leu Ala Ser Gly Val Pro Ala Arg Phe Ser Gly Ser
    50                  55                  60

Gly Ser Gly Thr Ser Tyr Ser Leu Thr Ile Ser Ser Met Glu Thr Glu
65                  70                  75                  80

Asp Ala Ala Thr Tyr Tyr Cys Gln Gln Trp Ser Arg Asn Pro Pro Thr
                85                  90                  95

Phe Gly Gly Gly Thr Lys Leu Gln Ile Thr Arg
            100                 105
```

<210> SEQ ID NO 47
<211> LENGTH: 121
<212> TYPE: PRT
<213> ORGANISM: Artificial
<220> FEATURE:
<223> OTHER INFORMATION: DRA161 VH

<400> SEQUENCE: 47

```
Gln Val Gln Leu Val Gln Ser Gly Gly Gly Val Val Gln Pro Gly Arg
1               5                   10                  15

Ser Leu Arg Leu Ser Cys Lys Ala Ser Gly Tyr Thr Phe Thr Arg Ser
            20                  25                  30

Thr Met His Trp Val Arg Gln Ala Pro Gly Lys Gly Leu Glu Trp Ile
        35                  40                  45

Gly Tyr Ile Asn Pro Ser Ser Ala Tyr Thr Asn Tyr Asn Gln Lys Phe
    50                  55                  60

Lys Asp Arg Phe Thr Ile Ser Ala Asp Lys Ser Lys Ser Thr Ala Phe
65                  70                  75                  80

Leu Gln Met Asp Ser Leu Arg Pro Glu Asp Thr Gly Val Tyr Phe Cys
                85                  90                  95

Ala Arg Pro Gln Val His Tyr Asp Tyr Asn Gly Phe Pro Tyr Trp Gly
            100                 105                 110

Gln Gly Thr Pro Val Thr Val Ser Ser
        115                 120
```

<210> SEQ ID NO 48
<211> LENGTH: 107
<212> TYPE: PRT
<213> ORGANISM: Artificial
<220> FEATURE:
<223> OTHER INFORMATION: DRA161 VL

<400> SEQUENCE: 48

```
Asp Ile Gln Met Thr Gln Ser Pro Ser Ser Leu Ser Ala Ser Val Gly
1               5                   10                  15
```

Asp Arg Val Thr Met Thr Cys Ser Ala Ser Ser Ser Val Ser Tyr Met
20 25 30

Asn Trp Tyr Gln Gln Lys Pro Gly Lys Ala Pro Lys Arg Trp Ile Tyr
35 40 45

Asp Ser Ser Lys Leu Ala Ser Gly Val Pro Ala Arg Phe Ser Gly Ser
50 55 60

Gly Ser Gly Thr Asp Tyr Thr Leu Thr Ile Ser Ser Leu Gln Pro Glu
65 70 75 80

Asp Phe Ala Thr Tyr Tyr Cys Gln Gln Trp Ser Arg Asn Pro Pro Thr
85 90 95

Phe Gly Gly Gly Thr Lys Leu Gln Ile Thr Arg
100 105

<210> SEQ ID NO 49
<211> LENGTH: 5
<212> TYPE: PRT
<213> ORGANISM: Artificial
<220> FEATURE:
<223> OTHER INFORMATION: CRIS7 VH CDR1

<400> SEQUENCE: 49

Arg Ser Thr Met His
1 5

<210> SEQ ID NO 50
<211> LENGTH: 17
<212> TYPE: PRT
<213> ORGANISM: Artificial
<220> FEATURE:
<223> OTHER INFORMATION: CRIS7 VH CDR2

<400> SEQUENCE: 50

Tyr Ile Asn Pro Ser Ser Ala Tyr Thr Asn Tyr Asn Gln Lys Phe Lys
1 5 10 15

Asp

<210> SEQ ID NO 51
<211> LENGTH: 11
<212> TYPE: PRT
<213> ORGANISM: Artificial
<220> FEATURE:
<223> OTHER INFORMATION: CRIS7 VHCDR3

<400> SEQUENCE: 51

Gln Val His Tyr Asp Tyr Asn Gly Phe Pro Tyr
1 5 10

<210> SEQ ID NO 52
<211> LENGTH: 10
<212> TYPE: PRT
<213> ORGANISM: Artificial
<220> FEATURE:
<223> OTHER INFORMATION: CRIS7 VL CDR1

<400> SEQUENCE: 52

Ser Ala Ser Ser Ser Val Ser Tyr Met Asn
1 5 10

<210> SEQ ID NO 53
<211> LENGTH: 7
<212> TYPE: PRT
<213> ORGANISM: Artificial
<220> FEATURE:

<223> OTHER INFORMATION: CRIS7 VL CDR2

<400> SEQUENCE: 53

```
Asp Ser Ser Lys Leu Ala Ser
1               5
```

<210> SEQ ID NO 54
<211> LENGTH: 9
<212> TYPE: PRT
<213> ORGANISM: Artificial
<220> FEATURE:
<223> OTHER INFORMATION: CRIS7 VL CDR3

<400> SEQUENCE: 54

```
Gln Gln Trp Ser Arg Asn Pro Pro Thr
1               5
```

<210> SEQ ID NO 55
<211> LENGTH: 216
<212> TYPE: PRT
<213> ORGANISM: Artificial
<220> FEATURE:
<223> OTHER INFORMATION: DRA161 modified Fc domain

<400> SEQUENCE: 55

```
Ala Pro Glu Ala Ala Ala Pro Ser Val Phe Leu Phe Pro Pro Lys Pro
1               5                   10                  15

Lys Asp Thr Leu Met Ile Ser Arg Thr Pro Glu Val Thr Cys Val Val
            20                  25                  30

Val Asp Val Ser Gln Glu Asp Pro Glu Val Gln Phe Asn Trp Tyr Val
        35                  40                  45

Asp Gly Val Glu Val His Asn Ala Lys Thr Lys Pro Arg Glu Glu Gln
    50                  55                  60

Phe Ala Ser Thr Tyr Arg Val Val Ser Val Leu Thr Val Leu His Gln
65                  70                  75                  80

Asp Trp Leu Asn Gly Lys Glu Tyr Lys Cys Lys Val Ser Asn Lys Gly
                85                  90                  95

Leu Pro Ser Ser Ile Glu Lys Thr Ile Ser Lys Ala Lys Gly Gln Pro
            100                 105                 110

Arg Glu Pro Gln Val Tyr Thr Leu Pro Pro Ser Gln Glu Glu Met Thr
        115                 120                 125

Lys Asn Gln Val Ser Leu Thr Cys Leu Val Lys Gly Phe Tyr Pro Ser
    130                 135                 140

Asp Ile Ala Val Glu Trp Glu Ser Asn Gly Gln Pro Glu Asn Asn Tyr
145                 150                 155                 160

Lys Thr Thr Pro Pro Val Leu Asp Ser Asp Gly Ser Phe Phe Leu Tyr
                165                 170                 175

Ser Arg Leu Thr Val Asp Lys Ser Arg Trp Gln Glu Gly Asn Val Phe
            180                 185                 190

Ser Cys Ser Val Met His Glu Ala Leu His Asn His Tyr Thr Gln Lys
        195                 200                 205

Ser Leu Ser Leu Ser Pro Gly Lys
    210                 215
```

<210> SEQ ID NO 56
<211> LENGTH: 2289
<212> TYPE: DNA
<213> ORGANISM: Artificial
<220> FEATURE:
<223> OTHER INFORMATION: Humanized TSC249 Scorpion (huVL-VH#2 107-1A4

-continued scFv-Fc-DRA222 scFv)

<400> SEQUENCE: 56

```
atggaagcac cagcgcagct tctcttcctc ctgctactct ggctcccaga taccaccggt      60
gatatccaga tgacccagtc tccatccgcc atgtctgcat ctgtaggaga cagagtcacc     120
atcacttgcc gggcgagtaa gagcattagc aaatatttag cctggtttca gcagaaacca     180
gggaaagttc ctaagctccg catccattct ggatctactt tgcaatcagg ggtcccatct     240
cggttcagtg gcagtggatc tgggacagaa tttactctca ccatcagcag cctgcagcct     300
gaagattttg caacttatta ctgtcaacag catattgaat acccgtggac gttcggccaa     360
gggaccaagg tggaaatcaa acgaggtggc ggagggtctg gggtggcgg atccggaggt      420
ggtggctctc aggtccagct ggtacagtct ggggctgagg tgaagaagcc tggggcttca     480
gtgaaggtct cctgcaaggc ttctggatac acattcactg actactacat gcactgggtg     540
cgacaggccc ctggacaagg gcttgagtgg atgggatatt ttaatcctta taatgattat     600
actagatacg cacagaagtt ccagggcaga gtcaccatga ccagggacac gtctatcagc     660
acagcctaca tggagctgag cagcctgaga tctgacgaca cggccgtgta ttactgtgca     720
agatcggatg gttactacga tgctatggac tactggggtc aaggaaccac agtcaccgtc     780
tcctcgagtg agcccaaatc ttctgacaaa actcacacat gcccaccgtg cccagcacct     840
gaagccgcgg gtgcaccgtc agtcttcctc ttcccccaa aacccaagga caccctcatg      900
atctcccgga cccctgaggt cacatgcgtg gtggtggacg tgagccacga agaccctgag     960
gtcaagttca actggtacgt ggacggcgtg gaggtgcata atgccaagac aaagccgcgg    1020
gaggagcagt acaacagcac gtaccgtgtg gtcagcgtcc tcaccgtcct gcaccaggac    1080
tggctgaatg gcaaggcgta cgcgtgcgcg gtctccaaca aagccctccc agcccccatc    1140
gagaaaacca tctccaaagc caaagggcag ccccgagaac cacaggtgta caccctgccc    1200
ccatcccggg atgagctgac caagaaccag gtcagcctga cctgcctggt caaaggcttc    1260
tatccaagcg acatcgccgt ggagtgggag agcaatgggc agccggagaa caactacaag    1320
accacgcctc ccgtgctgga ctccgacggc tccttcttcc tctacagcaa gctcaccgtg    1380
gacaagagca ggtggcagca ggggaacgtc ttctcatgct ccgtgatgca tgaggctctg    1440
cacaaccact acacgcagaa gagcctctcc ctgtctccgg gtcagaggca caacaattct    1500
tccctgaata caggaactca gatggcaggt cattctccga attctcaggt ccagctggtg    1560
gagtctgggg gcggagtggt gcagcctggg cggtcactga ggctgtcctg caaggcttct    1620
ggctacacct ttactagatc tacgatgcac tgggtaaggc aggcccctgg acaaggtctg    1680
gaatggattg gatacattaa tcctagcagt gcttatacta attacaatca gaaattcaag    1740
gacaggttca caatcagcgc agacaaatcc aagagcacag ccttcctgca gatggacagc    1800
ctgaggcccg aggacaccgg cgtctatttc tgtgcacggc cccaagtcca ctatgattac    1860
aacgggtttc cttactgggg ccaagggact cccgtcactg tctctagcgg tggcggaggg    1920
tctgggggtg gcggatccgg aggtggtggc tctgcacaag acatccagat gacccagtct    1980
ccaagcagcc tgtctgcaag cgtgggggac agggtcacca tgacctgcag tgccagctca    2040
agtgtaagtt acatgaactg gtaccagcag aagccgggca aggcccccaa aagatggatt    2100
tatgactcat ccaaactggc ttctggagtc cctgctcgct tcagtggcag tgggtctggg    2160
accgactata ccctcacaat cagcagcctg cagcccgaag atttcgccac ttattactgc    2220
cagcagtgga gtcgtaaccc acccacgttc ggaggggga ccaagctaca aattacatcc     2280
```

tccagctaa 2289

<210> SEQ ID NO 57
<211> LENGTH: 742
<212> TYPE: PRT
<213> ORGANISM: Artificial
<220> FEATURE:
<223> OTHER INFORMATION: Humanized TSC249 Scorpion (huVL-VH#2 107-1A4 scFv-Fc-DRA222 scFV)

<400> SEQUENCE: 57

```
Asp Ile Gln Met Thr Gln Ser Pro Ser Ala Met Ser Ala Ser Val Gly
1               5                   10                  15

Asp Arg Val Thr Ile Thr Cys Arg Ala Ser Lys Ser Ile Ser Lys Tyr
            20                  25                  30

Leu Ala Trp Phe Gln Gln Lys Pro Gly Lys Val Pro Lys Leu Arg Ile
        35                  40                  45

His Ser Gly Ser Thr Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln His Ile Glu Tyr Pro Trp
                85                  90                  95

Thr Phe Gly Gln Gly Thr Lys Val Glu Ile Lys Arg Gly Gly Gly Gly
            100                 105                 110

Ser Gly Gly Gly Gly Ser Gly Gly Gly Gly Ser Gln Val Gln Leu Val
        115                 120                 125

Gln Ser Gly Ala Glu Val Lys Lys Pro Gly Ala Ser Val Lys Val Ser
    130                 135                 140

Cys Lys Ala Ser Gly Tyr Thr Phe Thr Asp Tyr Tyr Met His Trp Val
145                 150                 155                 160

Arg Gln Ala Pro Gly Gln Gly Leu Glu Trp Met Gly Tyr Phe Asn Pro
                165                 170                 175

Tyr Asn Asp Tyr Thr Arg Tyr Ala Gln Lys Phe Gln Gly Arg Val Thr
            180                 185                 190

Met Thr Arg Asp Thr Ser Ile Ser Thr Ala Tyr Met Glu Leu Ser Ser
        195                 200                 205

Leu Arg Ser Asp Asp Thr Ala Val Tyr Tyr Cys Ala Arg Ser Asp Gly
    210                 215                 220

Tyr Tyr Asp Ala Met Asp Tyr Trp Gly Gln Gly Thr Thr Val Thr Val
225                 230                 235                 240

Ser Ser Ser Glu Pro Lys Ser Ser Asp Lys Thr His Thr Cys Pro Pro
                245                 250                 255

Cys Pro Ala Pro Glu Ala Ala Gly Ala Pro Ser Val Phe Leu Phe Pro
            260                 265                 270

Pro Lys Pro Lys Asp Thr Leu Met Ile Ser Arg Thr Pro Glu Val Thr
        275                 280                 285

Cys Val Val Val Asp Val Ser His Glu Asp Pro Glu Val Lys Phe Asn
    290                 295                 300

Trp Tyr Val Asp Gly Val Glu Val His Asn Ala Lys Thr Lys Pro Arg
305                 310                 315                 320

Glu Glu Gln Tyr Asn Ser Thr Tyr Arg Val Val Ser Val Leu Thr Val
                325                 330                 335

Leu His Gln Asp Trp Leu Asn Gly Lys Ala Tyr Ala Cys Ala Val Ser
            340                 345                 350
```

```
Asn Lys Ala Leu Pro Ala Pro Ile Glu Lys Thr Ile Ser Lys Ala Lys
        355                 360                 365

Gly Gln Pro Arg Glu Pro Gln Val Tyr Thr Leu Pro Pro Ser Arg Asp
    370                 375                 380

Glu Leu Thr Lys Asn Gln Val Ser Leu Thr Cys Leu Val Lys Gly Phe
385                 390                 395                 400

Tyr Pro Ser Asp Ile Ala Val Glu Trp Glu Ser Asn Gly Gln Pro Glu
                405                 410                 415

Asn Asn Tyr Lys Thr Thr Pro Pro Val Leu Asp Ser Asp Gly Ser Phe
            420                 425                 430

Phe Leu Tyr Ser Lys Leu Thr Val Asp Lys Ser Arg Trp Gln Gln Gly
        435                 440                 445

Asn Val Phe Ser Cys Ser Val Met His Glu Ala Leu His Asn His Tyr
    450                 455                 460

Thr Gln Lys Ser Leu Ser Leu Ser Pro Gly Gln Arg His Asn Asn Ser
465                 470                 475                 480

Ser Leu Asn Thr Gly Thr Gln Met Ala Gly His Ser Pro Asn Ser Gln
                485                 490                 495

Val Gln Leu Val Glu Ser Gly Gly Gly Val Val Gln Pro Gly Arg Ser
            500                 505                 510

Leu Arg Leu Ser Cys Lys Ala Ser Gly Tyr Thr Phe Thr Arg Ser Thr
        515                 520                 525

Met His Trp Val Arg Gln Ala Pro Gly Gln Gly Leu Glu Trp Ile Gly
    530                 535                 540

Tyr Ile Asn Pro Ser Ser Ala Tyr Thr Asn Tyr Asn Gln Lys Phe Lys
545                 550                 555                 560

Asp Arg Phe Thr Ile Ser Ala Asp Lys Ser Lys Ser Thr Ala Phe Leu
                565                 570                 575

Gln Met Asp Ser Leu Arg Pro Glu Asp Thr Gly Val Tyr Phe Cys Ala
            580                 585                 590

Arg Pro Gln Val His Tyr Asp Tyr Asn Gly Phe Pro Tyr Trp Gly Gln
        595                 600                 605

Gly Thr Pro Val Thr Val Ser Ser Gly Gly Gly Gly Ser Gly Gly Gly
    610                 615                 620

Gly Ser Gly Gly Gly Gly Ser Ala Gln Asp Ile Gln Met Thr Gln Ser
625                 630                 635                 640

Pro Ser Ser Leu Ser Ala Ser Val Gly Asp Arg Val Thr Met Thr Cys
                645                 650                 655

Ser Ala Ser Ser Ser Val Ser Tyr Met Asn Trp Tyr Gln Gln Lys Pro
            660                 665                 670

Gly Lys Ala Pro Lys Arg Trp Ile Tyr Asp Ser Ser Lys Leu Ala Ser
        675                 680                 685

Gly Val Pro Ala Arg Phe Ser Gly Ser Gly Ser Gly Thr Asp Tyr Thr
    690                 695                 700

Leu Thr Ile Ser Ser Leu Gln Pro Glu Asp Phe Ala Thr Tyr Tyr Cys
705                 710                 715                 720

Gln Gln Trp Ser Arg Asn Pro Pro Thr Phe Gly Gly Gly Thr Lys Leu
                725                 730                 735

Gln Ile Thr Ser Ser Ser
            740
```

<210> SEQ ID NO 58
<211> LENGTH: 2268

```
<212> TYPE: DNA
<213> ORGANISM: Artificial
<220> FEATURE:
<223> OTHER INFORMATION: Humanized TSC250 Scorpion (huVL-VH#2 107-1A4
      scFv-Fc-DRA222 scFv, with H81 linker)

<400> SEQUENCE: 58

atggaagcac cagcgcagct tctcttcctc ctgctactct ggctcccaga taccaccggt     60
gatatccaga tgacccagtc tccatccgcc atgtctgcat ctgtaggaga cagagtcacc    120
atcacttgcc gggcgagtaa gagcattagc aaatatttag cctggtttca gcagaaacca    180
gggaaagttc ctaagctccg catccattct ggatctactt tgcaatcagg ggtcccatct    240
cggttcagtg gcagtggatc tgggacagaa tttactctca ccatcagcag cctgcagcct    300
gaagattttg caacttatta ctgtcaacag catattgaat acccgtggac gttcggccaa    360
gggaccaagg tggaaatcaa acgaggtggc ggagggtctg gggggtggcgg atccggaggt    420
ggtggctctc aggtccagct ggtacagtct ggggctgagg tgaagaagcc tggggcttca    480
gtgaaggtct cctgcaaggc ttctggatac acattcactg actactacat gcactgggtg    540
cgacaggccc ctggacaagg gcttgagtgg atgggatatt ttaatcctta taatgattat    600
actagatacg cacagaagtt ccagggcaga gtcaccatga ccagggacac gtctatcagc    660
acagcctaca tggagctgag cagcctgaga tctgacgaca cggccgtgta ttactgtgca    720
agatcggatg gttactacga tgctatggac tactggggtc aaggaaccac agtcaccgtc    780
tcctcgagtg agcccaaatc ttctgacaaa actcacacat gcccaccgtg cccagcacct    840
gaagccgcgg gtgcaccgtc agtcttcctc ttccccccaa aacccaagga caccctcatg    900
atctcccgga cccctgaggt cacatgcgtg gtggtggacg tgagccacga agaccctgag    960
gtcaagttca actggtacgt ggacggcgtg gaggtgcata atgccaagac aaagccgcgg   1020
gaggagcagt acaacagcac gtaccgtgtg gtcagcgtcc tcaccgtcct gcaccaggac   1080
tggctgaatg gcaaggcgta cgcgtgcgcg gtctccaaca aagccctccc agcccccatc   1140
gagaaaacca tctccaaagc caaagggcag ccccgagaac cacaggtgta caccctgccc   1200
ccatcccggg atgagctgac caagaaccag gtcagcctga cctgcctggt caaaggcttc   1260
tatccaagcg acatcgccgt ggagtgggag agcaatgggc agccggagaa caactacaag   1320
accacgcctc ccgtgctgga ctccgacggc tccttcttcc tctacagcaa gctcaccgtg   1380
gacaagagca ggtggcagca ggggaacgtc ttctcatgct ccgtgatgca tgaggctctg   1440
cacaaccact acacgcagaa gagcctctcc ctgtctccgg gtgaagttca aattcccttg   1500
accgaaagtt acagcccgaa ttctcaggtc cagctggtgg agtctggggg cggagtggtg   1560
cagcctgggc ggtcactgag gctgtcctgc aaggcttctg gctacacctt tactagatct   1620
acgatgcact gggtaaggca ggcccctgga caaggtctgg aatggattgg atacattaat   1680
cctagcagtg cttatactaa ttacaatcag aaattcaagg acaggttcac aatcagcgca   1740
gacaaatcca agagcacagc cttcctgcag atggacagcc tgaggcccga ggacaccggc   1800
gtctatttct gtgcacggcc ccaagtccac tatgattaca acgggtttcc ttactggggc   1860
caagggactc ccgtcactgt ctctagcggt ggcggagggt ctgggggtgg cggatccgga   1920
ggtggtggct ctgcacaaga catccagatg acccagtctc caagcagcct gtctgcaagc   1980
gtgggggaca gggtcaccat gacctgcagt gccagctcaa gtgtaagtta catgaactgg   2040
taccagcaga agccgggcaa ggcccccaaa agatggattt atgactcatc caaactggct   2100
tctggagtcc ctgctcgctt cagtggcagt gggtctggga ccgactatac cctcacaatc   2160
```

```
agcagcctgc agcccgaaga tttcgccact tattactgcc agcagtggag tcgtaaccca   2220

cccacgttcg gagggggac caagctacaa attacatcct ccagctaa                 2268


<210> SEQ ID NO 59
<211> LENGTH: 1477
<212> TYPE: PRT
<213> ORGANISM: Artificial
<220> FEATURE:
<223> OTHER INFORMATION: Humanized TSC250 Scorpion (huVL-VH#2 107-1A4
      scFv-Fc-DRA222 scFv, with H81 linker)

<400> SEQUENCE: 59

Asp Ile Gln Met Thr Gln Ser Pro Ser Ala Met Ser Ala Ser Val Gly
1               5                   10                  15

Asp Arg Val Thr Ile Thr Cys Arg Ala Ser Lys Ser Ile Ser Lys Tyr
            20                  25                  30

Leu Ala Trp Phe Gln Gln Lys Pro Gly Lys Val Pro Lys Leu Arg Ile
        35                  40                  45

His Ser Gly Ser Thr Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln His Ile Glu Tyr Pro Trp
                85                  90                  95

Thr Phe Gly Gln Gly Thr Lys Val Glu Ile Lys Arg Gly Gly Gly Gly
            100                 105                 110

Ser Gly Gly Gly Gly Ser Gly Gly Gly Gly Ser Gln Val Gln Leu Val
        115                 120                 125

Gln Ser Gly Ala Glu Val Lys Lys Pro Gly Ala Ser Val Lys Val Ser
    130                 135                 140

Cys Lys Ala Ser Gly Tyr Thr Phe Thr Asp Tyr Tyr Met His Trp Val
145                 150                 155                 160

Arg Gln Ala Pro Gly Gln Gly Leu Glu Trp Met Gly Tyr Phe Asn Pro
                165                 170                 175

Tyr Asn Asp Tyr Thr Arg Tyr Ala Gln Lys Phe Gln Gly Arg Val Thr
            180                 185                 190

Met Thr Arg Asp Thr Ser Ile Ser Thr Ala Tyr Met Glu Leu Ser Ser
        195                 200                 205

Leu Arg Ser Asp Asp Thr Ala Val Tyr Tyr Cys Ala Arg Ser Asp Gly
    210                 215                 220

Tyr Tyr Asp Ala Met Asp Tyr Trp Gly Gln Gly Thr Thr Val Thr Val
225                 230                 235                 240

Ser Ser Ser Glu Pro Lys Ser Ser Asp Lys Thr His Thr Cys Pro Pro
                245                 250                 255

Cys Pro Ala Pro Glu Ala Ala Gly Ala Pro Ser Val Phe Leu Phe Pro
            260                 265                 270

Pro Lys Pro Lys Asp Thr Leu Met Ile Ser Arg Thr Pro Glu Val Thr
        275                 280                 285

Cys Val Val Val Asp Val Ser His Glu Asp Pro Glu Val Lys Phe Asn
    290                 295                 300

Trp Tyr Val Asp Gly Val Glu Val His Asn Ala Lys Thr Lys Pro Arg
305                 310                 315                 320

Glu Glu Gln Tyr Asn Ser Thr Tyr Arg Val Val Ser Val Leu Thr Val
                325                 330                 335
```

```
Leu His Gln Asp Trp Leu Asn Gly Lys Ala Tyr Ala Cys Ala Val Ser
            340                 345                 350

Asn Lys Ala Leu Pro Ala Pro Ile Glu Lys Thr Ile Ser Lys Ala Lys
        355                 360                 365

Gly Gln Pro Arg Glu Pro Gln Val Tyr Thr Leu Pro Pro Ser Arg Asp
    370                 375                 380

Glu Leu Thr Lys Asn Gln Val Ser Leu Thr Cys Leu Val Lys Gly Phe
385                 390                 395                 400

Tyr Pro Ser Asp Ile Ala Val Glu Trp Glu Ser Asn Gly Gln Pro Glu
                405                 410                 415

Asn Asn Tyr Lys Thr Thr Pro Pro Val Leu Asp Ser Asp Gly Ser Phe
            420                 425                 430

Phe Leu Tyr Ser Lys Leu Thr Val Asp Lys Ser Arg Trp Gln Gln Gly
        435                 440                 445

Asn Val Phe Ser Cys Ser Val Met His Glu Ala Leu His Asn His Tyr
    450                 455                 460

Thr Gln Lys Ser Leu Ser Leu Ser Pro Gly Gln Arg His Asn Asn Ser
465                 470                 475                 480

Ser Leu Asn Thr Gly Thr Gln Met Ala Gly His Ser Pro Asn Ser Gln
                485                 490                 495

Val Gln Leu Val Glu Ser Gly Gly Gly Val Val Gln Pro Gly Arg Ser
            500                 505                 510

Leu Arg Leu Ser Cys Lys Ala Ser Gly Tyr Thr Phe Thr Arg Ser Thr
        515                 520                 525

Met His Trp Val Arg Gln Ala Pro Gly Gln Gly Leu Glu Trp Ile Gly
    530                 535                 540

Tyr Ile Asn Pro Ser Ser Ala Tyr Thr Asn Tyr Asn Gln Lys Phe Lys
545                 550                 555                 560

Asp Arg Phe Thr Ile Ser Ala Asp Lys Ser Lys Ser Thr Ala Phe Leu
                565                 570                 575

Gln Met Asp Ser Leu Arg Pro Glu Asp Thr Gly Val Tyr Phe Cys Ala
            580                 585                 590

Arg Pro Gln Val His Tyr Asp Tyr Asn Gly Phe Pro Tyr Trp Gly Gln
        595                 600                 605

Gly Thr Pro Val Thr Val Ser Ser Gly Gly Gly Gly Ser Gly Gly Gly
    610                 615                 620

Gly Ser Gly Gly Gly Gly Ser Ala Gln Asp Ile Gln Met Thr Gln Ser
625                 630                 635                 640

Pro Ser Ser Leu Ser Ala Ser Val Gly Asp Arg Val Thr Met Thr Cys
                645                 650                 655

Ser Ala Ser Ser Ser Val Ser Tyr Met Asn Trp Tyr Gln Gln Lys Pro
            660                 665                 670

Gly Lys Ala Pro Lys Arg Trp Ile Tyr Asp Ser Ser Lys Leu Ala Ser
        675                 680                 685

Gly Val Pro Ala Arg Phe Ser Gly Ser Gly Ser Gly Thr Asp Tyr Thr
    690                 695                 700

Leu Thr Ile Ser Ser Leu Gln Pro Glu Asp Phe Ala Thr Tyr Tyr Cys
705                 710                 715                 720

Gln Gln Trp Ser Arg Asn Pro Pro Thr Phe Gly Gly Gly Thr Lys Leu
                725                 730                 735

Gln Ile Thr Ser Ser Ser Asp Ile Gln Met Thr Gln Ser Pro Ser Ala
            740                 745                 750

Met Ser Ala Ser Val Gly Asp Arg Val Thr Ile Thr Cys Arg Ala Ser
```

```
        755                 760                 765

Lys Ser Ile Ser Lys Tyr Leu Ala Trp Phe Gln Gln Lys Pro Gly Lys
    770                 775                 780

Val Pro Lys Leu Arg Ile His Ser Gly Ser Thr Leu Gln Ser Gly Val
785                 790                 795                 800

Pro Ser Arg Phe Ser Gly Ser Gly Ser Gly Thr Glu Phe Thr Leu Thr
                805                 810                 815

Ile Ser Ser Leu Gln Pro Glu Asp Phe Ala Thr Tyr Tyr Cys Gln Gln
            820                 825                 830

His Ile Glu Tyr Pro Trp Thr Phe Gly Gln Gly Thr Lys Val Glu Ile
        835                 840                 845

Lys Arg Gly Gly Gly Gly Ser Gly Gly Gly Gly Ser Gly Gly Gly Gly
    850                 855                 860

Ser Gln Val Gln Leu Val Gln Ser Gly Ala Glu Val Lys Lys Pro Gly
865                 870                 875                 880

Ala Ser Val Lys Val Ser Cys Lys Ala Ser Gly Tyr Thr Phe Thr Asp
                885                 890                 895

Tyr Tyr Met His Trp Val Arg Gln Ala Pro Gly Gln Gly Leu Glu Trp
            900                 905                 910

Met Gly Tyr Phe Asn Pro Tyr Asn Asp Tyr Thr Arg Tyr Ala Gln Lys
        915                 920                 925

Phe Gln Gly Arg Val Thr Met Thr Arg Asp Thr Ser Ile Ser Thr Ala
    930                 935                 940

Tyr Met Glu Leu Ser Ser Leu Arg Ser Asp Asp Thr Ala Val Tyr Tyr
945                 950                 955                 960

Cys Ala Arg Ser Asp Gly Tyr Tyr Asp Ala Met Asp Tyr Trp Gly Gln
                965                 970                 975

Gly Thr Thr Val Thr Val Ser Ser Ser Glu Pro Lys Ser Ser Asp Lys
            980                 985                 990

Thr His Thr Cys Pro Pro Cys Pro  Ala Pro Glu Ala Ala  Gly Ala Pro
        995                 1000                1005

Ser Val  Phe Leu Phe Pro Pro  Lys Pro Lys Asp Thr  Leu Met Ile
    1010                1015                1020

Ser Arg  Thr Pro Glu Val Thr  Cys Val Val Val Asp  Val Ser His
    1025                1030                1035

Glu Asp  Pro Glu Val Lys Phe  Asn Trp Tyr Val Asp  Gly Val Glu
    1040                1045                1050

Val His  Asn Ala Lys Thr Lys  Pro Arg Glu Glu Gln  Tyr Asn Ser
    1055                1060                1065

Thr Tyr  Arg Val Val Ser Val  Leu Thr Val Leu His  Gln Asp Trp
    1070                1075                1080

Leu Asn  Gly Lys Ala Tyr Ala  Cys Ala Val Ser Asn  Lys Ala Leu
    1085                1090                1095

Pro Ala  Pro Ile Glu Lys Thr  Ile Ser Lys Ala Lys  Gly Gln Pro
    1100                1105                1110

Arg Glu  Pro Gln Val Tyr Thr  Leu Pro Pro Ser Arg  Asp Glu Leu
    1115                1120                1125

Thr Lys  Asn Gln Val Ser Leu  Thr Cys Leu Val Lys  Gly Phe Tyr
    1130                1135                1140

Pro Ser  Asp Ile Ala Val Glu  Trp Glu Ser Asn Gly  Gln Pro Glu
    1145                1150                1155

Asn Asn  Tyr Lys Thr Thr Pro  Pro Val Leu Asp Ser  Asp Gly Ser
    1160                1165                1170
```

```
Phe Phe  Leu Tyr Ser Lys Leu  Thr Val Asp Lys Ser  Arg Trp Gln
    1175                 1180                 1185

Gln Gly  Asn Val Phe Ser Cys  Ser Val Met His Glu  Ala Leu His
    1190                 1195                 1200

Asn His  Tyr Thr Gln Lys Ser  Leu Ser Leu Ser Pro  Gly Glu Val
    1205                 1210                 1215

Gln Ile  Pro Leu Thr Glu Ser  Tyr Ser Pro Asn Ser  Gln Val Gln
    1220                 1225                 1230

Leu Val  Glu Ser Gly Gly Gly  Val Val Gln Pro Gly  Arg Ser Leu
    1235                 1240                 1245

Arg Leu  Ser Cys Lys Ala Ser  Gly Tyr Thr Phe Thr  Arg Ser Thr
    1250                 1255                 1260

Met His  Trp Val Arg Gln Ala  Pro Gly Gln Gly Leu  Glu Trp Ile
    1265                 1270                 1275

Gly Tyr  Ile Asn Pro Ser Ser  Ala Tyr Thr Asn Tyr  Asn Gln Lys
    1280                 1285                 1290

Phe Lys  Asp Arg Phe Thr Ile  Ser Ala Asp Lys Ser  Lys Ser Thr
    1295                 1300                 1305

Ala Phe  Leu Gln Met Asp Ser  Leu Arg Pro Glu Asp  Thr Gly Val
    1310                 1315                 1320

Tyr Phe  Cys Ala Arg Pro Gln  Val His Tyr Asp Tyr  Asn Gly Phe
    1325                 1330                 1335

Pro Tyr  Trp Gly Gln Gly Thr  Pro Val Thr Val Ser  Ser Gly Gly
    1340                 1345                 1350

Gly Gly  Ser Gly Gly Gly Gly  Ser Gly Gly Gly Gly  Ser Ala Gln
    1355                 1360                 1365

Asp Ile  Gln Met Thr Gln Ser  Pro Ser Ser Leu Ser  Ala Ser Val
    1370                 1375                 1380

Gly Asp  Arg Val Thr Met Thr  Cys Ser Ala Ser Ser  Ser Val Ser
    1385                 1390                 1395

Tyr Met  Asn Trp Tyr Gln Gln  Lys Pro Gly Lys Ala  Pro Lys Arg
    1400                 1405                 1410

Trp Ile  Tyr Asp Ser Ser Lys  Leu Ala Ser Gly Val  Pro Ala Arg
    1415                 1420                 1425

Phe Ser  Gly Ser Gly Ser Gly  Thr Asp Tyr Thr Leu  Thr Ile Ser
    1430                 1435                 1440

Ser Leu  Gln Pro Glu Asp Phe  Ala Thr Tyr Tyr Cys  Gln Gln Trp
    1445                 1450                 1455

Ser Arg  Asn Pro Pro Thr Phe  Gly Gly Gly Thr Lys  Leu Gln Ile
    1460                 1465                 1470

Thr Ser  Ser Ser
    1475
```

<210> SEQ ID NO 60
<211> LENGTH: 2274
<212> TYPE: DNA
<213> ORGANISM: Artificial
<220> FEATURE:
<223> OTHER INFORMATION: Humanized TSC251 Scorpion (huVL-VH#2 107-1A4 scFv-Fc-DRA222 scFv, with H83 linker)

<400> SEQUENCE: 60

```
atggaagcac cagcgcagct tctcttcctc ctgctactct ggctcccaga taccaccggt      60

gatatccaga tgacccagtc tccatccgcc atgtctgcat ctgtaggaga cagagtcacc     120
```

-continued

```
atcacttgcc gggcgagtaa gagcattagc aaatatttag cctggtttca gcagaaacca    180
gggaaagttc ctaagctccg catccattct ggatctactt tgcaatcagg ggtcccatct    240
cggttcagtg gcagtggatc tgggacagaa tttactctca ccatcagcag cctgcagcct    300
gaagattttg caacttatta ctgtcaacag catattgaat acccgtggac gttcggccaa    360
gggaccaagg tggaaatcaa acgaggtggc ggagggtctg gggtggcgg atccggaggt    420
ggtggctctc aggtccagct ggtacagtct ggggctgagg tgaagaagcc tggggcttca    480
gtgaaggtct cctgcaaggc ttctggatac acattcactg actactacat gcactgggtg    540
cgacaggccc ctggacaagg gcttgagtgg atgggatatt ttaatcctta taatgattat    600
actagatacg cacagaagtt ccagggcaga gtcaccatga ccagggacac gtctatcagc    660
acagcctaca tggagctgag cagcctgaga tctgacgaca cggccgtgta ttactgtgca    720
agatcggatg gttactacga tgctatggac tactggggtc aaggaaccac agtcaccgtc    780
tcctcgagtg agcccaaatc ttctgacaaa actcacacat gcccaccgtg cccagcacct    840
gaagccgcgg gtgcaccgtc agtcttcctc ttccccccaa aacccaagga caccctcatg    900
atctcccgga cccctgaggt cacatgcgtg gtggtggacg tgagccacga agaccctgag    960
gtcaagttca actggtacgt ggacggcgtg gaggtgcata atgccaagac aaagccgcgg   1020
gaggagcagt acaacagcac gtaccgtgtg gtcagcgtcc tcaccgtcct gcaccaggac   1080
tggctgaatg gcaaggcgta cgcgtgcgcg gtctccaaca aagccctccc agcccccatc   1140
gagaaaacca tctccaaagc caaagggcag ccccgagaac cacaggtgta caccctgccc   1200
ccatcccggg atgagctgac caagaaccag gtcagcctga cctgcctggt caaaggcttc   1260
tatccaagcg acatcgccgt ggagtgggag agcaatgggc agccggagaa caactacaag   1320
accacgcctc ccgtgctgga ctccgacggc tccttcttcc tctacagcaa gctcaccgtg   1380
gacaagagca ggtggcagca ggggaacgtc ttctcatgct ccgtgatgca tgaggctctg   1440
cacaaccact acacgcagaa gagcctctcc ctgtctccgg gttcttccct gaatacagga   1500
actcagatgg caggtcattc tccgaattct caggtccagc tggtggagtc tgggggcgga   1560
gtggtgcagc ctgggcggtc actgaggctg tcctgcaagg cttctggcta cacctttact   1620
agatctacga tgcactgggt aaggcaggcc cctggacaag gtctggaatg gattggatac   1680
attaatccta gcagtgctta tactaattac aatcagaaat tcaaggacag gttcacaatc   1740
agcgcagaca aatccaagag cacagccttc ctgcagatgg acagcctgag gcccgaggac   1800
accggcgtct atttctgtgc acggccccaa gtccactatg attacaacgg gtttccttac   1860
tggggccaag ggactcccgt cactgtctct agcggtggcg gagggtctgg gggtggcgga   1920
tccggaggtg gtggctctgc acaagacatc cagatgaccc agtctccaag cagcctgtct   1980
gcaagcgtgg gggacagggt caccatgacc tgcagtgcca gctcaagtgt aagttacatg   2040
aactggtacc agcagaagcc gggcaaggcc cccaaaagat ggatttatga ctcatccaaa   2100
ctggcttctg gagtccctgc tcgcttcagt ggcagtgggt ctgggaccga ctataccctc   2160
acaatcagca gcctgcagcc cgaagatttc gccacttatt actgccagca gtggagtcgt   2220
aacccaccca cgttcggagg ggggaccaag ctacaaatta catcctccag ctaa         2274
```

<210> SEQ ID NO 61
<211> LENGTH: 737
<212> TYPE: PRT
<213> ORGANISM: Artificial
<220> FEATURE:
<223> OTHER INFORMATION: Humanized TSC251 Scorpion (huVL-VH#2 107-1A4

-continued scFv-Fc-DRA222 scFv, with H83 linker)

<400> SEQUENCE: 61

```
Asp Ile Gln Met Thr Gln Ser Pro Ser Ala Met Ser Ala Ser Val Gly
1               5                   10                  15

Asp Arg Val Thr Ile Thr Cys Arg Ala Ser Lys Ser Ile Ser Lys Tyr
            20                  25                  30

Leu Ala Trp Phe Gln Gln Lys Pro Gly Lys Val Pro Lys Leu Arg Ile
        35                  40                  45

His Ser Gly Ser Thr Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln His Ile Glu Tyr Pro Trp
                85                  90                  95

Thr Phe Gly Gln Gly Thr Lys Val Glu Ile Lys Arg Gly Gly Gly Gly
            100                 105                 110

Ser Gly Gly Gly Gly Ser Gly Gly Gly Gly Ser Gln Val Gln Leu Val
        115                 120                 125

Gln Ser Gly Ala Glu Val Lys Lys Pro Gly Ala Ser Val Lys Val Ser
    130                 135                 140

Cys Lys Ala Ser Gly Tyr Thr Phe Thr Asp Tyr Tyr Met His Trp Val
145                 150                 155                 160

Arg Gln Ala Pro Gly Gln Gly Leu Glu Trp Met Gly Tyr Phe Asn Pro
                165                 170                 175

Tyr Asn Asp Tyr Thr Arg Tyr Ala Gln Lys Phe Gln Gly Arg Val Thr
            180                 185                 190

Met Thr Arg Asp Thr Ser Ile Ser Thr Ala Tyr Met Glu Leu Ser Ser
        195                 200                 205

Leu Arg Ser Asp Asp Thr Ala Val Tyr Tyr Cys Ala Arg Ser Asp Gly
    210                 215                 220

Tyr Tyr Asp Ala Met Asp Tyr Trp Gly Gln Gly Thr Thr Val Thr Val
225                 230                 235                 240

Ser Ser Ser Glu Pro Lys Ser Ser Asp Lys Thr His Thr Cys Pro Pro
                245                 250                 255

Cys Pro Ala Pro Glu Ala Ala Gly Ala Pro Ser Val Phe Leu Phe Pro
            260                 265                 270

Pro Lys Pro Lys Asp Thr Leu Met Ile Ser Arg Thr Pro Glu Val Thr
        275                 280                 285

Cys Val Val Val Asp Val Ser His Glu Asp Pro Glu Val Lys Phe Asn
    290                 295                 300

Trp Tyr Val Asp Gly Val Glu Val His Asn Ala Lys Thr Lys Pro Arg
305                 310                 315                 320

Glu Glu Gln Tyr Asn Ser Thr Tyr Arg Val Val Ser Val Leu Thr Val
                325                 330                 335

Leu His Gln Asp Trp Leu Asn Gly Lys Ala Tyr Ala Cys Ala Val Ser
            340                 345                 350

Asn Lys Ala Leu Pro Ala Pro Ile Glu Lys Thr Ile Ser Lys Ala Lys
        355                 360                 365

Gly Gln Pro Arg Glu Pro Gln Val Tyr Thr Leu Pro Pro Ser Arg Asp
    370                 375                 380

Glu Leu Thr Lys Asn Gln Val Ser Leu Thr Cys Leu Val Lys Gly Phe
385                 390                 395                 400
```

```
Tyr Pro Ser Asp Ile Ala Val Glu Trp Glu Ser Asn Gly Gln Pro Glu
                405                 410                 415

Asn Asn Tyr Lys Thr Thr Pro Pro Val Leu Asp Ser Asp Gly Ser Phe
            420                 425                 430

Phe Leu Tyr Ser Lys Leu Thr Val Asp Lys Ser Arg Trp Gln Gln Gly
        435                 440                 445

Asn Val Phe Ser Cys Ser Val Met His Glu Ala Leu His Asn His Tyr
    450                 455                 460

Thr Gln Lys Ser Leu Ser Leu Ser Pro Gly Ser Ser Leu Asn Thr Gly
465                 470                 475                 480

Thr Gln Met Ala Gly His Ser Pro Asn Ser Gln Val Gln Leu Val Glu
                485                 490                 495

Ser Gly Gly Gly Val Val Gln Pro Gly Arg Ser Leu Arg Leu Ser Cys
            500                 505                 510

Lys Ala Ser Gly Tyr Thr Phe Thr Arg Ser Thr Met His Trp Val Arg
        515                 520                 525

Gln Ala Pro Gly Gln Gly Leu Glu Trp Ile Gly Tyr Ile Asn Pro Ser
    530                 535                 540

Ser Ala Tyr Thr Asn Tyr Asn Gln Lys Phe Lys Asp Arg Phe Thr Ile
545                 550                 555                 560

Ser Ala Asp Lys Ser Lys Ser Thr Ala Phe Leu Gln Met Asp Ser Leu
                565                 570                 575

Arg Pro Glu Asp Thr Gly Val Tyr Phe Cys Ala Arg Pro Gln Val His
            580                 585                 590

Tyr Asp Tyr Asn Gly Phe Pro Tyr Trp Gly Gln Gly Thr Pro Val Thr
        595                 600                 605

Val Ser Ser Gly Gly Gly Gly Ser Gly Gly Gly Gly Ser Gly Gly Gly
    610                 615                 620

Gly Ser Ala Gln Asp Ile Gln Met Thr Gln Ser Pro Ser Ser Leu Ser
625                 630                 635                 640

Ala Ser Val Gly Asp Arg Val Thr Met Thr Cys Ser Ala Ser Ser Ser
                645                 650                 655

Val Ser Tyr Met Asn Trp Tyr Gln Gln Lys Pro Gly Lys Ala Pro Lys
            660                 665                 670

Arg Trp Ile Tyr Asp Ser Ser Lys Leu Ala Ser Gly Val Pro Ala Arg
        675                 680                 685

Phe Ser Gly Ser Gly Ser Gly Thr Asp Tyr Thr Leu Thr Ile Ser Ser
    690                 695                 700

Leu Gln Pro Glu Asp Phe Ala Thr Tyr Tyr Cys Gln Gln Trp Ser Arg
705                 710                 715                 720

Asn Pro Pro Thr Phe Gly Gly Gly Thr Lys Leu Gln Ile Thr Ser Ser
                725                 730                 735

Ser
```

<210> SEQ ID NO 62
<211> LENGTH: 2286
<212> TYPE: DNA
<213> ORGANISM: Artificial
<220> FEATURE:
<223> OTHER INFORMATION: Huamnized TSC252 Scorpion (huVL-VH#2 107-1A4 scFv-Fc-DRA222 scFv, with H91 linker)

<400> SEQUENCE: 62

```
atggaagcac cagcgcagct tctcttcctc ctgctactct ggctcccaga taccaccggt      60

gatatccaga tgacccagtc tccatccgcc atgtctgcat ctgtaggaga cagagtcacc     120
```

```
atcacttgcc gggcgagtaa gagcattagc aaatatttag cctggtttca gcagaaacca    180
gggaaagttc ctaagctccg catccattct ggatctactt tgcaatcagg ggtcccatct    240
cggttcagtg gcagtggatc tgggacagaa tttactctca ccatcagcag cctgcagcct    300
gaagattttg caacttatta ctgtcaacag catattgaat acccgtggac gttcggccaa    360
gggaccaagg tggaaatcaa acgaggtggc ggagggtctg gggtggcgg atccggaggt    420
ggtggctctc aggtccagct ggtacagtct ggggctgagg tgaagaagcc tggggcttca    480
gtgaaggtct cctgcaaggc ttctggatac acattcactg actactacat gcactgggtg    540
cgacaggccc ctggacaagg gcttgagtgg atgggatatt ttaatcctta taatgattat    600
actagatacg cacagaagtt ccagggcaga gtcaccatga ccagggacac gtctatcagc    660
acagcctaca tggagctgag cagcctgaga tctgacgaca cggccgtgta ttactgtgca    720
agatcggatg gttactacga tgctatggac tactggggtc aaggaaccac agtcaccgtc    780
tcctcgagtg agcccaaatc ttctgacaaa actcacacat gcccaccgtg cccagcacct    840
gaagccgcgg gtgcaccgtc agtcttcctc ttccccccaa aacccaagga caccctcatg    900
atctcccgga cccctgaggt cacatgcgtg gtggtggacg tgagccacga agaccctgag    960
gtcaagttca actggtacgt ggacggcgtg gaggtgcata atgccaagac aaagccgcgg   1020
gaggagcagt acaacagcac gtaccgtgtg gtcagcgtcc tcaccgtcct gcaccaggac   1080
tggctgaatg gcaaggcgta cgcgtgcgcg gtctccaaca aagccctccc agcccccatc   1140
gagaaaacca tctccaaagc caaagggcag ccccgagaac cacaggtgta caccctgccc   1200
ccatcccggg atgagctgac caagaaccag gtcagcctga cctgcctggt caaaggcttc   1260
tatccaagcg acatcgccgt ggagtgggag agcaatgggc agccggagaa caactacaag   1320
accacgcctc ccgtgctgga ctccgacggc tccttcttcc tctacagcaa gctcaccgtg   1380
gacaagagca ggtggcagca ggggaacgtc ttctcatgct ccgtgatgca tgaggctctg   1440
cacaaccact acacgcagaa gagcctctcc ctgtctccgg gtaactcatt agcaaaccaa   1500
gaagttcaaa ttcccttgac cgaaagttac agcccgaatt ctcaggtcca gctggtggag   1560
tctgggggcg gagtggtgca gcctgggcgg tcactgaggc tgtcctgcaa ggcttctggc   1620
tacaccttta ctagatctac gatgcactgg gtaaggcagg cccctggaca aggtctggaa   1680
tggattggat acattaatcc tagcagtgct tatactaatt acaatcagaa attcaaggac   1740
aggttcacaa tcagcgcaga caaatccaag agcacagcct tcctgcagat ggacagcctg   1800
aggcccgagg acaccggcgt ctatttctgt gcacggcccc aagtccacta tgattacaac   1860
gggtttcctt actggggcca agggactccc gtcactgtct ctagcggtgg cggagggtct   1920
gggggtggcg gatccggagg tggtggctct gcacaagaca tccagatgac ccagtctcca   1980
agcagcctgt ctgcaagcgt gggggacagg gtcaccatga cctgcagtgc cagctcaagt   2040
gtaagttaca tgaactggta ccagcagaag ccgggcaagg cccccaaaag atggatttat   2100
gactcatcca aactggcttc tggagtccct gctcgcttca gtggcagtgg gtctgggacc   2160
gactataccc tcacaatcag cagcctgcag cccgaagatt tcgccactta ttactgccag   2220
cagtggagtc gtaacccacc cacgttcgga gggggacca agctacaaat tacatcctcc   2280
agctaa                                                              2286
```

<210> SEQ ID NO 63
<211> LENGTH: 741
<212> TYPE: PRT

<213> ORGANISM: Artificial
<220> FEATURE:
<223> OTHER INFORMATION: Humanized TSC252 Scorpion (huVL-VH#2 107-1A4 scFv-Fc-DRA222 scFv, with H91 linker)

<400> SEQUENCE: 63

Asp Ile Gln Met Thr Gln Ser Pro Ser Ala Met Ser Ala Ser Val Gly
1 5 10 15

Asp Arg Val Thr Ile Thr Cys Arg Ala Ser Lys Ser Ile Ser Lys Tyr
20 25 30

Leu Ala Trp Phe Gln Gln Lys Pro Gly Lys Val Pro Lys Leu Arg Ile
35 40 45

His Ser Gly Ser Thr Leu Gln Ser Gly Val Pro Ser Arg Phe Ser Gly
50 55 60

Ser Gly Ser Gly Thr Glu Phe Thr Leu Thr Ile Ser Ser Leu Gln Pro
65 70 75 80

Glu Asp Phe Ala Thr Tyr Tyr Cys Gln Gln His Ile Glu Tyr Pro Trp
85 90 95

Thr Phe Gly Gln Gly Thr Lys Val Glu Ile Lys Arg Gly Gly Gly Gly
100 105 110

Ser Gly Gly Gly Gly Ser Gly Gly Gly Gly Ser Gln Val Gln Leu Val
115 120 125

Gln Ser Gly Ala Glu Val Lys Lys Pro Gly Ala Ser Val Lys Val Ser
130 135 140

Cys Lys Ala Ser Gly Tyr Thr Phe Thr Asp Tyr Tyr Met His Trp Val
145 150 155 160

Arg Gln Ala Pro Gly Gln Gly Leu Glu Trp Met Gly Tyr Phe Asn Pro
165 170 175

Tyr Asn Asp Tyr Thr Arg Tyr Ala Gln Lys Phe Gln Gly Arg Val Thr
180 185 190

Met Thr Arg Asp Thr Ser Ile Ser Thr Ala Tyr Met Glu Leu Ser Ser
195 200 205

Leu Arg Ser Asp Asp Thr Ala Val Tyr Tyr Cys Ala Arg Ser Asp Gly
210 215 220

Tyr Tyr Asp Ala Met Asp Tyr Trp Gly Gln Gly Thr Thr Val Thr Val
225 230 235 240

Ser Ser Ser Glu Pro Lys Ser Ser Asp Lys Thr His Thr Cys Pro Pro
245 250 255

Cys Pro Ala Pro Glu Ala Ala Gly Ala Pro Ser Val Phe Leu Phe Pro
260 265 270

Pro Lys Pro Lys Asp Thr Leu Met Ile Ser Arg Thr Pro Glu Val Thr
275 280 285

Cys Val Val Val Asp Val Ser His Glu Asp Pro Glu Val Lys Phe Asn
290 295 300

Trp Tyr Val Asp Gly Val Glu Val His Asn Ala Lys Thr Lys Pro Arg
305 310 315 320

Glu Glu Gln Tyr Asn Ser Thr Tyr Arg Val Val Ser Val Leu Thr Val
325 330 335

Leu His Gln Asp Trp Leu Asn Gly Lys Ala Tyr Ala Cys Ala Val Ser
340 345 350

Asn Lys Ala Leu Pro Ala Pro Ile Glu Lys Thr Ile Ser Lys Ala Lys
355 360 365

Gly Gln Pro Arg Glu Pro Gln Val Tyr Thr Leu Pro Pro Ser Arg Asp
370 375 380

```
Glu Leu Thr Lys Asn Gln Val Ser Leu Thr Cys Leu Val Lys Gly Phe
385                 390                 395                 400

Tyr Pro Ser Asp Ile Ala Val Glu Trp Glu Ser Asn Gly Gln Pro Glu
                405                 410                 415

Asn Asn Tyr Lys Thr Thr Pro Pro Val Leu Asp Ser Asp Gly Ser Phe
            420                 425                 430

Phe Leu Tyr Ser Lys Leu Thr Val Asp Lys Ser Arg Trp Gln Gln Gly
        435                 440                 445

Asn Val Phe Ser Cys Ser Val Met His Glu Ala Leu His Asn His Tyr
    450                 455                 460

Thr Gln Lys Ser Leu Ser Leu Ser Pro Gly Asn Ser Leu Ala Asn Gln
465                 470                 475                 480

Glu Val Gln Ile Pro Leu Thr Glu Ser Tyr Ser Pro Asn Ser Gln Val
                485                 490                 495

Gln Leu Val Glu Ser Gly Gly Gly Val Val Gln Pro Gly Arg Ser Leu
            500                 505                 510

Arg Leu Ser Cys Lys Ala Ser Gly Tyr Thr Phe Thr Arg Ser Thr Met
        515                 520                 525

His Trp Val Arg Gln Ala Pro Gly Gln Gly Leu Glu Trp Ile Gly Tyr
    530                 535                 540

Ile Asn Pro Ser Ser Ala Tyr Thr Asn Tyr Asn Gln Lys Phe Lys Asp
545                 550                 555                 560

Arg Phe Thr Ile Ser Ala Asp Lys Ser Lys Ser Thr Ala Phe Leu Gln
                565                 570                 575

Met Asp Ser Leu Arg Pro Glu Asp Thr Gly Val Tyr Phe Cys Ala Arg
            580                 585                 590

Pro Gln Val His Tyr Asp Tyr Asn Gly Phe Pro Tyr Trp Gly Gln Gly
        595                 600                 605

Thr Pro Val Thr Val Ser Ser Gly Gly Gly Gly Ser Gly Gly Gly Gly
    610                 615                 620

Ser Gly Gly Gly Gly Ser Ala Gln Asp Ile Gln Met Thr Gln Ser Pro
625                 630                 635                 640

Ser Ser Leu Ser Ala Ser Val Gly Asp Arg Val Thr Met Thr Cys Ser
                645                 650                 655

Ala Ser Ser Ser Val Ser Tyr Met Asn Trp Tyr Gln Gln Lys Pro Gly
            660                 665                 670

Lys Ala Pro Lys Arg Trp Ile Tyr Asp Ser Ser Lys Leu Ala Ser Gly
        675                 680                 685

Val Pro Ala Arg Phe Ser Gly Ser Gly Ser Gly Thr Asp Tyr Thr Leu
    690                 695                 700

Thr Ile Ser Ser Leu Gln Pro Glu Asp Phe Ala Thr Tyr Tyr Cys Gln
705                 710                 715                 720

Gln Trp Ser Arg Asn Pro Pro Thr Phe Gly Gly Gly Thr Lys Leu Gln
                725                 730                 735

Ile Thr Ser Ser Ser
            740
```

<210> SEQ ID NO 64
<211> LENGTH: 2250
<212> TYPE: DNA
<213> ORGANISM: Artificial
<220> FEATURE:
<223> OTHER INFORMATION: Humanized TSC295 Scorpion (huVL-VH#2 107-1A4 scFv-Fc-DRA222 scFv, with H9 linker)

<400> SEQUENCE: 64

```
atggaagcac cagcgcagct tctcttcctc ctgctactct ggctcccaga taccaccggt     60
gatatccaga tgacccagtc tccatccgcc atgtctgcat ctgtaggaga cagagtcacc    120
atcacttgcc gggcgagtaa gagcattagc aaatatttag cctggtttca gcagaaacca    180
gggaaagttc ctaagctccg catccattct ggatctactt tgcaatcagg ggtcccatct    240
cggttcagtg gcagtggatc tgggacagaa tttactctca ccatcagcag cctgcagcct    300
gaagattttg caacttatta ctgtcaacag catattgaat acccgtggac gttcggccaa    360
gggaccaagg tggaaatcaa acgaggtggc ggagggtctg gggggtggcgg atccggaggt    420
ggtggctctc aggtccagct ggtacagtct ggggctgagg tgaagaagcc tggggcttca    480
gtgaaggtct cctgcaaggc ttctggatac acattcactg actactacat gcactgggtg    540
cgacaggccc ctggacaagg gcttgagtgg atgggatatt ttaatcctta taatgattat    600
actagatacg cacagaagtt ccagggcaga gtcaccatga ccagggacac gtctatcagc    660
acagcctaca tggagctgag cagcctgaga tctgacgaca cggccgtgta ttactgtgca    720
agatcggatg gttactacga tgctatggac tactggggtc aaggaaccac agtcaccgtc    780
tcctcgagtg agcccaaatc ttctgacaaa actcacacat gcccaccgtg cccagcacct    840
gaagccgcgg gtgcaccgtc agtcttcctc ttccccccaa aacccaagga caccctcatg    900
atctcccgga cccctgaggt cacatgcgtg gtggtggacg tgagccacga agaccctgag    960
gtcaagttca actggtacgt ggacggcgtg gaggtgcata atgccaagac aaagccgcgg   1020
gaggagcagt acaacagcac gtaccgtgtg gtcagcgtcc tcaccgtcct gcaccaggac   1080
tggctgaatg gcaaggcgta cgcgtgcgcg gtctccaaca aagccctccc agcccccatc   1140
gagaaaacca tctccaaagc caaagggcag ccccgagaac cacaggtgta caccctgccc   1200
ccatcccggg atgagctgac caagaaccag gtcagcctga cctgcctggt caaaggcttc   1260
tatccaagcg acatcgccgt ggagtgggag agcaatgggc agccggagaa caactacaag   1320
accacgcctc ccgtgctgga ctccgacggc tccttcttcc tctacagcaa gctcaccgtg   1380
gacaagagca ggtggcagca ggggaacgtc ttctcatgct ccgtgatgca tgaggctctg   1440
cacaaccact acacgcagaa gagcctctcc ctgtctccgg gtgggagccc accttcaccg   1500
aattctcagg tccagctggt ggagtctggg ggcggagtgg tgcagcctgg gcggtcactg   1560
aggctgtcct gcaaggcttc tggctacacc tttactagat ctacgatgca ctgggtaagg   1620
caggcccctg gacaaggtct ggaatggatt ggatacatta atcctagcag tgcttatact   1680
aattacaatc agaaattcaa ggacaggttc acaatcagcg cagacaaatc caagagcaca   1740
gccttcctgc agatggacag cctgaggccc gaggacaccg gcgtctattt ctgtgcacgg   1800
ccccaagtcc actatgatta caacgggttt ccttactggg gccaagggac tcccgtcact   1860
gtctctagcg gtggcggagg gtctgggggt ggcggatccg gaggtggtgg ctctgcacaa   1920
gacatccaga tgacccagtc tccaagcagc ctgtctgcaa gcgtggggga cagggtcacc   1980
atgacctgca gtgccagctc aagtgtaagt tacatgaact ggtaccagca gaagccgggc   2040
aaggccccca aaagatggat ttatgactca tccaaactgg cttctggagt ccctgctcgc   2100
ttcagtggca gtgggtctgg gaccgactat accctcacaa tcagcagcct gcagcccgaa   2160
gatttcgcca cttattactg ccagcagtgg agtcgtaacc cacccacgtt cggagggggg   2220
accaagctac aaattacatc ctccagctaa                                    2250
```

<210> SEQ ID NO 65

```
<211> LENGTH: 729
<212> TYPE: PRT
<213> ORGANISM: Artificial
<220> FEATURE:
<223> OTHER INFORMATION: Humanized TSC295 Scorpion (huVL-VH#2 107-1A4
      scFv-Fc-DRA222 scFv, with H9 linker)

<400> SEQUENCE: 65

Asp Ile Gln Met Thr Gln Ser Pro Ser Ala Met Ser Ala Ser Val Gly
1               5                   10                  15

Asp Arg Val Thr Ile Thr Cys Arg Ala Ser Lys Ser Ile Ser Lys Tyr
            20                  25                  30

Leu Ala Trp Phe Gln Gln Lys Pro Gly Lys Val Pro Lys Leu Arg Ile
        35                  40                  45

His Ser Gly Ser Thr Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln His Ile Glu Tyr Pro Trp
                85                  90                  95

Thr Phe Gly Gln Gly Thr Lys Val Glu Ile Lys Arg Gly Gly Gly Gly
            100                 105                 110

Ser Gly Gly Gly Gly Ser Gly Gly Gly Gly Ser Gln Val Gln Leu Val
        115                 120                 125

Gln Ser Gly Ala Glu Val Lys Lys Pro Gly Ala Ser Val Lys Val Ser
    130                 135                 140

Cys Lys Ala Ser Gly Tyr Thr Phe Thr Asp Tyr Tyr Met His Trp Val
145                 150                 155                 160

Arg Gln Ala Pro Gly Gln Gly Leu Glu Trp Met Gly Tyr Phe Asn Pro
                165                 170                 175

Tyr Asn Asp Tyr Thr Arg Tyr Ala Gln Lys Phe Gln Gly Arg Val Thr
            180                 185                 190

Met Thr Arg Asp Thr Ser Ile Ser Thr Ala Tyr Met Glu Leu Ser Ser
        195                 200                 205

Leu Arg Ser Asp Asp Thr Ala Val Tyr Tyr Cys Ala Arg Ser Asp Gly
    210                 215                 220

Tyr Tyr Asp Ala Met Asp Tyr Trp Gly Gln Gly Thr Thr Val Thr Val
225                 230                 235                 240

Ser Ser Ser Glu Pro Lys Ser Ser Asp Lys Thr His Thr Cys Pro Pro
                245                 250                 255

Cys Pro Ala Pro Glu Ala Ala Gly Ala Pro Ser Val Phe Leu Phe Pro
            260                 265                 270

Pro Lys Pro Lys Asp Thr Leu Met Ile Ser Arg Thr Pro Glu Val Thr
        275                 280                 285

Cys Val Val Val Asp Val Ser His Glu Asp Pro Glu Val Lys Phe Asn
    290                 295                 300

Trp Tyr Val Asp Gly Val Glu Val His Asn Ala Lys Thr Lys Pro Arg
305                 310                 315                 320

Glu Glu Gln Tyr Asn Ser Thr Tyr Arg Val Val Ser Val Leu Thr Val
                325                 330                 335

Leu His Gln Asp Trp Leu Asn Gly Lys Ala Tyr Ala Cys Ala Val Ser
            340                 345                 350

Asn Lys Ala Leu Pro Ala Pro Ile Glu Lys Thr Ile Ser Lys Ala Lys
        355                 360                 365

Gly Gln Pro Arg Glu Pro Gln Val Tyr Thr Leu Pro Pro Ser Arg Asp
```

```
    370                 375                 380

Glu Leu Thr Lys Asn Gln Val Ser Leu Thr Cys Leu Val Lys Gly Phe
385                 390                 395                 400

Tyr Pro Ser Asp Ile Ala Val Glu Trp Glu Ser Asn Gly Gln Pro Glu
                405                 410                 415

Asn Asn Tyr Lys Thr Thr Pro Pro Val Leu Asp Ser Asp Gly Ser Phe
            420                 425                 430

Phe Leu Tyr Ser Lys Leu Thr Val Asp Lys Ser Arg Trp Gln Gln Gly
        435                 440                 445

Asn Val Phe Ser Cys Ser Val Met His Glu Ala Leu His Asn His Tyr
    450                 455                 460

Thr Gln Lys Ser Leu Ser Leu Ser Pro Gly Gly Ser Pro Pro Ser Pro
465                 470                 475                 480

Asn Ser Gln Val Gln Leu Val Glu Ser Gly Gly Gly Val Val Gln Pro
                485                 490                 495

Gly Arg Ser Leu Arg Leu Ser Cys Lys Ala Ser Gly Tyr Thr Phe Thr
            500                 505                 510

Arg Ser Thr Met His Trp Val Arg Gln Ala Pro Gly Gln Gly Leu Glu
        515                 520                 525

Trp Ile Gly Tyr Ile Asn Pro Ser Ser Ala Tyr Thr Asn Tyr Asn Gln
    530                 535                 540

Lys Phe Lys Asp Arg Phe Thr Ile Ser Ala Asp Lys Ser Lys Ser Thr
545                 550                 555                 560

Ala Phe Leu Gln Met Asp Ser Leu Arg Pro Glu Asp Thr Gly Val Tyr
                565                 570                 575

Phe Cys Ala Arg Pro Gln Val His Tyr Asp Tyr Asn Gly Phe Pro Tyr
            580                 585                 590

Trp Gly Gln Gly Thr Pro Val Thr Val Ser Ser Gly Gly Gly Gly Ser
        595                 600                 605

Gly Gly Gly Gly Ser Gly Gly Gly Gly Ser Ala Gln Asp Ile Gln Met
    610                 615                 620

Thr Gln Ser Pro Ser Ser Leu Ser Ala Ser Val Gly Asp Arg Val Thr
625                 630                 635                 640

Met Thr Cys Ser Ala Ser Ser Ser Val Ser Tyr Met Asn Trp Tyr Gln
                645                 650                 655

Gln Lys Pro Gly Lys Ala Pro Lys Arg Trp Ile Tyr Asp Ser Ser Lys
            660                 665                 670

Leu Ala Ser Gly Val Pro Ala Arg Phe Ser Gly Ser Gly Ser Gly Thr
        675                 680                 685

Asp Tyr Thr Leu Thr Ile Ser Ser Leu Gln Pro Glu Asp Phe Ala Thr
    690                 695                 700

Tyr Tyr Cys Gln Gln Trp Ser Arg Asn Pro Pro Thr Phe Gly Gly Gly
705                 710                 715                 720

Thr Lys Leu Gln Ile Thr Ser Ser Ser
                725
```

<210> SEQ ID NO 66
<211> LENGTH: 2283
<212> TYPE: DNA
<213> ORGANISM: Artificial
<220> FEATURE:
<223> OTHER INFORMATION: Humanized TSC296 Scorpion (huVL-VH#2 107-1A4 scFv-Fc-DRA222 scFv, with H94 linker)

<400> SEQUENCE: 66

-continued

```
atggaagcac cagcgcagct tctcttcctc ctgctactct ggctcccaga taccaccggt     60
gatatccaga tgacccagtc tccatccgcc atgtctgcat ctgtaggaga cagagtcacc    120
atcacttgcc gggcgagtaa gagcattagc aaatatttag cctggtttca gcagaaacca    180
gggaaagttc ctaagctccg catccattct ggatctactt tgcaatcagg ggtcccatct    240
cggttcagtg gcagtggatc tgggacagaa tttactctca ccatcagcag cctgcagcct    300
gaagattttg caacttatta ctgtcaacag catattgaat acccgtggac gttcggccaa    360
gggaccaagg tggaaatcaa acgaggtggc ggagggtctg gggtggcgg atccggaggt     420
ggtggctctc aggtccagct ggtacagtct ggggctgagg tgaagaagcc tggggcttca    480
gtgaaggtct cctgcaaggc ttctggatac acattcactg actactacat gcactgggtg    540
cgacaggccc ctggacaagg gcttgagtgg atgggatatt ttaatcctta taatgattat    600
actagatacg cacagaagtt ccagggcaga gtcaccatga ccagggacac gtctatcagc    660
acagcctaca tggagctgag cagcctgaga tctgacgaca cggccgtgta ttactgtgca    720
agatcggatg gttactacga tgctatggac tactggggtc aaggaaccac agtcaccgtc    780
tcctcgagtg agcccaaatc ttctgacaaa actcacacat gcccaccgtg cccagcacct    840
gaagccgcgg gtgcaccgtc agtcttcctc ttccccccaa aacccaagga caccctcatg    900
atctcccgga cccctgaggt cacatgcgtg gtggtggacg tgagccacga agaccctgag    960
gtcaagttca actggtacgt ggacggcgtg gaggtgcata atgccaagac aaagccgcgg   1020
gaggagcagt acaacagcac gtaccgtgtg gtcagcgtcc tcaccgtcct gcaccaggac   1080
tggctgaatg gcaaggcgta cgcgtgcgcg gtctccaaca aagccctccc agcccccatc   1140
gagaaaacca tctccaaagc caaagggcag ccccgagaac cacaggtgta caccctgccc   1200
ccatcccggg atgagctgac caagaaccag gtcagcctga cctgcctggt caaaggcttc   1260
tatccaagcg acatcgccgt ggagtgggag agcaatgggc agccggagaa caactacaag   1320
accacgcctc ccgtgctgga ctccgacggc tccttcttcc tctacagcaa gctcaccgtg   1380
gacaagagca ggtggcagca ggggaacgtc ttctcatgct ccgtgatgca tgaggctctg   1440
cacaaccact acacgcagaa gagcctctcc ctgtctccgg gttctggtgg aggcggttca   1500
ggcggaggtg gctccggcgg tggcggatcg ccgaattctc aggtccagct ggtggagtct   1560
gggggcggag tggtgcagcc tgggcggtca ctgaggctgt cctgcaaggc ttctggctac   1620
acctttacta gatctacgat gcactgggta aggcaggccc ctggacaagg tctggaatgg   1680
attggataca ttaatcctag cagtgcttat actaattaca atcagaaatt caaggacagg   1740
ttcacaatca gcgcagacaa atccaagagc acagccttcc tgcagatgga cagcctgagg   1800
cccgaggaca ccggcgtcta tttctgtgca cggccccaag tccactatga ttacaacggg   1860
tttccttact ggggccaagg gactcccgtc actgtctcta gcggtggcgg agggtctggg   1920
ggtggcggat ccggaggtgg tggctctgca caagacatcc agatgaccca gtctccaagc   1980
agcctgtctg caagcgtggg ggacagggtc accatgacct gcagtgccag ctcaagtgta   2040
agttacatga actggtacca gcagaagccg ggcaaggccc ccaaaagatg gatttatgac   2100
tcatccaaac tggcttctgg agtccctgct cgcttcagtg gcagtgggtc tgggaccgac   2160
tataccctca caatcagcag cctgcagccc gaagatttcg ccacttatta ctgccagcag   2220
tggagtcgta acccacccac gttcggaggg gggaccaagc tacaaattac atcctccagc   2280
taa                                                                 2283
```

<210> SEQ ID NO 67
<211> LENGTH: 740
<212> TYPE: PRT
<213> ORGANISM: Artificial
<220> FEATURE:
<223> OTHER INFORMATION: Humanized TSC296 Scorpion (huVL-VH#2 107-1A4 scFv-Fc-DRA222 scFv, with H94 linker)

<400> SEQUENCE: 67

```
Asp Ile Gln Met Thr Gln Ser Pro Ser Ala Met Ser Ala Ser Val Gly
1               5                   10                  15

Asp Arg Val Thr Ile Thr Cys Arg Ala Ser Lys Ser Ile Ser Lys Tyr
            20                  25                  30

Leu Ala Trp Phe Gln Gln Lys Pro Gly Lys Val Pro Lys Leu Arg Ile
        35                  40                  45

His Ser Gly Ser Thr Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln His Ile Glu Tyr Pro Trp
                85                  90                  95

Thr Phe Gly Gln Gly Thr Lys Val Glu Ile Lys Arg Gly Gly Gly Gly
            100                 105                 110

Ser Gly Gly Gly Gly Ser Gly Gly Gly Gly Ser Gln Val Gln Leu Val
        115                 120                 125

Gln Ser Gly Ala Glu Val Lys Lys Pro Gly Ala Ser Val Lys Val Ser
    130                 135                 140

Cys Lys Ala Ser Gly Tyr Thr Phe Thr Asp Tyr Tyr Met His Trp Val
145                 150                 155                 160

Arg Gln Ala Pro Gly Gln Gly Leu Glu Trp Met Gly Tyr Phe Asn Pro
                165                 170                 175

Tyr Asn Asp Tyr Thr Arg Tyr Ala Gln Lys Phe Gln Gly Arg Val Thr
            180                 185                 190

Met Thr Arg Asp Thr Ser Ile Ser Thr Ala Tyr Met Glu Leu Ser Ser
        195                 200                 205

Leu Arg Ser Asp Asp Thr Ala Val Tyr Tyr Cys Ala Arg Ser Asp Gly
    210                 215                 220

Tyr Tyr Asp Ala Met Asp Tyr Trp Gly Gln Gly Thr Thr Val Thr Val
225                 230                 235                 240

Ser Ser Ser Glu Pro Lys Ser Ser Asp Lys Thr His Thr Cys Pro Pro
                245                 250                 255

Cys Pro Ala Pro Glu Ala Ala Gly Ala Pro Ser Val Phe Leu Phe Pro
            260                 265                 270

Pro Lys Pro Lys Asp Thr Leu Met Ile Ser Arg Thr Pro Glu Val Thr
        275                 280                 285

Cys Val Val Val Asp Val Ser His Glu Asp Pro Glu Val Lys Phe Asn
    290                 295                 300

Trp Tyr Val Asp Gly Val Glu Val His Asn Ala Lys Thr Lys Pro Arg
305                 310                 315                 320

Glu Glu Gln Tyr Asn Ser Thr Tyr Arg Val Val Ser Val Leu Thr Val
                325                 330                 335

Leu His Gln Asp Trp Leu Asn Gly Lys Ala Tyr Ala Cys Ala Val Ser
            340                 345                 350

Asn Lys Ala Leu Pro Ala Pro Ile Glu Lys Thr Ile Ser Lys Ala Lys
        355                 360                 365
```

```
Gly Gln Pro Arg Glu Pro Gln Val Tyr Thr Leu Pro Pro Ser Arg Asp
    370                 375                 380

Glu Leu Thr Lys Asn Gln Val Ser Leu Thr Cys Leu Val Lys Gly Phe
385                 390                 395                 400

Tyr Pro Ser Asp Ile Ala Val Glu Trp Glu Ser Asn Gly Gln Pro Glu
                405                 410                 415

Asn Asn Tyr Lys Thr Thr Pro Pro Val Leu Asp Ser Asp Gly Ser Phe
            420                 425                 430

Phe Leu Tyr Ser Lys Leu Thr Val Asp Lys Ser Arg Trp Gln Gln Gly
        435                 440                 445

Asn Val Phe Ser Cys Ser Val Met His Glu Ala Leu His Asn His Tyr
    450                 455                 460

Thr Gln Lys Ser Leu Ser Leu Ser Pro Gly Ser Gly Gly Gly Gly Ser
465                 470                 475                 480

Gly Gly Gly Gly Ser Gly Gly Gly Gly Ser Pro Asn Ser Gln Val Gln
                485                 490                 495

Leu Val Glu Ser Gly Gly Gly Val Val Gln Pro Gly Arg Ser Leu Arg
            500                 505                 510

Leu Ser Cys Lys Ala Ser Gly Tyr Thr Phe Thr Arg Ser Thr Met His
        515                 520                 525

Trp Val Arg Gln Ala Pro Gly Gln Gly Leu Glu Trp Ile Gly Tyr Ile
    530                 535                 540

Asn Pro Ser Ser Ala Tyr Thr Asn Tyr Asn Gln Lys Phe Lys Asp Arg
545                 550                 555                 560

Phe Thr Ile Ser Ala Asp Lys Ser Lys Ser Thr Ala Phe Leu Gln Met
                565                 570                 575

Asp Ser Leu Arg Pro Glu Asp Thr Gly Val Tyr Phe Cys Ala Arg Pro
            580                 585                 590

Gln Val His Tyr Asp Tyr Asn Gly Phe Pro Tyr Trp Gly Gln Gly Thr
        595                 600                 605

Pro Val Thr Val Ser Ser Gly Gly Gly Gly Ser Gly Gly Gly Gly Ser
    610                 615                 620

Gly Gly Gly Gly Ser Ala Gln Asp Ile Gln Met Thr Gln Ser Pro Ser
625                 630                 635                 640

Ser Leu Ser Ala Ser Val Gly Asp Arg Val Thr Met Thr Cys Ser Ala
                645                 650                 655

Ser Ser Ser Val Ser Tyr Met Asn Trp Tyr Gln Gln Lys Pro Gly Lys
            660                 665                 670

Ala Pro Lys Arg Trp Ile Tyr Asp Ser Ser Lys Leu Ala Ser Gly Val
        675                 680                 685

Pro Ala Arg Phe Ser Gly Ser Gly Ser Gly Thr Asp Tyr Thr Leu Thr
    690                 695                 700

Ile Ser Ser Leu Gln Pro Glu Asp Phe Ala Thr Tyr Tyr Cys Gln Gln
705                 710                 715                 720

Trp Ser Arg Asn Pro Pro Thr Phe Gly Gly Gly Thr Lys Leu Gln Ile
                725                 730                 735

Thr Ser Ser Ser
            740
```

<210> SEQ ID NO 68
<211> LENGTH: 2274
<212> TYPE: DNA
<213> ORGANISM: Artificial
<220> FEATURE:
<223> OTHER INFORMATION: Humanized TSC301 Scorpion (huVL-VH#2 107-1A4

-continued scFv-Fc-DRA222 scFv, with H105 linker)

<400> SEQUENCE: 68

```
atggaagcac cagcgcagct tctcttcctc ctgctactct ggctcccaga taccaccggt     60
gatatccaga tgacccagtc tccatccgcc atgtctgcat ctgtaggaga cagagtcacc    120
atcacttgcc gggcgagtaa gagcattagc aaatatttag cctggtttca gcagaaacca    180
gggaaagttc ctaagctccg catccattct ggatctactt tgcaatcagg ggtcccatct    240
cggttcagtg gcagtggatc tgggacagaa tttactctca ccatcagcag cctgcagcct    300
gaagattttg caacttatta ctgtcaacag catattgaat acccgtggac gttcggccaa    360
gggaccaagg tggaaatcaa acgaggtggc ggagggtctg gggtggcgg atccggaggt     420
ggtggctctc aggtccagct ggtacagtct ggggctgagg tgaagaagcc tggggcttca    480
gtgaaggtct cctgcaaggc ttctggatac acattcactg actactacat gcactgggtg    540
cgacaggccc ctggacaagg gcttgagtgg atgggatatt ttaatcctta taatgattat    600
actagatacg cacagaagtt ccagggcaga gtcaccatga ccagggacac gtctatcagc    660
acagcctaca tggagctgag cagcctgaga tctgacgaca cggccgtgta ttactgtgca    720
agatcggatg gttactacga tgctatggac tactggggtc aaggaaccac agtcaccgtc    780
tcctcgagtg agcccaaatc ttctgacaaa actcacacat gcccaccgtg cccagcacct    840
gaagccgcgg gtgcaccgtc agtcttcctc ttccccccaa aacccaagga caccctcatg    900
atctcccgga cccctgaggt cacatgcgtg gtggtggacg tgagccacga agaccctgag    960
gtcaagttca actggtacgt ggacggcgtg gaggtgcata atgccaagac aaagccgcgg   1020
gaggagcagt acaacagcac gtaccgtgtg gtcagcgtcc tcaccgtcct gcaccaggac   1080
tggctgaatg gcaaggcgta cgcgtgcgcg gtctccaaca aagccctccc agcccccatc   1140
gagaaaacca tctccaaagc caaagggcag ccccgagaac cacaggtgta caccctgccc   1200
ccatcccggg atgagctgac caagaaccag gtcagcctga cctgcctggt caaaggcttc   1260
tatccaagcg acatcgccgt ggagtgggag agcaatgggc agccggagaa caactacaag   1320
accacgcctc ccgtgctgga ctccgacggc tccttcttcc tctacagcaa gctcaccgtg   1380
gacaagagca ggtggcagca ggggaacgtc ttctcatgct ccgtgatgca tgaggctctg   1440
cacaaccact acacgcagaa gagcctctcc ctgtctccgg gttctggtgg aggcggttca   1500
ggcggaggtg gctccggcgg tggcggatcg caggtccagc tggtggagtc tgggggcgga   1560
gtggtgcagc ctgggcggtc actgaggctg tcctgcaagg cttctggcta cacctttact   1620
agatctacga tgcactgggt aaggcaggcc cctggacaag gtctggaatg gattggatac   1680
attaatccta gcagtgctta tactaattac aatcagaaat tcaaggacag gttcacaatc   1740
agcgcagaca aatccaagag cacagccttc ctgcagatgg acagcctgag gcccgaggac   1800
accggcgtct atttctgtgc acggccccaa gtccactatg attacaacgg gtttccttac   1860
tggggccaag ggactcccgt cactgtctct agcggtggcg gagggtctgg gggtggcgga   1920
tccggaggtg gtggctctgc acaagacatc cagatgaccc agtctccaag cagcctgtct   1980
gcaagcgtgg gggacagggt caccatgacc tgcagtgcca gctcaagtgt aagttacatg   2040
aactggtacc agcagaagcc gggcaaggcc cccaaaagat ggatttatga ctcatccaaa   2100
ctggcttctg gagtccctgc tcgcttcagt ggcagtgggt ctgggaccga ctataccctc   2160
acaatcagca gcctgcagcc cgaagatttc gccacttatt actgccagca gtggagtcgt   2220
aacccaccca cgttcggagg ggggaccaag ctacaaatta catcctccag ctaa         2274
```

<210> SEQ ID NO 69
<211> LENGTH: 737
<212> TYPE: PRT
<213> ORGANISM: Artificial
<220> FEATURE:
<223> OTHER INFORMATION: Humanized TSC301 Scorpion (huVL-VH#2 107-1A4 scFv-Fc-DRA222 scFv, with H105 linker)

<400> SEQUENCE: 69

Asp Ile Gln Met Thr Gln Ser Pro Ser Ala Met Ser Ala Ser Val Gly
1 5 10 15

Asp Arg Val Thr Ile Thr Cys Arg Ala Ser Lys Ser Ile Ser Lys Tyr
20 25 30

Leu Ala Trp Phe Gln Gln Lys Pro Gly Lys Val Pro Lys Leu Arg Ile
35 40 45

His Ser Gly Ser Thr Leu Gln Ser Gly Val Pro Ser Arg Phe Ser Gly
50 55 60

Ser Gly Ser Gly Thr Glu Phe Thr Leu Thr Ile Ser Ser Leu Gln Pro
65 70 75 80

Glu Asp Phe Ala Thr Tyr Tyr Cys Gln Gln His Ile Glu Tyr Pro Trp
85 90 95

Thr Phe Gly Gln Gly Thr Lys Val Glu Ile Lys Arg Gly Gly Gly Gly
100 105 110

Ser Gly Gly Gly Gly Ser Gly Gly Gly Gly Ser Gln Val Gln Leu Val
115 120 125

Gln Ser Gly Ala Glu Val Lys Lys Pro Gly Ala Ser Val Lys Val Ser
130 135 140

Cys Lys Ala Ser Gly Tyr Thr Phe Thr Asp Tyr Tyr Met His Trp Val
145 150 155 160

Arg Gln Ala Pro Gly Gln Gly Leu Glu Trp Met Gly Tyr Phe Asn Pro
165 170 175

Tyr Asn Asp Tyr Thr Arg Tyr Ala Gln Lys Phe Gln Gly Arg Val Thr
180 185 190

Met Thr Arg Asp Thr Ser Ile Ser Thr Ala Tyr Met Glu Leu Ser Ser
195 200 205

Leu Arg Ser Asp Asp Thr Ala Val Tyr Tyr Cys Ala Arg Ser Asp Gly
210 215 220

Tyr Tyr Asp Ala Met Asp Tyr Trp Gly Gln Gly Thr Thr Val Thr Val
225 230 235 240

Ser Ser Ser Glu Pro Lys Ser Ser Asp Lys Thr His Thr Cys Pro Pro
245 250 255

Cys Pro Ala Pro Glu Ala Ala Gly Ala Pro Ser Val Phe Leu Phe Pro
260 265 270

Pro Lys Pro Lys Asp Thr Leu Met Ile Ser Arg Thr Pro Glu Val Thr
275 280 285

Cys Val Val Val Asp Val Ser His Glu Asp Pro Glu Val Lys Phe Asn
290 295 300

Trp Tyr Val Asp Gly Val Glu Val His Asn Ala Lys Thr Lys Pro Arg
305 310 315 320

Glu Glu Gln Tyr Asn Ser Thr Tyr Arg Val Val Ser Val Leu Thr Val
325 330 335

Leu His Gln Asp Trp Leu Asn Gly Lys Ala Tyr Ala Cys Ala Val Ser
340 345 350

Asn Lys Ala Leu Pro Ala Pro Ile Glu Lys Thr Ile Ser Lys Ala Lys

-continued

```
        355                 360                 365

Gly Gln Pro Arg Glu Pro Gln Val Tyr Thr Leu Pro Pro Ser Arg Asp
    370                 375                 380

Glu Leu Thr Lys Asn Gln Val Ser Leu Thr Cys Leu Val Lys Gly Phe
385                 390                 395                 400

Tyr Pro Ser Asp Ile Ala Val Glu Trp Glu Ser Asn Gly Gln Pro Glu
                405                 410                 415

Asn Asn Tyr Lys Thr Thr Pro Pro Val Leu Asp Ser Asp Gly Ser Phe
            420                 425                 430

Phe Leu Tyr Ser Lys Leu Thr Val Asp Lys Ser Arg Trp Gln Gln Gly
        435                 440                 445

Asn Val Phe Ser Cys Ser Val Met His Glu Ala Leu His Asn His Tyr
    450                 455                 460

Thr Gln Lys Ser Leu Ser Leu Ser Pro Gly Ser Gly Gly Gly Gly Ser
465                 470                 475                 480

Gly Gly Gly Gly Ser Gly Gly Gly Gly Ser Gln Val Gln Leu Val Glu
                485                 490                 495

Ser Gly Gly Gly Val Val Gln Pro Gly Arg Ser Leu Arg Leu Ser Cys
            500                 505                 510

Lys Ala Ser Gly Tyr Thr Phe Thr Arg Ser Thr Met His Trp Val Arg
        515                 520                 525

Gln Ala Pro Gly Gln Gly Leu Glu Trp Ile Gly Tyr Ile Asn Pro Ser
    530                 535                 540

Ser Ala Tyr Thr Asn Tyr Asn Gln Lys Phe Lys Asp Arg Phe Thr Ile
545                 550                 555                 560

Ser Ala Asp Lys Ser Lys Ser Thr Ala Phe Leu Gln Met Asp Ser Leu
                565                 570                 575

Arg Pro Glu Asp Thr Gly Val Tyr Phe Cys Ala Arg Pro Gln Val His
            580                 585                 590

Tyr Asp Tyr Asn Gly Phe Pro Tyr Trp Gly Gln Gly Thr Pro Val Thr
        595                 600                 605

Val Ser Ser Gly Gly Gly Gly Ser Gly Gly Gly Gly Ser Gly Gly Gly
    610                 615                 620

Gly Ser Ala Gln Asp Ile Gln Met Thr Gln Ser Pro Ser Ser Leu Ser
625                 630                 635                 640

Ala Ser Val Gly Asp Arg Val Thr Met Thr Cys Ser Ala Ser Ser Ser
                645                 650                 655

Val Ser Tyr Met Asn Trp Tyr Gln Gln Lys Pro Gly Lys Ala Pro Lys
            660                 665                 670

Arg Trp Ile Tyr Asp Ser Ser Lys Leu Ala Ser Gly Val Pro Ala Arg
        675                 680                 685

Phe Ser Gly Ser Gly Ser Gly Thr Asp Tyr Thr Leu Thr Ile Ser Ser
    690                 695                 700

Leu Gln Pro Glu Asp Phe Ala Thr Tyr Tyr Cys Gln Gln Trp Ser Arg
705                 710                 715                 720

Asn Pro Pro Thr Phe Gly Gly Gly Thr Lys Leu Gln Ile Thr Ser Ser
                725                 730                 735

Ser
```

<210> SEQ ID NO 70
<211> LENGTH: 2280
<212> TYPE: DNA
<213> ORGANISM: Artificial
<220> FEATURE:

<223> OTHER INFORMATION: Humanized TSC302 Scorpion (huVL-VH#2 107-1A4
      scFv-Fc-DRA222 scFv, with H106 linker)

<400> SEQUENCE: 70

```
atggaagcac cagcgcagct tctcttcctc ctgctactct ggctcccaga taccaccggt      60
gatatccaga tgacccagtc tccatccgcc atgtctgcat ctgtaggaga cagagtcacc     120
atcacttgcc gggcgagtaa gagcattagc aaatatttag cctggtttca gcagaaacca     180
gggaaagttc ctaagctccg catccattct ggatctactt tgcaatcagg ggtcccatct     240
cggttcagtg gcagtggatc tgggacagaa tttactctca ccatcagcag cctgcagcct     300
gaagattttg caacttatta ctgtcaacag catattgaat acccgtggac gttcggccaa     360
gggaccaagg tggaaatcaa acgaggtggc ggagggtctg gggtggcgg atccggaggt     420
ggtggctctc aggtccagct ggtacagtct ggggctgagg tgaagaagcc tggggcttca     480
gtgaaggtct cctgcaaggc ttctggatac acattcactg actactacat gcactgggtg     540
cgacaggccc ctggacaagg gcttgagtgg atgggatatt ttaatcctta taatgattat     600
actagatacg cacagaagtt ccagggcaga gtcaccatga ccagggacac gtctatcagc     660
acagcctaca tggagctgag cagcctgaga tctgacgaca cggccgtgta ttactgtgca     720
agatcggatg gttactacga tgctatggac tactggggtc aaggaaccac agtcaccgtc     780
tcctcgagtg agcccaaatc ttctgacaaa actcacacat gcccaccgtg cccagcacct     840
gaagccgcgg gtgcaccgtc agtcttcctc ttccccccaa aacccaagga caccctcatg     900
atctcccgga cccctgaggt cacatgcgtg gtggtggacg tgagccacga agaccctgag     960
gtcaagttca actggtacgt ggacggcgtg gaggtgcata atgccaagac aaagccgcgg    1020
gaggagcagt acaacagcac gtaccgtgtg gtcagcgtcc tcaccgtcct gcaccaggac    1080
tggctgaatg gcaaggcgta cgcgtgcgcg gtctccaaca aagccctccc agcccccatc    1140
gagaaaacca tctccaaagc caaagggcag ccccgagaac cacaggtgta caccctgccc    1200
ccatcccggg atgagctgac caagaaccag gtcagcctga cctgcctggt caaaggcttc    1260
tatccaagcg acatcgccgt ggagtgggag agcaatgggc agccggagaa caactacaag    1320
accacgcctc ccgtgctgga ctccgacggc tccttcttcc tctacagcaa gctcaccgtg    1380
gacaagagca ggtggcagca ggggaacgtc ttctcatgct ccgtgatgca tgaggctctg    1440
cacaaccact acacgcagaa gagcctctcc ctgtctccgg gtcagaggca caacaattct    1500
tccctgaata caggaactca gatggcaggt cattctcagg tccagctggt ggagtctggg    1560
ggcggagtgg tgcagcctgg gcggtcactg aggctgtcct gcaaggcttc tggctacacc    1620
tttactagat ctacgatgca ctgggtaagg caggcccctg gacaaggtct ggaatggatt    1680
ggatacatta atcctagcag tgcttatact aattacaatc agaaattcaa ggacaggttc    1740
acaatcagcg cagacaaatc caagagcaca gccttcctgc agatggacag cctgaggccc    1800
gaggacaccg gcgtctattt ctgtgcacgg ccccaagtcc actatgatta caacgggttt    1860
ccttactggg gccaagggac tcccgtcact gtctctagcg gtggcggagg gtctgggggt    1920
ggcggatccg gaggtggtgg ctctgcacaa gacatccaga tgacccagtc tccaagcagc    1980
ctgtctgcaa gcgtggggga cagggtcacc atgacctgca gtgccagctc aagtgtaagt    2040
tacatgaact ggtaccagca gaagccgggc aaggccccca aaagatggat ttatgactca    2100
tccaaactgg cttctggagt ccctgctcgc ttcagtggca gtgggtctgg gaccgactat    2160
accctcacaa tcagcagcct gcagcccgaa gatttcgcca cttattactg ccagcagtgg    2220
```

```
agtcgtaacc cacccacgtt cggagggggg accaagctac aaattacatc ctccagctaa   2280


<210> SEQ ID NO 71
<211> LENGTH: 739
<212> TYPE: PRT
<213> ORGANISM: Artificial
<220> FEATURE:
<223> OTHER INFORMATION: Humanizede TSC302 Scorpion (huVL-VH#2 107-1A4
      scFv-Fc-DRA222 scFv, with H106 linker)

<400> SEQUENCE: 71

Asp Ile Gln Met Thr Gln Ser Pro Ser Ala Met Ser Ala Ser Val Gly
1               5                   10                  15

Asp Arg Val Thr Ile Thr Cys Arg Ala Ser Lys Ser Ile Ser Lys Tyr
            20                  25                  30

Leu Ala Trp Phe Gln Gln Lys Pro Gly Lys Val Pro Lys Leu Arg Ile
        35                  40                  45

His Ser Gly Ser Thr Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln His Ile Glu Tyr Pro Trp
                85                  90                  95

Thr Phe Gly Gln Gly Thr Lys Val Glu Ile Lys Arg Gly Gly Gly Gly
            100                 105                 110

Ser Gly Gly Gly Gly Ser Gly Gly Gly Gly Ser Gln Val Gln Leu Val
        115                 120                 125

Gln Ser Gly Ala Glu Val Lys Lys Pro Gly Ala Ser Val Lys Val Ser
    130                 135                 140

Cys Lys Ala Ser Gly Tyr Thr Phe Thr Asp Tyr Tyr Met His Trp Val
145                 150                 155                 160

Arg Gln Ala Pro Gly Gln Gly Leu Glu Trp Met Gly Tyr Phe Asn Pro
                165                 170                 175

Tyr Asn Asp Tyr Thr Arg Tyr Ala Gln Lys Phe Gln Gly Arg Val Thr
            180                 185                 190

Met Thr Arg Asp Thr Ser Ile Ser Thr Ala Tyr Met Glu Leu Ser Ser
        195                 200                 205

Leu Arg Ser Asp Asp Thr Ala Val Tyr Tyr Cys Ala Arg Ser Asp Gly
    210                 215                 220

Tyr Tyr Asp Ala Met Asp Tyr Trp Gly Gln Gly Thr Thr Val Thr Val
225                 230                 235                 240

Ser Ser Ser Glu Pro Lys Ser Ser Asp Lys Thr His Thr Cys Pro Pro
                245                 250                 255

Cys Pro Ala Pro Glu Ala Ala Gly Ala Pro Ser Val Phe Leu Phe Pro
            260                 265                 270

Pro Lys Pro Lys Asp Thr Leu Met Ile Ser Arg Thr Pro Glu Val Thr
        275                 280                 285

Cys Val Val Val Asp Val Ser His Glu Asp Pro Glu Val Lys Phe Asn
    290                 295                 300

Trp Tyr Val Asp Gly Val Glu Val His Asn Ala Lys Thr Lys Pro Arg
305                 310                 315                 320

Glu Glu Gln Tyr Asn Ser Thr Tyr Arg Val Val Ser Val Leu Thr Val
                325                 330                 335

Leu His Gln Asp Trp Leu Asn Gly Lys Ala Tyr Ala Cys Ala Val Ser
            340                 345                 350
```

```
Asn Lys Ala Leu Pro Ala Pro Ile Glu Lys Thr Ile Ser Lys Ala Lys
        355                 360                 365

Gly Gln Pro Arg Glu Pro Gln Val Tyr Thr Leu Pro Pro Ser Arg Asp
    370                 375                 380

Glu Leu Thr Lys Asn Gln Val Ser Leu Thr Cys Leu Val Lys Gly Phe
385                 390                 395                 400

Tyr Pro Ser Asp Ile Ala Val Glu Trp Glu Ser Asn Gly Gln Pro Glu
                405                 410                 415

Asn Asn Tyr Lys Thr Thr Pro Pro Val Leu Asp Ser Asp Gly Ser Phe
            420                 425                 430

Phe Leu Tyr Ser Lys Leu Thr Val Asp Lys Ser Arg Trp Gln Gln Gly
        435                 440                 445

Asn Val Phe Ser Cys Ser Val Met His Glu Ala Leu His Asn His Tyr
    450                 455                 460

Thr Gln Lys Ser Leu Ser Leu Ser Pro Gly Gln Arg His Asn Asn Ser
465                 470                 475                 480

Ser Leu Asn Thr Gly Thr Gln Met Ala Gly His Ser Gln Val Gln Leu
                485                 490                 495

Val Glu Ser Gly Gly Gly Val Val Gln Pro Gly Arg Ser Leu Arg Leu
            500                 505                 510

Ser Cys Lys Ala Ser Gly Tyr Thr Phe Thr Arg Ser Thr Met His Trp
        515                 520                 525

Val Arg Gln Ala Pro Gly Gln Gly Leu Glu Trp Ile Gly Tyr Ile Asn
    530                 535                 540

Pro Ser Ser Ala Tyr Thr Asn Tyr Asn Gln Lys Phe Lys Asp Arg Phe
545                 550                 555                 560

Thr Ile Ser Ala Asp Lys Ser Lys Ser Thr Ala Phe Leu Gln Met Asp
                565                 570                 575

Ser Leu Arg Pro Glu Asp Thr Gly Val Tyr Phe Cys Ala Arg Pro Gln
            580                 585                 590

Val His Tyr Asp Tyr Asn Gly Phe Pro Tyr Trp Gly Gln Gly Thr Pro
        595                 600                 605

Val Thr Val Ser Ser Gly Gly Gly Gly Ser Gly Gly Gly Gly Ser Gly
    610                 615                 620

Gly Gly Gly Ser Ala Gln Asp Ile Gln Met Thr Gln Ser Pro Ser Ser
625                 630                 635                 640

Leu Ser Ala Ser Val Gly Asp Arg Val Thr Met Thr Cys Ser Ala Ser
                645                 650                 655

Ser Ser Val Ser Tyr Met Asn Trp Tyr Gln Gln Lys Pro Gly Lys Ala
            660                 665                 670

Pro Lys Arg Trp Ile Tyr Asp Ser Ser Lys Leu Ala Ser Gly Val Pro
        675                 680                 685

Ala Arg Phe Ser Gly Ser Gly Ser Gly Thr Asp Tyr Thr Leu Thr Ile
    690                 695                 700

Ser Ser Leu Gln Pro Glu Asp Phe Ala Thr Tyr Tyr Cys Gln Gln Trp
705                 710                 715                 720

Ser Arg Asn Pro Pro Thr Phe Gly Gly Gly Thr Lys Leu Gln Ile Thr
                725                 730                 735

Ser Ser Ser
```

<210> SEQ ID NO 72
<211> LENGTH: 106
<212> TYPE: PRT
<213> ORGANISM: Artificial

<220> FEATURE:
<223> OTHER INFORMATION: HuM291 VL

<400> SEQUENCE: 72

```
Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Ser Val Ser Tyr Met
            20                  25                  30

Asn Trp Tyr Gln Gln Lys Pro Gly Lys Ala Pro Lys Arg Leu Ile Tyr
        35                  40                  45

Asp Thr Ser Lys Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Ser Ser Asn Pro Pro Thr
                85                  90                  95

Phe Gly Gly Gly Thr Lys Val Glu Ile Lys
            100                 105
```

<210> SEQ ID NO 73
<211> LENGTH: 120
<212> TYPE: PRT
<213> ORGANISM: Artificial
<220> FEATURE:
<223> OTHER INFORMATION: HuM291 VH

<400> SEQUENCE: 73

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ile Ser Tyr
            20                  25                  30

Thr Met His Trp Val Arg Gln Ala Pro Gly Gln Gly Leu Glu Trp Met
        35                  40                  45

Gly Tyr Ile Asn Pro Arg Ser Gly Tyr Thr His Tyr Asn Gln Lys Leu
    50                  55                  60

Lys Asp Lys Ala Thr Leu Thr Ala Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Ala Tyr Tyr Asp Tyr Asp Gly Phe Ala Tyr Trp Gly Gln
            100                 105                 110

Gly Thr Leu Val Thr Val Ser Ser
        115                 120
```

<210> SEQ ID NO 74
<211> LENGTH: 5
<212> TYPE: PRT
<213> ORGANISM: Artificial
<220> FEATURE:
<223> OTHER INFORMATION: Linker

<400> SEQUENCE: 74

```
Gly Gly Gly Gly Ser
1               5
```

<210> SEQ ID NO 75
<211> LENGTH: 10
<212> TYPE: PRT
<213> ORGANISM: Artificial
<220> FEATURE:

-continued

<223> OTHER INFORMATION: Linker

<400> SEQUENCE: 75

Gly Gly Gly Gly Ser Gly Gly Gly Gly Ser
1               5                   10

<210> SEQ ID NO 76
<211> LENGTH: 15
<212> TYPE: PRT
<213> ORGANISM: Artificial
<220> FEATURE:
<223> OTHER INFORMATION: Linker

<400> SEQUENCE: 76

Gly Gly Gly Gly Ser Gly Gly Gly Gly Ser Gly Gly Gly Gly Ser
1               5                   10                  15

<210> SEQ ID NO 77
<211> LENGTH: 20
<212> TYPE: PRT
<213> ORGANISM: Artificial
<220> FEATURE:
<223> OTHER INFORMATION: Linker

<400> SEQUENCE: 77

Gly Gly Gly Gly Ser Gly Gly Gly Gly Ser Gly Gly Gly Gly Ser Gly
1               5                   10                  15

Gly Gly Gly Ser
            20

<210> SEQ ID NO 78
<211> LENGTH: 25
<212> TYPE: PRT
<213> ORGANISM: Artificial
<220> FEATURE:
<223> OTHER INFORMATION: Linker

<400> SEQUENCE: 78

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25

<210> SEQ ID NO 79
<211> LENGTH: 20
<212> TYPE: PRT
<213> ORGANISM: Artificial
<220> FEATURE:
<223> OTHER INFORMATION: a secretory signal sequence

<400> SEQUENCE: 79

Met Glu Ala Pro Ala Gln Leu Leu Phe Leu Leu Leu Leu Trp Leu Pro
1               5                   10                  15

Asp Thr Thr Gly
            20

<210> SEQ ID NO 80
<211> LENGTH: 98
<212> TYPE: PRT
<213> ORGANISM: Artificial
<220> FEATURE:
<223> OTHER INFORMATION: a wild-type human igG1 CH1 domain

<400> SEQUENCE: 80

Ala Ser Thr Lys Gly Pro Ser Val Phe Pro Leu Ala Pro Ser Ser Lys

-continued

```
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val


<210> SEQ ID NO 81
<211> LENGTH: 107
<212> TYPE: PRT
<213> ORGANISM: Artificial
<220> FEATURE:
<223> OTHER INFORMATION: a wild-type human CK domain

<400> SEQUENCE: 81

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105


<210> SEQ ID NO 82
<211> LENGTH: 106
<212> TYPE: PRT
<213> ORGANISM: Artificial
<220> FEATURE:
<223> OTHER INFORMATION: a wild-type human CA domain

<400> SEQUENCE: 82

Gly Gln Pro Lys Ala Asn Pro Thr Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Gly Ser Pro
        35                  40                  45

Val Lys Ala Gly Val Glu Thr Thr Lys Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
```

```
            100                 105


<210> SEQ ID NO 83
<211> LENGTH: 105
<212> TYPE: PRT
<213> ORGANISM: Artificial
<220> FEATURE:
<223> OTHER INFORMATION: a CK domain

<400> SEQUENCE: 83

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu
            100                 105


<210> SEQ ID NO 84
<211> LENGTH: 105
<212> TYPE: PRT
<213> ORGANISM: Artificial
<220> FEATURE:
<223> OTHER INFORMATION: a CA domain

<400> SEQUENCE: 84

Gln Pro Lys Ala Asn Pro Thr Val Thr Leu Phe Pro Pro Ser Ser Glu
1               5                   10                  15

Glu Leu Gln Ala Asn Lys Ala Thr Leu Val Cys Leu Ile Ser Asp Phe
            20                  25                  30

Tyr Pro Gly Ala Val Thr Val Ala Trp Lys Ala Asp Gly Ser Pro Val
        35                  40                  45

Lys Ala Gly Val Glu Thr Thr Lys Pro Ser Lys Gln Ser Asn Asn Lys
    50                  55                  60

Tyr Ala Ala Ser Ser Tyr Leu Ser Leu Thr Pro Glu Gln Trp Lys Ser
65                  70                  75                  80

His Arg Ser Tyr Ser Cys Gln Val Thr His Glu Gly Ser Thr Val Glu
                85                  90                  95

Lys Thr Val Ala Pro Thr Glu Ser Ser
            100                 105


<210> SEQ ID NO 85
<211> LENGTH: 110
<212> TYPE: PRT
<213> ORGANISM: Artificial
<220> FEATURE:
<223> OTHER INFORMATION: a wild-type human IgG1 CH2 domain

<400> SEQUENCE: 85

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30
```

```
Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys
            100                 105                 110


<210> SEQ ID NO 86
<211> LENGTH: 110
<212> TYPE: PRT
<213> ORGANISM: Artificial
<220> FEATURE:
<223> OTHER INFORMATION: a wild-type human IgG1 CH2 domain

<400> SEQUENCE: 86

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Ala Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys
            100                 105                 110


<210> SEQ ID NO 87
<211> LENGTH: 13
<212> TYPE: PRT
<213> ORGANISM: Artificial
<220> FEATURE:
<223> OTHER INFORMATION: RON-e01 VL CDR1

<400> SEQUENCE: 87

Arg Ala Ser Gln Asp Ile Gly Ser Ser Leu Ser Trp Leu
1               5                   10


<210> SEQ ID NO 88
<211> LENGTH: 11
<212> TYPE: PRT
<213> ORGANISM: Artificial
<220> FEATURE:
<223> OTHER INFORMATION: RON-e01 VL CDR2

<400> SEQUENCE: 88

Arg Leu Ile Tyr Ser Thr Ser Ser Leu Asp Ser
1               5                   10


<210> SEQ ID NO 89
<211> LENGTH: 9
<212> TYPE: PRT
<213> ORGANISM: Artificial
<220> FEATURE:
```

<223> OTHER INFORMATION: RON-e01 VL CDR3

<400> SEQUENCE: 89

Leu Gln Tyr Ala Ser Ser Pro Trp Thr
1 5

<210> SEQ ID NO 90
<211> LENGTH: 13
<212> TYPE: PRT
<213> ORGANISM: Artificial
<220> FEATURE:
<223> OTHER INFORMATION: RON-f01 VL CDR1

<400> SEQUENCE: 90

Leu Ala Ser Gln Thr Ile Gly Thr Trp Leu Ala Trp Tyr
1 5 10

<210> SEQ ID NO 91
<211> LENGTH: 11
<212> TYPE: PRT
<213> ORGANISM: Artificial
<220> FEATURE:
<223> OTHER INFORMATION: RON-f01 VL CDR2

<400> SEQUENCE: 91

Leu Leu Ile Tyr Ala Ala Thr Ser Leu Ala Asp
1 5 10

<210> SEQ ID NO 92
<211> LENGTH: 9
<212> TYPE: PRT
<213> ORGANISM: Artificial
<220> FEATURE:
<223> OTHER INFORMATION: RON-f01 VL CDR3

<400> SEQUENCE: 92

Gln Gln Leu Tyr Asn Thr Pro Trp Thr
1 5

<210> SEQ ID NO 93
<211> LENGTH: 10
<212> TYPE: PRT
<213> ORGANISM: Artificial
<220> FEATURE:
<223> OTHER INFORMATION: RON-e01 VH CDR1

<400> SEQUENCE: 93

Gly Tyr Thr Phe Thr Ser Tyr Trp Ile His
1 5 10

<210> SEQ ID NO 94
<211> LENGTH: 20
<212> TYPE: PRT
<213> ORGANISM: Artificial
<220> FEATURE:
<223> OTHER INFORMATION: RON-e01 VH CDR2

<400> SEQUENCE: 94

Trp Ile Gly Tyr Ile Tyr Pro Thr Thr Gly Tyr Thr Glu Ser Asn Gln
1 5 10 15

Lys Phe Lys Asp
20

<210> SEQ ID NO 95
<211> LENGTH: 10
<212> TYPE: PRT

```
<213> ORGANISM: Artificial
<220> FEATURE:
<223> OTHER INFORMATION: RON-e01 VH CDR3

<400> SEQUENCE: 95

Phe Leu Leu Arg Pro Trp Tyr Phe Asp Val
1               5                   10


<210> SEQ ID NO 96
<211> LENGTH: 10
<212> TYPE: PRT
<213> ORGANISM: Artificial
<220> FEATURE:
<223> OTHER INFORMATION: RON-f01 VH CDR1

<400> SEQUENCE: 96

Asp Tyr Thr Leu Thr Asp Phe Tyr Met Asn
1               5                   10


<210> SEQ ID NO 97
<211> LENGTH: 20
<212> TYPE: PRT
<213> ORGANISM: Artificial
<220> FEATURE:
<223> OTHER INFORMATION: RON-f01 VH CDR2

<400> SEQUENCE: 97

Trp Ile Gly Arg Ile Tyr Pro Gly Thr Asp Lys Thr Arg Tyr Asn Glu
1               5                   10                  15

Lys Phe Arg Asp
            20


<210> SEQ ID NO 98
<211> LENGTH: 14
<212> TYPE: PRT
<213> ORGANISM: Artificial
<220> FEATURE:
<223> OTHER INFORMATION: RON-f01 VH CDR3

<400> SEQUENCE: 98

Ala Arg Ser Ala Tyr Tyr Gly Asn Tyr Val Ala Met Asp Tyr
1               5                   10


<210> SEQ ID NO 99
<211> LENGTH: 107
<212> TYPE: PRT
<213> ORGANISM: Artificial
<220> FEATURE:
<223> OTHER INFORMATION: RON-e01 murine VL

<400> SEQUENCE: 99

Asp Ile Gln Met Thr Gln Ser Pro Ser Ser Leu Ser Ala Ser Leu Gly
1               5                   10                  15

Glu Arg Val Ser Leu Thr Cys Arg Ala Ser Gln Asp Ile Gly Ser Ser
            20                  25                  30

Leu Ser Trp Leu Gln Gln Glu Pro Asp Gly Thr Ile Lys Arg Leu Ile
        35                  40                  45

Tyr Ser Thr Ser Ser Leu Asp Ser Gly Val Pro Lys Arg Phe Ser Gly
    50                  55                  60

Ser Arg Ser Gly Ser Asp Tyr Ser Leu Thr Ile Ser Ser Leu Glu Ser
65                  70                  75                  80

Glu Asp Phe Val Asp Tyr Tyr Cys Leu Gln Tyr Ala Ser Ser Pro Trp
                85                  90                  95
```

```
Thr Phe Gly Gly Gly Thr Lys Leu Glu Ile Lys
            100                 105


<210> SEQ ID NO 100
<211> LENGTH: 107
<212> TYPE: PRT
<213> ORGANISM: Artificial
<220> FEATURE:
<223> OTHER INFORMATION: RON-f01 murine VL

<400> SEQUENCE: 100

Asp Ile Gln Met Thr Gln Ser Pro Ala Ser Gln Ser Ala Ser Leu Gly
1               5                   10                  15

Glu Ser Val Thr Ile Thr Cys Leu Ala Ser Gln Thr Ile Gly Thr Trp
            20                  25                  30

Leu Ala Trp Tyr Gln Gln Lys Pro Gly Lys Ser Pro Gln Leu Leu Ile
        35                  40                  45

Tyr Ala Ala Thr Ser Leu Ala Asp Gly Val Pro Ser Arg Phe Ser Ala
    50                  55                  60

Ser Gly Ser Gly Thr Lys Phe Ser Phe Lys Ile Asp Ser Leu Gln Ser
65                  70                  75                  80

Glu Asp Phe Val Ser Tyr Tyr Cys Gln Gln Leu Tyr Asn Thr Pro Trp
                85                  90                  95

Thr Phe Gly Gly Gly Thr Lys Leu Glu Ile Lys
            100                 105


<210> SEQ ID NO 101
<211> LENGTH: 117
<212> TYPE: PRT
<213> ORGANISM: Artificial
<220> FEATURE:
<223> OTHER INFORMATION: RON-e01 murine VH

<400> SEQUENCE: 101

Gln Val Gln Leu Gln Gln Ser Gly Ala Glu Leu Ala Lys Pro Gly Ala
1               5                   10                  15

Ser Val Lys Met Ser Cys Lys Ser Ser Gly Tyr Thr Phe Thr Ser Tyr
            20                  25                  30

Trp Ile His Trp Val Lys Glu Arg Pro Gly Gln Gly Leu Glu Trp Ile
        35                  40                  45

Gly Tyr Ile Tyr Pro Thr Thr Gly Tyr Thr Glu Ser Asn Gln Lys Phe
    50                  55                  60

Lys Asp Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Phe Leu Leu Arg Pro Trp Tyr Phe Asp Val Trp Gly Ala Gly Thr Thr
            100                 105                 110

Val Thr Val Ser Ser
        115


<210> SEQ ID NO 102
<211> LENGTH: 121
<212> TYPE: PRT
<213> ORGANISM: Artificial
<220> FEATURE:
<223> OTHER INFORMATION: RON-f01 murine VH

<400> SEQUENCE: 102

Gln Ile Gln Leu Gln Gln Ser Gly Pro Glu Leu Val Lys Pro Gly Thr
```

```
1               5                   10                  15

Ser Val Lys Ile Ser Cys Lys Ala Ser Asp Tyr Thr Leu Thr Asp Phe
            20                  25                  30

Tyr Met Asn Trp Val Arg Gln Lys Pro Gly Gln Gly Leu Glu Trp Ile
        35                  40                  45

Gly Arg Ile Tyr Pro Gly Thr Asp Lys Thr Arg Tyr Asn Glu Lys Phe
    50                  55                  60

Arg Asp Lys Ala Ile Leu Thr Val Asp Thr Ser Ser Ser Thr Ala Tyr
65                  70                  75                  80

Met Gln Leu Ser Ser Leu Thr Ser Glu Asp Thr Ala Val Tyr Phe Cys
                85                  90                  95

Ala Arg Ser Ala Tyr Tyr Gly Asn Tyr Val Ala Met Asp Tyr Trp Gly
            100                 105                 110

Gln Gly Thr Ser Val Thr Val Ser Leu
        115                 120


<210> SEQ ID NO 103
<211> LENGTH: 121
<212> TYPE: PRT
<213> ORGANISM: Artificial
<220> FEATURE:
<223> OTHER INFORMATION: RON-f01 murine VH variant

<400> SEQUENCE: 103

Gln Ile Gln Leu Gln Gln Ser Gly Pro Glu Leu Val Lys Pro Gly Thr
1               5                   10                  15

Ser Val Lys Ile Ser Cys Lys Ala Ser Asp Tyr Thr Leu Thr Asp Phe
            20                  25                  30

Tyr Met Asn Trp Val Arg Gln Lys Pro Gly Gln Gly Leu Glu Trp Ile
        35                  40                  45

Gly Arg Ile Tyr Pro Gly Thr Asp Lys Thr Arg Tyr Asn Glu Lys Phe
    50                  55                  60

Arg Asp Lys Ala Ile Leu Thr Val Asp Thr Ser Ser Ser Thr Ala Tyr
65                  70                  75                  80

Met Gln Leu Ser Ser Leu Thr Ser Glu Asp Thr Ala Val Tyr Phe Cys
                85                  90                  95

Ala Arg Ser Ala Tyr Tyr Gly Asn Tyr Val Ala Met Asp Tyr Trp Gly
            100                 105                 110

Gln Gly Thr Ser Val Thr Val Ser Ser
        115                 120


<210> SEQ ID NO 104
<211> LENGTH: 107
<212> TYPE: PRT
<213> ORGANISM: Artificial
<220> FEATURE:
<223> OTHER INFORMATION: RON-e01h6 humanized VL

<400> SEQUENCE: 104

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Asp Ile Gly Ser Ser
            20                  25                  30

Leu Ser Trp Leu Gln Gln Lys Pro Gly Lys Ala Pro Lys Arg Leu Ile
        35                  40                  45

Tyr Ser Thr Ser Ser Leu Asp Ser Gly Val Pro Ser Arg Phe Ser Gly
    50                  55                  60
```

```
Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Ala Ser Ser Pro Trp
                85                  90                  95

Thr Phe Gly Gln Gly Thr Lys Val Glu Ile Lys
            100                 105


<210> SEQ ID NO 105
<211> LENGTH: 107
<212> TYPE: PRT
<213> ORGANISM: Artificial
<220> FEATURE:
<223> OTHER INFORMATION: RON-e01h7 humanized VL

<400> SEQUENCE: 105

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Gly Ser Ser
            20                  25                  30

Leu Ser Trp Leu Gln Gln Lys Pro Gly Lys Ala Pro Lys Arg Leu Ile
        35                  40                  45

Tyr Ser Thr Ser Ser Leu Asp Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Leu Gln Tyr Ala Ser Ser Pro Trp
                85                  90                  95

Thr Phe Gly Gln Gly Thr Lys Val Glu Ile Lys
            100                 105


<210> SEQ ID NO 106
<211> LENGTH: 107
<212> TYPE: PRT
<213> ORGANISM: Artificial
<220> FEATURE:
<223> OTHER INFORMATION: RON-f01h2 humanized VL

<400> SEQUENCE: 106

Asp Ile Gln Met Thr Gln Ser Pro Ser Ser Leu Ser Ala Ser Val Gly
1               5                   10                  15

Asp Arg Val Thr Ile Thr Cys Leu Ala Ser Gln Thr Ile Gly Thr Trp
            20                  25                  30

Leu Ala Trp Tyr Gln Gln Lys Pro Gly Lys Ala Pro Lys Leu Leu Ile
        35                  40                  45

Tyr Ala Ala Thr Ser Leu Ala Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Leu Tyr Asn Thr Pro Trp
                85                  90                  95

Thr Phe Gly Gly Gly Thr Lys Val Glu Ile Lys
            100                 105


<210> SEQ ID NO 107
<211> LENGTH: 117
<212> TYPE: PRT
<213> ORGANISM: Artificial
<220> FEATURE:
<223> OTHER INFORMATION: RON-e01h8 humanized VH
```

-continued

<400> SEQUENCE: 107

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Ile His Trp Val Arg Gln Ala Pro Gly Gln Gly Leu Glu Trp Ile
        35                  40                  45

Gly Tyr Ile Tyr Pro Thr Thr Gly Tyr Thr Glu Ser Asn Gln Lys Phe
    50                  55                  60

Lys Asp Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Phe Leu Leu Arg Pro Trp Tyr Phe Asp Val Trp Gly Gln Gly Thr Thr
            100                 105                 110

Val Thr Val Ser Ser
        115
```

<210> SEQ ID NO 108
<211> LENGTH: 117
<212> TYPE: PRT
<213> ORGANISM: Artificial
<220> FEATURE:
<223> OTHER INFORMATION: RON-e01h9 humanized VH

<400> SEQUENCE: 108

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Ile His Trp Val Arg Gln Ala Thr Gly Gln Gly Leu Glu Trp Ile
        35                  40                  45

Gly Tyr Ile Tyr Pro Thr Thr Gly Tyr Thr Glu Ser Asn Gln Lys Phe
    50                  55                  60

Lys Asp Arg Val Thr Met Thr Arg Asn Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Phe Leu Leu Arg Pro Trp Tyr Phe Asp Val Trp Gly Gln Gly Thr Thr
            100                 105                 110

Val Thr Val Ser Ser
        115
```

<210> SEQ ID NO 109
<211> LENGTH: 117
<212> TYPE: PRT
<213> ORGANISM: Artificial
<220> FEATURE:
<223> OTHER INFORMATION: RON-e01h10 humanized VH

<400> SEQUENCE: 109

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Ile His Trp Val Arg Gln Ala Pro Gly Gln Gly Leu Glu Trp Ile
        35                  40                  45
```

Gly Tyr Ile Tyr Pro Thr Thr Gly Tyr Thr Glu Ser Asn Gln Lys Phe
50 55 60

Lys Asp Arg Val Thr Met Thr Arg Asp Thr Ser Thr Ser Thr Val Tyr
65 70 75 80

Met Glu Leu Ser Ser Leu Arg Ser Glu Asp Thr Ala Val Tyr Tyr Cys
85 90 95

Phe Leu Leu Arg Pro Trp Tyr Phe Asp Val Trp Gly Gln Gly Thr Thr
100 105 110

Val Thr Val Ser Ser
115

<210> SEQ ID NO 110
<211> LENGTH: 121
<212> TYPE: PRT
<213> ORGANISM: Artificial
<220> FEATURE:
<223> OTHER INFORMATION: RON-f01h4 humanized VH

<400> SEQUENCE: 110

Glu Val Gln Leu Val Gln Ser Gly Ala Glu Val Lys Lys Pro Gly Ala
1 5 10 15

Thr Val Lys Ile Ser Cys Lys Val Ser Asp Tyr Thr Leu Thr Asp Phe
20 25 30

Tyr Met Asn Trp Val Gln Gln Ala Pro Gly Lys Gly Leu Glu Trp Ile
35 40 45

Gly Arg Ile Tyr Pro Gly Thr Asp Lys Thr Arg Tyr Asn Glu Lys Phe
50 55 60

Arg Asp Arg Val Thr Ile Thr Ala Asp Thr Ser Thr Asp Thr Ala Tyr
65 70 75 80

Met Glu Leu Ser Ser Leu Arg Ser Glu Asp Thr Ala Val Tyr Tyr Cys
85 90 95

Ala Arg Ser Ala Tyr Tyr Gly Asn Tyr Val Ala Met Asp Tyr Trp Gly
100 105 110

Gln Gly Thr Thr Val Thr Val Ser Ser
115 120

<210> SEQ ID NO 111
<211> LENGTH: 121
<212> TYPE: PRT
<213> ORGANISM: Artificial
<220> FEATURE:
<223> OTHER INFORMATION: RON-f01h5 humanized VH

<400> SEQUENCE: 111

Gln Val Gln Leu Val Gln Ser Gly Ala Glu Val Lys Lys Pro Gly Ser
1 5 10 15

Ser Val Lys Val Ser Cys Lys Ala Ser Asp Tyr Thr Leu Thr Asp Phe
20 25 30

Tyr Met Asn Trp Val Arg Gln Ala Pro Gly Gln Gly Leu Glu Trp Ile
35 40 45

Gly Arg Ile Tyr Pro Gly Thr Asp Lys Thr Arg Tyr Asn Glu Lys Phe
50 55 60

Arg Asp Arg Val Thr Ile Thr Ala Asp Lys Ser Thr Ser Thr Ala Tyr
65 70 75 80

Met Glu Leu Ser Ser Leu Arg Ser Glu Asp Thr Ala Val Tyr Tyr Cys
85 90 95

Ala Arg Ser Ala Tyr Tyr Gly Asn Tyr Val Ala Met Asp Tyr Trp Gly
100 105 110

Gln Gly Thr Thr Val Thr Val Ser Ser
115 120

<210> SEQ ID NO 112
<211> LENGTH: 15
<212> TYPE: PRT
<213> ORGANISM: Artificial
<220> FEATURE:
<223> OTHER INFORMATION: sss(s)-hlgG1 hinge

<400> SEQUENCE: 112

Glu Pro Lys Ser Ser Asp Lys Thr His Thr Ser Pro Pro Ser Ser
1 5 10 15

<210> SEQ ID NO 113
<211> LENGTH: 15
<212> TYPE: PRT
<213> ORGANISM: Artificial
<220> FEATURE:
<223> OTHER INFORMATION: csc(s)-hlgG1 hinge

<400> SEQUENCE: 113

Glu Pro Lys Ser Cys Asp Lys Thr His Thr Ser Pro Pro Cys Ser
1 5 10 15

<210> SEQ ID NO 114
<211> LENGTH: 15
<212> TYPE: PRT
<213> ORGANISM: Artificial
<220> FEATURE:
<223> OTHER INFORMATION: ssc(s)-hlgG1 hinge

<400> SEQUENCE: 114

Glu Pro Lys Ser Ser Asp Lys Thr His Thr Ser Pro Pro Cys Ser
1 5 10 15

<210> SEQ ID NO 115
<211> LENGTH: 15
<212> TYPE: PRT
<213> ORGANISM: Artificial
<220> FEATURE:
<223> OTHER INFORMATION: scc(s)-hlg1 hinge

<400> SEQUENCE: 115

Glu Pro Lys Ser Ser Asp Lys Thr His Thr Cys Pro Pro Cys Ser
1 5 10 15

<210> SEQ ID NO 116
<211> LENGTH: 15
<212> TYPE: PRT
<213> ORGANISM: Artificial
<220> FEATURE:
<223> OTHER INFORMATION: css(s)-hlgG1 hinge

<400> SEQUENCE: 116

Glu Pro Lys Ser Cys Asp Lys Thr His Thr Ser Pro Pro Ser Ser
1 5 10 15

<210> SEQ ID NO 117
<211> LENGTH: 15
<212> TYPE: PRT
<213> ORGANISM: Artificial
<220> FEATURE:
<223> OTHER INFORMATION: scs(s)-hlgG1 hinge

<400> SEQUENCE: 117

Glu Pro Lys Ser Ser Asp Lys Thr His Thr Cys Pro Pro Ser Ser
1 5 10 15

<210> SEQ ID NO 118
<211> LENGTH: 15
<212> TYPE: PRT
<213> ORGANISM: Artificial
<220> FEATURE:
<223> OTHER INFORMATION: ccc(s)-hlgG1 hinge

<400> SEQUENCE: 118

Glu Pro Lys Ser Cys Asp Lys Thr His Thr Ser Pro Pro Cys Ser
1 5 10 15

<210> SEQ ID NO 119
<211> LENGTH: 15
<212> TYPE: PRT
<213> ORGANISM: Artificial
<220> FEATURE:
<223> OTHER INFORMATION: ccc(p)-hlgG1 hinge

<400> SEQUENCE: 119

Glu Pro Lys Ser Cys Asp Lys Thr His Thr Ser Pro Pro Cys Pro
1 5 10 15

<210> SEQ ID NO 120
<211> LENGTH: 15
<212> TYPE: PRT
<213> ORGANISM: Artificial
<220> FEATURE:
<223> OTHER INFORMATION: sss(p)-hlgG1 hinge

<400> SEQUENCE: 120

Glu Pro Lys Ser Ser Asp Lys Thr His Thr Ser Pro Pro Ser Pro
1 5 10 15

<210> SEQ ID NO 121
<211> LENGTH: 15
<212> TYPE: PRT
<213> ORGANISM: Artificial
<220> FEATURE:
<223> OTHER INFORMATION: csc(p)-hlgG1 hinge

<400> SEQUENCE: 121

Glu Pro Lys Ser Cys Asp Lys Thr His Thr Ser Pro Pro Cys Pro
1 5 10 15

<210> SEQ ID NO 122
<211> LENGTH: 15
<212> TYPE: PRT
<213> ORGANISM: Artificial
<220> FEATURE:
<223> OTHER INFORMATION: ssc(p)-hlgG1 hinge

<400> SEQUENCE: 122

Glu Pro Lys Ser Ser Asp Lys Thr His Thr Ser Pro Pro Cys Pro
1 5 10 15

<210> SEQ ID NO 123
<211> LENGTH: 15
<212> TYPE: PRT
<213> ORGANISM: Artificial
<220> FEATURE:
<223> OTHER INFORMATION: scc(p)-hlgG1 hinge

<400> SEQUENCE: 123

Glu Pro Lys Ser Ser Asp Lys Thr His Thr Cys Pro Pro Cys Pro 1 5 10 15

<210> SEQ ID NO 124
<211> LENGTH: 15
<212> TYPE: PRT
<213> ORGANISM: Artificial
<220> FEATURE:
<223> OTHER INFORMATION: css(p)-hlgG1 hinge

<400> SEQUENCE: 124

Glu Pro Lys Ser Cys Asp Lys Thr His Thr Ser Pro Pro Ser Pro
1 5 10 15

<210> SEQ ID NO 125
<211> LENGTH: 15
<212> TYPE: PRT
<213> ORGANISM: Artificial
<220> FEATURE:
<223> OTHER INFORMATION: scs(p)-hlgG1 hinge

<400> SEQUENCE: 125

Glu Pro Lys Ser Ser Asp Lys Thr His Thr Cys Pro Pro Ser Pro
1 5 10 15

<210> SEQ ID NO 126
<211> LENGTH: 6
<212> TYPE: PRT
<213> ORGANISM: Artificial
<220> FEATURE:
<223> OTHER INFORMATION: Scppcp

<400> SEQUENCE: 126

Ser Cys Pro Pro Cys Pro
1 5

<210> SEQ ID NO 127
<211> LENGTH: 20
<212> TYPE: PRT
<213> ORGANISM: Artificial
<220> FEATURE:
<223> OTHER INFORMATION: STD1

<400> SEQUENCE: 127

Asn Tyr Gly Gly Gly Gly Ser Gly Gly Gly Gly Ser Gly Gly Gly Gly
1 5 10 15

Ser Gly Asn Ser
20

<210> SEQ ID NO 128
<211> LENGTH: 38
<212> TYPE: PRT
<213> ORGANISM: Artificial
<220> FEATURE:
<223> OTHER INFORMATION: STD2

<400> SEQUENCE: 128

Asn Tyr Gly Gly Gly Gly Ser Gly Gly Gly Gly Ser Gly Gly Gly Gly
1 5 10 15

Ser Gly Asn Tyr Gly Gly Gly Gly Ser Gly Gly Gly Gly Ser Gly Gly
20 25 30

Gly Gly Ser Gly Asn Ser
35

<210> SEQ ID NO 129
<211> LENGTH: 2

<212> TYPE: PRT
<213> ORGANISM: Artificial
<220> FEATURE:
<223> OTHER INFORMATION: H1

<400> SEQUENCE: 129

Asn Ser
1

<210> SEQ ID NO 130
<211> LENGTH: 8
<212> TYPE: PRT
<213> ORGANISM: Artificial
<220> FEATURE:
<223> OTHER INFORMATION: H2

<400> SEQUENCE: 130

Gly Gly Gly Gly Ser Gly Asn Ser
1               5

<210> SEQ ID NO 131
<211> LENGTH: 10
<212> TYPE: PRT
<213> ORGANISM: Artificial
<220> FEATURE:
<223> OTHER INFORMATION: H3

<400> SEQUENCE: 131

Asn Tyr Gly Gly Gly Gly Ser Gly Asn Ser
1               5                   10

<210> SEQ ID NO 132
<211> LENGTH: 13
<212> TYPE: PRT
<213> ORGANISM: Artificial
<220> FEATURE:
<223> OTHER INFORMATION: H4

<400> SEQUENCE: 132

Gly Gly Gly Gly Ser Gly Gly Gly Gly Ser Gly Asn Ser
1               5                   10

<210> SEQ ID NO 133
<211> LENGTH: 15
<212> TYPE: PRT
<213> ORGANISM: Artificial
<220> FEATURE:
<223> OTHER INFORMATION: H5

<400> SEQUENCE: 133

Asn Tyr Gly Gly Gly Gly Ser Gly Gly Gly Gly Ser Gly Asn Ser
1               5                   10                  15

<210> SEQ ID NO 134
<211> LENGTH: 18
<212> TYPE: PRT
<213> ORGANISM: Artificial
<220> FEATURE:
<223> OTHER INFORMATION: H6

<400> SEQUENCE: 134

Gly Gly Gly Gly Ser Gly Gly Gly Gly Ser Gly Gly Gly Gly Ser Gly
1               5                   10                  15

Asn Ser

<210> SEQ ID NO 135

<211> LENGTH: 8
<212> TYPE: PRT
<213> ORGANISM: Artificial
<220> FEATURE:
<223> OTHER INFORMATION: H7

<400> SEQUENCE: 135

Gly Cys Pro Pro Cys Pro Asn Ser
1               5

<210> SEQ ID NO 136
<211> LENGTH: 8
<212> TYPE: PRT
<213> ORGANISM: Artificial
<220> FEATURE:
<223> OTHER INFORMATION: H9

<400> SEQUENCE: 136

Gly Ser Pro Pro Ser Pro Asn Ser
1               5

<210> SEQ ID NO 137
<211> LENGTH: 15
<212> TYPE: PRT
<213> ORGANISM: Artificial
<220> FEATURE:
<223> OTHER INFORMATION: (G4S)3

<400> SEQUENCE: 137

Gly Gly Gly Gly Ser Gly Gly Gly Gly Ser Gly Gly Gly Gly Ser
1               5                   10                  15

<210> SEQ ID NO 138
<211> LENGTH: 16
<212> TYPE: PRT
<213> ORGANISM: Artificial
<220> FEATURE:
<223> OTHER INFORMATION: H105

<400> SEQUENCE: 138

Ser Gly Gly Gly Gly Ser Gly Gly Gly Gly Ser Gly Gly Gly Gly Ser
1               5                   10                  15

<210> SEQ ID NO 139
<211> LENGTH: 20
<212> TYPE: PRT
<213> ORGANISM: Artificial
<220> FEATURE:
<223> OTHER INFORMATION: (G4S)4

<400> SEQUENCE: 139

Gly Gly Gly Gly Ser Gly Gly Gly Gly Ser Gly Gly Gly Gly Ser Gly
1               5                   10                  15

Gly Gly Gly Ser
            20

<210> SEQ ID NO 140
<211> LENGTH: 21
<212> TYPE: PRT
<213> ORGANISM: Artificial
<220> FEATURE:
<223> OTHER INFORMATION: H75 (NKG2A quadruple mutant)

<400> SEQUENCE: 140

Gln Arg His Asn Asn Ser Ser Leu Asn Thr Gly Thr Gln Met Ala Gly
1               5                   10                  15

His Ser Pro Asn Ser
            20

<210> SEQ ID NO 141
<211> LENGTH: 16
<212> TYPE: PRT
<213> ORGANISM: Artificial
<220> FEATURE:
<223> OTHER INFORMATION: H83 (NKG2A derived)

<400> SEQUENCE: 141

Ser Ser Leu Asn Thr Gly Thr Gln Met Ala Gly His Ser Pro Asn Ser
1               5                   10                  15

<210> SEQ ID NO 142
<211> LENGTH: 18
<212> TYPE: PRT
<213> ORGANISM: Artificial
<220> FEATURE:
<223> OTHER INFORMATION: H106 (NKG2A derived)

<400> SEQUENCE: 142

Gln Arg His Asn Asn Ser Ser Leu Asn Thr Gly Thr Gln Met Ala Gly
1               5                   10                  15

His Ser

<210> SEQ ID NO 143
<211> LENGTH: 14
<212> TYPE: PRT
<213> ORGANISM: Artificial
<220> FEATURE:
<223> OTHER INFORMATION: H81 (NKG2D derived)

<400> SEQUENCE: 143

Glu Val Gln Ile Pro Leu Thr Glu Ser Tyr Ser Pro Asn Ser
1               5                   10

<210> SEQ ID NO 144
<211> LENGTH: 20
<212> TYPE: PRT
<213> ORGANISM: Artificial
<220> FEATURE:
<223> OTHER INFORMATION: H91 (NKG2D derived)

<400> SEQUENCE: 144

Asn Ser Leu Ala Asn Gln Glu Val Gln Ile Pro Leu Thr Glu Ser Tyr
1               5                   10                  15

Ser Pro Asn Ser
            20

<210> SEQ ID NO 145
<211> LENGTH: 19
<212> TYPE: PRT
<213> ORGANISM: Artificial
<220> FEATURE:
<223> OTHER INFORMATION: H94

<400> SEQUENCE: 145

Ser Gly Gly Gly Gly Ser Gly Gly Gly Gly Ser Gly Gly Gly Gly Ser
1               5                   10                  15

Pro Asn Ser

<210> SEQ ID NO 146
<211> LENGTH: 15
<212> TYPE: PRT

<213> ORGANISM: Artificial
<220> FEATURE:
<223> OTHER INFORMATION: H16

<400> SEQUENCE: 146

Leu Ser Val Lys Ala Asp Phe Leu Thr Pro Ser Ile Gly Asn Ser
1 5 10 15

<210> SEQ ID NO 147
<211> LENGTH: 20
<212> TYPE: PRT
<213> ORGANISM: Artificial
<220> FEATURE:
<223> OTHER INFORMATION: H17

<400> SEQUENCE: 147

Leu Ser Val Lys Ala Asp Phe Leu Thr Pro Ser Ile Ser Cys Pro Pro
1 5 10 15

Cys Pro Asn Ser
20

<210> SEQ ID NO 148
<211> LENGTH: 15
<212> TYPE: PRT
<213> ORGANISM: Artificial
<220> FEATURE:
<223> OTHER INFORMATION: H18

<400> SEQUENCE: 148

Leu Ser Val Leu Ala Asn Phe Ser Gln Pro Glu Ile Gly Asn Ser
1 5 10 15

<210> SEQ ID NO 149
<211> LENGTH: 20
<212> TYPE: PRT
<213> ORGANISM: Artificial
<220> FEATURE:
<223> OTHER INFORMATION: H19

<400> SEQUENCE: 149

Leu Ser Val Leu Ala Asn Phe Ser Gln Pro Glu Ile Ser Cys Pro Pro
1 5 10 15

Cys Pro Asn Ser
20

<210> SEQ ID NO 150
<211> LENGTH: 15
<212> TYPE: PRT
<213> ORGANISM: Artificial
<220> FEATURE:
<223> OTHER INFORMATION: H20

<400> SEQUENCE: 150

Leu Lys Ile Gln Glu Arg Val Ser Lys Pro Lys Ile Ser Asn Ser
1 5 10 15

<210> SEQ ID NO 151
<211> LENGTH: 20
<212> TYPE: PRT
<213> ORGANISM: Artificial
<220> FEATURE:
<223> OTHER INFORMATION: H21

<400> SEQUENCE: 151

Leu Lys Ile Gln Glu Arg Val Ser Lys Pro Lys Ile Ser Cys Pro Pro
1 5 10 15

Cys Pro Asn Ser
20

<210> SEQ ID NO 152
<211> LENGTH: 15
<212> TYPE: PRT
<213> ORGANISM: Artificial
<220> FEATURE:
<223> OTHER INFORMATION: H22

<400> SEQUENCE: 152

Leu Asn Val Ser Glu Arg Pro Phe Pro Pro His Ile Gln Asn Ser
1 5 10 15

<210> SEQ ID NO 153
<211> LENGTH: 21
<212> TYPE: PRT
<213> ORGANISM: Artificial
<220> FEATURE:
<223> OTHER INFORMATION: H23

<400> SEQUENCE: 153

Leu Asp Val Ser Glu Arg Pro Phe Pro Pro His Ile Gln Ser Cys Pro
1 5 10 15

Pro Cys Pro Asn Ser
20

<210> SEQ ID NO 154
<211> LENGTH: 15
<212> TYPE: PRT
<213> ORGANISM: Artificial
<220> FEATURE:
<223> OTHER INFORMATION: H24

<400> SEQUENCE: 154

Arg Glu Gln Leu Ala Glu Val Thr Leu Ser Leu Lys Ala Asn Ser
1 5 10 15

<210> SEQ ID NO 155
<211> LENGTH: 20
<212> TYPE: PRT
<213> ORGANISM: Artificial
<220> FEATURE:
<223> OTHER INFORMATION: H25

<400> SEQUENCE: 155

Arg Glu Gln Leu Ala Glu Val Thr Leu Ser Leu Lys Ala Cys Pro Pro
1 5 10 15

Cys Pro Asn Ser
20

<210> SEQ ID NO 156
<211> LENGTH: 15
<212> TYPE: PRT
<213> ORGANISM: Artificial
<220> FEATURE:
<223> OTHER INFORMATION: H26

<400> SEQUENCE: 156

Arg Ile His Gln Met Asn Ser Glu Leu Ser Val Leu Ala Asn Ser
1 5 10 15

<210> SEQ ID NO 157
<211> LENGTH: 20
<212> TYPE: PRT

<213> ORGANISM: Artificial
<220> FEATURE:
<223> OTHER INFORMATION: H27

<400> SEQUENCE: 157

Arg Ile His Gln Met Asn Ser Glu Leu Ser Val Leu Ala Cys Pro Pro
1 5 10 15

Cys Pro Asn Ser
20

<210> SEQ ID NO 158
<211> LENGTH: 15
<212> TYPE: PRT
<213> ORGANISM: Artificial
<220> FEATURE:
<223> OTHER INFORMATION: H28

<400> SEQUENCE: 158

Asp Thr Lys Gly Lys Asn Val Leu Glu Lys Ile Phe Ser Asn Ser
1 5 10 15

<210> SEQ ID NO 159
<211> LENGTH: 15
<212> TYPE: PRT
<213> ORGANISM: Artificial
<220> FEATURE:
<223> OTHER INFORMATION: H30

<400> SEQUENCE: 159

Leu Pro Pro Glu Thr Gln Glu Ser Gln Glu Val Thr Leu Asn Ser
1 5 10 15

<210> SEQ ID NO 160
<211> LENGTH: 15
<212> TYPE: PRT
<213> ORGANISM: Artificial
<220> FEATURE:
<223> OTHER INFORMATION: H32

<400> SEQUENCE: 160

Arg Ile His Leu Asn Val Ser Glu Arg Pro Phe Pro Pro Asn Ser
1 5 10 15

<210> SEQ ID NO 161
<211> LENGTH: 20
<212> TYPE: PRT
<213> ORGANISM: Artificial
<220> FEATURE:
<223> OTHER INFORMATION: H33

<400> SEQUENCE: 161

Arg Ile His Leu Asn Val Ser Glu Arg Pro Phe Pro Pro Cys Pro Pro
1 5 10 15

Cys Pro Asn Ser
20

<210> SEQ ID NO 162
<211> LENGTH: 13
<212> TYPE: PRT
<213> ORGANISM: Artificial
<220> FEATURE:
<223> OTHER INFORMATION: H36

<400> SEQUENCE: 162

Gly Cys Pro Pro Cys Pro Gly Gly Gly Gly Ser Asn Ser
1 5 10

<210> SEQ ID NO 163
<211> LENGTH: 9
<212> TYPE: PRT
<213> ORGANISM: Artificial
<220> FEATURE:
<223> OTHER INFORMATION: H40

<400> SEQUENCE: 163

Gly Cys Pro Pro Cys Pro Ala Asn Ser
1 5

<210> SEQ ID NO 164
<211> LENGTH: 9
<212> TYPE: PRT
<213> ORGANISM: Artificial
<220> FEATURE:
<223> OTHER INFORMATION: H41

<400> SEQUENCE: 164

Gly Cys Pro Pro Cys Pro Ala Asn Ser
1 5

<210> SEQ ID NO 165
<211> LENGTH: 8
<212> TYPE: PRT
<213> ORGANISM: Artificial
<220> FEATURE:
<223> OTHER INFORMATION: H42

<400> SEQUENCE: 165

Gly Cys Pro Pro Cys Pro Asn Ser
1 5

<210> SEQ ID NO 166
<211> LENGTH: 13
<212> TYPE: PRT
<213> ORGANISM: Artificial
<220> FEATURE:
<223> OTHER INFORMATION: H44

<400> SEQUENCE: 166

Gly Gly Gly Ala Ser Cys Pro Pro Cys Pro Gly Asn Ser
1 5 10

<210> SEQ ID NO 167
<211> LENGTH: 13
<212> TYPE: PRT
<213> ORGANISM: Artificial
<220> FEATURE:
<223> OTHER INFORMATION: H45

<400> SEQUENCE: 167

Gly Gly Gly Ala Ser Cys Pro Pro Cys Ala Gly Asn Ser
1 5 10

<210> SEQ ID NO 168
<211> LENGTH: 12
<212> TYPE: PRT
<213> ORGANISM: Artificial
<220> FEATURE:
<223> OTHER INFORMATION: H46

<400> SEQUENCE: 168

Gly Gly Gly Ala Ser Cys Pro Pro Cys Ala Asn Ser
1 5 10

<210> SEQ ID NO 169
<211> LENGTH: 15
<212> TYPE: PRT
<213> ORGANISM: Artificial
<220> FEATURE:
<223> OTHER INFORMATION: H47

<400> SEQUENCE: 169

Leu Ser Val Lys Ala Asp Phe Leu Thr Pro Ser Ile Gly Asn Ser
1 5 10 15

<210> SEQ ID NO 170
<211> LENGTH: 11
<212> TYPE: PRT
<213> ORGANISM: Artificial
<220> FEATURE:
<223> OTHER INFORMATION: H48

<400> SEQUENCE: 170

Ala Asp Phe Leu Thr Pro Ser Ile Gly Asn Ser
1 5 10

<210> SEQ ID NO 171
<211> LENGTH: 15
<212> TYPE: PRT
<213> ORGANISM: Artificial
<220> FEATURE:
<223> OTHER INFORMATION: H50

<400> SEQUENCE: 171

Leu Ser Val Leu Ala Asn Phe Ser Gln Pro Glu Ile Gly Asn Ser
1 5 10 15

<210> SEQ ID NO 172
<211> LENGTH: 15
<212> TYPE: PRT
<213> ORGANISM: Artificial
<220> FEATURE:
<223> OTHER INFORMATION: H51

<400> SEQUENCE: 172

Leu Ser Val Leu Ala Asn Phe Ser Gln Pro Glu Ile Gly Asn Ser
1 5 10 15

<210> SEQ ID NO 173
<211> LENGTH: 11
<212> TYPE: PRT
<213> ORGANISM: Artificial
<220> FEATURE:
<223> OTHER INFORMATION: H52

<400> SEQUENCE: 173

Ser Gln Pro Glu Ile Val Pro Ile Ser Asn Ser
1 5 10

<210> SEQ ID NO 174
<211> LENGTH: 16
<212> TYPE: PRT
<213> ORGANISM: Artificial
<220> FEATURE:
<223> OTHER INFORMATION: H53

<400> SEQUENCE: 174

Ser Gln Pro Glu Ile Val Pro Ile Ser Cys Pro Pro Cys Pro Asn Ser
1 5 10 15

<210> SEQ ID NO 175
<211> LENGTH: 19
<212> TYPE: PRT
<213> ORGANISM: Artificial
<220> FEATURE:
<223> OTHER INFORMATION: H54

<400> SEQUENCE: 175

Ser Val Leu Ala Asn Phe Ser Gln Pro Glu Ile Ser Cys Pro Pro Cys
1 5 10 15

Pro Asn Ser

<210> SEQ ID NO 176
<211> LENGTH: 15
<212> TYPE: PRT
<213> ORGANISM: Artificial
<220> FEATURE:
<223> OTHER INFORMATION: H55

<400> SEQUENCE: 176

Arg Ile His Gln Met Asn Ser Glu Leu Ser Val Leu Ala Asn Ser
1 5 10 15

<210> SEQ ID NO 177
<211> LENGTH: 12
<212> TYPE: PRT
<213> ORGANISM: Artificial
<220> FEATURE:
<223> OTHER INFORMATION: H56

<400> SEQUENCE: 177

Gln Met Asn Ser Glu Leu Ser Val Leu Ala Asn Ser
1 5 10

<210> SEQ ID NO 178
<211> LENGTH: 10
<212> TYPE: PRT
<213> ORGANISM: Artificial
<220> FEATURE:
<223> OTHER INFORMATION: H57

<400> SEQUENCE: 178

Val Ser Glu Arg Pro Phe Pro Pro Asn Ser
1 5 10

<210> SEQ ID NO 179
<211> LENGTH: 15
<212> TYPE: PRT
<213> ORGANISM: Artificial
<220> FEATURE:
<223> OTHER INFORMATION: H58

<400> SEQUENCE: 179

Lys Pro Phe Phe Thr Cys Gly Ser Ala Asp Thr Cys Pro Asn Ser
1 5 10 15

<210> SEQ ID NO 180
<211> LENGTH: 15
<212> TYPE: PRT
<213> ORGANISM: Artificial
<220> FEATURE:
<223> OTHER INFORMATION: H59

<400> SEQUENCE: 180

Lys Pro Phe Phe Thr Cys Gly Ser Ala Asp Thr Cys Pro Asn Ser
1 5 10 15

<210> SEQ ID NO 181
<211> LENGTH: 15
<212> TYPE: PRT
<213> ORGANISM: Artificial
<220> FEATURE:
<223> OTHER INFORMATION: H60

<400> SEQUENCE: 181

```
Gln Tyr Asn Cys Pro Gly Gln Tyr Thr Phe Ser Met Pro Asn Ser
1               5                   10                  15
```

<210> SEQ ID NO 182
<211> LENGTH: 21
<212> TYPE: PRT
<213> ORGANISM: Artificial
<220> FEATURE:
<223> OTHER INFORMATION: H61

<400> SEQUENCE: 182

```
Glu Pro Ala Phe Thr Pro Gly Pro Asn Ile Glu Leu Gln Lys Asp Ser
1               5                   10                  15

Asp Cys Pro Asn Ser
            20
```

<210> SEQ ID NO 183
<211> LENGTH: 21
<212> TYPE: PRT
<213> ORGANISM: Artificial
<220> FEATURE:
<223> OTHER INFORMATION: H62

<400> SEQUENCE: 183

```
Gln Arg His Asn Asn Ser Ser Leu Asn Thr Arg Thr Gln Lys Ala Arg
1               5                   10                  15

His Cys Pro Asn Ser
            20
```

<210> SEQ ID NO 184
<211> LENGTH: 20
<212> TYPE: PRT
<213> ORGANISM: Artificial
<220> FEATURE:
<223> OTHER INFORMATION: H63

<400> SEQUENCE: 184

```
Asn Ser Leu Phe Asn Gln Glu Val Gln Ile Pro Leu Thr Glu Ser Tyr
1               5                   10                  15

Cys Pro Asn Ser
            20
```

<210> SEQ ID NO 185
<211> LENGTH: 2307
<212> TYPE: DNA
<213> ORGANISM: Artificial
<220> FEATURE:
<223> OTHER INFORMATION: TSC275 (hu4C04 x DRA222 null2 Scorpion)

<400> SEQUENCE: 185

```
atggaagcac cagcgcagct tctcttcctc ctgctactct ggctcccaga taccaccggt      60

gacatccaga tgacccagtc tccatcctcc ctgtctgcat ctgtaggaga cagagtcacc     120

atcacttgcc tggcaagtca gaccattggt acatggttag catggtatca gcagaaacca     180

gggaaagccc ctaagctcct gatttatgct gcaaccagct tggcagatgg ggtcccatca     240
```

```
aggttcagtg gcagtggatc tgggacagat ttcactctca ccatcagcag tctgcaacct    300

gaagattttg caacttacta ctgtcaacaa ctttacaata ctccgtggac gttcggcgga    360

gggaccaagg tggagatcaa agggggtgga ggctctggtg gcggtggctc tggcggaggt    420

ggatccggcg gggtggctc tgaggtccag ctggtacagt ctggggctga ggtgaagaag    480

cctggggcta cagtgaaaat ctcctgcaag gtttctgact acacactcac tgacttctat    540

atgaactggg tgcaacaggc ccctggaaaa gggcttgagt ggattgggag gatttatcct    600

ggaaccgata aaactagata caatgagaaa ttcagggaca gagtcaccat aaccgcggac    660

acgtctacag acacagccta catggagctg agcagcctga gatctgagga cacggccgtg    720

tattactgtg caagatccgc ctactatggt aactacgttg ctatggacta ctgggggcaa    780

gggaccacgg tcaccgtctc ctcgagtgag cccaaatctt ctgacaaaac tcacacatgc    840

ccaccgtgcc cagcacctga agccgcgggt gcaccgtcag tcttcctctt ccccccaaaa    900

cccaaggaca ccctcatgat ctcccggacc cctgaggtca catgcgtggt ggtggacgtg    960

agccacgaag accctgaggt caagttcaac tggtacgtgg acggcgtgga ggtgcataat   1020

gccaagacaa agccgcggga ggagcagtac aacagcacgt accgtgtggt cagcgtcctc   1080

accgtcctgc accaggactg gctgaatggc aaggcgtacg cgtgcgcggt ctccaacaaa   1140

gccctcccag cccccatcga gaaaaccatc tccaaagcca aagggcagcc ccgagaacca   1200

caggtgtaca ccctgccccc atcccgggat gagctgacca agaaccaggt cagcctgacc   1260

tgcctggtca aaggcttcta tccaagcgac atcgccgtgg agtgggagag caatgggcag   1320

ccggagaaca actacaagac cacgcctccc gtgctggact ccgacggctc cttcttcctc   1380

tacagcaagc tcaccgtgga caagagcagg tggcagcagg ggaacgtctt ctcatgctcc   1440

gtgatgcatg aggctctgca caaccactac acgcagaaga gcctctccct gtctccgggt   1500

cagaggcaca acaattcttc cctgaataca ggaactcaga tggcaggtca ttctccgaat   1560

tctcaggtcc agctggtgga gtctgggggc ggagtggtgc agcctgggcg gtcactgagg   1620

ctgtcctgca aggcttctgg ctacaccttt actagatcta cgatgcactg ggtaaggcag   1680

gcccctggac aaggtctgga atggattgga tacattaatc ctagcagtgc ttatactaat   1740

tacaatcaga aattcaagga caggttcaca atcagcgcag acaaatccaa gagcacagcc   1800

ttcctgcaga tggacagcct gaggcccgag gacaccggcg tctatttctg tgcacggccc   1860

caagtccact atgattacaa cgggtttcct tactggggcc aagggactcc cgtcactgtc   1920

tctagcggtg gcggagggtc tgggggtggc ggatccggag gtggtggctc tgcacaagac   1980

atccagatga cccagtctcc aagcagcctg tctgcaagcg tgggggacag ggtcaccatg   2040

acctgcagtg ccagctcaag tgtaagttac atgaactggt accagcagaa gccgggcaag   2100

gcccccaaaa gatggattta tgactcatcc aaactggctt ctggagtccc tgctcgcttc   2160

agtggcagtg ggtctgggac cgactatacc ctcacaatca gcagcctgca gcccgaagat   2220

ttcgccactt attactgcca gcagtggagt cgtaacccac ccacgttcgg agggggggacc   2280

aagctacaaa ttacatcctc cagctaa                                       2307
```

<210> SEQ ID NO 186
<211> LENGTH: 748
<212> TYPE: PRT
<213> ORGANISM: Artificial
<220> FEATURE:
<223> OTHER INFORMATION: TSC275 (hu4C04 x DRA222 null2 Scorpion)

<400> SEQUENCE: 186

-continued

```
Asp Ile Gln Met Thr Gln Ser Pro Ser Ser Leu Ser Ala Ser Val Gly
1               5                   10                  15

Asp Arg Val Thr Ile Thr Cys Leu Ala Ser Gln Thr Ile Gly Thr Trp
            20                  25                  30

Leu Ala Trp Tyr Gln Gln Lys Pro Gly Lys Ala Pro Lys Leu Leu Ile
        35                  40                  45

Tyr Ala Ala Thr Ser Leu Ala Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Leu Tyr Asn Thr Pro Trp
                85                  90                  95

Thr Phe Gly Gly Gly Thr Lys Val Glu Ile Lys Gly Gly Gly Gly Ser
            100                 105                 110

Gly Gly Gly Gly Ser Gly Gly Gly Gly Ser Gly Gly Gly Gly Ser Glu
        115                 120                 125

Val Gln Leu Val Gln Ser Gly Ala Glu Val Lys Lys Pro Gly Ala Thr
    130                 135                 140

Val Lys Ile Ser Cys Lys Val Ser Asp Tyr Thr Leu Thr Asp Phe Tyr
145                 150                 155                 160

Met Asn Trp Val Gln Gln Ala Pro Gly Lys Gly Leu Glu Trp Ile Gly
                165                 170                 175

Arg Ile Tyr Pro Gly Thr Asp Lys Thr Arg Tyr Asn Glu Lys Phe Arg
            180                 185                 190

Asp Arg Val Thr Ile Thr Ala Asp Thr Ser Thr Asp Thr Ala Tyr Met
        195                 200                 205

Glu Leu Ser Ser Leu Arg Ser Glu Asp Thr Ala Val Tyr Tyr Cys Ala
    210                 215                 220

Arg Ser Ala Tyr Tyr Gly Asn Tyr Val Ala Met Asp Tyr Trp Gly Gln
225                 230                 235                 240

Gly Thr Thr Val Thr Val Ser Ser Ser Glu Pro Lys Ser Ser Asp Lys
                245                 250                 255

Thr His Thr Cys Pro Pro Cys Pro Ala Pro Glu Ala Ala Gly Ala Pro
            260                 265                 270

Ser Val Phe Leu Phe Pro Pro Lys Pro Lys Asp Thr Leu Met Ile Ser
        275                 280                 285

Arg Thr Pro Glu Val Thr Cys Val Val Val Asp Val Ser His Glu Asp
    290                 295                 300

Pro Glu Val Lys Phe Asn Trp Tyr Val Asp Gly Val Glu Val His Asn
305                 310                 315                 320

Ala Lys Thr Lys Pro Arg Glu Glu Gln Tyr Asn Ser Thr Tyr Arg Val
                325                 330                 335

Val Ser Val Leu Thr Val Leu His Gln Asp Trp Leu Asn Gly Lys Ala
            340                 345                 350

Tyr Ala Cys Ala Val Ser Asn Lys Ala Leu Pro Ala Pro Ile Glu Lys
        355                 360                 365

Thr Ile Ser Lys Ala Lys Gly Gln Pro Arg Glu Pro Gln Val Tyr Thr
    370                 375                 380

Leu Pro Pro Ser Arg Asp Glu Leu Thr Lys Asn Gln Val Ser Leu Thr
385                 390                 395                 400

Cys Leu Val Lys Gly Phe Tyr Pro Ser Asp Ile Ala Val Glu Trp Glu
                405                 410                 415
```

-continued

```
Ser Asn Gly Gln Pro Glu Asn Asn Tyr Lys Thr Thr Pro Pro Val Leu
            420                 425                 430

Asp Ser Asp Gly Ser Phe Phe Leu Tyr Ser Lys Leu Thr Val Asp Lys
        435                 440                 445

Ser Arg Trp Gln Gln Gly Asn Val Phe Ser Cys Ser Val Met His Glu
    450                 455                 460

Ala Leu His Asn His Tyr Thr Gln Lys Ser Leu Ser Leu Ser Pro Gly
465                 470                 475                 480

Gln Arg His Asn Asn Ser Ser Leu Asn Thr Gly Thr Gln Met Ala Gly
                485                 490                 495

His Ser Pro Asn Ser Gln Val Gln Leu Val Glu Ser Gly Gly Gly Val
            500                 505                 510

Val Gln Pro Gly Arg Ser Leu Arg Leu Ser Cys Lys Ala Ser Gly Tyr
        515                 520                 525

Thr Phe Thr Arg Ser Thr Met His Trp Val Arg Gln Ala Pro Gly Gln
    530                 535                 540

Gly Leu Glu Trp Ile Gly Tyr Ile Asn Pro Ser Ser Ala Tyr Thr Asn
545                 550                 555                 560

Tyr Asn Gln Lys Phe Lys Asp Arg Phe Thr Ile Ser Ala Asp Lys Ser
                565                 570                 575

Lys Ser Thr Ala Phe Leu Gln Met Asp Ser Leu Arg Pro Glu Asp Thr
            580                 585                 590

Gly Val Tyr Phe Cys Ala Arg Pro Gln Val His Tyr Asp Tyr Asn Gly
        595                 600                 605

Phe Pro Tyr Trp Gly Gln Gly Thr Pro Val Thr Val Ser Ser Gly Gly
    610                 615                 620

Gly Gly Ser Gly Gly Gly Gly Ser Gly Gly Gly Gly Ser Ala Gln Asp
625                 630                 635                 640

Ile Gln Met Thr Gln Ser Pro Ser Ser Leu Ser Ala Ser Val Gly Asp
                645                 650                 655

Arg Val Thr Met Thr Cys Ser Ala Ser Ser Ser Val Ser Tyr Met Asn
            660                 665                 670

Trp Tyr Gln Gln Lys Pro Gly Lys Ala Pro Lys Arg Trp Ile Tyr Asp
        675                 680                 685

Ser Ser Lys Leu Ala Ser Gly Val Pro Ala Arg Phe Ser Gly Ser Gly
    690                 695                 700

Ser Gly Thr Asp Tyr Thr Leu Thr Ile Ser Ser Leu Gln Pro Glu Asp
705                 710                 715                 720

Phe Ala Thr Tyr Tyr Cys Gln Gln Trp Ser Arg Asn Pro Pro Thr Phe
                725                 730                 735

Gly Gly Gly Thr Lys Leu Gln Ile Thr Ser Ser Ser
            740                 745
```

<210> SEQ ID NO 187
<211> LENGTH: 107
<212> TYPE: PRT
<213> ORGANISM: Artificial
<220> FEATURE:
<223> OTHER INFORMATION: hu4C04 VL

<400> SEQUENCE: 187

```
Asp Ile Gln Met Thr Gln Ser Pro Ser Ser Leu Ser Ala Ser Val Gly
1               5                   10                  15

Asp Arg Val Thr Ile Thr Cys Leu Ala Ser Gln Thr Ile Gly Thr Trp
            20                  25                  30
```

```
Leu Ala Trp Tyr Gln Gln Lys Pro Gly Lys Ala Pro Lys Leu Leu Ile
        35                  40                  45

Tyr Ala Ala Thr Ser Leu Ala Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Leu Tyr Asn Thr Pro Trp
                85                  90                  95

Thr Phe Gly Gly Gly Thr Lys Val Glu Ile Lys
            100                 105


<210> SEQ ID NO 188
<211> LENGTH: 121
<212> TYPE: PRT
<213> ORGANISM: Artificial
<220> FEATURE:
<223> OTHER INFORMATION: hu4C04 VH

<400> SEQUENCE: 188

Glu Val Gln Leu Val Gln Ser Gly Ala Glu Val Lys Lys Pro Gly Ala
1               5                   10                  15

Thr Val Lys Ile Ser Cys Lys Val Ser Asp Tyr Thr Leu Thr Asp Phe
            20                  25                  30

Tyr Met Asn Trp Val Gln Gln Ala Pro Gly Lys Gly Leu Glu Trp Ile
        35                  40                  45

Gly Arg Ile Tyr Pro Gly Thr Asp Lys Thr Arg Tyr Asn Glu Lys Phe
    50                  55                  60

Arg Asp Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Ala Tyr Tyr Gly Asn Tyr Val Ala Met Asp Tyr Trp Gly
            100                 105                 110

Gln Gly Thr Thr Val Thr Val Ser Ser
        115                 120


<210> SEQ ID NO 189
<211> LENGTH: 2307
<212> TYPE: DNA
<213> ORGANISM: Artificial
<220> FEATURE:
<223> OTHER INFORMATION: TSC277 (hu4C04 (A43K Q240E) x DRA222 null2
      Scorpion)

<400> SEQUENCE: 189

atggaagcac cagcgcagct tctcttcctc ctgctactct ggctcccaga taccaccggt      60

gacatccaga tgacccagtc tccatcctcc ctgtctgcat ctgtaggaga cagagtcacc     120

atcacttgcc tggcaagtca gaccattggt acatggttag catggtatca gcagaaacca     180

gggaaaaagc ctaagctcct gatttatgct gcaaccagct tggcagatgg ggtcccatca     240

aggttcagtg gcagtggatc tgggacagat ttcactctca ccatcagcag tctgcaacct     300

gaagattttg caacttacta ctgtcaacaa ctttacaata ctccgtggac gttcggcgga     360

gggaccaagg tggagatcaa agggggtgga ggctctggtg gcggtggctc tggcggaggt     420

ggatccggcg ggggtggctc tgaggtccag ctggtacagt ctggggctga ggtgaagaag     480

cctggggcta cagtgaaaat ctcctgcaag gtttctgact acacactcac tgacttctat     540

atgaactggg tgcaacaggc ccctggaaaa gggcttgagt ggattgggag gatttatcct     600
```

ggaaccgata aaactagata caatgagaaa ttcagggaca gagtcaccat aaccgcggac 660
acgtctacag acacagccta catggagctg agcagcctga gatctgagga cacggccgtg 720
tattactgtg caagatccgc ctactatggt aactacgttg ctatggacta ctggggggag 780
gggaccacgg tcaccgtctc ctcgagtgag cccaaatctt ctgacaaaac tcacacatgc 840
ccaccgtgcc cagcacctga agccgcgggt gcaccgtcag tcttcctctt ccccccaaaa 900
cccaaggaca ccctcatgat ctcccggacc cctgaggtca catgcgtggt ggtggacgtg 960
agccacgaag accctgaggt caagttcaac tggtacgtgg acggcgtgga ggtgcataat 1020
gccaagacaa agccgcggga ggagcagtac aacagcacgt accgtgtggt cagcgtcctc 1080
accgtcctgc accaggactg gctgaatggc aaggcgtacg cgtgcgcggt ctccaacaaa 1140
gccctcccag cccccatcga gaaaaccatc tccaaagcca aagggcagcc ccgagaacca 1200
caggtgtaca ccctgccccc atcccgggat gagctgacca agaaccaggt cagcctgacc 1260
tgcctggtca aaggcttcta tccaagcgac atcgccgtgg agtgggagag caatgggcag 1320
ccggagaaca actacaagac cacgcctccc gtgctggact ccgacggctc cttcttcctc 1380
tacagcaagc tcaccgtgga caagagcagg tggcagcagg ggaacgtctt ctcatgctcc 1440
gtgatgcatg aggctctgca caaccactac acgcagaaga gcctctccct gtctccgggt 1500
cagaggcaca acaattcttc cctgaataca ggaactcaga tggcaggtca ttctccgaat 1560
tctcaggtcc agctggtgga gtctgggggc ggagtggtgc agcctgggcg gtcactgagg 1620
ctgtcctgca aggcttctgg ctacaccttt actagatcta cgatgcactg ggtaaggcag 1680
gcccctggac aaggtctgga atggattgga tacattaatc ctagcagtgc ttatactaat 1740
tacaatcaga aattcaagga caggttcaca atcagcgcag acaaatccaa gagcacagcc 1800
ttcctgcaga tggacagcct gaggcccgag gacaccggcg tctatttctg tgcacggccc 1860
caagtccact atgattacaa cgggtttcct tactggggcc aagggactcc cgtcactgtc 1920
tctagcggtg gcggagggtc tgggggtggc ggatccggag gtggtggctc tgcacaagac 1980
atccagatga cccagtctcc aagcagcctg tctgcaagcg tgggggacag ggtcaccatg 2040
acctgcagtg ccagctcaag tgtaagttac atgaactggt accagcagaa gccgggcaag 2100
gcccccaaaa gatggattta tgactcatcc aaactggctt ctggagtccc tgctcgcttc 2160
agtggcagtg ggtctgggac cgactatacc ctcacaatca gcagcctgca gcccgaagat 2220
ttcgccactt attactgcca gcagtggagt cgtaacccac ccacgttcgg aggggggacc 2280
aagctacaaa ttacatcctc cagctaa 2307

<210> SEQ ID NO 190
<211> LENGTH: 748
<212> TYPE: PRT
<213> ORGANISM: Artificial
<220> FEATURE:
<223> OTHER INFORMATION: TSC277 (hu4C04 (A43K Q240E) x DRA222 null2 Scorpion)

<400> SEQUENCE: 190

Asp Ile Gln Met Thr Gln Ser Pro Ser Ser Leu Ser Ala Ser Val Gly
1 5 10 15

Asp Arg Val Thr Ile Thr Cys Leu Ala Ser Gln Thr Ile Gly Thr Trp
20 25 30

Leu Ala Trp Tyr Gln Gln Lys Pro Gly Lys Lys Pro Lys Leu Leu Ile
35 40 45

-continued

```
Tyr Ala Ala Thr Ser Leu Ala Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Leu Tyr Asn Thr Pro Trp
                85                  90                  95

Thr Phe Gly Gly Gly Thr Lys Val Glu Ile Lys Gly Gly Gly Gly Ser
            100                 105                 110

Gly Gly Gly Gly Ser Gly Gly Gly Gly Ser Gly Gly Gly Gly Ser Glu
        115                 120                 125

Val Gln Leu Val Gln Ser Gly Ala Glu Val Lys Lys Pro Gly Ala Thr
    130                 135                 140

Val Lys Ile Ser Cys Lys Val Ser Asp Tyr Thr Leu Thr Asp Phe Tyr
145                 150                 155                 160

Met Asn Trp Val Gln Gln Ala Pro Gly Lys Gly Leu Glu Trp Ile Gly
                165                 170                 175

Arg Ile Tyr Pro Gly Thr Asp Lys Thr Arg Tyr Asn Glu Lys Phe Arg
            180                 185                 190

Asp Arg Val Thr Ile Thr Ala Asp Thr Ser Thr Asp Thr Ala Tyr Met
        195                 200                 205

Glu Leu Ser Ser Leu Arg Ser Glu Asp Thr Ala Val Tyr Tyr Cys Ala
    210                 215                 220

Arg Ser Ala Tyr Tyr Gly Asn Tyr Val Ala Met Asp Tyr Trp Gly Glu
225                 230                 235                 240

Gly Thr Thr Val Thr Val Ser Ser Ser Glu Pro Lys Ser Ser Asp Lys
                245                 250                 255

Thr His Thr Cys Pro Pro Cys Pro Ala Pro Glu Ala Ala Gly Ala Pro
            260                 265                 270

Ser Val Phe Leu Phe Pro Pro Lys Pro Lys Asp Thr Leu Met Ile Ser
        275                 280                 285

Arg Thr Pro Glu Val Thr Cys Val Val Val Asp Val Ser His Glu Asp
    290                 295                 300

Pro Glu Val Lys Phe Asn Trp Tyr Val Asp Gly Val Glu Val His Asn
305                 310                 315                 320

Ala Lys Thr Lys Pro Arg Glu Glu Gln Tyr Asn Ser Thr Tyr Arg Val
                325                 330                 335

Val Ser Val Leu Thr Val Leu His Gln Asp Trp Leu Asn Gly Lys Ala
            340                 345                 350

Tyr Ala Cys Ala Val Ser Asn Lys Ala Leu Pro Ala Pro Ile Glu Lys
        355                 360                 365

Thr Ile Ser Lys Ala Lys Gly Gln Pro Arg Glu Pro Gln Val Tyr Thr
    370                 375                 380

Leu Pro Pro Ser Arg Asp Glu Leu Thr Lys Asn Gln Val Ser Leu Thr
385                 390                 395                 400

Cys Leu Val Lys Gly Phe Tyr Pro Ser Asp Ile Ala Val Glu Trp Glu
                405                 410                 415

Ser Asn Gly Gln Pro Glu Asn Asn Tyr Lys Thr Thr Pro Pro Val Leu
            420                 425                 430

Asp Ser Asp Gly Ser Phe Phe Leu Tyr Ser Lys Leu Thr Val Asp Lys
        435                 440                 445

Ser Arg Trp Gln Gln Gly Asn Val Phe Ser Cys Ser Val Met His Glu
    450                 455                 460

Ala Leu His Asn His Tyr Thr Gln Lys Ser Leu Ser Leu Ser Pro Gly
```

```
465                 470                 475                 480

Gln Arg His Asn Asn Ser Ser Leu Asn Thr Gly Thr Gln Met Ala Gly
                485                 490                 495

His Ser Pro Asn Ser Gln Val Gln Leu Val Glu Ser Gly Gly Gly Val
            500                 505                 510

Val Gln Pro Gly Arg Ser Leu Arg Leu Ser Cys Lys Ala Ser Gly Tyr
        515                 520                 525

Thr Phe Thr Arg Ser Thr Met His Trp Val Arg Gln Ala Pro Gly Gln
    530                 535                 540

Gly Leu Glu Trp Ile Gly Tyr Ile Asn Pro Ser Ser Ala Tyr Thr Asn
545                 550                 555                 560

Tyr Asn Gln Lys Phe Lys Asp Arg Phe Thr Ile Ser Ala Asp Lys Ser
                565                 570                 575

Lys Ser Thr Ala Phe Leu Gln Met Asp Ser Leu Arg Pro Glu Asp Thr
            580                 585                 590

Gly Val Tyr Phe Cys Ala Arg Pro Gln Val His Tyr Asp Tyr Asn Gly
        595                 600                 605

Phe Pro Tyr Trp Gly Gln Gly Thr Pro Val Thr Val Ser Ser Gly Gly
    610                 615                 620

Gly Gly Ser Gly Gly Gly Gly Ser Gly Gly Gly Gly Ser Ala Gln Asp
625                 630                 635                 640

Ile Gln Met Thr Gln Ser Pro Ser Ser Leu Ser Ala Ser Val Gly Asp
                645                 650                 655

Arg Val Thr Met Thr Cys Ser Ala Ser Ser Ser Val Ser Tyr Met Asn
            660                 665                 670

Trp Tyr Gln Gln Lys Pro Gly Lys Ala Pro Lys Arg Trp Ile Tyr Asp
        675                 680                 685

Ser Ser Lys Leu Ala Ser Gly Val Pro Ala Arg Phe Ser Gly Ser Gly
    690                 695                 700

Ser Gly Thr Asp Tyr Thr Leu Thr Ile Ser Ser Leu Gln Pro Glu Asp
705                 710                 715                 720

Phe Ala Thr Tyr Tyr Cys Gln Gln Trp Ser Arg Asn Pro Pro Thr Phe
                725                 730                 735

Gly Gly Gly Thr Lys Leu Gln Ile Thr Ser Ser Ser
            740                 745


<210> SEQ ID NO 191
<211> LENGTH: 2307
<212> TYPE: DNA
<213> ORGANISM: Artificial
<220> FEATURE:
<223> OTHER INFORMATION: TSC278 (hu4C04 (A43T) x DRA222 null2 Scorpion)

<400> SEQUENCE: 191

atggaagcac cagcgcagct tctcttcctc ctgctactct ggctcccaga taccaccggt     60

gacatccaga tgacccagtc tccatcctcc ctgtctgcat ctgtaggaga cagagtcacc    120

atcacttgcc tggcaagtca gaccattggt acatggttag catggtatca gcagaaacca    180

gggaaaaccc ctaagctcct gatttatgct gcaaccagct tggcagatgg ggtcccatca    240

aggttcagtg gcagtggatc tgggacagat ttcactctca ccatcagcag tctgcaacct    300

gaagattttg caacttacta ctgtcaacaa ctttacaata ctccgtggac gttcggcgga    360

gggaccaagg tggagatcaa agggggtgga ggctctggtg gcggtggctc tggcggaggt    420

ggatccggcg gggtggctc tgaggtccag ctggtacagt ctggggctga ggtgaagaag    480
```

-continued

```
cctggggcta cagtgaaaat ctcctgcaag gtttctgact acacactcac tgacttctat    540

atgaactggg tgcaacaggc ccctggaaaa gggcttgagt ggattgggag gatttatcct    600

ggaaccgata aaactagata caatgagaaa ttcagggaca gagtcaccat aaccgcggac    660

acgtctacag acacagccta catggagctg agcagcctga gatctgagga cacggccgtg    720

tattactgtg caagatccgc ctactatggt aactacgttg ctatggacta ctgggggcaa    780

gggaccacgg tcaccgtctc ctcgagtgag cccaaatctt ctgacaaaac tcacacatgc    840

ccaccgtgcc cagcacctga agccgcgggt gcaccgtcag tcttcctctt ccccccaaaa    900

cccaaggaca ccctcatgat ctcccggacc cctgaggtca catgcgtggt ggtggacgtg    960

agccacgaag accctgaggt caagttcaac tggtacgtgg acggcgtgga ggtgcataat   1020

gccaagacaa agccgcggga ggagcagtac aacagcacgt accgtgtggt cagcgtcctc   1080

accgtcctgc accaggactg gctgaatggc aaggcgtacg cgtgcgcggt ctccaacaaa   1140

gccctcccag cccccatcga gaaaaccatc tccaaagcca aagggcagcc ccgagaacca   1200

caggtgtaca ccctgccccc atcccgggat gagctgacca agaaccaggt cagcctgacc   1260

tgcctggtca aaggcttcta tccaagcgac atcgccgtgg agtgggagag caatgggcag   1320

ccggagaaca actacaagac cacgcctccc gtgctggact ccgacggctc cttcttcctc   1380

tacagcaagc tcaccgtgga caagagcagg tggcagcagg ggaacgtctt ctcatgctcc   1440

gtgatgcatg aggctctgca caaccactac acgcagaaga gcctctccct gtctccgggt   1500

cagaggcaca acaattcttc cctgaataca ggaactcaga tggcaggtca ttctccgaat   1560

tctcaggtcc agctggtgga gtctgggggc ggagtggtgc agcctgggcg gtcactgagg   1620

ctgtcctgca aggcttctgg ctacaccttt actagatcta cgatgcactg ggtaaggcag   1680

gcccctggac aaggtctgga atggattgga tacattaatc ctagcagtgc ttatactaat   1740

tacaatcaga aattcaagga caggttcaca atcagcgcag acaaatccaa gagcacagcc   1800

ttcctgcaga tggacagcct gaggcccgag gacaccggcg tctatttctg tgcacggccc   1860

caagtccact atgattacaa cgggtttcct tactggggcc aagggactcc cgtcactgtc   1920

tctagcggtg gcggagggtc tgggggtggc ggatccggag gtggtggctc tgcacaagac   1980

atccagatga cccagtctcc aagcagcctg tctgcaagcg tgggggacag ggtcaccatg   2040

acctgcagtg ccagctcaag tgtaagttac atgaactggt accagcagaa gccgggcaag   2100

gcccccaaaa gatggattta tgactcatcc aaactggctt ctggagtccc tgctcgcttc   2160

agtggcagtg ggtctgggac cgactatacc ctcacaatca gcagcctgca gcccgaagat   2220

ttcgccactt attactgcca gcagtggagt cgtaacccac ccacgttcgg aggggggacc   2280

aagctacaaa ttacatcctc cagctaa                                       2307
```

<210> SEQ ID NO 192
<211> LENGTH: 748
<212> TYPE: PRT
<213> ORGANISM: Artificial
<220> FEATURE:
<223> OTHER INFORMATION: TSC278 (hu4C04 (A43T) x DRA222 null2 Scorpion)

<400> SEQUENCE: 192

```
Asp Ile Gln Met Thr Gln Ser Pro Ser Ser Leu Ser Ala Ser Val Gly
1               5                   10                  15

Asp Arg Val Thr Ile Thr Cys Leu Ala Ser Gln Thr Ile Gly Thr Trp
            20                  25                  30

Leu Ala Trp Tyr Gln Gln Lys Pro Gly Lys Thr Pro Lys Leu Leu Ile
```

-continued

```
        35                  40                  45

Tyr Ala Ala Thr Ser Leu Ala Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Leu Tyr Asn Thr Pro Trp
                85                  90                  95

Thr Phe Gly Gly Gly Thr Lys Val Glu Ile Lys Gly Gly Gly Gly Ser
            100                 105                 110

Gly Gly Gly Gly Ser Gly Gly Gly Gly Ser Gly Gly Gly Gly Ser Glu
        115                 120                 125

Val Gln Leu Val Gln Ser Gly Ala Glu Val Lys Lys Pro Gly Ala Thr
    130                 135                 140

Val Lys Ile Ser Cys Lys Val Ser Asp Tyr Thr Leu Thr Asp Phe Tyr
145                 150                 155                 160

Met Asn Trp Val Gln Gln Ala Pro Gly Lys Gly Leu Glu Trp Ile Gly
                165                 170                 175

Arg Ile Tyr Pro Gly Thr Asp Lys Thr Arg Tyr Asn Glu Lys Phe Arg
            180                 185                 190

Asp Arg Val Thr Ile Thr Ala Asp Thr Ser Thr Asp Thr Ala Tyr Met
        195                 200                 205

Glu Leu Ser Ser Leu Arg Ser Glu Asp Thr Ala Val Tyr Tyr Cys Ala
    210                 215                 220

Arg Ser Ala Tyr Tyr Gly Asn Tyr Val Ala Met Asp Tyr Trp Gly Gln
225                 230                 235                 240

Gly Thr Thr Val Thr Val Ser Ser Ser Glu Pro Lys Ser Ser Asp Lys
                245                 250                 255

Thr His Thr Cys Pro Pro Cys Pro Ala Pro Glu Ala Ala Gly Ala Pro
            260                 265                 270

Ser Val Phe Leu Phe Pro Pro Lys Pro Lys Asp Thr Leu Met Ile Ser
        275                 280                 285

Arg Thr Pro Glu Val Thr Cys Val Val Val Asp Val Ser His Glu Asp
    290                 295                 300

Pro Glu Val Lys Phe Asn Trp Tyr Val Asp Gly Val Glu Val His Asn
305                 310                 315                 320

Ala Lys Thr Lys Pro Arg Glu Glu Gln Tyr Asn Ser Thr Tyr Arg Val
                325                 330                 335

Val Ser Val Leu Thr Val Leu His Gln Asp Trp Leu Asn Gly Lys Ala
            340                 345                 350

Tyr Ala Cys Ala Val Ser Asn Lys Ala Leu Pro Ala Pro Ile Glu Lys
        355                 360                 365

Thr Ile Ser Lys Ala Lys Gly Gln Pro Arg Glu Pro Gln Val Tyr Thr
    370                 375                 380

Leu Pro Pro Ser Arg Asp Glu Leu Thr Lys Asn Gln Val Ser Leu Thr
385                 390                 395                 400

Cys Leu Val Lys Gly Phe Tyr Pro Ser Asp Ile Ala Val Glu Trp Glu
                405                 410                 415

Ser Asn Gly Gln Pro Glu Asn Asn Tyr Lys Thr Thr Pro Pro Val Leu
            420                 425                 430

Asp Ser Asp Gly Ser Phe Phe Leu Tyr Ser Lys Leu Thr Val Asp Lys
        435                 440                 445

Ser Arg Trp Gln Gln Gly Asn Val Phe Ser Cys Ser Val Met His Glu
    450                 455                 460
```

```
Ala Leu His Asn His Tyr Thr Gln Lys Ser Leu Ser Leu Ser Pro Gly
465                 470                 475                 480

Gln Arg His Asn Asn Ser Ser Leu Asn Thr Gly Thr Gln Met Ala Gly
                485                 490                 495

His Ser Pro Asn Ser Gln Val Gln Leu Val Glu Ser Gly Gly Gly Val
            500                 505                 510

Val Gln Pro Gly Arg Ser Leu Arg Leu Ser Cys Lys Ala Ser Gly Tyr
        515                 520                 525

Thr Phe Thr Arg Ser Thr Met His Trp Val Arg Gln Ala Pro Gly Gln
    530                 535                 540

Gly Leu Glu Trp Ile Gly Tyr Ile Asn Pro Ser Ser Ala Tyr Thr Asn
545                 550                 555                 560

Tyr Asn Gln Lys Phe Lys Asp Arg Phe Thr Ile Ser Ala Asp Lys Ser
                565                 570                 575

Lys Ser Thr Ala Phe Leu Gln Met Asp Ser Leu Arg Pro Glu Asp Thr
            580                 585                 590

Gly Val Tyr Phe Cys Ala Arg Pro Gln Val His Tyr Asp Tyr Asn Gly
        595                 600                 605

Phe Pro Tyr Trp Gly Gln Gly Thr Pro Val Thr Val Ser Ser Gly Gly
    610                 615                 620

Gly Gly Ser Gly Gly Gly Gly Ser Gly Gly Gly Gly Ser Ala Gln Asp
625                 630                 635                 640

Ile Gln Met Thr Gln Ser Pro Ser Ser Leu Ser Ala Ser Val Gly Asp
                645                 650                 655

Arg Val Thr Met Thr Cys Ser Ala Ser Ser Ser Val Ser Tyr Met Asn
            660                 665                 670

Trp Tyr Gln Gln Lys Pro Gly Lys Ala Pro Lys Arg Trp Ile Tyr Asp
        675                 680                 685

Ser Ser Lys Leu Ala Ser Gly Val Pro Ala Arg Phe Ser Gly Ser Gly
    690                 695                 700

Ser Gly Thr Asp Tyr Thr Leu Thr Ile Ser Ser Leu Gln Pro Glu Asp
705                 710                 715                 720

Phe Ala Thr Tyr Tyr Cys Gln Gln Trp Ser Arg Asn Pro Pro Thr Phe
                725                 730                 735

Gly Gly Gly Thr Lys Leu Gln Ile Thr Ser Ser Ser
            740                 745
```

<210> SEQ ID NO 193
<211> LENGTH: 2307
<212> TYPE: DNA
<213> ORGANISM: Artificial
<220> FEATURE:
<223> OTHER INFORMATION: TSC279 (hu4C04 (Q165R) x DRA222 null2 Scorpion)

<400> SEQUENCE: 193

```
atggaagcac cagcgcagct tctcttcctc ctgctactct ggctcccaga taccaccggt      60

gacatccaga tgacccagtc tccatcctcc ctgtctgcat ctgtaggaga cagagtcacc     120

atcacttgcc tggcaagtca gaccattggt acatggttag catggtatca gcagaaacca     180

gggaaagccc ctaagctcct gatttatgct gcaaccagct tggcagatgg ggtcccatca     240

aggttcagtg gcagtggatc tgggacagat ttcactctca ccatcagcag tctgcaacct     300

gaagattttg caacttacta ctgtcaacaa ctttacaata ctccgtggac gttcggcgga     360

gggaccaagg tggagatcaa agggggtgga ggctctggtg gcggtggctc tggcggaggt     420
```

-continued

```
ggatccggcg ggggtggctc tgaggtccag ctggtacagt ctggggctga ggtgaagaag    480

cctggggcta cagtgaaaat ctcctgcaag gtttctgact acacactcac tgacttctat    540

atgaactggg tgagacaggc ccctggaaaa gggcttgagt ggattgggag gatttatcct    600

ggaaccgata aaactagata caatgagaaa ttcagggaca gagtcaccat aaccgcggac    660

acgtctacag acacagccta catggagctg agcagcctga gatctgagga cacggccgtg    720

tattactgtg caagatccgc ctactatggt aactacgttg ctatggacta ctgggggcaa    780

gggaccacgg tcaccgtctc ctcgagtgag cccaaatctt ctgacaaaac tcacacatgc    840

ccaccgtgcc cagcacctga agccgcgggt gcaccgtcag tcttcctctt ccccccaaaa    900

cccaaggaca ccctcatgat ctcccggacc cctgaggtca catgcgtggt ggtggacgtg    960

agccacgaag accctgaggt caagttcaac tggtacgtgg acggcgtgga ggtgcataat   1020

gccaagacaa agccgcggga ggagcagtac aacagcacgt accgtgtggt cagcgtcctc   1080

accgtcctgc accaggactg gctgaatggc aaggcgtacg cgtgcgcggt ctccaacaaa   1140

gccctcccag cccccatcga gaaaaccatc tccaaagcca aagggcagcc ccgagaacca   1200

caggtgtaca ccctgccccc atcccgggat gagctgacca agaaccaggt cagcctgacc   1260

tgcctggtca aaggcttcta tccaagcgac atcgccgtgg agtgggagag caatgggcag   1320

ccggagaaca actacaagac cacgcctccc gtgctggact ccgacggctc cttcttcctc   1380

tacagcaagc tcaccgtgga caagagcagg tggcagcagg ggaacgtctt ctcatgctcc   1440

gtgatgcatg aggctctgca caaccactac acgcagaaga gcctctccct gtctccgggt   1500

cagaggcaca acaattcttc cctgaataca ggaactcaga tggcaggtca ttctccgaat   1560

tctcaggtcc agctggtgga gtctggggc ggagtggtgc agcctgggcg gtcactgagg    1620

ctgtcctgca aggcttctgg ctacaccttt actagatcta cgatgcactg ggtaaggcag   1680

gcccctggac aaggtctgga atggattgga tacattaatc ctagcagtgc ttatactaat   1740

tacaatcaga aattcaagga caggttcaca atcagcgcag acaaatccaa gagcacagcc   1800

ttcctgcaga tggacagcct gaggcccgag gacaccggcg tctatttctg tgcacggccc   1860

caagtccact atgattacaa cgggtttcct tactggggcc aagggactcc cgtcactgtc   1920

tctagcggtg gcggagggtc tgggggtggc ggatccggag gtggtggctc tgcacaagac   1980

atccagatga cccagtctcc aagcagcctg tctgcaagcg tgggggacag ggtcaccatg   2040

acctgcagtg ccagctcaag tgtaagttac atgaactggt accagcagaa gccgggcaag   2100

gcccccaaaa gatggattta tgactcatcc aaactggctt ctggagtccc tgctcgcttc   2160

agtggcagtg ggtctgggac cgactatacc ctcacaatca gcagcctgca gcccgaagat   2220

ttcgccactt attactgcca gcagtggagt cgtaacccac ccacgttcgg aggggggacc   2280

aagctacaaa ttacatcctc cagctaa                                       2307
```

<210> SEQ ID NO 194
<211> LENGTH: 748
<212> TYPE: PRT
<213> ORGANISM: Artificial
<220> FEATURE:
<223> OTHER INFORMATION: TSC279 (hu4C04 (Q165R) x DRA222 null2 Scorpion)

<400> SEQUENCE: 194

```
Asp Ile Gln Met Thr Gln Ser Pro Ser Ser Leu Ser Ala Ser Val Gly
1               5                   10                  15

Asp Arg Val Thr Ile Thr Cys Leu Ala Ser Gln Thr Ile Gly Thr Trp
            20                  25                  30
```

-continued

```
Leu Ala Trp Tyr Gln Gln Lys Pro Gly Lys Ala Pro Lys Leu Leu Ile
        35                  40                  45

Tyr Ala Ala Thr Ser Leu Ala Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Leu Tyr Asn Thr Pro Trp
                85                  90                  95

Thr Phe Gly Gly Gly Thr Lys Val Glu Ile Lys Gly Gly Gly Gly Ser
            100                 105                 110

Gly Gly Gly Gly Ser Gly Gly Gly Gly Ser Gly Gly Gly Gly Ser Glu
        115                 120                 125

Val Gln Leu Val Gln Ser Gly Ala Glu Val Lys Lys Pro Gly Ala Thr
    130                 135                 140

Val Lys Ile Ser Cys Lys Val Ser Asp Tyr Thr Leu Thr Asp Phe Tyr
145                 150                 155                 160

Met Asn Trp Val Arg Gln Ala Pro Gly Lys Gly Leu Glu Trp Ile Gly
                165                 170                 175

Arg Ile Tyr Pro Gly Thr Asp Lys Thr Arg Tyr Asn Glu Lys Phe Arg
            180                 185                 190

Asp Arg Val Thr Ile Thr Ala Asp Thr Ser Thr Asp Thr Ala Tyr Met
        195                 200                 205

Glu Leu Ser Ser Leu Arg Ser Glu Asp Thr Ala Val Tyr Tyr Cys Ala
    210                 215                 220

Arg Ser Ala Tyr Tyr Gly Asn Tyr Val Ala Met Asp Tyr Trp Gly Gln
225                 230                 235                 240

Gly Thr Thr Val Thr Val Ser Ser Ser Glu Pro Lys Ser Ser Asp Lys
                245                 250                 255

Thr His Thr Cys Pro Pro Cys Pro Ala Pro Glu Ala Ala Gly Ala Pro
            260                 265                 270

Ser Val Phe Leu Phe Pro Pro Lys Pro Lys Asp Thr Leu Met Ile Ser
        275                 280                 285

Arg Thr Pro Glu Val Thr Cys Val Val Val Asp Val Ser His Glu Asp
    290                 295                 300

Pro Glu Val Lys Phe Asn Trp Tyr Val Asp Gly Val Glu Val His Asn
305                 310                 315                 320

Ala Lys Thr Lys Pro Arg Glu Glu Gln Tyr Asn Ser Thr Tyr Arg Val
                325                 330                 335

Val Ser Val Leu Thr Val Leu His Gln Asp Trp Leu Asn Gly Lys Ala
            340                 345                 350

Tyr Ala Cys Ala Val Ser Asn Lys Ala Leu Pro Ala Pro Ile Glu Lys
        355                 360                 365

Thr Ile Ser Lys Ala Lys Gly Gln Pro Arg Glu Pro Gln Val Tyr Thr
    370                 375                 380

Leu Pro Pro Ser Arg Asp Glu Leu Thr Lys Asn Gln Val Ser Leu Thr
385                 390                 395                 400

Cys Leu Val Lys Gly Phe Tyr Pro Ser Asp Ile Ala Val Glu Trp Glu
                405                 410                 415

Ser Asn Gly Gln Pro Glu Asn Asn Tyr Lys Thr Thr Pro Pro Val Leu
            420                 425                 430

Asp Ser Asp Gly Ser Phe Phe Leu Tyr Ser Lys Leu Thr Val Asp Lys
        435                 440                 445
```

```
Ser Arg Trp Gln Gln Gly Asn Val Phe Ser Cys Ser Val Met His Glu
    450                 455                 460

Ala Leu His Asn His Tyr Thr Gln Lys Ser Leu Ser Leu Ser Pro Gly
465                 470                 475                 480

Gln Arg His Asn Asn Ser Ser Leu Asn Thr Gly Thr Gln Met Ala Gly
                485                 490                 495

His Ser Pro Asn Ser Gln Val Gln Leu Val Glu Ser Gly Gly Gly Val
            500                 505                 510

Val Gln Pro Gly Arg Ser Leu Arg Leu Ser Cys Lys Ala Ser Gly Tyr
        515                 520                 525

Thr Phe Thr Arg Ser Thr Met His Trp Val Arg Gln Ala Pro Gly Gln
    530                 535                 540

Gly Leu Glu Trp Ile Gly Tyr Ile Asn Pro Ser Ser Ala Tyr Thr Asn
545                 550                 555                 560

Tyr Asn Gln Lys Phe Lys Asp Arg Phe Thr Ile Ser Ala Asp Lys Ser
                565                 570                 575

Lys Ser Thr Ala Phe Leu Gln Met Asp Ser Leu Arg Pro Glu Asp Thr
            580                 585                 590

Gly Val Tyr Phe Cys Ala Arg Pro Gln Val His Tyr Asp Tyr Asn Gly
        595                 600                 605

Phe Pro Tyr Trp Gly Gln Gly Thr Pro Val Thr Val Ser Ser Gly Gly
    610                 615                 620

Gly Gly Ser Gly Gly Gly Gly Ser Gly Gly Gly Gly Ser Ala Gln Asp
625                 630                 635                 640

Ile Gln Met Thr Gln Ser Pro Ser Ser Leu Ser Ala Ser Val Gly Asp
                645                 650                 655

Arg Val Thr Met Thr Cys Ser Ala Ser Ser Ser Val Ser Tyr Met Asn
            660                 665                 670

Trp Tyr Gln Gln Lys Pro Gly Lys Ala Pro Lys Arg Trp Ile Tyr Asp
        675                 680                 685

Ser Ser Lys Leu Ala Ser Gly Val Pro Ala Arg Phe Ser Gly Ser Gly
    690                 695                 700

Ser Gly Thr Asp Tyr Thr Leu Thr Ile Ser Ser Leu Gln Pro Glu Asp
705                 710                 715                 720

Phe Ala Thr Tyr Tyr Cys Gln Gln Trp Ser Arg Asn Pro Pro Thr Phe
                725                 730                 735

Gly Gly Gly Thr Lys Leu Gln Ile Thr Ser Ser Ser
            740                 745
```

<210> SEQ ID NO 195
<211> LENGTH: 2316
<212> TYPE: DNA
<213> ORGANISM: Artificial
<220> FEATURE:
<223> OTHER INFORMATION: TSC233 (HD37 x DRA221 scorpion, H75 linker)

<400> SEQUENCE: 195

```
atggaagcac cagcgcagct tctcttcctc ctgctactct ggctcccaga taccaccggt     60

gacattgtgc tgacccaatc tccagcttct ttggctgtgt ctctagggca gagggccacc    120

atctcctgca aggccagcca aagtgttgat tatgatggtg atagttattt gaactggtac    180

caacagattc caggacagcc acccaaactc ctcatctatg atgcatccaa tctagtttct    240

gggatcccac ccaggtttag tggcagtggg tctgggacag acttcaccct caacatccat    300

cctgtggaga aggtggatgc tgcaacctat cactgccagc aaagtactga ggatccgtgg    360
```

```
acgttcggtg gaggcaccaa gctggaaatc aaaggtggcg gtggttcggg cggtggtggg    420

tcgggtggcg gcggagctag ccaggttcag ctgcagcagt ctggggctga gctggtgagg    480

cctgggtcct cagtgaagat ttcctgcaag gcttctggct atgcattcag tagctactgg    540

atgaactggg tgaagcagag gcctggacag ggtcttgagt ggattggaca gatttggcct    600

ggagatggtg atactaacta caatggaaag ttcaagggta aagccactct gactgcagac    660

gaatcctcca gcacagccta catgcaactc agcagcctag catctgagga ctctgcggtc    720

tatttctgtg caagacggga gactacgacg gtaggccgtt attactatgc tatggactac    780

tggggtcaag gaacctcagt caccgtctcc tcgagtgagc ccaaatcttc tgacaaaact    840

cacacatgcc caccgtgccc agcacctgaa gccgcgggtg caccgtcagt cttcctcttc    900

cccccaaaac ccaaggacac cctcatgatc tcccggaccc ctgaggtcac atgcgtggtg    960

gtggacgtga gccacgaaga ccctgaggtc aagttcaact ggtacgtgga cggcgtggag   1020

gtgcataatg ccaagacaaa gccgcgggag gagcagtaca acagcacgta ccgtgtggtc   1080

agcgtcctca ccgtcctgca ccaggactgg ctgaatggca aggcgtacgc gtgcgcggtc   1140

tccaacaaag ccctcccagc ccccatcgag aaaaccatct ccaaagccaa agggcagccc   1200

cgagaaccac aggtgtacac cctgccccca tcccgggatg agctgaccaa gaaccaggtc   1260

agcctgacct gcctggtcaa aggcttctat ccaagcgaca tcgccgtgga gtgggagagc   1320

aatgggcagc cggagaacaa ctacaagacc acgcctcccg tgctggactc cgacggctcc   1380

ttcttcctct acagcaagct caccgtggac aagagcaggt ggcagcaggg gaacgtcttc   1440

tcatgctccg tgatgcatga ggctctgcac aaccactaca cgcagaagag cctctccctg   1500

tctccgggtc agaggcacaa caattcttcc ctgaatacag gaactcagat ggcaggtcat   1560

tctccgaatt ctcaggtcca gctggtggag tctgggggcg gagtggtgca gcctgggcgg   1620

tcactgaggc tgtcctgcaa ggcttctggc tacaccttta ctagatctac gatgcactgg   1680

gtaaggcagg cccctggaca aggtctggaa tggattggat acattaatcc tagcagtgct   1740

tatactaatt acaatcagaa attcaaggac aggttcacaa tcagcgcaga caaatccaag   1800

agcacagcct tcctgcagat ggacagcctg aggcccgagg acaccggcgt ctatttctgt   1860

gcacggcccc aagtccacta tgattacaac gggtttcctt actggggcca agggactccc   1920

gtcactgtct ctagcggtgg cggagggtct gggggtggcg gatccggagg tggtggctct   1980

gcacaagaca tccagatgac ccagtctcca agcagcctgt ctgcaagcgt gggggacagg   2040

gtcaccatga cctgcagtgc cagctcaagt gtaagttaca tgaactggta ccagcagaag   2100

ccgggcaagg cccccaaact cctcatttat gactcatcca aactggcttc tggagtccct   2160

gctcgcttca gtggcagtgg gtctgggacc gactataccc tcacaatcag cagcctgcag   2220

cccgaagatt tcgccactta ttactgccag cagtggagtc gtaacccacc cactttcggc   2280

ggagggacca aggtggagat caaatcctcc agctaa                             2316
```

<210> SEQ ID NO 196
<211> LENGTH: 751
<212> TYPE: PRT
<213> ORGANISM: Artificial
<220> FEATURE:
<223> OTHER INFORMATION: TSC233 (HD37 x DRA221 scorpion, H75 linker)

<400> SEQUENCE: 196

```
Asp Ile Val Leu Thr Gln Ser Pro Ala Ser Leu Ala Val Ser Leu Gly
1               5                   10                  15
```

-continued

```
Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
    50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys Gly
            100                 105                 110

Gly Gly Gly Ser Gly Gly Gly Gly Ser Gly Gly Gly Gly Ala Ser Gln
        115                 120                 125

Val Gln Leu Gln Gln Ser Gly Ala Glu Leu Val Arg Pro Gly Ser Ser
    130                 135                 140

Val Lys Ile Ser Cys Lys Ala Ser Gly Tyr Ala Phe Ser Ser Tyr Trp
145                 150                 155                 160

Met Asn Trp Val Lys Gln Arg Pro Gly Gln Gly Leu Glu Trp Ile Gly
                165                 170                 175

Gln Ile Trp Pro Gly Asp Gly Asp Thr Asn Tyr Asn Gly Lys Phe Lys
            180                 185                 190

Gly Lys Ala Thr Leu Thr Ala Asp Glu Ser Ser Ser Thr Ala Tyr Met
        195                 200                 205

Gln Leu Ser Ser Leu Ala Ser Glu Asp Ser Ala Val Tyr Phe Cys Ala
    210                 215                 220

Arg Arg Glu Thr Thr Thr Val Gly Arg Tyr Tyr Tyr Ala Met Asp Tyr
225                 230                 235                 240

Trp Gly Gln Gly Thr Ser Val Thr Val Ser Ser Ser Glu Pro Lys Ser
                245                 250                 255

Ser Asp Lys Thr His Thr Cys Pro Pro Cys Pro Ala Pro Glu Ala Ala
            260                 265                 270

Gly Ala Pro Ser Val Phe Leu Phe Pro Pro Lys Pro Lys Asp Thr Leu
        275                 280                 285

Met Ile Ser Arg Thr Pro Glu Val Thr Cys Val Val Val Asp Val Ser
    290                 295                 300

His Glu Asp Pro Glu Val Lys Phe Asn Trp Tyr Val Asp Gly Val Glu
305                 310                 315                 320

Val His Asn Ala Lys Thr Lys Pro Arg Glu Glu Gln Tyr Asn Ser Thr
                325                 330                 335

Tyr Arg Val Val Ser Val Leu Thr Val Leu His Gln Asp Trp Leu Asn
            340                 345                 350

Gly Lys Ala Tyr Ala Cys Ala Val Ser Asn Lys Ala Leu Pro Ala Pro
        355                 360                 365

Ile Glu Lys Thr Ile Ser Lys Ala Lys Gly Gln Pro Arg Glu Pro Gln
    370                 375                 380

Val Tyr Thr Leu Pro Pro Ser Arg Asp Glu Leu Thr Lys Asn Gln Val
385                 390                 395                 400

Ser Leu Thr Cys Leu Val Lys Gly Phe Tyr Pro Ser Asp Ile Ala Val
                405                 410                 415

Glu Trp Glu Ser Asn Gly Gln Pro Glu Asn Asn Tyr Lys Thr Thr Pro
            420                 425                 430

Pro Val Leu Asp Ser Asp Gly Ser Phe Phe Leu Tyr Ser Lys Leu Thr
```

```
        435                 440                 445

Val Asp Lys Ser Arg Trp Gln Gln Gly Asn Val Phe Ser Cys Ser Val
    450                 455                 460

Met His Glu Ala Leu His Asn His Tyr Thr Gln Lys Ser Leu Ser Leu
465                 470                 475                 480

Ser Pro Gly Gln Arg His Asn Asn Ser Ser Leu Asn Thr Gly Thr Gln
                485                 490                 495

Met Ala Gly His Ser Pro Asn Ser Gln Val Gln Leu Val Glu Ser Gly
            500                 505                 510

Gly Gly Val Val Gln Pro Gly Arg Ser Leu Arg Leu Ser Cys Lys Ala
        515                 520                 525

Ser Gly Tyr Thr Phe Thr Arg Ser Thr Met His Trp Val Arg Gln Ala
    530                 535                 540

Pro Gly Gln Gly Leu Glu Trp Ile Gly Tyr Ile Asn Pro Ser Ser Ala
545                 550                 555                 560

Tyr Thr Asn Tyr Asn Gln Lys Phe Lys Asp Arg Phe Thr Ile Ser Ala
                565                 570                 575

Asp Lys Ser Lys Ser Thr Ala Phe Leu Gln Met Asp Ser Leu Arg Pro
            580                 585                 590

Glu Asp Thr Gly Val Tyr Phe Cys Ala Arg Pro Gln Val His Tyr Asp
        595                 600                 605

Tyr Asn Gly Phe Pro Tyr Trp Gly Gln Gly Thr Pro Val Thr Val Ser
    610                 615                 620

Ser Gly Gly Gly Gly Ser Gly Gly Gly Gly Ser Gly Gly Gly Gly Ser
625                 630                 635                 640

Ala Gln Asp Ile Gln Met Thr Gln Ser Pro Ser Ser Leu Ser Ala Ser
                645                 650                 655

Val Gly Asp Arg Val Thr Met Thr Cys Ser Ala Ser Ser Ser Val Ser
            660                 665                 670

Tyr Met Asn Trp Tyr Gln Gln Lys Pro Gly Lys Ala Pro Lys Leu Leu
        675                 680                 685

Ile Tyr Asp Ser Ser Lys Leu Ala Ser Gly Val Pro Ala Arg Phe Ser
    690                 695                 700

Gly Ser Gly Ser Gly Thr Asp Tyr Thr Leu Thr Ile Ser Ser Leu Gln
705                 710                 715                 720

Pro Glu Asp Phe Ala Thr Tyr Tyr Cys Gln Gln Trp Ser Arg Asn Pro
                725                 730                 735

Pro Thr Phe Gly Gly Gly Thr Lys Val Glu Ile Lys Ser Ser Ser
            740                 745                 750
```

<210> SEQ ID NO 197
<211> LENGTH: 2316
<212> TYPE: DNA
<213> ORGANISM: Artificial
<220> FEATURE:
<223> OTHER INFORMATION: TSC234 (HD37 x DRA222 scorpion, H75 linker)

<400> SEQUENCE: 197

```
atggaagcac cagcgcagct tctcttcctc ctgctactct ggctcccaga taccaccggt      60

gacattgtgc tgacccaatc tccagcttct ttggctgtgt ctctagggca gagggccacc     120

atctcctgca aggccagcca aagtgttgat tatgatggtg atagttattt gaactggtac     180

caacagattc caggacagcc acccaaactc ctcatctatg atgcatccaa tctagtttct     240

gggatcccac ccaggtttag tggcagtggg tctgggacag acttcaccct caacatccat     300
```

```
cctgtggaga aggtggatgc tgcaacctat cactgccagc aaagtactga ggatccgtgg    360
acgttcggtg gaggcaccaa gctggaaatc aaaggtggcg gtggttcggg cggtggtggg    420
tcgggtggcg gcggagctag ccaggttcag ctgcagcagt ctggggctga gctggtgagg    480
cctgggtcct cagtgaagat ttcctgcaag gcttctggct atgcattcag tagctactgg    540
atgaactggg tgaagcagag gcctggacag ggtcttgagt ggattggaca gatttggcct    600
ggagatggtg atactaacta caatggaaag ttcaagggta aagccactct gactgcagac    660
gaatcctcca gcacagccta catgcaactc agcagcctag catctgagga ctctgcggtc    720
tatttctgtg caagacggga gactacgacg gtaggccgtt attactatgc tatggactac    780
tggggtcaag gaacctcagt caccgtctcc tcgagtgagc ccaaatcttc tgacaaaact    840
cacacatgcc caccgtgccc agcacctgaa gccgcgggtg caccgtcagt cttcctcttc    900
cccccaaaac ccaaggacac cctcatgatc tcccggaccc ctgaggtcac atgcgtggtg    960
gtggacgtga gccacgaaga ccctgaggtc aagttcaact ggtacgtgga cggcgtggag   1020
gtgcataatg ccaagacaaa gccgcgggag gagcagtaca acagcacgta ccgtgtggtc   1080
agcgtcctca ccgtcctgca ccaggactgg ctgaatggca aggcgtacgc gtgcgcggtc   1140
tccaacaaag ccctcccagc ccccatcgag aaaaccatct ccaaagccaa agggcagccc   1200
cgagaaccac aggtgtacac cctgccccca tcccgggatg agctgaccaa gaaccaggtc   1260
agcctgacct gcctggtcaa aggcttctat ccaagcgaca tcgccgtgga gtgggagagc   1320
aatgggcagc cggagaacaa ctacaagacc acgcctcccg tgctggactc cgacggctcc   1380
ttcttcctct acagcaagct caccgtggac aagagcaggt ggcagcaggg gaacgtcttc   1440
tcatgctccg tgatgcatga ggctctgcac aaccactaca cgcagaagag cctctccctg   1500
tctccgggtc agaggcacaa caattcttcc ctgaatacag gaactcagat ggcaggtcat   1560
tctccgaatt ctcaggtcca gctggtggag tctgggggcg gagtggtgca gcctgggcgg   1620
tcactgaggc tgtcctgcaa ggcttctggc tacaccttta ctagatctac gatgcactgg   1680
gtaaggcagg cccctggaca aggtctggaa tggattggat acattaatcc tagcagtgct   1740
tatactaatt acaatcagaa attcaaggac aggttcacaa tcagcgcaga caaatccaag   1800
agcacagcct tcctgcagat ggacagcctg aggcccgagg acaccggcgt ctatttctgt   1860
gcacggcccc aagtccacta tgattacaac gggtttcctt actggggcca agggactccc   1920
gtcactgtct ctagcggtgg cggagggtct gggggtggcg gatccggagg tggtggctct   1980
gcacaagaca tccagatgac ccagtctcca agcagcctgt ctgcaagcgt gggggacagg   2040
gtcaccatga cctgcagtgc cagctcaagt gtaagttaca tgaactggta ccagcagaag   2100
ccgggcaagg cccccaaaag atggatttat gactcatcca aactggcttc tggagtccct   2160
gctcgcttca gtggcagtgg gtctgggacc gactataccc tcacaatcag cagcctgcag   2220
cccgaagatt tcgccactta ttactgccag cagtggagtc gtaacccacc cacgttcgga   2280
ggggggacca agctacaaat tacatcctcc agctaa                            2316
```

<210> SEQ ID NO 198
<211> LENGTH: 751
<212> TYPE: PRT
<213> ORGANISM: Artificial
<220> FEATURE:
<223> OTHER INFORMATION: TSC234 (HD37 x DRA222 scorpion, H75 linker)

<400> SEQUENCE: 198

Asp Ile Val Leu Thr Gln Ser Pro Ala Ser Leu Ala Val Ser Leu Gly

-continued

```
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
    50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys Gly
            100                 105                 110

Gly Gly Gly Ser Gly Gly Gly Gly Ser Gly Gly Gly Gly Ala Ser Gln
        115                 120                 125

Val Gln Leu Gln Gln Ser Gly Ala Glu Leu Val Arg Pro Gly Ser Ser
    130                 135                 140

Val Lys Ile Ser Cys Lys Ala Ser Gly Tyr Ala Phe Ser Ser Tyr Trp
145                 150                 155                 160

Met Asn Trp Val Lys Gln Arg Pro Gly Gln Gly Leu Glu Trp Ile Gly
                165                 170                 175

Gln Ile Trp Pro Gly Asp Gly Asp Thr Asn Tyr Asn Gly Lys Phe Lys
            180                 185                 190

Gly Lys Ala Thr Leu Thr Ala Asp Glu Ser Ser Ser Thr Ala Tyr Met
        195                 200                 205

Gln Leu Ser Ser Leu Ala Ser Glu Asp Ser Ala Val Tyr Phe Cys Ala
    210                 215                 220

Arg Arg Glu Thr Thr Thr Val Gly Arg Tyr Tyr Tyr Ala Met Asp Tyr
225                 230                 235                 240

Trp Gly Gln Gly Thr Ser Val Thr Val Ser Ser Ser Glu Pro Lys Ser
                245                 250                 255

Ser Asp Lys Thr His Thr Cys Pro Pro Cys Pro Ala Pro Glu Ala Ala
            260                 265                 270

Gly Ala Pro Ser Val Phe Leu Phe Pro Pro Lys Pro Lys Asp Thr Leu
        275                 280                 285

Met Ile Ser Arg Thr Pro Glu Val Thr Cys Val Val Val Asp Val Ser
    290                 295                 300

His Glu Asp Pro Glu Val Lys Phe Asn Trp Tyr Val Asp Gly Val Glu
305                 310                 315                 320

Val His Asn Ala Lys Thr Lys Pro Arg Glu Glu Gln Tyr Asn Ser Thr
                325                 330                 335

Tyr Arg Val Val Ser Val Leu Thr Val Leu His Gln Asp Trp Leu Asn
            340                 345                 350

Gly Lys Ala Tyr Ala Cys Ala Val Ser Asn Lys Ala Leu Pro Ala Pro
        355                 360                 365

Ile Glu Lys Thr Ile Ser Lys Ala Lys Gly Gln Pro Arg Glu Pro Gln
    370                 375                 380

Val Tyr Thr Leu Pro Pro Ser Arg Asp Glu Leu Thr Lys Asn Gln Val
385                 390                 395                 400

Ser Leu Thr Cys Leu Val Lys Gly Phe Tyr Pro Ser Asp Ile Ala Val
                405                 410                 415

Glu Trp Glu Ser Asn Gly Gln Pro Glu Asn Asn Tyr Lys Thr Thr Pro
            420                 425                 430
```

-continued

```
Pro Val Leu Asp Ser Asp Gly Ser Phe Phe Leu Tyr Ser Lys Leu Thr
        435                 440                 445

Val Asp Lys Ser Arg Trp Gln Gln Gly Asn Val Phe Ser Cys Ser Val
    450                 455                 460

Met His Glu Ala Leu His Asn His Tyr Thr Gln Lys Ser Leu Ser Leu
465                 470                 475                 480

Ser Pro Gly Gln Arg His Asn Asn Ser Ser Leu Asn Thr Gly Thr Gln
                485                 490                 495

Met Ala Gly His Ser Pro Asn Ser Gln Val Gln Leu Val Glu Ser Gly
            500                 505                 510

Gly Gly Val Val Gln Pro Gly Arg Ser Leu Arg Leu Ser Cys Lys Ala
        515                 520                 525

Ser Gly Tyr Thr Phe Thr Arg Ser Thr Met His Trp Val Arg Gln Ala
    530                 535                 540

Pro Gly Gln Gly Leu Glu Trp Ile Gly Tyr Ile Asn Pro Ser Ser Ala
545                 550                 555                 560

Tyr Thr Asn Tyr Asn Gln Lys Phe Lys Asp Arg Phe Thr Ile Ser Ala
                565                 570                 575

Asp Lys Ser Lys Ser Thr Ala Phe Leu Gln Met Asp Ser Leu Arg Pro
            580                 585                 590

Glu Asp Thr Gly Val Tyr Phe Cys Ala Arg Pro Gln Val His Tyr Asp
        595                 600                 605

Tyr Asn Gly Phe Pro Tyr Trp Gly Gln Gly Thr Pro Val Thr Val Ser
    610                 615                 620

Ser Gly Gly Gly Gly Ser Gly Gly Gly Gly Ser Gly Gly Gly Gly Ser
625                 630                 635                 640

Ala Gln Asp Ile Gln Met Thr Gln Ser Pro Ser Ser Leu Ser Ala Ser
                645                 650                 655

Val Gly Asp Arg Val Thr Met Thr Cys Ser Ala Ser Ser Ser Val Ser
            660                 665                 670

Tyr Met Asn Trp Tyr Gln Gln Lys Pro Gly Lys Ala Pro Lys Arg Trp
        675                 680                 685

Ile Tyr Asp Ser Ser Lys Leu Ala Ser Gly Val Pro Ala Arg Phe Ser
    690                 695                 700

Gly Ser Gly Ser Gly Thr Asp Tyr Thr Leu Thr Ile Ser Ser Leu Gln
705                 710                 715                 720

Pro Glu Asp Phe Ala Thr Tyr Tyr Cys Gln Gln Trp Ser Arg Asn Pro
                725                 730                 735

Pro Thr Phe Gly Gly Gly Thr Lys Leu Gln Ile Thr Ser Ser Ser
            740                 745                 750
```

<210> SEQ ID NO 199
<211> LENGTH: 2325
<212> TYPE: DNA
<213> ORGANISM: Artificial
<220> FEATURE:
<223> OTHER INFORMATION: TSC235 (HD37 x DRA224 scorpion, H75 linker)

<400> SEQUENCE: 199

```
atggaagcac cagcgcagct tctcttcctc ctgctactct ggctcccaga taccaccggt      60

gacattgtgc tgacccaatc tccagcttct ttggctgtgt ctctagggca gagggccacc     120

atctcctgca aggccagcca aagtgttgat tatgatggtg atagttattt gaactggtac     180

caacagattc caggacagcc acccaaactc ctcatctatg atgcatccaa tctagtttct     240
```

```
gggatcccac ccaggtttag tggcagtggg tctgggacag acttcaccct caacatccat    300
cctgtggaga aggtggatgc tgcaacctat cactgccagc aaagtactga ggatccgtgg    360
acgttcggtg gaggcaccaa gctggaaatc aaaggtggcg gtggttcggg cggtggtggg    420
tcgggtggcg gcggagctag ccaggttcag ctgcagcagt ctggggctga gctggtgagg    480
cctgggtcct cagtgaagat ttcctgcaag gcttctggct atgcattcag tagctactgg    540
atgaactggg tgaagcagag gcctggacag ggtcttgagt ggattggaca gatttggcct    600
ggagatggtg atactaacta caatggaaag ttcaagggta aagccactct gactgcagac    660
gaatcctcca gcacagccta catgcaactc agcagcctag catctgagga ctctgcggtc    720
tatttctgtg caagacggga gactacgacg gtaggccgtt attactatgc tatggactac    780
tggggtcaag gaacctcagt caccgtctcc tcgagtgagc ccaaatcttc tgacaaaact    840
cacacatgcc caccgtgccc agcacctgaa gccgcgggtg caccgtcagt cttcctcttc    900
cccccaaaac ccaaggacac cctcatgatc tcccggaccc ctgaggtcac atgcgtggtg    960
gtggacgtga gccacgaaga ccctgaggtc aagttcaact ggtacgtgga cggcgtggag   1020
gtgcataatg ccaagacaaa gccgcgggag gagcagtaca acagcacgta ccgtgtggtc   1080
agcgtcctca ccgtcctgca ccaggactgg ctgaatggca aggcgtacgc gtgcgcggtc   1140
tccaacaaag ccctcccagc ccccatcgag aaaaccatct ccaaagccaa agggcagccc   1200
cgagaaccac aggtgtacac cctgccccca tcccgggatg agctgaccaa gaaccaggtc   1260
agcctgacct gcctggtcaa aggcttctat ccaagcgaca tcgccgtgga gtgggagagc   1320
aatgggcagc cggagaacaa ctacaagacc acgcctcccg tgctggactc cgacggctcc   1380
ttcttcctct acagcaagct caccgtggac aagagcaggt ggcagcaggg gaacgtcttc   1440
tcatgctccg tgatgcatga ggctctgcac aaccactaca cgcagaagag cctctccctg   1500
tctccgggtc agaggcacaa caattcttcc ctgaatacag gaactcagat ggcaggtcat   1560
tctccgaatt ctcaggtcca gcttgtgcag tctggggctg aggtgaagaa gcctggggcc   1620
tcagtgaagg tttcctgcaa ggcttctgga tacaccttca ctagatctac gatgcactgg   1680
gtgcgccagg cccccggaca aaggcttgag tggatgggat acattaatcc tagcagtgct   1740
tatactaatt acaatcagaa attcaaggac agagtcacca ttaccaggga cacatccgcg   1800
agcacagcct acatggagct gagcagcctg agatctgaag acacggctgt gtattactgt   1860
gcgagacccc aagtccacta tgattacaac gggtttcctt actggggcca aggaaccctg   1920
gtcaccgtct cctcaggtgg aggcggttca ggcggaggtg gatccggcgg tggcggatcg   1980
ggtggcggcg gatctgaaat tgtgttgaca cagtctccag ccaccctgtc tttgtctcca   2040
ggggaaagag ccaccctctc ctgcagtgcc agctcaagtg taagttacat gaactggtac   2100
caacagaaac ctggccaggc tcccaggctc ctcatctatg actcatccaa actggcttct   2160
ggcatcccag ccaggttcag tggcagtggg tctgggacag acttcactct caccatcagc   2220
agcctagagc ctgaagattt tgcagtttat tactgtcagc agtggagtcg taacccaccc   2280
actttcggcg gagggaccaa ggtggagatc aaatcctcca gctaa                   2325
```

<210> SEQ ID NO 200
<211> LENGTH: 754
<212> TYPE: PRT
<213> ORGANISM: Artificial
<220> FEATURE:
<223> OTHER INFORMATION: TSC235 (HD37 x DRA224 scorpion, H75 linker)

<400> SEQUENCE: 200

```
Asp Ile Val Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
    50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys Gly
            100                 105                 110

Gly Gly Gly Ser Gly Gly Gly Gly Ser Gly Gly Gly Gly Ala Ser Gln
        115                 120                 125

Val Gln Leu Gln Gln Ser Gly Ala Glu Leu Val Arg Pro Gly Ser Ser
    130                 135                 140

Val Lys Ile Ser Cys Lys Ala Ser Gly Tyr Ala Phe Ser Ser Tyr Trp
145                 150                 155                 160

Met Asn Trp Val Lys Gln Arg Pro Gly Gln Gly Leu Glu Trp Ile Gly
                165                 170                 175

Gln Ile Trp Pro Gly Asp Gly Asp Thr Asn Tyr Asn Gly Lys Phe Lys
            180                 185                 190

Gly Lys Ala Thr Leu Thr Ala Asp Glu Ser Ser Ser Thr Ala Tyr Met
        195                 200                 205

Gln Leu Ser Ser Leu Ala Ser Glu Asp Ser Ala Val Tyr Phe Cys Ala
    210                 215                 220

Arg Arg Glu Thr Thr Thr Val Gly Arg Tyr Tyr Tyr Ala Met Asp Tyr
225                 230                 235                 240

Trp Gly Gln Gly Thr Ser Val Thr Val Ser Ser Ser Glu Pro Lys Ser
                245                 250                 255

Ser Asp Lys Thr His Thr Cys Pro Pro Cys Pro Ala Pro Glu Ala Ala
            260                 265                 270

Gly Ala Pro Ser Val Phe Leu Phe Pro Pro Lys Pro Lys Asp Thr Leu
        275                 280                 285

Met Ile Ser Arg Thr Pro Glu Val Thr Cys Val Val Val Asp Val Ser
    290                 295                 300

His Glu Asp Pro Glu Val Lys Phe Asn Trp Tyr Val Asp Gly Val Glu
305                 310                 315                 320

Val His Asn Ala Lys Thr Lys Pro Arg Glu Glu Gln Tyr Asn Ser Thr
                325                 330                 335

Tyr Arg Val Val Ser Val Leu Thr Val Leu His Gln Asp Trp Leu Asn
            340                 345                 350

Gly Lys Ala Tyr Ala Cys Ala Val Ser Asn Lys Ala Leu Pro Ala Pro
        355                 360                 365

Ile Glu Lys Thr Ile Ser Lys Ala Lys Gly Gln Pro Arg Glu Pro Gln
    370                 375                 380

Val Tyr Thr Leu Pro Pro Ser Arg Asp Glu Leu Thr Lys Asn Gln Val
385                 390                 395                 400

Ser Leu Thr Cys Leu Val Lys Gly Phe Tyr Pro Ser Asp Ile Ala Val
                405                 410                 415
```

```
Glu Trp Glu Ser Asn Gly Gln Pro Glu Asn Asn Tyr Lys Thr Thr Pro
            420                 425                 430

Pro Val Leu Asp Ser Asp Gly Ser Phe Phe Leu Tyr Ser Lys Leu Thr
        435                 440                 445

Val Asp Lys Ser Arg Trp Gln Gln Gly Asn Val Phe Ser Cys Ser Val
    450                 455                 460

Met His Glu Ala Leu His Asn His Tyr Thr Gln Lys Ser Leu Ser Leu
465                 470                 475                 480

Ser Pro Gly Gln Arg His Asn Asn Ser Ser Leu Asn Thr Gly Thr Gln
                485                 490                 495

Met Ala Gly His Ser Pro Asn Ser Gln Val Gln Leu Val Gln Ser Gly
            500                 505                 510

Ala Glu Val Lys Lys Pro Gly Ala Ser Val Lys Val Ser Cys Lys Ala
        515                 520                 525

Ser Gly Tyr Thr Phe Thr Arg Ser Thr Met His Trp Val Arg Gln Ala
    530                 535                 540

Pro Gly Gln Arg Leu Glu Trp Met Gly Tyr Ile Asn Pro Ser Ser Ala
545                 550                 555                 560

Tyr Thr Asn Tyr Asn Gln Lys Phe Lys Asp Arg Val Thr Ile Thr Arg
                565                 570                 575

Asp Thr Ser Ala Ser Thr Ala Tyr Met Glu Leu Ser Ser Leu Arg Ser
            580                 585                 590

Glu Asp Thr Ala Val Tyr Tyr Cys Ala Arg Pro Gln Val His Tyr Asp
        595                 600                 605

Tyr Asn Gly Phe Pro Tyr Trp Gly Gln Gly Thr Leu Val Thr Val Ser
    610                 615                 620

Ser Gly Gly Gly Gly Ser Gly Gly Gly Gly Ser Gly Gly Gly Gly Ser
625                 630                 635                 640

Gly Gly Gly Gly Ser Glu Ile Val Leu Thr Gln Ser Pro Ala Thr Leu
                645                 650                 655

Ser Leu Ser Pro Gly Glu Arg Ala Thr Leu Ser Cys Ser Ala Ser Ser
            660                 665                 670

Ser Val Ser Tyr Met Asn Trp Tyr Gln Gln Lys Pro Gly Gln Ala Pro
        675                 680                 685

Arg Leu Leu Ile Tyr Asp Ser Ser Lys Leu Ala Ser Gly Ile Pro Ala
    690                 695                 700

Arg Phe Ser Gly Ser Gly Ser Gly Thr Asp Phe Thr Leu Thr Ile Ser
705                 710                 715                 720

Ser Leu Glu Pro Glu Asp Phe Ala Val Tyr Tyr Cys Gln Gln Trp Ser
                725                 730                 735

Arg Asn Pro Pro Thr Phe Gly Gly Gly Thr Lys Val Glu Ile Lys Ser
            740                 745                 750

Ser Ser
```

<210> SEQ ID NO 201
<211> LENGTH: 2295
<212> TYPE: DNA
<213> ORGANISM: Artificial
<220> FEATURE:
<223> OTHER INFORMATION: TSC240 (HD37 x DRA222 scorpion, H81 linker)

<400> SEQUENCE: 201

```
atggaagcac cagcgcagct tctcttcctc ctgctactct ggctcccaga taccaccggt      60

gacattgtgc tgacccaatc tccagcttct ttggctgtgt ctctagggca gagggccacc     120
```

```
atctcctgca aggccagcca aagtgttgat tatgatggtg atagttattt gaactggtac    180
caacagattc caggacagcc acccaaactc ctcatctatg atgcatccaa tctagtttct    240
gggatcccac ccaggtttag tggcagtggg tctgggacag acttcaccct caacatccat    300
cctgtggaga aggtggatgc tgcaacctat cactgccagc aaagtactga ggatccgtgg    360
acgttcggtg gaggcaccaa gctggaaatc aaaggtggcg gtggttcggg cggtggtggg    420
tcgggtggcg gcggagctag ccaggttcag ctgcagcagt ctggggctga gctggtgagg    480
cctgggtcct cagtgaagat ttcctgcaag gcttctggct atgcattcag tagctactgg    540
atgaactggg tgaagcagag gcctggacag ggtcttgagt ggattggaca gatttggcct    600
ggagatggtg atactaacta caatggaaag ttcaagggta aagccactct gactgcagac    660
gaatcctcca gcacagccta catgcaactc agcagcctag catctgagga ctctgcggtc    720
tatttctgtg caagacggga gactacgacg gtaggccgtt attactatgc tatggactac    780
tggggtcaag gaacctcagt caccgtctcc tcgagtgagc ccaaatcttc tgacaaaact    840
cacacatgcc caccgtgccc agcacctgaa gccgcgggtg caccgtcagt cttcctcttc    900
cccccaaaac ccaaggacac cctcatgatc tcccggaccc ctgaggtcac atgcgtggtg    960
gtggacgtga gccacgaaga ccctgaggtc aagttcaact ggtacgtgga cggcgtggag   1020
gtgcataatg ccaagacaaa gccgcgggag gagcagtaca acagcacgta ccgtgtggtc   1080
agcgtcctca ccgtcctgca ccaggactgg ctgaatggca aggcgtacgc gtgcgcggtc   1140
tccaacaaag ccctcccagc ccccatcgag aaaaccatct ccaaagccaa agggcagccc   1200
cgagaaccac aggtgtacac cctgccccca tcccgggatg agctgaccaa gaaccaggtc   1260
agcctgacct gcctggtcaa aggcttctat ccaagcgaca tcgccgtgga gtgggagagc   1320
aatgggcagc cggagaacaa ctacaagacc acgcctcccg tgctggactc cgacggctcc   1380
ttcttcctct acagcaagct caccgtggac aagagcaggt ggcagcaggg gaacgtcttc   1440
tcatgctccg tgatgcatga ggctctgcac aaccactaca cgcagaagag cctctccctg   1500
tctccgggtg aagttcaaat tcccttgacc gaaagttaca gcccgaattc tcaggtccag   1560
ctggtggagt ctgggggcgg agtggtgcag cctgggcggt cactgaggct gtcctgcaag   1620
gcttctggct acacctttac tagatctacg atgcactggg taaggcaggc ccctggacaa   1680
ggtctggaat ggattggata cattaatcct agcagtgctt atactaatta caatcagaaa   1740
ttcaaggaca ggttcacaat cagcgcagac aaatccaaga gcacagcctt cctgcagatg   1800
gacagcctga ggcccgagga caccggcgtc tatttctgtg cacggcccca agtccactat   1860
gattacaacg ggtttcctta ctggggccaa gggactcccg tcactgtctc tagcggtggc   1920
ggagggtctg ggggtggcgg atccggaggt ggtggctctg cacaagacat ccagatgacc   1980
cagtctccaa gcagcctgtc tgcaagcgtg ggggacaggg tcaccatgac ctgcagtgcc   2040
agctcaagtg taagttacat gaactggtac cagcagaagc cgggcaaggc ccccaaaaga   2100
tggatttatg actcatccaa actggcttct ggagtccctg ctcgcttcag tggcagtggg   2160
tctgggaccg actataccct cacaatcagc agcctgcagc ccgaagattt cgccacttat   2220
tactgccagc agtggagtcg taacccaccc acgttcggag gggggaccaa gctacaaatt   2280
acatcctcca gctaa                                                    2295
```

<210> SEQ ID NO 202
<211> LENGTH: 744
<212> TYPE: PRT
<213> ORGANISM: Artificial
<220> FEATURE:
<223> OTHER INFORMATION: TSC240 (HD37 x DRA222 scorpion, H81 linker)

<400> SEQUENCE: 202

```
Asp Ile Val Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
    50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys Gly
            100                 105                 110

Gly Gly Gly Ser Gly Gly Gly Gly Ser Gly Gly Gly Gly Ala Ser Gln
        115                 120                 125

Val Gln Leu Gln Gln Ser Gly Ala Glu Leu Val Arg Pro Gly Ser Ser
    130                 135                 140

Val Lys Ile Ser Cys Lys Ala Ser Gly Tyr Ala Phe Ser Ser Tyr Trp
145                 150                 155                 160

Met Asn Trp Val Lys Gln Arg Pro Gly Gln Gly Leu Glu Trp Ile Gly
                165                 170                 175

Gln Ile Trp Pro Gly Asp Gly Asp Thr Asn Tyr Asn Gly Lys Phe Lys
            180                 185                 190

Gly Lys Ala Thr Leu Thr Ala Asp Glu Ser Ser Ser Thr Ala Tyr Met
        195                 200                 205

Gln Leu Ser Ser Leu Ala Ser Glu Asp Ser Ala Val Tyr Phe Cys Ala
    210                 215                 220

Arg Arg Glu Thr Thr Thr Val Gly Arg Tyr Tyr Tyr Ala Met Asp Tyr
225                 230                 235                 240

Trp Gly Gln Gly Thr Ser Val Thr Val Ser Ser Ser Glu Pro Lys Ser
                245                 250                 255

Ser Asp Lys Thr His Thr Cys Pro Pro Cys Pro Ala Pro Glu Ala Ala
            260                 265                 270

Gly Ala Pro Ser Val Phe Leu Phe Pro Pro Lys Pro Lys Asp Thr Leu
        275                 280                 285

Met Ile Ser Arg Thr Pro Glu Val Thr Cys Val Val Val Asp Val Ser
    290                 295                 300

His Glu Asp Pro Glu Val Lys Phe Asn Trp Tyr Val Asp Gly Val Glu
305                 310                 315                 320

Val His Asn Ala Lys Thr Lys Pro Arg Glu Glu Gln Tyr Asn Ser Thr
                325                 330                 335

Tyr Arg Val Val Ser Val Leu Thr Val Leu His Gln Asp Trp Leu Asn
            340                 345                 350

Gly Lys Ala Tyr Ala Cys Ala Val Ser Asn Lys Ala Leu Pro Ala Pro
        355                 360                 365

Ile Glu Lys Thr Ile Ser Lys Ala Lys Gly Gln Pro Arg Glu Pro Gln
    370                 375                 380

Val Tyr Thr Leu Pro Pro Ser Arg Asp Glu Leu Thr Lys Asn Gln Val
385                 390                 395                 400
```

```
Ser Leu Thr Cys Leu Val Lys Gly Phe Tyr Pro Ser Asp Ile Ala Val
                405                 410                 415

Glu Trp Glu Ser Asn Gly Gln Pro Glu Asn Asn Tyr Lys Thr Thr Pro
            420                 425                 430

Pro Val Leu Asp Ser Asp Gly Ser Phe Phe Leu Tyr Ser Lys Leu Thr
        435                 440                 445

Val Asp Lys Ser Arg Trp Gln Gln Gly Asn Val Phe Ser Cys Ser Val
    450                 455                 460

Met His Glu Ala Leu His Asn His Tyr Thr Gln Lys Ser Leu Ser Leu
465                 470                 475                 480

Ser Pro Gly Glu Val Gln Ile Pro Leu Thr Glu Ser Tyr Ser Pro Asn
                485                 490                 495

Ser Gln Val Gln Leu Val Glu Ser Gly Gly Gly Val Val Gln Pro Gly
            500                 505                 510

Arg Ser Leu Arg Leu Ser Cys Lys Ala Ser Gly Tyr Thr Phe Thr Arg
        515                 520                 525

Ser Thr Met His Trp Val Arg Gln Ala Pro Gly Gln Gly Leu Glu Trp
    530                 535                 540

Ile Gly Tyr Ile Asn Pro Ser Ser Ala Tyr Thr Asn Tyr Asn Gln Lys
545                 550                 555                 560

Phe Lys Asp Arg Phe Thr Ile Ser Ala Asp Lys Ser Lys Ser Thr Ala
                565                 570                 575

Phe Leu Gln Met Asp Ser Leu Arg Pro Glu Asp Thr Gly Val Tyr Phe
            580                 585                 590

Cys Ala Arg Pro Gln Val His Tyr Asp Tyr Asn Gly Phe Pro Tyr Trp
        595                 600                 605

Gly Gln Gly Thr Pro Val Thr Val Ser Ser Gly Gly Gly Gly Ser Gly
    610                 615                 620

Gly Gly Gly Ser Gly Gly Gly Gly Ser Ala Gln Asp Ile Gln Met Thr
625                 630                 635                 640

Gln Ser Pro Ser Ser Leu Ser Ala Ser Val Gly Asp Arg Val Thr Met
                645                 650                 655

Thr Cys Ser Ala Ser Ser Ser Val Ser Tyr Met Asn Trp Tyr Gln Gln
            660                 665                 670

Lys Pro Gly Lys Ala Pro Lys Arg Trp Ile Tyr Asp Ser Ser Lys Leu
        675                 680                 685

Ala Ser Gly Val Pro Ala Arg Phe Ser Gly Ser Gly Ser Gly Thr Asp
    690                 695                 700

Tyr Thr Leu Thr Ile Ser Ser Leu Gln Pro Glu Asp Phe Ala Thr Tyr
705                 710                 715                 720

Tyr Cys Gln Gln Trp Ser Arg Asn Pro Pro Thr Phe Gly Gly Gly Thr
                725                 730                 735

Lys Leu Gln Ile Thr Ser Ser Ser
            740
```

<210> SEQ ID NO 203
<211> LENGTH: 2301
<212> TYPE: DNA
<213> ORGANISM: Artificial
<220> FEATURE:
<223> OTHER INFORMATION: TSC241 (HD37 x DRA222 scorpion, H83 linker)

<400> SEQUENCE: 203

```
atggaagcac cagcgcagct tctcttcctc ctgctactct ggctcccaga taccaccggt      60
```

-continued

```
gacattgtgc tgacccaatc tccagcttct ttggctgtgt ctctagggca gagggccacc    120
atctcctgca aggccagcca aagtgttgat tatgatggtg atagttattt gaactggtac    180
caacagattc caggacagcc acccaaactc ctcatctatg atgcatccaa tctagtttct    240
gggatcccac ccaggtttag tggcagtggg tctgggacag acttcaccct caacatccat    300
cctgtggaga aggtggatgc tgcaacctat cactgccagc aaagtactga ggatccgtgg    360
acgttcggtg gaggcaccaa gctggaaatc aaaggtggcg gtggttcggg cggtggtggg    420
tcgggtggcg gcggagctag ccaggttcag ctgcagcagt ctggggctga gctggtgagg    480
cctgggtcct cagtgaagat ttcctgcaag gcttctggct atgcattcag tagctactgg    540
atgaactggg tgaagcagag gcctggacag ggtcttgagt ggattggaca gatttggcct    600
ggagatggtg atactaacta caatggaaag ttcaagggta aagccactct gactgcagac    660
gaatcctcca gcacagccta catgcaactc agcagcctag catctgagga ctctgcggtc    720
tatttctgtg caagacggga gactacgacg gtaggccgtt attactatgc tatggactac    780
tggggtcaag gaacctcagt caccgtctcc tcgagtgagc ccaaatcttc tgacaaaact    840
cacacatgcc caccgtgccc agcacctgaa gccgcgggtg caccgtcagt cttcctcttc    900
cccccaaaac ccaaggacac cctcatgatc tcccggaccc ctgaggtcac atgcgtggtg    960
gtggacgtga gccacgaaga ccctgaggtc aagttcaact ggtacgtgga cggcgtggag   1020
gtgcataatg ccaagacaaa gccgcgggag gagcagtaca acagcacgta ccgtgtggtc   1080
agcgtcctca ccgtcctgca ccaggactgg ctgaatggca aggcgtacgc gtgcgcggtc   1140
tccaacaaag ccctcccagc ccccatcgag aaaaccatct ccaaagccaa agggcagccc   1200
cgagaaccac aggtgtacac cctgccccca tcccgggatg agctgaccaa gaaccaggtc   1260
agcctgacct gcctggtcaa aggcttctat ccaagcgaca tcgccgtgga gtgggagagc   1320
aatgggcagc cggagaacaa ctacaagacc acgcctcccg tgctggactc cgacggctcc   1380
ttcttcctct acagcaagct caccgtggac aagagcaggt ggcagcaggg gaacgtcttc   1440
tcatgctccg tgatgcatga ggctctgcac aaccactaca cgcagaagag cctctccctg   1500
tctccgggtt cttccctgaa tacaggaact cagatggcag gtcattctcc gaattctcag   1560
gtccagctgg tggagtctgg gggcggagtg gtgcagcctg ggcggtcact gaggctgtcc   1620
tgcaaggctt ctggctacac ctttactaga tctacgatgc actgggtaag gcaggcccct   1680
ggacaaggtc tggaatggat tggatacatt aatcctagca gtgcttatac taattacaat   1740
cagaaattca aggacaggtt cacaatcagc gcagacaaat ccaagagcac agccttcctg   1800
cagatggaca gcctgaggcc cgaggacacc ggcgtctatt tctgtgcacg gccccaagtc   1860
cactatgatt acaacgggtt tccttactgg ggccaaggga ctcccgtcac tgtctctagc   1920
ggtggcggag ggtctggggg tggcggatcc ggaggtggtg gctctgcaca agacatccag   1980
atgacccagt ctccaagcag cctgtctgca agcgtggggg acagggtcac catgacctgc   2040
agtgccagct caagtgtaag ttacatgaac tggtaccagc agaagccggg caaggccccc   2100
aaaagatgga tttatgactc atccaaactg gcttctggag tccctgctcg cttcagtggc   2160
agtgggtctg ggaccgacta taccctcaca atcagcagcc tgcagcccga agatttcgcc   2220
acttattact gccagcagtg gagtcgtaac ccacccacgt tcggaggggg gaccaagcta   2280
caaattacat cctccagcta a                                             2301
```

<210> SEQ ID NO 204
<211> LENGTH: 746

<212> TYPE: PRT
<213> ORGANISM: Artificial
<220> FEATURE:
<223> OTHER INFORMATION: TSC241 (HD37 x DRA222 scorpion, H83 linker)

<400> SEQUENCE: 204

```
Asp Ile Val Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
    50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys Gly
            100                 105                 110

Gly Gly Gly Ser Gly Gly Gly Gly Ser Gly Gly Gly Gly Ala Ser Gln
        115                 120                 125

Val Gln Leu Gln Gln Ser Gly Ala Glu Leu Val Arg Pro Gly Ser Ser
    130                 135                 140

Val Lys Ile Ser Cys Lys Ala Ser Gly Tyr Ala Phe Ser Ser Tyr Trp
145                 150                 155                 160

Met Asn Trp Val Lys Gln Arg Pro Gly Gln Gly Leu Glu Trp Ile Gly
                165                 170                 175

Gln Ile Trp Pro Gly Asp Gly Asp Thr Asn Tyr Asn Gly Lys Phe Lys
            180                 185                 190

Gly Lys Ala Thr Leu Thr Ala Asp Glu Ser Ser Ser Thr Ala Tyr Met
        195                 200                 205

Gln Leu Ser Ser Leu Ala Ser Glu Asp Ser Ala Val Tyr Phe Cys Ala
    210                 215                 220

Arg Arg Glu Thr Thr Thr Val Gly Arg Tyr Tyr Tyr Ala Met Asp Tyr
225                 230                 235                 240

Trp Gly Gln Gly Thr Ser Val Thr Val Ser Ser Ser Glu Pro Lys Ser
                245                 250                 255

Ser Asp Lys Thr His Thr Cys Pro Pro Cys Pro Ala Pro Glu Ala Ala
            260                 265                 270

Gly Ala Pro Ser Val Phe Leu Phe Pro Pro Lys Pro Lys Asp Thr Leu
        275                 280                 285

Met Ile Ser Arg Thr Pro Glu Val Thr Cys Val Val Val Asp Val Ser
    290                 295                 300

His Glu Asp Pro Glu Val Lys Phe Asn Trp Tyr Val Asp Gly Val Glu
305                 310                 315                 320

Val His Asn Ala Lys Thr Lys Pro Arg Glu Glu Gln Tyr Asn Ser Thr
                325                 330                 335

Tyr Arg Val Val Ser Val Leu Thr Val Leu His Gln Asp Trp Leu Asn
            340                 345                 350

Gly Lys Ala Tyr Ala Cys Ala Val Ser Asn Lys Ala Leu Pro Ala Pro
        355                 360                 365

Ile Glu Lys Thr Ile Ser Lys Ala Lys Gly Gln Pro Arg Glu Pro Gln
    370                 375                 380
```

```
Val Tyr Thr Leu Pro Pro Ser Arg Asp Glu Leu Thr Lys Asn Gln Val
385                 390                 395                 400

Ser Leu Thr Cys Leu Val Lys Gly Phe Tyr Pro Ser Asp Ile Ala Val
                405                 410                 415

Glu Trp Glu Ser Asn Gly Gln Pro Glu Asn Asn Tyr Lys Thr Thr Pro
            420                 425                 430

Pro Val Leu Asp Ser Asp Gly Ser Phe Phe Leu Tyr Ser Lys Leu Thr
        435                 440                 445

Val Asp Lys Ser Arg Trp Gln Gln Gly Asn Val Phe Ser Cys Ser Val
    450                 455                 460

Met His Glu Ala Leu His Asn His Tyr Thr Gln Lys Ser Leu Ser Leu
465                 470                 475                 480

Ser Pro Gly Ser Ser Leu Asn Thr Gly Thr Gln Met Ala Gly His Ser
                485                 490                 495

Pro Asn Ser Gln Val Gln Leu Val Glu Ser Gly Gly Gly Val Val Gln
            500                 505                 510

Pro Gly Arg Ser Leu Arg Leu Ser Cys Lys Ala Ser Gly Tyr Thr Phe
        515                 520                 525

Thr Arg Ser Thr Met His Trp Val Arg Gln Ala Pro Gly Gln Gly Leu
    530                 535                 540

Glu Trp Ile Gly Tyr Ile Asn Pro Ser Ser Ala Tyr Thr Asn Tyr Asn
545                 550                 555                 560

Gln Lys Phe Lys Asp Arg Phe Thr Ile Ser Ala Asp Lys Ser Lys Ser
                565                 570                 575

Thr Ala Phe Leu Gln Met Asp Ser Leu Arg Pro Glu Asp Thr Gly Val
            580                 585                 590

Tyr Phe Cys Ala Arg Pro Gln Val His Tyr Asp Tyr Asn Gly Phe Pro
        595                 600                 605

Tyr Trp Gly Gln Gly Thr Pro Val Thr Val Ser Ser Gly Gly Gly Gly
    610                 615                 620

Ser Gly Gly Gly Gly Ser Gly Gly Gly Gly Ser Ala Gln Asp Ile Gln
625                 630                 635                 640

Met Thr Gln Ser Pro Ser Ser Leu Ser Ala Ser Val Gly Asp Arg Val
                645                 650                 655

Thr Met Thr Cys Ser Ala Ser Ser Ser Val Ser Tyr Met Asn Trp Tyr
            660                 665                 670

Gln Gln Lys Pro Gly Lys Ala Pro Lys Arg Trp Ile Tyr Asp Ser Ser
        675                 680                 685

Lys Leu Ala Ser Gly Val Pro Ala Arg Phe Ser Gly Ser Gly Ser Gly
    690                 695                 700

Thr Asp Tyr Thr Leu Thr Ile Ser Ser Leu Gln Pro Glu Asp Phe Ala
705                 710                 715                 720

Thr Tyr Tyr Cys Gln Gln Trp Ser Arg Asn Pro Pro Thr Phe Gly Gly
                725                 730                 735

Gly Thr Lys Leu Gln Ile Thr Ser Ser Ser
            740                 745
```

<210> SEQ ID NO 205
<211> LENGTH: 2313
<212> TYPE: DNA
<213> ORGANISM: Artificial
<220> FEATURE:
<223> OTHER INFORMATION: TSC242 (HD37 x DRA222 scorpion, H91 linker)

<400> SEQUENCE: 205

-continued

```
atggaagcac cagcgcagct tctcttcctc ctgctactct ggctcccaga taccaccggt     60
gacattgtgc tgacccaatc tccagcttct ttggctgtgt ctctagggca gagggccacc    120
atctcctgca aggccagcca aagtgttgat tatgatggtg atagttattt gaactggtac    180
caacagattc caggacagcc acccaaactc ctcatctatg atgcatccaa tctagtttct    240
gggatcccac ccaggtttag tggcagtggg tctgggacag acttcaccct caacatccat    300
cctgtggaga aggtggatgc tgcaacctat cactgccagc aaagtactga ggatccgtgg    360
acgttcggtg gaggcaccaa gctggaaatc aaaggtggcg gtggttcggg cggtggtggg    420
tcgggtggcg gcggagctag ccaggttcag ctgcagcagt ctggggctga gctggtgagg    480
cctgggtcct cagtgaagat ttcctgcaag gcttctggct atgcattcag tagctactgg    540
atgaactggg tgaagcagag gcctggacag ggtcttgagt ggattggaca gatttggcct    600
ggagatggtg atactaacta caatggaaag ttcaagggta aagccactct gactgcagac    660
gaatcctcca gcacagccta catgcaactc agcagcctag catctgagga ctctgcggtc    720
tatttctgtg caagacggga gactacgacg gtaggccgtt attactatgc tatggactac    780
tggggtcaag gaacctcagt caccgtctcc tcgagtgagc ccaaatcttc tgacaaaact    840
cacacatgcc caccgtgccc agcacctgaa gccgcgggtg caccgtcagt cttcctcttc    900
cccccaaaac ccaaggacac cctcatgatc tcccggaccc ctgaggtcac atgcgtggtg    960
gtggacgtga gccacgaaga ccctgaggtc aagttcaact ggtacgtgga cggcgtggag   1020
gtgcataatg ccaagacaaa gccgcgggag gagcagtaca acagcacgta ccgtgtggtc   1080
agcgtcctca ccgtcctgca ccaggactgg ctgaatggca aggcgtacgc gtgcgcggtc   1140
tccaacaaag ccctcccagc ccccatcgag aaaaccatct ccaaagccaa agggcagccc   1200
cgagaaccac aggtgtacac cctgccccca tcccgggatg agctgaccaa gaaccaggtc   1260
agcctgacct gcctggtcaa aggcttctat ccaagcgaca tcgccgtgga gtgggagagc   1320
aatgggcagc cggagaacaa ctacaagacc acgcctcccg tgctggactc cgacggctcc   1380
ttcttcctct acagcaagct caccgtggac aagagcaggt ggcagcaggg gaacgtcttc   1440
tcatgctccg tgatgcatga ggctctgcac aaccactaca cgcagaagag cctctccctg   1500
tctccgggta actcattagc aaaccaagaa gttcaaattc ccttgaccga aagttacagc   1560
ccgaattctc aggtccagct ggtggagtct gggggcggag tggtgcagcc tgggcggtca   1620
ctgaggctgt cctgcaaggc ttctggctac acctttacta gatctacgat gcactgggta   1680
aggcaggccc ctggacaagg tctggaatgg attggataca ttaatcctag cagtgcttat   1740
actaattaca atcagaaatt caaggacagg ttcacaatca gcgcagacaa atccaagagc   1800
acagccttcc tgcagatgga cagcctgagg cccgaggaca ccggcgtcta tttctgtgca   1860
cggccccaag tccactatga ttacaacggg tttccttact ggggccaagg gactcccgtc   1920
actgtctcta gcggtggcgg agggtctggg ggtggcggat ccggaggtgg tggctctgca   1980
caagacatcc agatgaccca gtctccaagc agcctgtctg caagcgtggg ggacagggtc   2040
accatgacct gcagtgccag ctcaagtgta agttacatga actggtacca gcagaagccg   2100
ggcaaggccc ccaaaagatg gatttatgac tcatccaaac tggcttctgg agtccctgct   2160
cgcttcagtg gcagtgggtc tgggaccgac tataccctca caatcagcag cctgcagccc   2220
gaagatttcg ccacttatta ctgccagcag tggagtcgta acccacccac gttcggaggg   2280
gggaccaagc tacaaattac atcctccagc taa                                2313
```

<210> SEQ ID NO 206
<211> LENGTH: 750
<212> TYPE: PRT
<213> ORGANISM: Artificial
<220> FEATURE:
<223> OTHER INFORMATION: TSC242 (HD37 x DRA222 scorpion, H91 linker)

<400> SEQUENCE: 206

```
Asp Ile Val Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
    50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys Gly
            100                 105                 110

Gly Gly Gly Ser Gly Gly Gly Gly Ser Gly Gly Gly Gly Ala Ser Gln
        115                 120                 125

Val Gln Leu Gln Gln Ser Gly Ala Glu Leu Val Arg Pro Gly Ser Ser
    130                 135                 140

Val Lys Ile Ser Cys Lys Ala Ser Gly Tyr Ala Phe Ser Ser Tyr Trp
145                 150                 155                 160

Met Asn Trp Val Lys Gln Arg Pro Gly Gln Gly Leu Glu Trp Ile Gly
                165                 170                 175

Gln Ile Trp Pro Gly Asp Gly Asp Thr Asn Tyr Asn Gly Lys Phe Lys
            180                 185                 190

Gly Lys Ala Thr Leu Thr Ala Asp Glu Ser Ser Ser Thr Ala Tyr Met
        195                 200                 205

Gln Leu Ser Ser Leu Ala Ser Glu Asp Ser Ala Val Tyr Phe Cys Ala
    210                 215                 220

Arg Arg Glu Thr Thr Thr Val Gly Arg Tyr Tyr Tyr Ala Met Asp Tyr
225                 230                 235                 240

Trp Gly Gln Gly Thr Ser Val Thr Val Ser Ser Ser Glu Pro Lys Ser
                245                 250                 255

Ser Asp Lys Thr His Thr Cys Pro Pro Cys Pro Ala Pro Glu Ala Ala
            260                 265                 270

Gly Ala Pro Ser Val Phe Leu Phe Pro Pro Lys Pro Lys Asp Thr Leu
        275                 280                 285

Met Ile Ser Arg Thr Pro Glu Val Thr Cys Val Val Val Asp Val Ser
    290                 295                 300

His Glu Asp Pro Glu Val Lys Phe Asn Trp Tyr Val Asp Gly Val Glu
305                 310                 315                 320

Val His Asn Ala Lys Thr Lys Pro Arg Glu Glu Gln Tyr Asn Ser Thr
                325                 330                 335

Tyr Arg Val Val Ser Val Leu Thr Val Leu His Gln Asp Trp Leu Asn
            340                 345                 350

Gly Lys Ala Tyr Ala Cys Ala Val Ser Asn Lys Ala Leu Pro Ala Pro
        355                 360                 365

Ile Glu Lys Thr Ile Ser Lys Ala Lys Gly Gln Pro Arg Glu Pro Gln
```

370 375 380

Val Tyr Thr Leu Pro Pro Ser Arg Asp Glu Leu Thr Lys Asn Gln Val
385 390 395 400

Ser Leu Thr Cys Leu Val Lys Gly Phe Tyr Pro Ser Asp Ile Ala Val
405 410 415

Glu Trp Glu Ser Asn Gly Gln Pro Glu Asn Asn Tyr Lys Thr Thr Pro
420 425 430

Pro Val Leu Asp Ser Asp Gly Ser Phe Phe Leu Tyr Ser Lys Leu Thr
435 440 445

Val Asp Lys Ser Arg Trp Gln Gln Gly Asn Val Phe Ser Cys Ser Val
450 455 460

Met His Glu Ala Leu His Asn His Tyr Thr Gln Lys Ser Leu Ser Leu
465 470 475 480

Ser Pro Gly Asn Ser Leu Ala Asn Gln Glu Val Gln Ile Pro Leu Thr
485 490 495

Glu Ser Tyr Ser Pro Asn Ser Gln Val Gln Leu Val Glu Ser Gly Gly
500 505 510

Gly Val Val Gln Pro Gly Arg Ser Leu Arg Leu Ser Cys Lys Ala Ser
515 520 525

Gly Tyr Thr Phe Thr Arg Ser Thr Met His Trp Val Arg Gln Ala Pro
530 535 540

Gly Gln Gly Leu Glu Trp Ile Gly Tyr Ile Asn Pro Ser Ser Ala Tyr
545 550 555 560

Thr Asn Tyr Asn Gln Lys Phe Lys Asp Arg Phe Thr Ile Ser Ala Asp
565 570 575

Lys Ser Lys Ser Thr Ala Phe Leu Gln Met Asp Ser Leu Arg Pro Glu
580 585 590

Asp Thr Gly Val Tyr Phe Cys Ala Arg Pro Gln Val His Tyr Asp Tyr
595 600 605

Asn Gly Phe Pro Tyr Trp Gly Gln Gly Thr Pro Val Thr Val Ser Ser
610 615 620

Gly Gly Gly Gly Ser Gly Gly Gly Gly Ser Gly Gly Gly Gly Ser Ala
625 630 635 640

Gln Asp Ile Gln Met Thr Gln Ser Pro Ser Ser Leu Ser Ala Ser Val
645 650 655

Gly Asp Arg Val Thr Met Thr Cys Ser Ala Ser Ser Ser Val Ser Tyr
660 665 670

Met Asn Trp Tyr Gln Gln Lys Pro Gly Lys Ala Pro Lys Arg Trp Ile
675 680 685

Tyr Asp Ser Ser Lys Leu Ala Ser Gly Val Pro Ala Arg Phe Ser Gly
690 695 700

Ser Gly Ser Gly Thr Asp Tyr Thr Leu Thr Ile Ser Ser Leu Gln Pro
705 710 715 720

Glu Asp Phe Ala Thr Tyr Tyr Cys Gln Gln Trp Ser Arg Asn Pro Pro
725 730 735

Thr Phe Gly Gly Gly Thr Lys Leu Gln Ile Thr Ser Ser Ser
740 745 750

<210> SEQ ID NO 207
<211> LENGTH: 1815
<212> TYPE: DNA
<213> ORGANISM: Artificial Sequence
<220> FEATURE:
<223> OTHER INFORMATION: TSC049

<400> SEQUENCE: 207

```
atggaagcac cagcgcagct tctcttcctc ctgctactct ggctcccaga taccaccggt      60
gacattgtgc tgacccaatc tccagcttct ttggctgtgt ctctagggca gagggccacc     120
atctcctgca aggccagcca aagtgttgat tatgatggtg atagttattt gaactggtac     180
caacagattc caggacagcc acccaaactc ctcatctatg atgcatccaa tctagtttct     240
gggatcccac ccaggtttag tggcagtggg tctgggacag acttcaccct caacatccat     300
cctgtggaga aggtggatgc tgcaacctat cactgccagc aaagtactga ggatccgtgg     360
acgttcggtg gaggcaccaa gctggaaatc aaaggtggcg gtggttcggg cggtggtggg     420
tcgggtggcg gcggagctag ccaggttcag ctgcagcagt ctggggctga gctggtgagg     480
cctgggtcct cagtgaagat ttcctgcaag gcttctggct atgcattcag tagctactgg     540
atgaactggg tgaagcagag gcctggacag ggtcttgagt ggattggaca gatttggcct     600
ggagatggtg atactaacta caatggaaag ttcaagggta aagccactct gactgcagac     660
gaatcctcca gcacagccta catgcaactc agcagcctag catctgagga ctctgcggtc     720
tatttctgtg caagacggga gactacgacg gtaggccgtt attactatgc tatggactac     780
tggggtcaag gaacctcagt caccgtctcc tcgagtgagc ccaaatcttc tgacaaaact     840
cacacatgcc caccgtgccc agcacctgaa gccgcgggtg caccgtcagt cttcctcttc     900
cccccaaaac ccaaggacac cctcatgatc tcccggaccc ctgaggtcac atgcgtggtg     960
gtggacgtga gccacgaaga ccctgaggtc aagttcaact ggtacgtgga cggcgtggag    1020
gtgcataatg ccaagacaaa gccgcgggag gagcagtaca acagcacgta ccgtgtggtc    1080
agcgtcctca ccgtcctgca ccaggactgg ctgaatggca aggcgtacgc gtgcgcggtc    1140
tccaacaaag ccctcccagc ccccatcgag aaaaccatct ccaaagccaa agggcagccc    1200
cgagaaccac aggtgtacac cctgccccca tcccgggatg agctgaccaa gaaccaggtc    1260
agcctgacct gcctggtcaa aggcttctat ccaagcgaca tcgccgtgga gtgggagagc    1320
aatgggcagc cggagaacaa ctacaagacc acgcctcccg tgctggactc cgacggctcc    1380
ttcttcctct acagcaagct caccgtggac aagagcaggt ggcagcaggg gaacgtcttc    1440
tcatgctccg tgatgcatga ggctctgcac aaccactaca cgcagaagag cctctccctg    1500
tctccgggta aatctagagc ctccaccaag ggcccatcgg tcttccccct ggcaccctcc    1560
tccaagagca cctctggggg cacagcggcc ctgggctgcc tggtcaagga ctacttcccc    1620
gagccggtga cggtgtcgtg gaactcaggc gccctgacca gcggcgtgca caccttcccg    1680
gctgtcctac agtcctcagg actctactcc ctcagcagcg tggtgaccgt gccctccagc    1740
agcttgggca cccagaccta catctgcaac gtgaatcaca agcccagcaa caccaaggtg    1800
gacaagaaag tttga                                                     1815
```

<210> SEQ ID NO 208
<211> LENGTH: 584
<212> TYPE: PRT
<213> ORGANISM: Artificial Sequence
<220> FEATURE:
<223> OTHER INFORMATION: TSC049

<400> SEQUENCE: 208

```
Asp Ile Val Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30
```

```
Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
    50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys Gly
            100                 105                 110

Gly Gly Gly Ser Gly Gly Gly Gly Ser Gly Gly Gly Gly Ala Ser Gln
        115                 120                 125

Val Gln Leu Gln Gln Ser Gly Ala Glu Leu Val Arg Pro Gly Ser Ser
    130                 135                 140

Val Lys Ile Ser Cys Lys Ala Ser Gly Tyr Ala Phe Ser Ser Tyr Trp
145                 150                 155                 160

Met Asn Trp Val Lys Gln Arg Pro Gly Gln Gly Leu Glu Trp Ile Gly
                165                 170                 175

Gln Ile Trp Pro Gly Asp Gly Asp Thr Asn Tyr Asn Gly Lys Phe Lys
            180                 185                 190

Gly Lys Ala Thr Leu Thr Ala Asp Glu Ser Ser Ser Thr Ala Tyr Met
        195                 200                 205

Gln Leu Ser Ser Leu Ala Ser Glu Asp Ser Ala Val Tyr Phe Cys Ala
    210                 215                 220

Arg Arg Glu Thr Thr Thr Val Gly Arg Tyr Tyr Tyr Ala Met Asp Tyr
225                 230                 235                 240

Trp Gly Gln Gly Thr Ser Val Thr Val Ser Ser Ser Glu Pro Lys Ser
                245                 250                 255

Ser Asp Lys Thr His Thr Cys Pro Pro Cys Pro Ala Pro Glu Ala Ala
            260                 265                 270

Gly Ala Pro Ser Val Phe Leu Phe Pro Pro Lys Pro Lys Asp Thr Leu
        275                 280                 285

Met Ile Ser Arg Thr Pro Glu Val Thr Cys Val Val Val Asp Val Ser
    290                 295                 300

His Glu Asp Pro Glu Val Lys Phe Asn Trp Tyr Val Asp Gly Val Glu
305                 310                 315                 320

Val His Asn Ala Lys Thr Lys Pro Arg Glu Glu Gln Tyr Asn Ser Thr
                325                 330                 335

Tyr Arg Val Val Ser Val Leu Thr Val Leu His Gln Asp Trp Leu Asn
            340                 345                 350

Gly Lys Ala Tyr Ala Cys Ala Val Ser Asn Lys Ala Leu Pro Ala Pro
        355                 360                 365

Ile Glu Lys Thr Ile Ser Lys Ala Lys Gly Gln Pro Arg Glu Pro Gln
    370                 375                 380

Val Tyr Thr Leu Pro Pro Ser Arg Asp Glu Leu Thr Lys Asn Gln Val
385                 390                 395                 400

Ser Leu Thr Cys Leu Val Lys Gly Phe Tyr Pro Ser Asp Ile Ala Val
                405                 410                 415

Glu Trp Glu Ser Asn Gly Gln Pro Glu Asn Asn Tyr Lys Thr Thr Pro
            420                 425                 430

Pro Val Leu Asp Ser Asp Gly Ser Phe Phe Leu Tyr Ser Lys Leu Thr
        435                 440                 445
```

Val Asp Lys Ser Arg Trp Gln Gln Gly Asn Val Phe Ser Cys Ser Val
450 455 460

Met His Glu Ala Leu His Asn His Tyr Thr Gln Lys Ser Leu Ser Leu
465 470 475 480

Ser Pro Gly Lys Ser Arg Ala Ser Thr Lys Gly Pro Ser Val Phe Pro
485 490 495

Leu Ala Pro Ser Ser Lys Ser Thr Ser Gly Gly Thr Ala Ala Leu Gly
500 505 510

Cys Leu Val Lys Asp Tyr Phe Pro Glu Pro Val Thr Val Ser Trp Asn
515 520 525

Ser Gly Ala Leu Thr Ser Gly Val His Thr Phe Pro Ala Val Leu Gln
530 535 540

Ser Ser Gly Leu Tyr Ser Leu Ser Ser Val Val Thr Val Pro Ser Ser
545 550 555 560

Ser Leu Gly Thr Gln Thr Tyr Ile Cys Asn Val Asn His Lys Pro Ser
565 570 575

Asn Thr Lys Val Asp Lys Lys Val
580

<210> SEQ ID NO 209
<211> LENGTH: 1836
<212> TYPE: DNA
<213> ORGANISM: Artificial Sequence
<220> FEATURE:
<223> OTHER INFORMATION: TSC096

<400> SEQUENCE: 209
atggaagcac cagcgcagct tctcttcctc ctgctactct ggctcccaga taccaccggt 60
gacattgtgc tgacccaatc tccagcttct ttggctgtgt ctctagggca gagggccacc 120
atctcctgca aggccagcca aagtgttgat tatgatggtg atagttattt gaactggtac 180
caacagattc caggacagcc acccaaactc ctcatctatg atgcatccaa tctagtttct 240
gggatcccac ccaggtttag tggcagtggg tctgggacag acttcaccct caacatccat 300
cctgtggaga aggtggatgc tgcaacctat cactgccagc aaagtactga ggatccgtgg 360
acgttcggtg gaggcaccaa gctggaaatc aaaggtggcg gtggttcggg cggtggtggg 420
tcgggtggcg gcggagctag ccaggttcag ctgcagcagt ctggggctga gctggtgagg 480
cctgggtcct cagtgaagat ttcctgcaag gcttctggct atgcattcag tagctactgg 540
atgaactggg tgaagcagag gcctggacag ggtcttgagt ggattggaca gatttggcct 600
ggagatggtg atactaacta caatggaaag ttcaagggta aagccactct gactgcagac 660
gaatcctcca gcacagccta catgcaactc agcagcctag catctgagga ctctgcggtc 720
tatttctgtg caagacggga gactacgacg gtaggccgtt attactatgc tatggactac 780
tggggtcaag gaacctcagt caccgtctcc tcgagtgagc ccaaatcttc tgacaaaact 840
cacacatgcc caccgtgccc agcacctgaa gccgcgggtg caccgtcagt cttcctcttc 900
cccccaaaac ccaaggacac cctcatgatc tcccggaccc ctgaggtcac atgcgtggtg 960
gtggacgtga gccacgaaga ccctgaggtc aagttcaact ggtacgtgga cggcgtggag 1020
gtgcataatg ccaagacaaa gccgcgggag gagcagtaca acagcacgta ccgtgtggtc 1080
agcgtcctca ccgtcctgca ccaggactgg ctgaatggca aggcgtacgc gtgcgcggtc 1140
tccaacaaag ccctcccagc ccccatcgag aaaaccatct ccaaagccaa agggcagccc 1200
cgagaaccac aggtgtacac cctgccccca tcccgggatg agctgaccaa gaaccaggtc 1260

```
agcctgacct gcctggtcaa aggcttctat ccaagcgaca tcgccgtgga gtgggagagc   1320

aatgggcagc cggagaacaa ctacaagacc acgcctcccg tgctggactc cgacggctcc   1380

ttcttcctct acagcaagct caccgtggac aagagcaggt ggcagcaggg gaacgtcttc   1440

tcatgctccg tgatgcatga ggctctgcac aaccactaca cgcagaagag cctctccctg   1500

tctccgggta aatctagaac tgtggctgca ccatctgtct tcatcttccc gccatctgat   1560

gagcagttga aatctggaac tgcctctgtt gtgtgcctgc tgaattactt ctatcccaga   1620

gaggccaaag tacagtggaa ggtggataac gccctccaat cgggtaactc ccaggagagt   1680

gccacagagc aggacagcaa ggacagcacc tacagcctca gcagcgagct gacgctgagc   1740

aaagcagact acgagaaaca caaagtctac gcctgcgaag tcacccatca gggcctgagc   1800

tcgcccgtca caaagagctt caacagggga gagtga                              1836
```

```
<210> SEQ ID NO 210
<211> LENGTH: 591
<212> TYPE: PRT
<213> ORGANISM: Artificial Sequence
<220> FEATURE:
<223> OTHER INFORMATION: TSC096

<400> SEQUENCE: 210

Asp Ile Val Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
    50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys Gly
            100                 105                 110

Gly Gly Gly Ser Gly Gly Gly Gly Ser Gly Gly Gly Gly Ala Ser Gln
        115                 120                 125

Val Gln Leu Gln Gln Ser Gly Ala Glu Leu Val Arg Pro Gly Ser Ser
    130                 135                 140

Val Lys Ile Ser Cys Lys Ala Ser Gly Tyr Ala Phe Ser Ser Tyr Trp
145                 150                 155                 160

Met Asn Trp Val Lys Gln Arg Pro Gly Gln Gly Leu Glu Trp Ile Gly
                165                 170                 175

Gln Ile Trp Pro Gly Asp Gly Asp Thr Asn Tyr Asn Gly Lys Phe Lys
            180                 185                 190

Gly Lys Ala Thr Leu Thr Ala Asp Glu Ser Ser Ser Thr Ala Tyr Met
        195                 200                 205

Gln Leu Ser Ser Leu Ala Ser Glu Asp Ser Ala Val Tyr Phe Cys Ala
    210                 215                 220

Arg Arg Glu Thr Thr Thr Val Gly Arg Tyr Tyr Tyr Ala Met Asp Tyr
225                 230                 235                 240

Trp Gly Gln Gly Thr Ser Val Thr Val Ser Ser Ser Glu Pro Lys Ser
                245                 250                 255

Ser Asp Lys Thr His Thr Cys Pro Pro Cys Pro Ala Pro Glu Ala Ala
```

-continued

```
            260                 265                 270

Gly Ala Pro Ser Val Phe Leu Phe Pro Pro Lys Pro Lys Asp Thr Leu
        275                 280                 285

Met Ile Ser Arg Thr Pro Glu Val Thr Cys Val Val Val Asp Val Ser
    290                 295                 300

His Glu Asp Pro Glu Val Lys Phe Asn Trp Tyr Val Asp Gly Val Glu
305                 310                 315                 320

Val His Asn Ala Lys Thr Lys Pro Arg Glu Glu Gln Tyr Asn Ser Thr
                325                 330                 335

Tyr Arg Val Val Ser Val Leu Thr Val Leu His Gln Asp Trp Leu Asn
            340                 345                 350

Gly Lys Ala Tyr Ala Cys Ala Val Ser Asn Lys Ala Leu Pro Ala Pro
        355                 360                 365

Ile Glu Lys Thr Ile Ser Lys Ala Lys Gly Gln Pro Arg Glu Pro Gln
    370                 375                 380

Val Tyr Thr Leu Pro Pro Ser Arg Asp Glu Leu Thr Lys Asn Gln Val
385                 390                 395                 400

Ser Leu Thr Cys Leu Val Lys Gly Phe Tyr Pro Ser Asp Ile Ala Val
                405                 410                 415

Glu Trp Glu Ser Asn Gly Gln Pro Glu Asn Asn Tyr Lys Thr Thr Pro
            420                 425                 430

Pro Val Leu Asp Ser Asp Gly Ser Phe Phe Leu Tyr Ser Lys Leu Thr
        435                 440                 445

Val Asp Lys Ser Arg Trp Gln Gln Gly Asn Val Phe Ser Cys Ser Val
    450                 455                 460

Met His Glu Ala Leu His Asn His Tyr Thr Gln Lys Ser Leu Ser Leu
465                 470                 475                 480

Ser Pro Gly Lys Ser Arg Thr Val Ala Ala Pro Ser Val Phe Ile Phe
                485                 490                 495

Pro Pro Ser Asp Glu Gln Leu Lys Ser Gly Thr Ala Ser Val Val Cys
            500                 505                 510

Leu Leu Asn Tyr Phe Tyr Pro Arg Glu Ala Lys Val Gln Trp Lys Val
        515                 520                 525

Asp Asn Ala Leu Gln Ser Gly Asn Ser Gln Glu Ser Ala Thr Glu Gln
    530                 535                 540

Asp Ser Lys Asp Ser Thr Tyr Ser Leu Ser Ser Glu Leu Thr Leu Ser
545                 550                 555                 560

Lys Ala Asp Tyr Glu Lys His Lys Val Tyr Ala Cys Glu Val Thr His
                565                 570                 575

Gln Gly Leu Ser Ser Pro Val Thr Lys Ser Phe Asn Arg Gly Glu
            580                 585                 590
```

<210> SEQ ID NO 211
<211> LENGTH: 1809
<212> TYPE: DNA
<213> ORGANISM: Artificial Sequence
<220> FEATURE:
<223> OTHER INFORMATION: TSC192

<400> SEQUENCE: 211

```
atggaagcac cagcgcagct tctcttcctc ctgctactct ggctcccaga taccaccggt      60

gatatccaga tgacccagtc tccatccgcc atgtctgcat ctgtaggaga cagagtcacc     120

atcacttgcc gggcgagtaa gagcattagc aaatatttag cctggtttca gcagaaacca     180

gggaaagttc ctaagctccg catccattct ggatctactt tgcaatcagg ggtcccatct     240
```

```
cggttcagtg gcagtggatc tgggacagaa tttactctca ccatcagcag cctgcagcct    300
gaagattttg caacttatta ctgtcaacag catattgaat acccgtggac gttcggccaa    360
gggaccaagg tggaaatcaa acgaggtggc ggagggtctg gggtggcgg atccggaggt     420
ggtggctctc aggtccagct ggtacagtct ggggctgagg tgaagaagcc tggggcttca    480
gtgaaggtct cctgcaaggc ttctggatac acattcactg actactacat gcactgggtg    540
cgacaggccc ctggacaagg gcttgagtgg atgggatatt ttaatcctta taatgattat    600
actagatacg cacagaagtt ccagggcaga gtcaccatga ccagggacac gtctatcagc    660
acagcctaca tggagctgag cagcctgaga tctgacgaca cggccgtgta ttactgtgca    720
agatcggatg gttactacga tgctatggac tactggggtc aaggaaccac agtcaccgtc    780
tcctcgagtg agcccaaatc ttctgacaaa actcacacat gcccaccgtg cccagcacct    840
gaagccgcgg gtgcaccgtc agtcttcctc ttccccccaa aacccaagga caccctcatg    900
atctcccgga cccctgaggt cacatgcgtg gtggtggacg tgagccacga agaccctgag    960
gtcaagttca actggtacgt ggacggcgtg gaggtgcata atgccaagac aaagccgcgg   1020
gaggagcagt acaacagcac gtaccgtgtg gtcagcgtcc tcaccgtcct gcaccaggac   1080
tggctgaatg gcaaggcgta cgcgtgcgcg gtctccaaca aagccctccc agcccccatc   1140
gagaaaacca tctccaaagc caaagggcag ccccgagaac cacaggtgta caccctgccc   1200
ccatcccggg atgagctgac caagaaccag gtcagcctga cctgcctggt caaaggcttc   1260
tatccaagcg acatcgccgt ggagtgggag agcaatgggc agccggagaa caactacaag   1320
accacgcctc ccgtgctgga ctccgacggc tccttcttcc tctacagcaa gctcaccgtg   1380
gacaagagca ggtggcagca ggggaacgtc ttctcatgct ccgtgatgca tgaggctctg   1440
cacaaccact acacgcagaa gagcctctcc ctgtctccgg gtaaatctag aactgtggct   1500
gcaccatctg tcttcatctt cccgccatct gatgagcagt tgaaatctgg aactgcctct   1560
gttgtgtgcc tgctgaatta cttctatccc agagaggcca aagtacagtg gaaggtggat   1620
aacgccctcc aatcgggtaa ctcccaggag agtgccacag agcaggacag caaggacagc   1680
acctacagcc tcagcagcga gctgacgctg agcaaagcag actacgagaa acacaaagtc   1740
tacgcctgcg aagtcaccca tcagggcctg agctcgcccg tcacaaagag cttcaacagg   1800
ggagagtga                                                           1809
```

<210> SEQ ID NO 212
<211> LENGTH: 582
<212> TYPE: PRT
<213> ORGANISM: Artificial Sequence
<220> FEATURE:
<223> OTHER INFORMATION: TSC192

<400> SEQUENCE: 212

```
Asp Ile Gln Met Thr Gln Ser Pro Ser Ala Met Ser Ala Ser Val Gly
1               5                   10                  15

Asp Arg Val Thr Ile Thr Cys Arg Ala Ser Lys Ser Ile Ser Lys Tyr
            20                  25                  30

Leu Ala Trp Phe Gln Gln Lys Pro Gly Lys Val Pro Lys Leu Arg Ile
        35                  40                  45

His Ser Gly Ser Thr Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80
```

```
Glu Asp Phe Ala Thr Tyr Tyr Cys Gln Gln His Ile Glu Tyr Pro Trp
                85                  90                  95

Thr Phe Gly Gln Gly Thr Lys Val Glu Ile Lys Arg Gly Gly Gly Gly
            100                 105                 110

Ser Gly Gly Gly Gly Ser Gly Gly Gly Gly Ser Gln Val Gln Leu Val
        115                 120                 125

Gln Ser Gly Ala Glu Val Lys Lys Pro Gly Ala Ser Val Lys Val Ser
    130                 135                 140

Cys Lys Ala Ser Gly Tyr Thr Phe Thr Asp Tyr Tyr Met His Trp Val
145                 150                 155                 160

Arg Gln Ala Pro Gly Gln Gly Leu Glu Trp Met Gly Tyr Phe Asn Pro
                165                 170                 175

Tyr Asn Asp Tyr Thr Arg Tyr Ala Gln Lys Phe Gln Gly Arg Val Thr
            180                 185                 190

Met Thr Arg Asp Thr Ser Ile Ser Thr Ala Tyr Met Glu Leu Ser Ser
        195                 200                 205

Leu Arg Ser Asp Asp Thr Ala Val Tyr Tyr Cys Ala Arg Ser Asp Gly
    210                 215                 220

Tyr Tyr Asp Ala Met Asp Tyr Trp Gly Gln Gly Thr Thr Val Thr Val
225                 230                 235                 240

Ser Ser Ser Glu Pro Lys Ser Ser Asp Lys Thr His Thr Cys Pro Pro
                245                 250                 255

Cys Pro Ala Pro Glu Ala Ala Gly Ala Pro Ser Val Phe Leu Phe Pro
            260                 265                 270

Pro Lys Pro Lys Asp Thr Leu Met Ile Ser Arg Thr Pro Glu Val Thr
        275                 280                 285

Cys Val Val Val Asp Val Ser His Glu Asp Pro Glu Val Lys Phe Asn
    290                 295                 300

Trp Tyr Val Asp Gly Val Glu Val His Asn Ala Lys Thr Lys Pro Arg
305                 310                 315                 320

Glu Glu Gln Tyr Asn Ser Thr Tyr Arg Val Val Ser Val Leu Thr Val
                325                 330                 335

Leu His Gln Asp Trp Leu Asn Gly Lys Ala Tyr Ala Cys Ala Val Ser
            340                 345                 350

Asn Lys Ala Leu Pro Ala Pro Ile Glu Lys Thr Ile Ser Lys Ala Lys
        355                 360                 365

Gly Gln Pro Arg Glu Pro Gln Val Tyr Thr Leu Pro Pro Ser Arg Asp
    370                 375                 380

Glu Leu Thr Lys Asn Gln Val Ser Leu Thr Cys Leu Val Lys Gly Phe
385                 390                 395                 400

Tyr Pro Ser Asp Ile Ala Val Glu Trp Glu Ser Asn Gly Gln Pro Glu
                405                 410                 415

Asn Asn Tyr Lys Thr Thr Pro Pro Val Leu Asp Ser Asp Gly Ser Phe
            420                 425                 430

Phe Leu Tyr Ser Lys Leu Thr Val Asp Lys Ser Arg Trp Gln Gln Gly
        435                 440                 445

Asn Val Phe Ser Cys Ser Val Met His Glu Ala Leu His Asn His Tyr
    450                 455                 460

Thr Gln Lys Ser Leu Ser Leu Ser Pro Gly Lys Ser Arg Thr Val Ala
465                 470                 475                 480

Ala Pro Ser Val Phe Ile Phe Pro Pro Ser Asp Glu Gln Leu Lys Ser
                485                 490                 495
```

```
Gly Thr Ala Ser Val Val Cys Leu Leu Asn Tyr Phe Tyr Pro Arg Glu
            500                 505                 510

Ala Lys Val Gln Trp Lys Val Asp Asn Ala Leu Gln Ser Gly Asn Ser
        515                 520                 525

Gln Glu Ser Ala Thr Glu Gln Asp Ser Lys Asp Ser Thr Tyr Ser Leu
    530                 535                 540

Ser Ser Glu Leu Thr Leu Ser Lys Ala Asp Tyr Glu Lys His Lys Val
545                 550                 555                 560

Tyr Ala Cys Glu Val Thr His Gln Gly Leu Ser Ser Pro Val Thr Lys
                565                 570                 575

Ser Phe Asn Arg Gly Glu
            580


<210> SEQ ID NO 213
<211> LENGTH: 1809
<212> TYPE: DNA
<213> ORGANISM: Artificial Sequence
<220> FEATURE:
<223> OTHER INFORMATION: TSC193

<400> SEQUENCE: 213

atggaagcac cagcgcagct tctcttcctc ctgctactct ggctcccaga taccaccggt      60

gatatccaga tgacccagtc tccatccgcc atgtctgcat ctgtaggaga cagagtcacc     120

atcacttgcc gggcgagtaa gagcattagc aaatatttag cctggtttca gcagaaacca     180

gggaaagttc ctaagctccg catccattct ggatctactt tgcaatcagg ggtcccatct     240

cggttcagtg gcagtggatc tgggacagaa tttactctca ccatcagcag cctgcagcct     300

gaagattttg caacttatta ctgtcaacag catattgaat acccgtggac gttcggccaa     360

gggaccaagg tggaaatcaa acgaggtggc ggagggtctg gggtggcgg atccggaggt     420

ggtggctctg aggtccagct ggtacagtct ggggctgagg tgaagaagcc tggggctaca     480

gtgaagatct cctgcaaggc ttctggatac acattcactg actactacat gcactgggtg     540

caacaggccc ctggaaaagg gcttgagtgg atgggatatt ttaatcctta taatgattat     600

actagatacg cagagaagtt ccagggcaga gtcaccataa ccgcggacac gtctacagac     660

acagcctaca tggagctgag cagcctgaga tctgaggaca cggccgtgta ttactgtgca     720

agatcggatg gttactacga tgctatggac tactggggtc aaggaaccac agtcaccgtc     780

tcctcgagtg agcccaaatc ttctgacaaa actcacacat gcccaccgtg cccagcacct     840

gaagccgcgg gtgcaccgtc agtcttcctc ttccccccaa aacccaagga caccctcatg     900

atctcccgga cccctgaggt cacatgcgtg gtggtggacg tgagccacga agaccctgag     960

gtcaagttca actggtacgt ggacggcgtg gaggtgcata atgccaagac aaagccgcgg    1020

gaggagcagt acaacagcac gtaccgtgtg gtcagcgtcc tcaccgtcct gcaccaggac    1080

tggctgaatg gcaaggcgta cgcgtgcgcg gtctccaaca aagccctccc agcccccatc    1140

gagaaaacca tctccaaagc caaagggcag ccccgagaac cacaggtgta caccctgccc    1200

ccatcccggg atgagctgac caagaaccag gtcagcctga cctgcctggt caaaggcttc    1260

tatccaagcg acatcgccgt ggagtgggag agcaatgggc agccggagaa caactacaag    1320

accacgcctc ccgtgctgga ctccgacggc tccttcttcc tctacagcaa gctcaccgtg    1380

gacaagagca ggtggcagca ggggaacgtc ttctcatgct ccgtgatgca tgaggctctg    1440

cacaaccact acacgcagaa gagcctctcc ctgtctccgg gtaaatctag aactgtggct    1500

gcaccatctg tcttcatctt cccgccatct gatgagcagt tgaaatctgg aactgcctct    1560
```

```
gttgtgtgcc tgctgaatta cttctatccc agagaggcca aagtacagtg gaaggtggat   1620

aacgccctcc aatcgggtaa ctcccaggag agtgccacag agcaggacag caaggacagc   1680

acctacagcc tcagcagcga gctgacgctg agcaaagcag actacgagaa acacaaagtc   1740

tacgcctgcg aagtcaccca tcagggcctg agctcgcccg tcacaaagag cttcaacagg   1800

ggagagtga                                                           1809


<210> SEQ ID NO 214
<211> LENGTH: 582
<212> TYPE: PRT
<213> ORGANISM: Artificial Sequence
<220> FEATURE:
<223> OTHER INFORMATION: TSC193

<400> SEQUENCE: 214

Asp Ile Gln Met Thr Gln Ser Pro Ser Ala Met Ser Ala Ser Val Gly
1               5                   10                  15

Asp Arg Val Thr Ile Thr Cys Arg Ala Ser Lys Ser Ile Ser Lys Tyr
            20                  25                  30

Leu Ala Trp Phe Gln Gln Lys Pro Gly Lys Val Pro Lys Leu Arg Ile
        35                  40                  45

His Ser Gly Ser Thr Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln His Ile Glu Tyr Pro Trp
                85                  90                  95

Thr Phe Gly Gln Gly Thr Lys Val Glu Ile Lys Arg Gly Gly Gly Gly
            100                 105                 110

Ser Gly Gly Gly Gly Ser Gly Gly Gly Gly Ser Glu Val Gln Leu Val
        115                 120                 125

Gln Ser Gly Ala Glu Val Lys Lys Pro Gly Ala Thr Val Lys Ile Ser
    130                 135                 140

Cys Lys Ala Ser Gly Tyr Thr Phe Thr Asp Tyr Tyr Met His Trp Val
145                 150                 155                 160

Gln Gln Ala Pro Gly Lys Gly Leu Glu Trp Met Gly Tyr Phe Asn Pro
                165                 170                 175

Tyr Asn Asp Tyr Thr Arg Tyr Ala Glu Lys Phe Gln Gly Arg Val Thr
            180                 185                 190

Ile Thr Ala Asp Thr Ser Thr Asp Thr Ala Tyr Met Glu Leu Ser Ser
        195                 200                 205

Leu Arg Ser Glu Asp Thr Ala Val Tyr Tyr Cys Ala Arg Ser Asp Gly
    210                 215                 220

Tyr Tyr Asp Ala Met Asp Tyr Trp Gly Gln Gly Thr Thr Val Thr Val
225                 230                 235                 240

Ser Ser Ser Glu Pro Lys Ser Ser Asp Lys Thr His Thr Cys Pro Pro
                245                 250                 255

Cys Pro Ala Pro Glu Ala Ala Gly Ala Pro Ser Val Phe Leu Phe Pro
            260                 265                 270

Pro Lys Pro Lys Asp Thr Leu Met Ile Ser Arg Thr Pro Glu Val Thr
        275                 280                 285

Cys Val Val Val Asp Val Ser His Glu Asp Pro Glu Val Lys Phe Asn
    290                 295                 300

Trp Tyr Val Asp Gly Val Glu Val His Asn Ala Lys Thr Lys Pro Arg
```

```
            305                 310                 315                 320
Glu Glu Gln Tyr Asn Ser Thr Tyr Arg Val Val Ser Val Leu Thr Val
                325                 330                 335

Leu His Gln Asp Trp Leu Asn Gly Lys Ala Tyr Ala Cys Ala Val Ser
                340                 345                 350

Asn Lys Ala Leu Pro Ala Pro Ile Glu Lys Thr Ile Ser Lys Ala Lys
                355                 360                 365

Gly Gln Pro Arg Glu Pro Gln Val Tyr Thr Leu Pro Pro Ser Arg Asp
370                 375                 380

Glu Leu Thr Lys Asn Gln Val Ser Leu Thr Cys Leu Val Lys Gly Phe
385                 390                 395                 400

Tyr Pro Ser Asp Ile Ala Val Glu Trp Glu Ser Asn Gly Gln Pro Glu
                405                 410                 415

Asn Asn Tyr Lys Thr Thr Pro Pro Val Leu Asp Ser Asp Gly Ser Phe
                420                 425                 430

Phe Leu Tyr Ser Lys Leu Thr Val Asp Lys Ser Arg Trp Gln Gln Gly
                435                 440                 445

Asn Val Phe Ser Cys Ser Val Met His Glu Ala Leu His Asn His Tyr
                450                 455                 460

Thr Gln Lys Ser Leu Ser Leu Ser Pro Gly Lys Ser Arg Thr Val Ala
465                 470                 475                 480

Ala Pro Ser Val Phe Ile Phe Pro Pro Ser Asp Glu Gln Leu Lys Ser
                485                 490                 495

Gly Thr Ala Ser Val Val Cys Leu Leu Asn Tyr Phe Tyr Pro Arg Glu
                500                 505                 510

Ala Lys Val Gln Trp Lys Val Asp Asn Ala Leu Gln Ser Gly Asn Ser
                515                 520                 525

Gln Glu Ser Ala Thr Glu Gln Asp Ser Lys Asp Ser Thr Tyr Ser Leu
                530                 535                 540

Ser Ser Glu Leu Thr Leu Ser Lys Ala Asp Tyr Glu Lys His Lys Val
545                 550                 555                 560

Tyr Ala Cys Glu Val Thr His Gln Gly Leu Ser Ser Pro Val Thr Lys
                565                 570                 575

Ser Phe Asn Arg Gly Glu
                580

<210> SEQ ID NO 215
<211> LENGTH: 1788
<212> TYPE: DNA
<213> ORGANISM: Artificial Sequence
<220> FEATURE:
<223> OTHER INFORMATION: TSC195

<400> SEQUENCE: 215

atggaagcac cagcgcagct tctcttcctc ctgctactct ggctcccaga taccaccggt      60

gatatccaga tgacccagtc tccatccgcc atgtctgcat ctgtaggaga cagagtcacc     120

atcacttgcc gggcgagtaa gagcattagc aaatatttag cctggtttca gcagaaacca     180

gggaaagttc ctaagctccg catccattct ggatctactt tgcaatcagg ggtcccatct     240

cggttcagtg gcagtggatc tgggacagaa tttactctca ccatcagcag cctgcagcct     300

gaagattttg caacttatta ctgtcaacag catattgaat acccgtggac gttcggccaa     360

gggaccaagg tggaaatcaa acgaggtggc ggagggtctg ggggtggcgg atccggaggt     420

ggtggctctc aggtccagct ggtacagtct ggggctgagg tgaagaagcc tggggcttca     480
```

```
gtgaaggtct cctgcaaggc ttctggatac acattcactg actactacat gcactgggtg    540

cgacaggccc ctggacaagg gcttgagtgg atgggatatt ttaatcctta taatgattat    600

actagatacg cacagaagtt ccagggcaga gtcaccatga ccagggacac gtctatcagc    660

acagcctaca tggagctgag cagcctgaga tctgacgaca cggccgtgta ttactgtgca    720

agatcggatg gttactacga tgctatggac tactggggtc aaggaaccac agtcaccgtc    780

tcctcgagtg agcccaaatc ttctgacaaa actcacacat gcccaccgtg cccagcacct    840

gaagccgcgg gtgcaccgtc agtcttcctc ttccccccaa aacccaagga caccctcatg    900

atctcccgga cccctgaggt cacatgcgtg gtggtggacg tgagccacga agaccctgag    960

gtcaagttca actggtacgt ggacggcgtg gaggtgcata atgccaagac aaagccgcgg   1020

gaggagcagt acaacagcac gtaccgtgtg gtcagcgtcc tcaccgtcct gcaccaggac   1080

tggctgaatg gcaaggcgta cgcgtgcgcg gtctccaaca aagccctccc agcccccatc   1140

gagaaaacca tctccaaagc caaagggcag ccccgagaac cacaggtgta caccctgccc   1200

ccatcccggg atgagctgac caagaaccag gtcagcctga cctgcctggt caaaggcttc   1260

tatccaagcg acatcgccgt ggagtgggag agcaatgggc agccggagaa caactacaag   1320

accacgcctc ccgtgctgga ctccgacggc tccttcttcc tctacagcaa gctcaccgtg   1380

gacaagagca ggtggcagca ggggaacgtc ttctcatgct ccgtgatgca tgaggctctg   1440

cacaaccact acacgcagaa gagcctctcc ctgtctccgg gtaaatctag agcctccacc   1500

aagggcccat cggtcttccc cctggcaccc tcctccaaga gcacctctgg gggcacagcg   1560

gccctgggct gcctggtcaa ggactacttc cccgagccgg tgacggtgtc gtggaactca   1620

ggcgccctga ccagcggcgt gcacaccttc ccggctgtcc tacagtcctc aggactctac   1680

tccctcagca gcgtggtgac cgtgccctcc agcagcttgg gcacccagac ctacatctgc   1740

aacgtgaatc acaagcccag caacaccaag gtggacaaga aagtttga                1788
```

```
<210> SEQ ID NO 216
<211> LENGTH: 575
<212> TYPE: PRT
<213> ORGANISM: Artificial Sequence
<220> FEATURE:
<223> OTHER INFORMATION: TSC195

<400> SEQUENCE: 216

Asp Ile Gln Met Thr Gln Ser Pro Ser Ala Met Ser Ala Ser Val Gly
1               5                   10                  15

Asp Arg Val Thr Ile Thr Cys Arg Ala Ser Lys Ser Ile Ser Lys Tyr
            20                  25                  30

Leu Ala Trp Phe Gln Gln Lys Pro Gly Lys Val Pro Lys Leu Arg Ile
        35                  40                  45

His Ser Gly Ser Thr Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln His Ile Glu Tyr Pro Trp
                85                  90                  95

Thr Phe Gly Gln Gly Thr Lys Val Glu Ile Lys Arg Gly Gly Gly Gly
            100                 105                 110

Ser Gly Gly Gly Gly Ser Gly Gly Gly Gly Ser Gln Val Gln Leu Val
        115                 120                 125

Gln Ser Gly Ala Glu Val Lys Lys Pro Gly Ala Ser Val Lys Val Ser
```

```
    130                 135                 140

Cys Lys Ala Ser Gly Tyr Thr Phe Thr Asp Tyr Tyr Met His Trp Val
145                 150                 155                 160

Arg Gln Ala Pro Gly Gln Gly Leu Glu Trp Met Gly Tyr Phe Asn Pro
                165                 170                 175

Tyr Asn Asp Tyr Thr Arg Tyr Ala Gln Lys Phe Gln Gly Arg Val Thr
            180                 185                 190

Met Thr Arg Asp Thr Ser Ile Ser Thr Ala Tyr Met Glu Leu Ser Ser
        195                 200                 205

Leu Arg Ser Asp Asp Thr Ala Val Tyr Tyr Cys Ala Arg Ser Asp Gly
    210                 215                 220

Tyr Tyr Asp Ala Met Asp Tyr Trp Gly Gln Gly Thr Thr Val Thr Val
225                 230                 235                 240

Ser Ser Ser Glu Pro Lys Ser Ser Asp Lys Thr His Thr Cys Pro Pro
                245                 250                 255

Cys Pro Ala Pro Glu Ala Ala Gly Ala Pro Ser Val Phe Leu Phe Pro
            260                 265                 270

Pro Lys Pro Lys Asp Thr Leu Met Ile Ser Arg Thr Pro Glu Val Thr
        275                 280                 285

Cys Val Val Val Asp Val Ser His Glu Asp Pro Glu Val Lys Phe Asn
    290                 295                 300

Trp Tyr Val Asp Gly Val Glu Val His Asn Ala Lys Thr Lys Pro Arg
305                 310                 315                 320

Glu Glu Gln Tyr Asn Ser Thr Tyr Arg Val Val Ser Val Leu Thr Val
                325                 330                 335

Leu His Gln Asp Trp Leu Asn Gly Lys Ala Tyr Ala Cys Ala Val Ser
            340                 345                 350

Asn Lys Ala Leu Pro Ala Pro Ile Glu Lys Thr Ile Ser Lys Ala Lys
        355                 360                 365

Gly Gln Pro Arg Glu Pro Gln Val Tyr Thr Leu Pro Pro Ser Arg Asp
    370                 375                 380

Glu Leu Thr Lys Asn Gln Val Ser Leu Thr Cys Leu Val Lys Gly Phe
385                 390                 395                 400

Tyr Pro Ser Asp Ile Ala Val Glu Trp Glu Ser Asn Gly Gln Pro Glu
                405                 410                 415

Asn Asn Tyr Lys Thr Thr Pro Pro Val Leu Asp Ser Asp Gly Ser Phe
            420                 425                 430

Phe Leu Tyr Ser Lys Leu Thr Val Asp Lys Ser Arg Trp Gln Gln Gly
        435                 440                 445

Asn Val Phe Ser Cys Ser Val Met His Glu Ala Leu His Asn His Tyr
    450                 455                 460

Thr Gln Lys Ser Leu Ser Leu Ser Pro Gly Lys Ser Arg Ala Ser Thr
465                 470                 475                 480

Lys Gly Pro Ser Val Phe Pro Leu Ala Pro Ser Ser Lys Ser Thr Ser
                485                 490                 495

Gly Gly Thr Ala Ala Leu Gly Cys Leu Val Lys Asp Tyr Phe Pro Glu
            500                 505                 510

Pro Val Thr Val Ser Trp Asn Ser Gly Ala Leu Thr Ser Gly Val His
        515                 520                 525

Thr Phe Pro Ala Val Leu Gln Ser Ser Gly Leu Tyr Ser Leu Ser Ser
    530                 535                 540

Val Val Thr Val Pro Ser Ser Ser Leu Gly Thr Gln Thr Tyr Ile Cys
545                 550                 555                 560
```

```
Asn Val Asn His Lys Pro Ser Asn Thr Lys Val Asp Lys Lys Val
                565                 570                 575


<210> SEQ ID NO 217
<211> LENGTH: 1806
<212> TYPE: DNA
<213> ORGANISM: Artificial Sequence
<220> FEATURE:
<223> OTHER INFORMATION: TSC219

<400> SEQUENCE: 217

atggatttc aagtgcagat tttcagcttc ctgctaatca gtgcttcagt cataatgtcg      60

cgaggacagg tccagctggt ggagtctggg ggcggagtgg tgcagcctgg gcggtcactg    120

aggctgtcct gcaaggcttc tggctacacc tttactagat ctacgatgca ctgggtaagg    180

caggcccctg gacaaggtct ggaatggatt ggatacatta atcctagcag tgcttatact    240

aattacaatc agaaattcaa ggacaggttc acaatcagcg cagacaaatc caagagcaca    300

gccttcctgc agatggacag cctgaggccc gaggacaccg gcgtctattt ctgtgcacgg    360

ccccaagtcc actatgatta caacgggttt ccttactggg gccaagggac tcccgtcact    420

gtctctagcg gtggcggagg gtctgggggt ggcggatccg gaggtggtgg ctctgcacaa    480

gacatccaga tgacccagtc tccaagcagc ctgtctgcaa gcgtggggga cagggtcacc    540

atgacctgca gtgccagctc aagtgtaagt tacatgaact ggtaccagca gaagccgggc    600

aaggccccca aaagatggat ttatgactca tccaaactgg cttctggagt ccctgctcgc    660

ttcagtggca gtgggtctgg gaccgactat accctcacaa tcagcagcct gcagcccgaa    720

gatttcgcca cttattactg ccagcagtgg agtcgtaacc cacccacgtt cggagggggg    780

accaagctac aaattacatc ctcgagtgag cccaaatctt ctgacaaaac tcacacatgc    840

ccaccgtgcc cagcacctga agccgcgggt gcaccgtcag tcttcctctt ccccccaaaa    900

cccaaggaca ccctcatgat ctcccggacc cctgaggtca catgcgtggt ggtggacgtg    960

agccacgaag accctgaggt caagttcaac tggtacgtgg acggcgtgga ggtgcataat   1020

gccaagacaa agccgcggga ggagcagtac aacagcacgt accgtgtggt cagcgtcctc   1080

accgtcctgc accaggactg gctgaatggc aaggcgtacg cgtgcgcggt ctccaacaaa   1140

gccctcccag cccccatcga gaaaaccatc tccaaagcca aagggcagcc ccgagaacca   1200

caggtgtaca ccctgccccc atcccgggat gagctgacca agaaccaggt cagcctgacc   1260

tgcctggtca aaggcttcta tccaagcgac atcgccgtgg agtgggagag caatgggcag   1320

ccggagaaca actacaagac cacgcctccc gtgctggact ccgacggctc cttcttcctc   1380

tacagcaagc tcaccgtgga caagagcagg tggcagcagg ggaacgtctt ctcatgctcc   1440

gtgatgcatg aggctctgca caaccactac acgcagaaga gcctctccct gtctccgggt   1500

aaatctagag cctccaccaa gggcccatcg gtcttccccc tggcaccctc ctccaagagc   1560

acctctgggg gcacagcggc cctgggctgc ctggtcaagg actacttccc cgagccggtg   1620

acggtgtcgt ggaactcagg cgccctgacc agcggcgtgc acaccttccc ggctgtccta   1680

cagtcctcag gactctactc cctcagcagc gtggtgaccg tgccctccag cagcttgggc   1740

acccagacct acatctgcaa cgtgaatcac aagcccagca acaccaaggt ggacaagaaa   1800

gtttga                                                              1806


<210> SEQ ID NO 218
<211> LENGTH: 579
```

-continued

<212> TYPE: PRT
<213> ORGANISM: Artificial Sequence
<220> FEATURE:
<223> OTHER INFORMATION: TSC219

<400> SEQUENCE: 218

```
Gln Val Gln Leu Val Glu Ser Gly Gly Gly Val Val Gln Pro Gly Arg
1               5                   10                  15

Ser Leu Arg Leu Ser Cys Lys Ala Ser Gly Tyr Thr Phe Thr Arg Ser
            20                  25                  30

Thr Met His Trp Val Arg Gln Ala Pro Gly Gln Gly Leu Glu Trp Ile
        35                  40                  45

Gly Tyr Ile Asn Pro Ser Ser Ala Tyr Thr Asn Tyr Asn Gln Lys Phe
    50                  55                  60

Lys Asp Arg Phe Thr Ile Ser Ala Asp Lys Ser Lys Ser Thr Ala Phe
65                  70                  75                  80

Leu Gln Met Asp Ser Leu Arg Pro Glu Asp Thr Gly Val Tyr Phe Cys
                85                  90                  95

Ala Arg Pro Gln Val His Tyr Asp Tyr Asn Gly Phe Pro Tyr Trp Gly
            100                 105                 110

Gln Gly Thr Pro Val Thr Val Ser Ser Gly Gly Gly Gly Ser Gly Gly
        115                 120                 125

Gly Gly Ser Gly Gly Gly Gly Ser Ala Gln Asp Ile Gln Met Thr Gln
    130                 135                 140

Ser Pro Ser Ser Leu Ser Ala Ser Val Gly Asp Arg Val Thr Met Thr
145                 150                 155                 160

Cys Ser Ala Ser Ser Ser Val Ser Tyr Met Asn Trp Tyr Gln Gln Lys
                165                 170                 175

Pro Gly Lys Ala Pro Lys Arg Trp Ile Tyr Asp Ser Ser Lys Leu Ala
            180                 185                 190

Ser Gly Val Pro Ala Arg Phe Ser Gly Ser Gly Ser Gly Thr Asp Tyr
        195                 200                 205

Thr Leu Thr Ile Ser Ser Leu Gln Pro Glu Asp Phe Ala Thr Tyr Tyr
    210                 215                 220

Cys Gln Gln Trp Ser Arg Asn Pro Pro Thr Phe Gly Gly Gly Thr Lys
225                 230                 235                 240

Leu Gln Ile Thr Ser Ser Ser Glu Pro Lys Ser Ser Asp Lys Thr His
                245                 250                 255

Thr Cys Pro Pro Cys Pro Ala Pro Glu Ala Ala Gly Ala Pro Ser Val
            260                 265                 270

Phe Leu Phe Pro Pro Lys Pro Lys Asp Thr Leu Met Ile Ser Arg Thr
        275                 280                 285

Pro Glu Val Thr Cys Val Val Val Asp Val Ser His Glu Asp Pro Glu
    290                 295                 300

Val Lys Phe Asn Trp Tyr Val Asp Gly Val Glu Val His Asn Ala Lys
305                 310                 315                 320

Thr Lys Pro Arg Glu Glu Gln Tyr Asn Ser Thr Tyr Arg Val Val Ser
                325                 330                 335

Val Leu Thr Val Leu His Gln Asp Trp Leu Asn Gly Lys Ala Tyr Ala
            340                 345                 350

Cys Ala Val Ser Asn Lys Ala Leu Pro Ala Pro Ile Glu Lys Thr Ile
        355                 360                 365

Ser Lys Ala Lys Gly Gln Pro Arg Glu Pro Gln Val Tyr Thr Leu Pro
    370                 375                 380
```

```
Pro Ser Arg Asp Glu Leu Thr Lys Asn Gln Val Ser Leu Thr Cys Leu
385                 390                 395                 400

Val Lys Gly Phe Tyr Pro Ser Asp Ile Ala Val Glu Trp Glu Ser Asn
                405                 410                 415

Gly Gln Pro Glu Asn Asn Tyr Lys Thr Thr Pro Pro Val Leu Asp Ser
            420                 425                 430

Asp Gly Ser Phe Phe Leu Tyr Ser Lys Leu Thr Val Asp Lys Ser Arg
        435                 440                 445

Trp Gln Gln Gly Asn Val Phe Ser Cys Ser Val Met His Glu Ala Leu
    450                 455                 460

His Asn His Tyr Thr Gln Lys Ser Leu Ser Leu Ser Pro Gly Lys Ser
465                 470                 475                 480

Arg Ala Ser Thr Lys Gly Pro Ser Val Phe Pro Leu Ala Pro Ser Ser
                485                 490                 495

Lys Ser Thr Ser Gly Gly Thr Ala Ala Leu Gly Cys Leu Val Lys Asp
            500                 505                 510

Tyr Phe Pro Glu Pro Val Thr Val Ser Trp Asn Ser Gly Ala Leu Thr
        515                 520                 525

Ser Gly Val His Thr Phe Pro Ala Val Leu Gln Ser Ser Gly Leu Tyr
    530                 535                 540

Ser Leu Ser Ser Val Val Thr Val Pro Ser Ser Ser Leu Gly Thr Gln
545                 550                 555                 560

Thr Tyr Ile Cys Asn Val Asn His Lys Pro Ser Asn Thr Lys Val Asp
                565                 570                 575

Lys Lys Val


<210> SEQ ID NO 219
<211> LENGTH: 1809
<212> TYPE: DNA
<213> ORGANISM: Artificial Sequence
<220> FEATURE:
<223> OTHER INFORMATION: TSC220

<400> SEQUENCE: 219

atggaagcac cagcgcagct tctcttcctc ctgctactct ggctcccaga taccaccggt      60

caggtccagc ttgtgcagtc tggggctgag gtgaagaagc ctggggcctc agtgaaggtt     120

tcctgcaagg cttctggata caccttcact agatctacga tgcactgggt gcgccaggcc     180

cccggacaaa ggcttgagtg gatgggatac attaatccta gcagtgctta tactaattac     240

aatcagaaat tcaaggacag agtcaccatt accagggaca catccgcgag cacagcctac     300

atggagctga gcagcctgag atctgaagac acggctgtgt attactgtgc gagaccccaa     360

gtccactatg attacaacgg gtttccttac tggggccaag gaaccctggt caccgtctcc     420

tcaggtggag gcggttcagg cggaggtgga tccggcggtg gcggatcggg tggcggcgga     480

tctgaaattg tgttgacaca gtctccagcc accctgtctt tgtctccagg ggaaagagcc     540

accctctcct gcagtgccag ctcaagtgta agttacatga actggtacca acagaaacct     600

ggccaggctc ccaggctcct catctatgac tcatccaaac tggcttctgg catcccagcc     660

aggttcagtg gcagtgggtc tgggacagac ttcactctca ccatcagcag cctagagcct     720

gaagattttg cagtttatta ctgtcagcag tggagtcgta acccacccac tttcggcgga     780

gggaccaagg tggagatcaa atcctcgagt gagcccaaat cttctgacaa aactcacaca     840

tgcccaccgt gcccagcacc tgaagccgcg ggtgcaccgt cagtcttcct cttcccccca     900

aaacccaagg acaccctcat gatctcccgg acccctgagg tcacatgcgt ggtggtggac     960
```

```
gtgagccacg aagaccctga ggtcaagttc aactggtacg tggacggcgt ggaggtgcat   1020

aatgccaaga caaagccgcg ggaggagcag tacaacagca cgtaccgtgt ggtcagcgtc   1080

ctcaccgtcc tgcaccagga ctggctgaat ggcaaggcgt acgcgtgcgc ggtctccaac   1140

aaagccctcc cagcccccat cgagaaaacc atctccaaag ccaaagggca gccccgagaa   1200

ccacaggtgt acaccctgcc cccatcccgg gatgagctga ccaagaacca ggtcagcctg   1260

acctgcctgg tcaaaggctt ctatccaagc gacatcgccg tggagtggga gagcaatggg   1320

cagccggaga acaactacaa gaccacgcct cccgtgctgg actccgacgg ctccttcttc   1380

ctctacagca agctcaccgt ggacaagagc aggtggcagc aggggaacgt cttctcatgc   1440

tccgtgatgc atgaggctct gcacaaccac tacacgcaga agagcctctc cctgtctccg   1500

ggtaaatcta gagcctccac caagggccca tcggtcttcc ccctggcacc ctcctccaag   1560

agcacctctg ggggcacagc ggccctgggc tgcctggtca aggactactt ccccgagccg   1620

gtgacggtgt cgtggaactc aggcgccctg accagcggcg tgcacacctt cccggctgtc   1680

ctacagtcct caggactcta ctccctcagc agcgtggtga ccgtgccctc cagcagcttg   1740

ggcacccaga cctacatctg caacgtgaat cacaagccca gcaacaccaa ggtggacaag   1800

aaagtttga                                                           1809
```

<210> SEQ ID NO 220
<211> LENGTH: 582
<212> TYPE: PRT
<213> ORGANISM: Artificial Sequence
<220> FEATURE:
<223> OTHER INFORMATION: TSC220

<400> SEQUENCE: 220

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Arg Ser
            20                  25                  30

Thr Met His Trp Val Arg Gln Ala Pro Gly Gln Arg Leu Glu Trp Met
        35                  40                  45

Gly Tyr Ile Asn Pro Ser Ser Ala Tyr Thr Asn Tyr Asn Gln Lys Phe
    50                  55                  60

Lys Asp Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Pro Gln Val His Tyr Asp Tyr Asn Gly Phe Pro Tyr Trp Gly
            100                 105                 110

Gln Gly Thr Leu Val Thr Val Ser Ser Gly Gly Gly Gly Ser Gly Gly
        115                 120                 125

Gly Gly Ser Gly Gly Gly Gly Ser Gly Gly Gly Gly Ser Glu Ile Val
    130                 135                 140

Leu Thr Gln Ser Pro Ala Thr Leu Ser Leu Ser Pro Gly Glu Arg Ala
145                 150                 155                 160

Thr Leu Ser Cys Ser Ala Ser Ser Ser Val Ser Tyr Met Asn Trp Tyr
                165                 170                 175

Gln Gln Lys Pro Gly Gln Ala Pro Arg Leu Leu Ile Tyr Asp Ser Ser
            180                 185                 190

Lys Leu Ala Ser Gly Ile Pro Ala Arg Phe Ser Gly Ser Gly Ser Gly
        195                 200                 205
```

Thr Asp Phe Thr Leu Thr Ile Ser Ser Leu Glu Pro Glu Asp Phe Ala
    210                 215                 220

Val Tyr Tyr Cys Gln Gln Trp Ser Arg Asn Pro Pro Thr Phe Gly Gly
225                 230                 235                 240

Gly Thr Lys Val Glu Ile Lys Ser Ser Ser Glu Pro Lys Ser Ser Asp
                245                 250                 255

Lys Thr His Thr Cys Pro Pro Cys Pro Ala Pro Glu Ala Ala Gly Ala
            260                 265                 270

Pro Ser Val Phe Leu Phe Pro Pro Lys Pro Lys Asp Thr Leu Met Ile
        275                 280                 285

Ser Arg Thr Pro Glu Val Thr Cys Val Val Val Asp Val Ser His Glu
    290                 295                 300

Asp Pro Glu Val Lys Phe Asn Trp Tyr Val Asp Gly Val Glu Val His
305                 310                 315                 320

Asn Ala Lys Thr Lys Pro Arg Glu Glu Gln Tyr Asn Ser Thr Tyr Arg
                325                 330                 335

Val Val Ser Val Leu Thr Val Leu His Gln Asp Trp Leu Asn Gly Lys
            340                 345                 350

Ala Tyr Ala Cys Ala Val Ser Asn Lys Ala Leu Pro Ala Pro Ile Glu
        355                 360                 365

Lys Thr Ile Ser Lys Ala Lys Gly Gln Pro Arg Glu Pro Gln Val Tyr
    370                 375                 380

Thr Leu Pro Pro Ser Arg Asp Glu Leu Thr Lys Asn Gln Val Ser Leu
385                 390                 395                 400

Thr Cys Leu Val Lys Gly Phe Tyr Pro Ser Asp Ile Ala Val Glu Trp
                405                 410                 415

Glu Ser Asn Gly Gln Pro Glu Asn Asn Tyr Lys Thr Thr Pro Pro Val
            420                 425                 430

Leu Asp Ser Asp Gly Ser Phe Phe Leu Tyr Ser Lys Leu Thr Val Asp
        435                 440                 445

Lys Ser Arg Trp Gln Gln Gly Asn Val Phe Ser Cys Ser Val Met His
    450                 455                 460

Glu Ala Leu His Asn His Tyr Thr Gln Lys Ser Leu Ser Leu Ser Pro
465                 470                 475                 480

Gly Lys Ser Arg Ala Ser Thr Lys Gly Pro Ser Val Phe Pro Leu Ala
                485                 490                 495

Pro Ser Ser Lys Ser Thr Ser Gly Gly Thr Ala Ala Leu Gly Cys Leu
            500                 505                 510

Val Lys Asp Tyr Phe Pro Glu Pro Val Thr Val Ser Trp Asn Ser Gly
        515                 520                 525

Ala Leu Thr Ser Gly Val His Thr Phe Pro Ala Val Leu Gln Ser Ser
    530                 535                 540

Gly Leu Tyr Ser Leu Ser Ser Val Val Thr Val Pro Ser Ser Ser Leu
545                 550                 555                 560

Gly Thr Gln Thr Tyr Ile Cys Asn Val Asn His Lys Pro Ser Asn Thr
                565                 570                 575

Lys Val Asp Lys Lys Val
            580

<210> SEQ ID NO 221
<211> LENGTH: 1827
<212> TYPE: DNA
<213> ORGANISM: Artificial Sequence
<220> FEATURE:

<223> OTHER INFORMATION: TSC222

<400> SEQUENCE: 221 atggatttc aagtgcagat tttcagcttc ctgctaatca gtgcttcagt cataatgtcg 60
cgaggacagg tccagctggt ggagtctggg ggcggagtgg tgcagcctgg gcggtcactg 120
aggctgtcct gcaaggcttc tggctacacc tttactagat ctacgatgca ctgggtaagg 180
caggcccctg gacaaggtct ggaatggatt ggatacatta atcctagcag tgcttatact 240
aattacaatc agaaattcaa ggacaggttc acaatcagcg cagacaaatc caagagcaca 300
gccttcctgc agatggacag cctgaggccc gaggacaccg gcgtctattt ctgtgcacgg 360
ccccaagtcc actatgatta caacgggttt ccttactggg gccaagggac tcccgtcact 420
gtctctagcg gtggcggagg gtctgggggt ggcggatccg gaggtggtgg ctctgcacaa 480
gacatccaga tgacccagtc tccaagcagc ctgtctgcaa gcgtggggga cagggtcacc 540
atgacctgca gtgccagctc aagtgtaagt tacatgaact ggtaccagca gaagccgggc 600
aaggccccca aaagatggat ttatgactca tccaaactgg cttctggagt ccctgctcgc 660
ttcagtggca gtgggtctgg gaccgactat accctcacaa tcagcagcct gcagcccgaa 720
gatttcgcca cttattactg ccagcagtgg agtcgtaacc cacccacgtt cggagggggg 780
accaagctac aaattacatc ctcgagtgag cccaaatctt ctgacaaaac tcacacatgc 840
ccaccgtgcc cagcacctga agccgcgggt gcaccgtcag tcttcctctt ccccccaaaa 900
cccaaggaca ccctcatgat ctcccggacc cctgaggtca catgcgtggt ggtggacgtg 960
agccacgaag accctgaggt caagttcaac tggtacgtgg acggcgtgga ggtgcataat 1020
gccaagacaa agccgcggga ggagcagtac aacagcacgt accgtgtggt cagcgtcctc 1080
accgtcctgc accaggactg gctgaatggc aaggcgtacg cgtgcgcggt ctccaacaaa 1140
gccctcccag cccccatcga gaaaaccatc tccaaagcca aagggcagcc ccgagaacca 1200
caggtgtaca ccctgccccc atcccgggat gagctgacca agaaccaggt cagcctgacc 1260
tgcctggtca aaggcttcta tccaagcgac atcgccgtgg agtgggagag caatgggcag 1320
ccggagaaca actacaagac cacgcctccc gtgctggact ccgacggctc cttcttcctc 1380
tacagcaagc tcaccgtgga caagagcagg tggcagcagg ggaacgtctt ctcatgctcc 1440
gtgatgcatg aggctctgca caaccactac acgcagaaga gcctctccct gtctccgggt 1500
aaatctagaa ctgtggctgc accatctgtc ttcatcttcc cgccatctga tgagcagttg 1560
aaatctggaa ctgcctctgt tgtgtgcctg ctgaattact tctatcccag agaggccaaa 1620
gtacagtgga aggtggataa cgccctccaa tcgggtaact cccaggagag tgccacagag 1680
caggacagca aggacagcac ctacagcctc agcagcgagc tgacgctgag caaagcagac 1740
tacgagaaac acaaagtcta cgcctgcgaa gtcacccatc agggcctgag ctcgcccgtc 1800
acaaagagct tcaacagggg agagtga 1827

<210> SEQ ID NO 222
<211> LENGTH: 586
<212> TYPE: PRT
<213> ORGANISM: Artificial Sequence
<220> FEATURE:
<223> OTHER INFORMATION: TSC222

<400> SEQUENCE: 222

Gln Val Gln Leu Val Glu Ser Gly Gly Gly Val Val Gln Pro Gly Arg
1 5 10 15

```
Ser Leu Arg Leu Ser Cys Lys Ala Ser Gly Tyr Thr Phe Thr Arg Ser
            20                  25                  30

Thr Met His Trp Val Arg Gln Ala Pro Gly Gln Gly Leu Glu Trp Ile
        35                  40                  45

Gly Tyr Ile Asn Pro Ser Ser Ala Tyr Thr Asn Tyr Asn Gln Lys Phe
    50                  55                  60

Lys Asp Arg Phe Thr Ile Ser Ala Asp Lys Ser Lys Ser Thr Ala Phe
65                  70                  75                  80

Leu Gln Met Asp Ser Leu Arg Pro Glu Asp Thr Gly Val Tyr Phe Cys
                85                  90                  95

Ala Arg Pro Gln Val His Tyr Asp Tyr Asn Gly Phe Pro Tyr Trp Gly
            100                 105                 110

Gln Gly Thr Pro Val Thr Val Ser Ser Gly Gly Gly Gly Ser Gly Gly
        115                 120                 125

Gly Gly Ser Gly Gly Gly Gly Ser Ala Gln Asp Ile Gln Met Thr Gln
    130                 135                 140

Ser Pro Ser Ser Leu Ser Ala Ser Val Gly Asp Arg Val Thr Met Thr
145                 150                 155                 160

Cys Ser Ala Ser Ser Ser Val Ser Tyr Met Asn Trp Tyr Gln Gln Lys
                165                 170                 175

Pro Gly Lys Ala Pro Lys Arg Trp Ile Tyr Asp Ser Ser Lys Leu Ala
            180                 185                 190

Ser Gly Val Pro Ala Arg Phe Ser Gly Ser Gly Ser Gly Thr Asp Tyr
        195                 200                 205

Thr Leu Thr Ile Ser Ser Leu Gln Pro Glu Asp Phe Ala Thr Tyr Tyr
    210                 215                 220

Cys Gln Gln Trp Ser Arg Asn Pro Pro Thr Phe Gly Gly Gly Thr Lys
225                 230                 235                 240

Leu Gln Ile Thr Ser Ser Ser Glu Pro Lys Ser Ser Asp Lys Thr His
                245                 250                 255

Thr Cys Pro Pro Cys Pro Ala Pro Glu Ala Ala Gly Ala Pro Ser Val
            260                 265                 270

Phe Leu Phe Pro Pro Lys Pro Lys Asp Thr Leu Met Ile Ser Arg Thr
        275                 280                 285

Pro Glu Val Thr Cys Val Val Val Asp Val Ser His Glu Asp Pro Glu
    290                 295                 300

Val Lys Phe Asn Trp Tyr Val Asp Gly Val Glu Val His Asn Ala Lys
305                 310                 315                 320

Thr Lys Pro Arg Glu Glu Gln Tyr Asn Ser Thr Tyr Arg Val Val Ser
                325                 330                 335

Val Leu Thr Val Leu His Gln Asp Trp Leu Asn Gly Lys Ala Tyr Ala
            340                 345                 350

Cys Ala Val Ser Asn Lys Ala Leu Pro Ala Pro Ile Glu Lys Thr Ile
        355                 360                 365

Ser Lys Ala Lys Gly Gln Pro Arg Glu Pro Gln Val Tyr Thr Leu Pro
    370                 375                 380

Pro Ser Arg Asp Glu Leu Thr Lys Asn Gln Val Ser Leu Thr Cys Leu
385                 390                 395                 400

Val Lys Gly Phe Tyr Pro Ser Asp Ile Ala Val Glu Trp Glu Ser Asn
                405                 410                 415

Gly Gln Pro Glu Asn Asn Tyr Lys Thr Thr Pro Pro Val Leu Asp Ser
            420                 425                 430

Asp Gly Ser Phe Phe Leu Tyr Ser Lys Leu Thr Val Asp Lys Ser Arg
```

```
        435                 440                 445

Trp Gln Gln Gly Asn Val Phe Ser Cys Ser Val Met His Glu Ala Leu
    450                 455                 460

His Asn His Tyr Thr Gln Lys Ser Leu Ser Leu Ser Pro Gly Lys Ser
465                 470                 475                 480

Arg Thr Val Ala Ala Pro Ser Val Phe Ile Phe Pro Pro Ser Asp Glu
                485                 490                 495

Gln Leu Lys Ser Gly Thr Ala Ser Val Val Cys Leu Leu Asn Tyr Phe
            500                 505                 510

Tyr Pro Arg Glu Ala Lys Val Gln Trp Lys Val Asp Asn Ala Leu Gln
        515                 520                 525

Ser Gly Asn Ser Gln Glu Ser Ala Thr Glu Gln Asp Ser Lys Asp Ser
    530                 535                 540

Thr Tyr Ser Leu Ser Ser Glu Leu Thr Leu Ser Lys Ala Asp Tyr Glu
545                 550                 555                 560

Lys His Lys Val Tyr Ala Cys Glu Val Thr His Gln Gly Leu Ser Ser
                565                 570                 575

Pro Val Thr Lys Ser Phe Asn Arg Gly Glu
            580                 585


<210> SEQ ID NO 223
<211> LENGTH: 1830
<212> TYPE: DNA
<213> ORGANISM: Artificial Sequence
<220> FEATURE:
<223> OTHER INFORMATION: TSC223

<400> SEQUENCE: 223

atggaagcac cagcgcagct tctcttcctc ctgctactct ggctcccaga taccaccggt     60

caggtccagc ttgtgcagtc tggggctgag gtgaagaagc ctggggcctc agtgaaggtt    120

tcctgcaagg cttctggata caccttcact agatctacga tgcactgggt gcgccaggcc    180

cccggacaaa ggcttgagtg gatgggatac attaatccta gcagtgctta tactaattac    240

aatcagaaat tcaaggacag agtcaccatt accagggaca catccgcgag cacagcctac    300

atggagctga gcagcctgag atctgaagac acggctgtgt attactgtgc gagaccccaa    360

gtccactatg attacaacgg gtttccttac tggggccaag gaaccctggt caccgtctcc    420

tcaggtggag gcggttcagg cggaggtgga tccggcggtg gcggatcggg tggcggcgga    480

tctgaaattg tgttgacaca gtctccagcc accctgtctt tgtctccagg ggaaagagcc    540

accctctcct gcagtgccag ctcaagtgta agttacatga actggtacca acagaaacct    600

ggccaggctc ccaggctcct catctatgac tcatccaaac tggcttctgg catcccagcc    660

aggttcagtg gcagtgggtc tgggacagac ttcactctca ccatcagcag cctagagcct    720

gaagattttg cagtttatta ctgtcagcag tggagtcgta acccacccac tttcggcgga    780

gggaccaagg tggagatcaa atcctcgagt gagcccaaat cttctgacaa aactcacaca    840

tgcccaccgt gcccagcacc tgaagccgcg ggtgcaccgt cagtcttcct cttcccccca    900

aaacccaagg acaccctcat gatctcccgg acccctgagg tcacatgcgt ggtggtggac    960

gtgagccacg aagaccctga ggtcaagttc aactggtacg tggacggcgt ggaggtgcat   1020

aatgccaaga caaagccgcg ggaggagcag tacaacagca cgtaccgtgt ggtcagcgtc   1080

ctcaccgtcc tgcaccagga ctggctgaat ggcaaggcgt acgcgtgcgc ggtctccaac   1140

aaagccctcc cagcccccat cgagaaaacc atctccaaag ccaaagggca gccccgagaa   1200
```

```
ccacaggtgt acaccctgcc cccatcccgg gatgagctga ccaagaacca ggtcagcctg   1260

acctgcctgg tcaaaggctt ctatccaagc gacatcgccg tggagtggga gagcaatggg   1320

cagccggaga acaactacaa gaccacgcct cccgtgctgg actccgacgg ctccttcttc   1380

ctctacagca agctcaccgt ggacaagagc aggtggcagc aggggaacgt cttctcatgc   1440

tccgtgatgc atgaggctct gcacaaccac tacacgcaga agagcctctc cctgtctccg   1500

ggtaaatcta gaactgtggc tgcaccatct gtcttcatct tcccgccatc tgatgagcag   1560

ttgaaatctg gaactgcctc tgttgtgtgc ctgctgaatt acttctatcc cagagaggcc   1620

aaagtacagt ggaaggtgga taacgccctc caatcgggta actcccagga gagtgccaca   1680

gagcaggaca gcaaggacag cacctacagc ctcagcagcg agctgacgct gagcaaagca   1740

gactacgaga aacacaaagt ctacgcctgc gaagtcaccc atcagggcct gagctcgccc   1800

gtcacaaaga gcttcaacag gggagagtga                                    1830
```

<210> SEQ ID NO 224
<211> LENGTH: 589
<212> TYPE: PRT
<213> ORGANISM: Artificial Sequence
<220> FEATURE:
<223> OTHER INFORMATION: TSC223

<400> SEQUENCE: 224

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Arg Ser
            20                  25                  30

Thr Met His Trp Val Arg Gln Ala Pro Gly Gln Arg Leu Glu Trp Met
        35                  40                  45

Gly Tyr Ile Asn Pro Ser Ser Ala Tyr Thr Asn Tyr Asn Gln Lys Phe
    50                  55                  60

Lys Asp Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Pro Gln Val His Tyr Asp Tyr Asn Gly Phe Pro Tyr Trp Gly
            100                 105                 110

Gln Gly Thr Leu Val Thr Val Ser Ser Gly Gly Gly Gly Ser Gly Gly
        115                 120                 125

Gly Gly Ser Gly Gly Gly Gly Ser Gly Gly Gly Gly Ser Glu Ile Val
    130                 135                 140

Leu Thr Gln Ser Pro Ala Thr Leu Ser Leu Ser Pro Gly Glu Arg Ala
145                 150                 155                 160

Thr Leu Ser Cys Ser Ala Ser Ser Ser Val Ser Tyr Met Asn Trp Tyr
                165                 170                 175

Gln Gln Lys Pro Gly Gln Ala Pro Arg Leu Leu Ile Tyr Asp Ser Ser
            180                 185                 190

Lys Leu Ala Ser Gly Ile Pro Ala Arg Phe Ser Gly Ser Gly Ser Gly
        195                 200                 205

Thr Asp Phe Thr Leu Thr Ile Ser Ser Leu Glu Pro Glu Asp Phe Ala
    210                 215                 220

Val Tyr Tyr Cys Gln Gln Trp Ser Arg Asn Pro Pro Thr Phe Gly Gly
225                 230                 235                 240

Gly Thr Lys Val Glu Ile Lys Ser Ser Ser Glu Pro Lys Ser Ser Asp
                245                 250                 255
```

```
Lys Thr His Thr Cys Pro Pro Cys Pro Ala Pro Glu Ala Ala Gly Ala
            260                 265                 270

Pro Ser Val Phe Leu Phe Pro Pro Lys Pro Lys Asp Thr Leu Met Ile
        275                 280                 285

Ser Arg Thr Pro Glu Val Thr Cys Val Val Val Asp Val Ser His Glu
    290                 295                 300

Asp Pro Glu Val Lys Phe Asn Trp Tyr Val Asp Gly Val Glu Val His
305                 310                 315                 320

Asn Ala Lys Thr Lys Pro Arg Glu Glu Gln Tyr Asn Ser Thr Tyr Arg
                325                 330                 335

Val Val Ser Val Leu Thr Val Leu His Gln Asp Trp Leu Asn Gly Lys
            340                 345                 350

Ala Tyr Ala Cys Ala Val Ser Asn Lys Ala Leu Pro Ala Pro Ile Glu
        355                 360                 365

Lys Thr Ile Ser Lys Ala Lys Gly Gln Pro Arg Glu Pro Gln Val Tyr
    370                 375                 380

Thr Leu Pro Pro Ser Arg Asp Glu Leu Thr Lys Asn Gln Val Ser Leu
385                 390                 395                 400

Thr Cys Leu Val Lys Gly Phe Tyr Pro Ser Asp Ile Ala Val Glu Trp
                405                 410                 415

Glu Ser Asn Gly Gln Pro Glu Asn Asn Tyr Lys Thr Thr Pro Pro Val
            420                 425                 430

Leu Asp Ser Asp Gly Ser Phe Phe Leu Tyr Ser Lys Leu Thr Val Asp
        435                 440                 445

Lys Ser Arg Trp Gln Gln Gly Asn Val Phe Ser Cys Ser Val Met His
    450                 455                 460

Glu Ala Leu His Asn His Tyr Thr Gln Lys Ser Leu Ser Leu Ser Pro
465                 470                 475                 480

Gly Lys Ser Arg Thr Val Ala Ala Pro Ser Val Phe Ile Phe Pro Pro
                485                 490                 495

Ser Asp Glu Gln Leu Lys Ser Gly Thr Ala Ser Val Val Cys Leu Leu
            500                 505                 510

Asn Tyr Phe Tyr Pro Arg Glu Ala Lys Val Gln Trp Lys Val Asp Asn
        515                 520                 525

Ala Leu Gln Ser Gly Asn Ser Gln Glu Ser Ala Thr Glu Gln Asp Ser
    530                 535                 540

Lys Asp Ser Thr Tyr Ser Leu Ser Ser Glu Leu Thr Leu Ser Lys Ala
545                 550                 555                 560

Asp Tyr Glu Lys His Lys Val Tyr Ala Cys Glu Val Thr His Gln Gly
                565                 570                 575

Leu Ser Ser Pro Val Thr Lys Ser Phe Asn Arg Gly Glu
            580                 585
```

<210> SEQ ID NO 225
<211> LENGTH: 1803
<212> TYPE: DNA
<213> ORGANISM: Artificial Sequence
<220> FEATURE:
<223> OTHER INFORMATION: TSC254

<400> SEQUENCE: 225

```
atggaagcac cagcgcagct tctcttcctc ctgctactct ggctcccaga taccaccggt     60

gatatccaga tgacccagtc tccatccgcc atgtctgcat ctgtaggaga cagagtcacc    120

atcacttgcc gggcgagtaa gagcattagc aaatatttag cctggtttca gcagaaacca    180
```

```
gggaaagttc ctaagctccg catccattct ggatctactt tgcaatcagg ggtcccatct    240

cggttcagtg gcagtggatc tgggacagaa tttactctca ccatcagcag cctgcagcct    300

gaagattttg caacttatta ctgtcaacag catattgaat acccgtggac gttcggccaa    360

gggaccaagg tggaaatcaa acgaggtggc ggagggtctg ggggtggcgg atccggaggt    420

ggtggctctg aggtccagct ggtacagtct ggggctgagg tgaagaagcc tggggctaca    480

gtgaagatct cctgcaaggc ttctggatac acattcactg actactacat gcactgggtg    540

caacaggccc ctggaaaagg gcttgagtgg atgggatatt ttaatcctta taatgattat    600

actagatacg cagagaagtt ccagggcaga gtcaccataa ccgcggacac gtctacagac    660

acagcctaca tggagctgag cagcctgaga tctgaggaca cggccgtgta ttactgtgca    720

agatcggatg gttactacga tgctatggac tactggggtc aaggaaccac agtcaccgtc    780

tcctcgagtg agcccaaatc ttctgacaaa actcacacat gcccaccgtg cccagcacct    840

gaagccgcgg gtgcaccgtc agtcttcctc ttccccccaa aacccaagga caccctcatg    900

atctcccgga cccctgaggt cacatgcgtg gtggtggacg tgagccacga agaccctgag    960

gtcaagttca actggtacgt ggacggcgtg gaggtgcata atgccaagac aaagccgcgg   1020

gaggagcagt acaacagcac gtaccgtgtg gtcagcgtcc tcaccgtcct gcaccaggac   1080

tggctgaatg gcaaggcgta cgcgtgcgcg gtctccaaca aagccctccc agcccccatc   1140

gagaaaacca tctccaaagc caaagggcag ccccgagaac cacaggtgta caccctgccc   1200

ccatcccggg atgagctgac caagaaccag gtcagcctga cctgcctggt caaaggcttc   1260

tatccaagcg acatcgccgt ggagtgggag agcaatgggc agccggagaa caactacaag   1320

accacgcctc ccgtgctgga ctccgacggc tccttcttcc tctacagcaa gctcaccgtg   1380

gacaagagca ggtggcagca ggggaacgtc ttctcatgct ccgtgatgca tgaggctctg   1440

cacaaccact acacgcagaa gagcctctcc ctgtctccgg gttcttccct gaatacaccg   1500

aactctgcct ccaccaaggg cccatcggtc ttccccctgg caccctcctc caagagcacc   1560

tctgggggca cagcggccct gggctgcctg gtcaaggact acttccccga gccggtgacg   1620

gtgtcgtgga actcaggcgc cctgaccagc ggcgtgcaca ccttcccggc tgtcctacag   1680

tcctcaggac tctactccct cagcagcgtg gtgaccgtgc cctccagcag cttgggcacc   1740

cagacctaca tctgcaacgt gaatcacaag cccagcaaca ccaaggtgga caagaaagtt   1800

tga                                                                 1803
```

```
<210> SEQ ID NO 226
<211> LENGTH: 580
<212> TYPE: PRT
<213> ORGANISM: Artificial Sequence
<220> FEATURE:
<223> OTHER INFORMATION: TSC254

<400> SEQUENCE: 226

Asp Ile Gln Met Thr Gln Ser Pro Ser Ala Met Ser Ala Ser Val Gly
1               5                   10                  15

Asp Arg Val Thr Ile Thr Cys Arg Ala Ser Lys Ser Ile Ser Lys Tyr
            20                  25                  30

Leu Ala Trp Phe Gln Gln Lys Pro Gly Lys Val Pro Lys Leu Arg Ile
        35                  40                  45

His Ser Gly Ser Thr Leu Gln Ser Gly Val Pro Ser Arg Phe Ser Gly
    50                  55                  60
```

```
Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln His Ile Glu Tyr Pro Trp
                85                  90                  95

Thr Phe Gly Gln Gly Thr Lys Val Glu Ile Lys Arg Gly Gly Gly Gly
            100                 105                 110

Ser Gly Gly Gly Gly Ser Gly Gly Gly Gly Ser Glu Val Gln Leu Val
        115                 120                 125

Gln Ser Gly Ala Glu Val Lys Lys Pro Gly Ala Thr Val Lys Ile Ser
    130                 135                 140

Cys Lys Ala Ser Gly Tyr Thr Phe Thr Asp Tyr Tyr Met His Trp Val
145                 150                 155                 160

Gln Gln Ala Pro Gly Lys Gly Leu Glu Trp Met Gly Tyr Phe Asn Pro
                165                 170                 175

Tyr Asn Asp Tyr Thr Arg Tyr Ala Glu Lys Phe Gln Gly Arg Val Thr
            180                 185                 190

Ile Thr Ala Asp Thr Ser Thr Asp Thr Ala Tyr Met Glu Leu Ser Ser
        195                 200                 205

Leu Arg Ser Glu Asp Thr Ala Val Tyr Tyr Cys Ala Arg Ser Asp Gly
    210                 215                 220

Tyr Tyr Asp Ala Met Asp Tyr Trp Gly Gln Gly Thr Thr Val Thr Val
225                 230                 235                 240

Ser Ser Ser Glu Pro Lys Ser Ser Asp Lys Thr His Thr Cys Pro Pro
                245                 250                 255

Cys Pro Ala Pro Glu Ala Ala Gly Ala Pro Ser Val Phe Leu Phe Pro
            260                 265                 270

Pro Lys Pro Lys Asp Thr Leu Met Ile Ser Arg Thr Pro Glu Val Thr
        275                 280                 285

Cys Val Val Val Asp Val Ser His Glu Asp Pro Glu Val Lys Phe Asn
    290                 295                 300

Trp Tyr Val Asp Gly Val Glu Val His Asn Ala Lys Thr Lys Pro Arg
305                 310                 315                 320

Glu Glu Gln Tyr Asn Ser Thr Tyr Arg Val Val Ser Val Leu Thr Val
                325                 330                 335

Leu His Gln Asp Trp Leu Asn Gly Lys Ala Tyr Ala Cys Ala Val Ser
            340                 345                 350

Asn Lys Ala Leu Pro Ala Pro Ile Glu Lys Thr Ile Ser Lys Ala Lys
        355                 360                 365

Gly Gln Pro Arg Glu Pro Gln Val Tyr Thr Leu Pro Pro Ser Arg Asp
    370                 375                 380

Glu Leu Thr Lys Asn Gln Val Ser Leu Thr Cys Leu Val Lys Gly Phe
385                 390                 395                 400

Tyr Pro Ser Asp Ile Ala Val Glu Trp Glu Ser Asn Gly Gln Pro Glu
                405                 410                 415

Asn Asn Tyr Lys Thr Thr Pro Pro Val Leu Asp Ser Asp Gly Ser Phe
            420                 425                 430

Phe Leu Tyr Ser Lys Leu Thr Val Asp Lys Ser Arg Trp Gln Gln Gly
        435                 440                 445

Asn Val Phe Ser Cys Ser Val Met His Glu Ala Leu His Asn His Tyr
    450                 455                 460

Thr Gln Lys Ser Leu Ser Leu Ser Pro Gly Ser Ser Leu Asn Thr Pro
465                 470                 475                 480

Asn Ser Ala Ser Thr Lys Gly Pro Ser Val Phe Pro Leu Ala Pro Ser
```

```
                485                 490                 495

Ser Lys Ser Thr Ser Gly Gly Thr Ala Ala Leu Gly Cys Leu Val Lys
            500                 505                 510

Asp Tyr Phe Pro Glu Pro Val Thr Val Ser Trp Asn Ser Gly Ala Leu
        515                 520                 525

Thr Ser Gly Val His Thr Phe Pro Ala Val Leu Gln Ser Ser Gly Leu
    530                 535                 540

Tyr Ser Leu Ser Ser Val Val Thr Val Pro Ser Ser Ser Leu Gly Thr
545                 550                 555                 560

Gln Thr Tyr Ile Cys Asn Val Asn His Lys Pro Ser Asn Thr Lys Val
                565                 570                 575

Asp Lys Lys Val
            580


<210> SEQ ID NO 227
<211> LENGTH: 1845
<212> TYPE: DNA
<213> ORGANISM: Artificial Sequence
<220> FEATURE:
<223> OTHER INFORMATION: TSC258

<400> SEQUENCE: 227

atggattttc aagtgcagat tttcagcttc ctgctaatca gtgcttcagt cataatgtcg     60

cgaggacagg tccagctggt ggagtctggg ggcggagtgg tgcagcctgg gcggtcactg    120

aggctgtcct gcaaggcttc tggctacacc tttactagat ctacgatgca ctgggtaagg    180

caggcccctg gacaaggtct ggaatggatt ggatacatta atcctagcag tgcttatact    240

aattacaatc agaaattcaa ggacaggttc acaatcagcg cagacaaatc caagagcaca    300

gccttcctgc agatggacag cctgaggccc gaggacaccg gcgtctattt ctgtgcacgg    360

ccccaagtcc actatgatta caacgggttt ccttactggg gccaagggac tcccgtcact    420

gtctctagcg gtggcggagg gtctgggggt ggcggatccg gaggtggtgg ctctgcacaa    480

gacatccaga tgacccagtc tccaagcagc ctgtctgcaa gcgtggggga cagggtcacc    540

atgacctgca gtgccagctc aagtgtaagt tacatgaact ggtaccagca gaagccgggc    600

aaggccccca aaagatggat ttatgactca tccaaactgg cttctggagt ccctgctcgc    660

ttcagtggca gtgggtctgg gaccgactat accctcacaa tcagcagcct gcagcccgaa    720

gatttcgcca cttattactg ccagcagtgg agtcgtaacc cacccacgtt cggagggggg    780

accaagctac aaattacatc ctcgagtgag cccaaatctt ctgacaaaac tcacacatgc    840

ccaccgtgcc cagcacctga agccgcgggt gcaccgtcag tcttcctctt cccccccaaaa    900

cccaaggaca ccctcatgat ctcccggacc cctgaggtca catgcgtggt ggtggacgtg    960

agccacgaag accctgaggt caagttcaac tggtacgtgg acggcgtgga ggtgcataat   1020

gccaagacaa agccgcggga ggagcagtac aacagcacgt accgtgtggt cagcgtcctc   1080

accgtcctgc accaggactg gctgaatggc aaggcgtacg cgtgcgcggt ctccaacaaa   1140

gccctcccag cccccatcga gaaaaccatc tccaaagcca aagggcagcc ccgagaacca   1200

caggtgtaca ccctgccccc atcccgggat gagctgacca agaaccaggt cagcctgacc   1260

tgcctggtca aaggcttcta tccaagcgac atcgccgtgg agtgggagag caatgggcag   1320

ccggagaaca actacaagac cacgcctccc gtgctggact ccgacggctc cttcttcctc   1380

tacagcaagc tcaccgtgga caagagcagg tggcagcagg ggaacgtctt ctcatgctcc   1440

gtgatgcatg aggctctgca caaccactac acgcagaaga gcctctccct gtctccgggt   1500
```

```
tcttccctga atacaccgaa ctctaggact gtggctgcac catctgtctt catcttcccg   1560

ccatctgatg agcagttgaa atctggaact gcctctgttg tgtgcctgct gaattacttc   1620

tatcccagag aggccaaagt acagtggaag gtggataacg ccctccaatc gggtaactcc   1680

caggagagtg ccacagagca ggacagcaag gacagcacct acagcctcag cagcgagctg   1740

acgctgagca aagcagacta cgagaaacac aaagtctacg cctgcgaagt cacccatcag   1800

ggcctgagct cgcccgtcac aaagagcttc aacaggggag agtga                    1845
```

<210> SEQ ID NO 228
<211> LENGTH: 592
<212> TYPE: PRT
<213> ORGANISM: Artificial Sequence
<220> FEATURE:
<223> OTHER INFORMATION: TSC258

<400> SEQUENCE: 228

```
Gln Val Gln Leu Val Glu Ser Gly Gly Gly Val Val Gln Pro Gly Arg
1               5                   10                  15

Ser Leu Arg Leu Ser Cys Lys Ala Ser Gly Tyr Thr Phe Thr Arg Ser
            20                  25                  30

Thr Met His Trp Val Arg Gln Ala Pro Gly Gln Gly Leu Glu Trp Ile
        35                  40                  45

Gly Tyr Ile Asn Pro Ser Ser Ala Tyr Thr Asn Tyr Asn Gln Lys Phe
    50                  55                  60

Lys Asp Arg Phe Thr Ile Ser Ala Asp Lys Ser Lys Ser Thr Ala Phe
65                  70                  75                  80

Leu Gln Met Asp Ser Leu Arg Pro Glu Asp Thr Gly Val Tyr Phe Cys
                85                  90                  95

Ala Arg Pro Gln Val His Tyr Asp Tyr Asn Gly Phe Pro Tyr Trp Gly
            100                 105                 110

Gln Gly Thr Pro Val Thr Val Ser Ser Gly Gly Gly Gly Ser Gly Gly
        115                 120                 125

Gly Gly Ser Gly Gly Gly Gly Ser Ala Gln Asp Ile Gln Met Thr Gln
    130                 135                 140

Ser Pro Ser Ser Leu Ser Ala Ser Val Gly Asp Arg Val Thr Met Thr
145                 150                 155                 160

Cys Ser Ala Ser Ser Ser Val Ser Tyr Met Asn Trp Tyr Gln Gln Lys
                165                 170                 175

Pro Gly Lys Ala Pro Lys Arg Trp Ile Tyr Asp Ser Ser Lys Leu Ala
            180                 185                 190

Ser Gly Val Pro Ala Arg Phe Ser Gly Ser Gly Ser Gly Thr Asp Tyr
        195                 200                 205

Thr Leu Thr Ile Ser Ser Leu Gln Pro Glu Asp Phe Ala Thr Tyr Tyr
    210                 215                 220

Cys Gln Gln Trp Ser Arg Asn Pro Pro Thr Phe Gly Gly Gly Thr Lys
225                 230                 235                 240

Leu Gln Ile Thr Ser Ser Ser Glu Pro Lys Ser Ser Asp Lys Thr His
                245                 250                 255

Thr Cys Pro Pro Cys Pro Ala Pro Glu Ala Ala Gly Ala Pro Ser Val
            260                 265                 270

Phe Leu Phe Pro Pro Lys Pro Lys Asp Thr Leu Met Ile Ser Arg Thr
        275                 280                 285

Pro Glu Val Thr Cys Val Val Val Asp Val Ser His Glu Asp Pro Glu
    290                 295                 300
```

```
Val Lys Phe Asn Trp Tyr Val Asp Gly Val Glu Val His Asn Ala Lys
305                 310                 315                 320

Thr Lys Pro Arg Glu Glu Gln Tyr Asn Ser Thr Tyr Arg Val Val Ser
                325                 330                 335

Val Leu Thr Val Leu His Gln Asp Trp Leu Asn Gly Lys Ala Tyr Ala
            340                 345                 350

Cys Ala Val Ser Asn Lys Ala Leu Pro Ala Pro Ile Glu Lys Thr Ile
        355                 360                 365

Ser Lys Ala Lys Gly Gln Pro Arg Glu Pro Gln Val Tyr Thr Leu Pro
    370                 375                 380

Pro Ser Arg Asp Glu Leu Thr Lys Asn Gln Val Ser Leu Thr Cys Leu
385                 390                 395                 400

Val Lys Gly Phe Tyr Pro Ser Asp Ile Ala Val Glu Trp Glu Ser Asn
                405                 410                 415

Gly Gln Pro Glu Asn Asn Tyr Lys Thr Thr Pro Pro Val Leu Asp Ser
            420                 425                 430

Asp Gly Ser Phe Phe Leu Tyr Ser Lys Leu Thr Val Asp Lys Ser Arg
        435                 440                 445

Trp Gln Gln Gly Asn Val Phe Ser Cys Ser Val Met His Glu Ala Leu
    450                 455                 460

His Asn His Tyr Thr Gln Lys Ser Leu Ser Leu Ser Pro Gly Ser Ser
465                 470                 475                 480

Leu Asn Thr Pro Asn Ser Arg Thr Val Ala Ala Pro Ser Val Phe Ile
                485                 490                 495

Phe Pro Pro Ser Asp Glu Gln Leu Lys Ser Gly Thr Ala Ser Val Val
            500                 505                 510

Cys Leu Leu Asn Tyr Phe Tyr Pro Arg Glu Ala Lys Val Gln Trp Lys
        515                 520                 525

Val Asp Asn Ala Leu Gln Ser Gly Asn Ser Gln Glu Ser Ala Thr Glu
    530                 535                 540

Gln Asp Ser Lys Asp Ser Thr Tyr Ser Leu Ser Ser Glu Leu Thr Leu
545                 550                 555                 560

Ser Lys Ala Asp Tyr Glu Lys His Lys Val Tyr Ala Cys Glu Val Thr
                565                 570                 575

His Gln Gly Leu Ser Ser Pro Val Thr Lys Ser Phe Asn Arg Gly Glu
            580                 585                 590
```

<210> SEQ ID NO 229
<211> LENGTH: 121
<212> TYPE: PRT
<213> ORGANISM: Artificial Sequence
<220> FEATURE:
<223> OTHER INFORMATION: Consensus sequence from Figure 3
<220> FEATURE:
<221> NAME/KEY: misc_feature
<223> OTHER INFORMATION: Xaa is a position that was not a consensus in Figure 3 with Ala and Phe being equally prevalent at that position and Val occuring in 1 out of 7 of the sequences
<220> FEATURE:
<221> NAME/KEY: misc_feature
<222> LOCATION: (68)..(68)
<223> OTHER INFORMATION: Xaa can be any naturally occurring amino acid

<400> SEQUENCE: 229

```
Gln Val Gln Leu Val Gln Ser Gly Gly Gly Val Val Lys Pro Gly Ala
1               5                   10                  15

Ser Leu Arg Leu Ser Cys Lys Ala Ser Gly Tyr Thr Phe Thr Arg Ser
            20                  25                  30
```

```
Thr Met His Trp Val Arg Gln Ala Pro Gly Gln Gly Leu Glu Trp Ile
        35                  40                  45

Gly Tyr Ile Asn Pro Ser Ser Ala Tyr Thr Asn Tyr Asn Gln Lys Phe
    50                  55                  60

Lys Asp Arg Xaa Thr Ile Thr Ala Asp Lys Ser Lys Ser Thr Ala Tyr
65                  70                  75                  80

Met Gln Leu Ser Ser Leu Arg Ser Glu Asp Thr Ala Val Tyr Tyr Cys
                85                  90                  95

Ala Arg Pro Gln Val His Tyr Asp Tyr Asn Gly Phe Pro Tyr Trp Gly
            100                 105                 110

Gln Gly Thr Leu Val Thr Val Ser Ser
        115                 120


<210> SEQ ID NO 230
<211> LENGTH: 108
<212> TYPE: PRT
<213> ORGANISM: Artificial Sequence
<220> FEATURE:
<223> OTHER INFORMATION: consensus sequence from Figure 4

<400> SEQUENCE: 230

Ala Gln Asp Ile Gln Met Thr Gln Ser Pro Ser Ser Leu Ser Ala Ser
1               5                   10                  15

Val Gly Asp Arg Val Thr Met Thr Cys Ser Ala Ser Ser Ser Val Ser
            20                  25                  30

Tyr Met Asn Trp Tyr Gln Gln Lys Pro Gly Lys Ala Pro Lys Arg Trp
        35                  40                  45

Ile Tyr Asp Ser Ser Lys Leu Ala Ser Gly Val Pro Ala Arg Phe Ser
    50                  55                  60

Gly Ser Gly Ser Gly Thr Asp Tyr Thr Leu Thr Ile Ser Ser Leu Gln
65                  70                  75                  80

Pro Glu Asp Phe Ala Thr Tyr Tyr Cys Gln Gln Trp Ser Arg Asn Pro
                85                  90                  95

Pro Thr Phe Gly Gly Gly Thr Lys Leu Gln Ile Thr
            100                 105


<210> SEQ ID NO 231
<211> LENGTH: 98
<212> TYPE: PRT
<213> ORGANISM: Artificial Sequence
<220> FEATURE:
<223> OTHER INFORMATION: Consensus sequence from Figure 5
<220> FEATURE:
<221> NAME/KEY: misc_feature
<223> OTHER INFORMATION: This is the consensus seqeunce from figure 5. X
      represents where there was no consequence, so X could equally be
      one of the amino acids shown in that position in the other
      sequences
<220> FEATURE:
<221> NAME/KEY: misc_feature
<222> LOCATION: (50)..(50)
<223> OTHER INFORMATION: Xaa can be any naturally occurring amino acid
<220> FEATURE:
<221> NAME/KEY: misc_feature
<222> LOCATION: (52)..(52)
<223> OTHER INFORMATION: Xaa can be any naturally occurring amino acid
<220> FEATURE:
<221> NAME/KEY: misc_feature
<222> LOCATION: (54)..(55)
<223> OTHER INFORMATION: Xaa can be any naturally occurring amino acid
<220> FEATURE:
<221> NAME/KEY: misc_feature
<222> LOCATION: (57)..(58)
<223> OTHER INFORMATION: Xaa can be any naturally occurring amino acid
```

<220> FEATURE:
<221> NAME/KEY: misc_feature
<222> LOCATION: (74)..(74)
<223> OTHER INFORMATION: Xaa can be any naturally occurring amino acid
<220> FEATURE:
<221> NAME/KEY: misc_feature
<222> LOCATION: (84)..(84)
<223> OTHER INFORMATION: Xaa can be any naturally occurring amino acid

<400> SEQUENCE: 231

```
Gln Val Gln Leu Val Gln Ser Gly Gly Gly Val Val Gln Pro Gly Arg
1               5                   10                  15

Ser Leu Arg Leu Ser Cys Lys Ala Ser Gly Phe Thr Phe Ser Ser Tyr
            20                  25                  30

Ala Met His Trp Val Arg Gln Ala Pro Gly Lys Gly Leu Glu Trp Ile
        35                  40                  45

Gly Xaa Ile Xaa Pro Xaa Xaa Ala Xaa Xaa Asn Tyr Ala Gln Lys Phe
    50                  55                  60

Lys Gly Arg Phe Thr Ile Ser Ala Asp Xaa Ser Lys Ser Thr Ala Tyr
65                  70                  75                  80

Leu Gln Met Xaa Ser Leu Arg Ala Glu Asp Thr Ala Val Tyr Tyr Cys
                85                  90                  95

Ala Arg
```

<210> SEQ ID NO 232
<211> LENGTH: 95
<212> TYPE: PRT
<213> ORGANISM: Artificial Sequence
<220> FEATURE:
<223> OTHER INFORMATION: IGKV1-5*01

<400> SEQUENCE: 232

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Ser
                85                  90                  95
```

<210> SEQ ID NO 233
<211> LENGTH: 91
<212> TYPE: PRT
<213> ORGANISM: Artificial Sequence
<220> FEATURE:
<223> OTHER INFORMATION: Consensus sequence from Figure 6
<220> FEATURE:
<221> NAME/KEY: misc_feature
<223> OTHER INFORMATION: This is the consensus seqeunce from figure 6. X represents where there was no consequence, so X could equally be one of the amino acids shown in that position in the other sequences
<220> FEATURE:
<221> NAME/KEY: misc_feature
<222> LOCATION: (24)..(24)
<223> OTHER INFORMATION: Xaa can be any naturally occurring amino acid
<220> FEATURE:
<221> NAME/KEY: misc_feature
<222> LOCATION: (27)..(27)

<223> OTHER INFORMATION: Xaa can be any naturally occurring amino acid
<220> FEATURE:
<221> NAME/KEY: misc_feature
<222> LOCATION: (31)..(31)
<223> OTHER INFORMATION: Xaa can be any naturally occurring amino acid
<220> FEATURE:
<221> NAME/KEY: misc_feature
<222> LOCATION: (34)..(34)
<223> OTHER INFORMATION: Xaa can be any naturally occurring amino acid
<220> FEATURE:
<221> NAME/KEY: misc_feature
<222> LOCATION: (46)..(47)
<223> OTHER INFORMATION: Xaa can be any naturally occurring amino acid
<220> FEATURE:
<221> NAME/KEY: misc_feature
<222> LOCATION: (53)..(53)
<223> OTHER INFORMATION: Xaa can be any naturally occurring amino acid
<220> FEATURE:
<221> NAME/KEY: misc_feature
<222> LOCATION: (55)..(55)
<223> OTHER INFORMATION: Xaa can be any naturally occurring amino acid

<400> SEQUENCE: 233

```
Asp Ile Gln Met Thr Gln Ser Pro Ser Ser Leu Ser Ala Ser Val Gly
1               5                   10                  15

Asp Arg Val Thr Ile Thr Cys Xaa Ala Ser Xaa Ser Ile Ser Xaa Trp
            20                  25                  30

Leu Xaa Trp Tyr Gln Gln Lys Pro Gly Lys Ala Pro Lys Xaa Xaa Ile
        35                  40                  45

Tyr Asp Ala Ser Xaa Leu Xaa Ser Gly Val Pro Ala Arg Phe Ser Gly
    50                  55                  60

Ser Gly Ser Gly Thr Asp Phe Thr Leu Thr Ile Ser Ser Leu Gln Pro
65                  70                  75                  80

Asp Asp Phe Ala Thr Tyr Tyr Cys Gln Gln Trp
                85                  90
```

<210> SEQ ID NO 234
<211> LENGTH: 12
<212> TYPE: PRT
<213> ORGANISM: Artificial Sequence
<220> FEATURE:
<223> OTHER INFORMATION: IGKJ1*01

<400> SEQUENCE: 234

```
Trp Thr Phe Gly Gln Gly Thr Lys Val Glu Ile Lys
1               5                   10
```

<210> SEQ ID NO 235
<211> LENGTH: 12
<212> TYPE: PRT
<213> ORGANISM: Artificial Sequence
<220> FEATURE:
<223> OTHER INFORMATION: IGKJ2*01

<400> SEQUENCE: 235

```
Tyr Thr Phe Gly Gln Gly Thr Lys Leu Glu Ile Lys
1               5                   10
```

<210> SEQ ID NO 236
<211> LENGTH: 12
<212> TYPE: PRT
<213> ORGANISM: Artificial Sequence
<220> FEATURE:
<223> OTHER INFORMATION: IGKJ3*01

<400> SEQUENCE: 236

```
Phe Thr Phe Gly Pro Gly Thr Lys Val Asp Ile Lys
```

```
1               5                   10


<210> SEQ ID NO 237
<211> LENGTH: 12
<212> TYPE: PRT
<213> ORGANISM: Artificial Sequence
<220> FEATURE:
<223> OTHER INFORMATION: IGKJ4*01

<400> SEQUENCE: 237

Leu Thr Phe Gly Gly Gly Thr Lys Val Glu Ile Lys
1               5                   10


<210> SEQ ID NO 238
<211> LENGTH: 12
<212> TYPE: PRT
<213> ORGANISM: Artificial Sequence
<220> FEATURE:
<223> OTHER INFORMATION: IGKJ5*01

<400> SEQUENCE: 238

Ile Thr Phe Gly Gln Gly Thr Arg Leu Glu Ile Lys
1               5                   10


<210> SEQ ID NO 239
<211> LENGTH: 423
<212> TYPE: PRT
<213> ORGANISM: Artificial Sequence
<220> FEATURE:
<223> OTHER INFORMATION: Figure 7 consensus sequence

<400> SEQUENCE: 239

Gln Val Gln Leu Val Gln Ser Gly Gly Gly Val Val Gln Pro Gly Arg
1               5                   10                  15

Ser Leu Arg Leu Ser Cys Lys Ala Ser Gly Tyr Thr Phe Thr Arg Ser
            20                  25                  30

Thr Met His Trp Val Arg Gln Ala Pro Gly Lys Gly Leu Glu Trp Ile
        35                  40                  45

Gly Tyr Ile Asn Pro Ser Ser Ala Tyr Thr Asn Tyr Asn Gln Lys Phe
    50                  55                  60

Lys Asp Arg Phe Thr Ile Ser Ala Asp Lys Ser Lys Ser Thr Ala Phe
65                  70                  75                  80

Leu Gln Met Asp Ser Leu Arg Pro Glu Asp Thr Gly Val Tyr Phe Cys
                85                  90                  95

Ala Arg Pro Gln Val His Tyr Asp Tyr Asn Gly Phe Pro Tyr Trp Gly
            100                 105                 110

Gln Gly Thr Pro Val Thr Val Ser Ser Gly Gly Gly Gly Ser Gly Gly
        115                 120                 125

Gly Gly Ser Gly Gly Gly Gly Ser Ala Gln Asp Ile Gln Met Thr Gln
    130                 135                 140

Ser Pro Ser Ser Leu Ser Ala Ser Val Gly Asp Arg Val Thr Met Thr
145                 150                 155                 160

Cys Ser Ala Ser Ser Ser Val Ser Tyr Met Asn Trp Tyr Gln Gln Lys
                165                 170                 175

Pro Gly Lys Ala Pro Lys Leu Leu Ile Tyr Asp Ser Ser Lys Leu Ala
            180                 185                 190

Ser Gly Val Pro Ala Arg Phe Ser Gly Ser Gly Ser Gly Thr Asp Tyr
        195                 200                 205

Thr Leu Thr Ile Ser Ser Leu Gln Pro Glu Asp Phe Ala Thr Tyr Tyr
    210                 215                 220
```

Cys Gln Gln Trp Ser Arg Asn Pro Pro Thr Phe Gly Gly Gly Thr Lys
225 230 235 240

Val Glu Ile Lys Ser Ser Ser Glu Pro Lys Ser Ser Asp Lys Thr His
245 250 255

Thr Cys Pro Pro Cys Pro Ala Pro Glu Ala Ala Ala Pro Ser Val Phe
260 265 270

Leu Phe Pro Pro Lys Pro Lys Asp Thr Leu Met Ile Ser Arg Thr Pro
275 280 285

Glu Val Thr Cys Val Val Val Asp Val Ser Gln Glu Asp Pro Glu Val
290 295 300

Gln Phe Asn Trp Tyr Val Asp Gly Val Glu Val His Asn Ala Lys Thr
305 310 315 320

Lys Pro Arg Glu Glu Gln Phe Asn Ser Thr Tyr Arg Val Val Ser Val
325 330 335

Leu Thr Val Leu His Gln Asp Trp Leu Asn Gly Lys Ala Tyr Ala Cys
340 345 350

Ala Val Ser Asn Lys Gly Leu Pro Ser Ser Ile Glu Lys Thr Ile Ser
355 360 365

Lys Ala Lys Gly Gln Pro Arg Glu Pro Gln Val Tyr Thr Leu Pro Pro
370 375 380

Ser Gln Glu Glu Met Thr Lys Asn Gln Val Ser Leu Thr Cys Leu Val
385 390 395 400

Lys Gly Phe Tyr Pro Ser Asp Ile Ala Val Glu Trp Glu Ser Asn Gly
405 410 415

Gln Pro Glu Asn Asn Tyr Lys
420

<210> SEQ ID NO 240
<211> LENGTH: 478
<212> TYPE: PRT
<213> ORGANISM: Artificial Sequence
<220> FEATURE:
<223> OTHER INFORMATION: DRA161

<400> SEQUENCE: 240

Gln Val Gln Leu Val Gln Ser Gly Gly Gly Val Val Gln Pro Gly Arg
1 5 10 15

Ser Leu Arg Leu Ser Cys Lys Ala Ser Gly Tyr Thr Phe Thr Arg Ser
20 25 30

Thr Met His Trp Val Arg Gln Ala Pro Gly Lys Gly Leu Glu Trp Ile
35 40 45

Gly Tyr Ile Asn Pro Ser Ser Ala Tyr Thr Asn Tyr Asn Gln Lys Phe
50 55 60

Lys Asp Arg Phe Thr Ile Ser Ala Asp Lys Ser Lys Ser Thr Ala Phe
65 70 75 80

Leu Gln Met Asp Ser Leu Arg Pro Glu Asp Thr Gly Val Tyr Phe Cys
85 90 95

Ala Arg Pro Gln Val His Tyr Asp Tyr Asn Gly Phe Pro Tyr Trp Gly
100 105 110

Gln Gly Thr Pro Val Thr Val Ser Ser Gly Gly Gly Gly Ser Gly Gly
115 120 125

Gly Gly Ser Gly Gly Gly Gly Ser Ala Gln Asp Ile Gln Met Thr Gln
130 135 140

Ser Pro Ser Ser Leu Ser Ala Ser Val Gly Asp Arg Val Thr Met Thr
145 150 155 160

Cys Ser Ala Ser Ser Ser Val Ser Tyr Met Asn Trp Tyr Gln Gln Lys
165 170 175

Pro Gly Lys Ala Pro Lys Arg Trp Ile Tyr Asp Ser Ser Lys Leu Ala
180 185 190

Ser Gly Val Pro Ala Arg Phe Ser Gly Ser Gly Ser Gly Thr Asp Tyr
195 200 205

Thr Leu Thr Ile Ser Ser Leu Gln Pro Glu Asp Phe Ala Thr Tyr Tyr
210 215 220

Cys Gln Gln Trp Ser Arg Asn Pro Pro Thr Phe Gly Gly Gly Thr Lys
225 230 235 240

Leu Gln Ile Thr Arg Arg Thr Ser Pro Lys Ser Ser Asp Lys Thr His
245 250 255

Thr Cys Pro Pro Cys Pro Ala Pro Glu Ala Ala Ala Pro Ser Val Phe
260 265 270

Leu Phe Pro Pro Lys Pro Lys Asp Thr Leu Met Ile Ser Arg Thr Pro
275 280 285

Glu Val Thr Cys Val Val Val Asp Val Ser Gln Glu Asp Pro Glu Val
290 295 300

Gln Phe Asn Trp Tyr Val Asp Gly Val Glu Val His Asn Ala Lys Thr
305 310 315 320

Lys Pro Arg Glu Glu Gln Phe Ala Ser Thr Tyr Arg Val Val Ser Val
325 330 335

Leu Thr Val Leu His Gln Asp Trp Leu Asn Gly Lys Glu Tyr Lys Cys
340 345 350

Lys Val Ser Asn Lys Gly Leu Pro Ser Ser Ile Glu Lys Thr Ile Ser
355 360 365

Lys Ala Lys Gly Gln Pro Arg Glu Pro Gln Val Tyr Thr Leu Pro Pro
370 375 380

Ser Gln Glu Glu Met Thr Lys Asn Gln Val Ser Leu Thr Cys Leu Val
385 390 395 400

Lys Gly Phe Tyr Pro Ser Asp Ile Ala Val Glu Trp Glu Ser Asn Gly
405 410 415

Gln Pro Glu Asn Asn Tyr Lys Thr Thr Pro Pro Val Leu Asp Ser Asp
420 425 430

Gly Ser Phe Phe Leu Tyr Ser Arg Leu Thr Val Asp Lys Ser Arg Trp
435 440 445

Gln Glu Gly Asn Val Phe Ser Cys Ser Val Met His Glu Ala Leu His
450 455 460

Asn His Tyr Thr Gln Lys Ser Leu Ser Leu Ser Pro Gly Lys
465 470 475

<210> SEQ ID NO 241
<211> LENGTH: 478
<212> TYPE: PRT
<213> ORGANISM: Artificial Sequence
<220> FEATURE:
<223> OTHER INFORMATION: Consensus sequence of Figure 8

<400> SEQUENCE: 241

Gln Val Gln Leu Val Gln Ser Gly Gly Gly Val Val Gln Pro Gly Arg
1 5 10 15

Ser Leu Arg Leu Ser Cys Lys Ala Ser Gly Tyr Thr Phe Thr Arg Ser
20 25 30

Thr Met His Trp Val Arg Gln Ala Pro Gly Lys Gly Leu Glu Trp Ile
35 40 45

```
Gly Tyr Ile Asn Pro Ser Ser Ala Tyr Thr Asn Tyr Asn Gln Lys Phe
    50                  55                  60

Lys Asp Arg Phe Thr Ile Ser Ala Asp Lys Ser Lys Ser Thr Ala Phe
65                  70                  75                  80

Leu Gln Met Asp Ser Leu Arg Pro Glu Asp Thr Gly Val Tyr Phe Cys
                85                  90                  95

Ala Arg Pro Gln Val His Tyr Asp Tyr Asn Gly Phe Pro Tyr Trp Gly
            100                 105                 110

Gln Gly Thr Pro Val Thr Val Ser Ser Gly Gly Gly Gly Ser Gly Gly
        115                 120                 125

Gly Gly Ser Gly Gly Gly Gly Ser Ala Gln Asp Ile Gln Met Thr Gln
    130                 135                 140

Ser Pro Ser Ser Leu Ser Ala Ser Val Gly Asp Arg Val Thr Met Thr
145                 150                 155                 160

Cys Ser Ala Ser Ser Ser Val Ser Tyr Met Asn Trp Tyr Gln Gln Lys
                165                 170                 175

Pro Gly Lys Ala Pro Lys Arg Trp Ile Tyr Asp Ser Ser Lys Leu Ala
            180                 185                 190

Ser Gly Val Pro Ala Arg Phe Ser Gly Ser Gly Ser Gly Thr Asp Tyr
        195                 200                 205

Thr Leu Thr Ile Ser Ser Leu Gln Pro Glu Asp Phe Ala Thr Tyr Tyr
    210                 215                 220

Cys Gln Gln Trp Ser Arg Asn Pro Pro Thr Phe Gly Gly Gly Thr Lys
225                 230                 235                 240

Leu Gln Ile Thr Ser Ser Ser Glu Pro Lys Ser Ser Asp Lys Thr His
                245                 250                 255

Thr Cys Pro Pro Cys Pro Ala Pro Glu Ala Ala Ala Pro Ser Val Phe
            260                 265                 270

Leu Phe Pro Pro Lys Pro Lys Asp Thr Leu Met Ile Ser Arg Thr Pro
        275                 280                 285

Glu Val Thr Cys Val Val Val Asp Val Ser Gln Glu Asp Pro Glu Val
    290                 295                 300

Gln Phe Asn Trp Tyr Val Asp Gly Val Glu Val His Asn Ala Lys Thr
305                 310                 315                 320

Lys Pro Arg Glu Glu Gln Phe Ala Ser Thr Tyr Arg Val Val Ser Val
                325                 330                 335

Leu Thr Val Leu His Gln Asp Trp Leu Asn Gly Lys Glu Tyr Lys Cys
            340                 345                 350

Lys Val Ser Asn Lys Gly Leu Pro Ser Ser Ile Glu Lys Thr Ile Ser
        355                 360                 365

Lys Ala Lys Gly Gln Pro Arg Glu Pro Gln Val Tyr Thr Leu Pro Pro
    370                 375                 380

Ser Gln Glu Glu Met Thr Lys Asn Gln Val Ser Leu Thr Cys Leu Val
385                 390                 395                 400

Lys Gly Phe Tyr Pro Ser Asp Ile Ala Val Glu Trp Glu Ser Asn Gly
                405                 410                 415

Gln Pro Glu Asn Asn Tyr Lys Thr Thr Pro Pro Val Leu Asp Ser Asp
            420                 425                 430

Gly Ser Phe Phe Leu Tyr Ser Arg Leu Thr Val Asp Lys Ser Arg Trp
        435                 440                 445

Gln Glu Gly Asn Val Phe Ser Cys Ser Val Met His Glu Ala Leu His
    450                 455                 460
```

Asn His Tyr Thr Gln Lys Ser Leu Ser Leu Ser Pro Gly Lys
465 470 475

<210> SEQ ID NO 242
<211> LENGTH: 1800
<212> TYPE: DNA
<213> ORGANISM: Artificial Sequence
<220> FEATURE:
<223> OTHER INFORMATION: TSC125

<400> SEQUENCE: 242
atggaagcac cagcgcagct tctcttcctc ctgctactct ggctcccaga taccaccggt 60
caggtccagc tggtgcagtc tgggggcgga gtggtgcagc ctgggcggtc actgaggctg 120
tcctgcaagg cttctggcta cacctttact agatctacga tgcactgggt aaggcaggcc 180
cctggaaagg gtctggaatg gattggatac attaatccta gcagtgctta tactaattac 240
aatcagaaat tcaaggacag gttcacaatc agcgcagaca aatccaagag cacagccttc 300
ctgcagatgg acagcctgag gcccgaggac accggcgtct atttctgtgc acggccccaa 360
gtccactatg attacaacgg gtttccttac tggggccaag ggactcccgt cactgtctct 420
agcggtggcg gagggtctgg gggtggcgga tccggaggtg gtggctctgc acaagacatc 480
cagatgaccc agtctccaag cagcctgtct gcaagcgtgg gggacagggt caccatgacc 540
tgcagtgcca gctcaagtgt aagttacatg aactggtacc agcagaagcc cggcaaggcc 600
cccaaaagat ggatttatga ctcatccaaa ctggcttctg gagtccctgc tcgcttcagt 660
ggcagtgggt ctgggaccga ctataccctc acaatcagca gcctgcagcc cgaagatttc 720
gccacttatt actgccagca gtggagtcgt aacccaccca cgttcggagg ggggaccaag 780
ctacaaatta cacgctcgag tgagcccaaa tcttctgaca aaactcacac atgcccaccg 840
tgcccagcac ctgaagccgc gggtgcaccg tcagtcttcc tcttcccccc aaaacccaag 900
gacaccctca tgatctcccg gacccctgag gtcacatgcg tggtggtgga cgtgagccac 960
gaagaccctg aggtcaagtt caactggtac gtggacggcg tggaggtgca taatgccaag 1020
acaaagccgc gggaggagca gtacaacagc acgtaccgtg tggtcagcgt cctcaccgtc 1080
ctgcaccagg actggctgaa tggcaaggcg tacgcgtgcg cggtctccaa caaagccctc 1140
ccagccccca tcgagaaaac catctccaaa gccaaagggc agccccgaga accacaggtg 1200
tacaccctgc ccccatcccg ggatgagctg accaagaacc aggtcagcct gacctgcctg 1260
gtcaaaggct tctatccaag cgacatcgcc gtggagtggg agagcaatgg gcagccggag 1320
aacaactaca agaccacgcc tcccgtgctg gactccgacg gctccttctt cctctacagc 1380
aagctcaccg tggacaagag caggtggcag caggggaacg tcttctcatg ctccgtgatg 1440
catgaggctc tgcacaacca ctacacgcag aagagcctct ccctgtctcc gggtaaatct 1500
agagcctcca ccaagggccc atcggtcttc cccctggcac cctcctccaa gagcacctct 1560
gggggcacag cggccctggg ctgcctggtc aaggactact tccccgagcc ggtgacggtg 1620
tcgtggaact caggcgccct gaccagcggc gtgcacacct tcccggctgt cctacagtcc 1680
tcaggactct actccctcag cagcgtggtg accgtgccct ccagcagctt gggcacccag 1740
acctacatct gcaacgtgaa tcacaagccc agcaacacca aggtggacaa gaaagtttga 1800

<210> SEQ ID NO 243
<211> LENGTH: 579
<212> TYPE: PRT
<213> ORGANISM: Artificial Sequence
<220> FEATURE:

<223> OTHER INFORMATION: TSC125 mature protein

<400> SEQUENCE: 243

```
Gln Val Gln Leu Val Gln Ser Gly Gly Gly Val Val Gln Pro Gly Arg
1               5                   10                  15

Ser Leu Arg Leu Ser Cys Lys Ala Ser Gly Tyr Thr Phe Thr Arg Ser
            20                  25                  30

Thr Met His Trp Val Arg Gln Ala Pro Gly Lys Gly Leu Glu Trp Ile
        35                  40                  45

Gly Tyr Ile Asn Pro Ser Ser Ala Tyr Thr Asn Tyr Asn Gln Lys Phe
    50                  55                  60

Lys Asp Arg Phe Thr Ile Ser Ala Asp Lys Ser Lys Ser Thr Ala Phe
65                  70                  75                  80

Leu Gln Met Asp Ser Leu Arg Pro Glu Asp Thr Gly Val Tyr Phe Cys
                85                  90                  95

Ala Arg Pro Gln Val His Tyr Asp Tyr Asn Gly Phe Pro Tyr Trp Gly
            100                 105                 110

Gln Gly Thr Pro Val Thr Val Ser Ser Gly Gly Gly Gly Ser Gly Gly
        115                 120                 125

Gly Gly Ser Gly Gly Gly Gly Ser Ala Gln Asp Ile Gln Met Thr Gln
    130                 135                 140

Ser Pro Ser Ser Leu Ser Ala Ser Val Gly Asp Arg Val Thr Met Thr
145                 150                 155                 160

Cys Ser Ala Ser Ser Ser Val Ser Tyr Met Asn Trp Tyr Gln Gln Lys
                165                 170                 175

Pro Gly Lys Ala Pro Lys Arg Trp Ile Tyr Asp Ser Ser Lys Leu Ala
            180                 185                 190

Ser Gly Val Pro Ala Arg Phe Ser Gly Ser Gly Ser Gly Thr Asp Tyr
        195                 200                 205

Thr Leu Thr Ile Ser Ser Leu Gln Pro Glu Asp Phe Ala Thr Tyr Tyr
    210                 215                 220

Cys Gln Gln Trp Ser Arg Asn Pro Pro Thr Phe Gly Gly Gly Thr Lys
225                 230                 235                 240

Leu Gln Ile Thr Arg Ser Ser Glu Pro Lys Ser Ser Asp Lys Thr His
                245                 250                 255

Thr Cys Pro Pro Cys Pro Ala Pro Glu Ala Ala Gly Ala Pro Ser Val
            260                 265                 270

Phe Leu Phe Pro Pro Lys Pro Lys Asp Thr Leu Met Ile Ser Arg Thr
        275                 280                 285

Pro Glu Val Thr Cys Val Val Val Asp Val Ser His Glu Asp Pro Glu
    290                 295                 300

Val Lys Phe Asn Trp Tyr Val Asp Gly Val Glu Val His Asn Ala Lys
305                 310                 315                 320

Thr Lys Pro Arg Glu Glu Gln Tyr Asn Ser Thr Tyr Arg Val Val Ser
                325                 330                 335

Val Leu Thr Val Leu His Gln Asp Trp Leu Asn Gly Lys Ala Tyr Ala
            340                 345                 350

Cys Ala Val Ser Asn Lys Ala Leu Pro Ala Pro Ile Glu Lys Thr Ile
        355                 360                 365

Ser Lys Ala Lys Gly Gln Pro Arg Glu Pro Gln Val Tyr Thr Leu Pro
    370                 375                 380

Pro Ser Arg Asp Glu Leu Thr Lys Asn Gln Val Ser Leu Thr Cys Leu
385                 390                 395                 400
```

-continued

```
Val Lys Gly Phe Tyr Pro Ser Asp Ile Ala Val Glu Trp Glu Ser Asn
                405                 410                 415

Gly Gln Pro Glu Asn Asn Tyr Lys Thr Thr Pro Pro Val Leu Asp Ser
            420                 425                 430

Asp Gly Ser Phe Phe Leu Tyr Ser Lys Leu Thr Val Asp Lys Ser Arg
        435                 440                 445

Trp Gln Gln Gly Asn Val Phe Ser Cys Ser Val Met His Glu Ala Leu
    450                 455                 460

His Asn His Tyr Thr Gln Lys Ser Leu Ser Leu Ser Pro Gly Lys Ser
465                 470                 475                 480

Arg Ala Ser Thr Lys Gly Pro Ser Val Phe Pro Leu Ala Pro Ser Ser
                485                 490                 495

Lys Ser Thr Ser Gly Gly Thr Ala Ala Leu Gly Cys Leu Val Lys Asp
            500                 505                 510

Tyr Phe Pro Glu Pro Val Thr Val Ser Trp Asn Ser Gly Ala Leu Thr
        515                 520                 525

Ser Gly Val His Thr Phe Pro Ala Val Leu Gln Ser Ser Gly Leu Tyr
    530                 535                 540

Ser Leu Ser Ser Val Val Thr Val Pro Ser Ser Ser Leu Gly Thr Gln
545                 550                 555                 560

Thr Tyr Ile Cys Asn Val Asn His Lys Pro Ser Asn Thr Lys Val Asp
                565                 570                 575

Lys Lys Val
```

```
<210> SEQ ID NO 244
<211> LENGTH: 2310
<212> TYPE: DNA
<213> ORGANISM: Artificial Sequence
<220> FEATURE:
<223> OTHER INFORMATION: TSC129a DNA

<400> SEQUENCE: 244

atggaagcac cagcgcagct tctcttcctc ctgctactct ggctcccaga taccaccggt     60

gacattgtgc tgacccaatc tccagcttct ttggctgtgt ctctagggca gagggccacc    120

atctcctgca aggccagcca aagtgttgat tatgatggtg atagttattt gaactggtac    180

caacagattc caggacagcc acccaaactc ctcatctatg atgcatccaa tctagtttct    240

gggatcccac ccaggtttag tggcagtggg tctgggacag acttcaccct caacatccat    300

cctgtggaga aggtggatgc tgcaacctat cactgccagc aaagtactga ggatccgtgg    360

acgttcggtg gaggcaccaa gctggaaatc aaaggtggcg gtggttcggg cggtggtggg    420

tcgggtggcg gcggagctag ccaggttcag ctgcagcagt ctggggctga gctggtgagg    480

cctgggtcct cagtgaagat ttcctgcaag gcttctggct atgcattcag tagctactgg    540

atgaactggg tgaagcagag gcctggacag ggtcttgagt ggattggaca gatttggcct    600

ggagatggtg atactaacta caatggaaag ttcaagggta aagccactct gactgcagac    660

gaatcctcca gcacagccta catgcaactc agcagcctag catctgagga ctctgcggtc    720

tatttctgtg caagacggga gactacgacg gtaggccgtt attactatgc tatggactac    780

tggggtcaag gaacctcagt caccgtctcc tcgagtgagc ccaaatcttc tgacaaaact    840

cacacatgcc caccgtgccc agcacctgaa gccgcgggtg caccgtcagt cttcctcttc    900

cccccaaaac ccaaggacac cctcatgatc tcccggaccc ctgaggtcac atgcgtggtg    960

gtggacgtga gccacgaaga ccctgaggtc aagttcaact ggtacgtgga cggcgtggag   1020
```

```
gtgcataatg ccaagacaaa gccgcgggag gagcagtaca acagcacgta ccgtgtggtc   1080

agcgtcctca ccgtcctgca ccaggactgg ctgaatggca aggcgtacgc gtgcgcggtc   1140

tccaacaaag ccctcccagc ccccatcgag aaaaccatct ccaaagccaa agggcagccc   1200

cgagaaccac aggtgtacac cctgcccccca tcccgggatg agctgaccaa gaaccaggtc   1260

agcctgacct gcctggtcaa aggcttctat ccaagcgaca tcgccgtgga gtgggagagc   1320

aatgggcagc cggagaacaa ctacaagacc acgcctcccg tgctggactc cgacggctcc   1380

ttcttcctct acagcaagct caccgtggac aagagcaggt ggcagcaggg gaacgtcttc   1440

tcatgctccg tgatgcatga ggctctgcac aaccactaca cgcagaagag cctctccctg   1500

tctccgggtc agaggcacaa caattcttcc ctgaatacag gaactcagat ggcaggtcat   1560

tctccgaatt ctcaggtcca gctggtgcag tctgggggcg gagtggtgca gcctgggcgg   1620

tcactgaggc tgtcctgcaa ggcttctggc tacaccttta ctagatctac gatgcactgg   1680

gtaaggcagg cccctggaaa gggtctggaa tggattggat acattaatcc tagcagtgct   1740

tatactaatt acaatcagaa attcaaggac aggttcacaa tcagcgcaga caaatccaag   1800

agcacagcct tcctgcagat ggacagcctg aggcccgagg acaccggcgt ctatttctgt   1860

gcacggcccc aagtccacta tgattacaac gggtttcctt actggggcca agggactccc   1920

gtcactgtct ctagcggtgg cggagggtct gggggtggcg gatccggagg tggtggctct   1980

gcacaagaca tccagatgac ccagtctcca agcagcctgt ctgcaagcgt gggggacagg   2040

gtcaccatga cctgcagtgc cagctcaagt gtaagttaca tgaactggta ccagcagaag   2100

cccggcaagg cccccaaaag atggatttat gactcatcca aactggcttc tggagtccct   2160

gctcgcttca gtggcagtgg gtctgggacc gactataccc tcacaatcag cagcctgcag   2220

cccgaagatt tcgccactta ttactgccag cagtggagtc gtaacccacc cacgttcgga   2280

ggggggacca agctacaaat tacacgataa                                    2310
```

<210> SEQ ID NO 245
<211> LENGTH: 749
<212> TYPE: PRT
<213> ORGANISM: Artificial Sequence
<220> FEATURE:
<223> OTHER INFORMATION: TSC129a mature protein

<400> SEQUENCE: 245

```
Asp Ile Val Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
    50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys Gly
            100                 105                 110

Gly Gly Gly Ser Gly Gly Gly Gly Ser Gly Gly Gly Gly Ala Ser Gln
        115                 120                 125

Val Gln Leu Gln Gln Ser Gly Ala Glu Leu Val Arg Pro Gly Ser Ser
```

```
    130                 135                 140

Val Lys Ile Ser Cys Lys Ala Ser Gly Tyr Ala Phe Ser Ser Tyr Trp
145                 150                 155                 160

Met Asn Trp Val Lys Gln Arg Pro Gly Gln Gly Leu Glu Trp Ile Gly
                165                 170                 175

Gln Ile Trp Pro Gly Asp Gly Asp Thr Asn Tyr Asn Gly Lys Phe Lys
            180                 185                 190

Gly Lys Ala Thr Leu Thr Ala Asp Glu Ser Ser Ser Thr Ala Tyr Met
        195                 200                 205

Gln Leu Ser Ser Leu Ala Ser Glu Asp Ser Ala Val Tyr Phe Cys Ala
    210                 215                 220

Arg Arg Glu Thr Thr Thr Val Gly Arg Tyr Tyr Tyr Ala Met Asp Tyr
225                 230                 235                 240

Trp Gly Gln Gly Thr Ser Val Thr Val Ser Ser Ser Glu Pro Lys Ser
                245                 250                 255

Ser Asp Lys Thr His Thr Cys Pro Pro Cys Pro Ala Pro Glu Ala Ala
            260                 265                 270

Gly Ala Pro Ser Val Phe Leu Phe Pro Pro Lys Pro Lys Asp Thr Leu
        275                 280                 285

Met Ile Ser Arg Thr Pro Glu Val Thr Cys Val Val Val Asp Val Ser
    290                 295                 300

His Glu Asp Pro Glu Val Lys Phe Asn Trp Tyr Val Asp Gly Val Glu
305                 310                 315                 320

Val His Asn Ala Lys Thr Lys Pro Arg Glu Glu Gln Tyr Asn Ser Thr
                325                 330                 335

Tyr Arg Val Val Ser Val Leu Thr Val Leu His Gln Asp Trp Leu Asn
            340                 345                 350

Gly Lys Ala Tyr Ala Cys Ala Val Ser Asn Lys Ala Leu Pro Ala Pro
        355                 360                 365

Ile Glu Lys Thr Ile Ser Lys Ala Lys Gly Gln Pro Arg Glu Pro Gln
    370                 375                 380

Val Tyr Thr Leu Pro Pro Ser Arg Asp Glu Leu Thr Lys Asn Gln Val
385                 390                 395                 400

Ser Leu Thr Cys Leu Val Lys Gly Phe Tyr Pro Ser Asp Ile Ala Val
                405                 410                 415

Glu Trp Glu Ser Asn Gly Gln Pro Glu Asn Asn Tyr Lys Thr Thr Pro
            420                 425                 430

Pro Val Leu Asp Ser Asp Gly Ser Phe Phe Leu Tyr Ser Lys Leu Thr
        435                 440                 445

Val Asp Lys Ser Arg Trp Gln Gln Gly Asn Val Phe Ser Cys Ser Val
    450                 455                 460

Met His Glu Ala Leu His Asn His Tyr Thr Gln Lys Ser Leu Ser Leu
465                 470                 475                 480

Ser Pro Gly Gln Arg His Asn Asn Ser Ser Leu Asn Thr Gly Thr Gln
                485                 490                 495

Met Ala Gly His Ser Pro Asn Ser Gln Val Gln Leu Val Gln Ser Gly
            500                 505                 510

Gly Gly Val Val Gln Pro Gly Arg Ser Leu Arg Leu Ser Cys Lys Ala
        515                 520                 525

Ser Gly Tyr Thr Phe Thr Arg Ser Thr Met His Trp Val Arg Gln Ala
    530                 535                 540

Pro Gly Lys Gly Leu Glu Trp Ile Gly Tyr Ile Asn Pro Ser Ser Ala
545                 550                 555                 560
```

Tyr Thr Asn Tyr Asn Gln Lys Phe Lys Asp Arg Phe Thr Ile Ser Ala
565 570 575

Asp Lys Ser Lys Ser Thr Ala Phe Leu Gln Met Asp Ser Leu Arg Pro
580 585 590

Glu Asp Thr Gly Val Tyr Phe Cys Ala Arg Pro Gln Val His Tyr Asp
595 600 605

Tyr Asn Gly Phe Pro Tyr Trp Gly Gln Gly Thr Pro Val Thr Val Ser
610 615 620

Ser Gly Gly Gly Gly Ser Gly Gly Gly Gly Ser Gly Gly Gly Gly Ser
625 630 635 640

Ala Gln Asp Ile Gln Met Thr Gln Ser Pro Ser Ser Leu Ser Ala Ser
645 650 655

Val Gly Asp Arg Val Thr Met Thr Cys Ser Ala Ser Ser Ser Val Ser
660 665 670

Tyr Met Asn Trp Tyr Gln Gln Lys Pro Gly Lys Ala Pro Lys Arg Trp
675 680 685

Ile Tyr Asp Ser Ser Lys Leu Ala Ser Gly Val Pro Ala Arg Phe Ser
690 695 700

Gly Ser Gly Ser Gly Thr Asp Tyr Thr Leu Thr Ile Ser Ser Leu Gln
705 710 715 720

Pro Glu Asp Phe Ala Thr Tyr Tyr Cys Gln Gln Trp Ser Arg Asn Pro
725 730 735

Pro Thr Phe Gly Gly Gly Thr Lys Leu Gln Ile Thr Arg
740 745

<210> SEQ ID NO 246
<211> LENGTH: 1806
<212> TYPE: DNA
<213> ORGANISM: Artificial Sequence
<220> FEATURE:
<223> OTHER INFORMATION: TSC218 DNA

<400> SEQUENCE: 246 atggatttc aagtgcagat tttcagcttc ctgctaatca gtgcttcagt cataatgtcg 60
cgaggacagg tccagctggt ggagtctggg ggcggagtgg tgcagcctgg gcggtcactg 120
aggctgtcct gcaaggcttc tggctacacc tttactagat ctacgatgca ctgggtaagg 180
caggcccctg gacaaggtct ggaatggatt ggatacatta atcctagcag tgcttatact 240
aattacaatc agaaattcaa ggacaggttc acaatcagcg cagacaaatc caagagcaca 300
gccttcctgc agatggacag cctgaggccc gaggacaccg gcgtctattt ctgtgcacgg 360
ccccaagtcc actatgatta caacgggttt ccttactggg gccaagggac tcccgtcact 420
gtctctagcg gtggcggagg gtctgggggt ggcggatccg gaggtggtgg ctctgcacaa 480
gacatccaga tgacccagtc tccaagcagc ctgtctgcaa gcgtggggga cagggtcacc 540
atgacctgca gtgccagctc aagtgtaagt tacatgaact ggtaccagca gaagccgggc 600
aaggccccca aactcctcat ttatgactca tccaaactgg cttctggagt ccctgctcgc 660
ttcagtggca gtgggtctgg gaccgactat accctcacaa tcagcagcct gcagcccgaa 720
gatttcgcca cttattactg ccagcagtgg agtcgtaacc cacccacttt cggcggaggg 780
accaaggtgg agatcaaatc ctcgagtgag cccaaatctt ctgacaaaac tcacacatgc 840
ccaccgtgcc cagcacctga agccgcgggt gcaccgtcag tcttcctctt ccccccaaaa 900
cccaaggaca ccctcatgat ctcccggacc cctgaggtca catgcgtggt ggtggacgtg 960

-continued

```
agccacgaag accctgaggt caagttcaac tggtacgtgg acggcgtgga ggtgcataat   1020

gccaagacaa agccgcggga ggagcagtac aacagcacgt accgtgtggt cagcgtcctc   1080

accgtcctgc accaggactg gctgaatggc aaggcgtacg cgtgcgcggt ctccaacaaa   1140

gccctcccag cccccatcga gaaaaccatc tccaaagcca aagggcagcc ccgagaacca   1200

caggtgtaca ccctgccccc atcccgggat gagctgacca agaaccaggt cagcctgacc   1260

tgcctggtca aaggcttcta tccaagcgac atcgccgtgg agtgggagag caatgggcag   1320

ccggagaaca actacaagac cacgcctccc gtgctggact ccgacggctc cttcttcctc   1380

tacagcaagc tcaccgtgga caagagcagg tggcagcagg ggaacgtctt ctcatgctcc   1440

gtgatgcatg aggctctgca caaccactac acgcagaaga gcctctccct gtctccgggt   1500

aaatctagag cctccaccaa gggcccatcg gtcttccccc tggcaccctc ctccaagagc   1560

acctctgggg gcacagcggc cctgggctgc ctggtcaagg actacttccc cgagccggtg   1620

acggtgtcgt ggaactcagg cgccctgacc agcggcgtgc acaccttccc ggctgtccta   1680

cagtcctcag gactctactc cctcagcagc gtggtgaccg tgccctccag cagcttgggc   1740

acccagacct acatctgcaa cgtgaatcac aagcccagca acaccaaggt ggacaagaaa   1800

gtttga                                                              1806
```

<210> SEQ ID NO 247
<211> LENGTH: 579
<212> TYPE: PRT
<213> ORGANISM: Artificial Sequence
<220> FEATURE:
<223> OTHER INFORMATION: TSC218 mature protein

<400> SEQUENCE: 247

```
Gln Val Gln Leu Val Glu Ser Gly Gly Gly Val Val Gln Pro Gly Arg
1               5                   10                  15

Ser Leu Arg Leu Ser Cys Lys Ala Ser Gly Tyr Thr Phe Thr Arg Ser
            20                  25                  30

Thr Met His Trp Val Arg Gln Ala Pro Gly Gln Gly Leu Glu Trp Ile
        35                  40                  45

Gly Tyr Ile Asn Pro Ser Ser Ala Tyr Thr Asn Tyr Asn Gln Lys Phe
    50                  55                  60

Lys Asp Arg Phe Thr Ile Ser Ala Asp Lys Ser Lys Ser Thr Ala Phe
65                  70                  75                  80

Leu Gln Met Asp Ser Leu Arg Pro Glu Asp Thr Gly Val Tyr Phe Cys
                85                  90                  95

Ala Arg Pro Gln Val His Tyr Asp Tyr Asn Gly Phe Pro Tyr Trp Gly
            100                 105                 110

Gln Gly Thr Pro Val Thr Val Ser Ser Gly Gly Gly Gly Ser Gly Gly
        115                 120                 125

Gly Gly Ser Gly Gly Gly Gly Ser Ala Gln Asp Ile Gln Met Thr Gln
    130                 135                 140

Ser Pro Ser Ser Leu Ser Ala Ser Val Gly Asp Arg Val Thr Met Thr
145                 150                 155                 160

Cys Ser Ala Ser Ser Ser Val Ser Tyr Met Asn Trp Tyr Gln Gln Lys
                165                 170                 175

Pro Gly Lys Ala Pro Lys Leu Leu Ile Tyr Asp Ser Ser Lys Leu Ala
            180                 185                 190

Ser Gly Val Pro Ala Arg Phe Ser Gly Ser Gly Ser Gly Thr Asp Tyr
        195                 200                 205
```

-continued

```
Thr Leu Thr Ile Ser Ser Leu Gln Pro Glu Asp Phe Ala Thr Tyr Tyr
    210                 215                 220

Cys Gln Gln Trp Ser Arg Asn Pro Pro Thr Phe Gly Gly Gly Thr Lys
225                 230                 235                 240

Val Glu Ile Lys Ser Ser Ser Glu Pro Lys Ser Ser Asp Lys Thr His
                245                 250                 255

Thr Cys Pro Pro Cys Pro Ala Pro Glu Ala Ala Gly Ala Pro Ser Val
            260                 265                 270

Phe Leu Phe Pro Pro Lys Pro Lys Asp Thr Leu Met Ile Ser Arg Thr
        275                 280                 285

Pro Glu Val Thr Cys Val Val Val Asp Val Ser His Glu Asp Pro Glu
    290                 295                 300

Val Lys Phe Asn Trp Tyr Val Asp Gly Val Glu Val His Asn Ala Lys
305                 310                 315                 320

Thr Lys Pro Arg Glu Glu Gln Tyr Asn Ser Thr Tyr Arg Val Val Ser
                325                 330                 335

Val Leu Thr Val Leu His Gln Asp Trp Leu Asn Gly Lys Ala Tyr Ala
            340                 345                 350

Cys Ala Val Ser Asn Lys Ala Leu Pro Ala Pro Ile Glu Lys Thr Ile
        355                 360                 365

Ser Lys Ala Lys Gly Gln Pro Arg Glu Pro Gln Val Tyr Thr Leu Pro
    370                 375                 380

Pro Ser Arg Asp Glu Leu Thr Lys Asn Gln Val Ser Leu Thr Cys Leu
385                 390                 395                 400

Val Lys Gly Phe Tyr Pro Ser Asp Ile Ala Val Glu Trp Glu Ser Asn
                405                 410                 415

Gly Gln Pro Glu Asn Asn Tyr Lys Thr Thr Pro Pro Val Leu Asp Ser
            420                 425                 430

Asp Gly Ser Phe Phe Leu Tyr Ser Lys Leu Thr Val Asp Lys Ser Arg
        435                 440                 445

Trp Gln Gln Gly Asn Val Phe Ser Cys Ser Val Met His Glu Ala Leu
    450                 455                 460

His Asn His Tyr Thr Gln Lys Ser Leu Ser Leu Ser Pro Gly Lys Ser
465                 470                 475                 480

Arg Ala Ser Thr Lys Gly Pro Ser Val Phe Pro Leu Ala Pro Ser Ser
                485                 490                 495

Lys Ser Thr Ser Gly Gly Thr Ala Ala Leu Gly Cys Leu Val Lys Asp
            500                 505                 510

Tyr Phe Pro Glu Pro Val Thr Val Ser Trp Asn Ser Gly Ala Leu Thr
        515                 520                 525

Ser Gly Val His Thr Phe Pro Ala Val Leu Gln Ser Ser Gly Leu Tyr
    530                 535                 540

Ser Leu Ser Ser Val Val Thr Val Pro Ser Ser Ser Leu Gly Thr Gln
545                 550                 555                 560

Thr Tyr Ile Cys Asn Val Asn His Lys Pro Ser Asn Thr Lys Val Asp
                565                 570                 575

Lys Lys Val
```

<210> SEQ ID NO 248
<211> LENGTH: 1827
<212> TYPE: DNA
<213> ORGANISM: Artificial Sequence
<220> FEATURE:
<223> OTHER INFORMATION: TSC221 DNA

<400> SEQUENCE: 248

```
atggattttc aagtgcagat tttcagcttc ctgctaatca gtgcttcagt cataatgtcg      60
cgaggacagg tccagctggt ggagtctggg ggcggagtgg tgcagcctgg gcggtcactg     120
aggctgtcct gcaaggcttc tggctacacc tttactagat ctacgatgca ctgggtaagg     180
caggcccctg gacaaggtct ggaatggatt ggatacatta atcctagcag tgcttatact     240
aattacaatc agaaattcaa ggacaggttc acaatcagcg cagacaaatc caagagcaca     300
gccttcctgc agatggacag cctgaggccc gaggacaccg gcgtctattt ctgtgcacgg     360
ccccaagtcc actatgatta caacgggttt ccttactggg gccaagggac tcccgtcact     420
gtctctagcg gtggcggagg gtctgggggt ggcggatccg gaggtggtgg ctctgcacaa     480
gacatccaga tgacccagtc tccaagcagc ctgtctgcaa gcgtgggggga cagggtcacc     540
atgacctgca gtgccagctc aagtgtaagt tacatgaact ggtaccagca gaagccgggc     600
aaggccccca aactcctcat ttatgactca tccaaactgg cttctggagt ccctgctcgc     660
ttcagtggca gtgggtctgg gaccgactat accctcacaa tcagcagcct gcagcccgaa     720
gatttcgcca cttattactg ccagcagtgg agtcgtaacc cacccacttt cggcggaggg     780
accaaggtgg agatcaaatc ctcgagtgag cccaaatctt ctgacaaaac tcacacatgc     840
ccaccgtgcc cagcacctga agccgcgggt gcaccgtcag tcttcctctt ccccccaaaa     900
cccaaggaca ccctcatgat ctcccggacc cctgaggtca catgcgtggt ggtggacgtg     960
agccacgaag accctgaggt caagttcaac tggtacgtgg acggcgtgga ggtgcataat    1020
gccaagacaa agccgcggga ggagcagtac aacagcacgt accgtgtggt cagcgtcctc    1080
accgtcctgc accaggactg gctgaatggc aaggcgtacg cgtgcgcggt ctccaacaaa    1140
gccctcccag cccccatcga gaaaaccatc tccaaagcca aagggcagcc ccgagaacca    1200
caggtgtaca ccctgccccc atcccgggat gagctgacca agaaccaggt cagcctgacc    1260
tgcctggtca aaggcttcta tccaagcgac atcgccgtgg agtgggagag caatgggcag    1320
ccggagaaca actacaagac cacgcctccc gtgctggact ccgacggctc cttcttcctc    1380
tacagcaagc tcaccgtgga caagagcagg tggcagcagg ggaacgtctt ctcatgctcc    1440
gtgatgcatg aggctctgca caaccactac acgcagaaga gcctctccct gtctccgggt    1500
aaatctagaa ctgtggctgc accatctgtc ttcatcttcc cgccatctga tgagcagttg    1560
aaatctggaa ctgcctctgt tgtgtgcctg ctgaattact tctatcccag agaggccaaa    1620
gtacagtgga aggtggataa cgccctccaa tcgggtaact cccaggagag tgccacagag    1680
caggacagca aggacagcac ctacagcctc agcagcgagc tgacgctgag caaagcagac    1740
tacgagaaac acaaagtcta cgcctgcgaa gtcacccatc agggcctgag ctcgcccgtc    1800
acaaagagct tcaacagggg agagtga                                       1827
```

<210> SEQ ID NO 249
<211> LENGTH: 586
<212> TYPE: PRT
<213> ORGANISM: Artificial Sequence
<220> FEATURE:
<223> OTHER INFORMATION: TSC221 mature protein

<400> SEQUENCE: 249

```
Gln Val Gln Leu Val Glu Ser Gly Gly Gly Val Val Gln Pro Gly Arg
1               5                   10                  15

Ser Leu Arg Leu Ser Cys Lys Ala Ser Gly Tyr Thr Phe Thr Arg Ser
            20                  25                  30
```

```
Thr Met His Trp Val Arg Gln Ala Pro Gly Gln Gly Leu Glu Trp Ile
        35                  40                  45

Gly Tyr Ile Asn Pro Ser Ser Ala Tyr Thr Asn Tyr Asn Gln Lys Phe
    50                  55                  60

Lys Asp Arg Phe Thr Ile Ser Ala Asp Lys Ser Lys Ser Thr Ala Phe
65                  70                  75                  80

Leu Gln Met Asp Ser Leu Arg Pro Glu Asp Thr Gly Val Tyr Phe Cys
                85                  90                  95

Ala Arg Pro Gln Val His Tyr Asp Tyr Asn Gly Phe Pro Tyr Trp Gly
            100                 105                 110

Gln Gly Thr Pro Val Thr Val Ser Ser Gly Gly Gly Gly Ser Gly Gly
        115                 120                 125

Gly Gly Ser Gly Gly Gly Gly Ser Ala Gln Asp Ile Gln Met Thr Gln
    130                 135                 140

Ser Pro Ser Ser Leu Ser Ala Ser Val Gly Asp Arg Val Thr Met Thr
145                 150                 155                 160

Cys Ser Ala Ser Ser Ser Val Ser Tyr Met Asn Trp Tyr Gln Gln Lys
                165                 170                 175

Pro Gly Lys Ala Pro Lys Leu Leu Ile Tyr Asp Ser Ser Lys Leu Ala
            180                 185                 190

Ser Gly Val Pro Ala Arg Phe Ser Gly Ser Gly Ser Gly Thr Asp Tyr
        195                 200                 205

Thr Leu Thr Ile Ser Ser Leu Gln Pro Glu Asp Phe Ala Thr Tyr Tyr
    210                 215                 220

Cys Gln Gln Trp Ser Arg Asn Pro Pro Thr Phe Gly Gly Gly Thr Lys
225                 230                 235                 240

Val Glu Ile Lys Ser Ser Ser Glu Pro Lys Ser Ser Asp Lys Thr His
                245                 250                 255

Thr Cys Pro Pro Cys Pro Ala Pro Glu Ala Ala Gly Ala Pro Ser Val
            260                 265                 270

Phe Leu Phe Pro Pro Lys Pro Lys Asp Thr Leu Met Ile Ser Arg Thr
        275                 280                 285

Pro Glu Val Thr Cys Val Val Val Asp Val Ser His Glu Asp Pro Glu
    290                 295                 300

Val Lys Phe Asn Trp Tyr Val Asp Gly Val Glu Val His Asn Ala Lys
305                 310                 315                 320

Thr Lys Pro Arg Glu Glu Gln Tyr Asn Ser Thr Tyr Arg Val Val Ser
                325                 330                 335

Val Leu Thr Val Leu His Gln Asp Trp Leu Asn Gly Lys Ala Tyr Ala
            340                 345                 350

Cys Ala Val Ser Asn Lys Ala Leu Pro Ala Pro Ile Glu Lys Thr Ile
        355                 360                 365

Ser Lys Ala Lys Gly Gln Pro Arg Glu Pro Gln Val Tyr Thr Leu Pro
    370                 375                 380

Pro Ser Arg Asp Glu Leu Thr Lys Asn Gln Val Ser Leu Thr Cys Leu
385                 390                 395                 400

Val Lys Gly Phe Tyr Pro Ser Asp Ile Ala Val Glu Trp Glu Ser Asn
                405                 410                 415

Gly Gln Pro Glu Asn Asn Tyr Lys Thr Thr Pro Pro Val Leu Asp Ser
            420                 425                 430

Asp Gly Ser Phe Phe Leu Tyr Ser Lys Leu Thr Val Asp Lys Ser Arg
        435                 440                 445
```

```
Trp Gln Gln Gly Asn Val Phe Ser Cys Ser Val Met His Glu Ala Leu
    450                 455                 460

His Asn His Tyr Thr Gln Lys Ser Leu Ser Leu Ser Pro Gly Lys Ser
465                 470                 475                 480

Arg Thr Val Ala Ala Pro Ser Val Phe Ile Phe Pro Pro Ser Asp Glu
                485                 490                 495

Gln Leu Lys Ser Gly Thr Ala Ser Val Val Cys Leu Leu Asn Tyr Phe
            500                 505                 510

Tyr Pro Arg Glu Ala Lys Val Gln Trp Lys Val Asp Asn Ala Leu Gln
        515                 520                 525

Ser Gly Asn Ser Gln Glu Ser Ala Thr Glu Gln Asp Ser Lys Asp Ser
    530                 535                 540

Thr Tyr Ser Leu Ser Ser Glu Leu Thr Leu Ser Lys Ala Asp Tyr Glu
545                 550                 555                 560

Lys His Lys Val Tyr Ala Cys Glu Val Thr His Gln Gly Leu Ser Ser
                565                 570                 575

Pro Val Thr Lys Ser Phe Asn Arg Gly Glu
            580                 585


<210> SEQ ID NO 250
<211> LENGTH: 2283
<212> TYPE: DNA
<213> ORGANISM: Artificial Sequence
<220> FEATURE:
<223> OTHER INFORMATION: TSC194 DNA

<400> SEQUENCE: 250

atggaagcac cagcgcagct tctcttcctc ctgctactct ggctcccaga taccaccggt     60

gatatccaga tgacccagtc tccatccgcc atgtctgcat ctgtaggaga cagagtcacc    120

atcacttgcc gggcgagtaa gagcattagc aaatatttag cctggtttca gcagaaacca    180

gggaaagttc ctaagctccg catccattct ggatctactt tgcaatcagg ggtcccatct    240

cggttcagtg gcagtggatc tgggacagaa tttactctca ccatcagcag cctgcagcct    300

gaagattttg caacttatta ctgtcaacag catattgaat acccgtggac gttcggccaa    360

gggaccaagg tggaaatcaa acgaggtggc ggagggtctg ggggtggcgg atccggaggt    420

ggtggctctc aggtccagct ggtacagtct ggggctgagg tgaagaagcc tggggcttca    480

gtgaaggtct cctgcaaggc ttctggatac acattcactg actactacat gcactgggtg    540

cgacaggccc ctggacaagg gcttgagtgg atgggatatt ttaatcctta taatgattat    600

actagatacg cacagaagtt ccagggcaga gtcaccatga ccagggacac gtctatcagc    660

acagcctaca tggagctgag cagcctgaga tctgacgaca cggccgtgta ttactgtgca    720

agatcggatg gttactacga tgctatggac tactggggtc aaggaaccac agtcaccgtc    780

tcctcgagtg agcccaaatc ttctgacaaa actcacacat gcccaccgtg cccagcacct    840

gaagccgcgg gtgcaccgtc agtcttcctc ttccccccaa aacccaagga caccctcatg    900

atctcccgga cccctgaggt cacatgcgtg gtggtggacg tgagccacga agaccctgag    960

gtcaagttca actggtacgt ggacggcgtg gaggtgcata atgccaagac aaagccgcgg   1020

gaggagcagt acaacagcac gtaccgtgtg gtcagcgtcc tcaccgtcct gcaccaggac   1080

tggctgaatg gcaaggcgta cgcgtgcgcg gtctccaaca aagccctccc agcccccatc   1140

gagaaaacca tctccaaagc caaagggcag ccccgagaac cacaggtgta caccctgccc   1200

ccatcccggg atgagctgac caagaaccag gtcagcctga cctgcctggt caaaggcttc   1260
```

```
tatccaagcg acatcgccgt ggagtgggag agcaatgggc agccggagaa caactacaag   1320

accacgcctc ccgtgctgga ctccgacggc tccttcttcc tctacagcaa gctcaccgtg   1380

gacaagagca ggtggcagca ggggaacgtc ttctcatgct ccgtgatgca tgaggctctg   1440

cacaaccact acacgcagaa gagcctctcc ctgtctccgg gtcagaggca caacaattct   1500

tccctgaata caggaactca gatggcaggt cattctccga attctcaggt ccagctggtg   1560

cagtctgggg gcggagtggt gcagcctggg cggtcactga ggctgtcctg caaggcttct   1620

ggctacacct ttactagatc tacgatgcac tgggtaaggc aggcccctgg aaagggtctg   1680

gaatggattg gatacattaa tcctagcagt gcttatacta attacaatca gaaattcaag   1740

gacaggttca caatcagcgc agacaaatcc aagagcacag ccttcctgca gatggacagc   1800

ctgaggcccg aggacaccgg cgtctatttc tgtgcacggc cccaagtcca ctatgattac   1860

aacgggtttc cttactgggg ccaagggact cccgtcactg tctctagcgg tggcggaggg   1920

tctgggggtg gcggatccgg aggtggtggc tctgcacaag acatccagat gacccagtct   1980

ccaagcagcc tgtctgcaag cgtgggggac agggtcacca tgacctgcag tgccagctca   2040

agtgtaagtt acatgaactg gtaccagcag aagcccggca aggcccccaa aagatggatt   2100

tatgactcat ccaaactggc ttctggagtc cctgctcgct tcagtggcag tgggtctggg   2160

accgactata ccctcacaat cagcagcctg cagcccgaag atttcgccac ttattactgc   2220

cagcagtgga gtcgtaaccc acccacgttc ggagggggga ccaagctaca aattacacga   2280

taa                                                                 2283
```

<210> SEQ ID NO 251
<211> LENGTH: 740
<212> TYPE: PRT
<213> ORGANISM: Artificial Sequence
<220> FEATURE:
<223> OTHER INFORMATION: TSC194 mature protein

<400> SEQUENCE: 251

```
Asp Ile Gln Met Thr Gln Ser Pro Ser Ala Met Ser Ala Ser Val Gly
1               5                   10                  15

Asp Arg Val Thr Ile Thr Cys Arg Ala Ser Lys Ser Ile Ser Lys Tyr
            20                  25                  30

Leu Ala Trp Phe Gln Gln Lys Pro Gly Lys Val Pro Lys Leu Arg Ile
        35                  40                  45

His Ser Gly Ser Thr Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln His Ile Glu Tyr Pro Trp
                85                  90                  95

Thr Phe Gly Gln Gly Thr Lys Val Glu Ile Lys Arg Gly Gly Gly Gly
            100                 105                 110

Ser Gly Gly Gly Gly Ser Gly Gly Gly Gly Ser Gln Val Gln Leu Val
        115                 120                 125

Gln Ser Gly Ala Glu Val Lys Lys Pro Gly Ala Ser Val Lys Val Ser
    130                 135                 140

Cys Lys Ala Ser Gly Tyr Thr Phe Thr Asp Tyr Tyr Met His Trp Val
145                 150                 155                 160

Arg Gln Ala Pro Gly Gln Gly Leu Glu Trp Met Gly Tyr Phe Asn Pro
                165                 170                 175
```

```
Tyr Asn Asp Tyr Thr Arg Tyr Ala Gln Lys Phe Gln Gly Arg Val Thr
            180                 185                 190

Met Thr Arg Asp Thr Ser Ile Ser Thr Ala Tyr Met Glu Leu Ser Ser
        195                 200                 205

Leu Arg Ser Asp Asp Thr Ala Val Tyr Tyr Cys Ala Arg Ser Asp Gly
    210                 215                 220

Tyr Tyr Asp Ala Met Asp Tyr Trp Gly Gln Gly Thr Thr Val Thr Val
225                 230                 235                 240

Ser Ser Ser Glu Pro Lys Ser Ser Asp Lys Thr His Thr Cys Pro Pro
                245                 250                 255

Cys Pro Ala Pro Glu Ala Ala Gly Ala Pro Ser Val Phe Leu Phe Pro
            260                 265                 270

Pro Lys Pro Lys Asp Thr Leu Met Ile Ser Arg Thr Pro Glu Val Thr
        275                 280                 285

Cys Val Val Val Asp Val Ser His Glu Asp Pro Glu Val Lys Phe Asn
    290                 295                 300

Trp Tyr Val Asp Gly Val Glu Val His Asn Ala Lys Thr Lys Pro Arg
305                 310                 315                 320

Glu Glu Gln Tyr Asn Ser Thr Tyr Arg Val Val Ser Val Leu Thr Val
                325                 330                 335

Leu His Gln Asp Trp Leu Asn Gly Lys Ala Tyr Ala Cys Ala Val Ser
            340                 345                 350

Asn Lys Ala Leu Pro Ala Pro Ile Glu Lys Thr Ile Ser Lys Ala Lys
        355                 360                 365

Gly Gln Pro Arg Glu Pro Gln Val Tyr Thr Leu Pro Pro Ser Arg Asp
    370                 375                 380

Glu Leu Thr Lys Asn Gln Val Ser Leu Thr Cys Leu Val Lys Gly Phe
385                 390                 395                 400

Tyr Pro Ser Asp Ile Ala Val Glu Trp Glu Ser Asn Gly Gln Pro Glu
                405                 410                 415

Asn Asn Tyr Lys Thr Thr Pro Pro Val Leu Asp Ser Asp Gly Ser Phe
            420                 425                 430

Phe Leu Tyr Ser Lys Leu Thr Val Asp Lys Ser Arg Trp Gln Gln Gly
        435                 440                 445

Asn Val Phe Ser Cys Ser Val Met His Glu Ala Leu His Asn His Tyr
    450                 455                 460

Thr Gln Lys Ser Leu Ser Leu Ser Pro Gly Gln Arg His Asn Asn Ser
465                 470                 475                 480

Ser Leu Asn Thr Gly Thr Gln Met Ala Gly His Ser Pro Asn Ser Gln
                485                 490                 495

Val Gln Leu Val Gln Ser Gly Gly Gly Val Val Gln Pro Gly Arg Ser
            500                 505                 510

Leu Arg Leu Ser Cys Lys Ala Ser Gly Tyr Thr Phe Thr Arg Ser Thr
        515                 520                 525

Met His Trp Val Arg Gln Ala Pro Gly Lys Gly Leu Glu Trp Ile Gly
    530                 535                 540

Tyr Ile Asn Pro Ser Ser Ala Tyr Thr Asn Tyr Asn Gln Lys Phe Lys
545                 550                 555                 560

Asp Arg Phe Thr Ile Ser Ala Asp Lys Ser Lys Ser Thr Ala Phe Leu
                565                 570                 575

Gln Met Asp Ser Leu Arg Pro Glu Asp Thr Gly Val Tyr Phe Cys Ala
            580                 585                 590

Arg Pro Gln Val His Tyr Asp Tyr Asn Gly Phe Pro Tyr Trp Gly Gln
```

595 600 605

Gly Thr Pro Val Thr Val Ser Ser Gly Gly Gly Gly Ser Gly Gly Gly
610 615 620

Gly Ser Gly Gly Gly Gly Ser Ala Gln Asp Ile Gln Met Thr Gln Ser
625 630 635 640

Pro Ser Ser Leu Ser Ala Ser Val Gly Asp Arg Val Thr Met Thr Cys
645 650 655

Ser Ala Ser Ser Ser Val Ser Tyr Met Asn Trp Tyr Gln Gln Lys Pro
660 665 670

Gly Lys Ala Pro Lys Arg Trp Ile Tyr Asp Ser Ser Lys Leu Ala Ser
675 680 685

Gly Val Pro Ala Arg Phe Ser Gly Ser Gly Ser Gly Thr Asp Tyr Thr
690 695 700

Leu Thr Ile Ser Ser Leu Gln Pro Glu Asp Phe Ala Thr Tyr Tyr Cys
705 710 715 720

Gln Gln Trp Ser Arg Asn Pro Pro Thr Phe Gly Gly Gly Thr Lys Leu
725 730 735

Gln Ile Thr Arg
740

<210> SEQ ID NO 252
<211> LENGTH: 4
<212> TYPE: PRT
<213> ORGANISM: Mus musculus

<400> SEQUENCE: 252

Leu Gln Ile Thr
1

<210> SEQ ID NO 253
<211> LENGTH: 4
<212> TYPE: PRT
<213> ORGANISM: Artificial Sequence
<220> FEATURE:
<223> OTHER INFORMATION: VEIK

<400> SEQUENCE: 253

Val Glu Ile Lys
1

<210> SEQ ID NO 254
<211> LENGTH: 6
<212> TYPE: PRT
<213> ORGANISM: Homo sapiens

<400> SEQUENCE: 254

Val Glu Pro Lys Ser Cys
1 5

<210> SEQ ID NO 255
<211> LENGTH: 6
<212> TYPE: PRT
<213> ORGANISM: Homo sapiens

<400> SEQUENCE: 255

Phe Asn Arg Gly Glu Cys
1 5

The invention claimed is:

1. A CD3 binding polypeptide comprising a CD3 binding domain, wherein the CD3 binding domain has a reduced isoelectric point as compared to the isoelectric point of a binding domain with the amino acid sequence of SEQ ID NO:41;

wherein the CD3 binding domain comprises a humanized variable heavy (VH) region and a humanized variable light (VL) region and wherein the humanized VH region and the humanized VL region comprise framework regions;

wherein the VH region comprises SEQ ID NO: 28, and the VL region comprises SEQ ID NO: 34 or an amino acid sequence from about 90% to less than 100% identical to SEQ ID NO: 34;

wherein the VL region comprises a CDR1 having a sequence of SEQ ID NO: 52, a CDR2 region having a sequence of SEQ ID NO: 53, and a CDR3 having a sequence of SEQ ID NO: 54; and wherein the CD3 binding polypeptide further comprises a second binding domain.

2. The CD3 binding polypeptide of claim 1, wherein two or more amino acids in the framework regions of VL are modified compared to SEQ ID NO: 34 by substituting positively charged amino acids with neutral amino acids and/or substituting neutral amino acids with negatively charged amino acids.

3. The CD3 binding polypeptide of claim 1, wherein at least one of the framework regions comprises an amino acid sequence from a human germline IgG sequence.

4. The CD3 binding polypeptide of claim 3, wherein the human germline IgG sequence comprises SEQ ID NO:43.

5. The CD3 binding polypeptide of claim 3, wherein the human germline IgG sequence comprises SEQ ID NO:44.

6. The CD3 binding polypeptide of claim 1 further comprising a prehinge region.

7. The CD3 binding polypeptide of claim 6, wherein the prehinge region has the sequence SSS, and the CD3 binding polypeptide has a reduced isoelectric point as compared to a CD3 binding polypeptide that is identical except for having a prehinge region having the sequence RRT.

8. A CD3 binding polypeptide comprising a CD3 binding domain with framework regions, a prehinge region and a hinge region, wherein the CD3 binding domain has a reduced isoelectric point as compared to the isoelectric point of the binding domain with the amino acid sequence of SEQ ID NO:41;

wherein the CD3 binding domain comprises a humanized VH region and a humanized VL region;

wherein the VH region comprises SEQ ID NO: 28, and the VL region comprises SEQ ID NO: 34 or an amino acid sequence from about 90% to less than 100% identical to SEQ ID NO: 34;

wherein the VL region comprises a CDR1 having a sequence of SEQ ID NO: 52, a CDR2 region having a sequence of SEQ ID NO: 53, and a CDR3 having a sequence of SEQ ID NO: 54; and wherein the CD3 binding polypeptide further comprises a second binding domain.

9. The CD3 binding polypeptide of claim 8, wherein at least two or more amino acids in the framework regions of VL are modified as compared to SEQ ID NO: 34 by substituting positively charged amino acids with neutral amino acids and/or substituting neutral amino acids with negatively charged amino acids.

10. The CD3 binding polypeptide of claim 8, wherein at least four or more amino acids in the framework regions of VL are modified as compared to SEQ ID NO: 34 by substituting positively charged amino acids with neutral amino acids and/or substituting neutral amino acids with negatively charged amino acids.

11. The CD3 binding polypeptide of claim 8, wherein three to five amino acids in the framework regions of VL are modified as compared to SEQ ID NO: 34 by substituting positively charged amino acids with neutral amino acids and/or substituting neutral amino acids with negatively charged amino acids.

12. The CD3 binding polypeptide of claim 8, wherein three to ten amino acids in the framework regions of VL are modified as compared to SEQ ID NO: 34 by substituting positively charged amino acids with neutral amino acids and/or substituting neutral amino acids with negatively charged amino acids.

13. The CD3 binding polypeptide of claim 8, wherein the CD3 binding polypeptide prehinge region comprises the amino acid sequence SSS or SST.

14. The CD3 binding polypeptide of claim 8, wherein the CD3 binding polypeptide has an empirical isoelectric point of at least 1 pI unit less than the empirical isoelectric point of a polypeptide of SEQ ID NO:4.

15. The CD3 binding polypeptide of claim 8 wherein the second binding domain binds or interacts with a target molecule and the CD3 binding polypeptide induces T-cell cytotoxicity.

16. The CD3 binding polypeptide of claim 15, wherein the second binding domain binds or interacts with a tumor associated antigen.

17. The CD3 binding polypeptide of claim 16, wherein the CD3 binding polypeptide induces T-cells to lyse tumor cells.

18. The CD3 binding polypeptide of claim 16, wherein the CD3 binding polypeptide induces polyclonal T-cell activation and expansion in the vicinity of a tumor.

19. The CD3 binding polypeptide of claim 8, wherein the CD3 binding domain comprises a VL region selected from the group consisting of SEQ ID NO:34, SEQ ID NO:36 and SEQ ID NO:38.

20. The CD3 binding polypeptide of claim 19, wherein the VL region comprises SEQ ID NO:34.

21. The CD3 binding polypeptide of claim 19, wherein the VH region comprises SEQ ID NO:28 and the VL region comprises SEQ ID NO:38.

22. The CD3 binding polypeptide of claim 8, wherein the CD3 binding polypeptide comprises an amino acid sequence selected from the group consisting of SEQ ID NO:8, SEQ ID NO:10, and SEQ ID NO:20.

23. A nucleic acid encoding a polypeptide of claim 8.

24. An expression vector comprising the nucleic acid of claim 23.

25. A recombinant host cell comprising the expression vector of claim 24.

26. A composition comprising the CD3 binding polypeptide of claim 8 and a pharmaceutically acceptable carrier, diluent or excipient.

27. A method for treating prostate cancer comprising administering a therapeutically effective amount of the composition of claim 26 to a patient in need thereof;

wherein the second binding domain binds or interacts with a tumor associated antigen.

28. The CD3 binding polypeptide of claim 8, wherein the CD3 binding polypeptide further comprises an immunoglobulin dimerization domain.

29. The CD3 binding polypeptide of claim 28, wherein the CD3 binding polypeptide forms a homodimer.

30. The CD3 binding polypeptide of claim 28, wherein the CD3 binding polypeptide forms a heterodimer.

31. The CD3 binding polypeptide of claim 8, wherein the CD3 binding domain is about 90% to about 99% identical to SEQ ID NO:41.

32. A CD3 binding polypeptide comprising a CD3 binding domain, wherein the CD3 binding domain comprises a humanized VH region and a humanized VL region;

wherein the VH region comprises an amino acid sequence of SEQ ID NO: 28, and the VL region comprises an amino acid sequence of SEQ ID NO: 34.

33. The CD3 binding polypeptide of claim 6, wherein the prehinge region is a short amino acid sequence that connects the binding domain to the hinge region.

* * * * *